United States Patent
Zhou et al.

(10) Patent No.: US 11,306,108 B2
(45) Date of Patent: Apr. 19, 2022

(54) CHEMICAL COMPOUNDS

(71) Applicant: Boragen, Inc., Durham, NC (US)

(72) Inventors: Yasheen Zhou, Moraga, CA (US); Chunliang Liu, Cary, NC (US); Yong-Kang Zhang, San Jose, CA (US); Marissa Aubrey, Durham, NC (US); Chun Yu Liu, Durham, NC (US)

(73) Assignee: Borah, Inc., Nashville, TN (US)

( * ) Notice: Subject to any disclaimer, the term of this patent is extended or adjusted under 35 U.S.C. 154(b) by 0 days.

(21) Appl. No.: 17/133,515

(22) Filed: Dec. 23, 2020

(65) Prior Publication Data
US 2021/0188879 A1 Jun. 24, 2021

Related U.S. Application Data

(63) Continuation of application No. PCT/US2020/070042, filed on May 12, 2020.

(60) Provisional application No. 62/949,353, filed on Dec. 17, 2019, provisional application No. 62/911,012, filed on Oct. 4, 2019, provisional application No. 62/846,785, filed on May 13, 2019.

(51) Int. Cl.
*C07F 5/02* (2006.01)

(52) U.S. Cl.
CPC ...................... *C07F 5/02* (2013.01)

(58) Field of Classification Search
CPC ........................................ C07F 5/02
See application file for complete search history.

(56) References Cited

U.S. PATENT DOCUMENTS

| | | |
|---|---|---|
| 2011/0294826 A1 | 12/2011 | Xie et al. |
| 2014/0023614 A1 | 1/2014 | Barawkar et al. |
| 2014/0200344 A1 | 7/2014 | Hayashi et al. |
| 2015/0291629 A1 | 10/2015 | Akama |
| 2015/0368245 A1 | 12/2015 | Takahashi et al. |

FOREIGN PATENT DOCUMENTS

| | | |
|---|---|---|
| CA | 02899888 A1 | 2/2016 |
| CN | 108329274 A | 7/2018 |
| CN | 108341835 A | 7/2018 |
| WO | 2011017125 A1 | 2/2010 |
| WO | 2012/085176 A1 | 6/2012 |
| WO | 2014066659 A1 | 5/2014 |
| WO | 2015083028 A1 | 6/2015 |
| WO | 2016024185 A1 | 2/2016 |
| WO | 2020008391 A1 | 1/2020 |
| WO | 2010027975 A1 | 3/2020 |

OTHER PUBLICATIONS

Cahn et al., Angew. Chem. 78:413-447 (1966).

Friedman, et al., "Structure activity optimization of 6H-pyrrolo[2,3-e][1,2,4]triazolo[4,3-a]pyrazines as Jak1 kinase inhibitors," Bioorganic & Medicinal Chemistry Letters 25 (2015) 4399-4404.
Hamaguchi, et al., "Discovery and structural characterization of peficitinib (ASP015K) as a novel and potent JAK inhibitor," Bioorganic & Medicinal Chemistry 26 (2018) 4971-4983.
International Search Report issued in corresponding PCT/US2020/070042 dated Aug. 18, 2020.
Kisseleva et al., Gene, 2002, 285, 1.
Kulagowski, et al., "Identification of Imidazo-Pyrrolopyridines as Novel and Potent JAK1 Inhibitors," J. Med. Chem. 2012, 55, 5901-5921.
Labadie, et al., "Design and evaluation of novel 8-oxo-pyridopyrimidine Jak1/2 inhibitors," Bioorganic & Medicinal Chemistry Letters 23 (2013) 5923-5930.
Parmentier, et al., "Invitro and in vivo characterization of the JAK1 selectivity of upadacitinib (ABT-494)," BMC Rheumatology (2018) 2:23.
Schwartz et al., "JAK inhibition as a therapeutic strategy for immune and inflammatory diseases," Nat. Reg. Drug Discov., Dec. 28, 2017, 17(1):78.
Vazquez, et al., "Identification of N-{cis-3-[Methyl(7H-pyrrolo[2,3-d]pyrimidin-4-yl)amino]cyclobutyl}propane-1-sulfonamide (PF-04965842): A Selective JAK1 Clinical Candidate for the Treatment of Autoimmune Diseases," J. Med. Chem 2018, 61, 1130-1152.
Yamagishi, et al., Discovery of 3,6-dihydroimidazo[4,5-d]pyrrolo[2,3-b]pyridin-2(1H)-one derivatives as novel JAK inhibitors, Bioorganic & Medicinal Chemistry 23 (2015) 4846-4859.
Yamaoka et al., Genome Biology 2004, 5, 253.
Zak, et al., "Discovery and Optimization of C-2 Methyl Imidazopyrrolopyridines as Potent and Orally Bioavailable JAK1 Inhibitors with Selectivity over JAK2," J. Med. Chem 2012, 55, 6176-6193.
Zak, et al., "Identification of C-2 Hydroxyethyl Imidazopyrrolopyridines as Potent JAK1 Inhibitors with Favorable Physicochemical Properties and High Selectivity over JAK2," J. Med. Chem. 2013, 56, 4764-4785.
Damsky, William et al., "JAK Inhibitors in Dermatology: The Promise of a New Drug Class", J. Am. Acad. Dermatol., (Apr. 2017), 76(4):736-744.
Liu, B., et al., "Discovery of Taniborcactam (VNRX-5133): A Broad-Spectrum Serine- and Metallo-beta-lactamase Inhibitor for Carbapenem-Resistant Bacterial Infections", J. Med. Chem. (2020), 63:2789-2801.
Park, E., et al., "Discovery and Biological Evaluation of N-Methyl-pyrrolo[2,3-b]pyridine-5-carboxamide Derivatives as JAK1-Selective Inhibitors", Journal of Medicinal Chemistry, (2021), 64:958-979.
International Search Report for PCT/US2020/070234, dated Oct. 23, 2020.

*Primary Examiner* — Golam M Shameem
(74) *Attorney, Agent, or Firm* — Barnes & Thornburg LLP

(57) ABSTRACT

The present invention describes novel compounds, or their pharmaceutically acceptable salts, pharmaceutical compositions containing them, and their medical uses. The compounds of the invention have activity as Janus kinase (JAK) inhibitors and are useful in the in the treatment or control of inflammation, auto-immune diseases, cancer, and other disorders and indications where modulation of JAK would be desirable. Also described herein are methods of treating inflammation, auto-immune diseases, cancer, and other conditions susceptible to inhibition of JAK by administering a compound herein described.

30 Claims, 32 Drawing Sheets

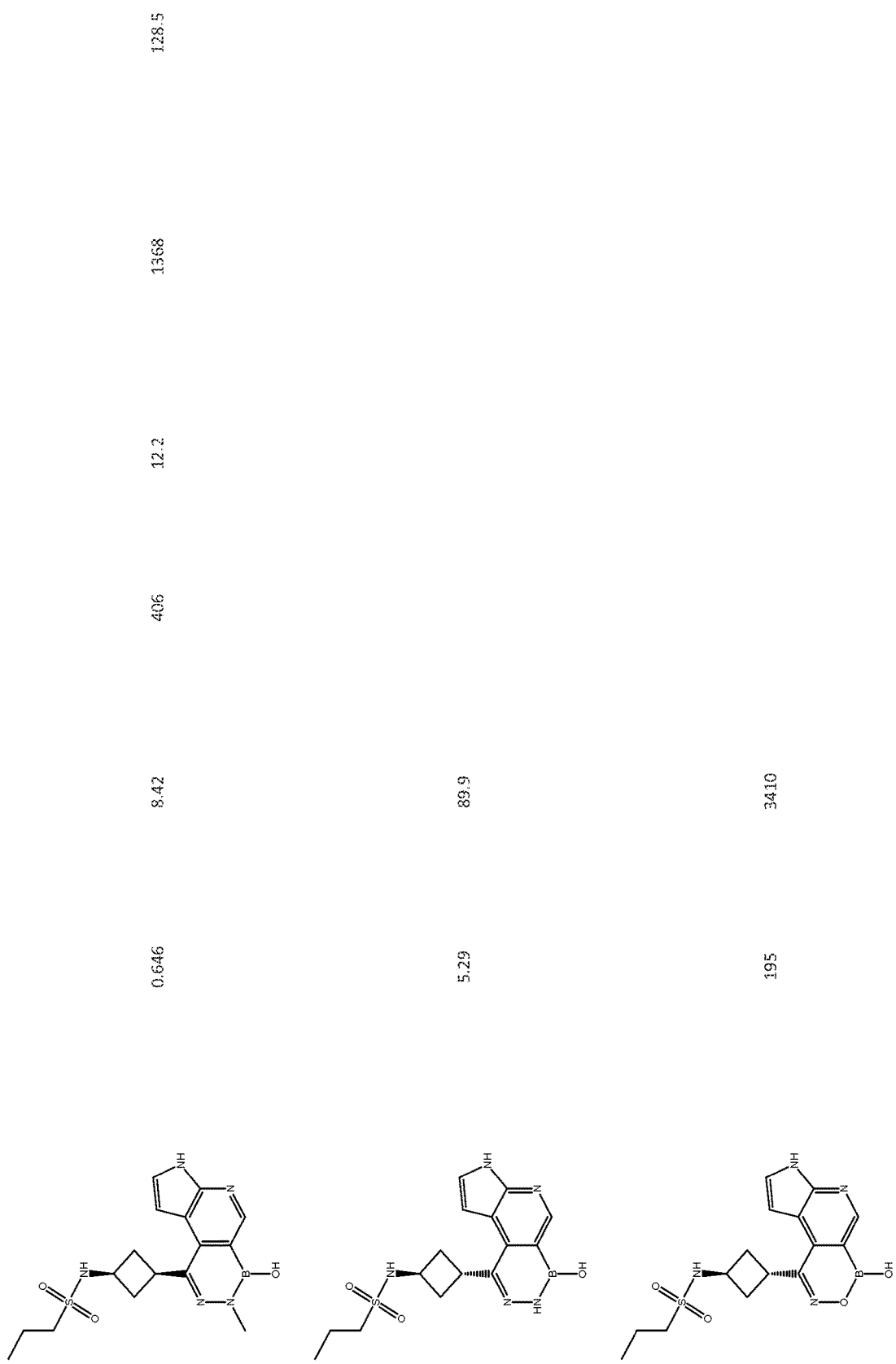

| | | |
|---|---|---|
| 87.4 | 301 | 59.6 |
| 1602 | 3700 | 2254 |
| | 9.89 | 0.4 |
| 0.658 | 1.2 | 0.295 |
| 2.28 | 22 | 1.15 |
| 0.56 | 8.35 | 0.473 |

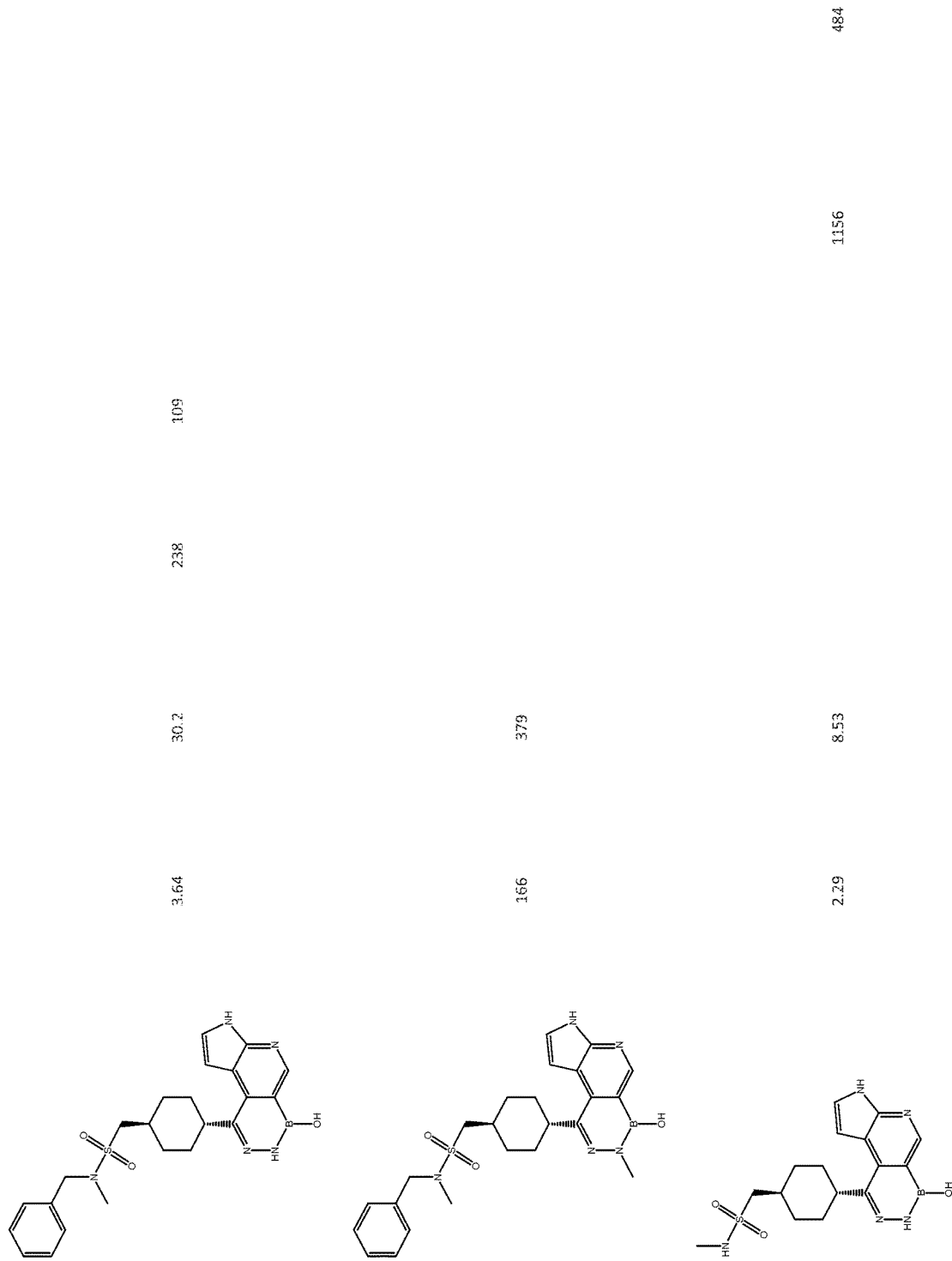

12.4    250

545    >1000

772    >1000

3.52    10.6    3624    144

| 14.8 | 60.8 | | |
| 166 | 687 | | |
| 0.882 | 2.91 | 1932 | 81.4 |
| 21.9 | 125 | | |

FIGURE 2

| structure | EC50: GM-CSF/pSTA T5_nM | EC50: IL-4/pSTAT6 _nM | IC50: JAK1_nM | IC50: JAK2_nM | IC50: JAK3_nM | IC50: TYK2_nM |
|---|---|---|---|---|---|---|
| (structure 1) | 5719 | 246 | 0.583 | 15.8 | | |
| (structure 2) | | | 941 | >1000 | | |

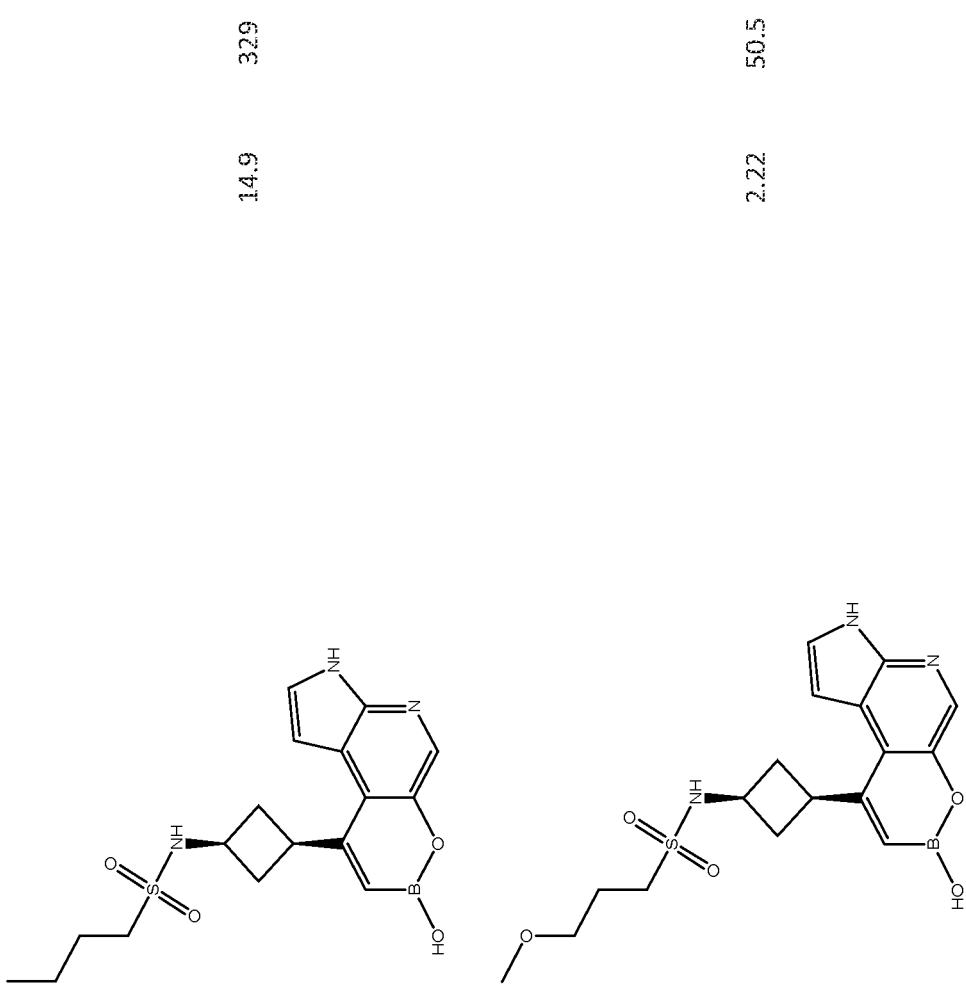

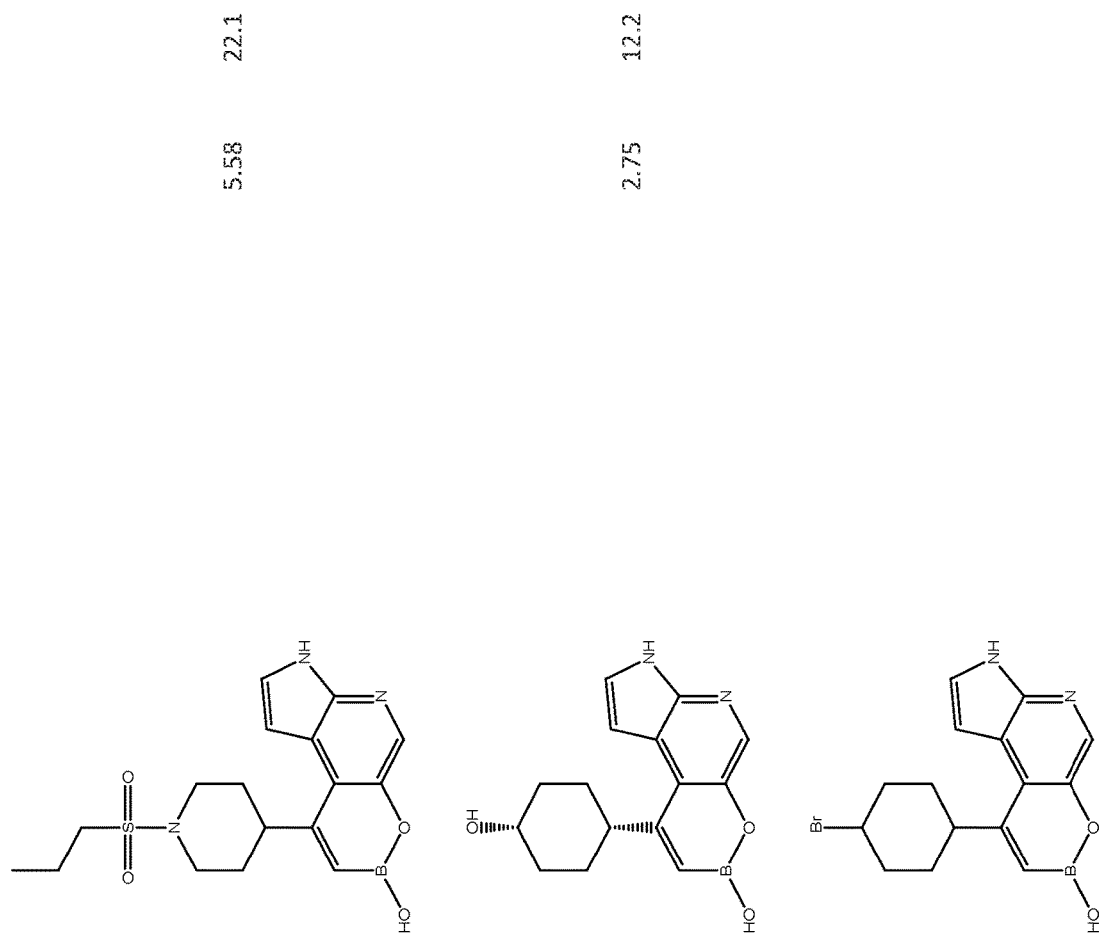

CHEMICAL COMPOUNDS

CROSS-REFERENCE TO RELATED APPLICATIONS

The present application is a continuation application of International Application No. PCT/US2020/070042, filed 12 May 2020, which claims the benefit of U.S. Provisional Patent Application No. 62/846,785, filed 13 May 2019, U.S. Provisional Patent Application No. 62/911,012, filed 4 Oct. 2019, and U.S. Provisional Patent Application No. 62/949,353, filed 17 Dec. 2019, each of which is incorporated by reference in its entirety.

FIELD OF THE INVENTION

The present invention describes novel boron-containing compounds, or their pharmaceutically acceptable salts, pharmaceutical compositions containing them, and their medical uses. The compounds of the invention have activity as Janus kinase (JAK) inhibitors and are useful in the treatment or control of inflammation, auto-immune diseases, cancer, and other disorders and indications where modulation of JAK would be desirable. Also described herein are methods of treating inflammation, auto-immune diseases, cancer, and other conditions susceptible to inhibition of JAK by administering a compound of the invention.

BACKGROUND

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation, or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases. Thus, protein kinases have emerged as an important class of enzymes as targets for therapeutic intervention. In particular, the JAK family of cellular protein tyrosine kinases (JAK-1, JAK-2, JAK-3, and Tyk-2) play a central role in cytokine signaling (Kisseleva et al, Gene, 2002, 285, 1; Yamaoka et al. Genome Biology 2004, 5, 253)). Upon binding to their receptors, cytokines activate JAK, which then phosphorylate the cytokine receptor, thereby creating docking sites for signaling molecules, notably, members of the signal transducer and activator of transcription (STAT) family that ultimately lead to gene expression, which stimulates biologic responses such as an itch signal. Activation of the JAK-STAT pathway also results in several other ancillary biologic activities that contribute to the inflammation and pruritic processes that contribute to acute allergy in animals but can also exacerbate clinical signs and contribute to chronic allergy.

Atopic dermatitis (AD), also known as eczema, is a common chronic inflammatory skin disease, affecting approximately 20% of children and up to 10% of adults and it imposes a significant financial and societal burden because of the direct medical costs and decreased productivity of individuals with AD. The burden of AD appears to be related mainly to the limited methods of treatment. Furthermore, according to the AD treatment guidelines, there is no standard of care and treatment may be tailored to an individual's needs. Topical interventions are the mainstay of AD therapy. Until now, topical corticosteroids have been the first-line treatment. Their use, however, may be limited by potential local and systemic adverse effects. Topical calcineurin inhibitors are classified as second-line anti-inflammatory therapy for AD, with advantages in long-term maintenance and application to special sites. Topical calcineurin inhibitors inhibit calcineurin-dependent T-cell activation; however, a black box warning about the potential for developing malignant neoplasms with the use of topical calcineurin inhibitors reduces patients' adherence to treatment.

Psoriasis and psoriatic arthritis are associated with aberrant inflammation and the production of proinflammatory mediators. Psoriasis and psoriatic arthritis are inflammatory diseases with overlapping features and shared immunologic mechanisms. Psoriasis is a systemic disease in that it primarily affects the skin but up to 40% of individuals with psoriasis may go on to develop psoriatic arthritis. Psoriatic arthritis typically affects the peripheral joints and may occasionally affect the spine and sacroiliac area. Enthesitis, dactylitis, and nail changes such as pitting and discoloration are also common manifestations of psoriatic disease in patients with joint involvement.

JAK inhibition may provide a therapeutic strategy for various immune and inflammatory diseases, including rheumatoid arthritis (RA), arthritis, ulcerative colitis, Crohn's disease, inflammatory bowel disease (IBD), psoriasis, alopecia areata, atopic dermatitis, vitiligo, palmoplantar pustulosis, mucocutaneous disease erythema multiforme, mycosis fungoides, graft-versus-host disease, cutaneous lupus, transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, artherosclerosis, and cancer. Reference is made to Schwartz et al., *JAK inhibition as a therapeutic strategy for immune and inflammatory diseases,* Nat Rev Drug Discov., 2017 Dec. 28, 17(1):78, herein incorporated by reference with regard to the rationale for targeting JAKs.

There remains a need for therapies targeting and modulating JAK kinases for the treatment or control of inflammation, auto-immune diseases, cancer, and other disorders and indications where modulation of JAK modulation would be desirable.

SUMMARY

One embodiment of the present disclosure includes a compound of formula (I) or (II):

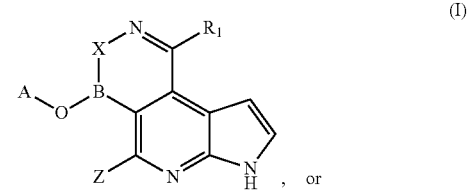

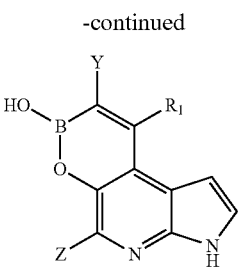

(II)

wherein:
each X independently is selected from the group consisting of O and NR$^a$;
each Z independently is selected from the group consisting of hydrogen, fluorine, and CH$_3$;
each Y independently is selected from the group consisting of hydrogen, halogen, C$_{1-6}$ alkyl, C$_{2-6}$, alkenyl, C$_{2-6}$ alkynyl, C$_{3-6}$ cycloalkyl, and (CH$_2$)$_3$OH, or Y and the oxygen atom depicted as OH together form a 6 to 8 membered ring;
each R$^a$ is independently selected from the group consisting of hydrogen, substituted or unsubstituted C$_1$-C$_{15}$ alkyl, substituted or unsubstituted C$_{2-15}$ alkenyl, substituted or unsubstituted C$_{2-15}$ alkynyl, substituted or unsubstituted C$_{3-15}$ cycloalkyl, and substituted or unsubstituted aryl;
A is
  (i) hydrogen, or
  (ii) when X is NR$^a$, A may be absent and R$^a$ and is taken together with the depicted oxygen to form a substituted or unsubstituted 6 to 8 membered ring; and
each R$^1$ independently is selected from the group consisting of unsubstituted or substituted:
  (i) C$_1$-C$_{15}$ alkyl,
  (ii) C$_{2-15}$ alkenyl,
  (iii) C$_{2-15}$ alkynyl,
  (iv) C$_1$-C$_{15}$ alkyl, wherein one or more carbon atom, including the carbon atom attached to the depicted ring, is replaced with a heteroatom selected from O, N, S, or Si, and wherein each N, S, or Si may be oxidized, and wherein the N may be quaternized,
  (v) C$_{2-15}$ alkenyl, wherein one or more carbon atom, including the carbon atom attached to the depicted ring, is replaced with a heteroatom selected from O, N, S, or Si, and wherein each N, S, or Si may be oxidized, and wherein the N may be quaternized,
  (vi) C$_{2-15}$ alkynyl, wherein one or more carbon atom, including the carbon atom attached to the depicted ring, is replaced with a heteroatom selected from O, N, S, or Si, and wherein each N, S, or Si may be oxidized, and wherein the N may be quaternized,
  (vii) C$_{3-15}$ cycloalkyl,
  (viii) heterocyclyl,
  (ix) aryl, and
  (x) heteroaryl,
or a stereoisomer, enantiomer, or tautomer thereof, or a veterinary or pharmaceutically acceptable salt thereof.

In one aspect, the compound is a compound of formula (I). In one aspect, the compound is a compound of formula (II). In one aspect, each Y is hydrogen. In one aspect, X is O. In one aspect, X is NR$^a$, and R$^a$ is hydrogen or C$_{1-8}$ alkyl. In one aspect, the compound is a compound of formula (I), A is hydrogen, X is NR$^a$, and R$^a$ is selected from the group consisting of: hydrogen, C$_1$-C$_6$ alkyl, and C$_{3-6}$ cycloalkyl. In one aspect, Z is hydrogen.

In one aspect, the compound is a compound of formula (I), X is NR$^a$, A is absent, and R$^a$ is taken together with the depicted oxygen to form a 6 membered ring. In one aspect, R$_1$ is C$_{3-15}$ cycloalkyl. In one aspect, the compound is selected from the group consisting of formulae (Ia), (Ib), (Ic), and (Id):

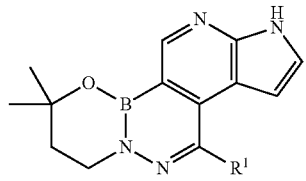

(Ia)

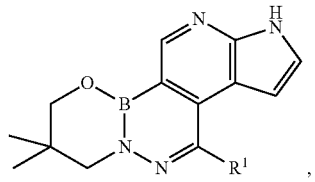

(Ib)

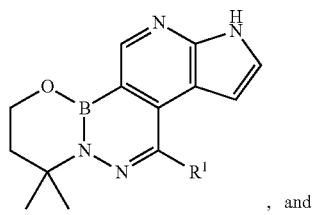

(Ic)

, and

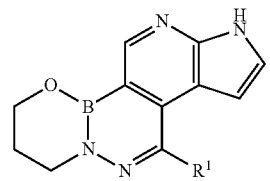

(Id)

In one aspect, each R$^1$ is unsubstituted or substituted C$_{3-15}$ cycloalkyl. In one aspect, R$^1$ is unsubstituted or substituted cyclobutyl, cyclohexyl, bicyclo[1.1.1]pentane, or adamantyl. In one aspect, the compound is of formula (I), R$^1$ is substituted adamantyl, and R$^a$ is substituted alkyl. In one aspect, each R$^1$ is unsubstituted or substituted heterocyclyl. In one aspect, each R$^1$ is a substituted 3- to 6-membered heterocyclyl, wherein at least one heteroatom is a N. In one aspect, R$^1$ is pyrrolidinyl or piperidinyl. In one aspect, R$^1$ is tetrahydropyranyl.

In one aspect, each R$^1$ individually is substituted with one or more substituent selected from the group consisting of halogen, haloalkyl, R', OR', OH, SH, SR', NO$_2$, CN, C(O)R', C(O)(alkyl substituted with one or more of halogen, haloalkyl, NH$_2$, OH, SH, CN, and NO$_2$), C(O)OR', OC(O)R', CON(R')$_2$, OC(O)N(R')$_2$, NH$_2$, NHR', N(R')$_2$, NHCOR', NHCOH, NHCONH$_2$, NHCONHR', NHCON(R')$_2$, NR'COR', NRCOH, NHCO$_2$H, NHCO$_2$R', NHC(S)NH$_2$, NHC(S)NHR', NHC(S)N(R')$_2$, NR'C(S)N(R')$_2$, CO$_2$R', CO$_2$H, CHO, CONH$_2$, CONHR', CON(R')$_2$, S(O)$_2$H, S(O)$_2$R', SO$_2$NH$_2$, S(O)H, S(O)R', SO$_2$NHR', SO$_2$N(R')$_2$, NHS(O)$_2$H, NR'S(O)$_2$H, NHS(O)$_2$R', NR'S(O)$_2$R', N(R')SO$_2$N(R')$_2$, Si(R')$_3$, =O, =S, =NNHR', =NNH$_2$, =NN(R')$_2$, =N—OR', =N—OH, =NNHCOR', =NNHCOH, =NNHCO$_2$R', =NNHCO$_2$H, =NNHSO$_2$R', =NNHSO$_2$H, =N—CN, =NH, and =NR'. In one aspect, each $R^1$ individually is substituted with one or more substituent selected from the group consisting of halogen, haloalkyl, R', OR', OH, SH, SR', $NO_2$, CN, C(O)R', C(O) (alkyl substituted with one or more of halogen, haloalkyl, $NH_2$, OH, SH, CN, and $NO_2$), C(O)OR', OC(O)R', CON(R')$_2$, OC(O)N(R')$_2$, $NH_2$, NHR', N(R')$_2$, NHCOR', NHCOH, NHCONH$_2$, NHCONHR', NHCON(R')$_2$, NR'CON(R')$_2$, NR'COR', NR'COH, NHCO$_2$H, NHCO$_2$R', NR'CO$_2$R', NHC(S)NH$_2$, NHC(S)NHR', NHC(S)N(R')$_2$, NR'C(S)N(R')$_2$, CO$_2$R', CO$_2$H, CHO, CONH$_2$, CONHR', CON(R')$_2$, S(O)$_2$H, S(O)$_2$R', SO$_2$NH$_2$, S(O)H, S(O)R', SO$_2$NHR', SO$_2$N(R')$_2$, NHS(O)$_2$H, NR'S(O)$_2$H, NHS(O)$_2$R', NR'S(O)$_2$R', N(R')SO$_2$N(R')$_2$, and =O. In one aspect, each of the preceding may be linked to $R^1$ through an alkylene linker, (CH$_2$)$_x$, where x is 1, 2, or 3. In one aspect, each R' is the same or different and is hydrogen, alkyl, alkenyl, alkynyl, haloalkyl, haloalkenyl, haloalkynyl, hydroxyalkyl, hydroxyalkenyl, hydroxyalkynyl, cycloalkyl, cycloalkyl substituted by one or more halogens, cycloalkylalkyl, aryl, aryl substituted with one or more halogen, CN, arylalkyl, heterocyclyl, heterocyclylalkyl, heteroaryl, or heteroarylalkyl.

In one aspect, the alkylene linker, (CH$_2$)$_x$, where x is 1, 2, or 3, may itself be further substituted with one or more of alkyl, cycloalkyl, aryl, aralkyl, heteroaryl, heteroarylalkyl, heteroicyclyl, or heterocyclylalkyl.

In one aspect, each $R^1$ is substituted with one substitutent. In one aspect, each $R^1$ is substituted with two substituents, each of which may be substituted from the same or different atoms, as valency allows.

In one aspect, $R^1$ is substituted with NHS(O)$_2$(C$_1$-C$_6$ alkyl), NHS(O)$_2$(C$_1$-C$_6$ partially or fully fluorinated alkyl), NHS(O)$_2$(C$_1$-C$_6$ cycloalkyl), NHS(O)$_2$(C$_1$-C$_6$ partially or fully fluorinated cycloalkyl), OH, CH$_2$S(O)$_2$NH(C$_1$-C$_6$ alkyl), CH$_2$S(O)$_2$NH(C$_1$-C$_6$ partially or fully fluorinated alkyl), CH$_2$S(O)$_2$N(C$_1$-C$_6$ alkyl)$_2$, CH$_2$S(O)$_2$N(C$_1$-C$_6$ partially fluorinated alkyl)$_2$, N(C$_1$-C$_6$ alkyl)$_2$ or N(C$_1$-C$_6$ partially fluorinated alkyl)$_2$. In one aspect, $R^1$ is substituted with NHSO$_2$R', wherein R' is hydrogen, alkyl, alkenyl, alkynyl, cycloalkyl, aryl, heterocyclyl, or heteroaryl. In one aspect, R' is C$_{1-8}$ alkyl, C$_{2-8}$ alkenyl, or C$_{2-8}$ alkynyl. In one aspect, the compound is of formula (I), $R^1$ is substituted adamantyl, and $R^a$ is substituted alkyl, and each of $R^1$ and $R^a$ is substituted with an OH.

In one embodiment, $R^1$ is $R^{1a}$-L-$R^{1b}$, wherein $R^{1a}$ is any $R^1$ group as defined herein, L is a polar linking group, and $R^{1b}$ is any $R^1$ group as defined herein. A "polar linking group," "L," is intended to create an appropriate linker between the $R^{1a}$ and $R^{1b}$ groups. The linker, L, itself may be a divalent linking group, for example —NHSO$_2$—. Alternatively, as will be described in more detail herein, an $R^{1a}$ group may be a heterocyclyl group. In such embodiments, for example, $R^{1a}$ may be attached to L through a nitrogen of the heterocycle, such that when combined with, for example, a divalent —SO$_2$— group, they together function as a polar linking group.

In one embodiment, $R^{1a}$ is C$_{3-15}$ cycloalkyl. In one embodiment, $R^{1a}$ is heterocyclyl.

In one embodiment, L is —(CH$_2$)$_p$-L$^1$-, wherein p is 0, 1, or 2, and L$^1$ is —O—, —C(O)—, —C(O)O—, —OC(O)—, —CON(R')—, —OC(O)N(R')—, —N(R')—, —NHCON(R')—, —NR'CO—, —NR'CO$_2$—, —NHC(S)NR'—, —CO$_2$—, —CONR'—, —S(O)$_2$—, —S(O)—, —SO$_2$N(R')—, —NR'S(O)$_2$—, Si(R')$_2$—, =NNR'—, =N—O—, =NNHCO—, =NNHCO$_2$—, =NNHCO$_2$—, =NNHSO$_2$—, and =N—.

In one embodiment, $R^{1b}$ is C$_{1-8}$ alkyl, C$_{2-8}$ alkenyl, C$_{2-8}$ alkynyl, C$_{3-15}$ cycloalkyl, heterocyclyl, aryl, or heteroaryl.

In one embodiment, $R^1$ is substituted with, or in other words, the group -L-$R^{1b}$ is selected from the group consisting of NHS(O)$_2$(C$_1$-C$_6$ alkyl), NHS(O)$_2$(C$_1$-C$_6$ partially or fully fluorinated alkyl), NHS(O)$_2$(C$_1$-C$_6$ cycloalkyl), NHS(O)$_2$(C$_1$-C$_6$ partially or fully fluorinated cycloalkyl), OH, CH$_2$S(O)$_2$NH(C$_1$-C$_6$ alkyl), CH$_2$S(O)$_2$NH(C$_1$-C$_6$ partially or fully fluorinated alkyl), CH$_2$S(O)$_2$N(C$_1$-C$_6$ alkyl)$_2$, CH$_2$S(O)$_2$N(C$_1$-C$_6$ partially fluorinated alkyl)$_2$, N(C$_1$-C$_6$ alkyl)$_2$, and N(C$_1$-C$_6$ partially fluorinated alkyl)$_2$.

In one embodiment, $R^1$ is substituted with NHSO$_2$R', wherein R' is hydrogen, alkyl, alkenyl, alkynyl, cycloalkyl, aryl, heterocyclyl, or heteroaryl. In other words, L is NHSO$_2$ and $R^{1b}$ is R', which is hydrogen, alkyl, alkenyl, alkynyl, cycloalkyl, aryl, heterocyclyl, or heteroaryl.

In one embodiment, the group L may be defined as —X—SO$_2$—, where: X is selected from —NR$^p$— and —(CR$^p$$_2$)$_p$—, where p is 0, 1, or 2, and each RP is independently hydrogen, alkyl, cycloalkyl, aryl, aralkyl, heteroaryl, heteroarylalkyl, heterocyclyl, or heterocyclylalkyl. In one embodiment, $R^{1b}$ is unsubstituted or substituted C$_{1-8}$ alkyl, C$_{2-8}$ alkenyl, C$_{2-8}$ alkynyl, C$_{3-15}$ cycloalkyl, heterocyclyl, aryl, arylalkyl, heteroaryl, or heteroarylalkyl.

In one embodiment, $R^{1b}$ is preceded by a group consisting of —NH—, —(CH$_2$)$_k$— or —(CD$_2$)$_k$-, where k is 1, 2, or 3.

In one aspect, $R^1$ is $R^{1a}$-L-$R^{1b}$, wherein $R^{1a}$ is independently any $R^1$ group as defined, L is a polar linking group, and $R^{1b}$ is independently any $R^1$ group as defined. In one aspect, (i) $R^{1a}$ is C$_{3-15}$ cycloalkyl, L is —(CH$_2$)$_p$-L$^1$-, wherein p is 0, 1, or 2, and L$^1$ is selected from —O—, —C(O)—, —C(O)O—, —OC(O)—, —C(O)N(R')—, —OC(O)N(R')—, —N(R')—, —N(R')C(O)N(R')—, —N(R')C(S)NR'—, —N(R')C(O)—, —NR'C(O)O—, —CONR'—, —S(O)$_2$—, —S(O)—, —SO$_2$N(R')—, —N(R')S(O)$_2$—, Si(R')$_2$—, =NNR'—, =N—O—, =NNHCO—, =NNHCO$_2$—, =NNHCO$_2$—, =NNHSO$_2$—, and =N—; and $R^{1b}$ is unsubstituted or substituted C$_{1-8}$ alkyl, C$_{2-8}$ alkenyl, C$_{2-8}$ alkynyl, C$_{3-15}$ cycloalkyl, heterocyclyl, aryl, arylalkyl, heteroaryl, or heteroarylalkyl; or (ii) $R^{1a}$ is heterocyclyl; L is —(CH$_2$)$_p$-L$^1$-, wherein p is 0, 1, or 2, and L$^1$ is selected from —O—, —C(O)—, —C(O)O—, —OC(O)—, —C(O)N(R')—, —OC(O)N(R')—, —N(R')—, —N(R')C(O)N(R')—, —N(R')C(S)NR'—, —N(R')C(O)—, —NR'C(O)O—, —CONR'—, —S(O)$_2$—, —S(O)—, —SO$_2$N(R')—, —N(R')S(O)$_2$—, Si(R')$_2$—, =NNR'—, =N—O—, =NNHCO—, =NNHCO$_2$—, =NNHCO$_2$—, =NNHSO$_2$—, and =N—; and $R^{1b}$ is unsubstituted or substituted C$_{1-8}$ alkyl, C$_{2-8}$ alkenyl, C$_{2-8}$ alkynyl, C$_{3-15}$ cycloalkyl, heterocyclyl, aryl, arylalkyl, heteroaryl, or heteroarylalkyl.

In one aspect, L$^1$ is selected from the group consisting of —O—, —C(O)—, —C(O)O—, —OC(O)—, —C(O)N(R')—, —OC(O)N(R')—, —N(R')—, —N(R')C(O)N(R')—, —N(R')C(S)N(R')—, —N(R')C(O)—, —N(R')C(O)O—, —SO$_2$—, —S(O)—, —SO$_2$N(R')—, —N(R')SO$_2$—, and —N(R')SO$_2$(NR')—. In one aspect, $R^{1b}$ is selected from the group consisting of unsubstituted or substituted C$_{1-8}$ alkyl, C$_{2-8}$ alkenyl, C$_{2-8}$ alkynyl, C$_{3-15}$ cycloalkyl, heterocyclyl, aryl, arylalkyl, heteroaryl, or heteroarylalkyl.

In one aspect, the compound is of formula (II) and wherein $R^1$ is $R^{1a}$-L-$R^{1b}$, as herein defined. In one aspect, L$^1$ is selected from the group consisting —O—, —C(O)—, —C(O)O—, —CON(R')—, —NR'C(O)—, —NR'CO$_2$—, —S(O)$_2$—, —SO$_2$N(R')—, —N(R')CON(R')—, and —NR'S(O)$_2$—. In one aspect, $R^{1a}$ is selected from the group consisting of unsubstituted or substituted cyclobutyl, cyclohexyl, bicyclo[1.1.1]pentyl, pyrrolidinyl, and piperidinyl. In one aspect, $R^{1b}$ is unsubstituted. In one aspect, $R^{1b}$ is substituted with at least one of fluorine, $OCH_3$, or CN. In one aspect, R' is hydrogen. In one aspect, Z and Y are both hydrogen.

One embodiment of the present disclosure includes a compound selected from the group consisting of:

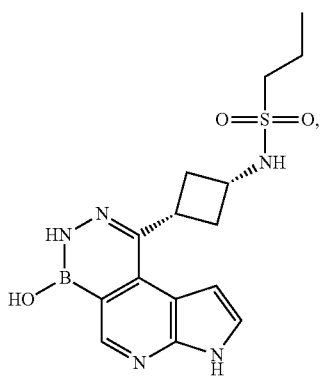

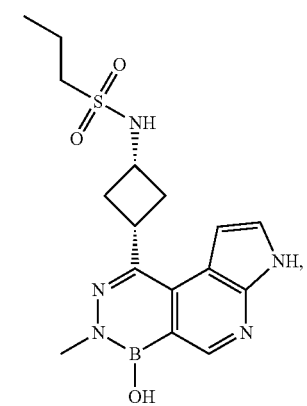

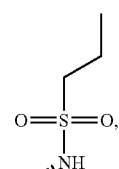

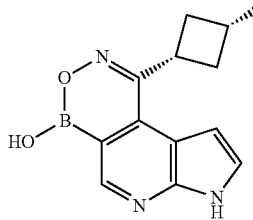

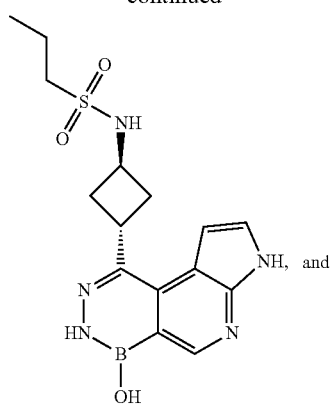

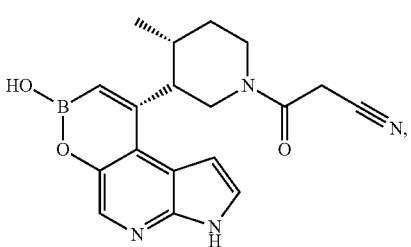

or a stereoisomer, enantiomer, or tautomer thereof, or a veterinary or pharmaceutically acceptable salt thereof.

One embodiment of the present disclosure includes a compound selected from the group consisting of:

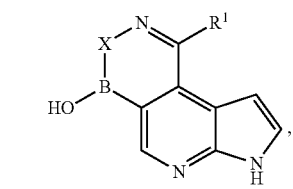

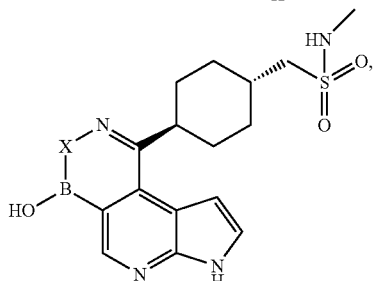

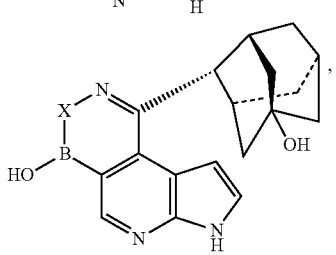

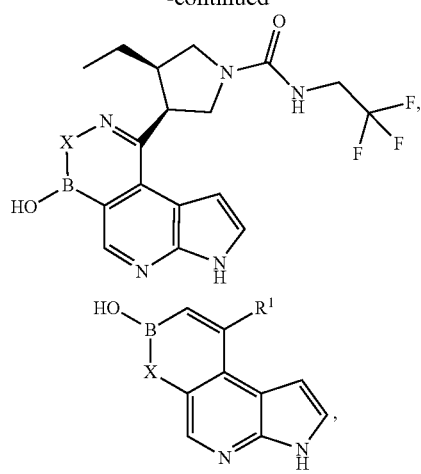
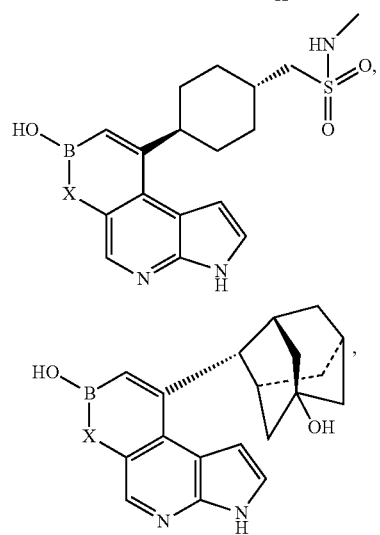
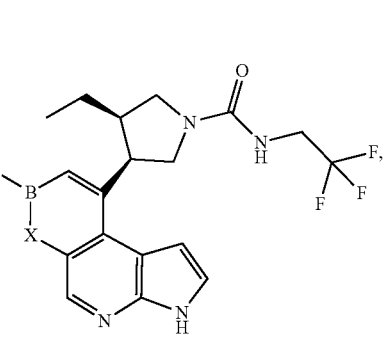
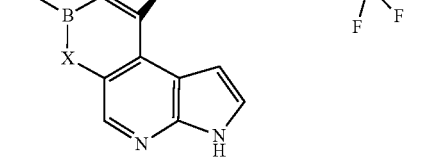
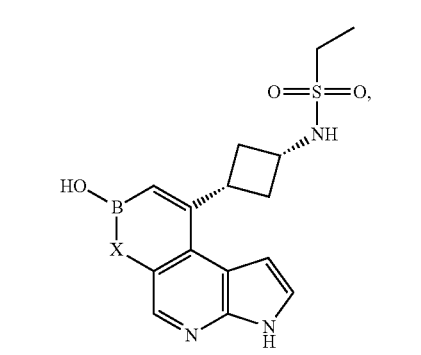
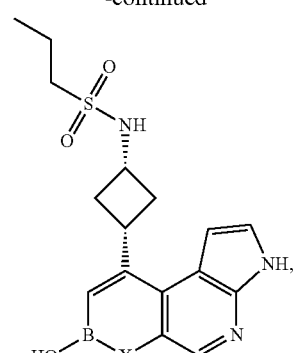
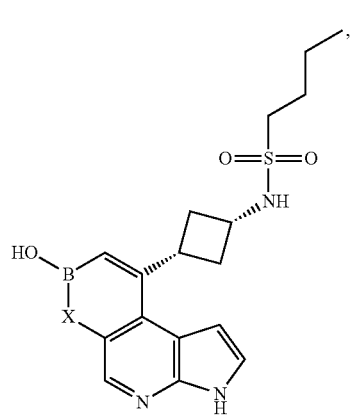
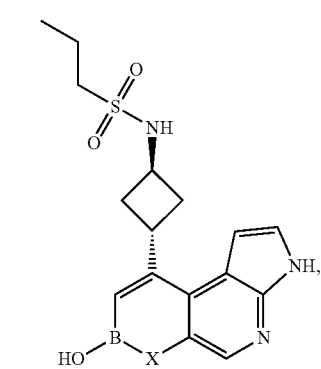
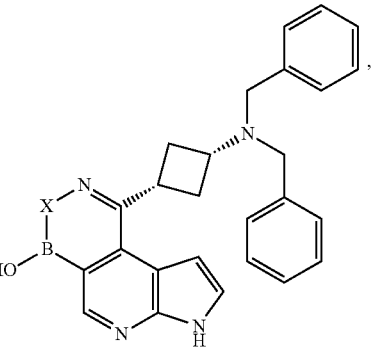

-continued

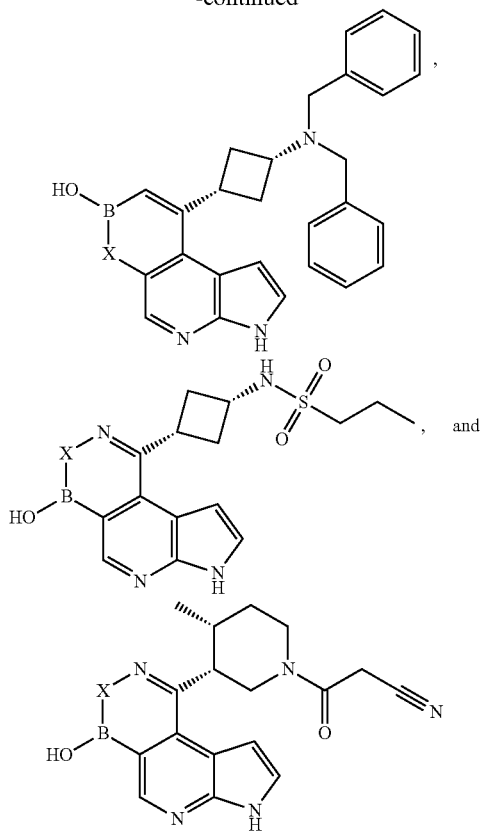

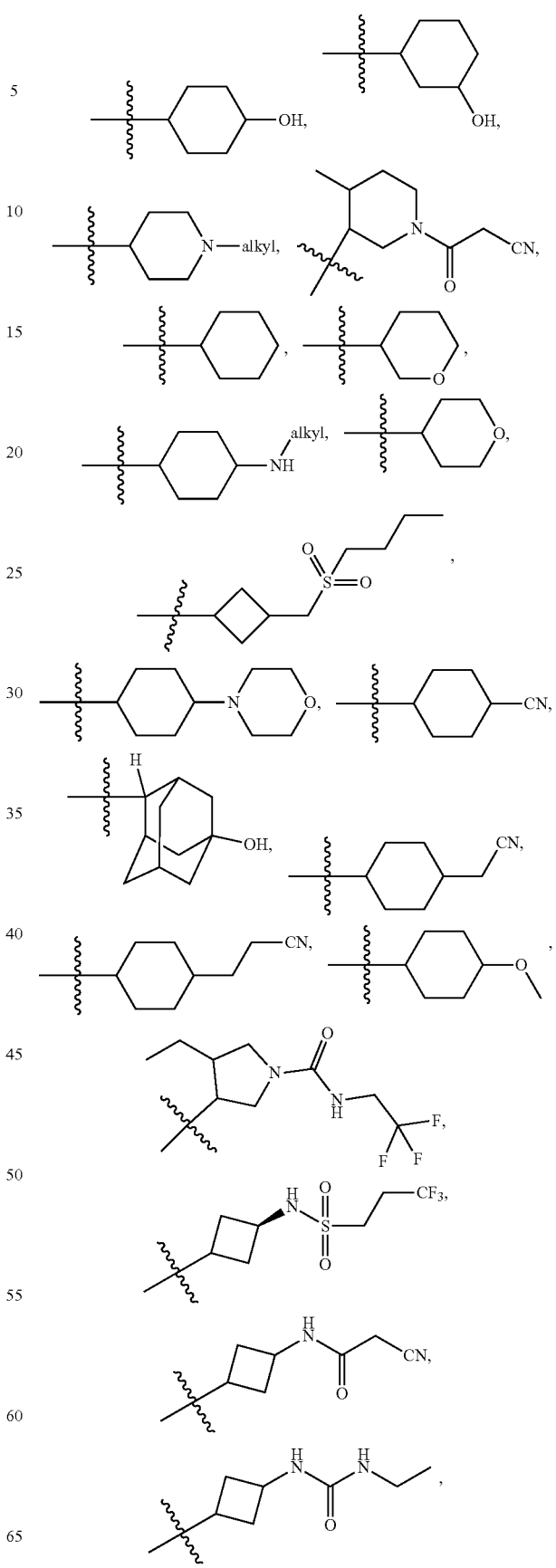

wherein each X independently is selected from the group consisting of O and $NR^a$;
each $R^a$ independently is selected from the group consisting of hydrogen, $C_1$-$C_{15}$ alkyl, $C_{2-15}$ alkenyl, $C_{2-15}$ alkynyl, $C_{3-15}$ cycloalkyl, and aryl; and
each $R^1$ independently is selected from the group consisting of unsubstituted or substituted:

(i) $C_1$-$C_{15}$ alkyl,
(ii) $C_{2-15}$ alkenyl,
(iii) $C_{2-15}$ alkynyl,
(iv) $C_1$-$C_{15}$ alkyl, wherein one or more carbon atom, including the carbon atom attached to the depicted ring, is replaced with a heteroatom selected from O, N, S, or Si, and wherein each N, S, or Si may be oxidized, and wherein the N may be quarternized,
(v) $C_{2-15}$ alkenyl, wherein one or more carbon atom, including the carbon atom attached to the depicted ring, is replaced with a heteroatom selected from O, N, S, or Si, and wherein each N, S, or Si may be oxidized, and wherein the N may be quarternized,
(vi) $C_{2-15}$ alkynyl, wherein one or more carbon atom, including the carbon atom attached to the depicted ring, is replaced with a heteroatom selected from O, N, S, or Si, and wherein each N, S, or Si may be oxidized, and wherein the N may be quarternized,
(vii) $C_{3-15}$ cycloalkyl,
(viii) heterocyclyl,
(ix) aryl, and
(x) heteroaryl, or a stereoisomer, enantiomer, or tautomer thereof, or a veterinary or pharmaceutically acceptable salt thereof.

In one aspect, X is $NR^a$ and $R^a$ is selected from the group consisting of: hydrogen, $C_1$-$C_6$ alkyl, and $C_{3-6}$ cycloalkyl. In one aspect, X is oxygen. In one aspect, $R^1$ is selected from the group consisting of:

13
-continued
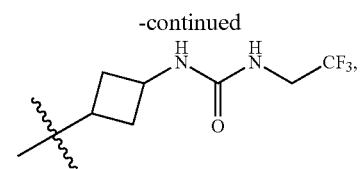
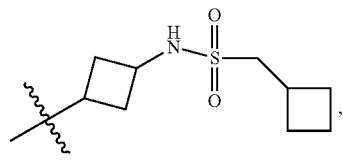
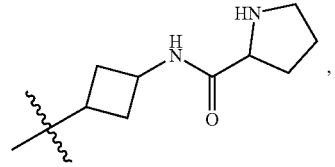
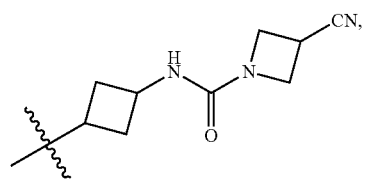
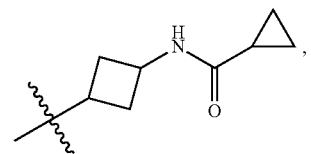
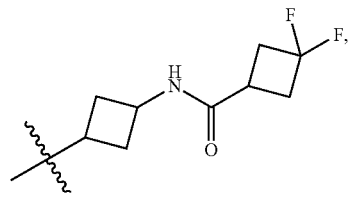
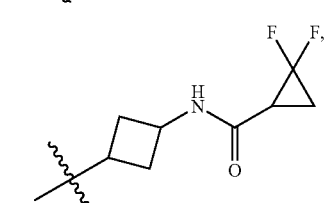
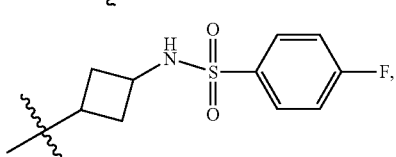
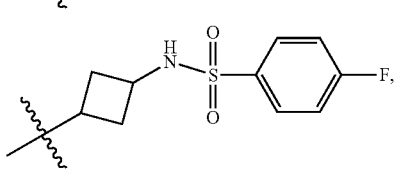
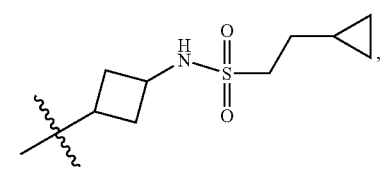
14
-continued
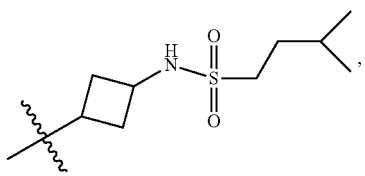
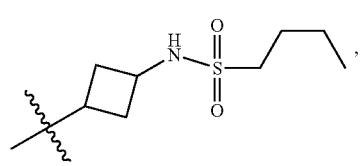
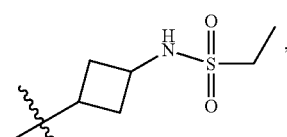
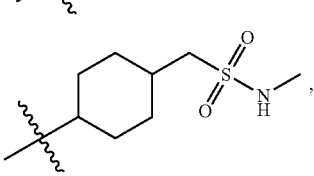
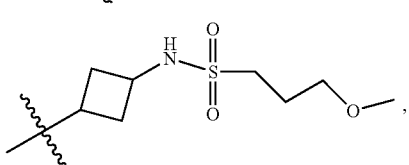
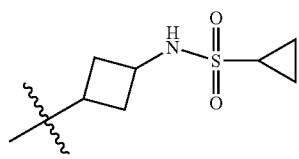
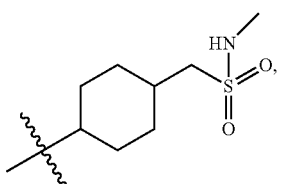
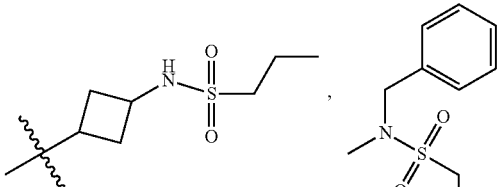
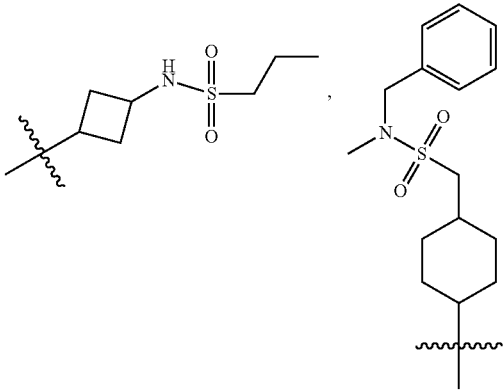

-continued
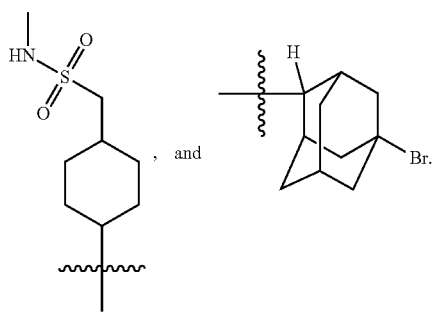, and
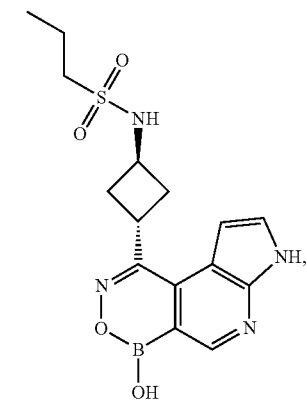
or a stereoisomer, enantiomer, or tautomer thereof, or a veterinary or pharmaceutically acceptable salt thereof.
One embodiment of the present disclosure includes a compound selected from the group consisting of:
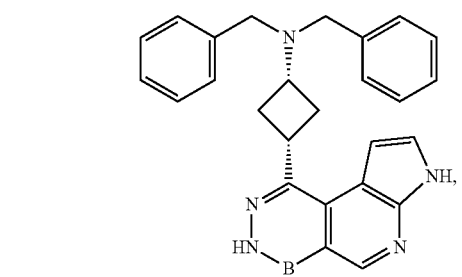
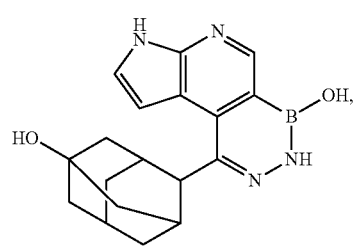
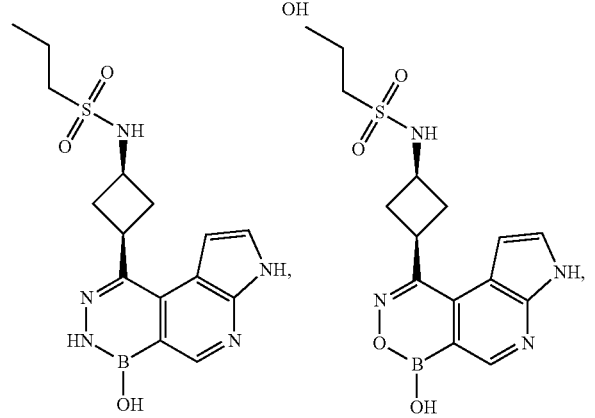
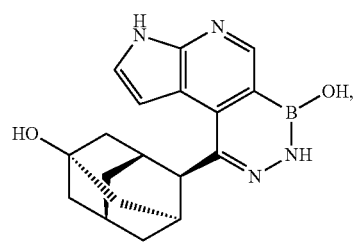
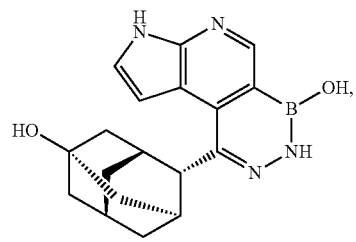
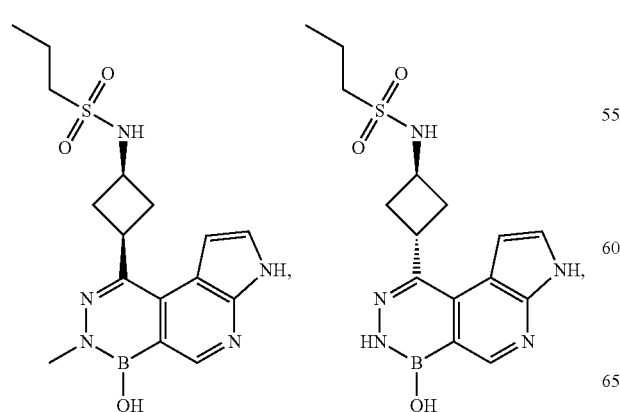
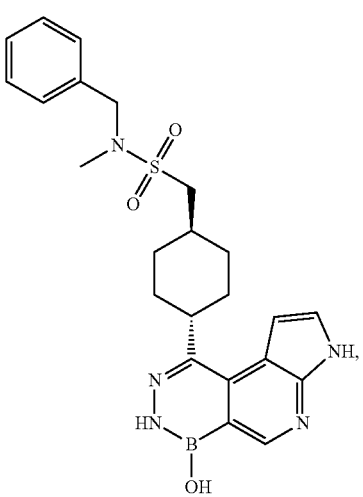

17
-continued
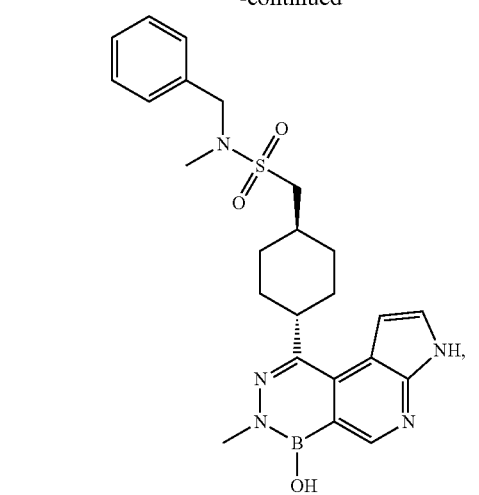
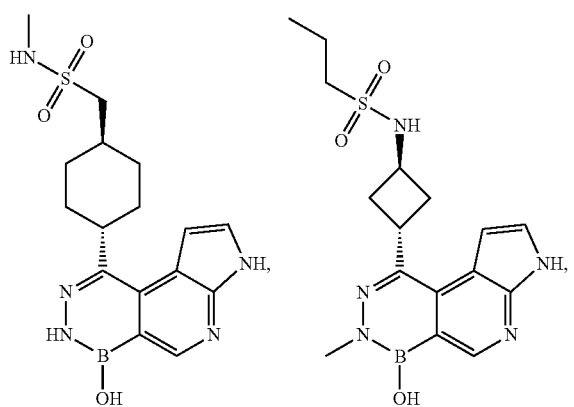
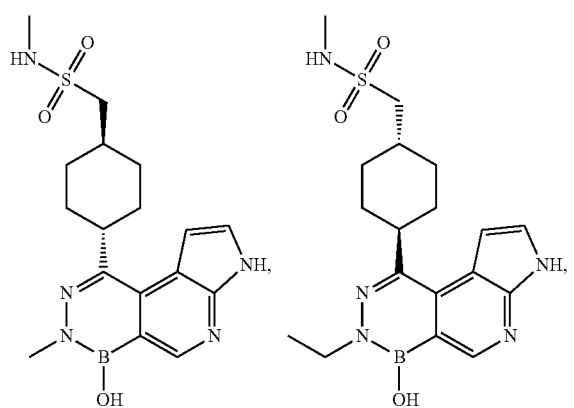
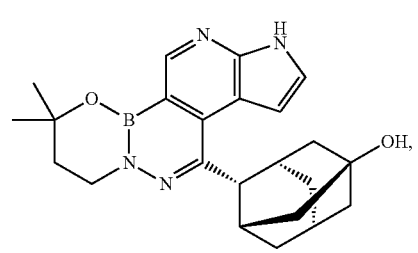
18
-continued
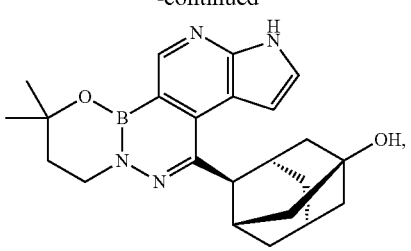
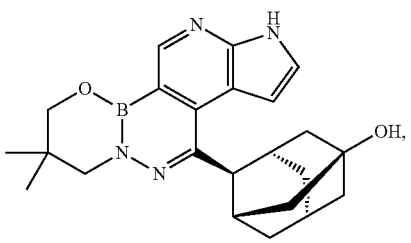
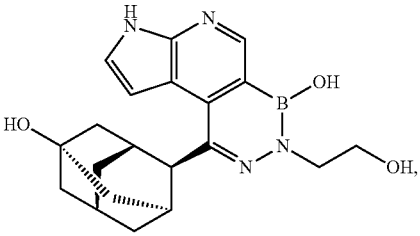
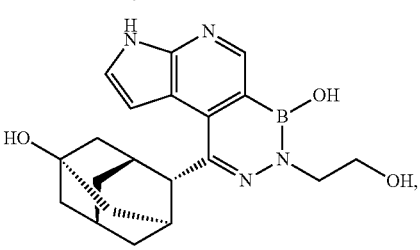
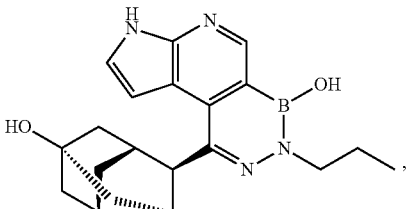
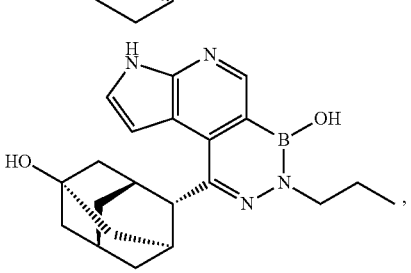
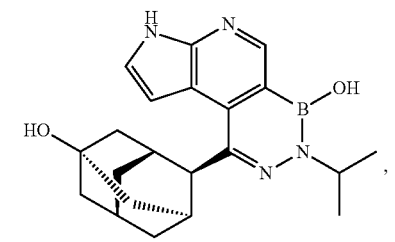

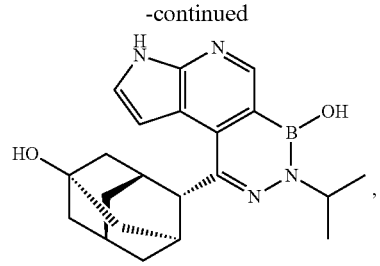
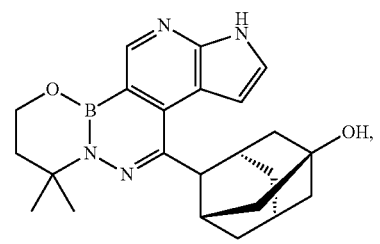
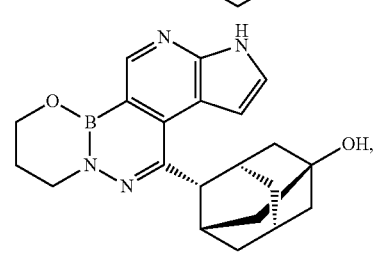
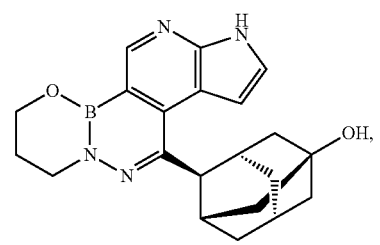
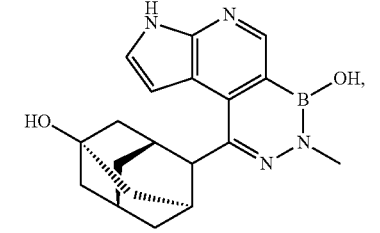
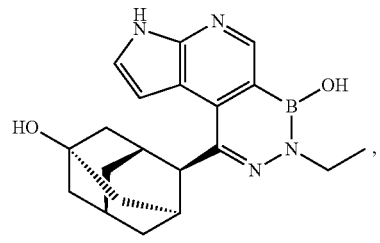
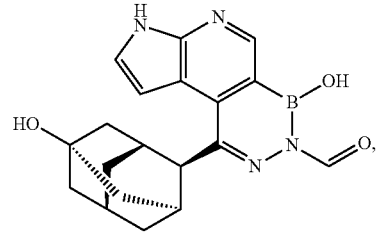
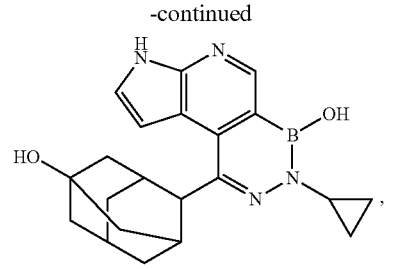
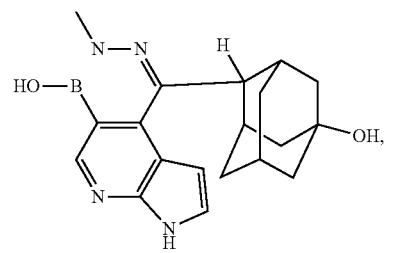
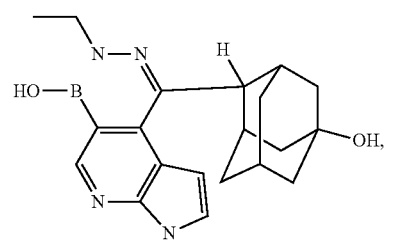
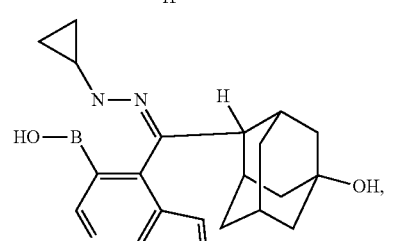
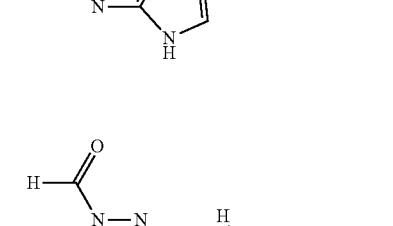
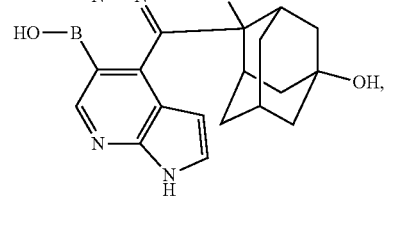
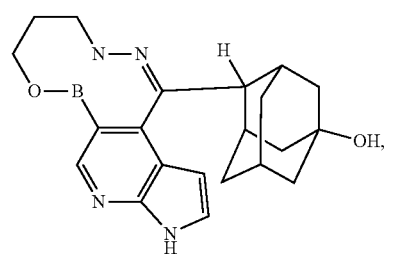

-continued
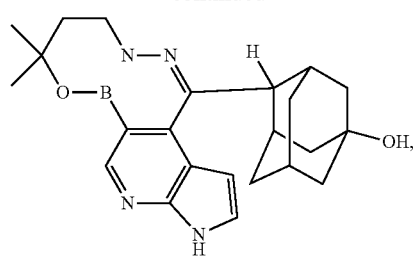
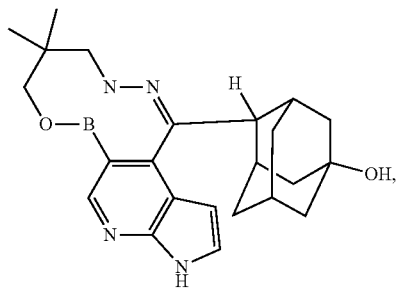
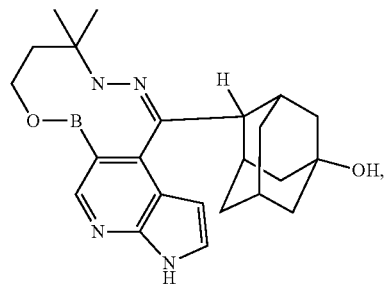
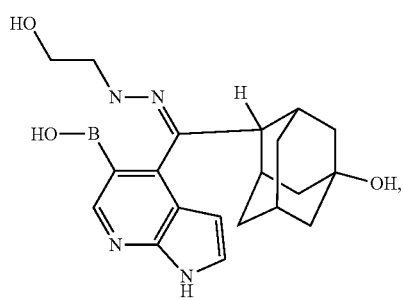
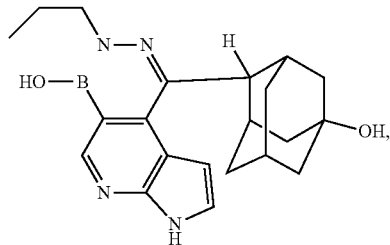
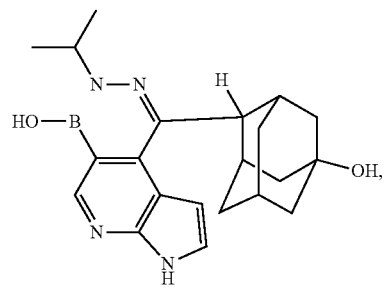
-continued
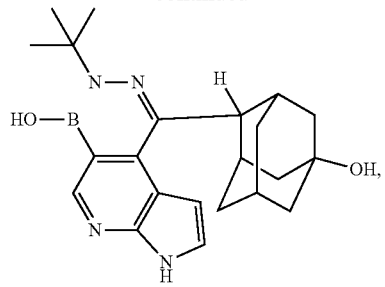
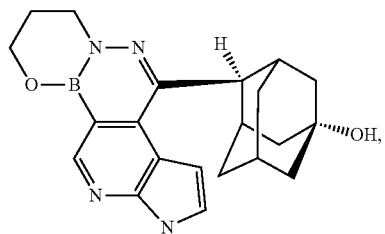
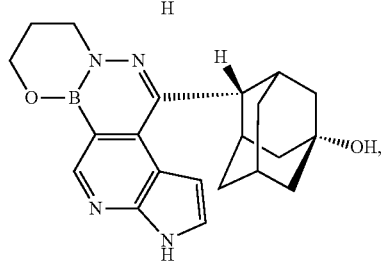
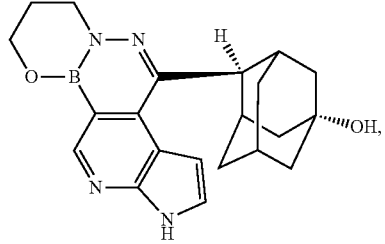
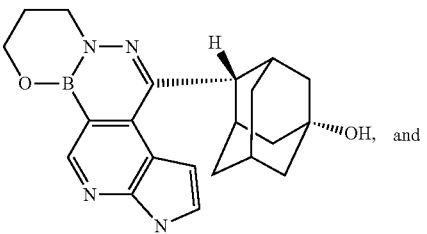
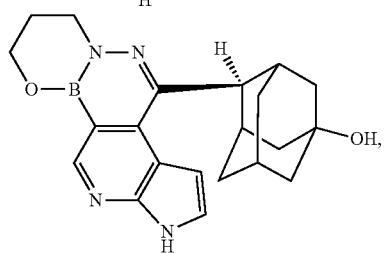
or a stereoisomer, enantiomer, or tautomer thereof, or a veterinary or pharmaceutically acceptable salt thereof.
In one aspect, the compound is selected from the group consisting of:

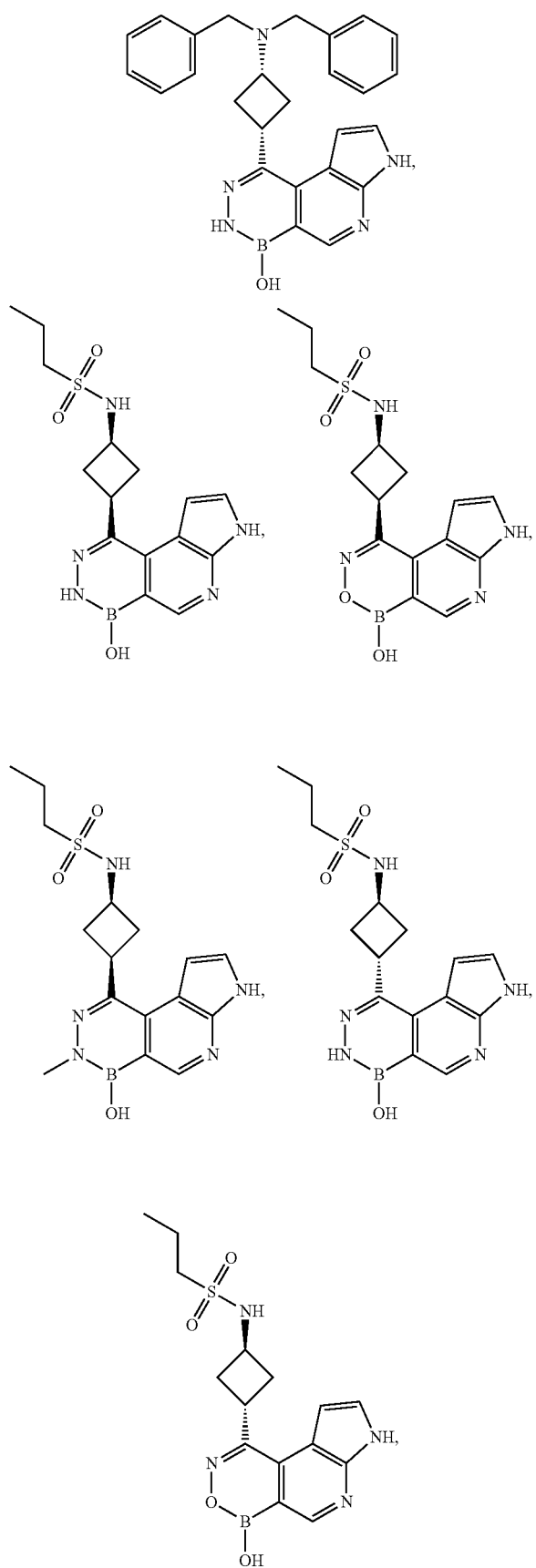
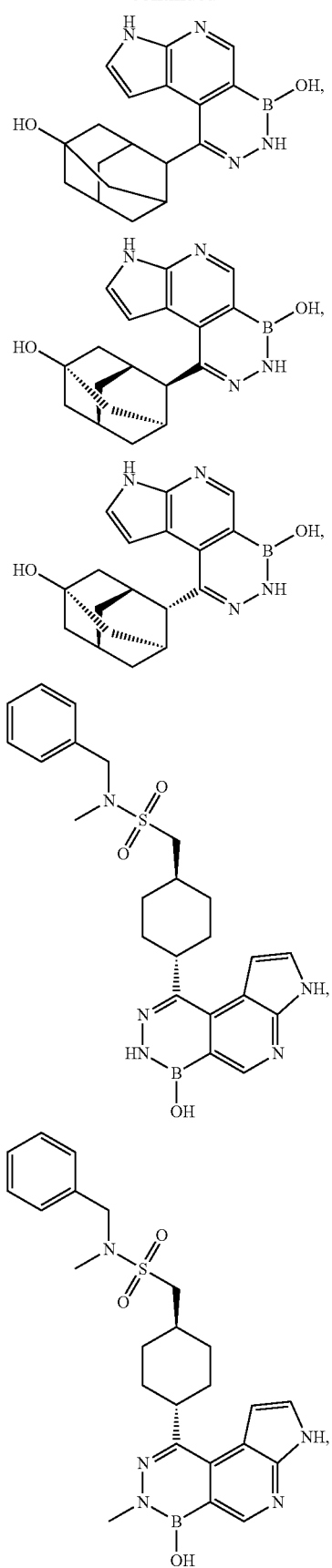

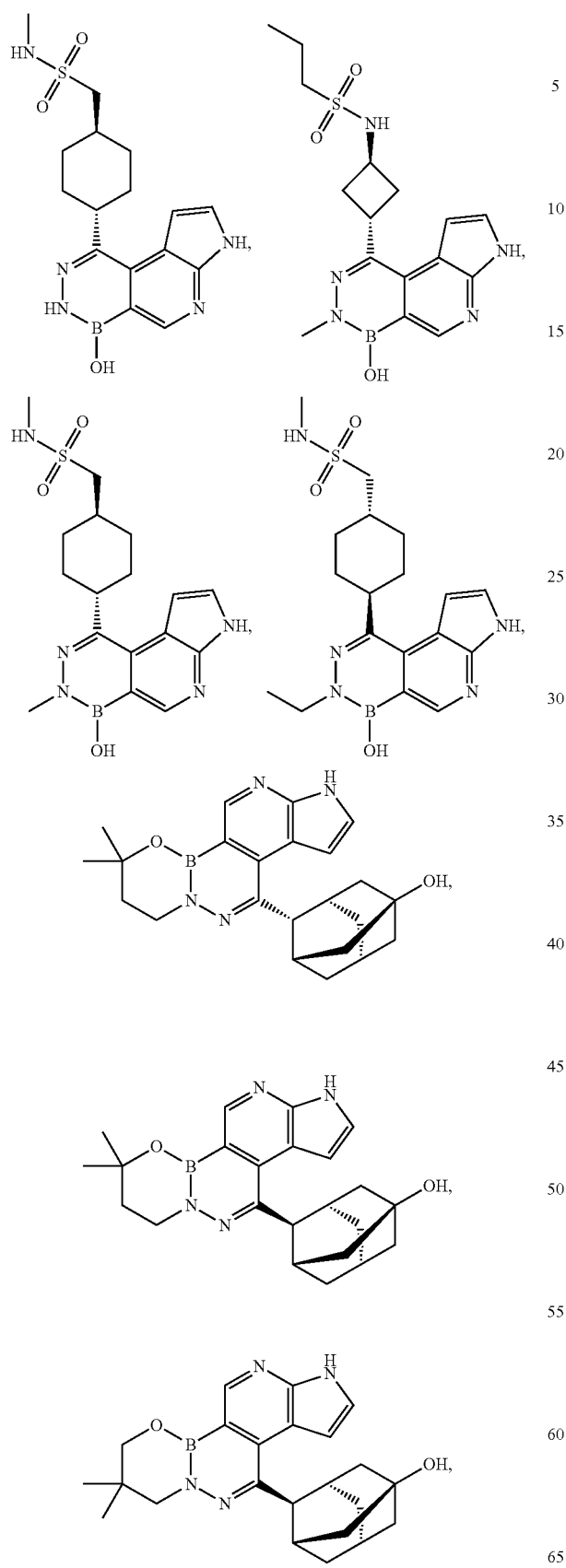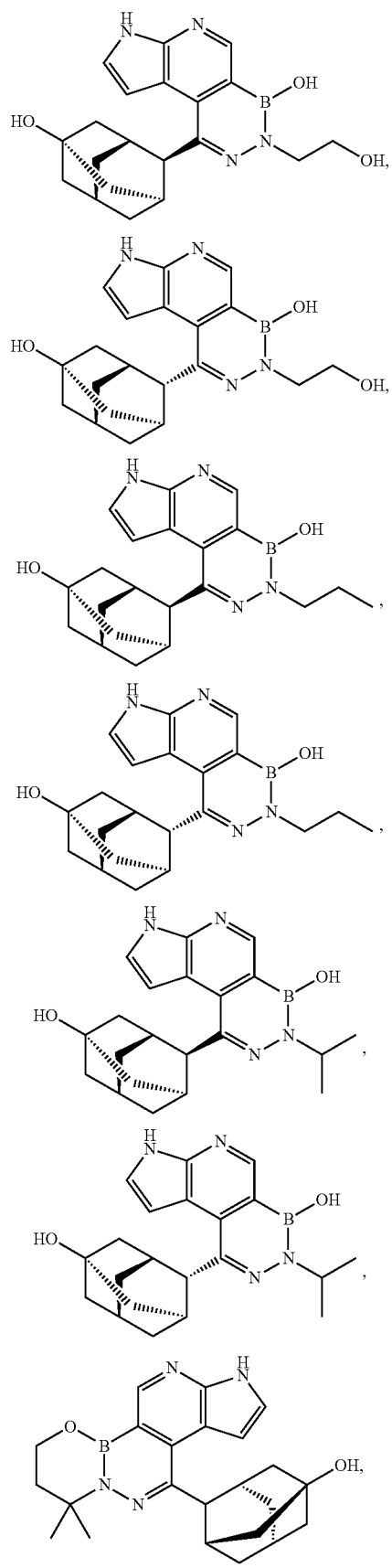

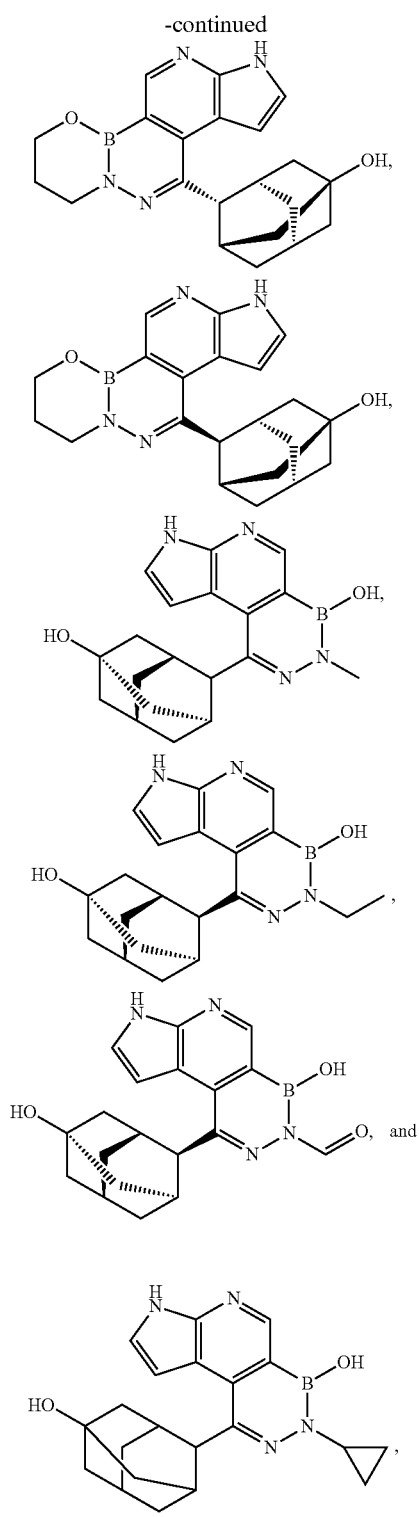
or a stereoisomer, enantiomer, or tautomer thereof, or a veterinary or pharmaceutically acceptable salt thereof.
In one aspect, the compound is selected from the group consisting of:
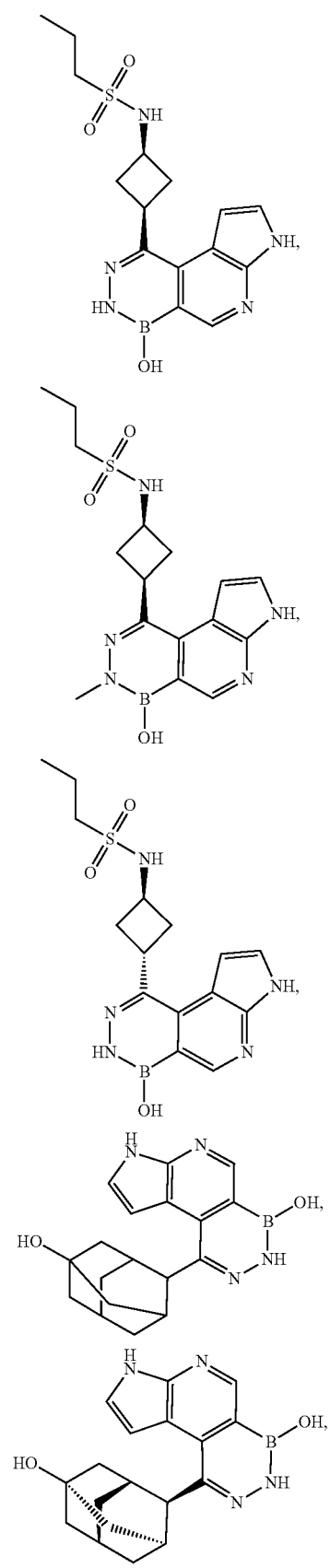

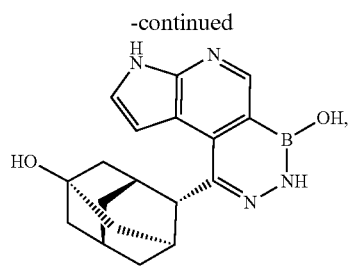
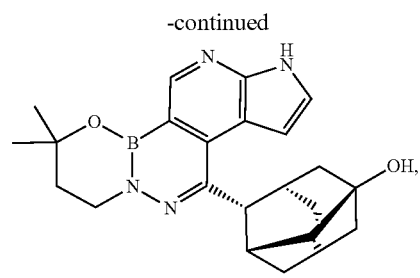
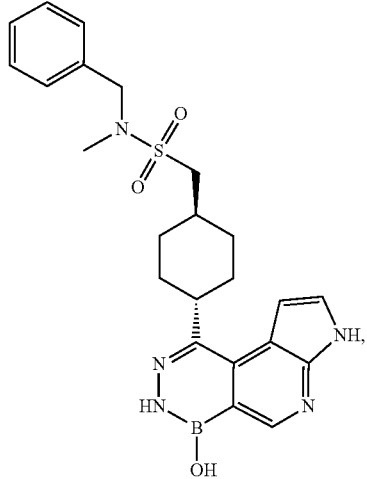
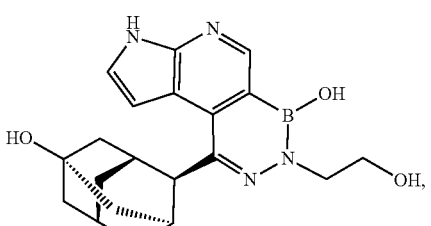
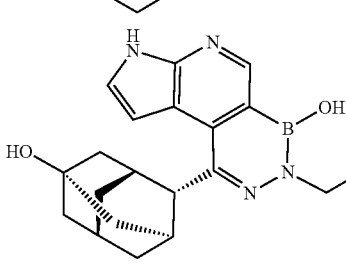
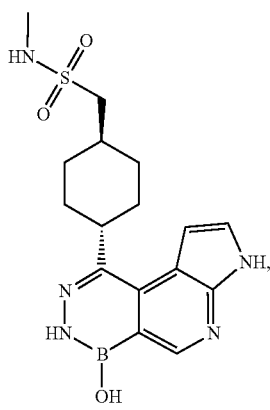
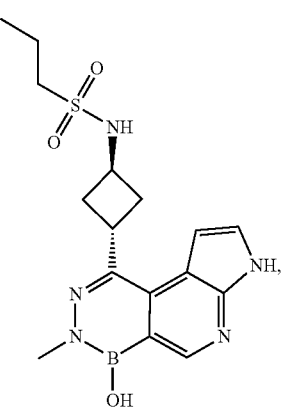
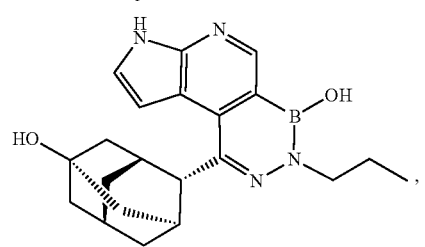
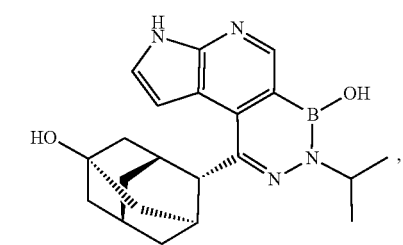
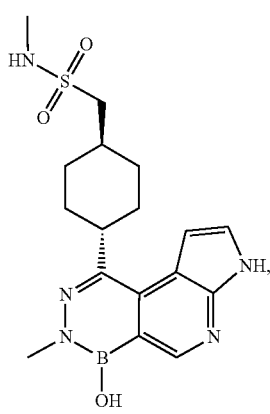
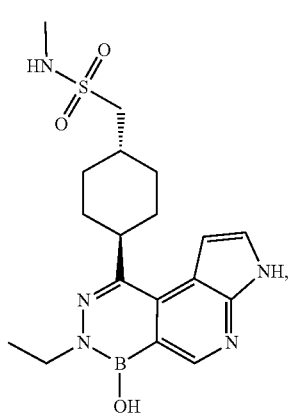
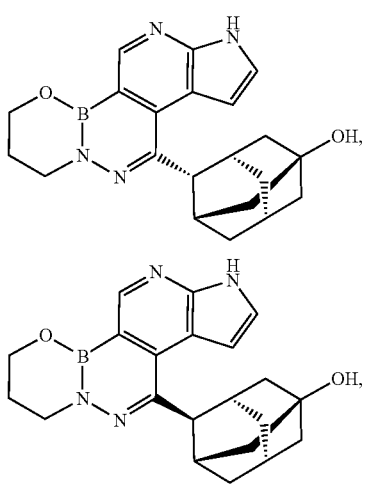

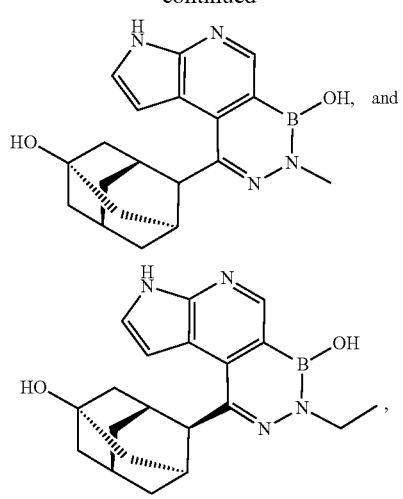
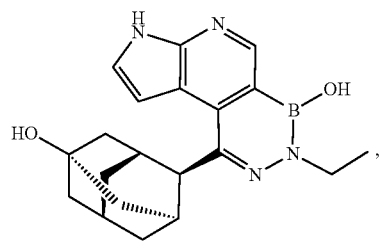
or a stereoisomer, enantiomer, or tautomer thereof, or a veterinary or pharmaceutically acceptable salt thereof.
One embodiment of the present disclosure includes a compound selected from the group consisting of:
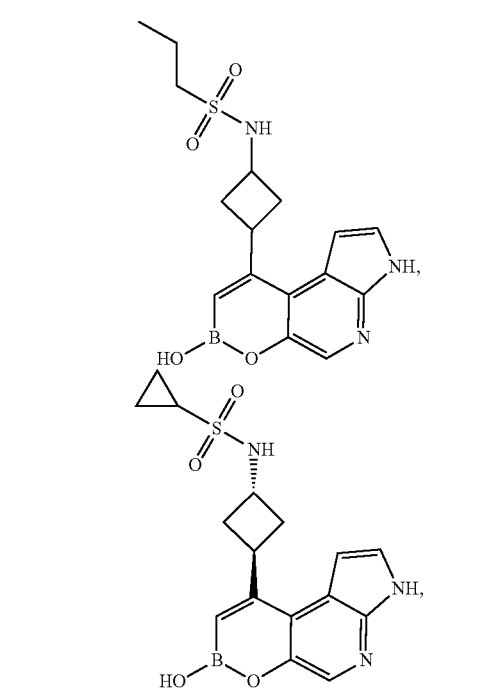
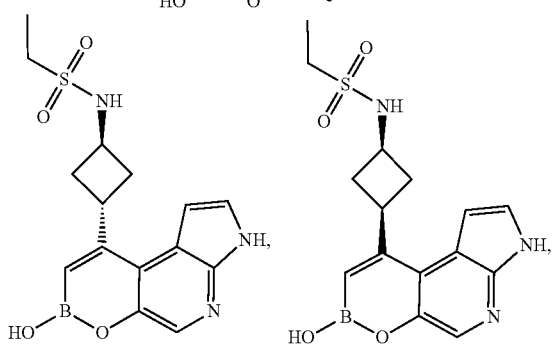
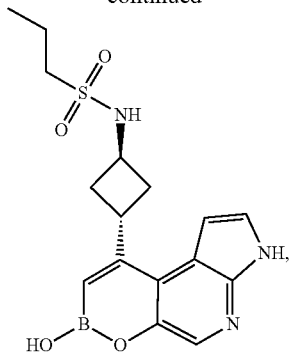
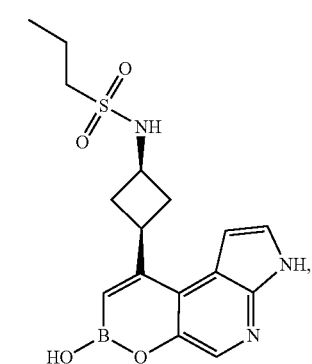
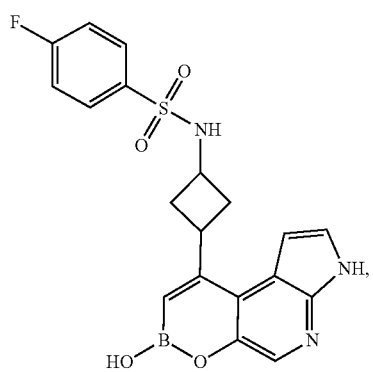
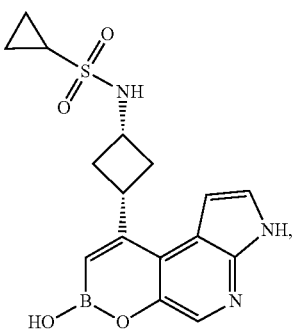

| 33 -continued | 34 -continued |
|---|---|
| 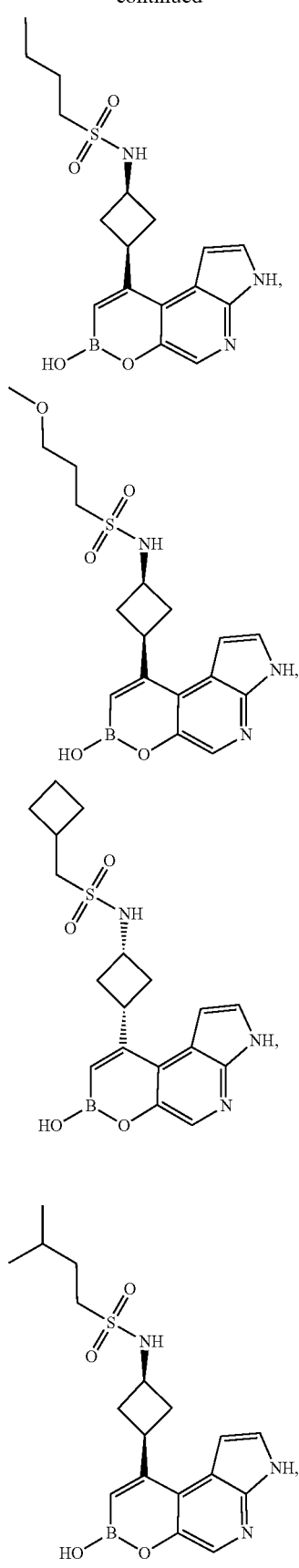 | 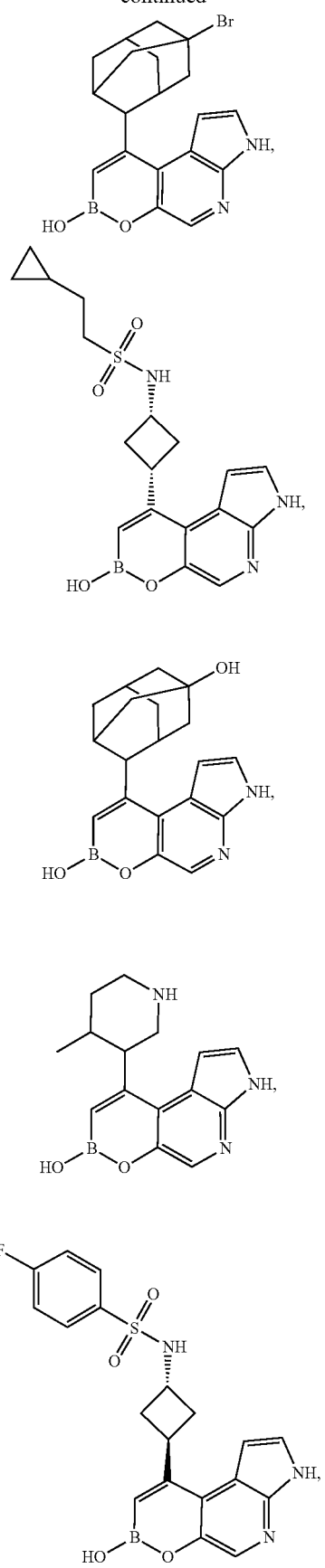 |

35
-continued
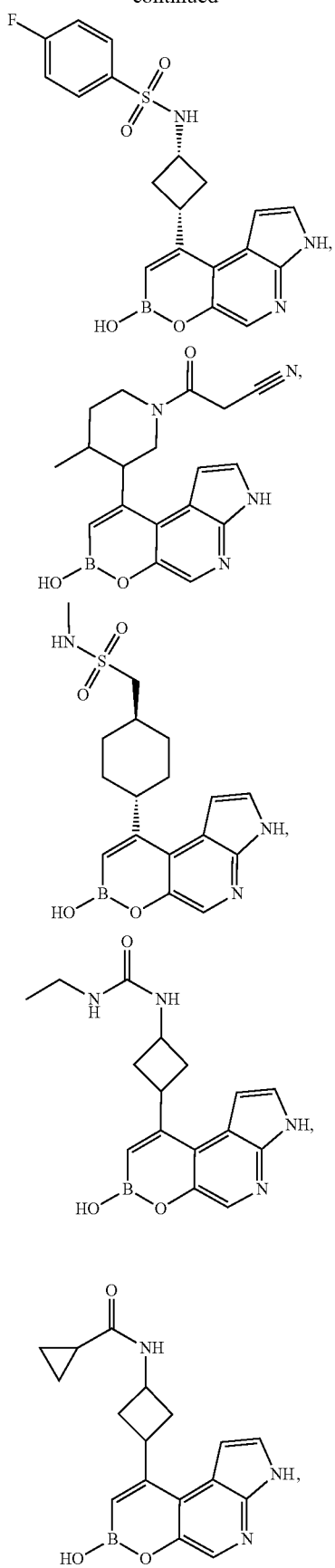
36
-continued
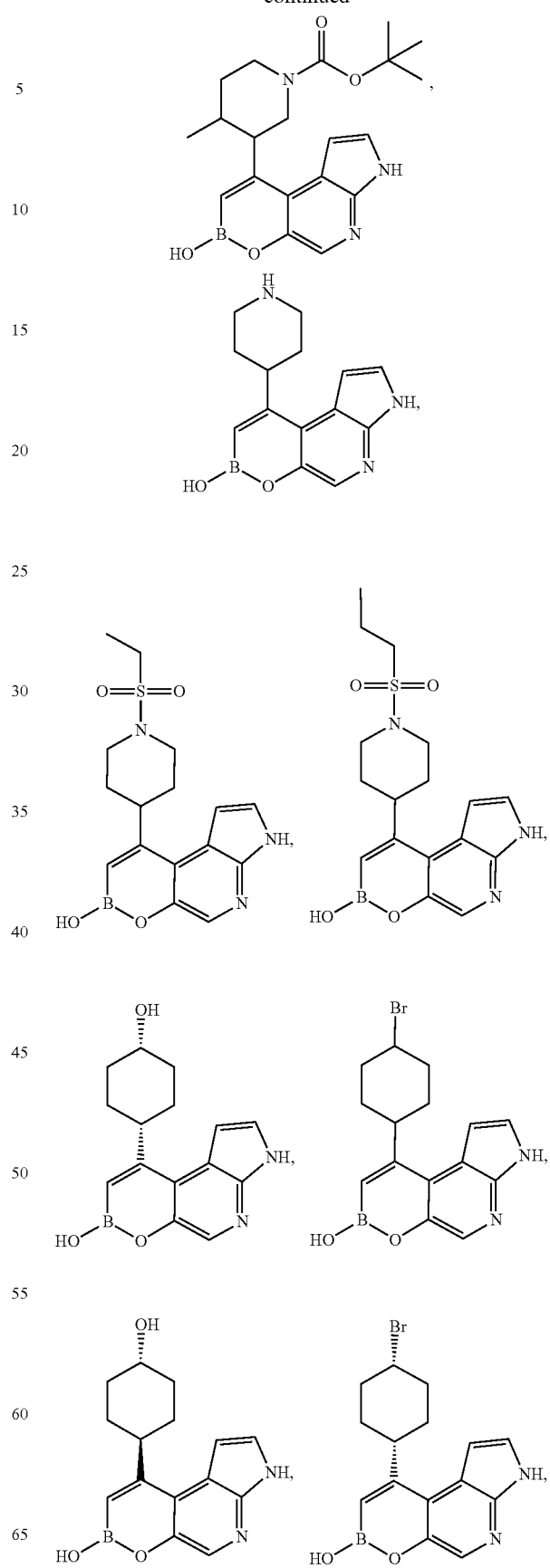

37
-continued
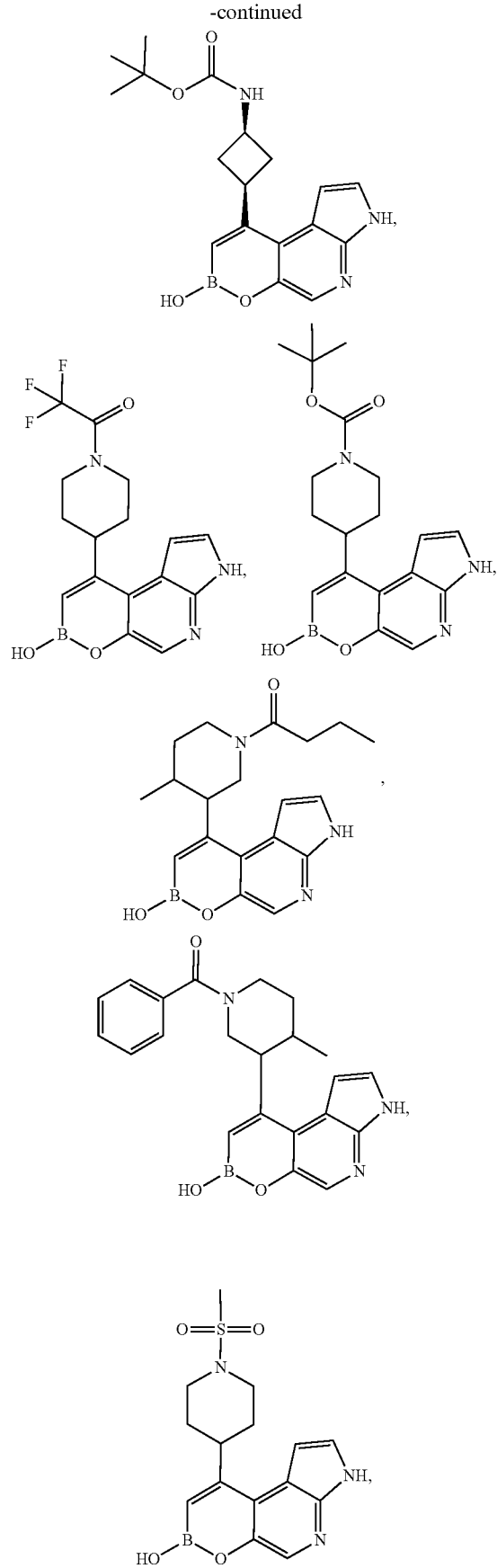
38
-continued
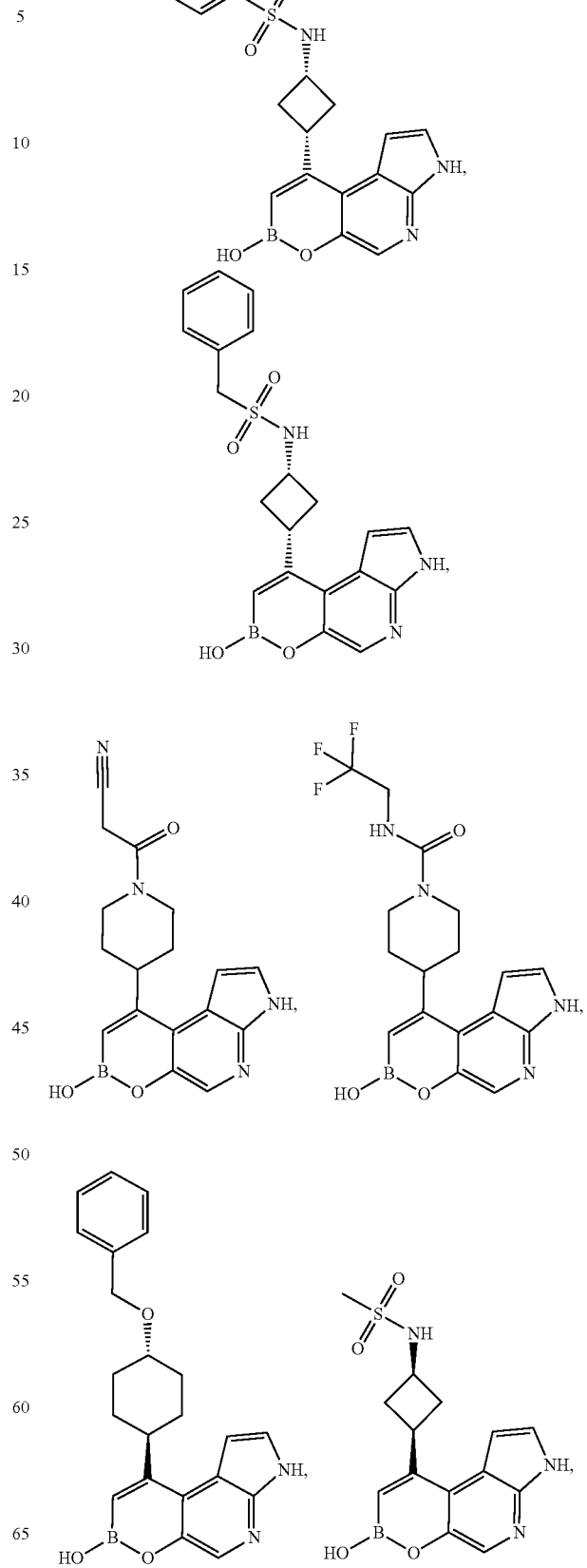

-continued
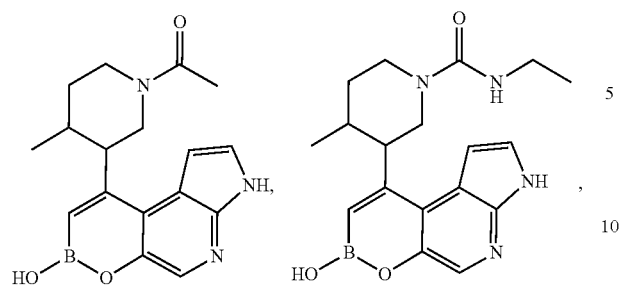
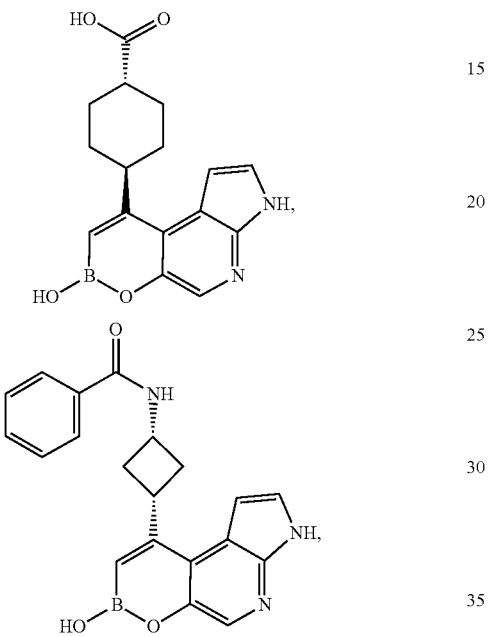
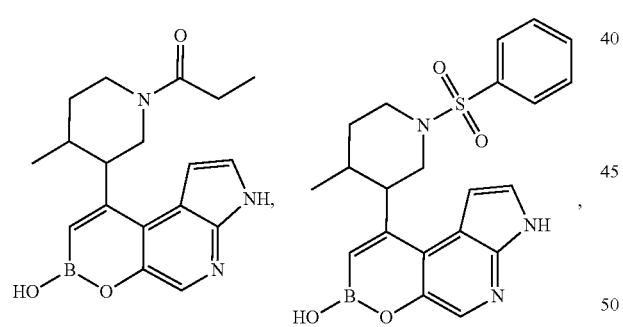
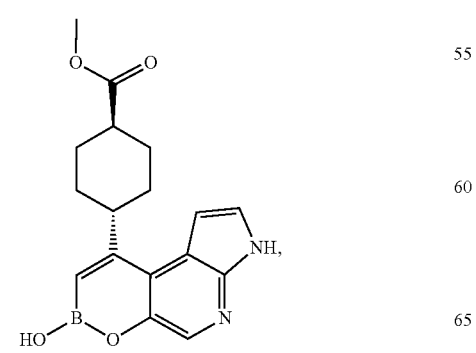
-continued
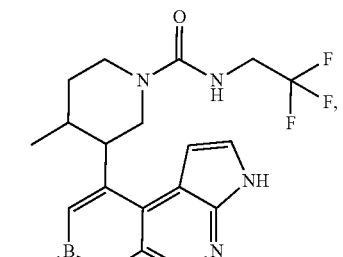
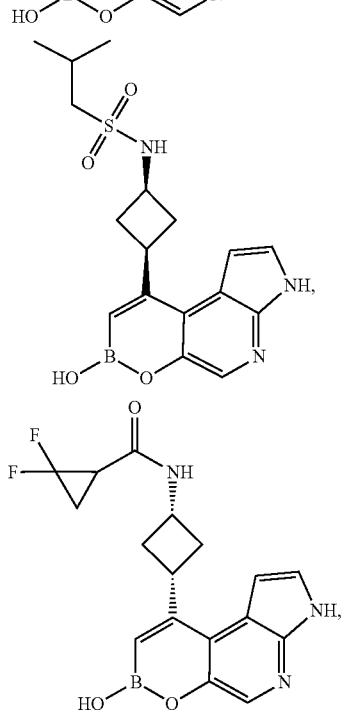
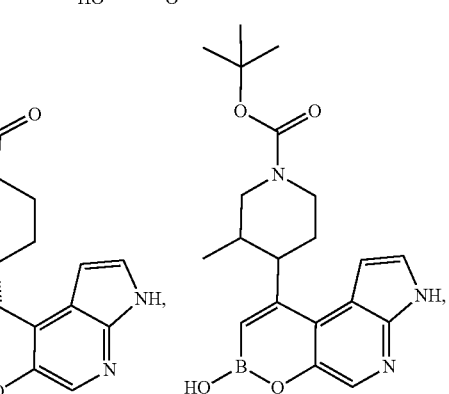
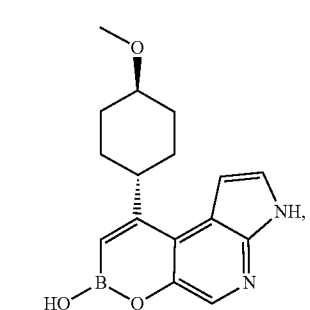

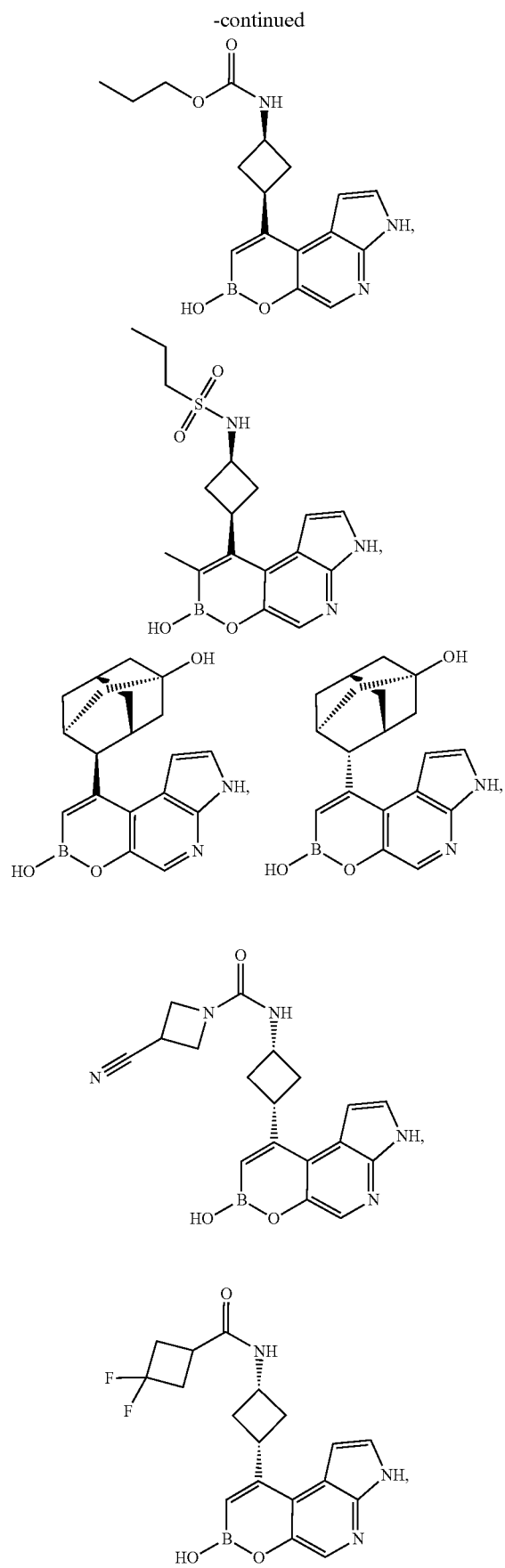
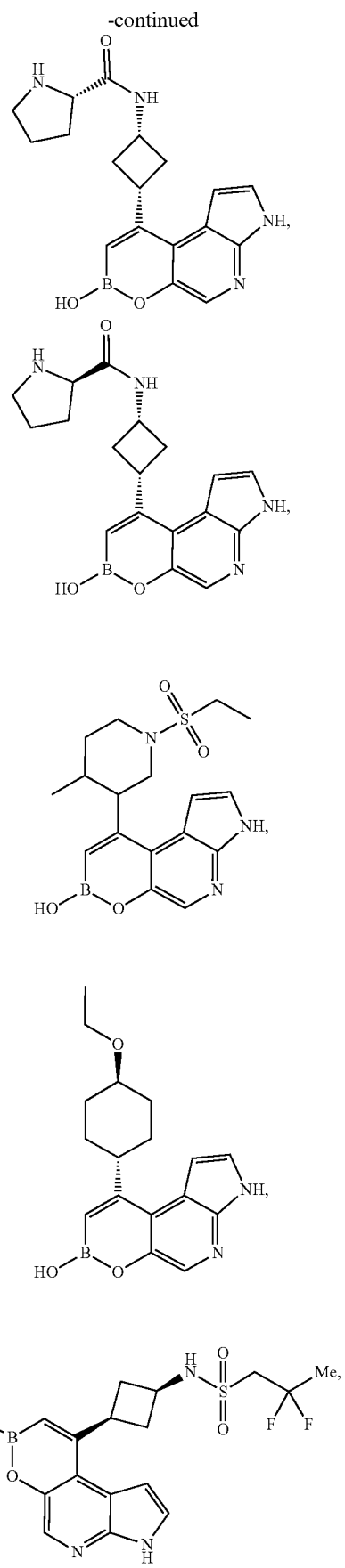

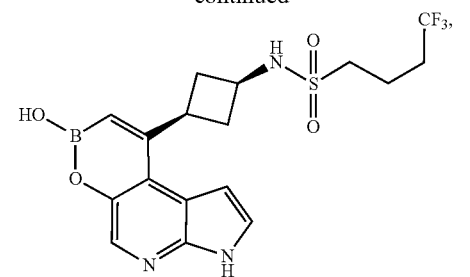
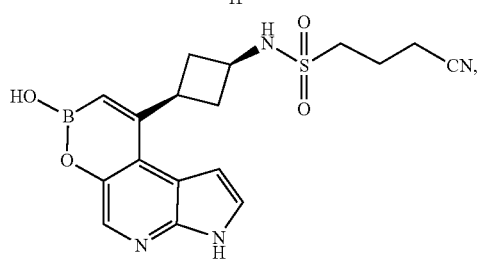
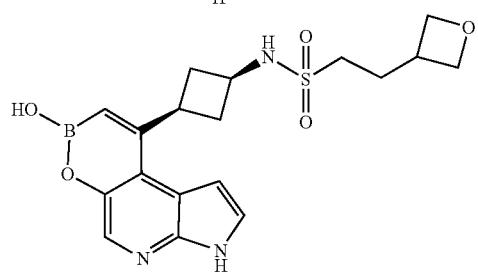
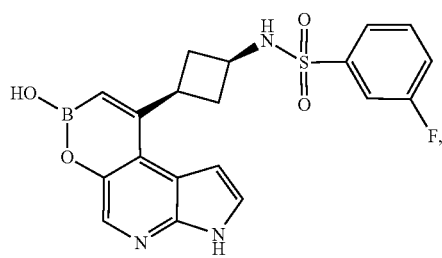
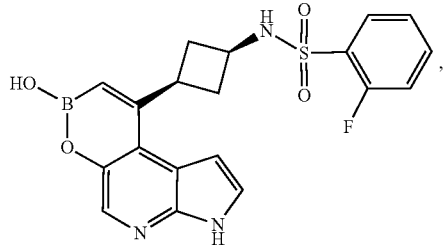
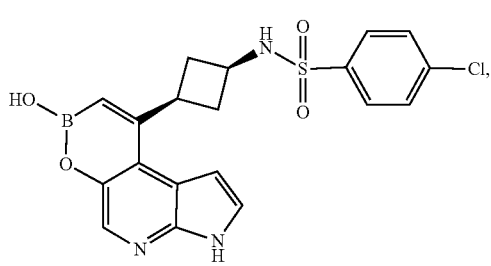
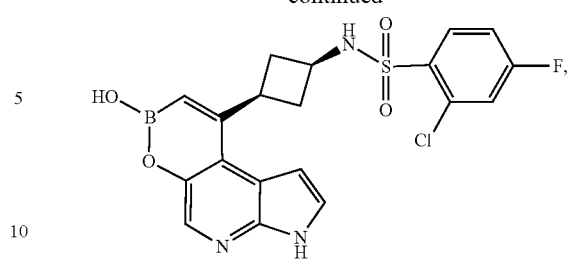
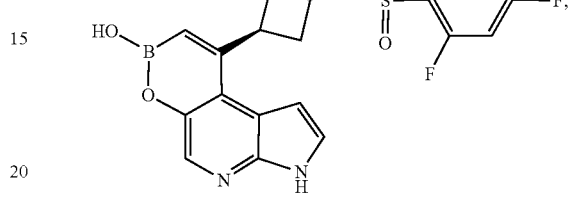
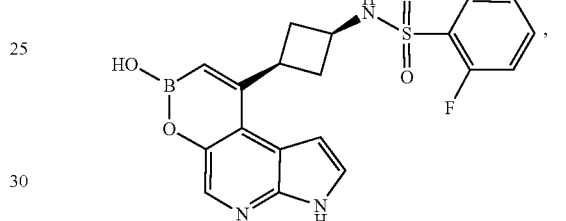
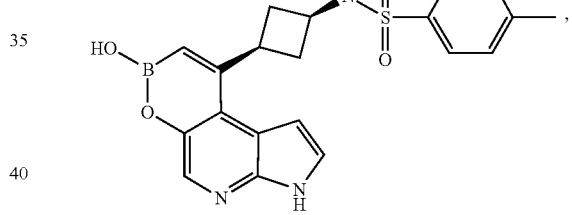
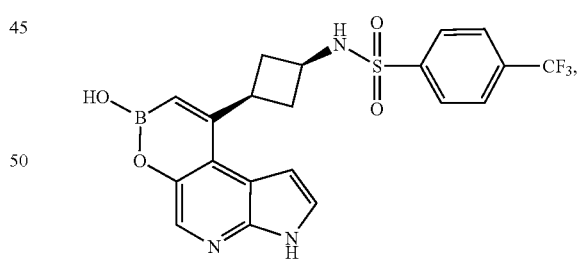
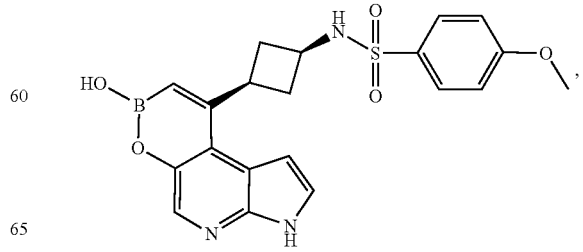

45
-continued
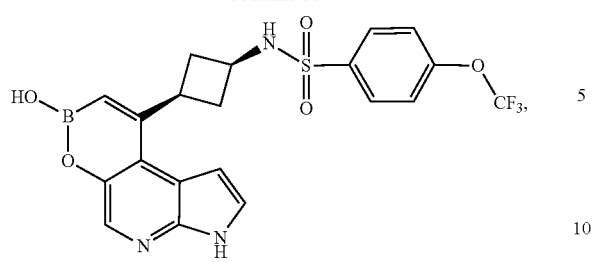
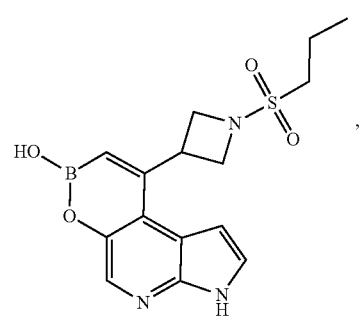
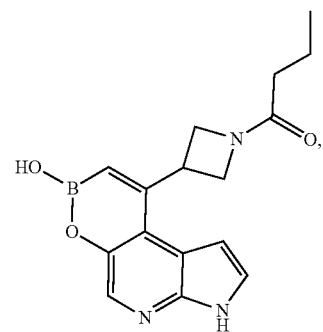
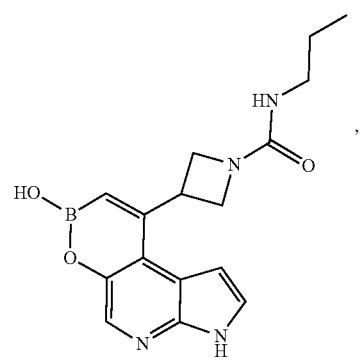
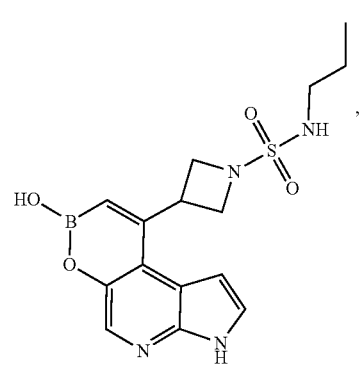
46
-continued
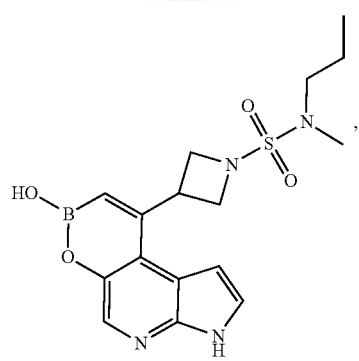
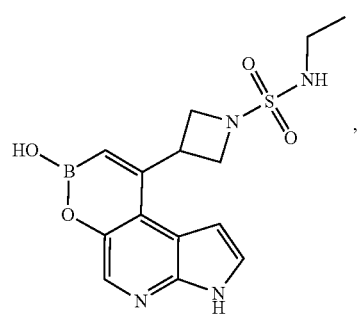
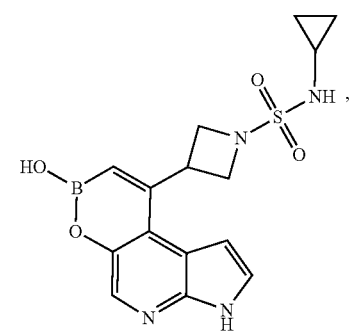
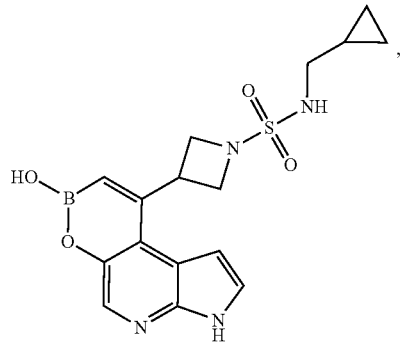
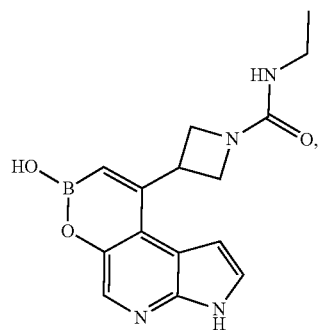

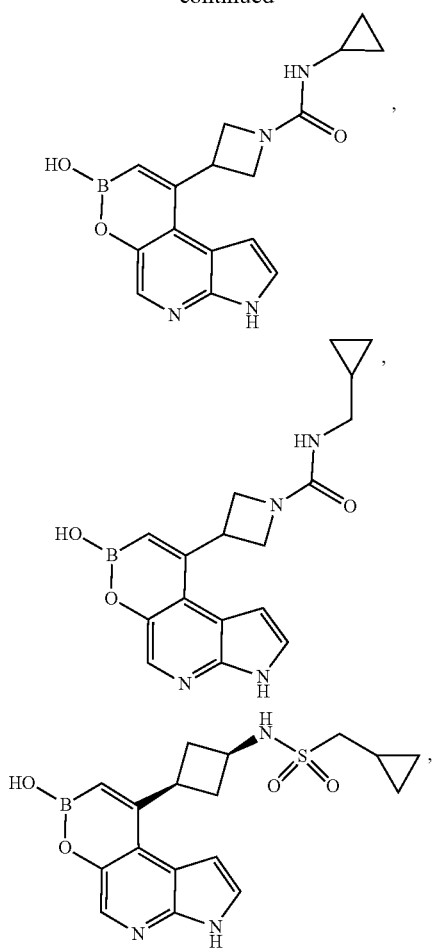
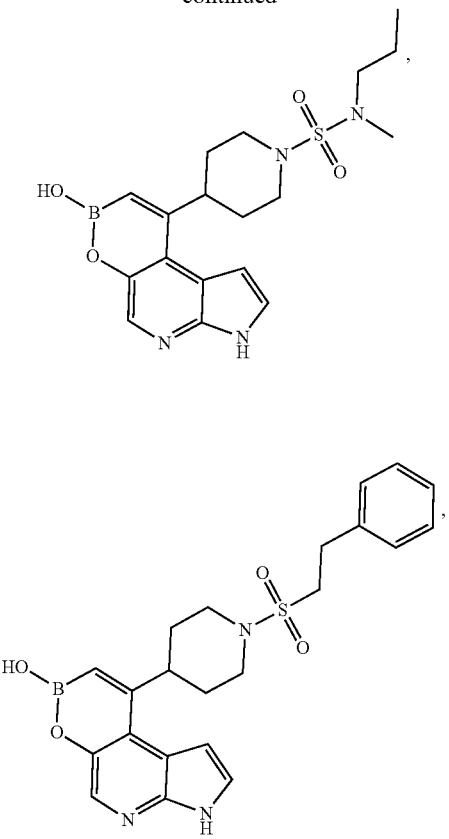
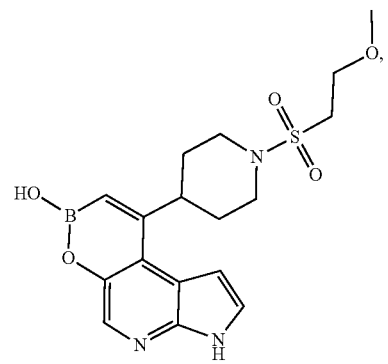
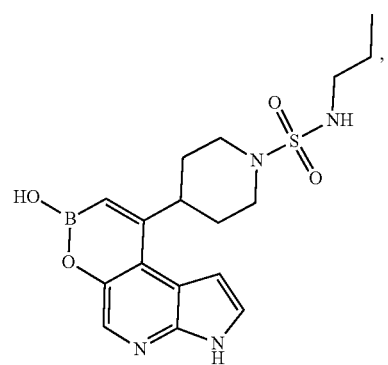

-continued
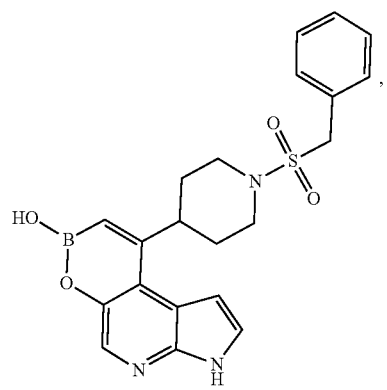
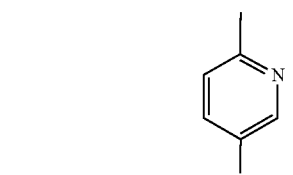
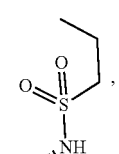
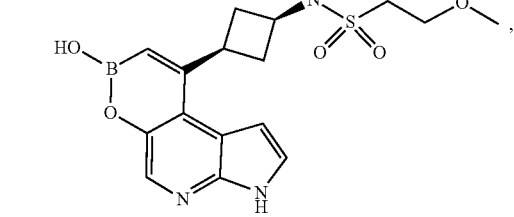
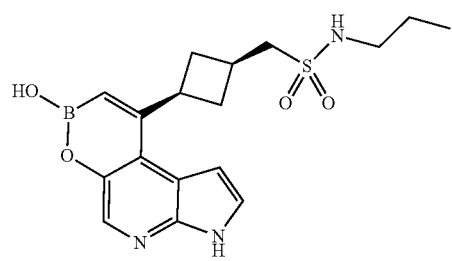
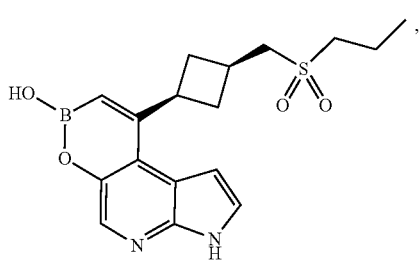
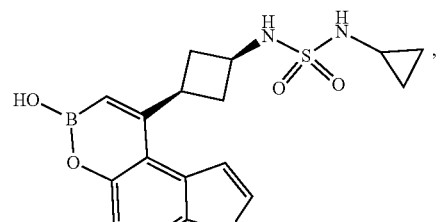
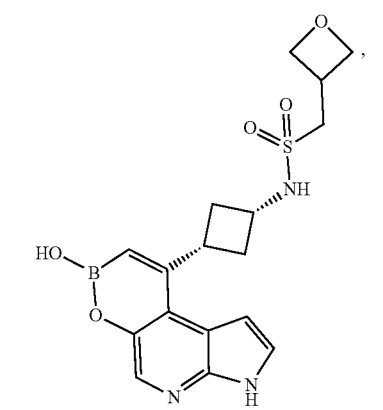
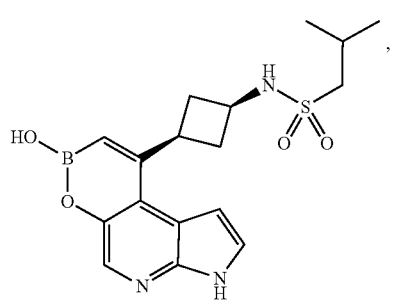
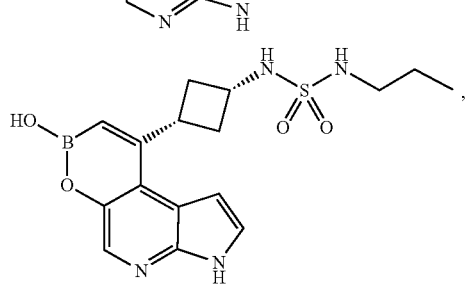

51
-continued
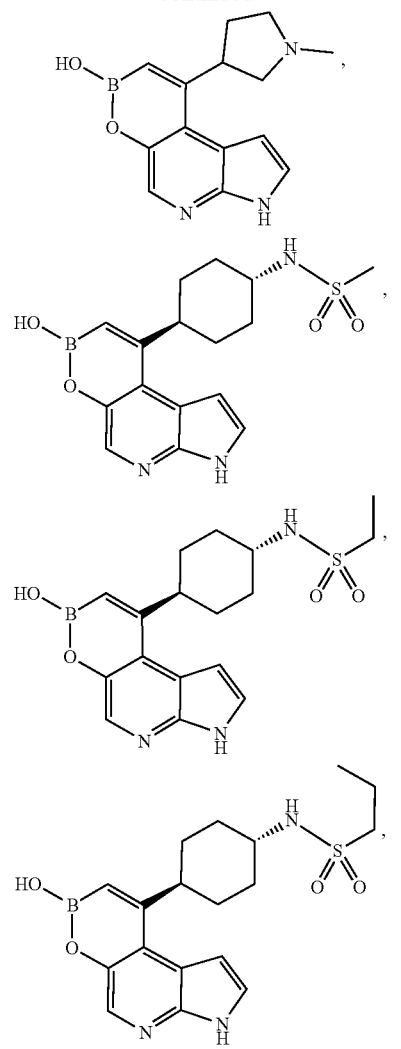
52
-continued
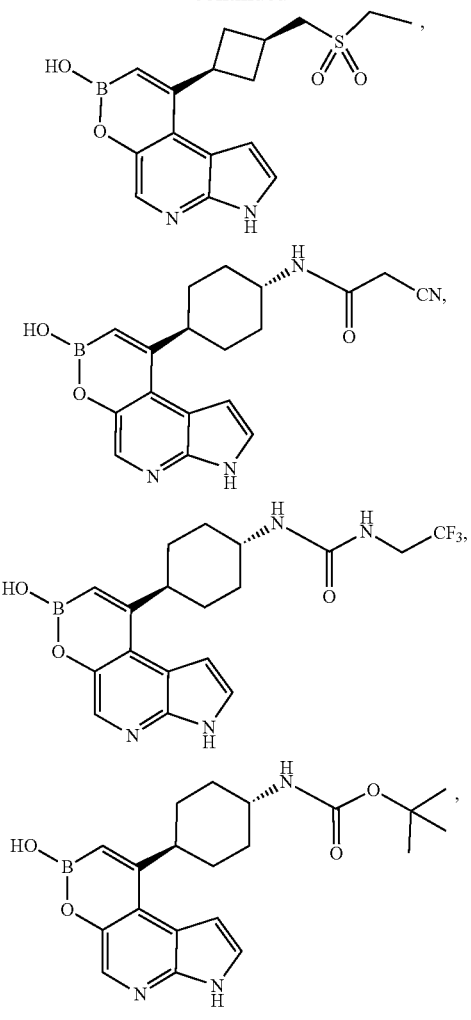
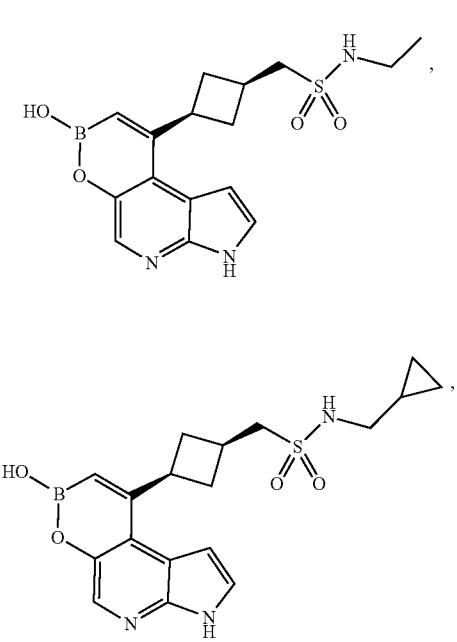
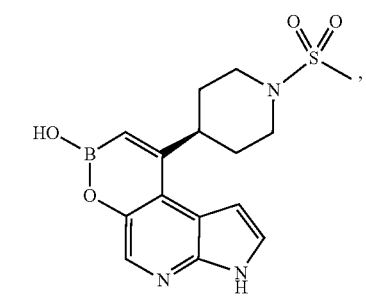
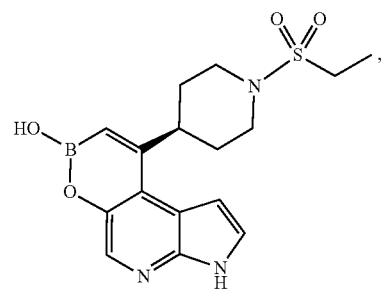

53
-continued
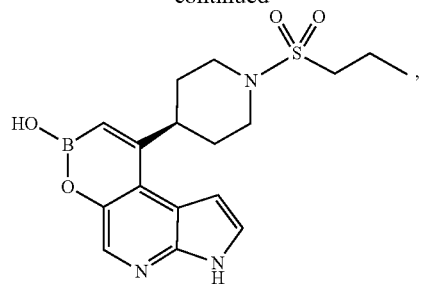
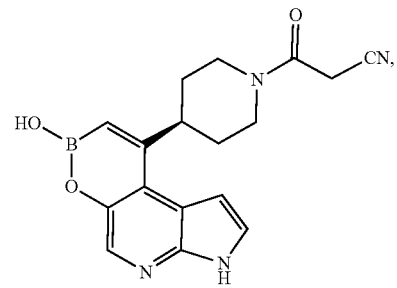
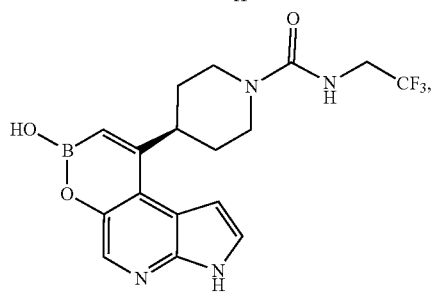
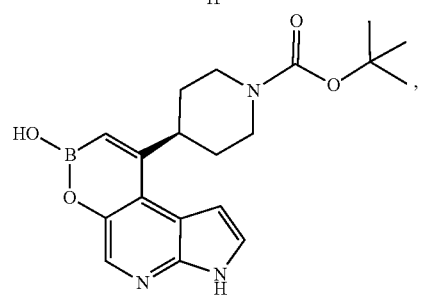
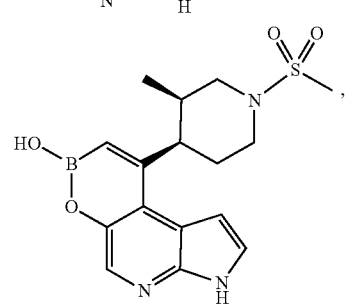
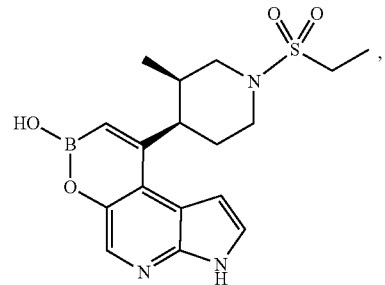
54
-continued
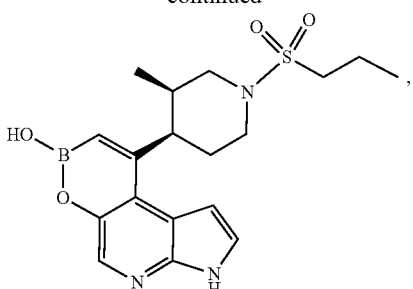
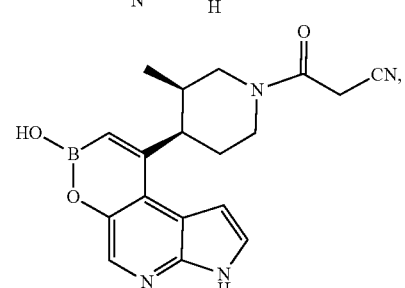
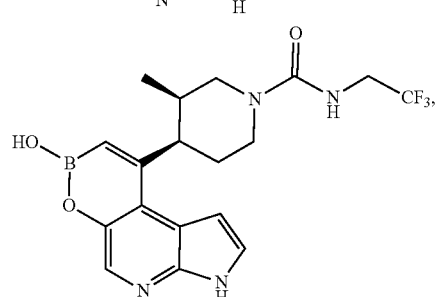
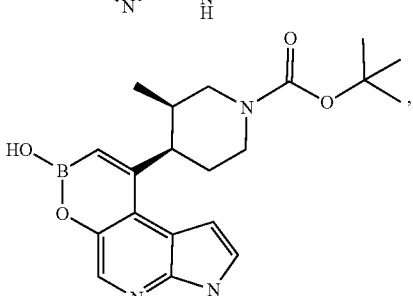
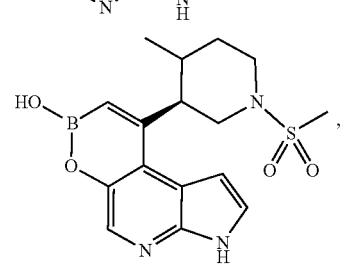
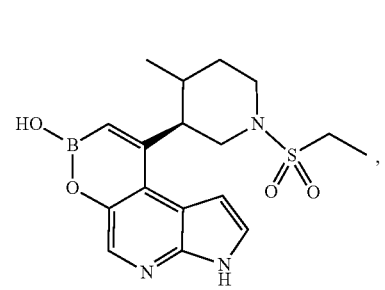

55
-continued
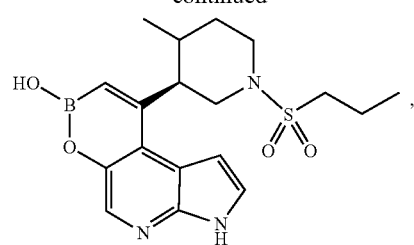,
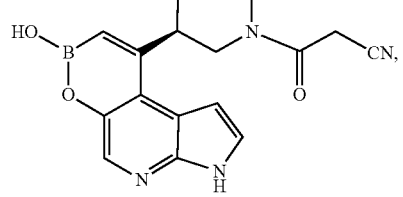,
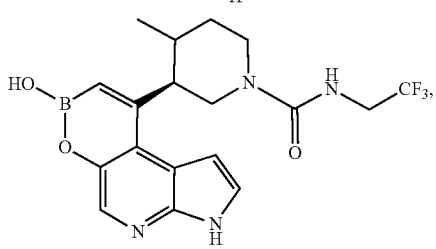,
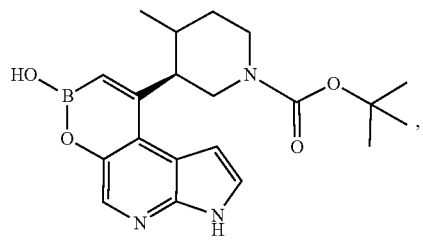,
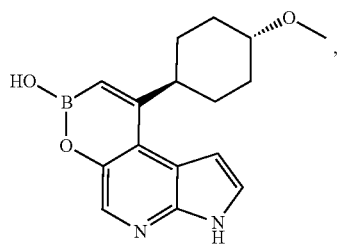,
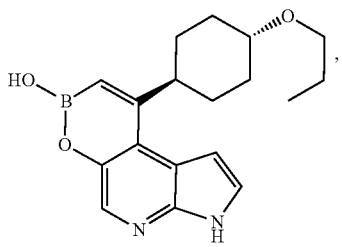,
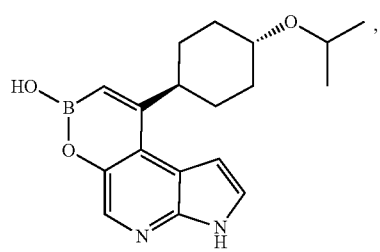,
56
-continued
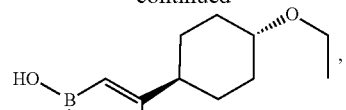,
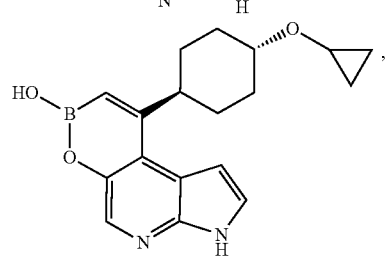,
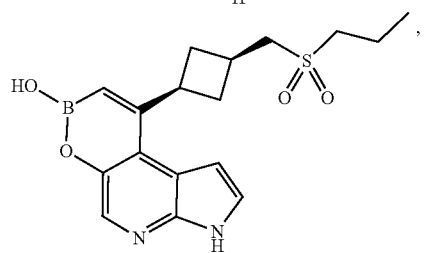,
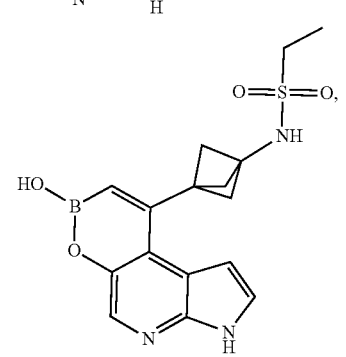,
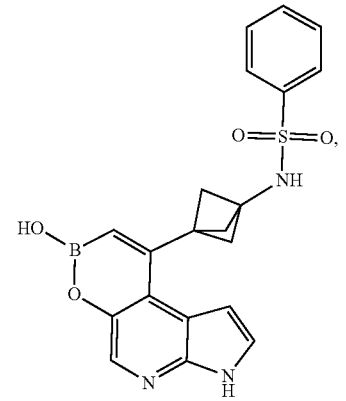, 57
-continued
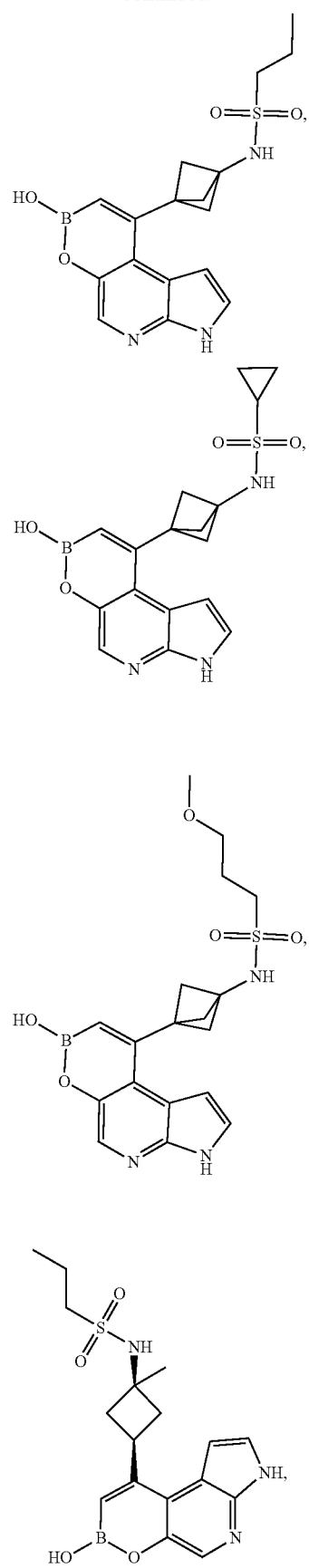
58
-continued
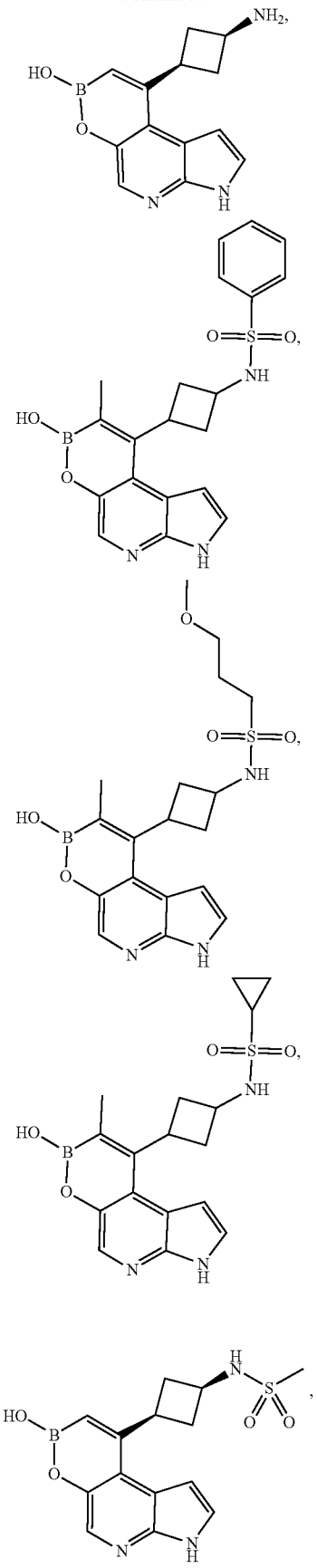

59
-continued
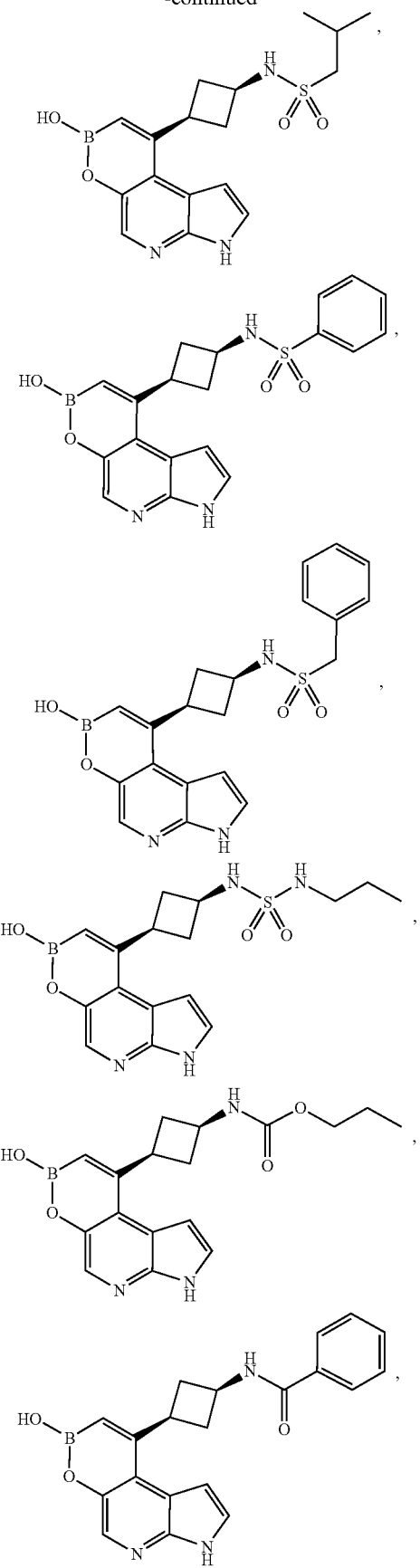
60
-continued
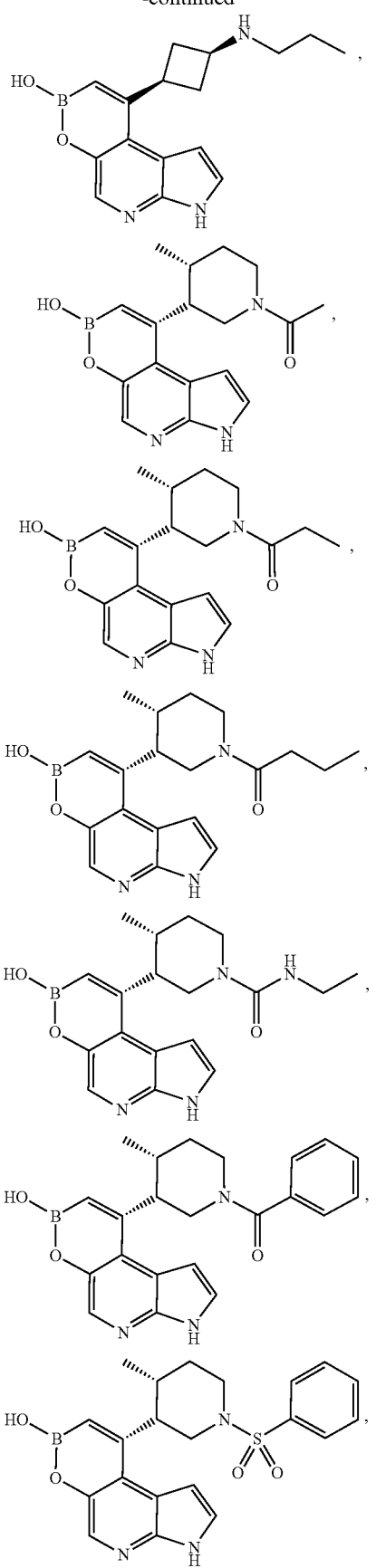

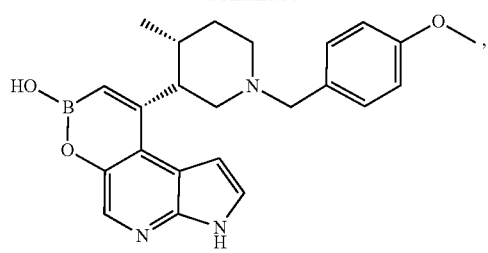
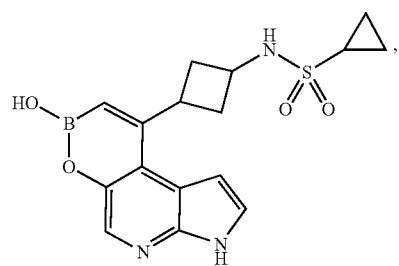
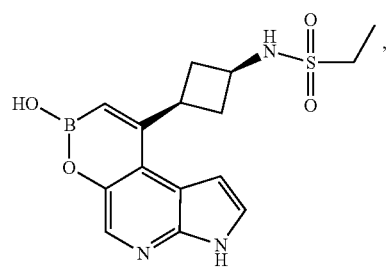
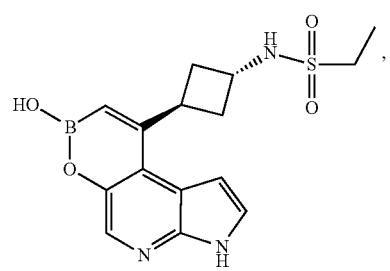
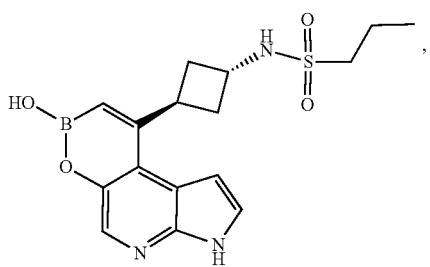
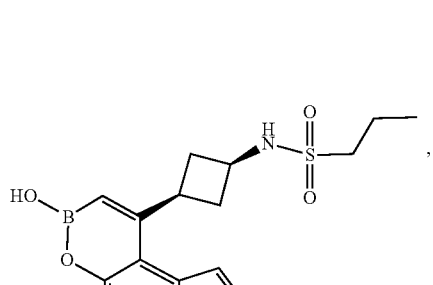
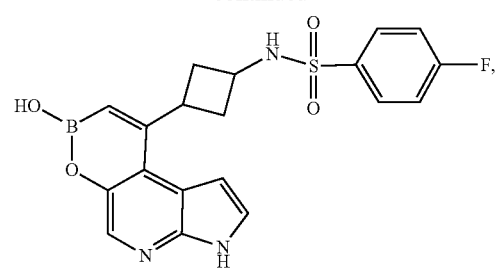
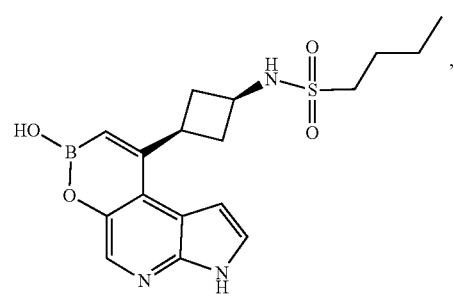
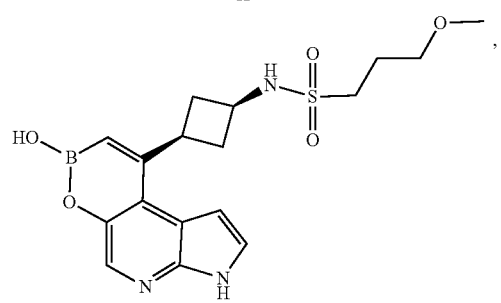
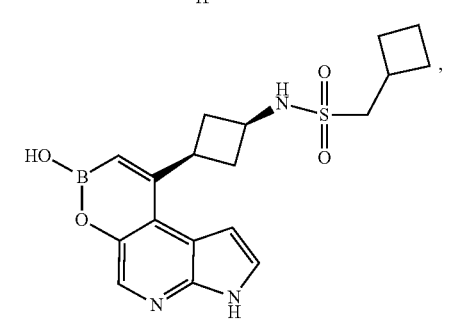
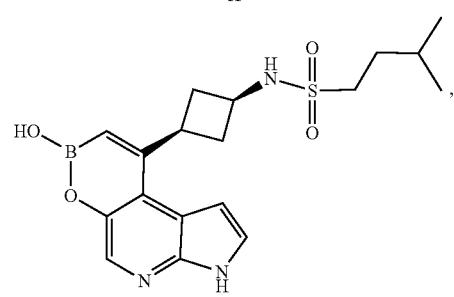
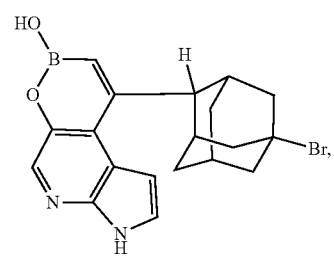

63
-continued
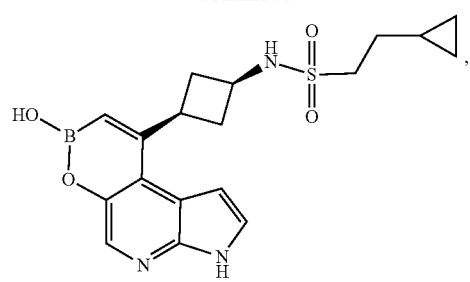
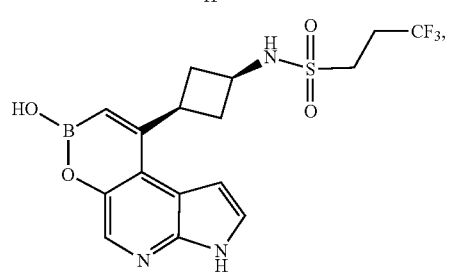
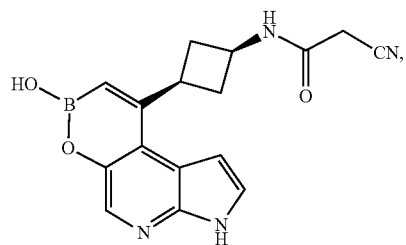
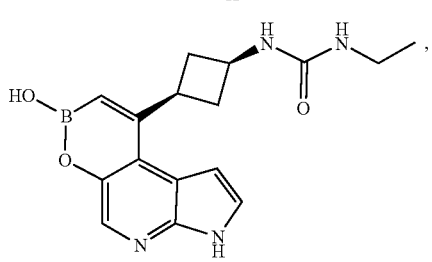
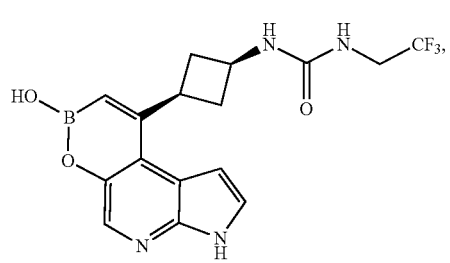
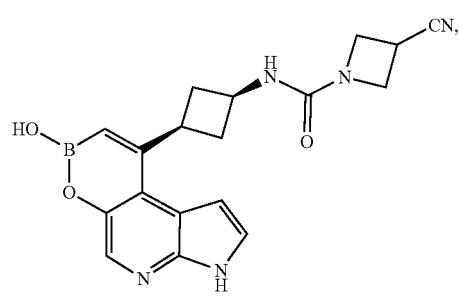
64
-continued
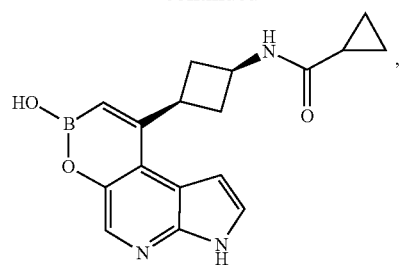
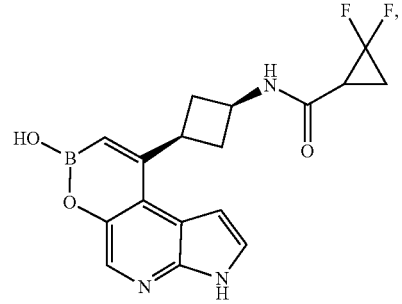
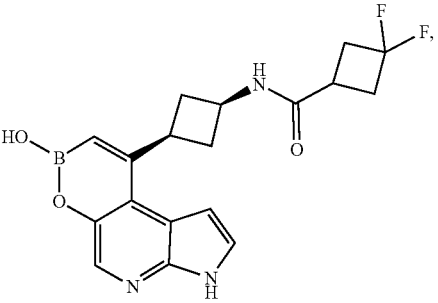
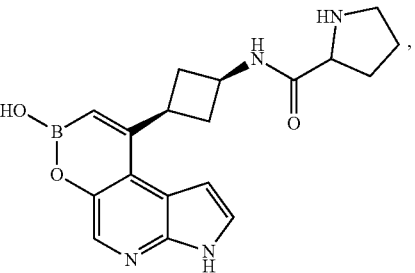
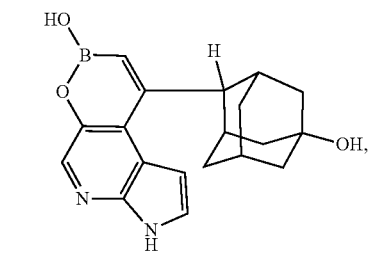
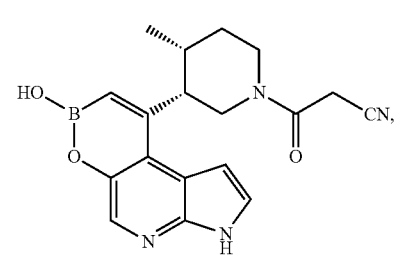

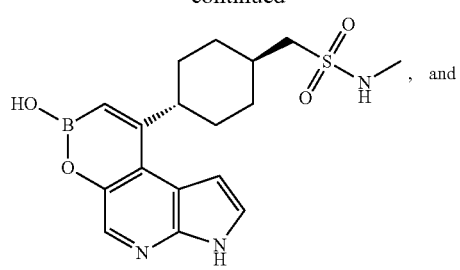
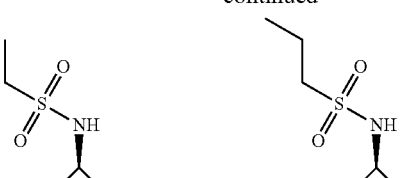
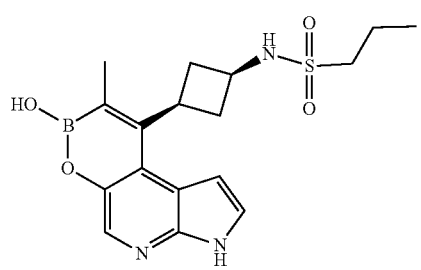
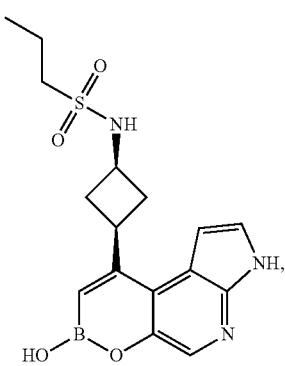
or a stereoisomer, enantiomer, or tautomer thereof, or a veterinary or pharmaceutically acceptable salt thereof.
In one aspect, the compound is selected from the group consisting of:
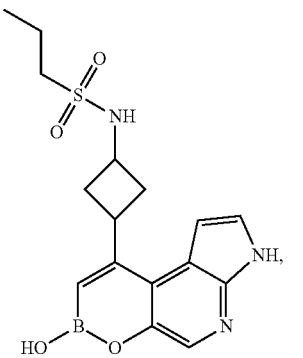
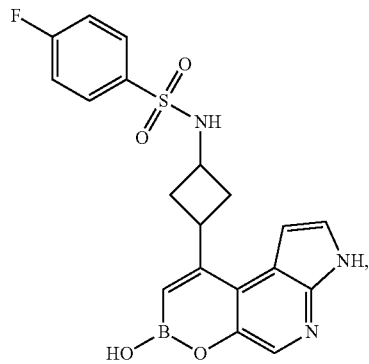
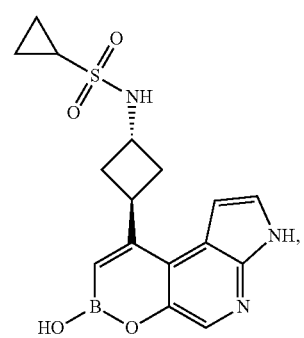
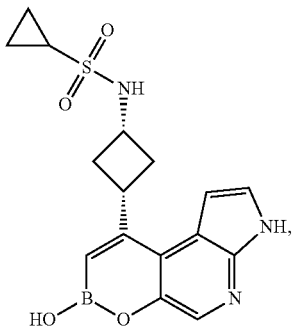

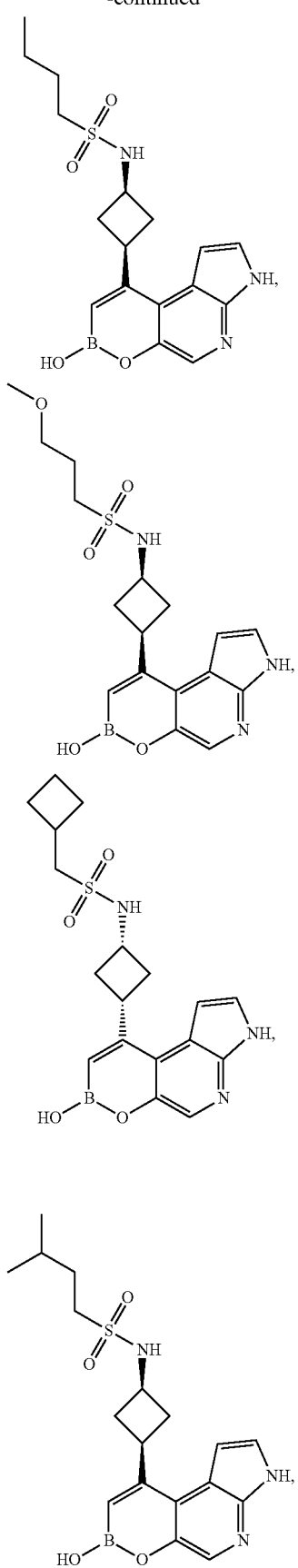
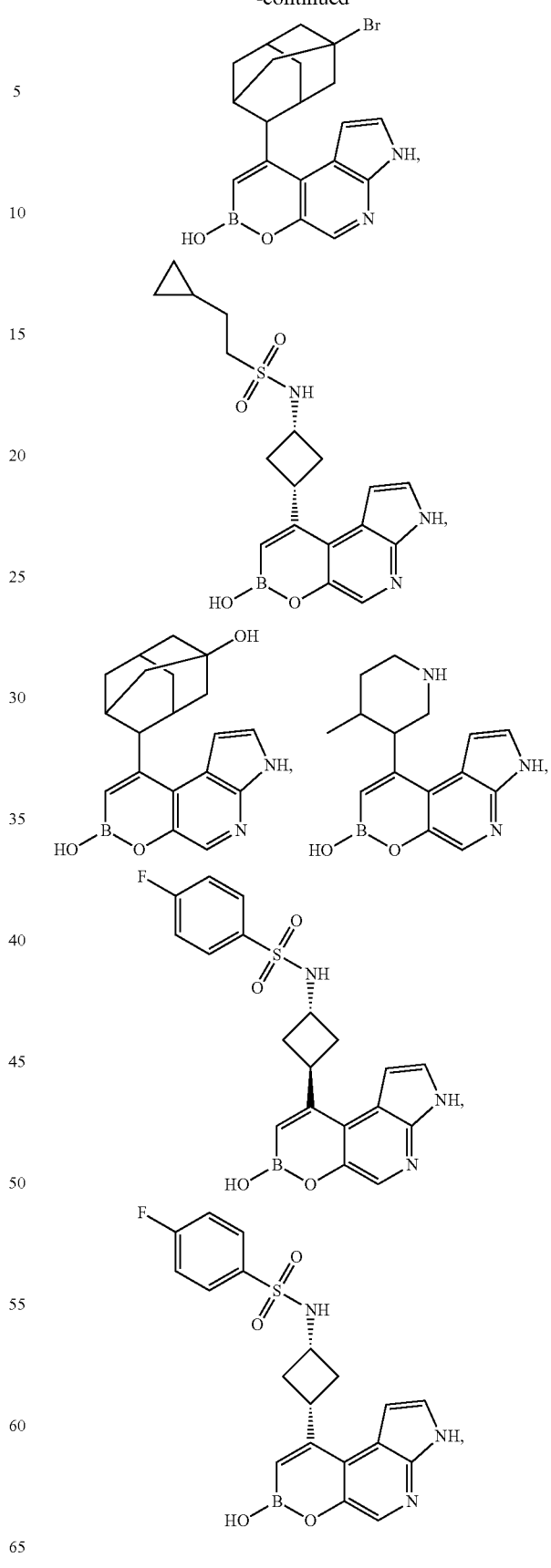

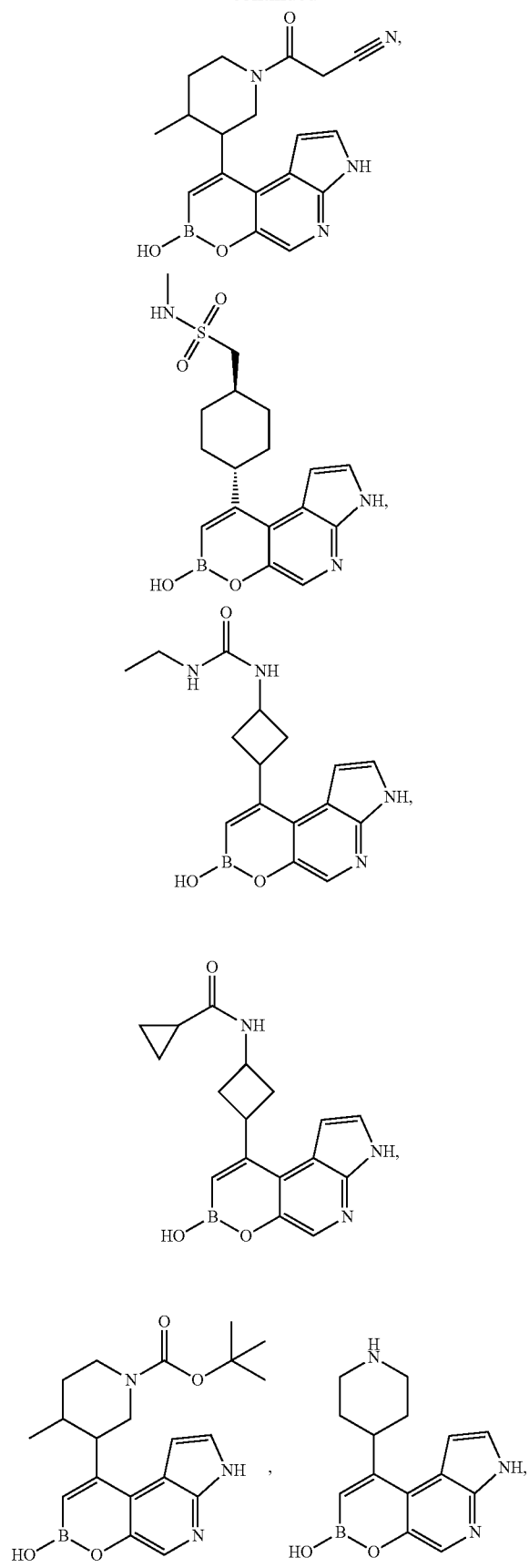

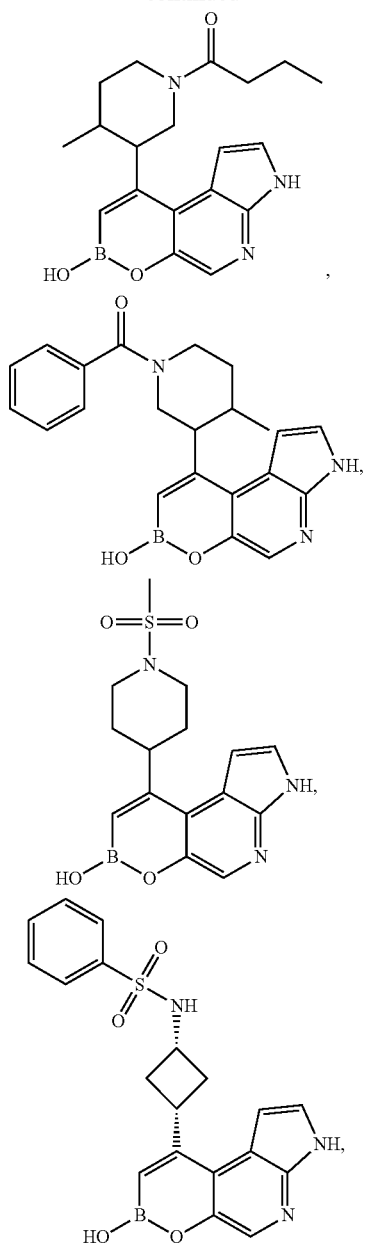
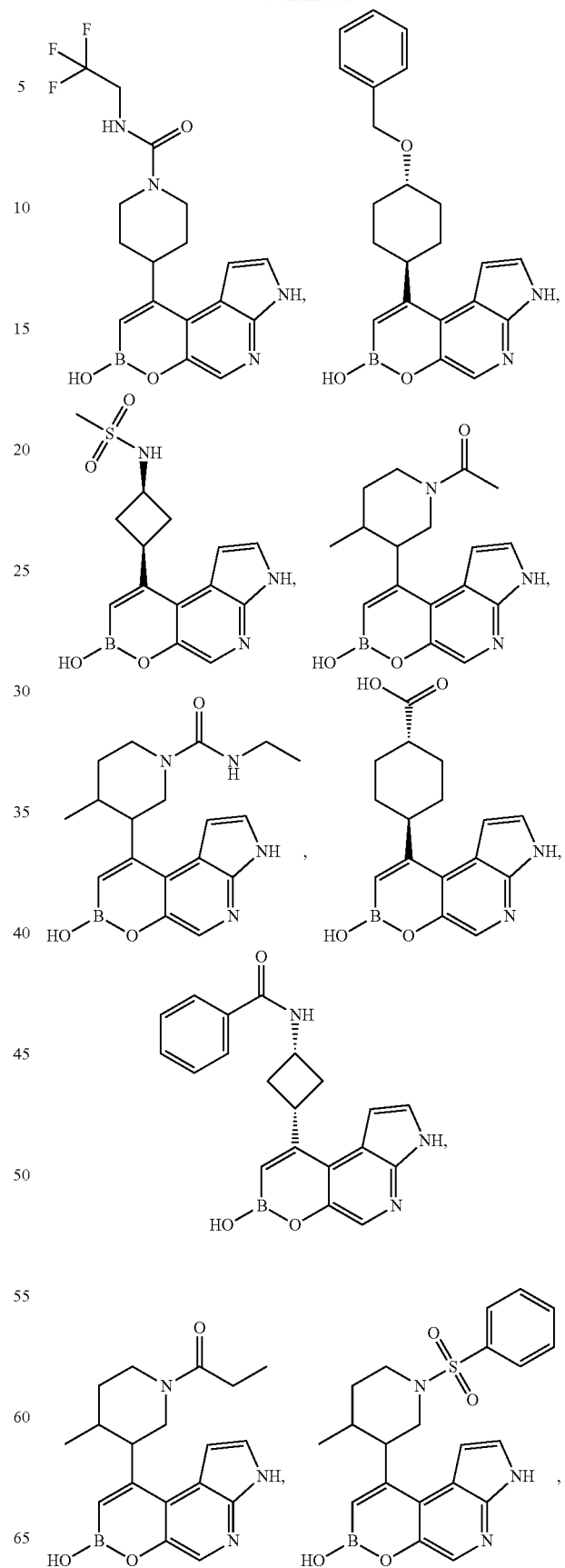

73
-continued
74
-continued
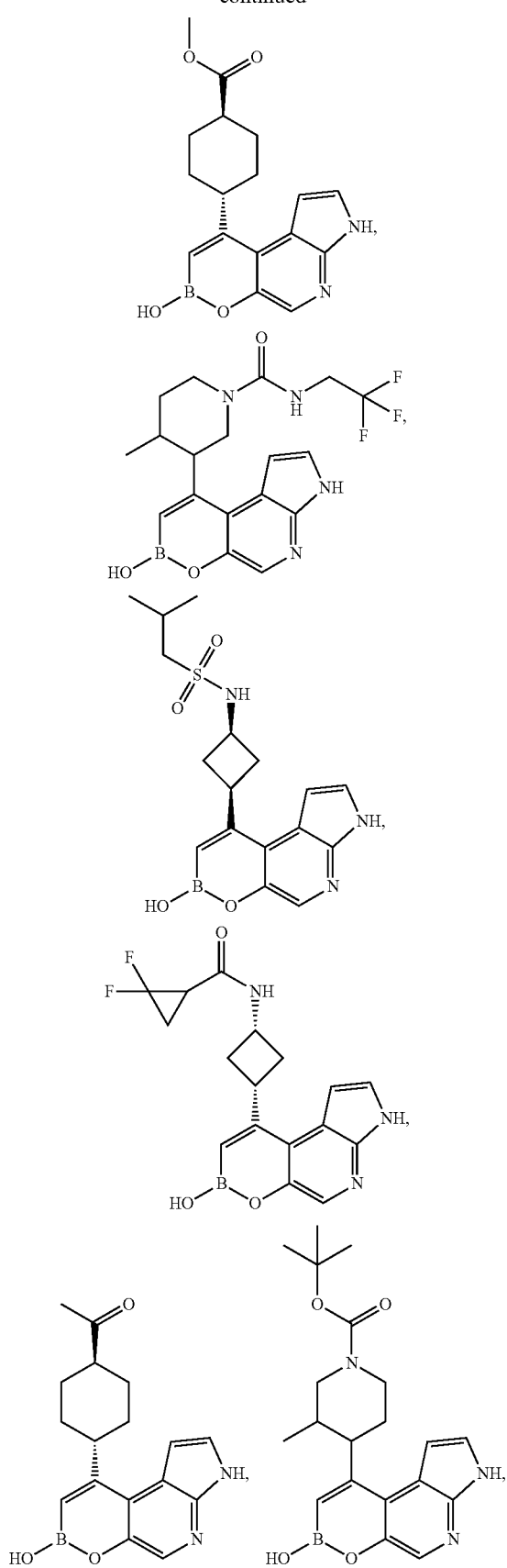
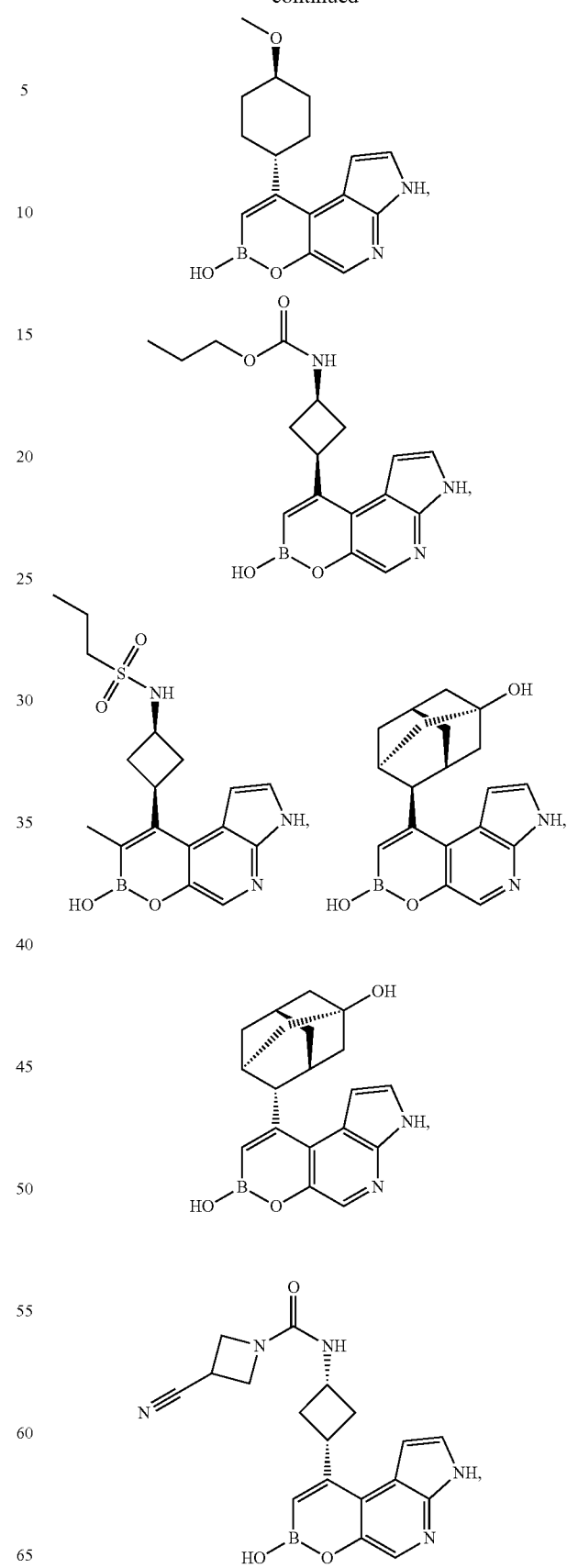

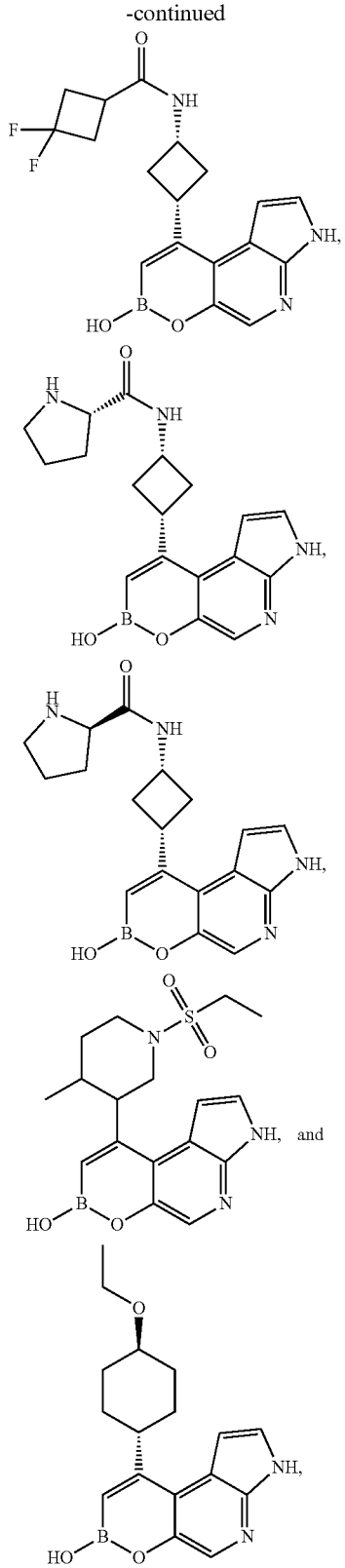
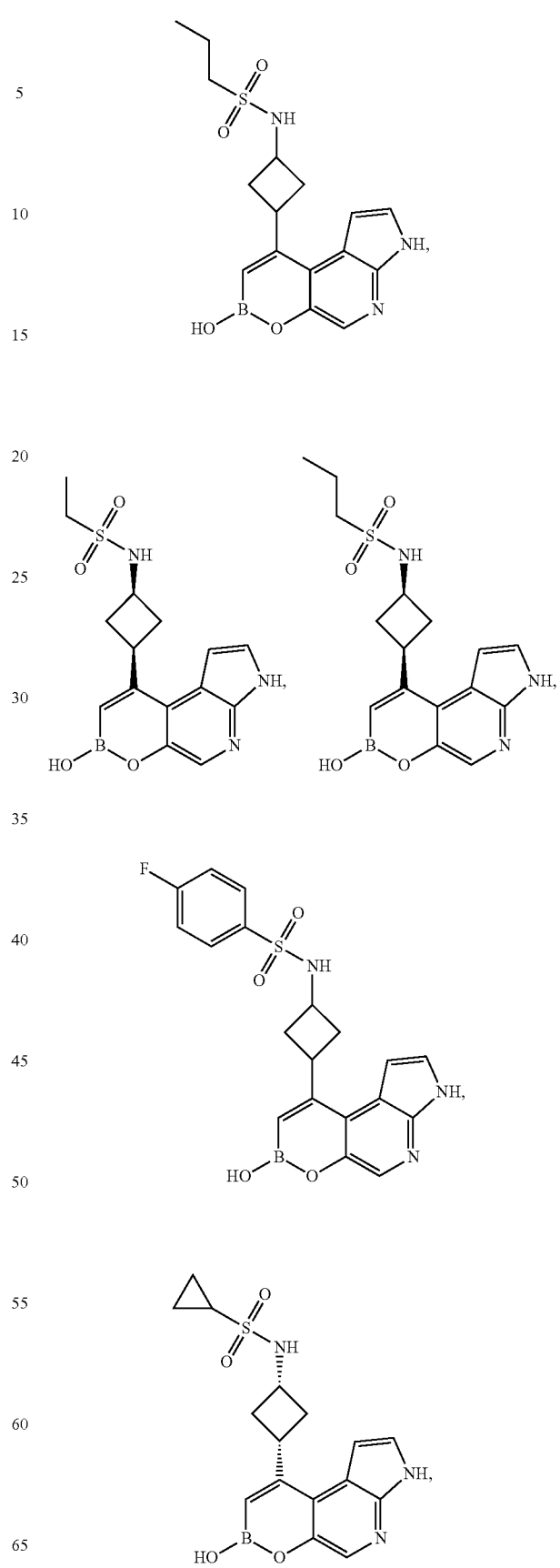
or a stereoisomer, enantiomer, or tautomer thereof, or a veterinary or pharmaceutically acceptable salt thereof.
In one aspect, the compound is selected from the group consisting of 77
-continued
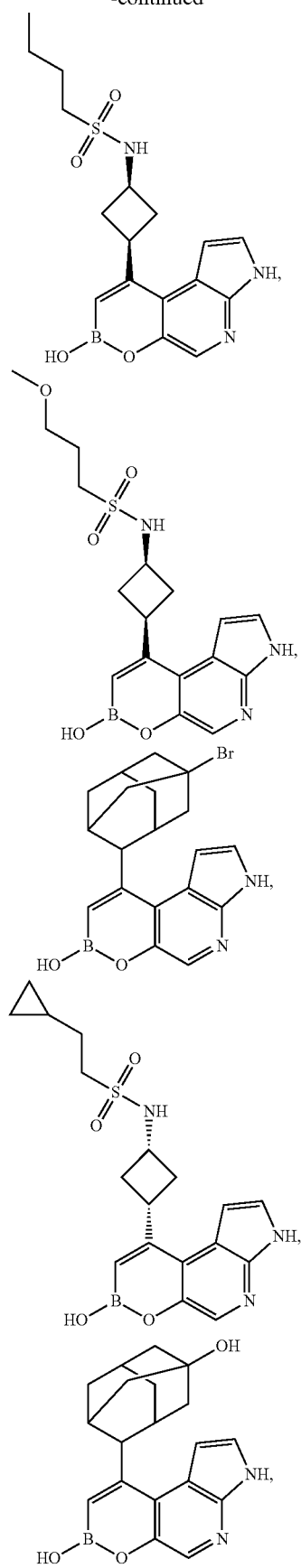
78
-continued
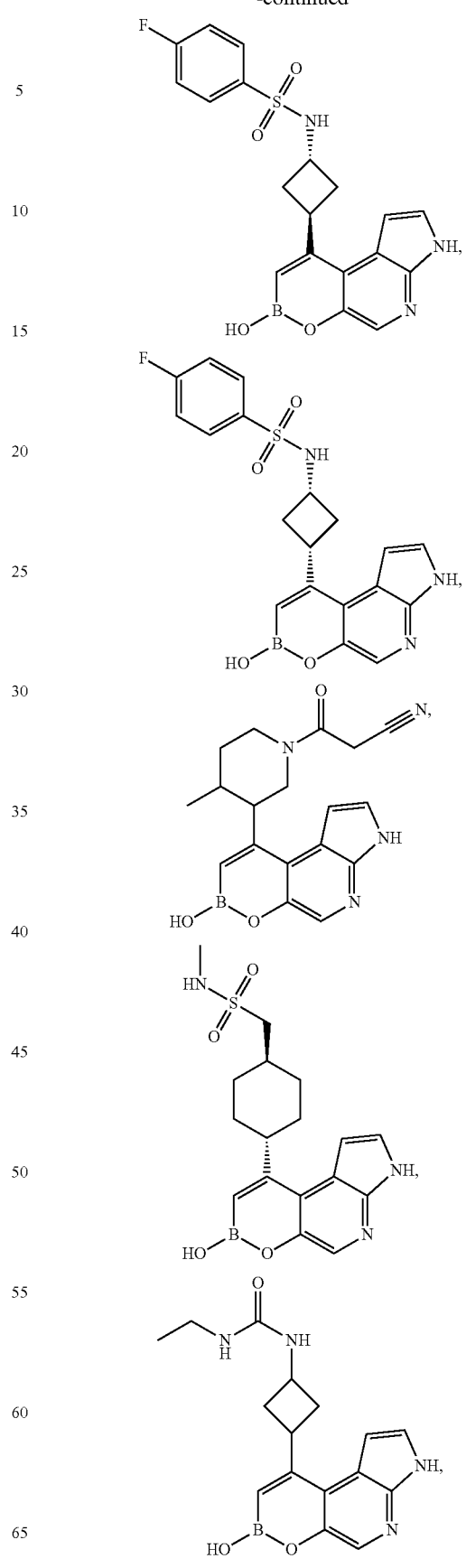

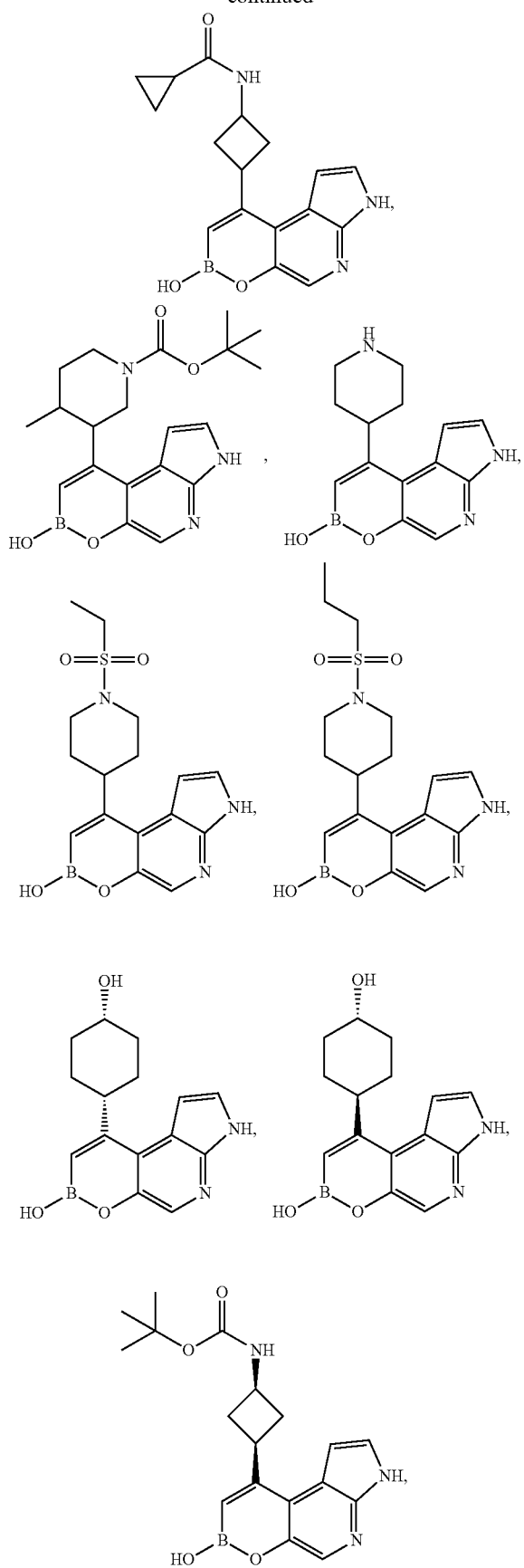
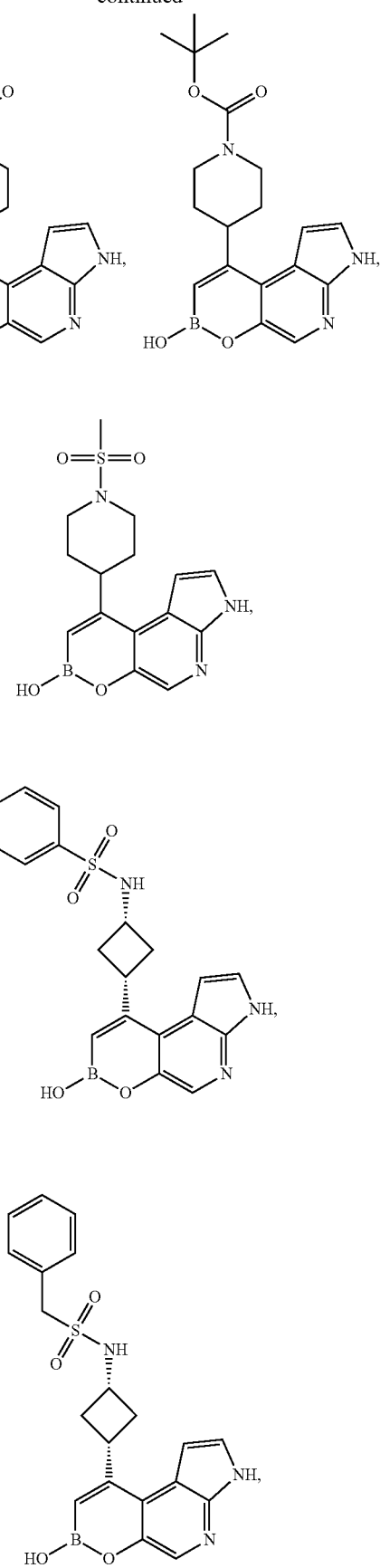

-continued

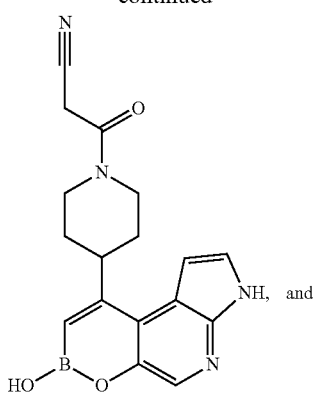

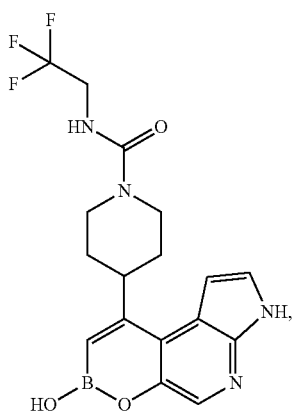

or a stereoisomer, enantiomer, or tautomer thereof, or a veterinary or pharmaceutically acceptable salt thereof.

One embodiment of the present disclosure includes a compound of formula (III), (IV), or (V):

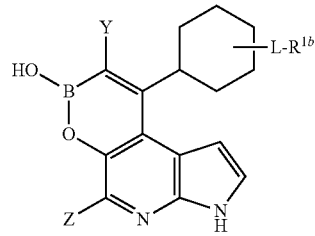
(III)

(IV)

-continued

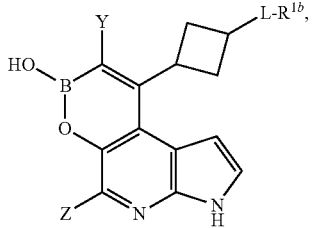
(V)

wherein
each Y independently is selected from the group consisting of hydrogen, $C_1$-$C_6$ alkyl, $C_{2\text{-}6}$ alkenyl, and $C_{2\text{-}6}$ alkynyl;
each Z independently is selected from the group consisting of hydrogen, $C_1$-$C_6$ alkyl, $C_{2\text{-}6}$ alkenyl, and $C_{2\text{-}6}$ alkynyl; and
each L independently is selected from the group consisting of —NR'SO$_2$—, —CH$_2$SO$_2$NR'—, —NR'C(O)—, and —NR'C(O)NR'—,
where each R' and $R^{1b}$ independently is selected from the group consisting of hydrogen, deuterium, $C_1$-$C_6$ alkyl, $C_2$-$C_6$ alkenyl, $C_2$-$C_6$ alkynyl, $C_3$-$C_6$ cycloalkyl, aryl, aryl-$C_1$-$C_6$ alkyl, aryl-$C_2$-$C_6$ alkenyl, aryl-$C_1$-$C_6$ alkynyl, heteroaryl, $C_1$-$C_6$ alkyl-heteroaryl, $C_2$-$C_6$ alkenyl-heteroaryl, $C_2$-$C_6$ alkynyl-heteroaryl, heteroaryl-$C_1$-$C_6$ alkyl, heteroaryl-$C_2$-$C_6$ alkenyl, heteroaryl-$C_1$-$C_6$ alkynyl, heterocyclyl-$C^1$-$C_6$ alkyl, heterocyclyl-$C_1$-$C_6$ alkenyl, and heterocyclyl-$C_1$-$C_6$ alkynyl, or a stereoisomer, enantiomer, or tautomer thereof, or a veterinary or pharmaceutically acceptable salt thereof.

In one aspect, the L-$R^{1b}$ substituent is located as depicted in formulae (III'), (IV'), or (V'):

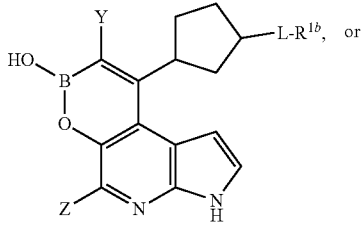
(III')

(IV')

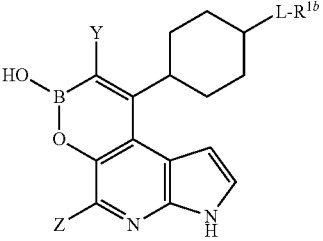
(V')

One embodiment of the present disclosure includes a compound selected from the group consisting of:

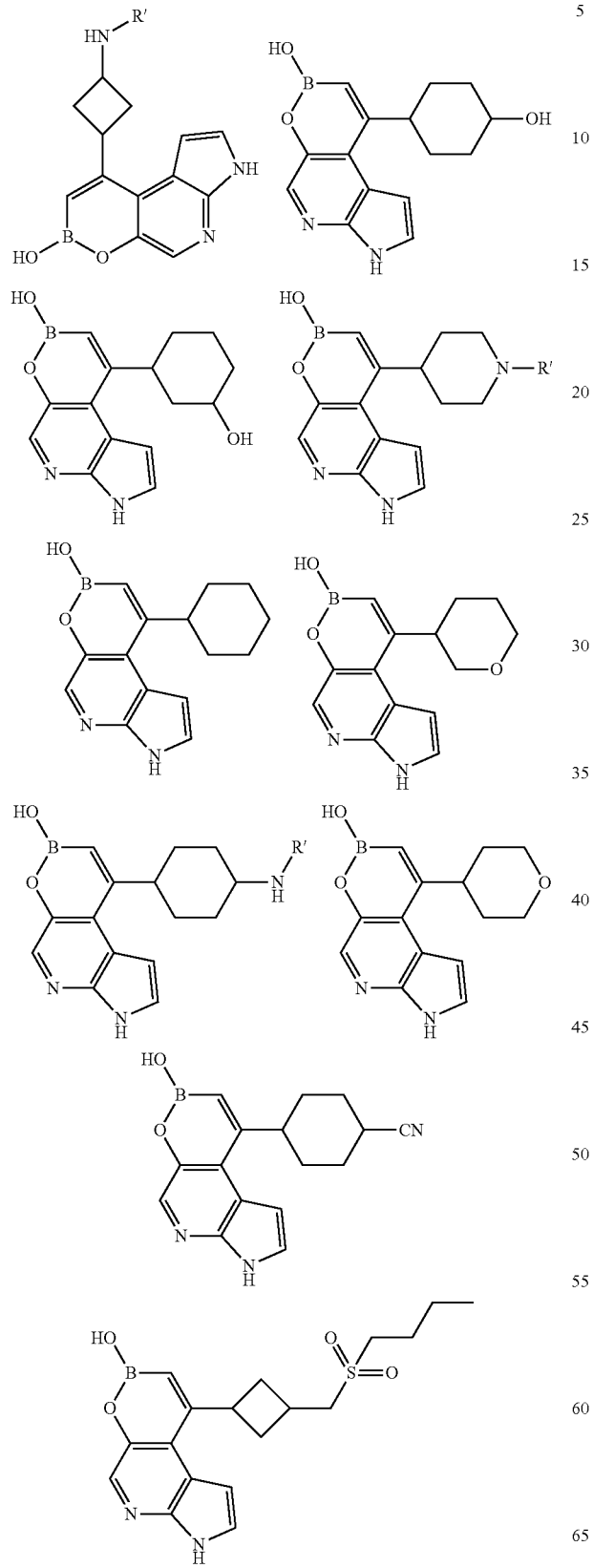

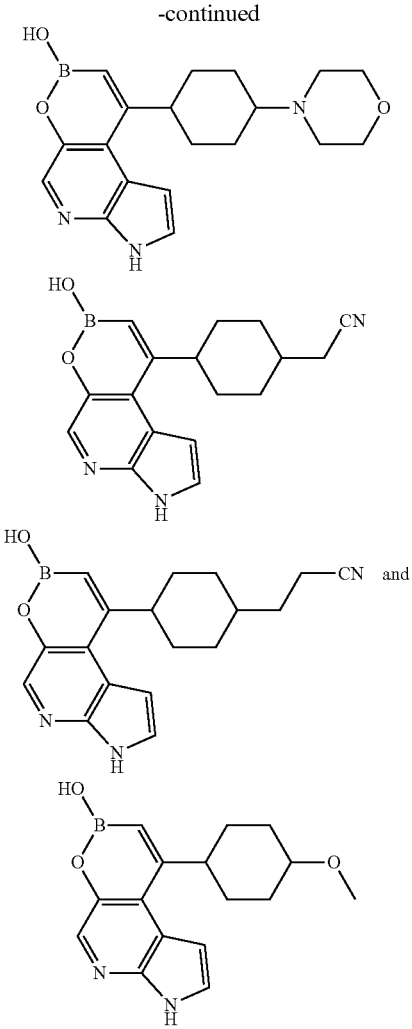

each R' independently is selected from the group consisting of hydrogen, substituted or unsubstituted $C_1$-$C_{15}$ alkyl, substituted or unsubstituted $C_{2-15}$ alkenyl, substituted or unsubstituted $C_{2-15}$ alkynyl, substituted or unsubstituted $C_{3-15}$ cycloalkyl, substituted or unsubstituted heteroaryl, substituted or unsubstituted heterocyclyl, and substituted or unsubstituted aryl, or a stereoisomer, enantiomer, or tautomer thereof, or a veterinary or pharmaceutically acceptable salt thereof.

One embodiment of the present disclosure includes a method for treating a patient having a disease or disorder susceptible to modulation of JAK comprising administering a therapeutically effective amount of a compound of the present disclosure. In one aspect, the disease or disorder is one or more of atopic dermatitis, psoriasis, psoriatic arthritis, Bechet's disease, *Pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, artherosclerosis, and cancer. In one aspect, the disease or disorder is one or more of atopic dermatitis, psoriasis, and rheumatoid arthritis. In one aspect, the compound is administered in an amount to perturb an immune regulatory pathway in a cell. In one aspect, the perturbation results in an effect on the JAK-STAT pathway.

One embodiment of the present disclosure includes a method of inhibiting JAK in a mammalian cell comprising contacting the mammalian cell with a compound of the present disclosure. In one aspect, the mammalian cell is a cell from a subject having an inflammatory condition.

One embodiment of the present disclosure includes a composition comprising a compound of the present invention and a pharmaceutically or veterinary acceptable carrier.

One embodiment of the present disclosure includes a combination comprising a compound of the present disclosure, and one or more other pharmaceutical or veterinary active substances.

One embodiment of the present disclosure a method for treating one or more diseases or disorders of inflammation, auto-immune dysfunction, and cancer comprising administering to a subject in need thereof an effective amount of a compound of the present disclosure. In one aspect, the disease or disorder is atopic dermatitis, psoriasis, or rheumatoid arthritis. In one aspect, the subject is a mammal. In one aspect, the subject is selected from livestock mammals, domestic mammals, or companion animals. In one aspect, the subject is selected from cattle, sheep, goats, llamas, alpacas, pigs, horses, donkeys, dogs, and cats. In one aspect, the subject is a human.

One embodiment of the present disclosure includes a compound of the present disclosure for use in medicine.

One embodiment of the present disclosure includes a compound of the present disclosure for the manufacture of a medicament for the treatment of one or more diseases or disorder of inflammation, auto-immune dysfunction, and cancer. In one aspect, the disease or disorder is atopic dermatitis, psoriasis, or rheumatoid arthritis.

One embodiment of the present disclosure includes a use of a compound of the present disclosure for the treatment of one or more diseases or disorders of inflammation, auto-immune dysfunction, and cancer. In one aspect, the disease or disorder is atopic dermatitis, psoriasis, or rheumatoid arthritis.

One or more aspects and embodiments may be incorporated in a different embodiment although not specifically described. That is, all aspects and embodiments may be combined in any way or combination.

BRIEF DESCRIPTION OF THE DRAWINGS

The foregoing and other aspects of the embodiments disclosed herein are best understood from the following detailed description when read in connection with the accompanying drawings. For the purposes of illustrating the embodiments disclosed herein, there is shown in the drawings embodiments that are presently preferred, it being understood, however, that the embodiments disclosed herein are not limited to the specific instrumentalities disclosed. Included in the drawings are the following figures.

Figure 1:
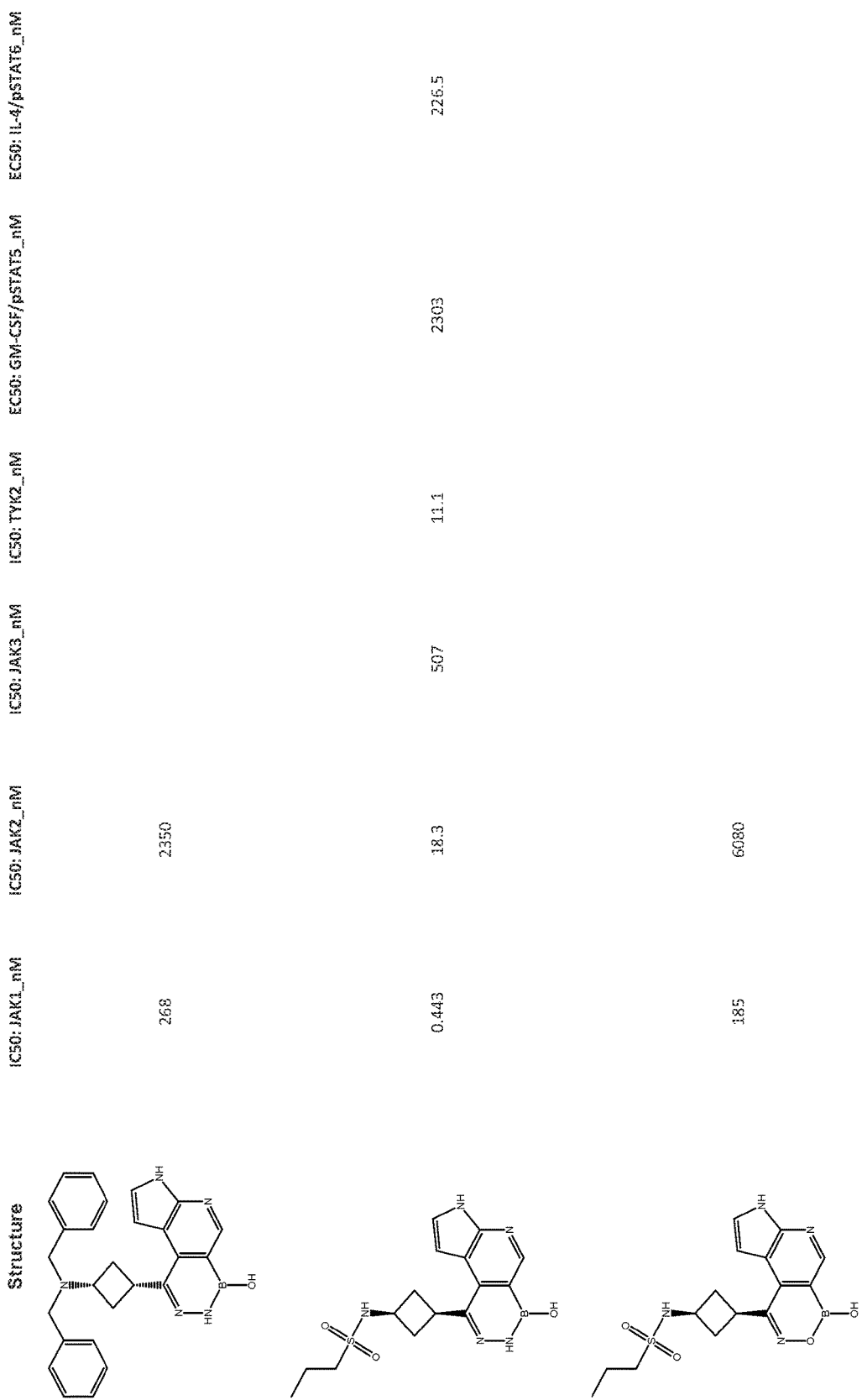
FIG. 1 represents a table of examples of biological activity of the compounds of the present disclosure.
Figure 1:
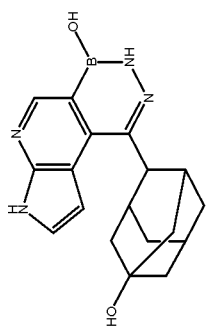
Figure 1:
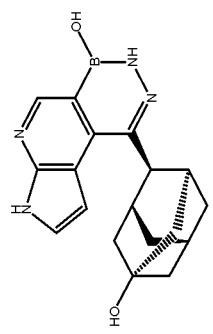
Figure 1:
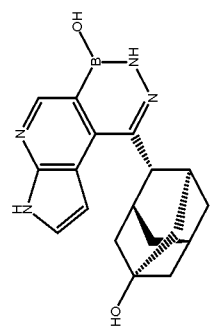
Figure 1:
Figure 1:
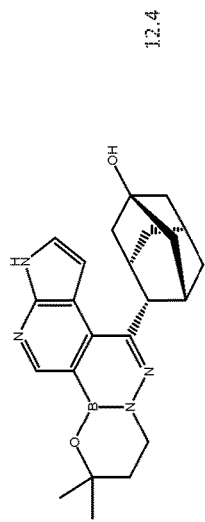
Figure 1:
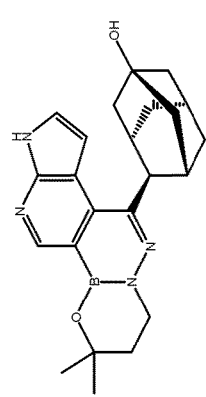
Figure 1:
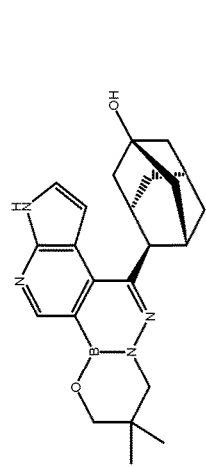
Figure 1:
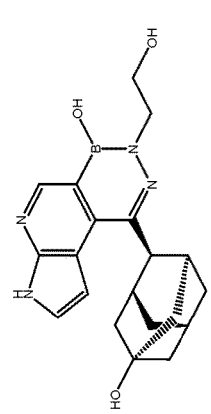
Figure 1:
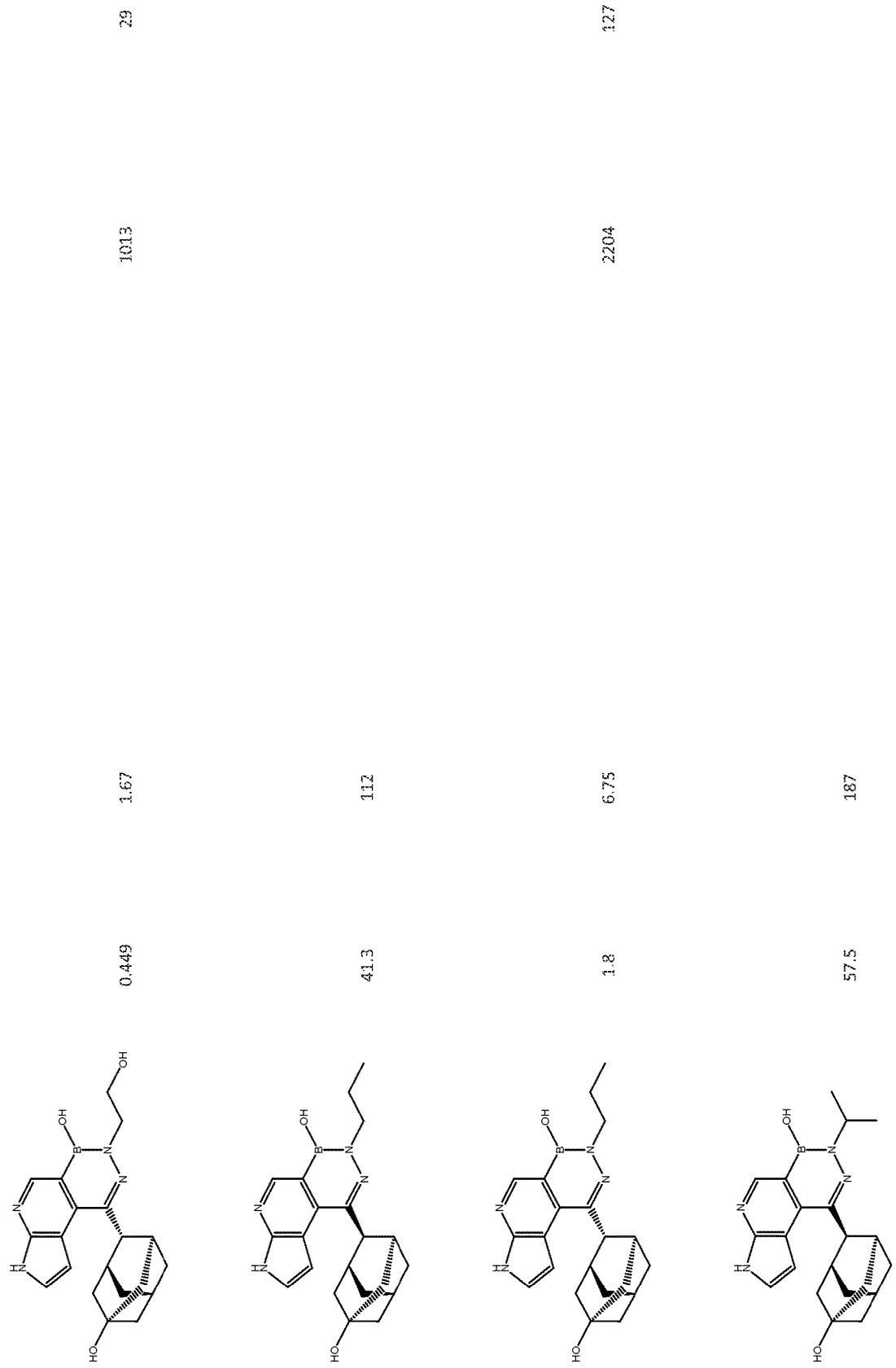
Figure 1:
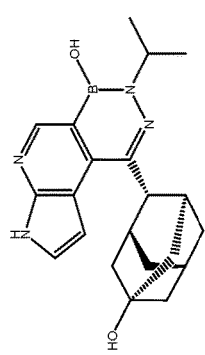
Figure 1:
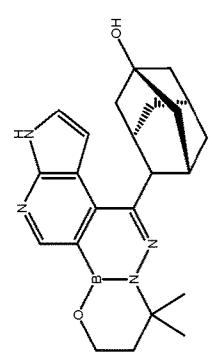
Figure 1:
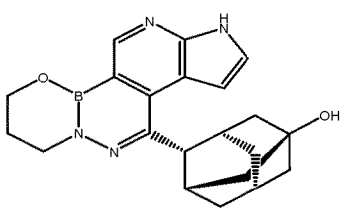
Figure 1:
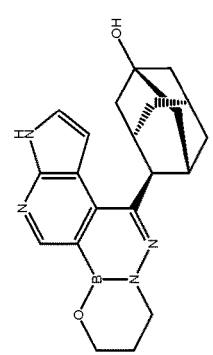
Figure 1:
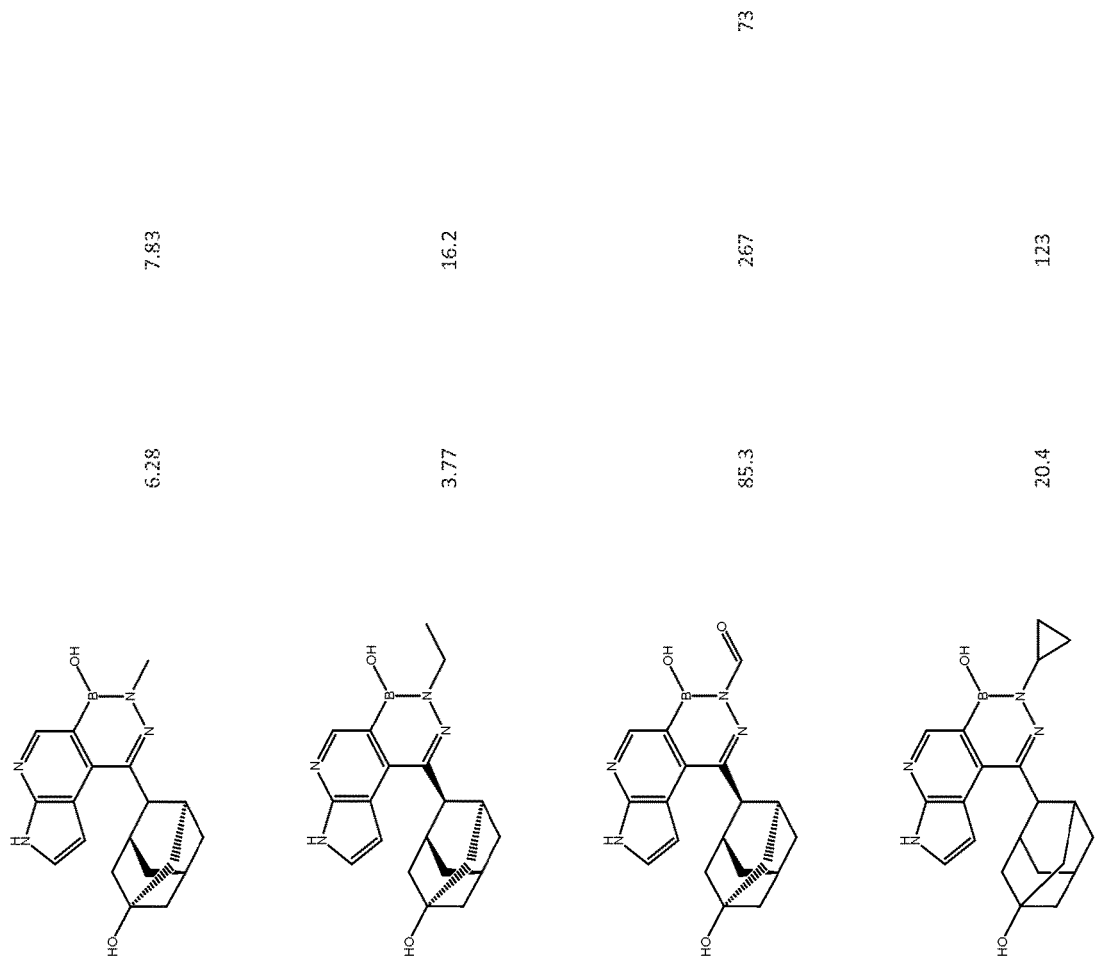

While embodiments of the present disclosure are described herein by way of example using several illustrative drawings, those skilled in the art will recognize the present disclosure is not limited to the embodiments or drawings described. It should be understood the drawings and the detailed description thereto are not intended to limit the present disclosure to the form disclosed, but to the contrary, the present disclosure is to cover all modification, equivalents and alternatives falling within the spirit and scope of embodiments of the present disclosure as recited by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to the described variable. To facilitate understanding, like reference numerals have been used, where possible, to designate like elements common to the figures.

DETAILED DESCRIPTION

Definitions

When referring to the compounds disclosed herein, the following terms have the following meanings unless indicated otherwise. The following definitions are meant to clarify, but not limit, the terms defined. If a particular term used herein is not specifically defined, such term should not be considered indefinite. Rather, terms are used within their accepted meanings.

As used herein, "alkyl" refers to monovalent saturated aliphatic hydrocarbon groups having from 1 to 20 carbon atoms, preferably 1-8 carbon atoms, preferably 1-6 carbon atoms. The hydrocarbon chain may be either straight-chained or branched. Illustrative alkyl groups include methyl, ethyl, n-propyl, iso-propyl, n-butyl, iso-butyl, and tert-butyl. Similarly, an "alkenyl" group refers to an alkyl group having one or more double bonds present in the chain, and an "alkynyl" group refers to an alkyl group having one or more triple bonds present in the chain.

As used herein "halogen" or "halo" refers to a halogen. In some embodiments, the halogen is preferably Br, Cl, or F.

As used herein, "haloalkyl" refers to monovalent saturated aliphatic hydrocarbon groups having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms. The haloalkyl chain can be either straight-chained or branched. Illustrative alkyl groups include trifluoromethyl, trifluoroethyl, trifluoropropyl, trifluorobutyl, and pentafluoroethyl. Similarly, a "haloalkenyl" group refers to a haloalkyl group having one or more double bonds present in the chain, and a "haloalkynyl" group refers to a haloalkyl group having one or more triple bonds present in the chain. Moreover, an "alkylene" linker group refers to a divalent alkyl group, namely $(CH_2)_x$, where x is 1 to 20, preferably 1 to 8, preferably 1 to 6, and more preferably 1 to 3.

As used herein, "hydroxyalkyl" refers to an alkyl group as herein defined substituted with one or more —OH group. Similarly, a "hydroxyalkenyl" group refers to a haloalkyl group having one or more double bonds present in the chain, and a "hydroxyalkynyl" group refers to a haloalkyl group having one or more triple bonds present in the chain.

As used herein, "aryl" refers to a substituted or unsubstituted carbocyclic aromatic ring system, either pendent or fused, such as phenyl, naphthyl, anthracenyl, phenanthryl, tetrahydronaphthyl, indane, or biphenyl. A preferred aryl group is phenyl.

As used herein, "cycloalkyl" refers to an unsaturated or partially saturated hydrocarbon ring, containing from 3 to 15 ring atoms. Illustrative cycloalkyl groups include cyclopropyl, cyclobutyl, cyclopentyl, cyclohexyl, as well as partially saturated versions thereof, such as cyclohexenyl, and cyclohexadienyl. Moreover, bridged rings, such as adamantane, are included within the definition of "cycloalkyl."

As used herein, the term "heterocyclyl" refers to an unsaturated or partially saturated hydrocarbon ring, containing from 3 to 15 ring atoms, wherein one or more carbon atom is replaced with a heteroatom selected from O, N, S, or Si, where each N, S, or Si may be oxidized, and where each N may be quarternized. A heterocyclyl group may be attached to the remainder of the molecule through a heteroatom. Heterocyclyl does not include heteroaryl.

As used herein, the term "heteroaryl" or "heteroaromatic" refers to aromatic ring groups having 5 to 14 ring atoms selected from carbon and at least one (typically 1-4, more typically 1 or 2) heteroatom (e.g., oxygen, nitrogen, sulfur, or silicon). They include monocyclic rings and polycyclic rings in which a monocyclic heteroaromatic ring is fused to one or more other carbocyclic aromatic or heteroaromatic rings. Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl) and thienyl (e.g., 2-thienyl, 3-thienyl. Examples of monocyclic six-membered nitrogen-containing heteroaryl groups include pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

The terms "arylalkyl," "heteroarylalkyl," and "heterocyclylalkyl" refers to those radicals in which an aryl, heteroaryl, or heterocyclyl group is linked through an alkyl group. Examples includes benzyl, phenethyl, pyridylmethyl, and the like. The terms also include alkyl linking groups in which a carbon atom, for example, a methylene group, has been replaced by, for example, an oxygen atom. Examples include phenoxymethyl, pyrid-2-yloxymethyl, 3-(naphth-1-yloxy)propyl, and the like. Similarly, the term "benzyl" as used herein is a radical in which a phenyl group is attached to a CH$_2$ group, thus, a CH$_2$Ph group. Benzyl groups may be substituted or unsubstituted. The term substituted benzyl refers to radicals in which the phenyl group or CH$_2$ contains one or more substituents. In one embodiment, the phenyl group may have 1 to 5 substituents, or in another embodiment 2 to 3 substituents.

As used herein "optionally substituted" refers to a substitution of a hydrogen atom, which would otherwise be present for the substituent. When discussing ring systems, the optional substitution is typically with 1, 2, or 3 substituents replacing the normally-present hydrogen. When referencing straight and branched moieties, however, the number of substitutions may be more, occurring wherever hydrogen is present. The substitutions may be the same or different.

Illustrative substituents, which with multiple substituents can be the same or different, include halogen, haloalkyl, R', OR', OH, SH, SR', NO$_2$, CN, C(O)R', C(O)(alkyl substituted with one or more of halogen, haloalkyl, NH$_2$, OH, SH, CN, and NO$_2$), C(O)OR', OC(O)R', CON(R')$_2$, OC(O)N(R')$_2$, NH$_2$, NHR', N(R')$_2$, NHCOR', NHCOH, NHCONH$_2$, NHCONHR', NHCON(R')$_2$, NRCOR', NRCOH, NHCO$_2$H, NHCO$_2$R', NHC(S)NH$_2$, NHC(S)NHR', NHC(S)N(R')$_2$, CO$_2$R', CO$_2$H, CHO, CONH$_2$, CONHR', CON(R')$_2$, S(O)$_2$H, S(O)$_2$R', SO$_2$NH$_2$, S(O)H, S(O)R', SO$_2$NHR', SO$_2$N(R')$_2$, NHS(O)$_2$H, NR'S(O)$_2$H, NHS(O)$_2$R', NR'S(O)$_2$R', Si(R')$_3$, where each of the preceding may be linked through a divalent alkylene linker, (CH$_2$)$_x$, where x is 1, 2, or 3. In embodiments where a saturated carbon atom is optionally substituted with one or more substituent groups, the substituents may be the same or different and also include =O, =S, =NNHR', =NNH$_2$, =NN(R')$_2$, =N—OR', =N—OH, =NNHCOR', =NNHCOH, =NNHCO$_2$R', =NNHCO$_2$H, =NNHSO$_2$R', =NNHSO$_2$H, =N—CN, =NH, or =NR'. For each of the preceding, each may be linked through an alkylene linker, (CH$_2$)$_x$, where x is 1, 2, or 3, Each occurrence of R' is the same or different and represents hydrogen, alkyl, alkenyl, alkynyl, cycloalkyl, aryl, heterocyclyl, or heteroaryl, or when two R' are each attached to a nitrogen atom, they may form a saturated or unsaturated heterocyclic ring containing from 4 to 6 ring atoms.

As used herein, the phrase veterinary or veterinarily, or pharmaceutical or pharmaceutically acceptable salt refers to any salt of a compound disclosed herein which retains its biological properties and which is not toxic or otherwise undesirable for veterinary or pharmaceutical use. The general use of the terms pharmaceutical or pharmaceutically is intended to reach either veterinary or veterinarily, as well. The terms may be used interchangeably as context allows.

Such salts may be derived from a variety of organic and inorganic counter-ions known in the art. Such salts include acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct- 2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

Examples of inorganic bases that may be used to form base addition salts include, but are not limited to, metal hydroxides, such as lithium hydroxide, sodium hydroxide, and potassium hydroxide; metal amides, such as lithium amide and sodium amide; metal carbonates, such as lithium carbonate, sodium carbonate, and potassium carbonate; and ammonium bases such as ammonium hydroxide and ammonium carbonate.

Examples of organic bases that may be used to form base addition salts include, but are not limited to, metal alkoxides, such as lithium, sodium, and potassium alkoxides including lithium methoxide, sodium methoxide, potassium methoxide, lithium ethoxide, sodium ethoxide, potassium ethoxide, and potassium tert-butoxide; quaternary ammonium hydroxides, such as choline hydroxide; and amines including, but not limited to, aliphatic amines (i.e., alkylamines, alkenylamines, alkynylamines, and alicyclic amines), heterocyclic amines, arylamines, heteroarylamines, basic amino acids, amino sugars, and polyamines.

The base may be a quaternary ammonium hydroxide, wherein one or more of the alkyl groups of the quaternary ammonium ion are optionally substituted with one or more suitable substituents. Preferably, at least one alkyl group is substituted with one or more hydroxyl groups. Non-limiting examples of quaternary ammonium hydroxides that may be used in accordance with the present invention include choline hydroxide, trimethylethylammonium hydroxide, tetramethylammonium hydroxide, and is preferably choline hydroxide. An alkylamine base may be substituted or unsubstituted. Non-limiting examples of unsubstituted alkylamine bases that may be used in accordance with the present invention include methylamine, ethylamine, diethylamine, and triethylamine. A substituted alkylamine base may be substituted with one or more hydroxyl groups, and preferably one to three hydroxyl groups. Non-limiting examples of substituted alkylamine bases that may be used in accordance with the present invention include 2-(diethylamino)ethanol, N,N-dimethylethanolamine (deanol), tromethamine, ethanolamine, and diolamine.

In certain cases, the depicted substituents may contribute to optical isomers and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example when it is bonded to four different groups, a pair of enantiomers is possible. A molecule with at least one stereocenter may be characterized by the absolute configuration of its asymmetric center and is designated (R) or (S) according to the rules of Cahn and Prelog (Cahn et al., 1966, Angew. Chem. 78: 413-447, Angew. Chem., Int. Ed. Engl. 5: 385-414 (errata: Angew. Chem., Int. Ed. Engl. 5:511); Prelog and Helmchen, 1982, Angew. Chem. 94: 614-631, Angew. Chem. Internat. Ed. Eng. 21: 567-583; Mata and Lobo, 1993, Tetrahedron: Asymmetry 4: 657-668) or may be characterized by the manner in which the molecule rotates the plane of polarized light and is designated dextrorotatory or levorotatory (namely, as (+)- or (−)-isomers, respectively). A chiral compound may exist as either an individual enantiomer or as a mixture thereof. A mixture containing equal proportions of enantiomers is called a "racemic mixture".

In certain embodiments, the compounds disclosed herein may possess one or more asymmetric centers, and such compounds may therefore be produced as a racemic mixture, an enantiomerically enriched mixture, or as an individual enantiomer. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art.

In certain embodiments, the compounds disclosed herein are "stereochemically pure". A stereochemically pure compound has a level of stereochemical purity that would be recognized as "pure" by those of skill in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

As used herein, the terms "subject" and "patient" may be used interchangeably herein. In one embodiment, the subject is a human. In one embodiment, the subject is a companion animal such as' a dog or cat. In a further embodiment, the subject is an animal such as a sheep, cow, horse, goat, fish, pig, or domestic fowl (e.g., chicken, turkey, duck, or goose). In another embodiment, the subject is a primate such as a monkey such as a cynomolgous monkey or a chimpanzee.

In addition, a pharmaceutically acceptable prodrug of the compound represented by the formula (I) and (II) is also included in the present invention. The pharmaceutically acceptable prodrug refers to a compound having a group which may be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. The term prodrug is used throughout the specification to describe any pharmaceutically acceptable form of a compound which, upon administration to a patient, provides the active compound. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that may be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound.

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labelled compounds of the invention, such as those incorporating a radioactive isotope, may be useful in drug or substrate tissue distribution studies. The radioactive isotopes tritium, i.e. $^{3}$H, and carbon-14, i.e. $^{14}$C, are particularly useful for this purpose in view of their ease of incorporation and ready means of detection. Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds of the invention may generally be prepared by conventional techniques known to those skilled in the art or by processes analogous to those described in the accompanying Examples using an appropriate isotopically-labeled reagent in place of the non-labeled reagent previously employed.

Compositions and Methods of Administration

The compounds of formula (I) and (II) used in the methods disclosed herein may be administered in certain embodiments using veterinary or pharmaceutical compositions including at least one compound of formula (I) and (II), if appropriate in the salt form, either used alone or in the form of a combination with one or more compatible and veterinary or pharmaceutically acceptable carriers, such as diluents or adjuvants, or with another agent. There are provided compositions which comprise a derivative of formula (I) and (II) or a salt thereof, and an acceptable excipient, carrier or diluent. The composition may also be in a variety of forms which include, but are not limited to, oral formulations, injectable formulations, and topical, dermal or subdermal formulations.

The composition may be in a form suitable for oral use, for example, as dietary supplements, troches, lozenges, chewables, tablets, hard or soft capsules, emulsions, aqueous or oily suspensions, aqueous or oily solutions, dispersible powders or granules, syrups, or elixirs. Compositions intended for oral use may be prepared according to any method known in the art for the manufacture of veterinary or pharmaceutical compositions and such compositions may contain one or more agents selected from the group consisting of sweetening agents, bittering agents, flavoring agents, coloring agents and preserving agents in order to provide elegant and palatable preparations.

Lozenges are solid compositions containing one or more active ingredients intended to dissolve or disintegrate slowly in the oral cavity by passive incubation in the oral cavity, or actively by sucking or chewing. They may be used for systemic effect if the drug is absorbed through the buccal or esophageal lining or is swallowed. In particular, soft lozenges may be chewed or allowed to dissolve slowly in the mouth. These dosage forms have the advantage of being flavored and thus easy to administer to both human and animal patients; have formulas that are easy to change and may be patient specific; may deliver accurate amounts of the active ingredient to the oral cavity and digestive system; and allow for the drug to remain in contact with the oral or esophageal cavity for an extended period of time.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example, peanut oil, liquid paraffin, or olive oil.

The compositions may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously. In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion. The aqueous phase includes, for example, water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol. Some compounds are common to the three components discussed above, for example, aqueous phase, surfactant and cosurfactant. However, it is well within the skill level of the practitioner to use different compounds for each component of the same formulation. In one embodiment, for example, for the amount of surfactant/cosurfactant, the cosurfactant to surfactant ratio may be from about 1/10 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxypropylmethylcellulose, sodium alginate, polvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents and/or bittering agents, such as those set forth herein.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and coloring agent(s).

The compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Topical, dermal and subdermal formulations may include emulsions, creams, ointments, gels or pastes.

Organic solvents that may be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, compositions of the present invention may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_3$-$C_{12}$) triglycerides.

Dosage forms may contain from about 0.5 mg to about 5 g of an active agent.

In one embodiment of the invention, the active agent is present in the formulation at a concentration of about 0.05 to 10% weight/volume.

A compound of formula (I) and (II) may be employed as such or in the form of their preparations or formulations as combinations.

A compound of formula (I) and (II) according to the invention may be combined with one or more agents having the same sphere of activity, for example, to increase activity, or with substances having another sphere of activity, for example, to broaden the range of activity. As an example, a combination of a compound of formula (I) and (II) with one or more of an additional JAK inhibitor or a JAK/Signal Transducer and Activator of Transcription (JAK/STAT) modulator may offer therapeutic advantage. Examples of JAK inhibitors that may be useful as combination agents include Baricitinib, Ruxolitinib, Filgotinib, CYT387, Upadacitinib, Fedratinib, Peficitinib, Lestaurtinib, Pacritinib, Oclacitinib, Cerdulatinib, and Tofacitinib.

The compounds of formula (I) and (II) according to the invention may be combined with one or more additional active agents. Further additional active agents which may be used in the methods provided herein in combination with a compound of formula (I) or (II) include, but are not limited to, disease-modifying anti-rheumatic drugs (DMARDs such as cyclosporine A and methotrexate), anti-inflammatory agents such as nonsteroidal anti-inflammatory drugs (NSAIDs), immnunosuppressants, mycophenolate mofetil, biologic agents, TNF-α inhibitors (such as etanercept), Cox-2 inhibitors, and analgesics. These agents may include but are not limited to cyclosporin A, e.g. Sandimmune® or Neoral®, rapamycin, FK-506 (tacrolimus), leflunomide, deoxyspergualin, mycophenolate, e.g., Cellcept®, azathioprine, e.g. Imuran®, daclizumab, e.g. Zenapax®, OKT3, e.g. Orthocolone®, AtGam, aspirin, acetaminophen, ibuprofen, naproxen, piroxicam, and anti-inflammatory steroids, e.g. prednisolone or dexamethasone.

In some embodiments, the second active agents may include, but are not limited to, anti-inflammatories such as NSAIDs including, but not limited to, diclofenac (e.g., ARTHROTEC®), diflunisal (e.g., DOLOBID®), etodolac (e.g., LODINE®), fenoprofen (e.g., NALFON®), ibuprofen (e.g., ADVIL®, CHILDREN'S ADVIL/MOTRIN®, MEDIPREN®, MOTRIN®, NUPRIN®, or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., MECLOMEN®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAY PRO®), piroxicam (e.g., FELDENE®), sulindac (e.g., CLINORIL®), and tolmetin (e.g., TOLECTIN® DS or TOLECTIN®).

In other embodiments, the second active agents may include, but are not limited to, disease-modifying antirheumatic drugs (e.g., DMARDs) or immnunosuppressants such as, but not limited to, methotrexate (e.g., RHEUMATREX®), sulfasalazine (e.g., AZULFIDINE®), and cyclosporine (e.g., SANDIMMUNE® or NEROAL®; and including cyclosporine A).

In other embodiments, the second active agents may include, but are not limited to, mycophenolate mofetil (e.g., CellCept®), an immunosuppressive agent widely used in organ transplantation and gaining favor in treating autoimmune and inflammatory skin disorders.

In further embodiments, the second active agents may include, but are not limited to, biologic agents such as etanercept (e.g., ENBREL®), infliximab (e.g., REMICADE®) and adalimumab (e.g., HUMIRA®).

In further embodiments of interest, the second active agents may include, but are not limited to Cox-2 inhibitors such as celecoxib (e.g., CELEBREX®), valdecoxib (e.g., BEXTRA®) and meloxicam (e.g., MOBIC®).

These one or more additional active agents may be administered as part of the same or separate dosage forms, via the same or different routes of administration, and on the same or different administration schedules according to standard pharmaceutical practice known to one skilled in the art.

The pharmaceutical preparation comprising the compounds of formula (I) and (II), for delivery to a human or other mammal, is preferably in unit dosage form, in which the preparation is subdivided into unit doses containing an appropriate quantity of the active component. The unit dosage form may be a packaged preparation containing discrete quantities of the preparation, such as packaged tablets, capsules, and powders in vials or ampoules. Also, the unit dosage form may be a capsule, tablet or lozenge itself, or it may be an appropriate number of any of these in packaged form.

The quantity of active component in a unit dose preparation may be varied or adjusted from about 0.1 mg to about 1000 mg, according to the particular application and the potency of the active component. The composition may, if desired, also contain other compatible therapeutic agents.

In therapeutic use for the treatment or alleviation of inflammation, auto-immune diseases, and cancer in a human or other mammal, the compounds utilized in the method of treatment are administered at an initial dosage of about 0.1 mg/kg to about 100 mg/kg per interval, about 0.1 mg/kg to about 50.0 mg/kg per interval, about 0.1 mg/kg to about 10.0 mg/kg per interval, about 0.1 mg/kg to about 5.0 mg/kg per interval, about 0.1 mg/kg to about 2.5 mg/kg per interval, about 0.1 mg/kg to about 2.0 mg/kg per interval, about 0.1 mg/kg to about 1.0 mg/kg per interval, about 0.4 mg/kg to about 1.0 mg/kg per interval, or about 0.4 mg/kg to about 0.6 mg/kg per interval. Preferred intervals may be daily, weekly, monthly, quarterly, semi-annually, or annually. The dosages may be varied depending on the requirements of the patient, for example, the size of the human or mammal being treated, the severity of the condition being treated, the route of administration, and the potency of the compound(s) being used. Determination of the proper dosage and route of administration for a particular situation is within the skill of the practitioner. Generally, the treatment will be initiated with smaller dosages, which are less than the optimum dose of the compound, which may be increased in small increments until the optimum effect under the particular circumstances of the condition is reached. For convenience, the total daily dosage may be divided and administered in portions during the day if desired.

In therapeutic use, the compounds of formula (I) and (II) are useful in manufacture of a medicament for a method of the treating any indication where inhibition of JAK would be desirable, including but not limited to cancer, neuroinflammation, inflammatory airway diseases, ankylosing spondylitis, inflammatory bowel diseases, rheumatoid arthritis, psoriasis, and atopic dermatitis. In one or more embodiments, one or more of a compound of formula (I) and (II) is useful in the treatment of one or more of atopic dermatitis, psoriasis, psoriatic arthritis, Bechet's disease, *Pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, asthma, vasculitis, multiple sclerosis, diabetic nephropathy, cardiovascular disease, artherosclerosis, and cancer. One route of administration may be oral. One route of administration may be topical.

While not intending to be bound by any theory, the inventors associated with the present disclosure believe the structure-activity relationship trends should be applicable between the two formulae of the present disclosure. Therefore, an exemplification with associated biological activity with regard to Formula I is believed to be extrapolative to a similar compound of Formula II, and vice versa.

The present invention explicitly encompasses those compounds presented below in Compound List 1 and Compound List 2, including salt forms thereof. The present invention also encompasses those compounds presented below, including stereoisomers thereof. A composition comprising a therapeutically acceptable amount of any of these compounds is also within the scope of the invention. The composition may further comprise a pharmaceutically or veterinary acceptable excipient, diluent, carrier, or mixture thereof. Such a composition may be administered to a subject in need thereof to treat or control a disease or disorder mediated, in whole or in part, directly or indirectly, by JAK. The composition may further comprise an additional active agent, as described herein.

Compound List 1
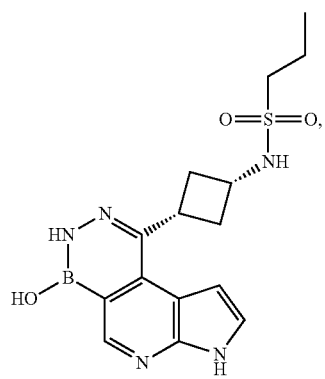
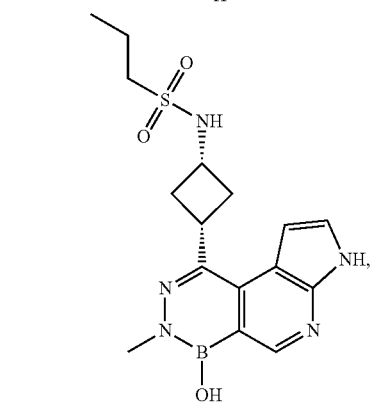
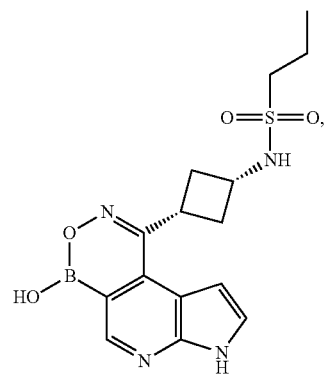
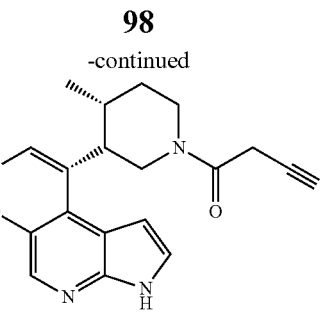
or a stereoisomer, enantiomer, or tautomer thereof, or a veterinary or pharmaceutically acceptable salt thereof.
Compound List 2
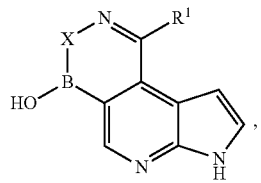
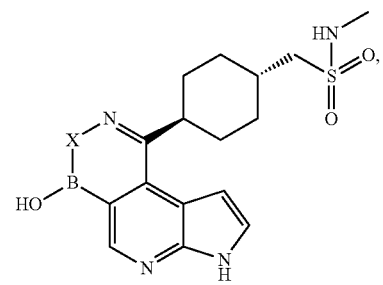
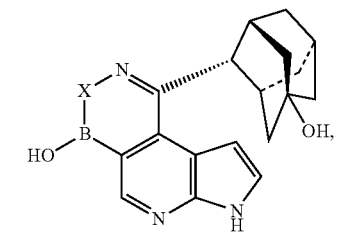
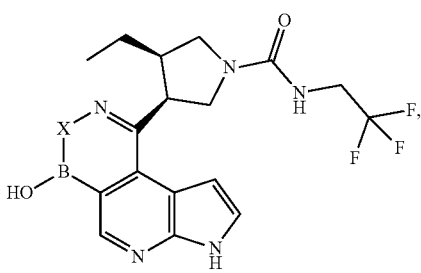
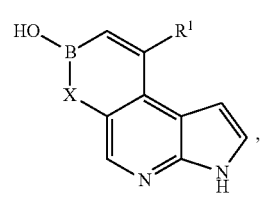

99
-continued
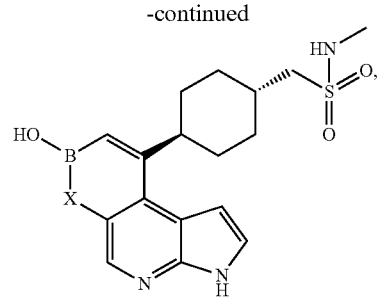
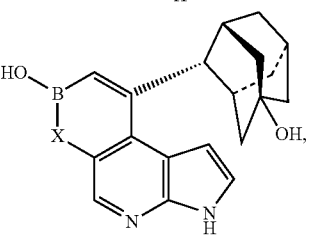
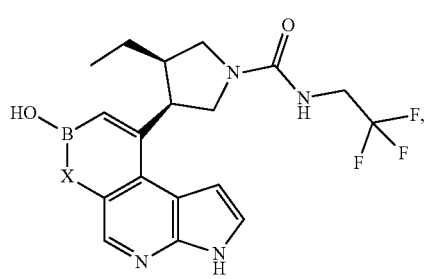
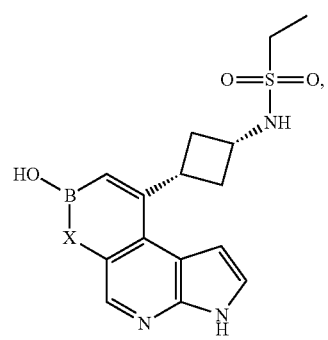
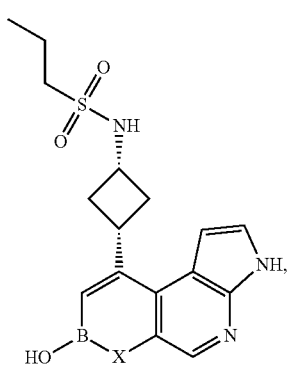
100
-continued
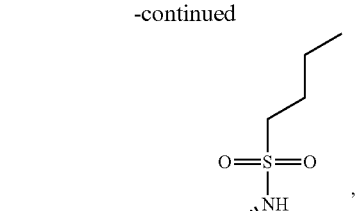
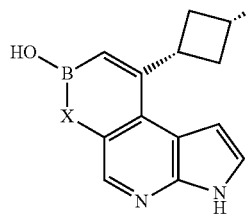
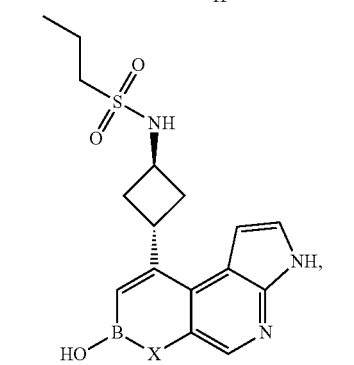
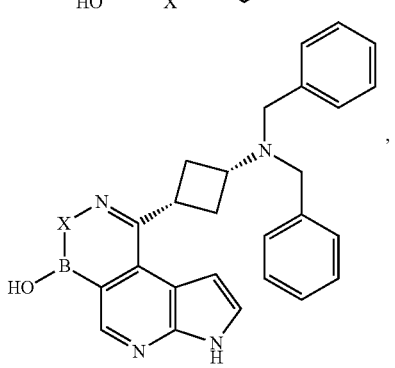
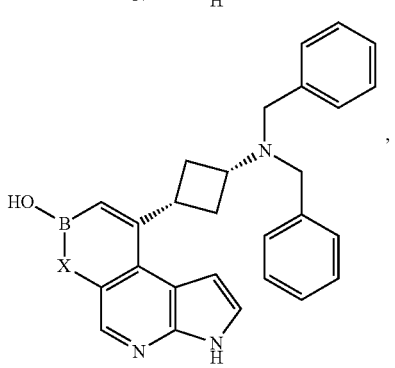, and
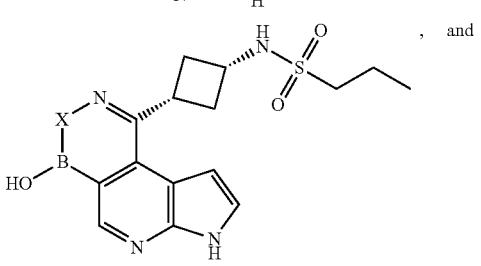

101

-continued

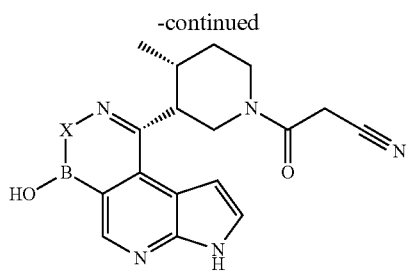

wherein each $R^1$ independently is as defined herein;
each X independently is selected from the group consisting of O and $NR^a$; and
each $R^a$ independently is selected from the group consisting of hydrogen, $C_1$-$C_{15}$ alkyl, $C_{2-15}$ alkenyl, $C_{2-15}$ alkynyl, $C_{3-15}$ cycloalkyl, and aryl.
or a stereoisomer, enantiomer, or tautomer thereof, or a veterinary or pharmaceutically acceptable salt thereof.

Compound List 3

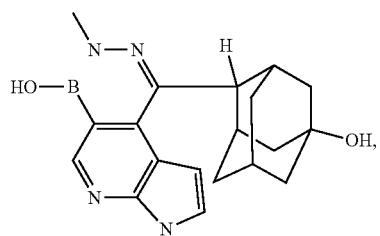

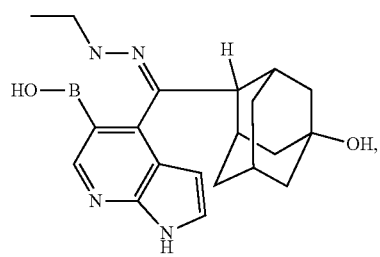

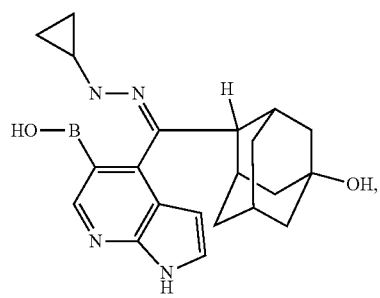

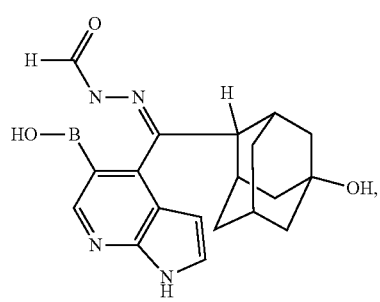

102

-continued

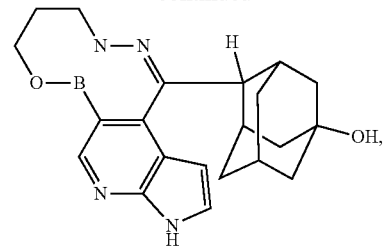

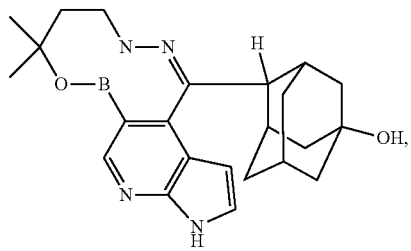

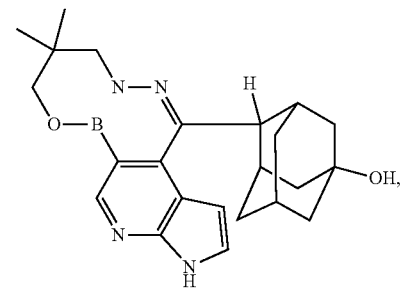

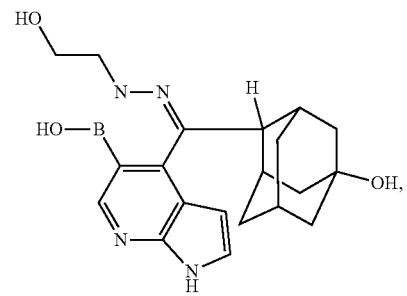

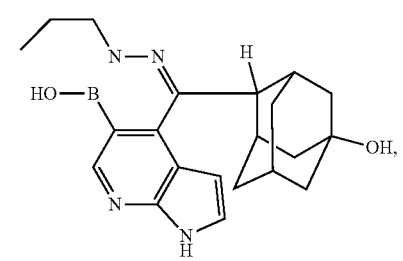

103
-continued
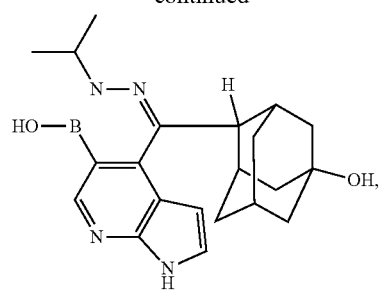
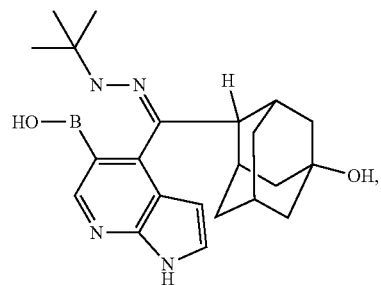
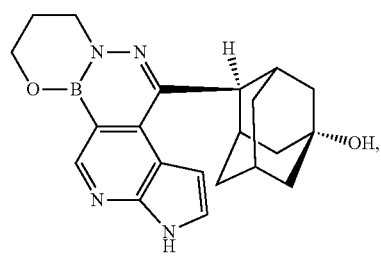
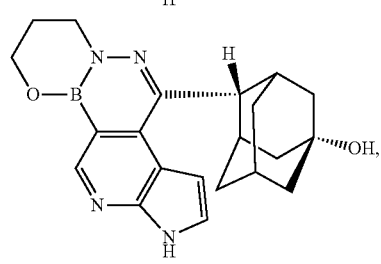
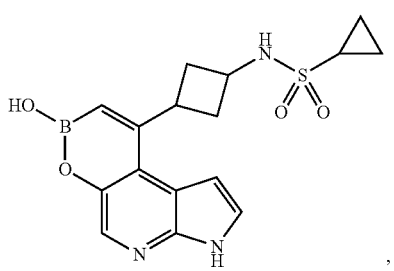
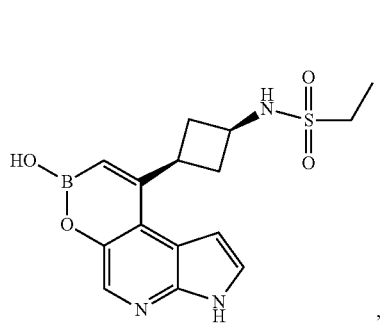
104
-continued
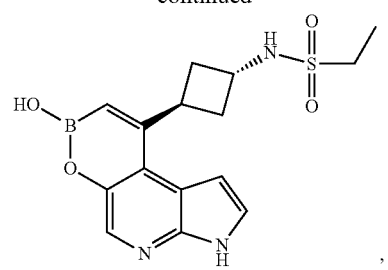
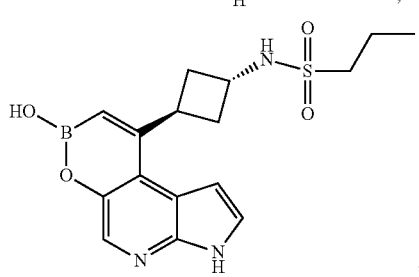
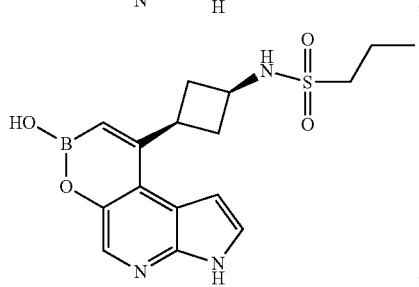
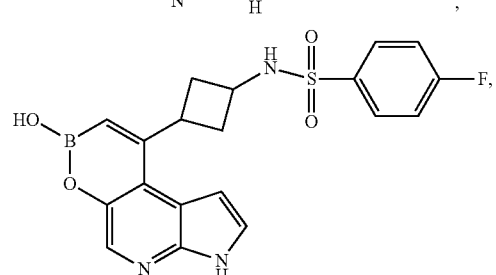
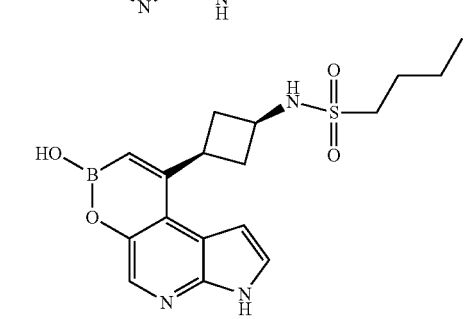
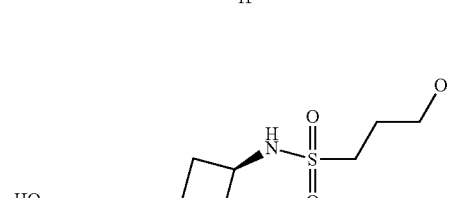
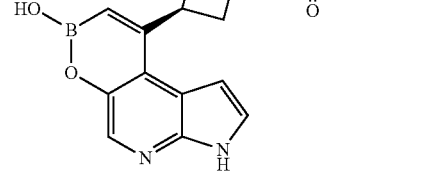

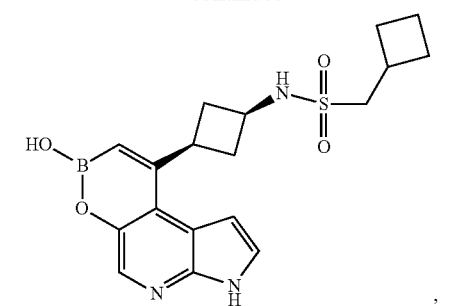
,
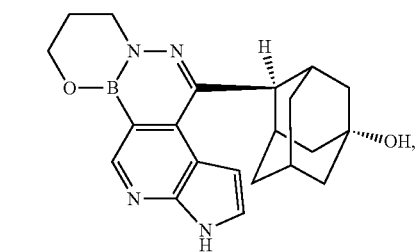
,
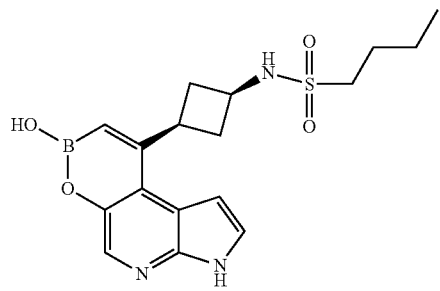
,
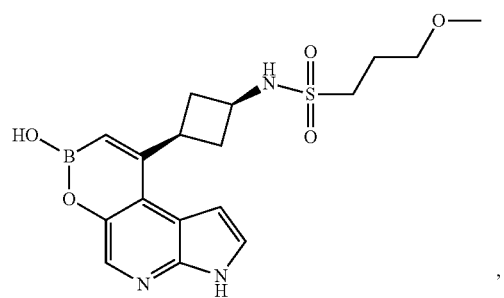
,
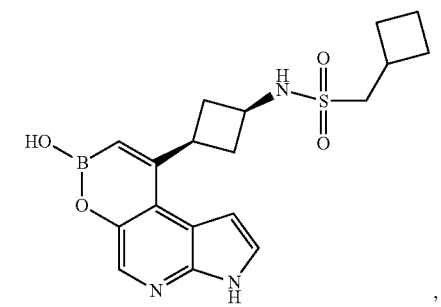
,
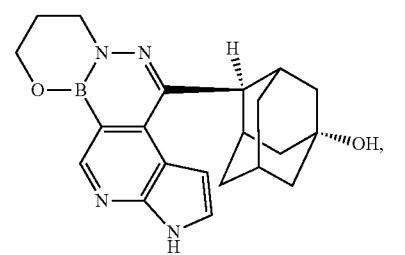
,
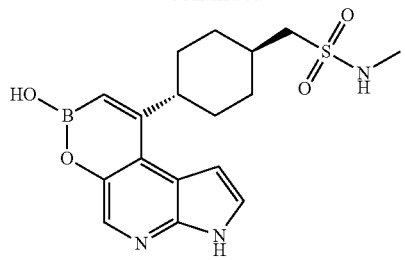
,
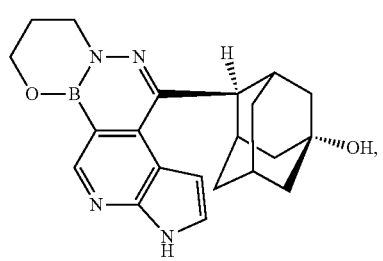
,
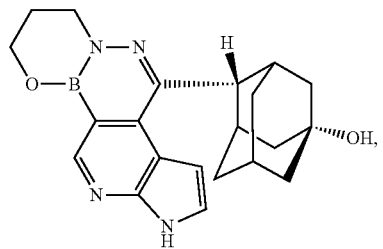
,
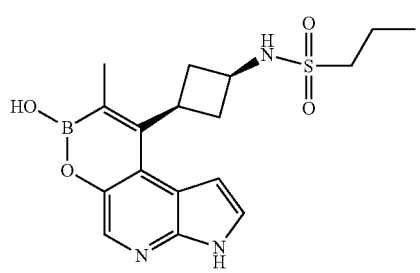
,
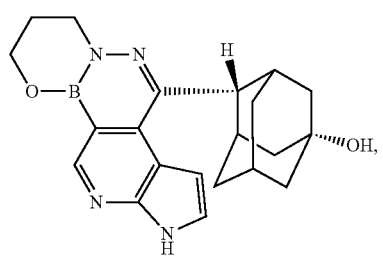
,
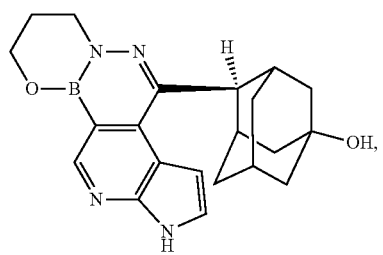

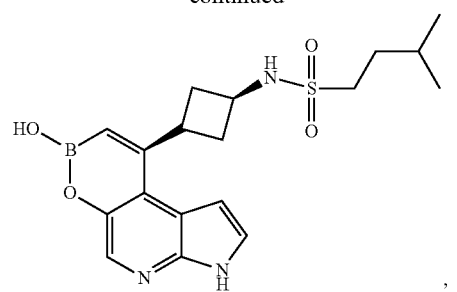
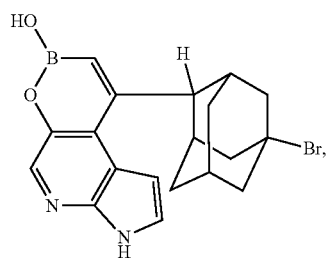
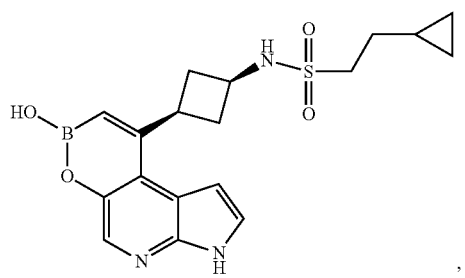
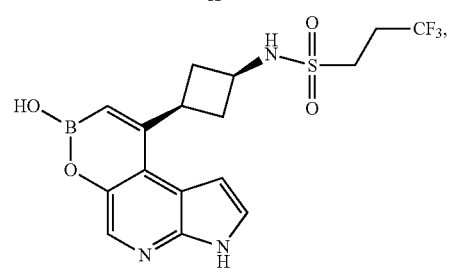
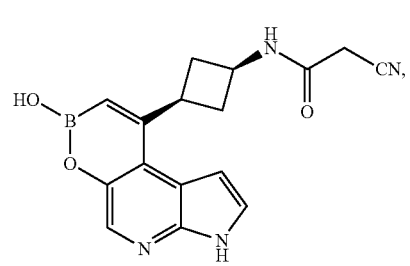
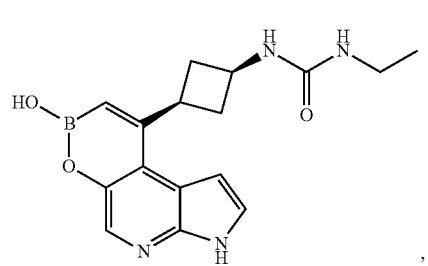
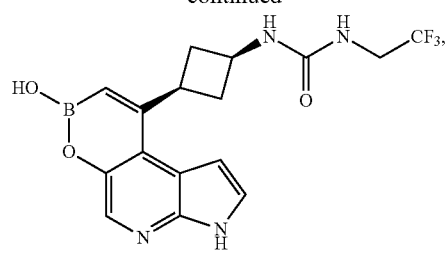
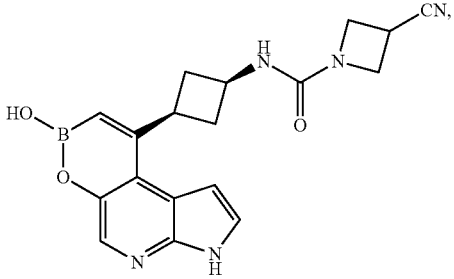
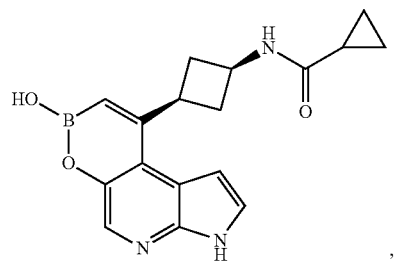
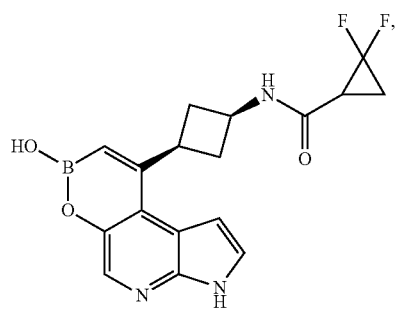
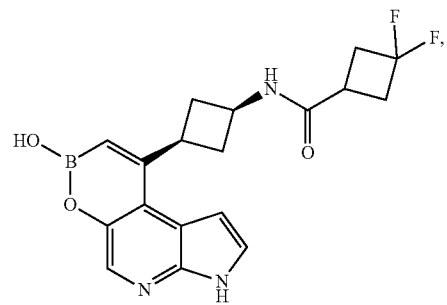
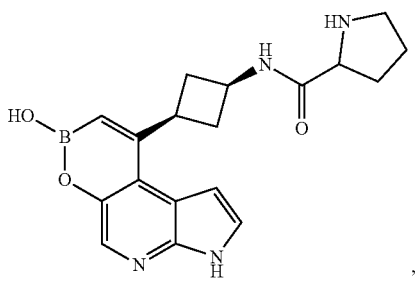

109
-continued
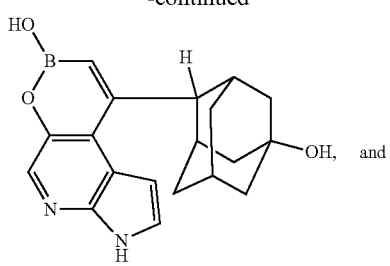
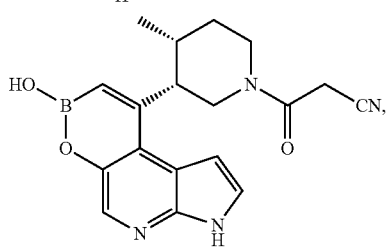
or a stereoisomer, enantiomer, or tautomer thereof, or a veterinary or pharmaceutically acceptable salt thereof.
Compound List 4
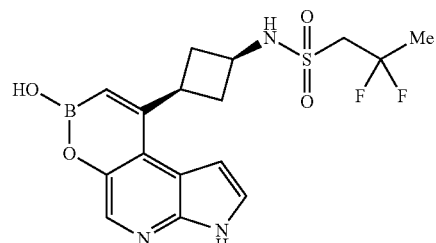
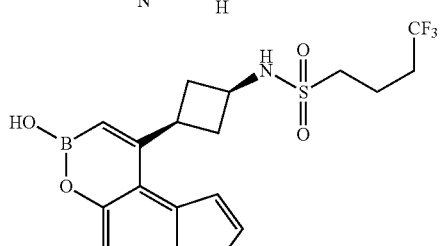
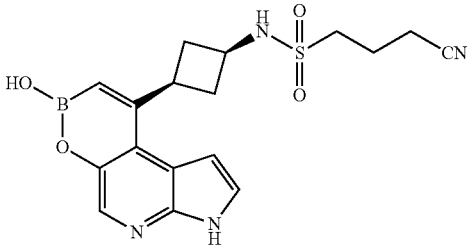
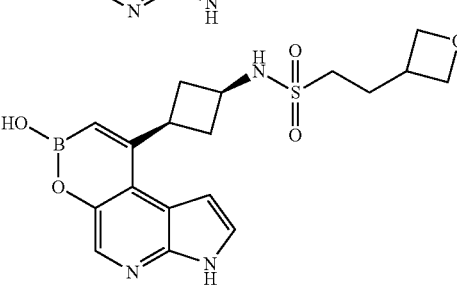
110
-continued
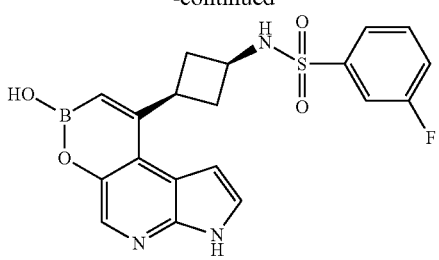
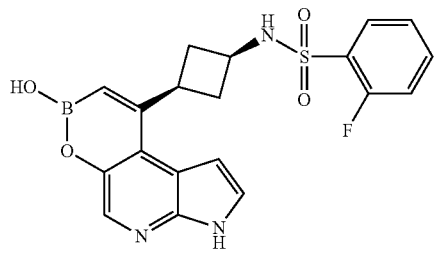
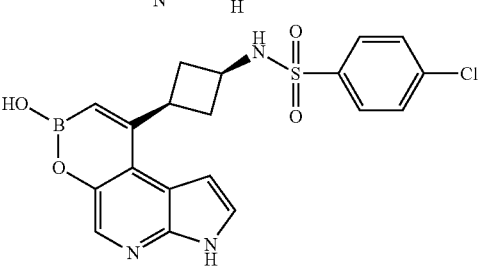
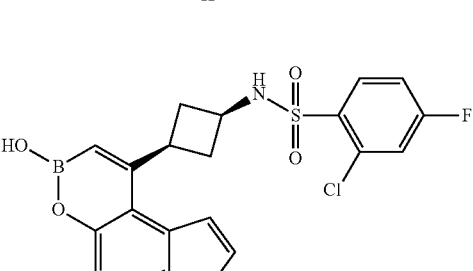
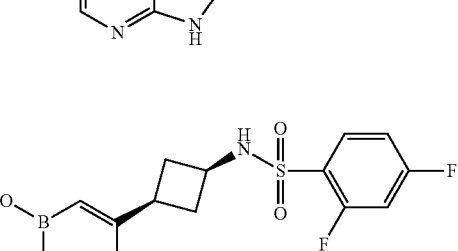
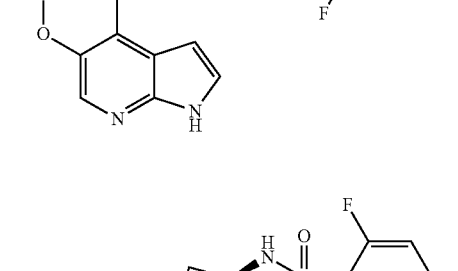
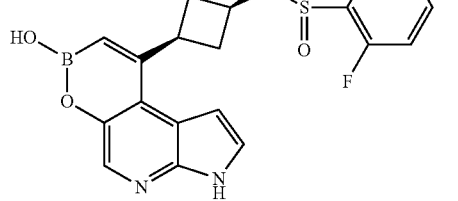

111
-continued
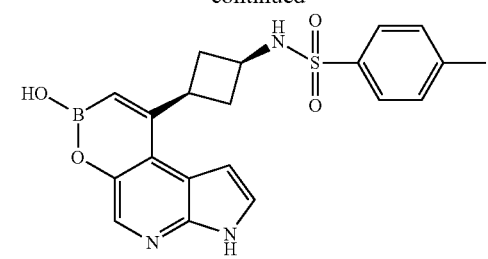
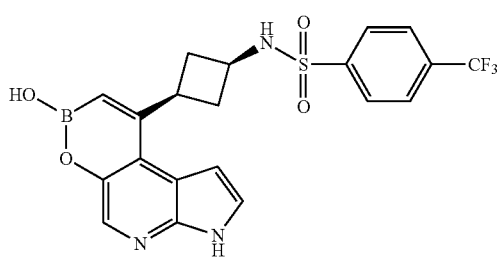
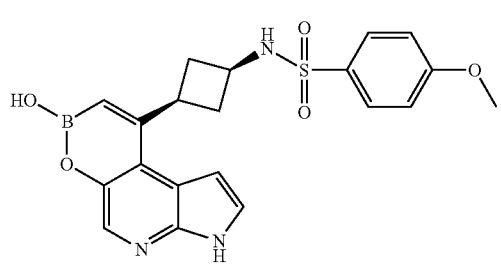
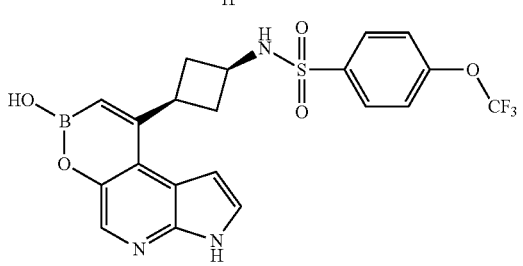
or a stereoisomer, enantiomer, or tautomer thereof, or a veterinary or pharmaceutically acceptable salt thereof.
Compound List 5
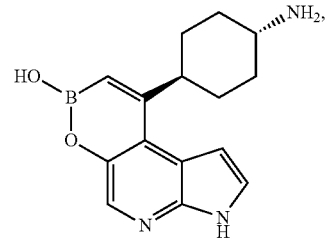
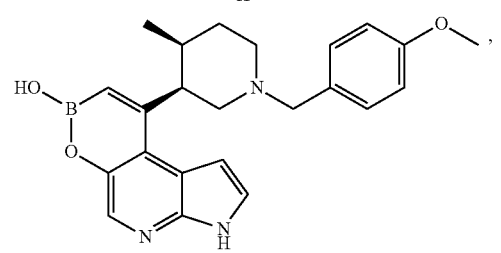
112
-continued
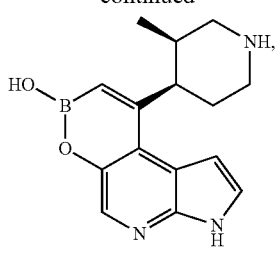
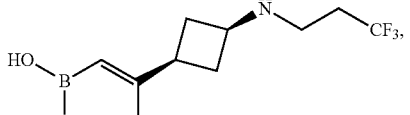
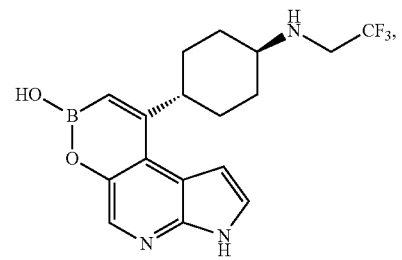
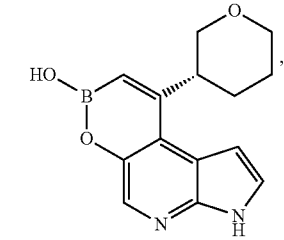
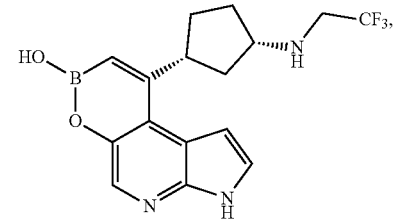
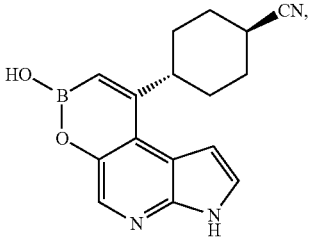
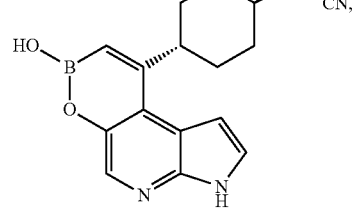

-continued

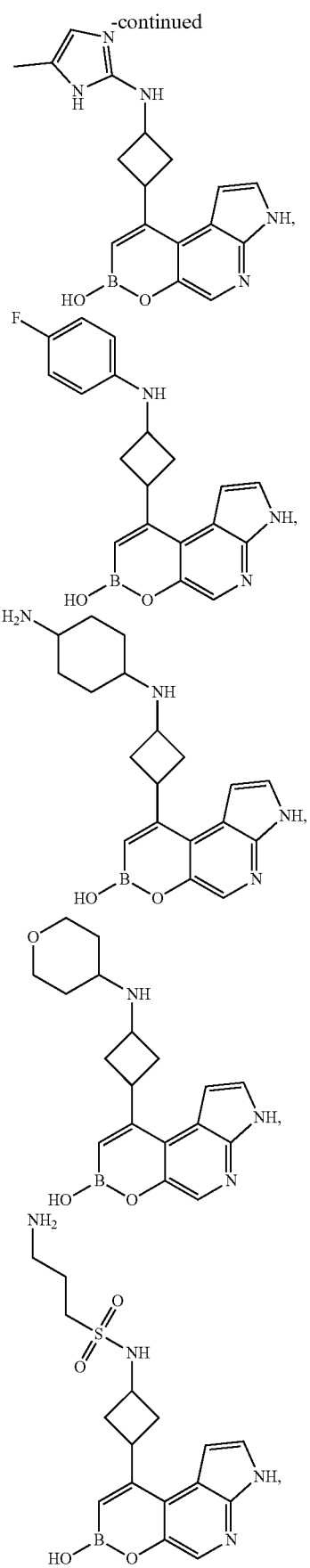

-continued

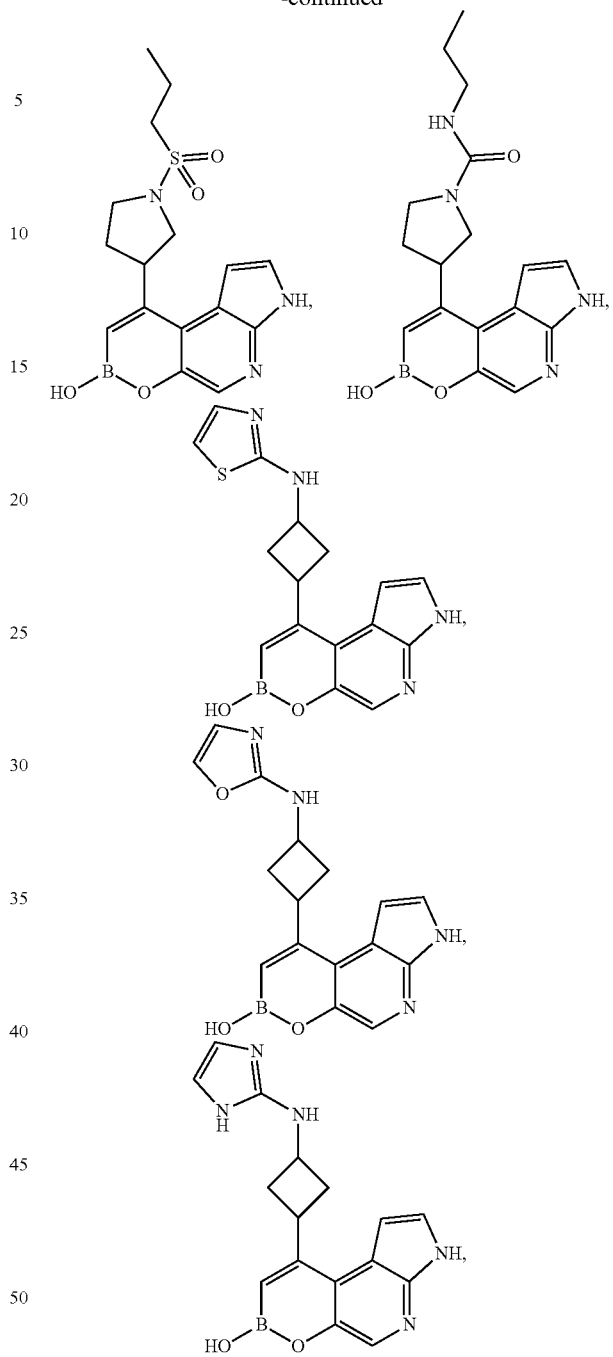

or a stereoisomer, enantiomer, or tautomer thereof, or a veterinary or pharmaceutically acceptable salt thereof.

EXAMPLES

Experimental Procedures:

The following examples provide a more detailed description of the process conditions for preparing compounds of the present invention. It is to be understood, however, that the invention, as fully described herein and as recited in the claims, is not intended to be limited by the details of the following schemes or modes of preparation.

Certain abbreviations may be used in describing the examples of the present disclosure. The abbreviations are believed to be used consistently within commonly accepted use of those skilled in the art.

In the following schemes, general substitutent groups are represented with assignments that may not align with the formulae of the present disclosure. The following schemes provide a key for such substituent groups that should be followed for the schemes and not applied to the formulae of the present disclosure.

Synthesis

Scheme 1

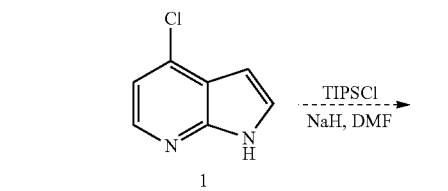

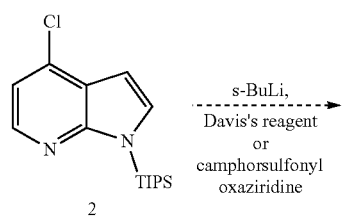

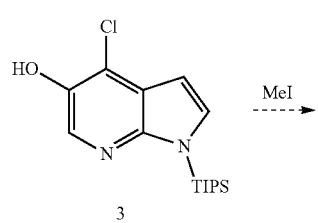

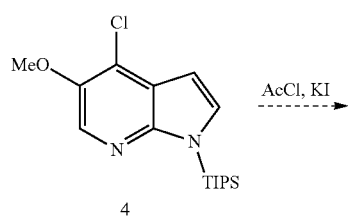

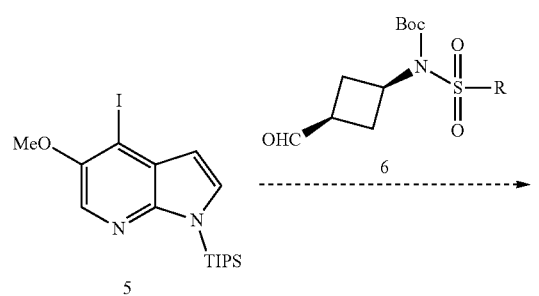

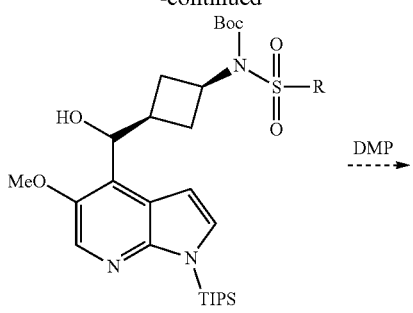

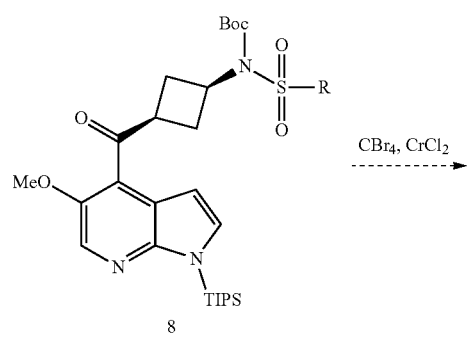

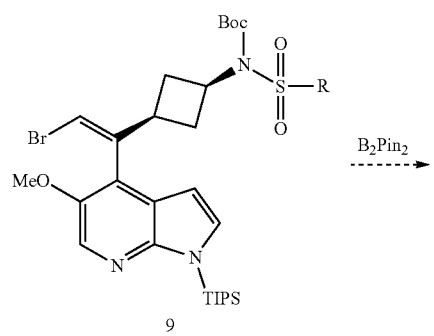

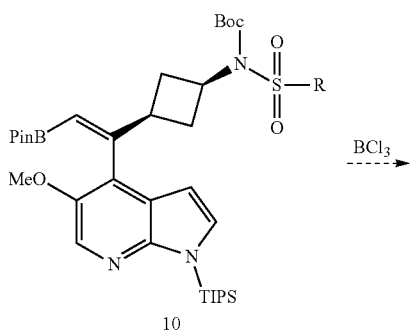

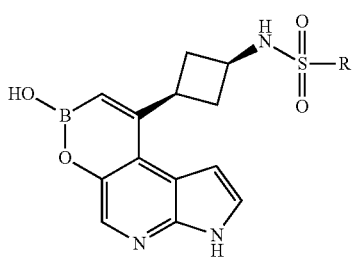

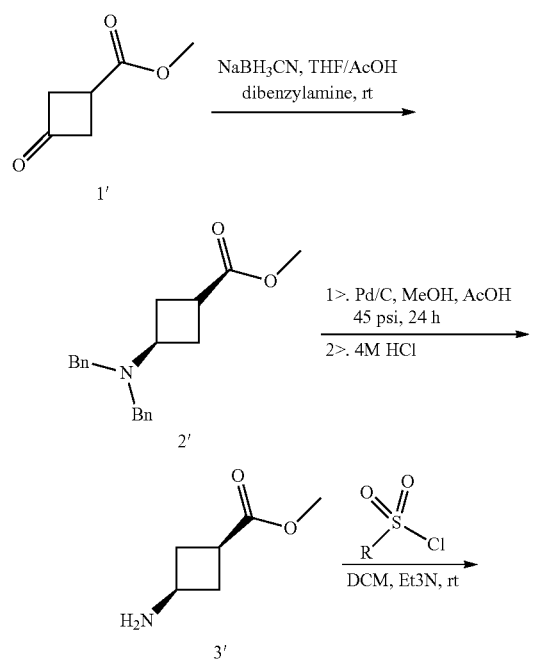
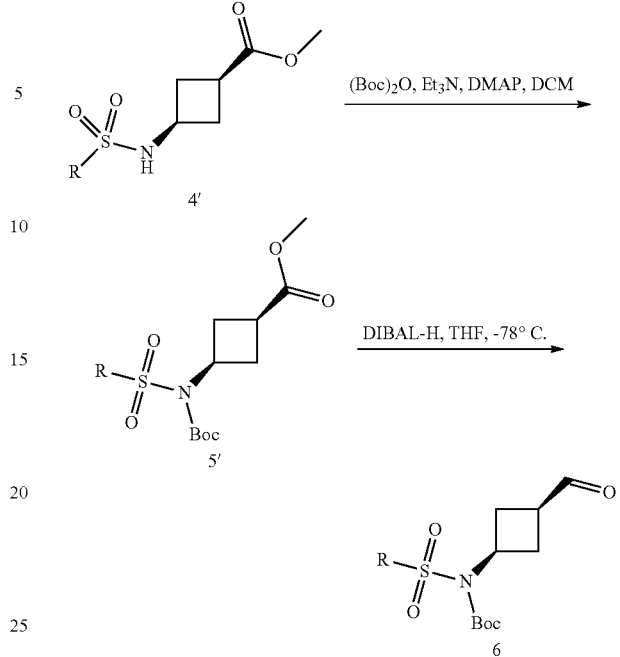
Scheme 2a
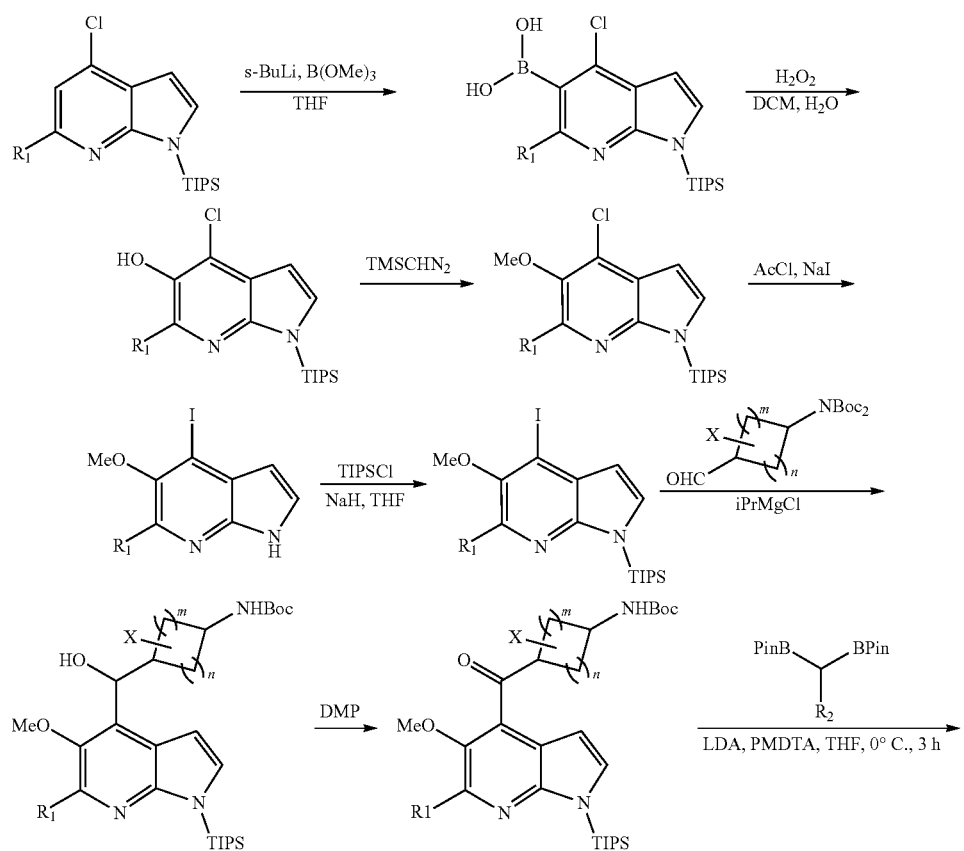

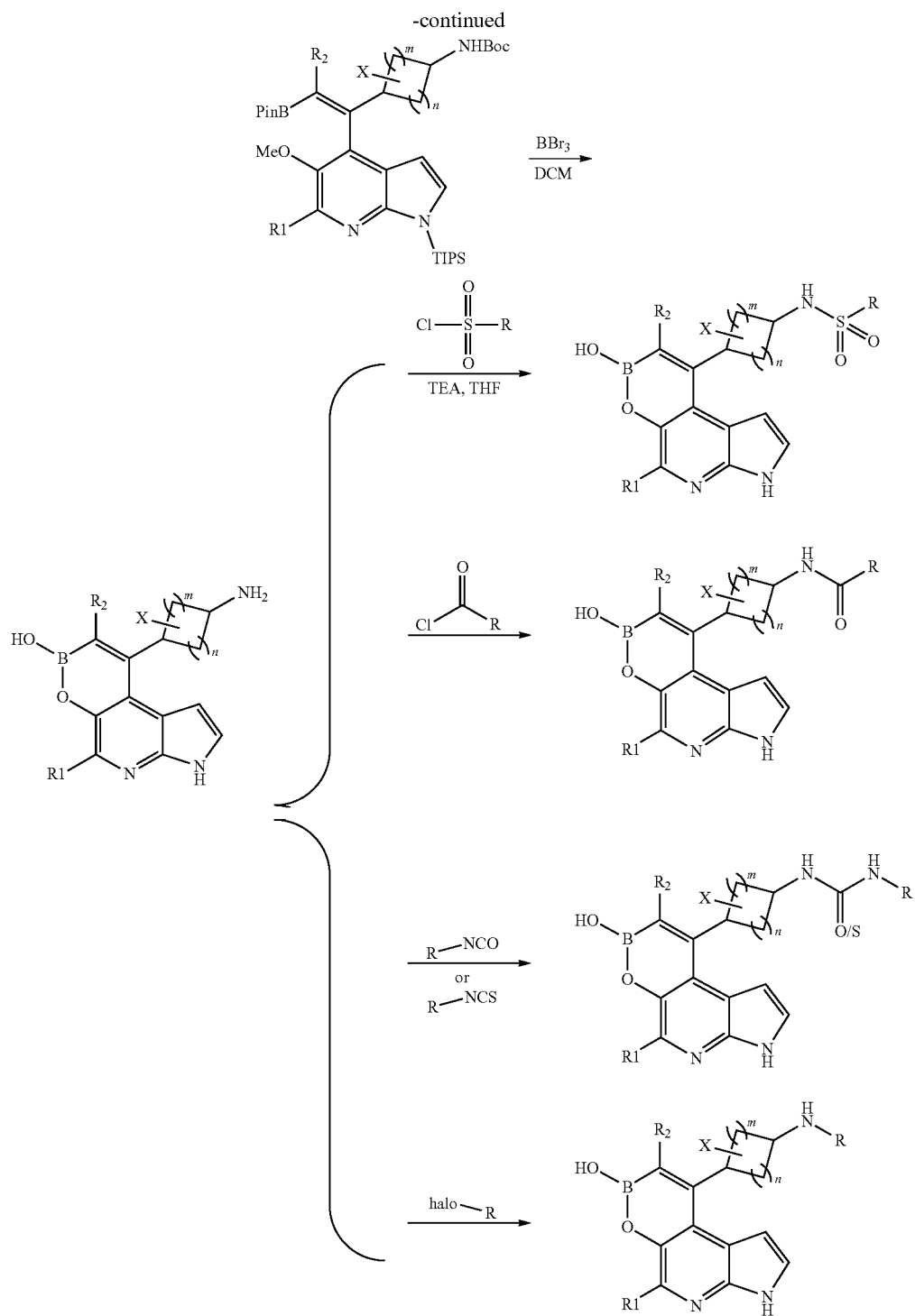
R₁ = H, Me, small alkyl, halo
R₂ = H, Me, small alkyl, halo
m, n = 1, 2
X = H, deuterium, C1-C6 linear or branched alkyl, C1-C6 linear or branched perfluoroalkyl, aryl, and alkylaryl;
R = —A—R₃, where A is a bond, —NH—, —O—, —(CH₂)k— or —(CD₂)k— and R₃ is C1-C6 linear or branched alkyl, C3-C6 cycloalkyl, aryl or —NR$_a$R$_b$, or is an unsaturated, saturated or partially saturated monocyclic or bicyclic ring structure

121
Scheme 2b - for variable definitions refer to labels as defined in Scheme 2a
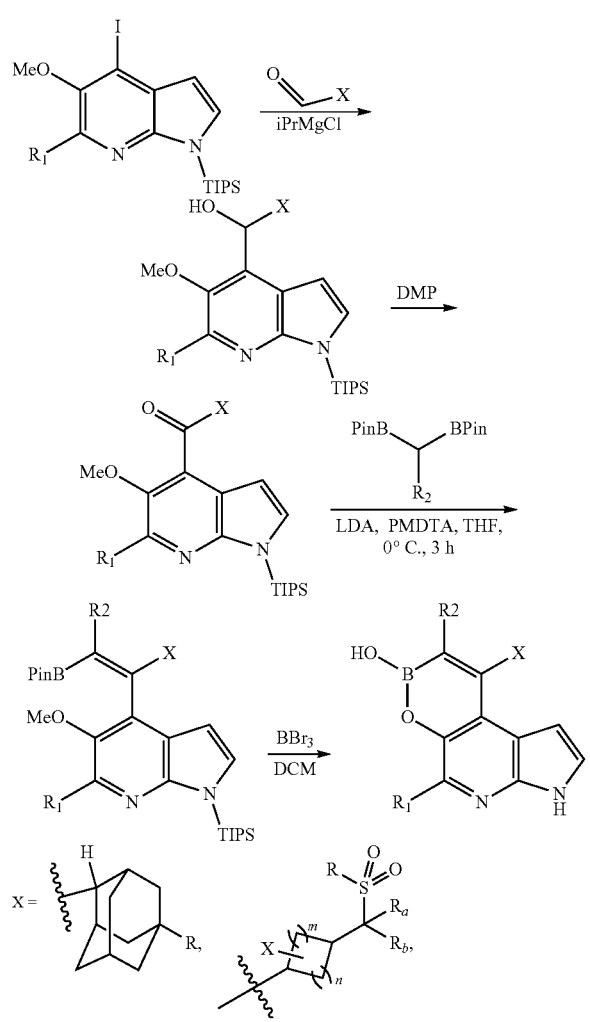
122
-continued
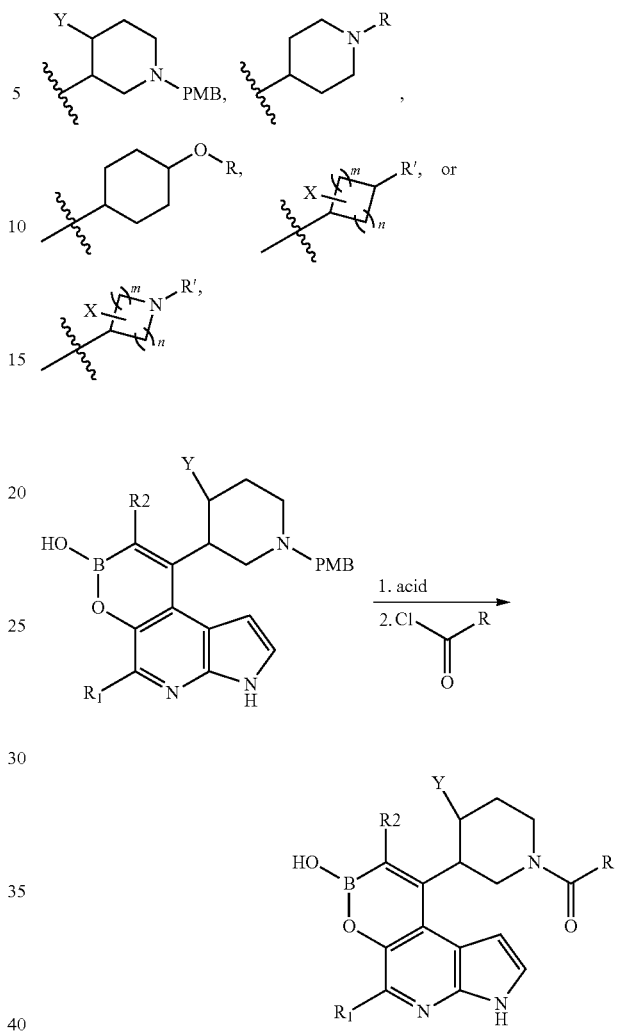
Scheme 3 - for variable definitions refer to labels as defined in Scheme 2a
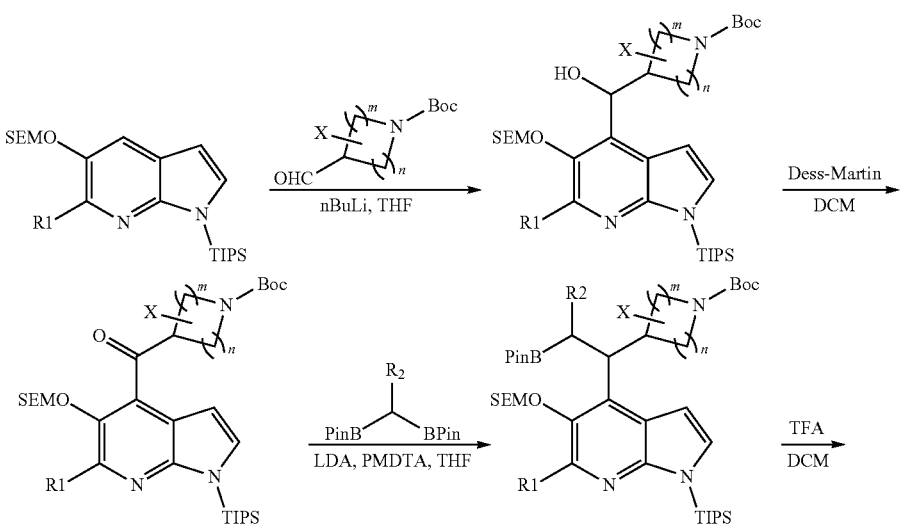

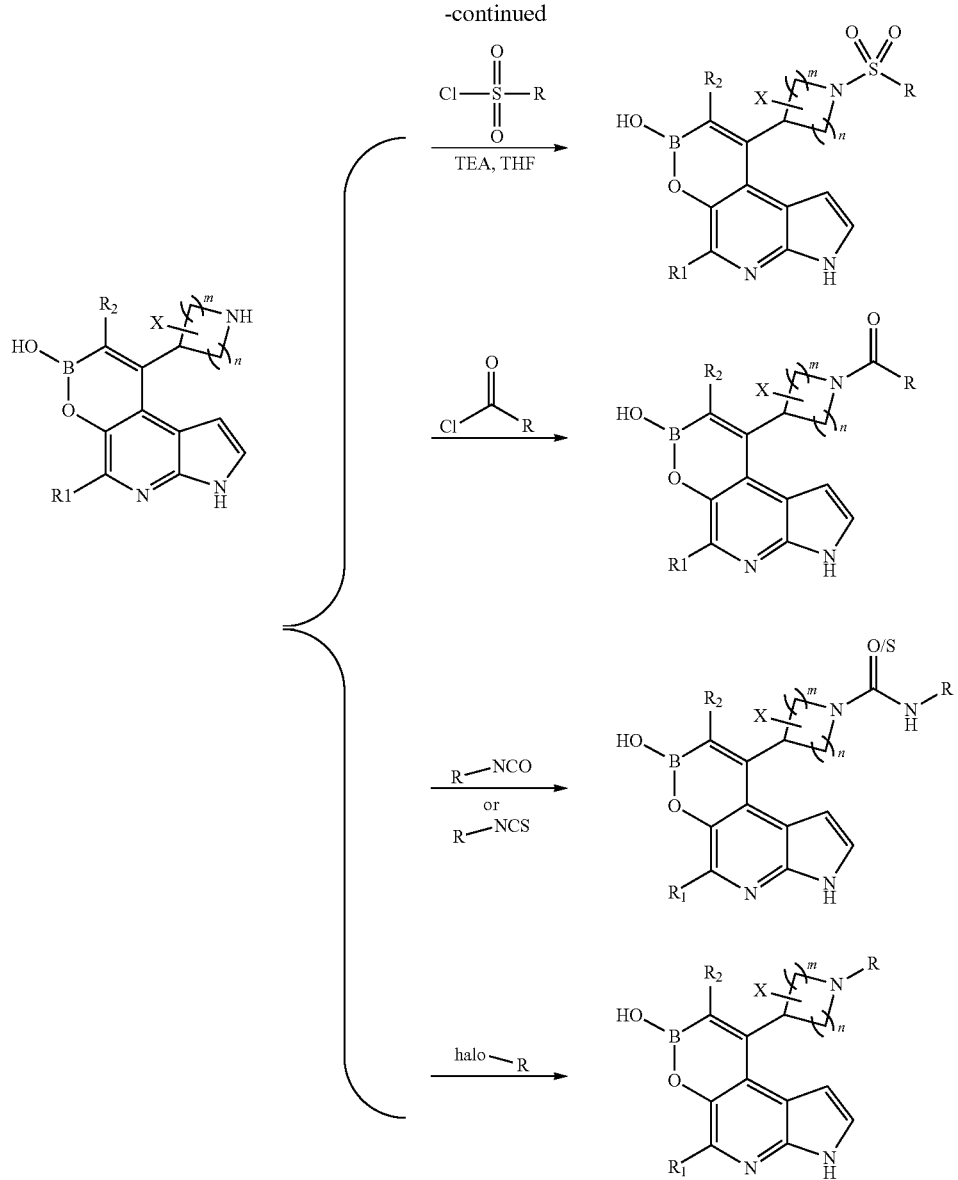
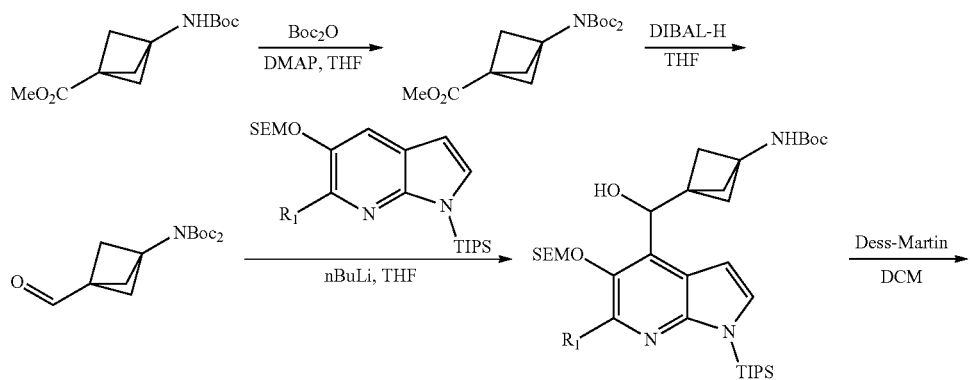
Scheme 4 - for variable definitions refer to labels as defined in Scheme 2a 125
-continued
126
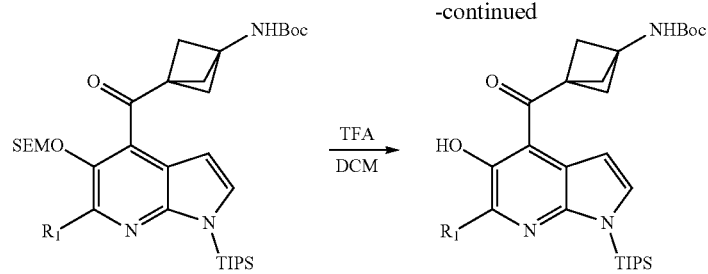
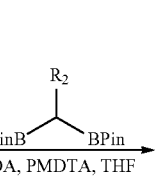
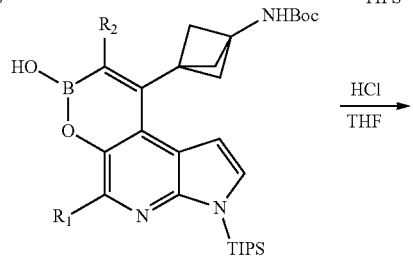
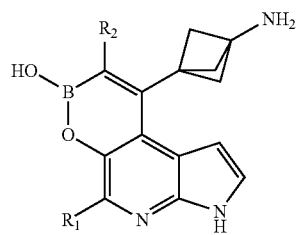
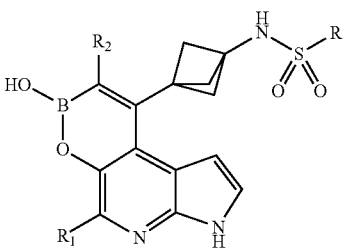
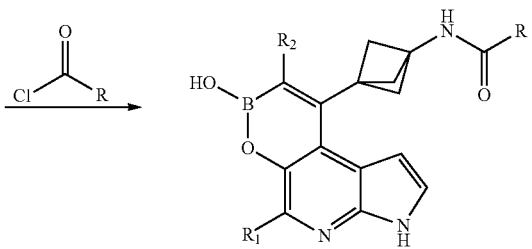
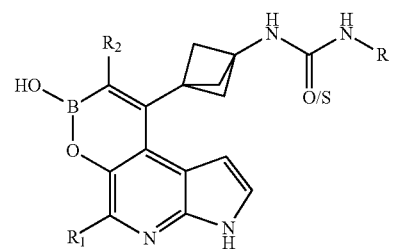
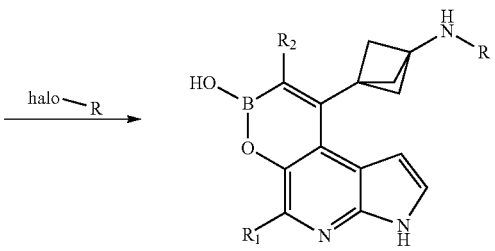

Scheme 5 - for variable definitions refer to labels as defined in Scheme 2a
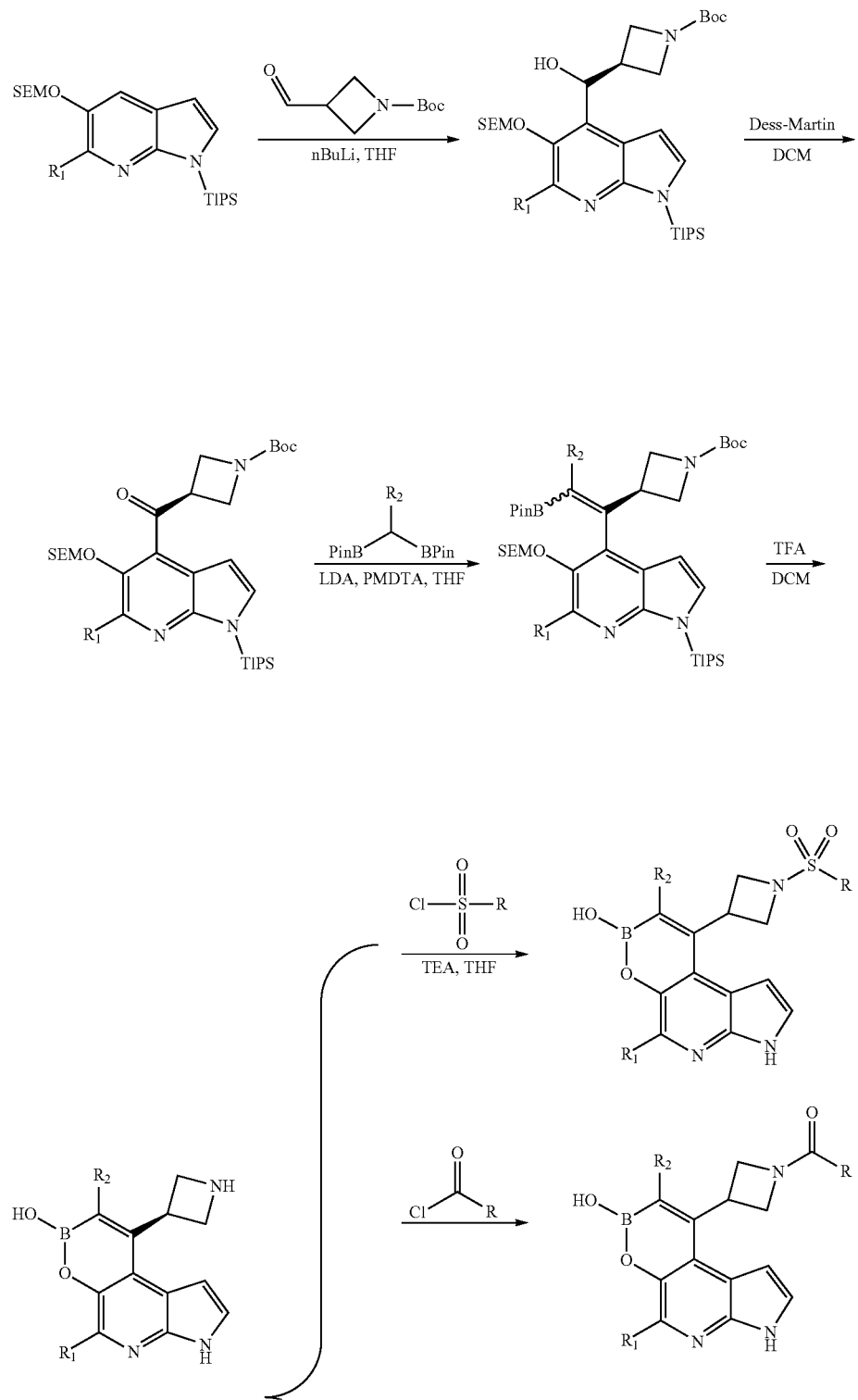

-continued
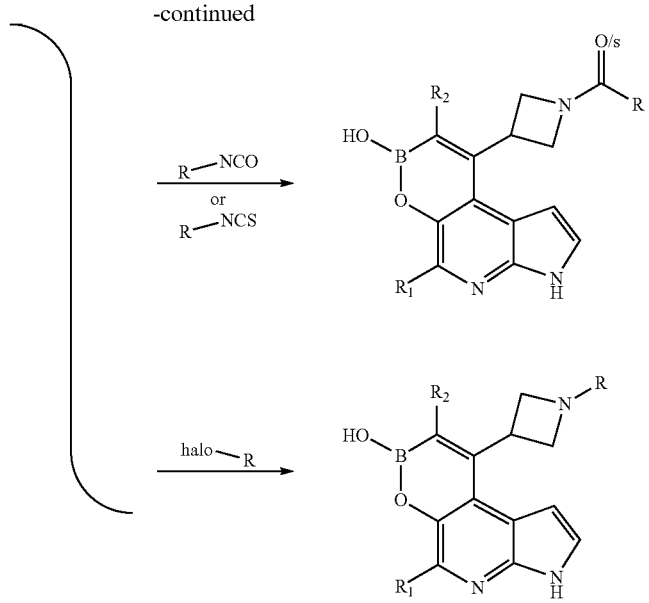
Example 1: 1-((1s,3s)-3-(dibenzylamino)cyclobutyl)-3,7-dihydro-4H-pyrrolo[3',2':5,6]pyrido[3,4-d][1,2,3]diazaborinin-4-ol
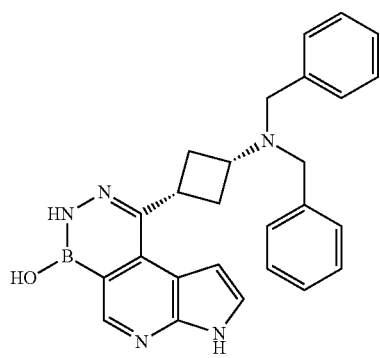 [SMILES: OB1NN=C([C@H]2C[C@@H](N(Cc3ccccc3)Cc3ccccc3)C2)c2c1cnc1[nH]ccc21]
The title compound was prepared by the scheme and procedures below:
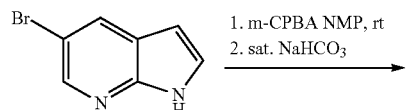
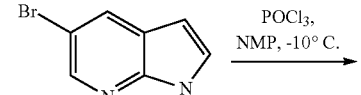
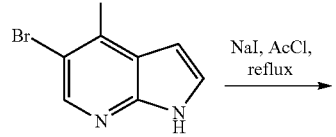
-continued
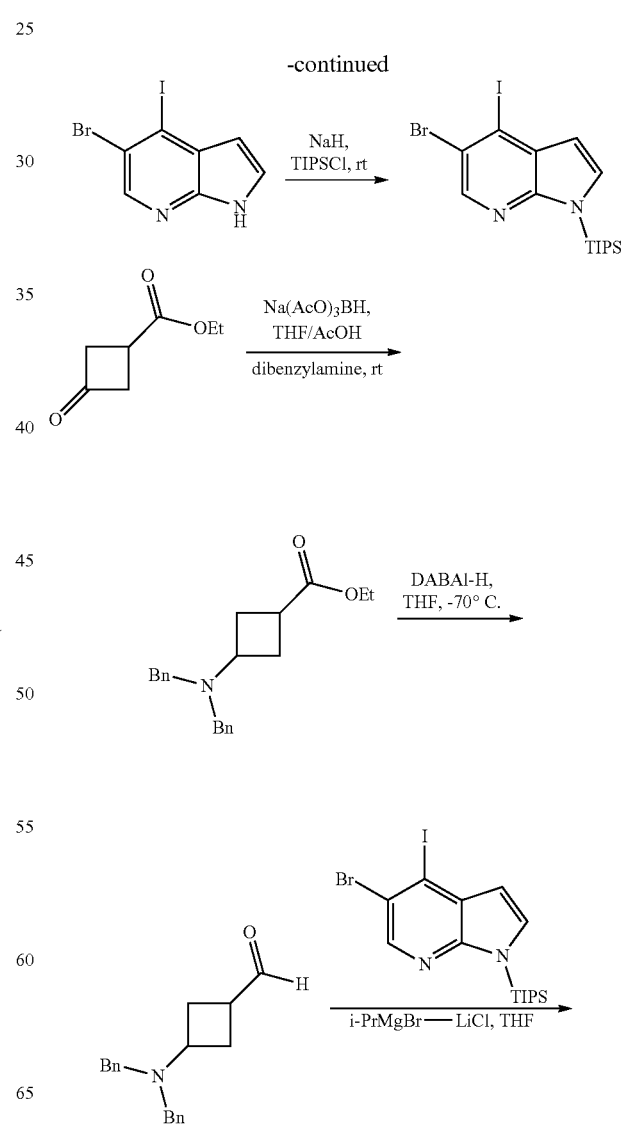

-continued

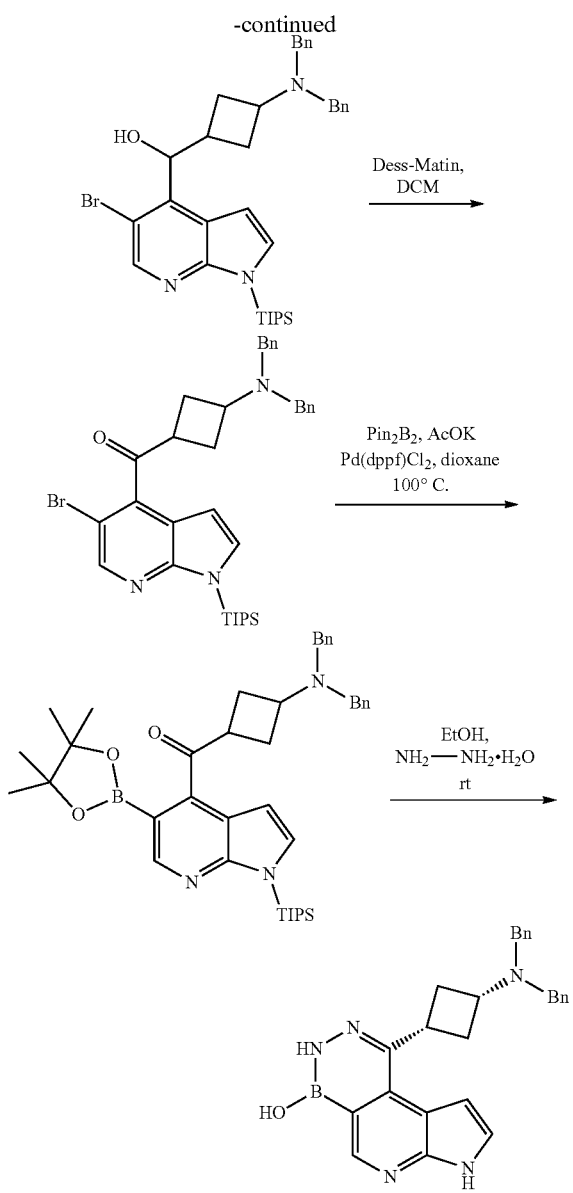

5-Bromo-1H-pyrrolo[2,3-b]pyridine (20 g, 0.1 mol) was suspended in 300 mL of NMP. A solution of m-CPBA (40 g, 0.16 mol) in 100 mL NMP was added dropwise over 30 min. The solution was stirred at 25° C. for 1 h, quenched with water (300 mL) and neutralized by sat. NaHCO$_3$ to pH=8. The solid formed was filtered and dried in vacuo to give 5-bromo-1H-pyrrolo[2,3-b]pyridine 7-oxide (18.0 g, yield 85%) as a yellow solid. MS: m/z=213.0 (M+H)$^+$. This intermediate (19.2 g, 90 mmol) was suspended in 200 mL NMP and cooled to −20° C. Phosphorus oxychloride (41 mL, 450 mmol) was added dropwise over 30 min. The mixture was warmed to 25° C. for 1 h and then it was cooled on an ice bath and quenched with water (800 mL). The solids were filtered and recrystallized from ethyl acetate and hexanes to give 5-bromo-4-chloro-1H-pyrrolo[2,3-b]pyridine (10 g, yield 48%). MS: m/z=230.9 (M+H)$^+$. This intermediate (6.00 g, 26.0 mmol) was mixed with sodium iodide (19.5 g, 130 mmol) in anhydrous acetonitrile (240 mL). Acetyl chloride (5.5 mL, 77.7 mmol) was added, and the reaction was stirred under reflux for 5 h. Aqueous saturated sodium bicarbonate solution (100 mL) was added. Solids were collected by filtration and washed with water (2×70 mL) to afford a crude intermediate 1-(5-bromo-4-iodo-pyrrolo[2,3-b]pyridin-1-yl)-ethanone (8.5 g). The intermediate was resuspended in a resulting mixture of methanol (200 mL) and aqueous sodium hydroxide (200 mL, 1N). The mixture was stirred for 1 h at 25° C. Solids were collected by filtration and rinsed with water (100 mL) to afford 5-bromo-4-iodo-1H-pyrrolo[2,3-b]pyridine (7.5 g, yield 90%) as a white solid. $^1$H NMR (400 MHz, DMSO-d$_6$): δ 12.20 (br. s, 1H), 8.30 (s, 1H), 7.63 (s, 1H), 6.30 (s, 1H) ppm. The solution of this intermediate (7.5 g, 23.0 mmol) in THF (50 mL) was cooled to 0° C., and NaH (1.8 g, 46 mmol, 60% oil dispersion) was added under N$_2$ atmosphere. After 15 minutes, triisopropylsilyl chloride ("TIPS-Cl"; 4.0 mL, 28 mmol) was added, and the reaction was stirred at rt for 1 h. A saturated ammonium chloride solution (20 mL) was added. The mixture was extracted with EtOAc (40 mL), washed with brine and dried over sodium sulfate. After filtration and removal of the solvent, the residue was purified by silica gel chromatography eluted with petroleum to give 5-bromo-4-iodo-1-(triisopropylsilyl)-1H-pyrrolo[2,3-b]pyridine (11.0 g, 100% yield) as a colorless oil. $^1$HNMR (400 MHz, DMSO-d$_6$): δ 8.31 (s, 1H), 7.61 (d, J=3.4 Hz, 1H), 6.48 (d, J=3.4 Hz, 1H), 1.85-1.75 (m, 3H), 1.04 (d, J=7.5 Hz, 18H) ppm. Sodium triacetoxyborohydride (30.0 g, 142 mmol) were added to a solution of ethyl 3-oxocyclobutane-1-carboxylate (10.0 g, 70 mmol) and dibenzylamine (15 mL, 77 mmol)) in acetic acid/THF (10%, 95 mL). It was stirred at room temperature for 2 h and concentrated in vacuo. The resulting residue was dissolved in dichloromethane, washed with water, saturated NaHCO$_3$ and brine, dried over Na$_2$SO$_4$ and filtered. The filtrate was concentrated in vacuo to give crude product. Purification by column chromatography (silica, 5% EtOAc in petroleum) provided ethyl 3-(dibenzylamino)cyclobutane-1-carboxylate (18.0 g, 73% yield, cis:trans ratio 10:1) as a yellow oil. To the solution of this intermediate (6.0 g, 19.0 mmol) in anhydrous THF (100 mL) was added DIBAL-H (25 mL, 1.5 M in toluene) at −78° C. under N$_2$ atmosphere dropwise. After the addition was completed, it was slowly warmed to rt, quenched by sat. NH$_4$Cl, and diluted with EtOAc. It was stirred at rt for 30 min and filtered through Celite. The filtrate was separated, and the organic layer was evaporated under reduced pressure. The residue was applied to flash chromatography using 10% EtOAc in petroleum to afford 3-(dibenzylamino)cyclobutane-1-carbaldehyde (2.4 g, 45%) as a colorless oil. MS: m/z=280.2 (M+H)$^+$. To a solution of 5-bromo-4-iodo-1-(triisopropylsilyl)-1H-pyrrolo[2,3-b]pyridine (1.8 g, 3.8 mmol) in THF (50 mL) was added i-PrMgBr—LiCl (5.6 mL, 1M in THF, 5.6 mmol) at −35° C. under N$_2$ atmosphere. It was stirred at −35° C. for 1 h. To this mixture was added the solution of 3-(dibenzylamino)cyclobutane-1-carbaldehyde (1.5 g, 5.6 mmol) in THF (5 mL), and the resulting mixture was stirred at −35° C. for another 1 h. It was allowed to warm to 0° C., quenched with H$_2$O, and extracted by EtOAc. The organic layer was washed by bine, dried over Na$_2$SO$_4$, and filtered. After evaporation, the residue was purified by column chromatography (30%-50% EtOAc in petroleum) to give the desired compound (5-bromo-1-(triisopropylsilyl)-1H-pyrrolo[2,3-b]pyridin-4-yl)(3-(dibenzylamino)cyclobutyl)methanol (1.2 g, yield 50%, cis:trans ratio 4:1) as a yellow oil. MS: m/z=475.8 (M-TIPS)$^+$. To a solution of this alcohol intermediate (1.2 g, 1.9 mmol) in DCM (15 mL) was added Dess-Martin reagent (784 mg, 1.9 mmol) in portions at 0° C., and then it was stirred at rt for 30 min. TLC showed the reaction was complete. The reaction mixture was diluted with EtOAc (25 mL) and filtered through a pad of Celite. The filtrate was concentrated in vacuo under reduce pressure to dryness. The residue was purified by silica gel column chromatography (5%-10% EtOAc in petroleum) to give the desired compound (5-bromo-1-(triisopropylsilyl)-1H-pyrrolo[2,3-b]pyridin-4-yl)(3-(dibenzyl amino)cyclobutyl)methanone (1.0 g, yield 84%) as a yellow oil. MS: m/z=501.9 (M-TIPS)$^+$. To a solution of this bromo ketone intermediate (1.0 g, 1.6 mmol) in 1,4-dioxane (15.0 mL) were added KOAc (706 mg, 3.0 mmol), Pin$_2$B$_2$ (828 mg, 3.2 mmol) and Pd(dppf)Cl$_2$ (175 mg, 0.24 mmol). The mixture was heated at 100° C. for 5 h under N$_2$. The reaction mixture was cooled to rt, and the solids were filtered off. The solvent was removed and the crude product was purified by silica gel column chromatography (10% EtOAc in petroleum) to afford the desired compound (3-(dibenzylamino)cyclobutyl)(5-(4,4,5,5-tetramethyl-1,3,2-dioxaborolan-2-yl)-1-(triisopropylsilyl)-1H-pyrrolo[2,3-b]pyridin-4-yl)methanone (400 mg, yield 36%). It was used to the next step without further purification. MS: m/z=440.2 (M-TIPS; BOH)$^+$. To a solution of this ketone boron intermediate (600 mg, 0.89 mmol) in EtOH (5 mL) at rt was added hydrazine hydrate (0.5 mL). It was stirred at rt for 30 min, and then 6N HCl (2 mL) was added to the mixture. The resulting mixture was stirred at rt for another 30 min, concentrated in vacuo to dryness, and neutralized with hydrazine hydrate to pH=7 to 8. The residue was purified by prep-HPLC (0.1% diethylamine in MeCN and H$_2$O) to afford the desired product 1-((1s,3s)-3-(dibenzylamino)cyclobutyl)-3,7-dihydro-4H-pyrrolo[3',2':5,6]pyrido[3,4-d][1,2,3]diazaborinin-4-ol (40 mg, yield 10%). $^1$HNMR (400 MHz, DMSO-d$_6$): δ 12.07 (s, 1H), 10.07 (s, 1H), 9.02 (s, 1H), 8.10 (s, 1H), 7.61 (s, 1H), 7.49-7.16 (m, 10H), 6.92 (s, 1H), 3.83-3.69 (m, 1H), 3.50 (s, 4H), 3.29 (s, 2H), 2.47-2.35 (m, 2H), 2.20-2.11 (m, 1H) ppm. HPLC purity: 97.1% at 210 nm and 99.4% at 254 nm. MS: m/z=435.9 (M+H)$^+$.

Example 2: N-((1s,3s)-3-(4-hydroxy-4,7-dihydro-3H-pyrrolo[3',2':5,6]pyrido[3,4-d][1,2,3]diazaborinin-1-yl)cyclobutyl)propane-1-sulfonamide and N-((1r,3r)-3-(4-hydroxy-4,7-dihydro-3H-pyrrolo[3',2':5,6]pyrido[3,4-d][1,2,3]diazaborinin-1-yl)cyclobutyl)propane-1-sulfonamide

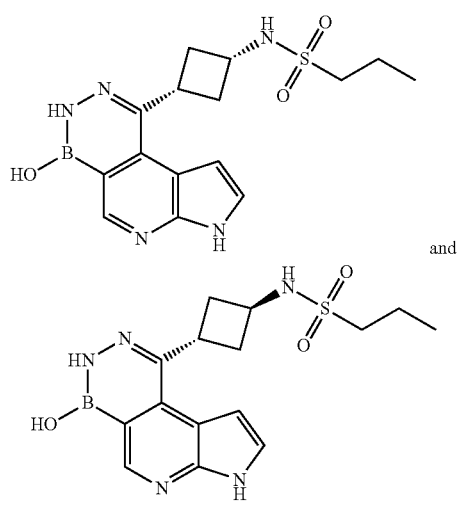

and

The title compounds were prepared by the scheme and procedures below:

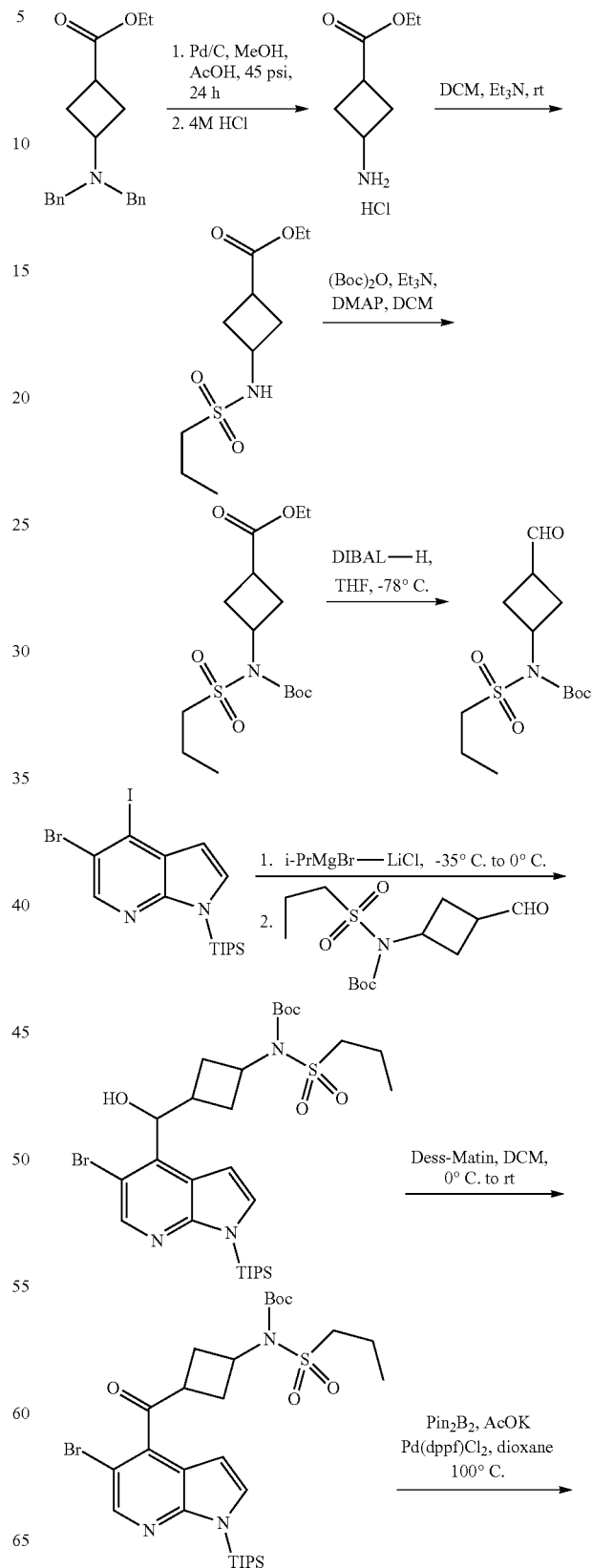

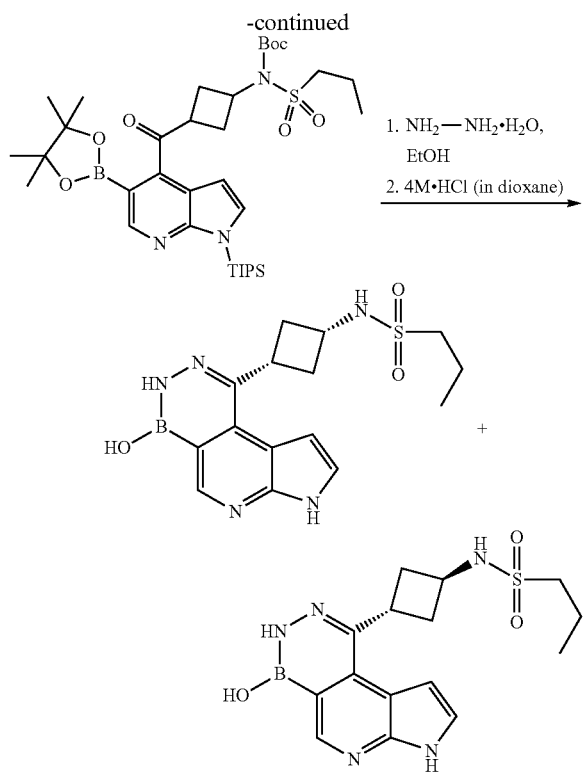

Pd/C (10% by wt., 7.0 g) was added to a solution of ethyl 3-(dibenzylamino)cyclobutane-1-carboxylate (22 g, 68 mmol), ethanol (250 mL), water (13 mL) and acetic acid (1 mL) in a Parr shaker bottle. The reaction mixture was pressurized to 45 psi with $H_2$ and agitated at room temperature for 18 h. The reaction mixture was filtered, and the filtrate was concentrated in vacuo. The resulting residue was taken up in ethanol (50 mL), and then HCl (2 M in $Et_2O$, 50 mL) was added. The slurry was filtered to provide ethyl 3-aminocyclobutane-1-carboxylate HCl salt (6.5 g, yield 53%). $^1$HNMR (400 MHz, DMSO-$d_6$): δ 8.26 (br. s, 3H), 4.08 (q, J=7.1 Hz, 2H), 3.60 (quintet, J=8.0 Hz, 1H), 2.96 (quintet, J=8.0 Hz, 1H), 2.47-2.37 (m, 2H), 2.34-2.21 (m, 2H), 1.19 (t, J=7.1 Hz, 3H) ppm. To a solution of this amino intermediate (6.5 g, 36 mmol) and triethylamine (5.0 mL, 36.0 mmol) in dichloromethane (50 mL) at 0° C. was gradually added propane-1-sulfonyl chloride (5.1 g, 36.0 mmol), and the mixture was stirred at rt for 3 h. To the reaction solution was added water (50 ml), and the resultant was extracted with dichloromethane (2×50 mL). The organic layer was dried over anhydrous magnesium sulfate and filtered. The filtrate was concentrated under reduced pressure. The residue was purified by silica gel chromatography eluted with PE/EtOAc (30:1 to 10:1, v/v) to give ethyl 3-(propylsulfonamido)cyclobutane-1-carboxylate (8.0 g, yield 89%). $^1$HNMR (400 MHz, DMSO-$d_6$): δ 7.49 (d, J=9.0 Hz, 1H), 4.05 (q, J=7.1 Hz, 2H), 3.76-3.59 (m, 1H), 2.95-2.82 (m, 2H), 2.80-2.70 (m, 1H), 2.49-2.40 (m, 2H), 2.17-2.03 (m, 2H), 1.71-1.58 (m, 2H), 1.18 (t, J=7.1 Hz, 3H), 0.97 (t, J=7.4 Hz, 3H) ppm. To the solution of this intermediate (8.0 g, 32 mmol), $Et_3N$ (9.0 mL, 94 mmol) and DMAP (8 mg) in $CH_2Cl_2$ (80 mL) was added a solution of $(Boc)_2O$ (1.5 eq) in $CH_2Cl_2$ (10 mL) at 0° C. under a $N_2$ atmosphere. The mixture was stirred at rt for 2 h. The reaction was quenched with $NaHCO_3$ (10 mL). The organic layer was separated, dried with anhydrous sodium sulfate, filtered and concentrated in vacuo to yield a crude product. It was purified by flash chromatography using 10% EtOAc in petroleum to afford ethyl 3-(N-(tert-butoxycarbonyl)propylsulfonamido) cyclobutane-1-carboxylate (11 g, yield 100%) as a colorless oil. $^1$HNMR (400 MHz, DMSO-$d_6$): δ 4.56-4.42 (m, 1H), 4.12-3.99 (m, 2H), 3.52-3.41 (m, 2H), 2.93-2.76 (m, 1H), 2.68 (qd, J=9.7, 2.3 Hz, 2H), 2.48-2.37 (m, 2H), 1.72-1.59 (m, 2H), 1.49 (s, 9H), 1.18 (t, J=7.1 Hz, 3H), 0.99 (t, J=7.4 Hz, 3H) ppm. To the solution of this intermediate (11.0 g, 32 mmol) in anhydrous THF (50 mL) was added DIBAL-H (41.7 mL, 1.5 M in toluene) at −78° C. under $N_2$ atmosphere dropwise. After the addition was completed, it was slowly warmed to rt, quenched by sat. $NH_4Cl$, diluted with EtOAc, and stirred at rt for 30 min. It was filtered through Celite, and the filtrate was separated. The organic layer was evaporated under reduce pressure, and the residue was purified by flash chromatography using 10% EtOAc in petroleum to afford tert-butyl (3-formylcyclobutyl)(propylsulfonyl)carbamate (4.1 g, yield 43%) as a colorless oil. $^1$HNMR (400 MHz, DMSO-$d_6$): δ 9.60 (d, J=1.5 Hz, 1H), 4.66-4.50 (m, 1H), 3.55-3.41 (m, 2H), 2.98-2.85 (m, 1H), 2.76-2.60 (m, 2H), 2.42-2.32 (m, 2H), 1.74-1.60 (m, 2H), 1.48 (s, 9H), 0.99 (t, J=7.4 Hz, 3H) ppm. To a solution of 5-bromo-4-iodo-1-(triisopropylsilyl)-1H-pyrrolo[2,3-b]pyridine (6.4 g, 13.4 mmol) in THF (30 mL) was added i-PrMgBr—LiCl (20 mL, 20.0 mmol, 1M in THF) at −35° C. under $N_2$ atmosphere, and the mixture was stirred at −35° C. for 1 h. A solution of tert-butyl (3-formylcyclobutyl)(propylsulfonyl)carbamate (4.1 g, 13.4 mmol) in THF (5 mL) was added to the mixture. The resulting mixture was stirred at −35° C. for another 1 h, allowed to warm to 0° C., quenched by $H_2O$, and extracted by EtOAc. It was washed by brine, dried over $Na_2SO_4$, filtered and evaporated in vacuo under reduce pressure. The residue was purified by column chromatography (30%-50% EtOAc in petroleum) to give the desired compound tert-butyl (3-((5-bromo-1-(triisopropylsilyl)-1H-pyrrolo[2,3-b]pyridin-4-yl)(hydroxy)methyl) cyclobutyl)(propylsulfonyl)carbamate (3.0 g, yield 34%, cis:trans ratio 4:1) as a yellow oil. MS: m/z=501.9 (M-TIPS)$^+$. To a solution of this intermediate (3.0 g, 4.6 mmol) in DCM (25 mL) was added Dess-Martin reagent (1.9 g, 4.6 mmol) in portions at 0° C., and then it was slowly warmed to rt. It was stirred at rt for 30 min and TLC showed no alcohol compound left. The reaction mixture was diluted with EtOAc (25 mL) and filtered by a pad of Celite. The filtrate was concentrated in vacuo under reduce pressure to dryness. The residue was purified to silica gel column chromatography (5%-10% EtOAc in petroleum) to give the desired ketone compound tert-butyl (3-(5-bromo-1-(triisopropylsilyl)-1H-pyrrolo[2,3-b]pyridine-4-carbonyl)cyclobutyl)(propylsulfonyl)carbamate (1.0 g, yield 33%) as a yellow oil. $^1$HNMR (400 MHz, DMSO-$d_6$): δ 8.45 (s, 1H), 7.72 (d, J=3.5 Hz, 1H), 6.62 (d, J=3.5 Hz, 1H), 4.59 (t, J=8.1 Hz, 1H), 3.69 (t, J=8.3 Hz, 1H), 3.58-3.47 (m, 2H), 2.88 (m, 2H), 2.53 (m, 3H), 1.91 (m, 3H), 1.70 (m, 3H), 1.54 (s, 9H), 1.12 (d, J=8 Hz, 18H), 1.03 (t, J=8 Hz, 3H) ppm. To a solution of this intermediate (1.6 g, 2.4 mmol) in 15.0 mL dioxane were added KOAc (706 mg, 3.0 mmol), and $Pin_2B_2$ (1.24 g, 4.88 mmol) followed by Pd(dppf)$Cl_2$ (175 mg, 0.24 mmol). The mixture was heated at 100° C. for 5 h under $N_2$. The reaction mixture was cooled to room temperature, and the solids were filtered off. The solvent was removed and the crude product was purified by silica gel column chromatography (10% EtOAc in petroleum) to afford the desired boron compound tert-butyl (propylsulfonyl)(3-(5-(4,4,5,5-tetramethyl-1,3,2-dioxaborolan-2-yl)-1-(triisopropylsilyl)-1H-pyrrolo[2,3-b]pyridine-4-carbonyl)cyclobutyl) carbamate (650 mg, yield 39%). To a solution of this intermediate (200 mg, 0.28 mmol) in EtOH (5 mL) at rt was added hydrazine hydrate (0.1 mL). It was stirred at rt for 30 min and then 6N HCl (0.5 mL) was added the mixture. The resulting mixture was stirred at rt for another 30 min and 4N HCl (3 mL) was added to the mixture. The reaction mixture was transferred into a sealed-tube and stirred at 40° C. overnight. LCMS indicated the reaction was completed. It was concentrated in vacuo to dryness, and neutralized by hydrazine hydrate to pH=7-8. The residue was purified by prep-HPLC (0.1% diethylamine in MeCN and H₂O) to afford the desired cis-compound N-((1s,3s)-3-(4-hydroxy-4,7-dihydro-3H-pyrrolo[3',2':5,6]pyrido[3,4-d][1,2,3]diazaborinin-1-yl)cyclobutyl)propane-1-sulfonamide (27 mg) and trans-compound N-((1r,3r)-3-(4-hydroxy-4,7-dihydro-3H-pyrrolo[3',2':5,6]pyrido[3,4-d][1,2,3]diazaborinin-1-yl)cyclobutyl)propane-1-sulfonamide (5 mg) as white solids (total yield 32%). Analytical data of the cis-isomer are shown as follows. ¹HNMR (400 MHz, DMSO-d₆): δ 12.08 (s, 1H), 10.11 (s, 1H), 9.03 (s, 1H), 8.12 (s, 1H), 7.62 (s, 1H), 7.41 (d, J=9.0 Hz, 1H), 7.03 (d, J=2.3 Hz, 1H), 4.01-3.72 (m, 2H), 2.98-2.89 (m, 2H), 2.77-2.63 (m, 2H), 2.38-2.19 (m, 2H), 1.75-1.57 (m, 2H), 0.96 (t, J=7.4 Hz, 3H) ppm. HPLC purity: 96.9% at 254 nm. MS: m/z=361.9 (M+H)⁺. Analytical data of the trans-isomer are shown as follows. ¹HNMR (400 MHz, DMSO-d₆): δ 12.10 (s, 1H), 10.10 (s, 1H), 9.04 (s, 1H), 8.14 (s, 1H), 7.66-7.59 (m, 1H), 6.73 (d, J=1.8 Hz, 1H), 4.01-3.83 (m, 2H), 2.91-2.77 (m, 2H), 2.72-2.62 (m, 2H), 2.48-2.41 (m, 2H), 1.71-1.59 (m, 2H), 0.94 (t, J=7.4 Hz, 3H) ppm. HPLC purity: 95.5% at 254 nm. MS: m/z=361.9 (M+H)⁺.

Example 3: N-((1s,3s)-3-(4-hydroxy-4,7-dihydropyrrolo[3',2':5,6]pyrido[4,3-d][1,2,6]oxazaborinin-1-yl)cyclobutyl)propane-1-sulfonamide and N-((1r,3r)-3-(4-hydroxy-4,7-dihydropyrrolo[3',2':5,6]pyrido[4,3-d][1,2,6]oxazaborinin-1-yl)cyclobutyl)propane-1-sulfonamide

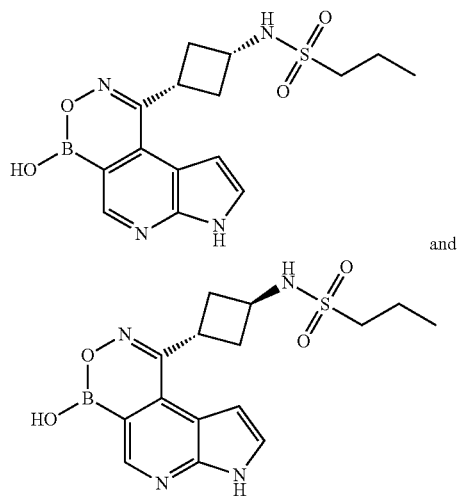

The title compounds were prepared by the scheme and procedures below:

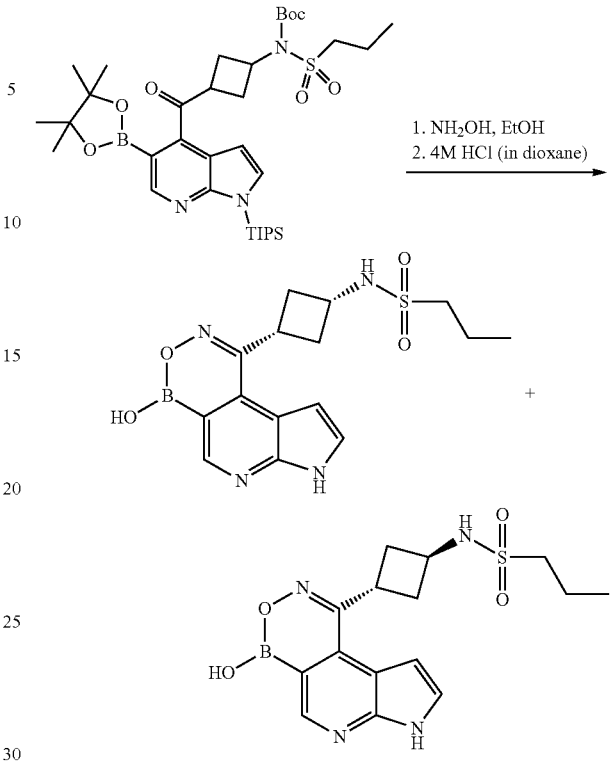

To a solution of tert-butyl (propylsulfonyl)(3-(5-(4,4,5,5-tetramethyl-1,3,2-dioxaborolan-2-yl)-1-(triisopropylsilyl)-1H-pyrrolo[2,3-b]pyridine-4-carbonyl)cyclobutyl)carbamate (200 mg, 0.28 mmol) in EtOH (5 mL) at rt was added hydroxylamine solution (0.25 mL, 40% solution in H₂O). It was stirred at rt for 30 min, and 6N HCl (0.5 mL) was added the mixture. The resulting mixture was stirred at rt for another 30 min. 4M HCl in 1,4-dioxane (3 mL) was added to the mixture, and the reaction mixture was transferred into a sealed-tube. It was stirred at 40° C. overnight and LCMS indicated the reaction was completed. It was neutralized by hydroxylamine solution to pH=7-8 and then concentrated in vacuo to dryness. The residue was purified by prep-HPLC (0.1% diethylamine in MeCN and H₂O) to afford the desired cis-compound N-((1s,3s)-3-(4-hydroxy-4,7-dihydropyrrolo[3',2':5,6]pyrido[4,3-d][1,2,6]oxazaborinin-1-yl)cyclobutyl)propane-1-sulfonamide (34 mg) and the trans-compound N-((1r,3r)-3-(4-hydroxy-4,7-dihydropyrrolo[3',2':5,6]pyrido[4,3-d][1,2,6]oxazaborinin-1-yl)cyclobutyl)propane-1-sulfonamide (11 mg) as a white solid (total yield 45%). Analytical data of the cis-isomer is shown as follows. ¹HNMR (400 MHz, DMSO-d₆): δ 9.27 (br. s, 1H), 8.89 (s, 1H), 7.78 (d, J=3.5 Hz, 1H), 7.44 (br. s, 1H), 7.05 (d, J=3.6 Hz, 1H), 3.99 (m, 1H), 3.93-3.78 (m, 1H), 2.92 (dd, J=8.8, 6.6 Hz, 2H), 2.78-2.63 (m, 2H), 2.38-2.23 (m, 2H), 1.67 (m, 2H), 0.96 (t, J=7.4 Hz, 3H) ppm. HPLC purity: 93.9% at 210 nm and 98.6% at 254 nm. MS: m/z=362.8 (M+H)⁺. Analytical data of the trans-isomer is shown as following. ¹HNMR (400 MHz, DMSO-d₆): δ 10.12 (s, 1H), 9.05 (s, 1H), 8.30 (br. s, 1H), 7.68-7.52 (m, 2H), 6.74 (d, J=1.5 Hz, 1H), 3.92-3.79 (m, 2H), 3.01-2.75 (m, 4H), 2.66 (m, 2H), 2.43 (m, 2H), 1.71-1.58 (m, 2H), 0.94 (t, J=7.4 Hz, 3H) ppm. HPLC purity: 91.8% at 210 nm and 98.0% at 254 nm. MS: m/z=362.8 (M+H)⁺.

Example 4: N-((1s,3s)-3-(4-hydroxy-3-methyl-4,7-dihydro-3H-pyrrolo[3',2':5,6]pyrido[3,4-d][1,2,3]diazaborinin-1-yl)cyclobutyl)propane-1-sulfonamide Example 5: Synthesis of N-(3-(7-hydroxy-3,7-dihydro-[1,2]oxaborinino[5,6-d]pyrrolo[2,3-b]pyridin-9-yl)cyclobutyl)propane-1-sulfonamide

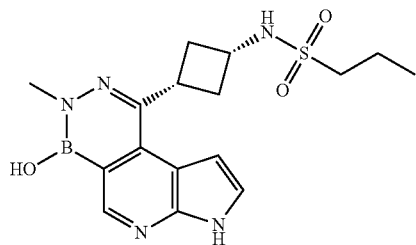 [SMILES: CCCS(=O)(=O)N[C@H]1C[C@@H](C2=NN(C)B(O)c3cnc4[nH]ccc4c32)C1]

The title compound was prepared by the scheme and procedures below:

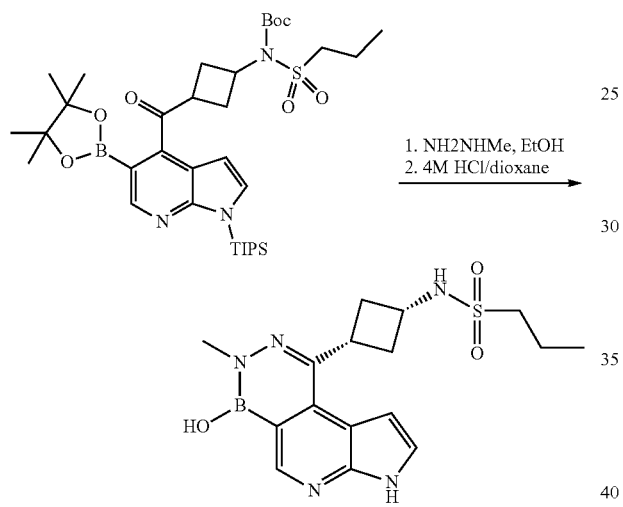

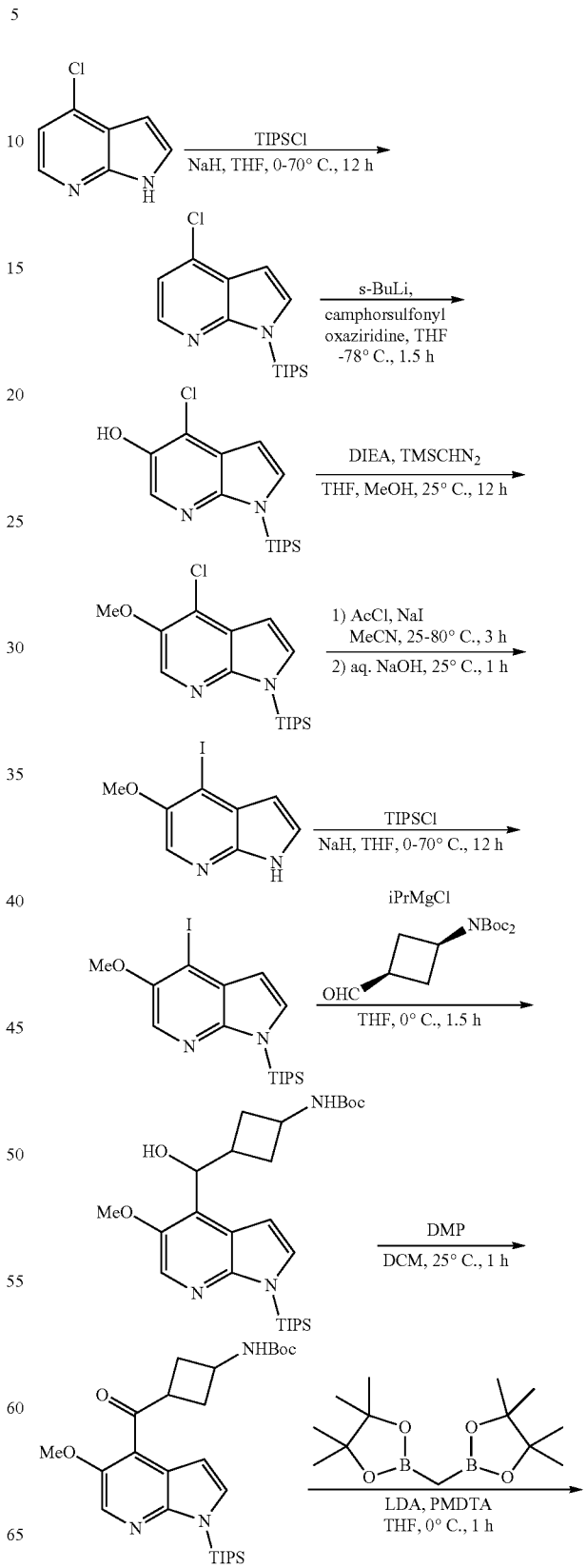

To a solution of tert-butyl (propylsulfonyl)(3-(5-(4,4,5,5-tetramethyl-1,3,2-dioxaborolan-2-yl)-1-(triisopropylsilyl)-1H-pyrrolo[2,3-b]pyridine-4-carbonyl)cyclobutyl)carbamate (200 mg, 0.28 mmol) in EtOH (5 mL) at rt was added methylhydrazine solution (0.3 mL, 25% solution in $H_2O$), and then it was stirred at rt for 30 min. 6N HCl (0.5 mL) was added to the mixture. The resulting mixture was stirred at rt for another 30 min. 4M HCl in 1,4-dioxane (3 mL) was added and the reaction mixture was transferred into a sealed-tube. It was stirred at 40° C. overnight. LCMS indicated the reaction was completed. It was neutralized by methylhydrazine solution to pH=7-8, and concentrated in vacuo to dryness. The residue was purified by prep-HPLC (0.1% diethylamine in MeCN and $H_2O$) to afford the desired compound N-((1s,3s)-3-(4-hydroxy-3-methyl-4,7-dihydro-3H-pyrrolo[3',2':5,6]pyrido[3,4-d][1,2,3]diazaborinin-1-yl)cyclobutyl) propane-1-sulfonamide (36 mg, yield 34%) as a white solid. $^1$HNMR (400 MHz, DMSO-$d_6$): δ 9.10 (s, 1H), 8.44 (s, 1H), 7.67-7.56 (m, 1H), 7.40 (d, J=8.9 Hz, 1H), 7.03 (dd, J=3.3, 1.6 Hz, 1H), 3.94 (m, 1H), 3.86-3.72 (m, 1H), 3.58 (s, 3H), 2.96-2.84 (m, 2H), 2.74-2.60 (m, 2H), 2.29 (m, 2H), 1.74-1.57 (m, 2H), 0.94 (t, J=7.2 Hz, 3H). ppm. HPLC purity: 94.9% at 210 nm and 96.5% at 254 nm. MS: m/z=375.9 (M+H)$^+$.

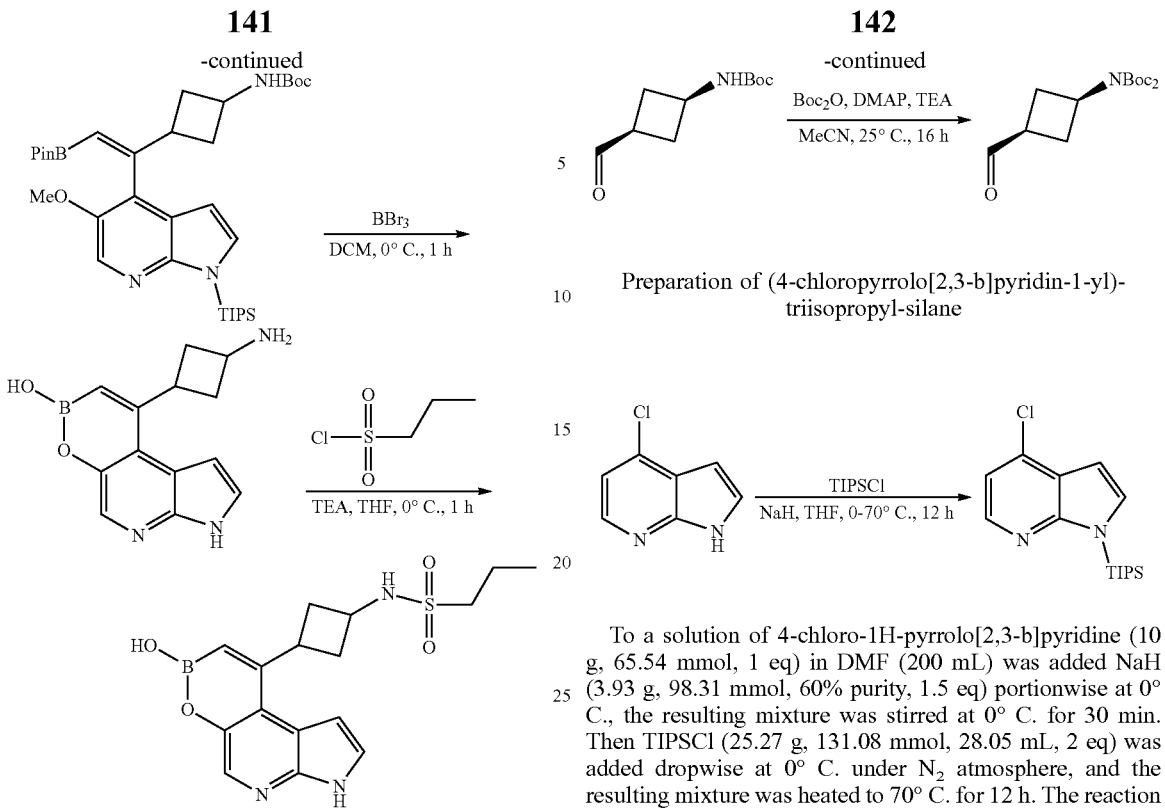

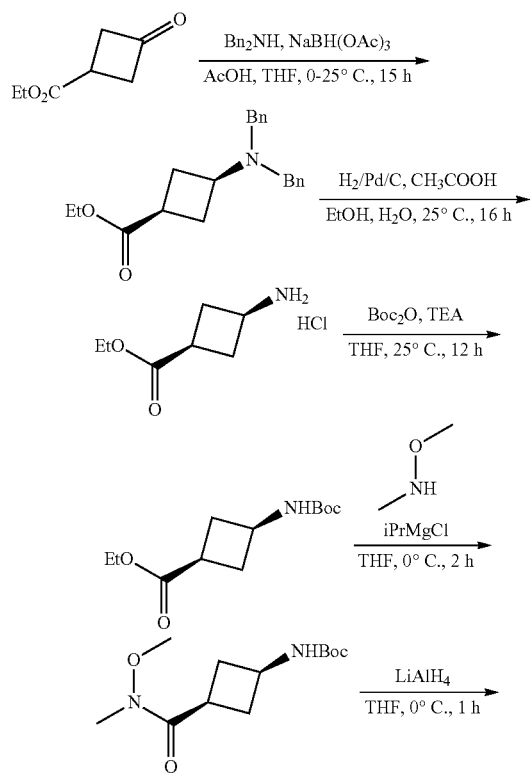

Synthesis of Intermediate Tert-Butyl N-tert-butoxy-carbonyl-N-(3-formylcyclobutyl)carbamate Preparation of (4-chloropyrrolo[2,3-b]pyridin-1-yl)-triisopropyl-silane

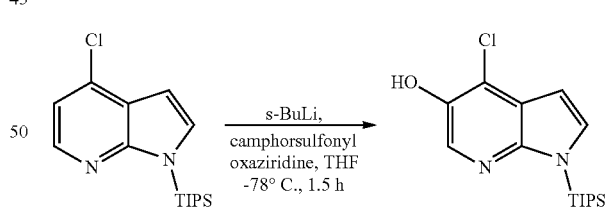

To a solution of 4-chloro-1H-pyrrolo[2,3-b]pyridine (10 g, 65.54 mmol, 1 eq) in DMF (200 mL) was added NaH (3.93 g, 98.31 mmol, 60% purity, 1.5 eq) portionwise at 0° C., the resulting mixture was stirred at 0° C. for 30 min. Then TIPSCl (25.27 g, 131.08 mmol, 28.05 mL, 2 eq) was added dropwise at 0° C. under $N_2$ atmosphere, and the resulting mixture was heated to 70° C. for 12 h. The reaction mixture was quenched by adding saturated aq. $NH_4Cl$ (100 mL) and extracted with EtOAc (100 mL×3). The combined organic layers were washed with brine (100 mL×2), dried over $Na_2SO_4$, filtered and concentrated under reduced pressure to give a residue, which was purified by column chromatography ($SiO_2$, Petroleum ether/Ethyl acetate=20/1 to 10/1) to give (4-chloropyrrolo[2,3-b]pyridin-1-yl)-triisopropyl-silane (19 g, 61.50 mmol, 93.84% yield) as a yellow oil. $^1H$ NMR ($CDCl_3$, 400 MHz) δ 8.05 (d, J=5.2 Hz, 1H), 7.24 (d, J=3.6 Hz, 1H), 6.97 (d, J=5.2 Hz, 1H), 6.57 (d, J=3.2 Hz, 1H), 1.79-1.73 (m, 3H), 1.03 (d, J=7.6 Hz, 18H).

Preparation of 4-chloro-1-triisopropylsilyl-pyrrolo[2,3-b]pyridin-5-ol

To a solution of (4-chloropyrrolo[2,3-b]pyridin-1-yl)-tri-isopropyl-silane (2 g, 6.47 mmol, 1 eq) in THF (40 mL) was added s-BuLi (1.3 M, 10.96 mL, 2.2 eq) dropwise at −78° C., the resulting mixture was stirred for 30 min under $N_2$ atmosphere. Then camphorsulfonyloxaziridine (2.15 g, 9.39 mmol, 1.45 eq) was added to the mixture at −78° C. under $N_2$ atmosphere, and the reaction mixture was stirred at −78° C. for 1 h. The reaction was quenched by adding saturated aq. $NH_4Cl$ (50 mL) and extracted with EtOAc (50 mL×3). The combined organic layers were washed with brine (100 mL×2), dried over $Na_2SO_4$, filtered and concentrated under reduced pressure to give a residue, which was purified by column chromatography ($SiO_2$, Petroleum ether/Ethyl acetate=10/1 to 5/1) to give 4-chloro-1-triisopropylsilyl-pyrrolo[2,3-b]pyridin-5-ol (0.9 g, 2.77 mmol, 42.78% yield) as a yellow oil. $^1$H NMR (CDCl$_3$, 400 MHz) δ 7.99 (s, 1H), 7.24 (d, J=3.2 Hz, 1H), 6.46 (d, J=3.6 Hz, 1H), 5.04 (s, 1H), 1.77-1.70 (m, 3H), 1.03 (d, J=7.6 Hz, 18H).

Preparation of Methyl (4-chloro-5-methoxy-pyrrolo[2,3-b]pyridin-1-yl)-triisopropyl-silane

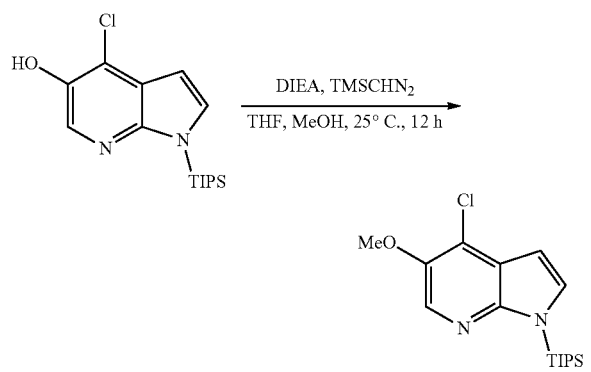

To a mixture of 4-chloro-1-triisopropylsilyl-pyrrolo[2,3-b]pyridin-5-ol (3 g, 9.23 mmol, 1 eq) and DIEA (1.19 g, 9.23 mmol, 1.61 mL, 1 eq) in THF (6 mL)/MeOH (2 mL) was added TMSCHN$_2$ (2 M, 9.23 mL, 2 eq) dropwise at 25° C. under N$_2$; the mixture was stirred at 25° C. for 12 h. The reaction mixture was quenched with H$_2$O (150 mL) and extracted with EtOAc (50 mL×3). The combined organic layers were washed with brine (20 mL×2), dried over Na$_2$SO$_4$, filtered and concentrated under reduced pressure to give a residue, which was purified by column chromatography (SiO$_2$, Petroleum ether/Ethyl acetate=15/1 to 5/1) give (4-chloro-5-methoxy-pyrrolo[2,3-b]pyridin-1-yl)-triisopropyl-silane (2.8 g, 8.26 mmol, 89.47% yield) as a yellow oil. $^1$H NMR (CDCl$_3$, 400 MHz) δ 7.98 (s, 1H), 7.25 (d, J=3.2 Hz, 1H), 6.51 (d, J=3.6 Hz, 1H), 3.92 (s, 3H), 1.79-1.72 (m, 3H), 1.04 (d, J=7.6 Hz, 18H).

Preparation of 4-iodo-5-methoxy-1H-pyrrolo[2,3-b]pyridine

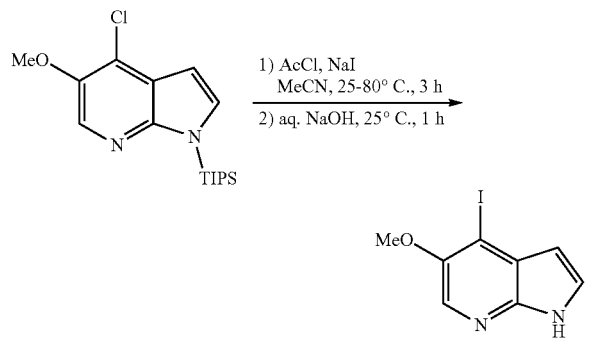

To a mixture of (4-chloro-5-methoxy-pyrrolo[2,3-b]pyridin-1-yl)-triisopropyl-silane (5.3 g, 15.64 mmol, 1 eq) and acetyl chloride (3.68 g, 46.91 mmol, 3.35 mL, 3 eq) in CH$_3$CN (20 mL) was added NaI (23.44 g, 156.37 mmol, 10 eq) in one portion at 25° C. under N$_2$ atmosphere. The mixture was stirred at 80° C. for 3 h. The reaction mixture was quenched by adding 2N aq. K$_2$CO$_3$ (50 mL) and was extracted with EtOAc (50 mL×3). The combined organic layers were washed with brine (20 mL×2), dried over Na$_2$SO$_4$, filtered and concentrated under reduced pressure to give a residue. To the residue in THF (50 mL) was added 2 N aq. NaOH (10 mL), and the mixture was stirred at 25° C. for 1 h. To the reaction mixture was added H$_2$O (50 mL), and the aqueous phase was extracted with EtOAc (50 mL×3). The combined organic layers were washed with brine (20 mL×2), dried over Na$_2$SO$_4$, filtered and concentrated under reduced pressure to give a residue, which was purified by trituration with MTBE (50 mL) to give 4-iodo-5-methoxy-1H-pyrrolo[2,3-b]pyridine (3.5 g, 12.77 mmol, 81.67% yield) as a yellow solid. $^1$H NMR (DMSO-d$_6$, 400 MHz) δ 11.82 (s, 1H), 7.97 (s, 1H), 7.55 (d, J=3.2 Hz, 1H), 6.16 (d, J=3.2 Hz, 1H), 3.90 (s, 3H).

Preparation of (4-iodo-5-methoxy-pyrrolo[2,3-b]pyridin-1-yl)-triisopropyl-silane

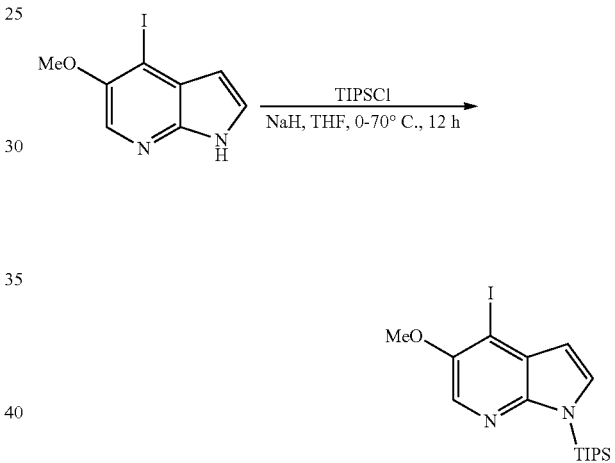

To a solution of 4-iodo-5-methoxy-1H-pyrrolo[2,3-b]pyridine (5 g, 18.24 mmol, 1 eq) in THF (200 mL) was added NaH (1.61 g, 40.14 mmol, 60% purity, 2.2 eq) portionwise at 0° C., and the mixture was stirred at 0° C. for 30 min. TIPSCl (5.28 g, 27.37 mmol, 5.86 mL, 1.5 eq) was added dropwise to the mixture at 0° C., then heated to 70° C. for 12 h. The reaction mixture was quenched by adding saturated aq. NH$_4$Cl (50 mL) and extracted with EtOAc (20 mL×3). The combined organic layers were washed with brine (100 mL×2), dried over Na$_2$SO$_4$, filtered and concentrated under reduced pressure to give a residue, which was purified by column chromatography (SiO$_2$, Petroleum ether/Ethyl acetate=20/1 to 10/1) to give (4-iodo-5-methoxy-pyrrolo[2,3-b]pyridin-1-yl)-triisopropyl-silane (6 g, 13.94 mmol, 76.41% yield) as a yellow oil. $^1$H NMR (CDCl$_3$, 400 MHz) δ 7.81 (s, 1H), 7.28 (d, J=3.2 Hz, 1H), 6.33 (d, J=3.6 Hz, 1H), 3.91 (s, 3H), 1.78-1.72 (m, 3H), 1.04 (d, J=7.2 Hz, 18H).

Preparation of Tert-Butyl N-[3-[hydroxy-(5-methoxy-1-triisopropylsilyl-pyrrolo [2,3-b]pyridin-4-yl)methyl]cyclobutyl]carbamate

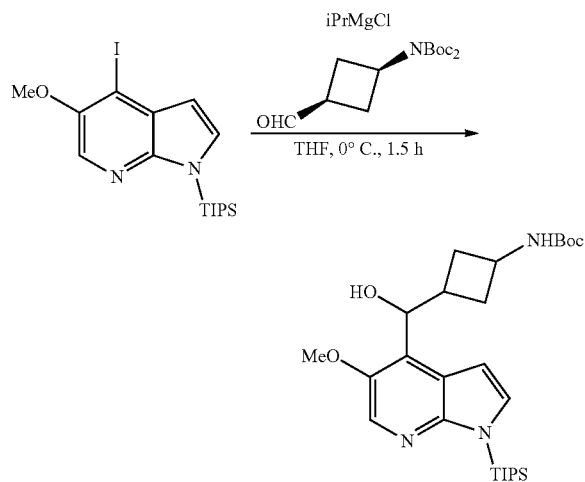

40) To a mixture of (4-iodo-5-methoxy-pyrrolo[2,3-b]pyridin-1-yl)-triisopropyl-silane (2 g, 4.65 mmol, 1 eq) in THF (30 mL) was added i-PrMgCl (2 M, 5.81 mL, 2.5 eq) dropwise at 0° C.; the resulting mixture was stirred at 0° C. for 30 min under $N_2$ atmosphere. Then tert-butyl N-tert-butoxycarbonyl-N-(3-formylcyclobutyl)carbamate (1.53 g, 5.11 mmol, 1.1 eq) was added in one portion, and the mixture was stirred at 0° C. for 1 h. The reaction mixture was quenched with saturated aq. $NH_4Cl$ (50 mL) and extracted with EtOAc (50 mL×3). The combined organic layers were washed with brine (50 mL×2), dried over $Na_2SO_4$, filtered and concentrated under reduced pressure to give a residue, which was purified by column chromatography ($SiO_2$, Petroleum ether/Ethyl acetate=10/1 to 3/1) to give tert-butyl N-[3-[hydroxy-(5-methoxy-1-triisopropylsilyl-pyrrolo[2,3-b]pyridin-4-yl)methyl]cyclobutyl]carbamate (1.8 g, 3.57 mmol, 76.90% yield) as a yellow oil. $^1$H NMR ($CDCl_3$, 400 MHz) δ 7.94 (s, 1H), 7.20 (d, J=3.6 Hz, 1H), 6.59 (d, J=3.6 Hz, 1H), 4.96 (d, J=6.4 Hz, 1H), 4.66-4.64 (m, 1H), 3.88 (s, 3H), 2.47-2.41 (m, 2H), 2.40-2.39 (m, 1H), 1.81-1.71 (m, 5H), 1.35 (s, 9H), 1.03 (d, J=7.6 Hz, 18H).

Preparation of Tert-Butyl N-[3-(5-methoxy-1-triisopropylsilyl-pyrrolo[2,3-b] pyridine-4-carbonyl)cyclobutyl]carbamate

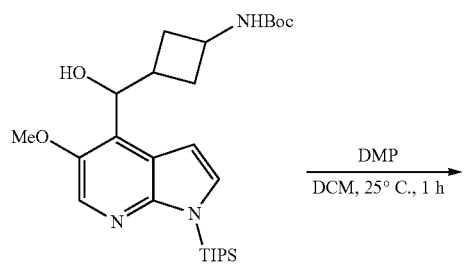

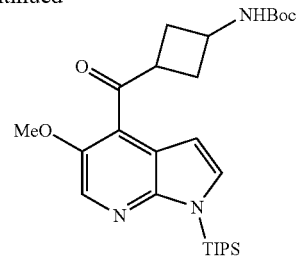

To a mixture of tert-butyl N-[3-[hydroxy-(5-methoxy-1-triisopropylsilyl-pyrrolo[2,3-b]pyridin-4-yl)methyl]cyclobutyl]carbamate (1.8 g, 3.57 mmol, 1 eq) in DCM (40 mL) was added DMP (1.82 g, 4.29 mmol, 1.33 mL, 1.2 eq) portionwise at 25° C. under $N_2$ atmosphere; the mixture was stirred at 25° C. for 1 h. $H_2O$ (50 mL) was added, and the reaction mixture was extracted with EtOAc (50 mL×3). The combined organic layers were washed with brine (50 mL×2), dried over $Na_2SO_4$, filtered and concentrated under reduced pressure to give a residue, which was purified by column chromatography ($SiO_2$, Petroleum ether/Ethyl acetate=10/1 to 5/1) to give tert-butyl N-[3-(5-methoxy-1-triisopropylsilyl-pyrrolo[2,3-b]pyridine-4-carbonyl)cyclobutyl]carbamate (1.5 g, 2.99 mmol, 83.67% yield) as a yellow oil. $^1$H NMR ($CDCl_3$, 400 MHz) δ 8.04 (s, 1H), 7.32 (d, J=3.2 Hz, 1H), 6.73 (d, J=3.6 Hz, 1H), 4.11-4.07 (m, 1H), 3.91 (s, 3H), 3.64-3.61 (m, 1H), 2.57-2.55 (m, 2H), 2.13-2.08 (m, 2H), 1.77-1.71 (m, 3H), 1.36 (s, 9H), 1.03 (d, J=7.6 Hz, 18H).

Preparation of Tert-Butyl N-[3-[(Z)-1-(5-methoxy-1-triisopropylsilyl-pyrrolo [2,3-b]pyridin-4-yl)-2-(4,4,5,5-tetramethyl-1,3,2-dioxaborolan-2-yl)vinyl]cyclobutyl]carbamate

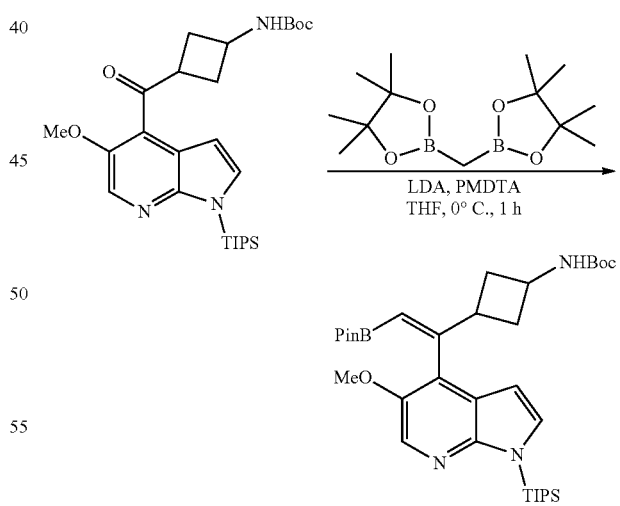

To a mixture of LDA (2 M, 6.98 mL, 7 eq) and N'-[2-(dimethylamino)ethyl]-N,N,N'-trimethyl-ethane-1,2-diamine (460.71 mg, 2.66 mmol, 555.08 uL, 4 eq) in THF (10 mL) was added a solution of 4,4,5,5-tetramethyl-2-[(4,4,5,5-tetramethyl-1,3,2-dioxaborolan-2-yl)methyl]-1,3,2-dioxaborolane (2.67 g, 9.97 mmol, 5 eq) in THF (10 mL) dropwise at 0° C.; the mixture was stirred at 0° C. for 10 min. Then tert-butyl N-[3-(5-methoxy-1-triisopropylsilylpyrrolo[2,3-b]pyridine-4-carbonyl) cyclobutyl]carbamate (1 g, 1.99 mmol, 1 eq) in THF (10 mL) was added to the mixture dropwise at 0° C.; the resulting mixture was stirred at 0° C. for 1 h. The reaction mixture was quenched by adding sat. aq. NH₄Cl (50 mL) and extracted with EtOAc (30 mL×3). The combined organic layers were washed with brine (30 mL×2), dried over Na₂SO₄, filtered and concentrated under reduced pressure to give a residue, which was purified by column chromatography (SiO₂, Petroleum ether/Ethyl acetate=12/1 to 8/1) to give tert-butyl N-[3-[(Z)-1-(5-methoxy-1-triisopropylsilyl-pyrrolo[2,3-b]pyridin-4-yl)-2-(4,4,5,5-tetramethyl-1,3,2-dioxaborolan-2-yl)vinyl] cyclobutyl]carbamate (0.95 g, 1.52 mmol, 76.18% yield) as yellow oil.

¹H NMR (CDCl₃, 400 MHz) δ 7.94 (s, 1H), 7.12 (d, J=3.6 Hz, 1H), 6.22 (d, J=3.6 Hz, 1H), 5.61 (s, 1H), 4.63-4.62 (m, 1H), 4.53-4.38 (m, 1H), 3.81 (s, 3H), 2.47-2.45 (m, 2H), 2.25-2.20 (m, 2H), 1.81-1.73 (m, 5H), 1.36 (s, 9H), 1.05 (s, 18H).

Preparation of 9-((1s,3s)-3-aminocyclobutyl)-[1,2] oxaborinino[5,6-d]pyrrolo[2,3-b] pyridin-7(3H)-ol

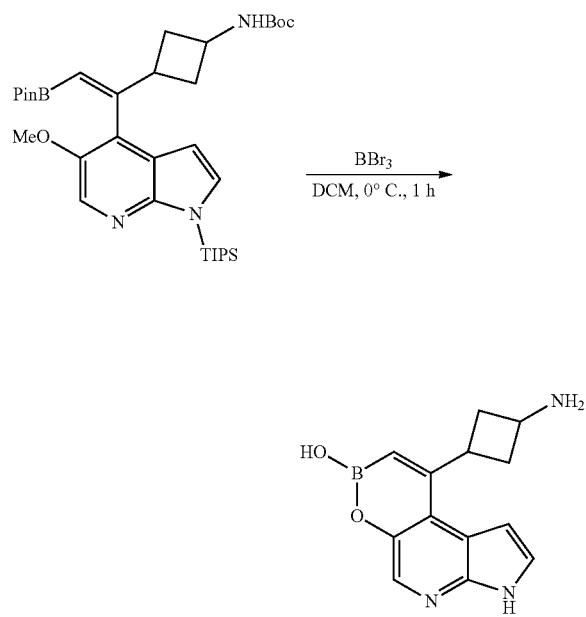

To a mixture of tert-butyl N-[3-[(E)-1-(5-methoxy-1-triisopropylsilyl-pyrrolo[2,3-b]pyridin-4-yl)-2-(4,4,5,5-tetramethyl-1,3,2-dioxaborolan-2-yl)vinyl]cyclobutyl]carbamate (0.9 g, 1.44 mmol, 1 eq) in DCM (10 mL) was added BBr₃ (1.08 g, 4.32 mmol, 415.77 uL, 3 eq) in one portion at 0° C. under N₂ atmosphere; the resulting mixture was stirred at 0° C. for 1 h. Then the reaction mixture was quenched by adding H₂O (10 mL) and extracted with EtOAc (10 mL×3) to remove the impurity. The aqueous layer was directly freeze-dried to give 9-((1s,3s)-3-aminocyclobutyl)-[1,2] oxaborinino[5,6-d]pyrrolo[2,3-b] pyridin-7(3H)-ol (0.5 g, crude) as a white solid, which was used for the next step. ¹H NMR (DMSO-d₆, 400 MHz) δ 8.25 (s, 1H), 7.56 (d, J=3.2 Hz, 1H), 6.89 (d, J=3.6 Hz, 1H), 6.27 (s, 1H), 4.20-4.01 (m, 1H), 3.89-3.85 (m, 2H), 2.64-2.62 (m, 1H), 2.17-2.08 (m, 2H).

Preparation of N-((1s,3s)-3-(7-hydroxy-3,7-dihydro-[1,2]oxaborinino[5,6-d]pyrrolo [2,3-b]pyridin-9-yl) cyclobutyl)propane-1-sulfonamide

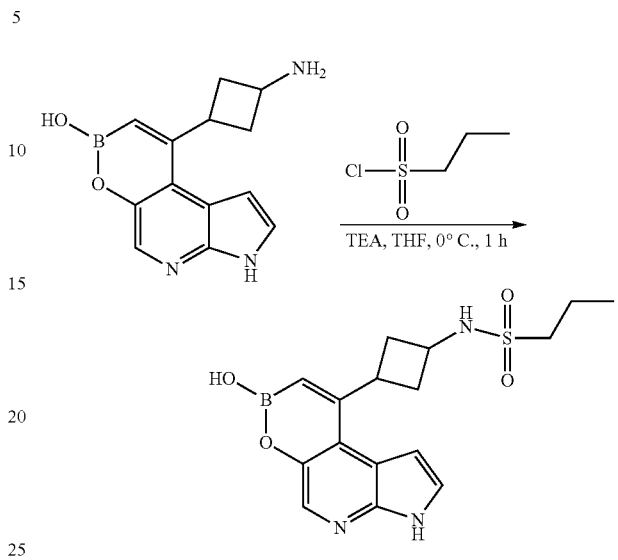

To a mixture of 9-((1s,3s)-3-aminocyclobutyl)-[1,2]oxaborinino[5,6-d]pyrrolo [2,3-b]pyridin-7(3H)-ol (250 mg, 980.09 umol, 1 eq) and TEA (99 mg, 980.09 umol, 136.42 uL, 1 eq) in THF (1 mL) was added propane-1-sulfonyl chloride (279 mg, 1.96 mmol, 220.10 uL, 2 eq) in one portion at 0° C.; the resulting mixture was stirred at 0° C. for 1 h. Then H₂O (10 mL) was added, and the reaction mixture was extracted with EtOAc (5 mL×3). The combined organic layers were washed with brine, dried over Na₂SO₄, filtered and concentrated under reduced pressure to give a residue, which was purified by twice prep-TLC (SiO₂, PE:EA=0:1) to give N-((1s,3s)-3-(7-hydroxy-3,7-dihydro-[1,2]oxaborinino[5,6-d]pyrrolo[2,3-b]pyridin-9-yl)cyclobutyl)propane-1-sulfonamide (32 mg, 88.59 μmol, 9.04% yield) as a white solid. ¹H NMR (DMSO-d₆, 400 MHz) δ 11.81 (s, 1H), 8.93 (s, 1H), 8.25 (s, 1H), 7.57 (s, 1H), 7.45 (d, J=8.4 Hz, 1H), 6.93 (s, 1H), 6.22 (s, 1H), 3.97-3.96 (m, 1H), 3.70-3.69 (m, 1H), 2.97-2.95 (m, 2H), 2.93-2.73 (m, 2H), 2.02-2.00 (m, 2H), 1.69-1.66 (m, 2H), 0.98 (t, J=7.6 Hz, 3H). MS (ESI): mass calcd. For C₁₆H₂₀BN₃O₄S, 361.13, m/z. found 362.1 [M+H]⁺. Purity by HPLC: 92.73% (220 nm), 96.17% (254 nm).

Preparation of Ethyl 3-(dibenzylamino)cyclobutanecarboxylate

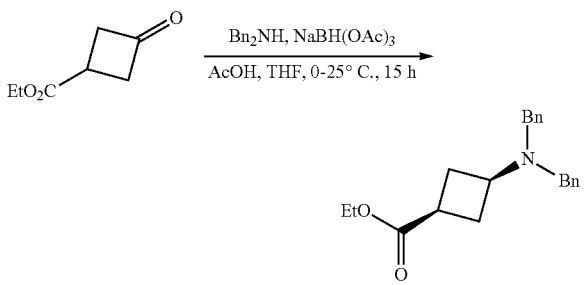

To a mixture of ethyl 3-oxocyclobutanecarboxylate (25 g, 175.87 mmol, 1 eq) and AcOH (15.84 g, 263.80 mmol, 15.09 mL, 1.5 eq) in THF (500 mL) was added N-benzyl-1-phenylmethanamine (52.04 g, 263.80 mmol, 50.53 mL, 1.5 eq) in one portion at 0° C.; the resulting mixture was stirred at 0° C. for 1 h. Then NaBH(OAc)₃ (55.91 g, 263.80 mmol, 1.5 eq) was added to the reaction in portions at 0° C., the resulting mixture was kept stirring at 25° C. for 14 h. The solvent was removed under reduced pressure, and the pH of the mixture was adjusted to 9 by adding saturated aq. Na₂CO₃, the mixture was extracted with EtOAc (500 mL×3). The combined organic layers were washed with brine (500 mL×2), dried over anhydrous Na₂SO₄, filtered and concentrated under reduced pressure to give a residue, which was purified by flash silica gel chromatography (ISCO®; 330 g SepaFlash® Silica Flash Column, Eluent of 0~10% Ethyl acetate/Petroleum ethergradient @ 100 mL/min) to give ethyl 3-(dibenzylamino)cyclobutanecarboxylate (150 g, 463.78 mmol, 65.93% yield) as a colorless oil.

¹H NMR (CDCl₃, 400 MHz) δ 7.32-7.26 (m, 8H), 7.24-7.22 (m, 2H), 4.13 (q, J=6.8 Hz, 2H), 3.51 (s, 4H), 3.14-3.09 (m, 1H), 2.67-2.62 (m, 1H), 2.23-2.14 (m, 4H), 1.23 (t, J=6.8 Hz, 3H).

Preparation of ethyl 3-aminocyclobutanecarboxylate

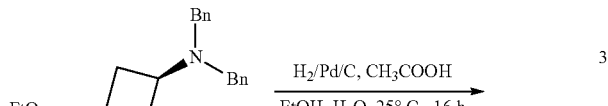

To a solution of ethyl 3-(dibenzylamino)cyclobutanecarboxylate (59 g, 182.42 mmol, 1 eq) in EtOH (1000 mL) and H₂O (60 mL) was added AcOH (10.95 g, 182.42 mmol, 10.43 mL, 1 eq) and Pd/C (20 g, 182.42 mmol, 10% purity). The suspension was degassed in vacuo and purged with H₂ three times. The mixture was stirred under H₂ (45 psi) at 25° C. for 16 h. Then the reaction mixture was filtered and concentrated under reduced pressure. 4 N HCl/EtOAc (300 mL) was added to the residue, and white solid was precipitated. The white solid was collected by filtration and dried in vacuo to give ethyl 3-aminocyclobutanecarboxylate (48 g, 267.19 mmol, 73.24% yield, HCl) as a white solid. ¹H NMR (DMSO-d₆, 400 MHz) δ 8.46 (br, 3H), 4.05 (q, J=6.8 Hz, 2H), 3.59-3.55 (m, 1H), 2.96-2.92 (m, 1H), 2.42-2.38 (m, 2H), 2.32-2.26 (m, 2H), 1.19-1.15 (t, J=6.8 Hz, 3H).

Preparation of Ethyl 3-(tert-butoxycarbonylamino)cyclobutanecarboxylate

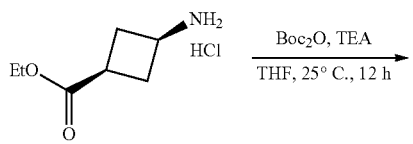

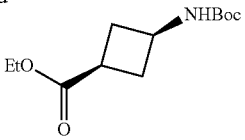

To a mixture of ethyl 3-aminocyclobutanecarboxylate (24 g, 133.60 mmol, 1 eq, HCl) and TEA (40.56 g, 400.79 mmol, 55.79 mL, 3 eq) in THF (300 mL) was added (Boc)₂O (43.74 g, 200.40 mmol, 46.04 mL, 1.5 eq) dropwise at 25° C. The mixture was stirred at 25° C. for 12 h under N₂ atmosphere. Then the reaction mixture was poured into saturated aq. NaHCO₃ (200 mL) and extracted with EtOAc (200 mL×3). The combined organic layers were washed with brine (200 mL×2), dried over anhydrous Na₂SO₄, filtered and concentrated in vacuo to give a residue, which was purified by flash silica gel chromatography (ISCO®; 330 g SepaFlash® Silica Flash Column, Eluent of 0~10% Ethyl acetate/Petroleum ethergradient @ 100 mL/min) to give ethyl 3-(tert-butoxycarbonylamino)cyclobutanecarboxylate (50 g, 205.51 mmol, 76.91% yield) as a white solid. ¹H NMR (CDCl₃, 400 MHz) δ 4.86 (br, 1H), 4.14-4.09 (m, 3H), 2.78-2.69 (m, 1H), 2.59-2.57 (m, 2H), 2.11-2.04 (m, 2H), 1.42 (s, 9H), 1.24 (t, J=6.8 Hz, 3H).

Preparation of Tert-Butyl N-[3-[methoxy(methyl)carbamoyl]cyclobutyl]carbamate

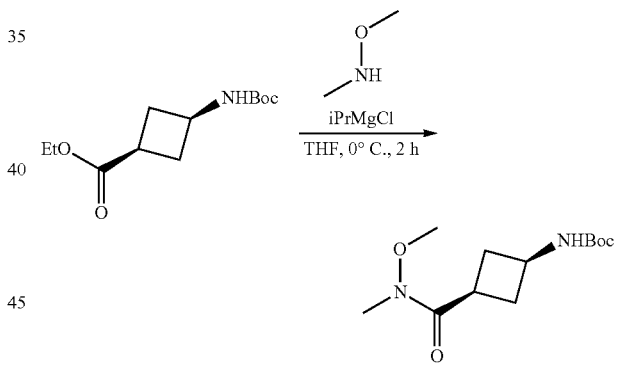

To a mixture of ethyl 3-(tert-butoxycarbonylamino)cyclobutanecarboxylate (25 g, 102.75 mmol, 1 eq) and N-methoxymethanamine (20.05 g, 205.51 mmol, 2 eq, HCl) in THF (250 mL) was added dropwise i-PrMgCl (2 M, 205.51 mL, 4 eq) at 0° C. The mixture was stirred at 0° C. for 2 h. The reaction mixture was poured into saturated aq. NH₄Cl (250 mL), extracted with EtOAc (200 mL×3). The combined organic layers were washed with brine (200 mL×2), dried over anhydrous Na₂SO₄, filtered and concentrated under reduced pressure to give a residue, which was purified by flash silica gel chromatography (ISCO®; 330 g SepaFlash® Silica Flash Column, Eluent of 0-30% Ethyl acetate/Petroleum ethergradient @ 100 mL/min) to give tert-butyl N-[3-[methoxy(methyl)carbamoyl]cyclobutyl]carbamate (44 g, 170.34 mmol, 82.88% yield) as a white solid. ¹H NMR (CDCl₃, 400 MHz) δ 5.03 (br, 1H), 4.20-4.00 (m, 1H), 3.63 (s, 3H), 3.16-3.15 (m, 4H), 2.51-2.49 (m, 2H), 2.15-2.07 (m, 2H), 1.41 (s, 9H).

Preparation of Tert-Butyl N-(3-formylcyclobutyl)carbamate

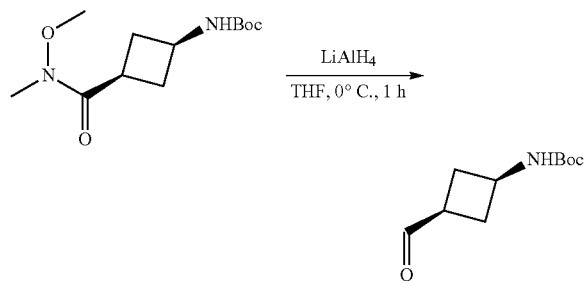

To a mixture of tert-butyl N-[3-[methoxy(methyl)carbamoyl]cyclobutyl]carbamate (15 g, 58.07 mmol, 1 eq) in THF (150 mL) was added LiAlH₄ (2.64 g, 69.68 mmol, 1.2 eq) in portions at 0° C. The mixture was kept stirring at 0° C. for 1 h, then quenched by adding Na₂SO₄.10H₂O (50 g) while stirring. The resulting mixture was filtered through pad of celite to remove the insoluble impurities, and the filtrate was washed with HCl 50 mL (1 N), dried over anhydrous Na₂SO₄, filtered and concentrated under reduced pressure to give a residue, which was purified by flash silica gel chromatography (ISCO®; 330 g SepaFlash® Silica Flash Column, Eluent of 0-30% Ethyl acetate/Petroleum ethergradient @ 100 mL/min) to give tert-butyl N-(3-formylcyclobutyl)carbamate (9 g, 45.17 mmol, 38.89% yield) as a white solid.

$^1$H NMR (CDCl₃, 400 MHz) δ 9.69 (s, 1H), 4.72 (br. s, 1H), 4.19-4.11 (m, 1H), 2.92-2.86 (m, 1H), 2.58-2.53 (m, 2H), 2.11-2.03 (m, 2H), 1.44 (s, 9H).

Preparation of Tert-Butyl N-tert-butoxycarbonyl-N-(3-formylcyclobutyl)carbamate

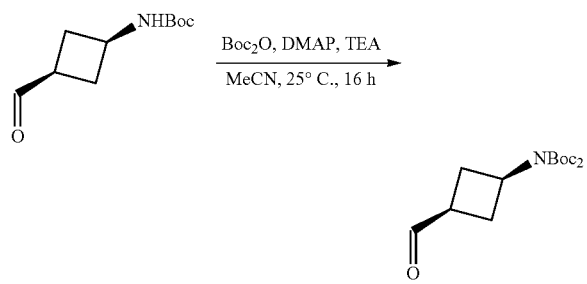

To a mixture of tert-butyl N-(3-formylcyclobutyl)carbamate (9 g, 45.17 mmol, 1 eq) in MeCN (90 mL) was added TEA (13.71 g, 135.51 mmol, 18.86 mL, 3 eq), DMAP (2.76 g, 22.59 mmol, 0.5 eq) and Boc₂O (14.79 g, 67.76 mmol, 15.57 mL, 1.5 eq) in one portion at 25° C. The resulting mixture was stirred at 25° C. for 16 h. Then the mixture was poured into H₂O (100 mL) and extracted with EtOAc (100 mL×3). The combined organic layers were washed with brine (100 mL×2), dried over anhydrous Na₂SO₄, filtered and concentrated under reduced pressure to give a residue, which was purified by flash silica gel chromatography (ISCO®; 120 g SepaFlash® Silica Flash Column, eluent of 0-30% Ethyl acetate/Petroleum ether gradient @100 mL/min) to give tert-butyl N-tert-butoxycarbonyl-N-(3-formylcyclobutyl)carbamate (4 g, 13.36 mmol, 29.58% yield) as a yellow oil. $^1$H NMR (CDCl₃, 400 MHz) δ 9.68 (s, 1H), 4.48-4.38 (m, 1H), 2.83-2.81 (m, 1H), 2.58-2.49 (m, 4H), 1.51 (s, 18H).

Example 6: Preparation of N-(3-(7-hydroxy-3,7-dihydro-[1,2]oxaborinino[5,6-d]pyrrolo[2,3-b] pyridin-9-yl)cyclobutyl)cyclopropanesulfonamide

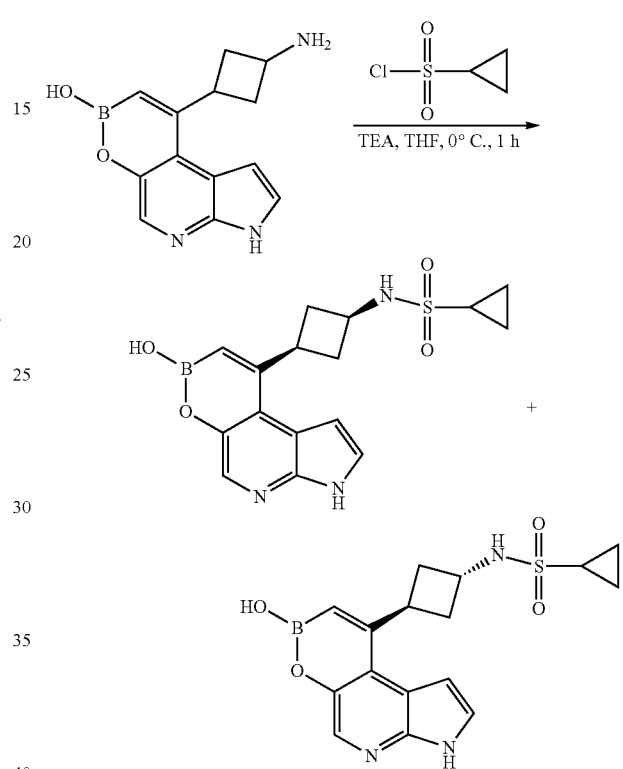

To a mixture of 9-((1 s,3s)-3-aminocyclobutyl)-[1,2]oxaborinino[5,6-d] pyrrolo[2,3-b]pyridin-7(3H)-ol (250 mg, 980.09 umol, 1 eq) and TEA (99 mg, 980.09 umol, 136.42 uL, 1 eq) in THF (4 mL) was added cyclopropanesulfonyl chloride (275 mg, 1.96 mmol, 79.24 uL, 2 eq) in one portion at 0° C.; the resulting mixture was stirred at 0° C. for 1 h. The reaction mixture was quenched with H₂O (10 mL), and extracted with EtOAc (5 mL×2). The combined organic layers were washed with brine, dried over Na₂SO₄, filtered and concentrated under reduced pressure to give a residue, which was purified by prep-HPLC (column: Nano-micro Kromasil C18 100*30 mm 8 um; mobile phase: [water (0.1% TFA)-ACN]; B %: 15%-35%,10 min) to give N-(3-(7-hydroxy-3,7-dihydro-[1,2]oxaborinino[5,6-d]pyrrolo[2,3-b]pyridin-9yl)cyclobutyl) cyclopropanesulfonamide (45 mg, 125.28 umol, 12.78% yield) as two diastereomers. Peak 1: (20 mg, 95% purity) as a white solid. Peak 2: (25 mg, 90% purity) as a white solid.

Peak 1: $^1$H NMR (DMSO-d₆, 400 MHz) δ 11.82 (s, 1H), 8.88 (br. s, 1H), 8.28 (s, 1H), 7.67 (d, J=9.6 Hz, 1H), 7.57 (s, 1H), 6.66 (s, 1H), 6.41 (s, 1H), 3.95-3.88 (m, 1H), 3.86-3.82 (m, 2H), 2.63-2.60 (m, 3H), 2.58-2.47 (m, 1H), 0.93-0.89 (m, 4H). MS (ESI): mass calcd. For C₁₈H₁₈BN₃O₄S, 359.11, m/z. found 361.0 [M+H]⁺. Purity by HPLC: 95.41% (220 nm), 95.07% (254 nm).

Peak 2: ¹H NMR (DMSO-d₆, 400 MHz) δ 11.80 (s, 1H), 8.26 (s, 1H), 7.57 (s, 1H), 7.67 (d, J=9.6 Hz, 1H), 6.94 (s, 1H), 6.24 (s, 1H), 4.02-3.99 (m, 1H), 3.73-3.71 (m, 2H), 2.76-2.75 (m, 2H), 2.25-2.20 (m, 1H), 2.07-2.04 (m, 1H), 0.95-0.93 (m, 4H). MS (ESI): mass calcd. For C₁₈H₁₈BN₃O₄S, 359.11, m/z. found 361.0 [M+H]⁺. Purity by HPLC: 94.92% (220 nm), 92.89% (254 nm).

Example 7: N-((1r,3r)-3-(4-hydroxy-3-methyl-4,7-dihydro-3H-pyrrolo[3',2':5,6]pyrido[3,4-d][1,2,3]diazaborinin-1-yl)cyclobutyl)propane-1-sulfonamide

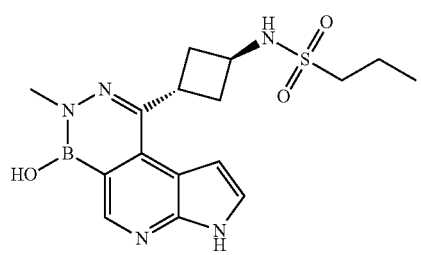 [SMILES: CCCS(=O)(=O)N[C@H]1C[C@H](C2=NN(C)B(O)c3cnc4[nH]ccc4c32)C1]

The title compound was prepared by following the experimental procedures in the Example above (in Example 4) and purified by preparative SFC. The analytical data of this compound are shown as following. ¹HNMR (400 MHz, DMSO-d₆): δ 12.11 (s, 1H), 9.12 (s, 1H), 8.46 (s, 1H), 7.63-7.58 (m, 2H), 6.74-6.73 (m, 1H), 4.05-3.95 (m, 1H), 3.90-3.80 (m, 1H), 3.59 (s, 3H), 2.89-2.85 (m, 2H), 2.74-2.60 (m, 2H), 2.55-2.42 (m, 2H), 1.75-1.60 (m, 2H), 0.94 (t, J=7.2 Hz, 3H). ppm. HPLC purity: 98.21% at 210 nm and 98.20% at 254 nm. MS: m/z=376.1 (M+H)⁺.

Example 8: 1-((1R,2s,3S,5s,7s)-5-hydroxyadamantan-2-yl)-3,7-dihydro-4H-pyrrolo[3',2':5,6]pyrido[3,4-d][1,2,3]diazaborinin-4-ol and 1-((1R,2r,3S,5s,7s)-5-hydroxyadamantan-2-yl)-3,7-dihydro-4H-pyrrolo[3',2':5,6]pyrido[3,4-d][1,2,3]diazaborinin-4-ol

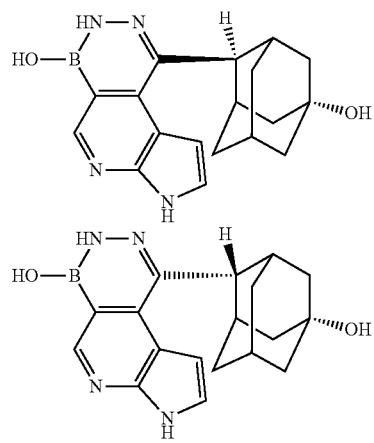

The title compounds were prepared by using the scheme and following procedures shown below:

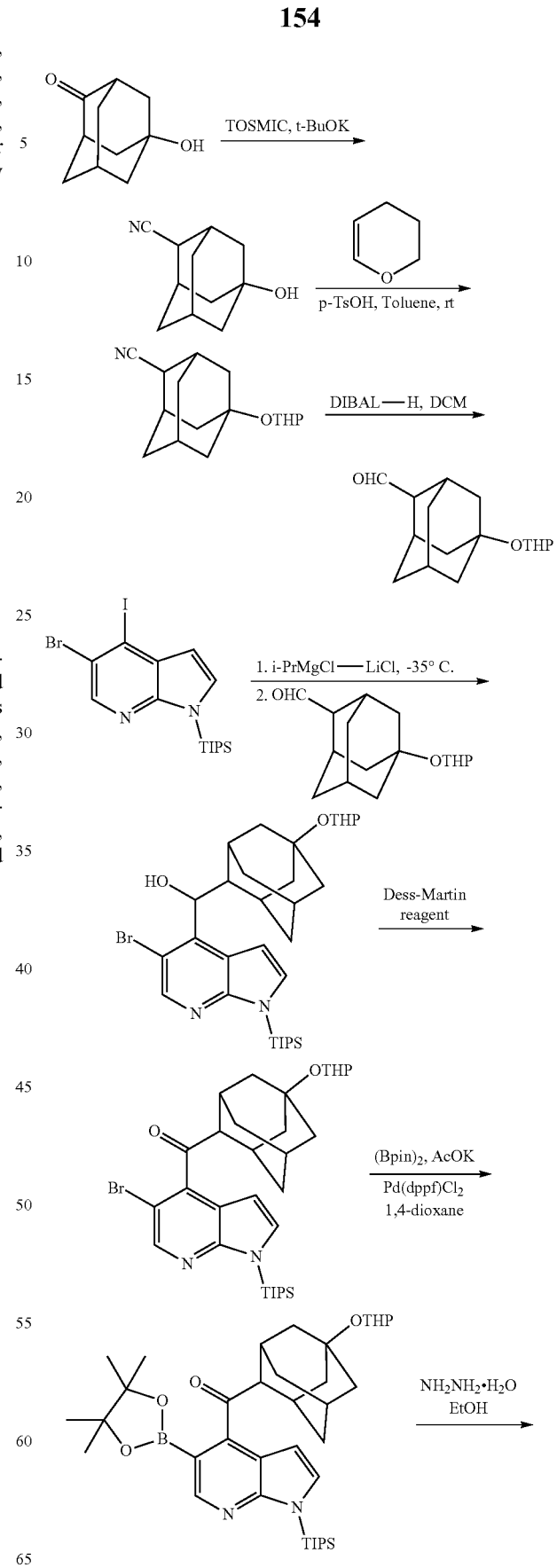

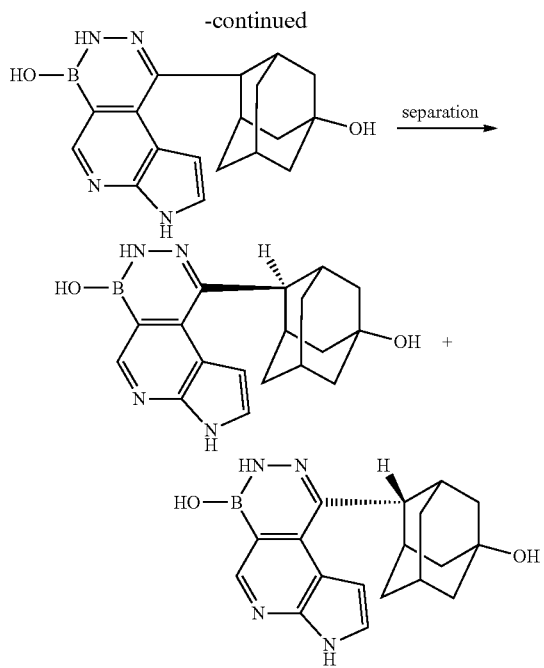

To a solution of (1R,3S,5s,7s)-5-hydroxyadamantan-2-one (10.0 g, 60.2 mmol) and toluenesulfonylmethyl isocyanide (TOSMIC, 15.2 g, 78.0 mol) in 1,2-dimethoxyethane (200 mL) and anhydrous EtOH (10 mL) at 0° C. was added t-BuOK (16.8 g, 150 mmol) in portions. After the addition was completed, the reaction mixture was slowly warmed to 40° C. with stirring for 2 h. TLC showed the reaction was completed. It was cooled to room temperature and filtered off the solid. The filtrate was concentrated in vacuo to give the crude product. Purification by column chorography (PE/EtOAc=10/1 to 5/1, v/v) gave the desired compound, (1R,2s,3S,5s,7s)-5-hydroxyadamantane-2-carbonitrile, as a white solid (4.8 g, yield 45%). $^1$H NMR (400 MHz, DMSO-$d_6$): δ 4.61 (s, 1H), 3.00 (s, 1H), 2.26 (s, 2H), 2.05-1.99 (m, 1H), 1.87-1.80 (m, 2H), 1.63-1.54 (m, 8H) ppm. To a solution of (1R,2s,3S,5s,7s)-5-hydroxyadamantane-2-carbonitrile (4.8 g, 27.1 mmol) and p-TsOH (462 mg, 2.7 mmol) in toluene (50 mL) at rt was added 3,4-dihydro-2H-pyran (11.4 g, 136 mmol) dropwise. The reaction mixture was stirred at rt for 1 h and TLC showed no starting materials left. The reaction mixture was concentrated at 30° under reduced pressure to dryness, and the residue was purified by column chromatography (PE/EtOAc=50/1, v/v) to afford (1R,2s,3S,5s,7s)-5-((tetrahydro-2H-pyran-2-yl)oxy)adamantane-2-carbonitrile as a yellow oil (3.8 g, 54%). $^1$HNMR (400 MHz, CDCl$_3$): δ 4.90-4.77 (m, 1H), 4.02-3.87 (m, 1H), 3.54-3.37 (m, 1H), 2.84-2.75 (m, 1H), 2.45-2.35 (m, 2H), 2.28-2.14 (m, 2H), 2.10-2.01 (m, 1H), 1.98-1.73 (m, 7H), 1.64 (t, J=11.1 Hz, 3H), 1.56-1.46 (m, 4H) ppm. To a solution of (1R,2s,3S,5s,7s)-5-((tetrahydro-2H-pyran-2-yl)oxy)adamantane-2-carbonitrile (3.8 g, 14.6 mmol) in dry DCM (48 mL) at −70° C. was added DIBAL-H (14.6 mL, 1.5 M in toluene) dropwise. After the addition was completed, the reaction mixture was slowly warmed to rt with stirring for 1 h and TLC showed the cyano compound was disappeared. The reaction mixture was re-cooled to 0° C. and quenched with saturated NH$_4$Cl (3 mL). The mixture was stirred at rt for 30 min and anhydrous Na$_2$SO$_4$ was added. It was filtered and the filtrate was concentrated under reduced pressure to dryness. Purification of the residue by column chromatography (PE/EtOAc=50/1, v/v) afforded (1R,2s,3S,5s,7s)-5-((tetrahydro-2H-pyran-2-yl)oxy)adamantane-2-carbaldehyde as a yellow oil (1.7 g, 44%, cis:trans ratio was about 1:1 by $^1$HNMR). $^1$HNMR (400 MHz, CDCl$_3$): δ 9.75 & 9.68 (two s, 1H), 4.93-4.72 (m, 1H), 4.02-3.84 (m, 1H), 3.55-3.34 (m, 1H), 2.70-2.55 (m, 2H), 2.39-2.08 (m, 2H), 1.95-1.45 (m, 16H) ppm. To a solution of 5-bromo-4-iodo-1-(triisopropylsilyl)-1H-pyrrolo[2,3-b]pyridine (3.16 g, 6.4 mmol) in THF (15 mL) was added i-PrMgCl.LiCl (8.3 mL, 8.3 mmol, 1 M in THF) at −35° C. under N$_2$ atmosphere. The mixture was stirred at −35° C. for 1 h. A solution of (1R,2s,3S,5s,7s)-5-((tetrahydro-2H-pyran-2-yl)oxy)adamantane-2-carbaldehyde (1.7 g, 6.4 mmol) in THF (5 mL) was added to the mixture and the resulting mixture was stirred at −35° C. for another 1 h. It was warmed to 0° C., quenched with H$_2$O and extracted with EtOAc. The organic layer was washed with brine, dried over Na$_2$SO$_4$, filtered and evaporated in vacuo. The residue was applied to column chromatography (30%-50% EtOAc in petroleum) to give the desired compound (5-bromo-1-(triisopropylsilyl)-1H-pyrrolo[2,3-b]pyridin-4-yl)((1R,2S,5R)-5-((tetrahydro-2H-pyran-2-yl)oxy)adamantan-2-yl)methanol (1.0 g, yield 26%) as a yellow oil. To a solution of (5-bromo-1-(triisopropylsilyl)-1H-pyrrolo[2,3-b]pyridin-4-yl)((1R,2S,5R)-5-((tetrahydro-2H-pyran-2-yl)oxy)adamantan-2-yl)methanol (1.0 g, 1.62 mmol) in DCM (15 mL) was added Dess-Martin reagent (800 mg, 2.4 mmol) in portions at 0° C. It was then slowly warmed to rt and stirred at rt for 30 min. TLC showed the oxidation reaction was completed. The reaction mixture was diluted with EtOAc (25 mL) and filtered through a pad of Celite. The filtrate was concentrated under reduce pressure to dryness. The residue was purified by column chromatography (5%-10% EtOAc in petroleum) to give the desired bromo ketone compound (5-bromo-1-(triisopropylsilyl)-1H-pyrrolo[2,3-b]pyridin-4-yl)((1R,2S,5R)-5-((tetrahydro-2H-pyran-2-yl)oxy)adamantan-2-yl)methanone (838 mg, 83%) as a yellow oil. To a solution of this bromo ketone intermediate (838 mg, 1.4 mmol) in 1,4-dioxane (15.0 mL) were added KOAc (412 mg, 4.2 mmol), Pin$_2$B$_2$ (427 mg, 1.68 mmol) and Pd(dppf)Cl$_2$ (116 mg, 0.14 mmol). The mixture under N$_2$ was heated at 100° C. for 3 h and cooled to room temperature. It was filtered and the filtrate was concentrated. The crude product was purified by column chromatography (10% EtOAc in petroleum) to afford the desired compound ((1R,2S,5R)-5-((tetrahydro-2H-pyran-2-yl)oxy)adamantan-2-yl)(5-(4,4,5,5-tetramethyl-1,3,2-dioxaborolan-2-yl)-1-(triisopropylsilyl)-1H-pyrrolo[2,3-b]pyridin-4-yl)methanone (940 mg, crude). It was used to the next step without further purification. To a solution of this boron intermediate (940 mg, 1.4 mmol) in EtOH (10 mL) at rt was added hydrazine hydrate (0.1 mL) and then it was stirred at rt for 30 min. 6N HCl (0.5 mL) was added to the mixture. The resulting mixture was stirred at rt for additional 30 min. Then 4N HCl (3 mL) was added and the mixture was stirred at rt for 30 min more. LCMS indicated the reaction was completed. It was concentrated in vacuo to dryness, neutralized with hydrazine hydrate to pH=7-8 and then concentrated. The residue was purified by prep-HPLC (0.1% TFA in MeCN and H$_2$O) to afford the desired final compounds 1-((1R,2s,3S,5s,7s)-5-hydroxyadamantan-2-yl)-3,7-dihydro-4H-pyrrolo[3',2':5,6]pyrido[3,4-d][1,2,3]diazaborinin-4-ol (48.9 mg) and 1-((1R,2r,3S,5s,7s)-5-hydroxyadamantan-2-yl)-3,7-dihydro-4H-pyrrolo[3',2':5,6]pyrido[3,4-d][1,2,3]diazaborinin-4-ol (56.9 mg) as yellow solids (total yield 26%). Analytical data for 1-((1R,2s,3S,5s,7s)-5-hydroxyadamantan-2-yl)-3,7-dihydro-4H-pyrrolo[3',2':5,6]pyrido[3,4-d][1,2,3]diazaborinin-4-ol: $^1$HNMR (400 MHz, DMSO-d$_6$): δ 12.14 (s, 1H), 10.09 (s, 1H), 9.04 (s, 1H), 7.66 (t, J=2.8 Hz, 1H), 6.73 (d, J=1.6 Hz, 1H), 3.63 (s, 1H), 2.40 (s, 2H), 2.22 (d, J=11.9 Hz, 2H), 2.07-1.91 (m, 3H), 1.76 (d, J=10.5 Hz, 2H), 1.64 (s, 2H), 1.30 (d, J=12.2 Hz, 2H) ppm. HPLC purity: 91.33% at 210 nm and 93.43% at 254 nm. MS (ESI): m/z=337.3 (M+H)$^+$. Analytical data for 1-((1R,2r,3S,5s,7s)-5-hydroxyadamantan-2-yl)-3,7-dihydro-4H-pyrrolo[3',2':5,6]pyrido[3,4-d][1,2,3]diazaborinin-4-ol: $^1$HNMR (400 MHz, DMSO-d$_6$): δ 12.14 (s, 1H), 10.09 (s, 1H), 9.04 (s, 1H), 7.64 (t, J=3.0 Hz, 1H), 6.79 (t, J=1.6 Hz, 1H), 3.55 (s, 1H), 2.46 (s, 2H), 2.20-2.17 (m, 3H), 1.97 (d, J=11.4 Hz, 2H), 1.74 (d, J=12.1 Hz, 2H), 1.61 (s, 2H), 1.34 (d, J=11.0 Hz, 2H) ppm. HPLC purity: 91.75% at 210 nm and 95.18% at 254 nm. MS (ESI): m/z=337.3 (M+H)$^+$.

Example 9: (1s,3R,4s,5S,7s)-4-(9,9-dimethyl-8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol and (1s,3R,4r,5S,7s)-4-(9,9-dimethyl-8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol

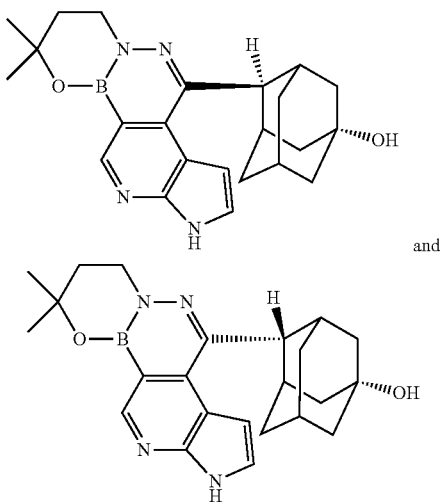

and

The title compounds were prepared by following the experimental procedures in Example 8 above. The analytical data of (1s,3R,4s,5S,7s)-4-(9,9-dimethyl-8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol are shown as follows. $^1$HNMR (400 MHz, DMSO-d$_6$): δ 12.22 (s, 1H), 8.80 (s, 1H), 7.67 (t, J=2.8 Hz, 1H), 6.79 (t, J=1.6 Hz, 1H), 3.96 (t, J=6.0 Hz, 2H), 3.57 (s, 1H), 2.50-2.46 (m, 2H), 2.27-2.22 (m, 3H), 2.06 (t, J=6.0 Hz, 2H), 1.97 (d, J=11.6 Hz, 2H), 1.75 (d, J=12.0 Hz, 2H), 1.62 (s, 2H), 1.40-1.34 (m, 8H) ppm. HPLC purity: 98.44% at 210 nm and 99.22% at 254 nm. MS (ESI): m/z=405.8 (M+H)$^+$. The analytical data of (1s,3R,4r,5S,7s)-4-(9,9-dimethyl-8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol are shown below. $^1$HNMR (400 MHz, DMSO-d$_6$): δ 12.18 (s, 1H), 8.80 (s, 1H), 7.68 (t, J=3.0 Hz, 1H), 6.72 (d, J=1.6 Hz, 1H), 3.94 (t, J=6.0 Hz, 2H), 3.65 (s, 1H), 2.41 (s, 2H), 2.29 (d, J=12.0 Hz, 2H), 2.06-1.97 (m, 5H), 1.78 (d, J=11.2 Hz, 2H), 1.66 (s, 2H), 1.39-1.31 (m, 8H) ppm. HPLC purity: 97.90% at 210 nm and 98.99% at 254 nm. MS (ESI): m/z=405.8 (M+H)$^+$.

Example 10: (1s,3R,4r,5S,7s)-4-(8,8-dimethyl-8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol

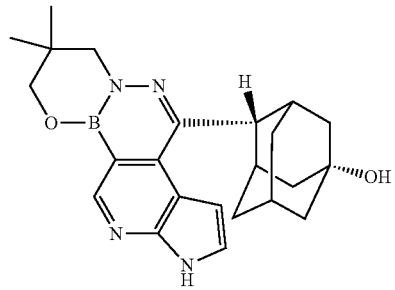 [SMILES: CC1(C)COB2c3cnc4[nH]ccc4c3C([C@H]3C4CC5CC3C[C@@](O)(C5)C4)=NN2C1]

The title compound was prepared by following the experimental procedures in Example 8 above. The analytical data of this compound are shown as following. $^1$HNMR (400 MHz, DMSO-d$_6$): δ 12.22 (s, 1H), 8.84 (s, 1H), 7.70 (t, J=2.8 Hz, 1H), 6.72 (d, J=1.6 Hz, 1H), 3.80 (s, 2H), 3.68-3.66 (s, 3H), 2.40 (s, 2H), 2.25 (d, J=12.0 Hz, 2H), 2.03-1.97 (m, 3H), 1.78 (d, J=11.2 Hz, 2H), 1.65 (s, 2H), 1.33 (d, J=12.4 Hz, 2H), 1.04 (s, 6H) ppm. HPLC purity: 98.75% at 210 nm and 99.81% at 254 nm. MS (ESI): m/z=405.2 (M+H)$^+$.

Example 11: 1-((1R,2s,3S,5s,7s)-5-hydroxyadamantan-2-yl)-3-(2-hydroxyethyl)-3,7-dihydro-4H-pyrrolo[3',2':5,6]pyrido[3,4-d][1,2,3]diazaborinin-4-ol and 1-((1R,2r,3S,5s,7s)-5-hydroxyadamantan-2-yl)-3-(2-hydroxyethyl)-3,7-dihydro-4H-pyrrolo[3',2':5,6]pyrido[3,4-d][1,2,3]diazaborinin-4-ol

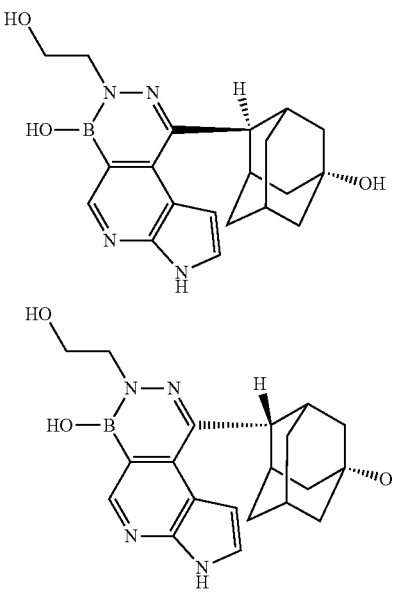

and

The title compounds were prepared by following the experimental procedures in Example 8 above. The analytical data of 1-((1R,2s,3S,5s,7s)-5-hydroxyadamantan-2-yl)-3-(2-hydroxyethyl)-3,7-dihydro-4H-pyrrolo[3',2':5,6]pyrido

[3,4-d][1,2,3]diazaborinin-4-ol are shown as following. ¹HNMR (400 MHz, DMSO-$d_6$): δ 12.09 (s, 1H), 9.11 (s, 1H), 8.31 (s, 1H), 7.65 (t, J=2.8 Hz, 1H), 6.71 (t, J=1.6 Hz, 1H), 4.70 (br s, 1H), 4.46 (br s, 1H), 3.95 (t, J=7.2 Hz, 2H), 3.69 (t, J=7.2 Hz, 2H), 3.63 (s, 1H), 2.39 (s, 2H), 2.28 (d, J=12.0 Hz, 2H), 2.04 (s, 1H), 1.98 (d, J=11.2 Hz, 2H), 1.78 (d, J=10.8 Hz, 2H), 1.66 (s, 2H), 1.33 (d, J=12.4 Hz, 2H) ppm. HPLC purity: 97.52% at 210 nm and 98.78% at 254 nm. MS (ESI): m/z=362 (M−18)⁻. And the analytical data of 1-((1R,2r,3S,5s,7s)-5-hydroxyadamantan-2-yl)-3-(2-hydroxyethyl)-3,7-dihydro-4H-pyrrolo[3',2':5,6]pyrido[3,4-d][1,2,3]diazaborinin-4-ol are shown below. ¹HNMR (400 MHz, DMSO-$d_6$): δ 12.07 (s, 1H), 9.10 (s, 1H), 8.31 (s, 1H), 7.62 (t, J=3.0 Hz, 1H), 6.76 (d, J=1.6 Hz, 1H), 4.68 (t, J=5.4 Hz, 1H), 4.21 (s, 1H), 3.96 (t, J=6.8 Hz, 2H), 3.71 (q, J=6.4 Hz, 2H), 3.54 (s, 1H), 2.45 (s, 2H), 2.23 (d, J=12.0 Hz, 2H), 2.21 (s, 1H), 1.97 (d, J=11.2 Hz, 2H), 1.74 (d, J=12.4 Hz, 2H), 1.62 (s, 2H), 1.36 (d, J=11.2 Hz, 2H) ppm. HPLC purity: 95.79% at 210 nm and 98.34% at 254 nm. MS (ESI): m/z=362 (M−18)⁻.

Example 12: 1-((1R,2s,3S,5s,7s)-5-hydroxyadamantan-2-yl)-3-propyl-3,7-dihydro-4H-pyrrolo[3',2':5,6]pyrido[3,4-d][1,2,3]diazaborinin-4-ol and 1-((1R,2r,3S,5s,7s)-5-hydroxyadamantan-2-yl)-3-propyl-3,7-dihydro-4H-pyrrolo[3',2':5,6]pyrido[3,4-d][1,2,3]diazaborinin-4-ol

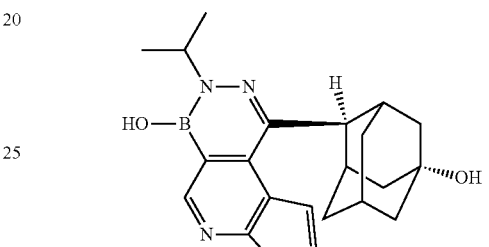

and

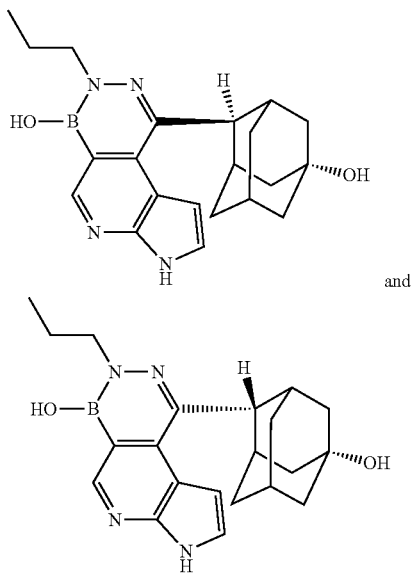

The title compounds were prepared by following the experimental procedures in Example 8 above. The analytical data of 1-((1R,2s,3S,5s,7s)-5-hydroxyadamantan-2-yl)-3-propyl-3,7-dihydro-4H-pyrrolo[3',2':5,6]pyrido[3,4-d][1,2,3]diazaborinin-4-ol are shown as following. ¹HNMR (400 MHz, DMSO-$d_6$): δ 12.17 (s, 1H), 9.13 (s, 1H), 8.35 (br s, 1H), 7.67 (t, J=2.8 Hz, 1H), 6.72 (d, J=1.6 Hz, 1H), 3.95 (br s, 1H), 3.85 (t, J=6.8 Hz, 2H), 3.64 (s, 1H), 2.39 (s, 2H), 2.28 (d, J=12.0 Hz, 2H), 2.04 (s, 1H), 1.98 (d, J=11.2 Hz, 2H), 1.79-1.72 (m, 4H), 1.65 (s, 2H), 1.33 (d, J=12.0 Hz, 2H), 0.89 (t, J=7.6 Hz, 3H) ppm. HPLC purity: 92.14% at 210 nm and 90.08% at 254 nm. MS (ESI+): m/z=379.3 (M+H)⁺. And the analytical data of 1-((1R,2r,3S,5s,7s)-5-hydroxyadamantan-2-yl)-3-propyl-3,7-dihydro-4H-pyrrolo[3',2':5,6]pyrido [3,4-d][1,2,3]diazaborinin-4-ol are shown below. ¹HNMR (400 MHz, DMSO-$d_6$): δ 12.08 (s, 1H), 9.11 (s, 1H), 8.28 (s, 1H), 7.62 (t, J=2.8 Hz, 1H), 6.77 (s, 1H), 4.21 (s, 1H), 3.86 (t, J=6.8 Hz, 2H), 3.55 (s, 1H), 2.45 (s, 2H), 2.25 (d, J=12.0 Hz, 2H), 2.22 (s, 1H), 1.97 (d, J=11.6 Hz, 2H), 1.78-1.72 (m, 4H), 1.62 (s, 2H), 1.36 (d, J=11.2 Hz, 2H), 0.89 (t, J=7.6 Hz, 3H) ppm. HPLC purity: 90.3% at 254 nm. MS (ESI+): m/z=379.2 (M+H)⁺.

Example 13: 1-((1R,2s,3S,5s,7s)-5-hydroxyadamantan-2-yl)-3-isopropyl-3,7-dihydro-4H-pyrrolo[3',2':5,6]pyrido[3,4-d][1,2,3]diazaborinin-4-ol and 1-((1R,2r,3S,5s,7s)-5-hydroxyadamantan-2-yl)-3-isopropyl-3,7-dihydro-4H-pyrrolo[3',2':5,6]pyrido[3,4-d][1,2,3]diazaborinin-4-ol

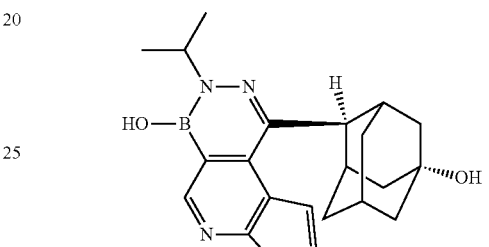

and

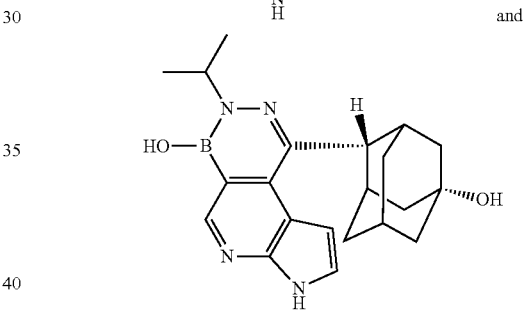

The title compounds were prepared by following the experimental procedures in Example 8 above. The analytical data of 1-((1R,2s,3S,5s,7s)-5-hydroxyadamantan-2-yl)-3-isopropyl-3,7-dihydro-4H-pyrrolo[3',2':5,6]pyrido[3,4-d][1,2,3]diazaborinin-4-ol are shown as following. ¹HNMR (400 MHz, DMSO-$d_6$): δ 12.17 (s, 1H), 9.13 (s, 1H), 8.40 (br s, 1H), 7.66 (t, J=2.8 Hz, 1H), 6.73 (s, 1H), 4.74-4.71 (m, 1H), 3.79 (br s, 1H), 3.67 (s, 1H), 2.39 (s, 2H), 2.32 (d, J=12.0 Hz, 2H), 2.06 (s, 2H), 2.00 (d, J=10.8 Hz, 2H), 1.79 (d, J=10.8 Hz, 2H), 1.66 (s, 2H), 1.38-1.32 (m, 2H), 1.24 (s, 6H) ppm. HPLC purity: 91.68% at 210 nm and 94.44% at 254 nm. MS (ESI+): m/z=379.2 (M+H)⁺. And the analytical data of 1-((1R,2r,3S,5s,7s)-5-hydroxyadamantan-2-yl)-3-isopropyl-3,7-dihydro-4H-pyrrolo[3',2':5,6]pyrido[3,4-d][1,2,3]diazaborinin-4-ol are shown below. ¹HNMR (400 MHz, DMSO-$d_6$): δ 12.13 (s, 1H), 9.12 (s, 1H), 8.36 (br s, 1H), 7.63 (t, J=3.0 Hz, 1H), 6.78 (t, J=1.6 Hz, 1H), 4.76-4.68 (m, 1H), 3.70 (br s, 1H), 3.58 (s, 1H), 2.45 (s, 2H), 2.30-2.20 (m, 4H), 2.10 (s, 2H), 1.98 (d, J=11.6 Hz, 2H), 1.76 (d, J=12.0 Hz, 2H), 1.64 (s, 2H), 1.41-1.35 (m, 2H), 1.34 (s, 6H) ppm. HPLC purity: 95.94% at 210 nm and 96.23% at 254 nm. MS (ESI+): m/z=379.2 (M+H)⁺.

Example 14: (1s,3R,4s,5S,7s)-4-(7,7-dimethyl-8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol

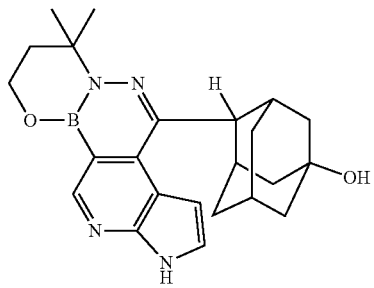 [SMILES: CC1(C)CCOB2c3cnc4[nH]ccc4c3C(C3C4CC5CC3CC(O)(C5)C4)=NN21]

The title compound was prepared by following the experimental procedures in Example 8 above. The analytical data of this compound are shown as follows. $^1$HNMR (400 MHz, DMSO-d$_6$): δ 12.19 (s, 1H), 8.80 (s, 1H), 7.69-7.65 (m, 1H), 6.80-6.72 (m, 1H), 4.40-4.10 (m, 3H), 3.69 & 3.60 (two s, 1H), 2.50-2.40 (m, 2H), 2.35-2.20 (m, 4H), 2.15-2.10 (m, 2H), 2.10-1.95 (m, 2H), 1.85-1.75 (m, 2H), 1.70-1.60 (m, 2H), 1.51 & 1.49 (two s, 6H), 1.45-1.35 (m, 2H) ppm. HPLC purity: 99.00% at 210 nm and 99.46% at 254 nm. MS (ESI): m/z=405.0 (M+H)$^+$.

Example 15: (1s,3R,4s,5S,7s)-4-(8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol and (1s,3R,4r,5S,7s)-4-(8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol

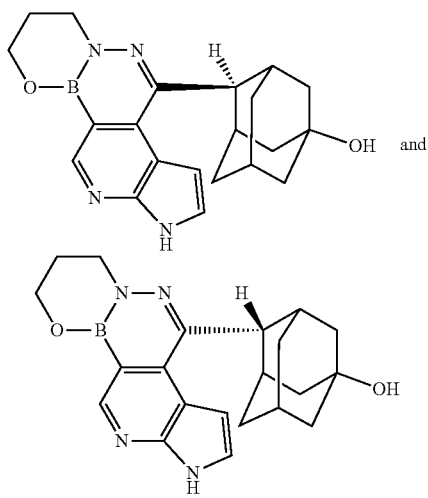

The title compounds were prepared by following the experimental procedures in Example 8 above. The analytical data of (1s,3R,4s,5S,7s)-4-(8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol are shown as following. $^1$HNMR (400 MHz, DMSO-d$_6$): δ 12.16 (s, 1H), 8.81 (s, 1H), 7.66 (s, 1H), 6.78 (s, 1H), 4.25 (s, 1H), 4.17 (t, J=4.8 Hz, 2H), 3.95 (t, J=5.6 Hz, 2H), 3.57 (s, 1H), 2.46 (s, 2H), 2.26-2.17 (m, 5H), 1.97 (d, J=11.6 Hz, 2H), 1.75 (d, J=12 Hz, 2H), 1.62 (s, 2H), 1.36 (d, J=11.2 Hz, 2H) ppm. HPLC purity: 98.72% at 210 nm and 99.71% at 254 nm. MS (ESI+): m/z=377.0 (M+H)$^+$. And the analytical data of (1s,3R,4r,5S,7s)-4-(8,9-dihydro-1H,7H-pyrrolo[3",2":5',6']pyrido[3',4':4,5][1,2,3]diazaborinino[3,2-b][1,3,2]oxazaborinin-4-yl)adamantan-1-ol are shown below. $^1$HNMR (400 MHz, DMSO-d$_6$): δ 12.17 (s, 1H), 8.81 (s, 1H), 7.68 (s, 1H), 6.72 (s, 1H), 4.48 (s, 1H), 4.16 (s, 2H), 3.94 (s, 2H), 3.65 (s, 1H), 2.41 (s, 2H), 2.28 (d, J=11.6 Hz, 2H), 2.17 (s, 2H), 2.04-1.97 (m, 3H), 1.78 (d, J=10.8 Hz, 2H), 1.65 (s, 2H), 1.35 (d, J=11.2 Hz, 2H) ppm. HPLC purity: 96.71% at 210 nm and 99.01% at 254 nm. MS (ESI+): m/z=377.0 (M+H)$^+$.

Example 16: 1-((1R,2s,3S,5s,7s)-5-hydroxyadamantan-2-yl)-3-methyl-3,7-dihydro-4H-pyrrolo[3',2':5,6]pyrido[3,4-d][1,2,3]diazaborinin-4-ol

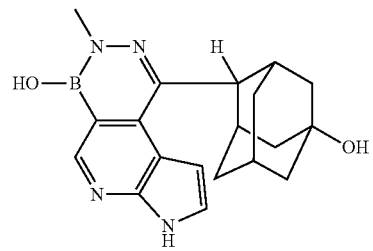 [SMILES: CN1N=C(C2C3CC4CC2CC(O)(C4)C3)c2c(cnc3[nH]ccc23)B1O]

The title compound was prepared by following the experimental procedures in Example 8 above. The analytical data of this compound are shown as following. $^1$HNMR (400 MHz, DMSO-d$_6$): δ 12.13 (s, 1H), 9.10 (s, 1H), 8.43 (s, 1H), 7.66-7.63 (m, 1H), 6.77 & 6.71 (two s, 1H), 3.59-3.51 (m, 4H), 2.39 (s, 2H), 2.22 (d, J=12.0 Hz, 2H), 2.05-1.94 (m, 3H), 1.80-1.70 (m, 2H), 1.62 (d, J=14.2 Hz, 2H), 1.33 (t, J=12.0 Hz, 2H) ppm. HPLC purity: 97.93% at 210 nm and 99.57% at 254 nm. MS (ESI): m/z=351.2 (M+H)$^+$.

Example 17: N-benzyl-1-((1r,4r)-4-(4-hydroxy-4,7-dihydro-3H-pyrrolo[3',2':5,6]pyrido[3,4-d][1,2,3]diazaborinin-1-yl)cyclohexyl)-N-methylmethanesulfonamide

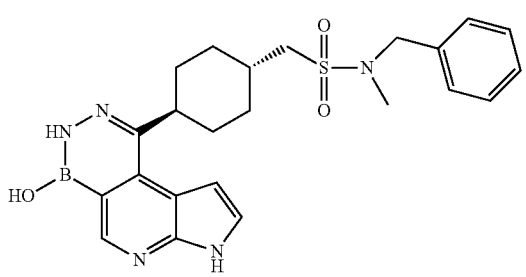 [SMILES: CN(Cc1ccccc1)S(=O)(=O)C[C@H]1CC[C@H](C2=NNB(O)c3cnc4[nH]ccc4c32)CC1]

The title compounds were prepared by using the scheme and following procedures shown below:

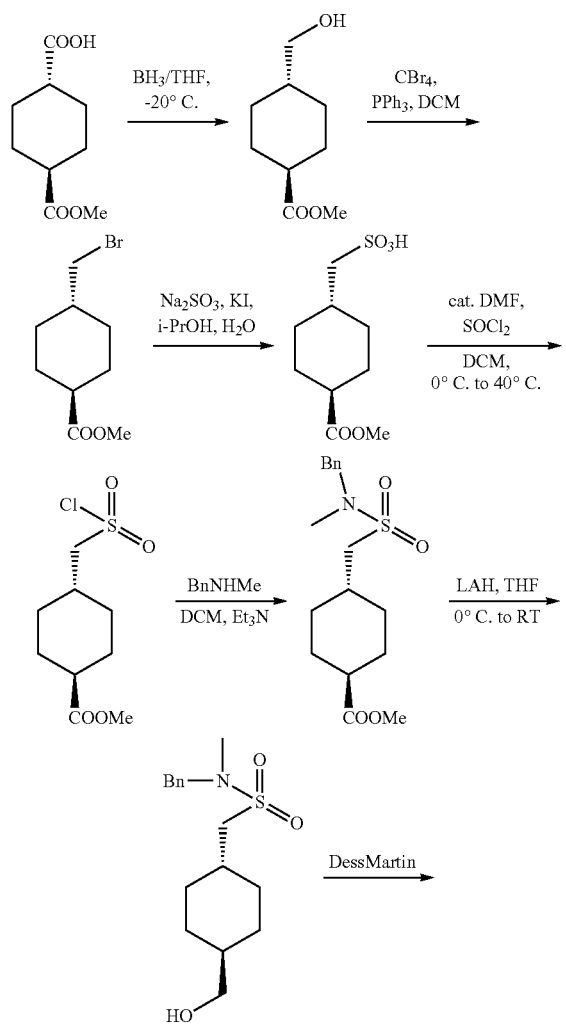

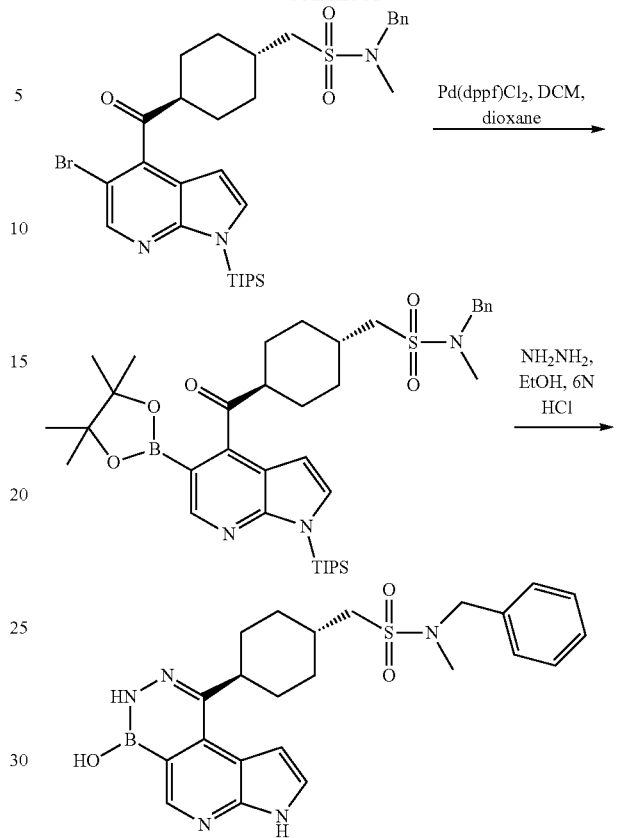

To a solution of (1r,4r)-4-(Methoxycarbonyl)cyclohexane-1-carboxylic acid (20 g, 108 mmol) in THF (120 mL) was added BH$_3$ complex solution (1.0 M in THF, 130 mL) dropwise at −20° C. under argon gas atmosphere over a period of 1 hour. The mixture was stirred at −10° C. for 1 hour. To the reaction mixture was added water (160 mL) under ice-cooling and the mixture was extracted with EtOAc. The organic layer was washed with saturated brine, dried over anhydrous sodium sulfate and concentrated in vacuo to give methyl (1r,4r)-4-(hydroxymethyl)cyclohexane-1-carboxylate, which was used in the next step directly (20 g, crude) as an oil. $^1$H NMR (400 MHz, CDCl$_3$): δ 3.67 (s, 3H), 3.46 (d, J=6.3 Hz, 2H), 2.35-2.18 (m, 1H), 2.12-1.96 (m, 2H), 1.96-1.80 (m, 2H), 1.61-1.33 (m, 4H), 1.08-0.85 (m, 2H) ppm. To a solution of methyl (1r,4r)-4-(hydroxymethyl)cyclohexane-1-carboxylate (6.0 g, 35 mmol) and CBr$_4$ (23.2 g, 70 mmol) in DCM (50 mL) was added PPh$_3$ (9.2 g, 35 mmol, in 50 mL DCM) dropwise at 0° C. The resulting mixture was stirred at room temperature overnight. It was concentrated and purified by silica chromatography to give the product methyl (1r,4r)-4-(bromomethyl)cyclohexane-1-carboxylate (3.8 g, yield 47%) as a colorless oil. LC-MS: (M+H)$^+$: m/z=235.0 and 237.0. To a solution of methyl (1r,4r)-4-(bromomethyl)cyclohexane-1-carboxylate (3.7 g, 15.7 mmol) in i-PrOH (15 mL) were added Na$_2$SO$_3$ (2.6 g, 20.4 mmol) and KI (200 mg, 1.2 mmol) in water (20 mL) at room temperature. The mixture was heated to 100° C. overnight and then monitored by LCMS. After the reaction was completed, it was evaporated and then dried by azeotropic distillation with toluene to give the product, ((1r,4r)-4-(methoxycarbonyl)cyclohexyl)methanesulfonic acid salt, as a white solid (6.3 g), which was used in the next step without further purification. MS (ESI–): m/z=235.1 (M–1)⁻. This compound (6.3 g, crude) and a drop of DMF were suspended in DCM (35 mL) and cooled with an ice-bath. SOCl$_2$ (3.5 mL) was added dropwise. The mixture was stirred at rt for 20 min and heated to 50° C. overnight. It was monitored by LCMS. Solid was filtered and the filtrate was concentrated. The residue was dissolved in DCM (30 mL) and concentrated to remove the excess of SOCl$_2$. The residue (5.0 g, a yellow oil), methyl (1r,4r)-4-((chlorosulfonyl)methyl)cyclohexane-1-carboxylate, was used in the next step without further purification. To a solution of methyl (1r,4r)-4-((chlorosulfonyl)methyl) cyclohexane-1-carboxylate (5.0 g, about 10 mmol) in THF (20 mL) was added Et$_3$N (2.0 g, 20.0 mmol). The mixture was cooled with an ice-water bath. Then, N-methyl-1-phenylmethanamine (1.5 g, 12 mmol) in THF (8 mL) was added dropwise, and the mixture was stirred at room temperature for 2h. It was monitored by TLC (PE/EA=5:1) and LCMS, quenched by water and extracted with EtOAc. The organic layer was concentrated and purified by silica chromatography to give methyl (1r,4r)-4-((N-benzyl-N-methylsulfamoyl)methyl)cyclohexane-1-carboxylate as an off-white solid (3.0 g, 80% yield). $^1$H NMR (400 MHz, CDCl$_3$): δ 7.40-7.28 (m, 5H), 4.32 (s, 2H), 3.67 (s, 3H), 2.81 (d, J=6.3 Hz, 2H), 2.76 (s, 3H), 2.31-2.19 (m, 1H), 2.16-1.94 (m, 5H), 1.55-1.40 (m, 2H), 1.20-1.03 (m, 2H) ppm. To a solution of methyl (1r,4r)-4-((N-benzyl-N-methylsulfamoyl)methyl)cyclohexane-1-carboxylate (3.0 g, 8.8 mmol) in THF (20 mL), cooled with an ice-bath, was added LiAlH$_4$ (501 mg, 13.2 mmol) in portions. The resulting mixture was warmed to rt and stirred at that temperature for 1.5 h. It was monitored by LCMS and TLC, and quenched with 2 mL water. Na$_2$SO$_4$ was added and filtered through a pad of Celite. The filtrate was concentrated in vacuo to give N-benzyl-1-((1r,4r)-4-(hydroxymethyl)cyclohexyl)-N-methylmethanesulfonamide (2.5 g, 83%) as a white solid, which was used in the next step without further purification. $^1$H NMR (400 MHz, CDCl$_3$): δ 7.41-7.28 (m, 5H), 4.32 (s, 2H), 3.47 (d, J=6.3 Hz, 2H), 2.82 (d, J=6.3 Hz, 2H), 2.76 (s, 3H), 2.14-2.03 (m, 2H), 2.03-1.91 (m, 1H), 1.85 (d, J=12.5 Hz, 2H), 1.54-1.39 (m, 1H), 1.33 (s, 1H), 1.21-0.93 (m, 4H) ppm. To a solution of N-benzyl-1-((1r,4r)-4-(hydroxymethyl)cyclohexyl)-N-methylmethanesulfonamide (2.5 g, 7.3 mmol) in DCM (25 mL) was added Dess-Martin reagent (5.0 g, 12 mmol) in portions at 0° C. It was then slowly warmed to rt and stirred at rt for 30 min. TLC showed no starting material left. The reaction mixture was diluted with EtOAc (25 mL) and filtered through a pad of Celite. The filtrate was concentrated in vacuo under reduce pressure to dryness. The residue was purified by column chromatography (5%-10% EtOAc in petroleum) to give the desired aldehyde N-benzyl-1-((1r,4r)-4-formylcyclohexyl)-N-methylmethanesulfonamide (2.0 g, 82%) as a white solid. $^1$H NMR (400 MHz, CDCl$_3$): δ 9.62 (s, 1H), 7.40-7.29 (m, 5H), 4.32 (s, 2H), 2.83 (d, J=6.3 Hz, 2H), 2.77 (s, 3H), 2.25-2.12 (m, 3H), 2.09-1.94 (m, 4H), 1.43-1.29 (m, 2H), 1.23-1.09 (m, 2H) ppm. To a solution of 5-bromo-4-iodo-1-(triisopropylsilyl)-1H-pyrrolo[2,3-b]pyridine (1.33 g, 3 mmol) in THF (30 mL) was added i-PrMgCl—LiCl (3 mL, 3.9 mmol, 1 M in THF) at –35° C. under N$_2$ atmosphere, and the mixture was stirred at –35° C. for 1 h. A solution of N-benzyl-1-((1r,4r)-4-formylcyclohexyl)-N-methylmethanesulfonamide (1.0 g, 3 mmol) in THF (5 mL) was added to the mixture, and the resulting mixture was stirred at –35° C. for another 1 h. It was allowed to warm to 0° C., quenched with H$_2$O, dried over Na$_2$SO$_4$, filtered and evaporated under reduce pressure. The residue was purified by column chromatography (0%-30% EtOAc in petroleum) to give N-benzyl-1-((1R,4r)-4-((R)-(5-bromo-1-(triisopropylsilyl)-1H-pyrrolo[2,3-b]pyridin-4-yl)(hydroxy)methyl) cyclohexyl)-N-methylmethanesulfonamide (1.0 g, yield 34%,) as a yellow oil. $^1$H NMR (400 MHz, CDCl$_3$): δ 8.26 (s, 1H), 7.38-7.29 (m, 5H), 7.28 (d, J=3.5 Hz, 1H), 6.83 (t, J=4.0 Hz, 1H), 5.30 (s, 2H), 5.07 (dd, J=7.0, 3.7 Hz, 1H), 4.30 (s, 2H), 2.82-2.75 (m, 3H), 2.74 (s, 3H), 2.20 (d, J=3.8 Hz, 1H), 2.11 (d, J=11.2 Hz, 2H), 2.02-1.92 (m, 3H), 1.10 (t, J=11.2 Hz, 18H), 1.08-0.80 (m, 4H) ppm. To a solution of N-benzyl-1-((1R,4r)-4-((R)-(5-bromo-1-(triisopropylsilyl)-1H-pyrrolo[2,3-b]pyridin-4-yl)(hydroxy)methyl)cyclohexyl)-N-methylmethanesulfonamide (830 mg, 1.25 mmol) in DCM (25 mL) was added Dess-Martin reagent (795 mg, 1.87 mmol) in portions at 0° C. It was then slowly warmed to rt and stirred at rt for 30 min. TLC showed no starting material left. The reaction mixture was diluted with EtOAc (25 mL) and filtered through a pad of Celite. The filtrate was concentrated under reduced pressure to dryness. The residue was purified by column chromatography (5%-10% EtOAc in petroleum) to give N-benzyl-1-((1r,4r)-4-(5-bromo-1-(triisopropylsilyl)-1H-pyrrolo[2,3-b]pyridine-4-carbonyl)cyclohexyl)-N-methylmethanesulfonamide (750 mg, 82%) as a white solid. To a solution of this ketone compound (750 mg, 1.1 mmol) in 1,4-dioxane (5 mL) were added KOAc (323 mg, 3.3 mmol), bis(pinacolato)diborane (558 mg, 2.2 mmol) and Pd(dppf)Cl$_2$ DCM (180 mg, 0.22 mmol) under nitrogen. The mixture was heated at 100° C. for 5 h and then cooled to room temperature. The solids were filtered off, and the solvent was removed. The crude product was purified by column chromatography (PE/EA=10:1 to 1:1) to afford N-benzyl-N-methyl-1-((1r,4r)-4-(5-(4,4,5,5-tetramethyl-1,3,2-dioxaborolan-2-yl)-1-(triisopropylsilyl)-1H-pyrrolo[2,3-b]pyridine-4-carbonyl)cyclohexyl)methanesulfonamide (650 mg, crude). To a solution of this boron ketone (650 mg, crude) in EtOH (5 mL) at rt was added hydrazine hydrate (0.1 mL), and then it was stirred at rt for 30 min. 6N HCl (0.5 mL) was added to the mixture. The resulting mixture was stirred at rt for another 30 min and LCMS indicated the reaction was completed. It was concentrated in vacuo to dryness and neutralized by hydrazine hydrate to pH=7-8. The residue was purified by prep-HPLC (0.1% TFA in water and MeCN) to afford the desired final product N-benzyl-1-((1r,4r)-4-(4-hydroxy-4,7-dihydro-3H-pyrrolo[3',2':5,6] pyrido[3,4-d][1,2,3]diazaborinin-1-yl)cyclohexyl)-N-methylmethane-sulfonamide (10 mg) as a light yellow solid. $^1$H NMR (400 MHz, DMSO-d$_6$): δ 12.16 (s, 1H), 10.06 (d, J=3.5 Hz, 1H), 9.05 (s, 1H), 8.20 (br s, 1H), 7.73-7.59 (m, 1H), 7.44-7.28 (m, 5H), 6.82 (d, J=8.5 Hz, 1H), 4.31 (s, 2H), 3.37 (t, J=11.3 Hz, 1H), 3.20-3.05 (m, 2H), 2.70 (s, 2H), 2.13-2.05 (m, 3H), 1.97-1.72 (m, 3H), 1.68-1.35 (m, 3H) ppm. HPLC purity: 94.12% at 210 nm and 98.68% at 254 nm. MS (ESI+): m/z=466.2 (M+H)$^+$.

Example 18: N-benzyl-1-((1r,4r)-4-(4-hydroxy-3-methyl-4,7-dihydro-3H-pyrrolo[3',2':5,6]pyrido[3,4-d][1,2,3]diazaborinin-1-yl)cyclohexyl)-N-methyl-methanesulfonamide

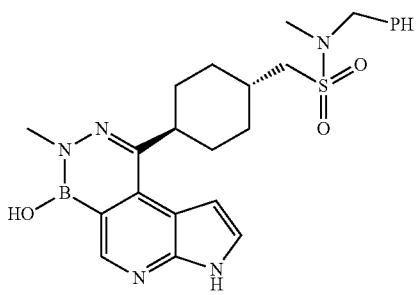

The title compound was prepared by following the experimental procedures in the Example above (in Example 17). The analytical data of this compound are shown as follows. $^1$H NMR (400 MHz, DMSO-d$_6$): δ 12.14 (s, 1H), 9.12 (s, 1H), 8.39 (br s, 1H), 7.66 (t, J=2.8 Hz, 1H), 7.45-7.30 (m, 6H), 6.79 (d, J=2.8 Hz, 1H), 4.32 (s, 2H), 3.54 (s, 3H), 3.36 (t, J=11.6 Hz, 1H), 3.12 (d, J=6.3 Hz, 2H), 2.71 (s, 3H), 2.19-2.05 (m, 3H), 1.74-1.51 (m, 2H), 1.53-1.33 (m, 2H), 1.33-1.17 (m, 2H) ppm. HPLC purity: 93.34% at 210 nm and 94.25% at 254 nm. MS: m/z=480.2 (M+H)$^+$.

Example 19: 1-((1r,4r)-4-(4-hydroxy-4,7-dihydro-3H-pyrrolo[3',2':5,6]pyrido[3,4-d][1,2,3]diazaborinin-1-yl)cyclohexyl)-N-methylmethanesulfonamide

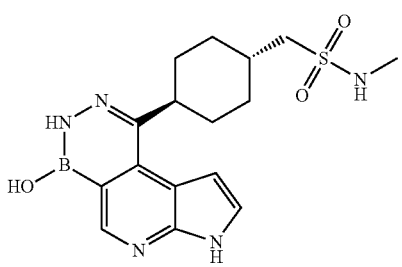 [SMILES: CNS(=O)(=O)C[C@H]1CC[C@H](C2=NNB(O)c3cnc4[nH]ccc4c32)CC1]

The title compound was prepared by adapting the experimental procedures in the Example above (in Example 17). The analytical data of this compound are shown as follows. $^1$H NMR (400 MHz, DMSO-d$_6$): δ 12.12 (s, 1H), 10.03 (s, 1H), 9.04 (s, 1H), 8.06 (s, 1H), 7.65 (t, J=2.8 Hz, 1H), 6.90 (q, J=5.2 Hz, 1H), 6.79 (d, J=2.0 Hz, 1H), 3.40-3.30 (m, 1H), 3.00 (d, J=6.4 Hz, 2H), 2.60 (d, J=4.8 Hz, 3H), 2.15-2.02 (m, 4H), 2.00-1.85 (m, 1H), 1.65-1.50 (m, 2H), 1.50-1.35 (m, 2H) ppm. HPLC purity: 93.94% at 210 nm and 98.49% at 254 nm. MS (ESI+): m/z=376.1 (M+H)$^+$.

Example 20: 1-((1r,4r)-4-(4-hydroxy-3-methyl-4,7-dihydro-3H-pyrrolo[3',2':5,6]pyrido[3,4-d][1,2,3]diazaborinin-1-yl)cyclohexyl)-N-methylmethanesulfonamide

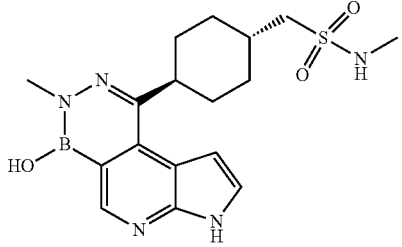 [SMILES: CNS(=O)(=O)C[C@H]1CC[C@H](C2=NN(C)B(O)c3cnc4[nH]ccc4c32)CC1]

The title compound was prepared by adapting the experimental procedures in the Example above (in Example 17). The analytical data of this compound are shown as follows. $^1$H NMR (400 MHz, DMSO-d$_6$): δ 12.12 (s, 1H), 9.11 (s, 1H), 8.37 (s, 1H), 7.65-7.63 (m, 1H), 6.90 (q, J=4.8 Hz, 1H), 6.81-6.78 (m, 1H), 3.56 (s, 3H), 3.01 (d, J=6.0 Hz, 2H), 2.60 (d, J=5.2 Hz, 3H), 2.15-2.02 (m, 3H), 2.00-1.80 (m, 2H), 1.70-1.55 (m, 2H), 1.50-1.35 (m, 2H) ppm. HPLC purity: 97.76% at 210 nm and 98.28% at 254 nm. MS (ESI+): m/z=390.2 (M+H)$^+$.

Example 21: 1-((1r,4r)-4-(3-ethyl-4-hydroxy-4,7-dihydro-3H-pyrrolo[3',2':5,6]pyrido[3,4-d][1,2,3]diazaborinin-1-yl)cyclohexyl)-N-methylmethanesulfonamide

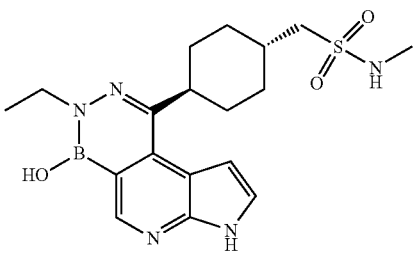 [SMILES: CCN1N=C([C@H]2CC[C@H](CS(=O)(=O)NC)CC2)c2c(cnc3[nH]ccc23)B1O]

The title compound was prepared by adapting the experimental procedures in the Example above (in Example 17). The analytical data of this compound are shown as follows. $^1$H NMR (400 MHz, DMSO-d$_6$): δ 12.11 (s, 1H), 9.11 (s, 1H), 8.32 (s, 1H), 7.65-7.63 (m, 1H), 6.91-6.87 (m, 1H), 6.79-6.78 (m, 1H), 3.88 (q, J=7.2 Hz, 2H), 3.45-3.30 (m, 1H), 3.01 (d, J=6.4 Hz, 2H), 2.60 (d, J=5.2 Hz, 3H), 2.15-2.02 (m, 4H), 2.00-1.80 (m, 1H), 1.70-1.55 (m, 2H), 1.50-1.35 (m, 2H), 1.28 (t, J=7.2 Hz, 3H) ppm. HPLC purity: 96.08% at 210 nm and 95.99% at 254 nm. MS (ESI+): m/z=404.2 (M+H)$^+$.

General Procedure A:

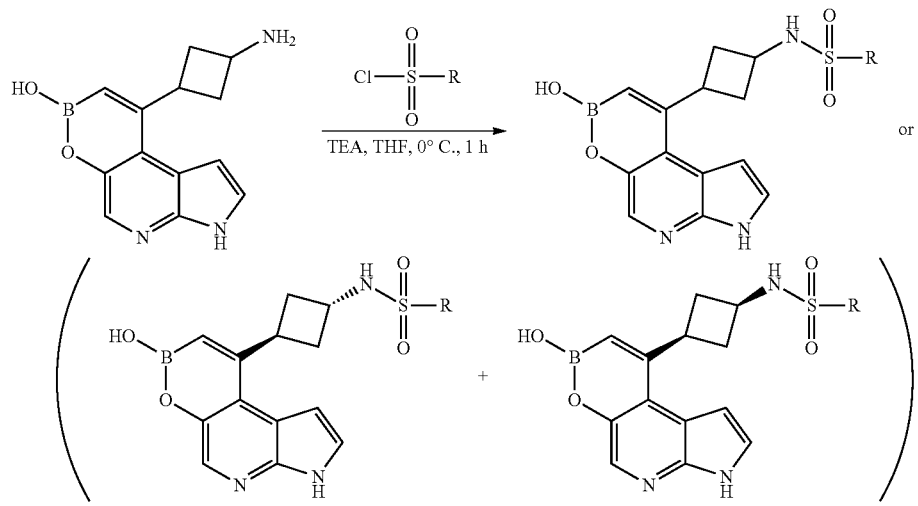

To a mixture of 9-(3-aminocyclobutyl)-[1,2]oxaborinino[5,6-d]pyrrolo[2,3-b]pyridin-7(3H)-ol (1 eq) and TEA (1 eq) in THF (1 mL) sulfonyl chloride (2 eq) was added in one portion at 0° C., and the resulting mixture was stirred at 0° C. for 1 h. Water was then added, and the reaction mixture was extracted with EtOAc. The combined organic layers were washed with brine, dried over anhydrous $Na_2SO_4$, filtered and concentrated in vacuo to give a residue, which was purified by prep-TLC to give the desired racemic sulfonamide mixture or purified by pre-HPLC to give the corresponding cis and trans isomers.

Synthesis of 9-(3-aminocyclobutyl)-[1,2]oxaborinino[5,6-d]pyrrolo[2,3-b]pyridin-7(3H)-ol

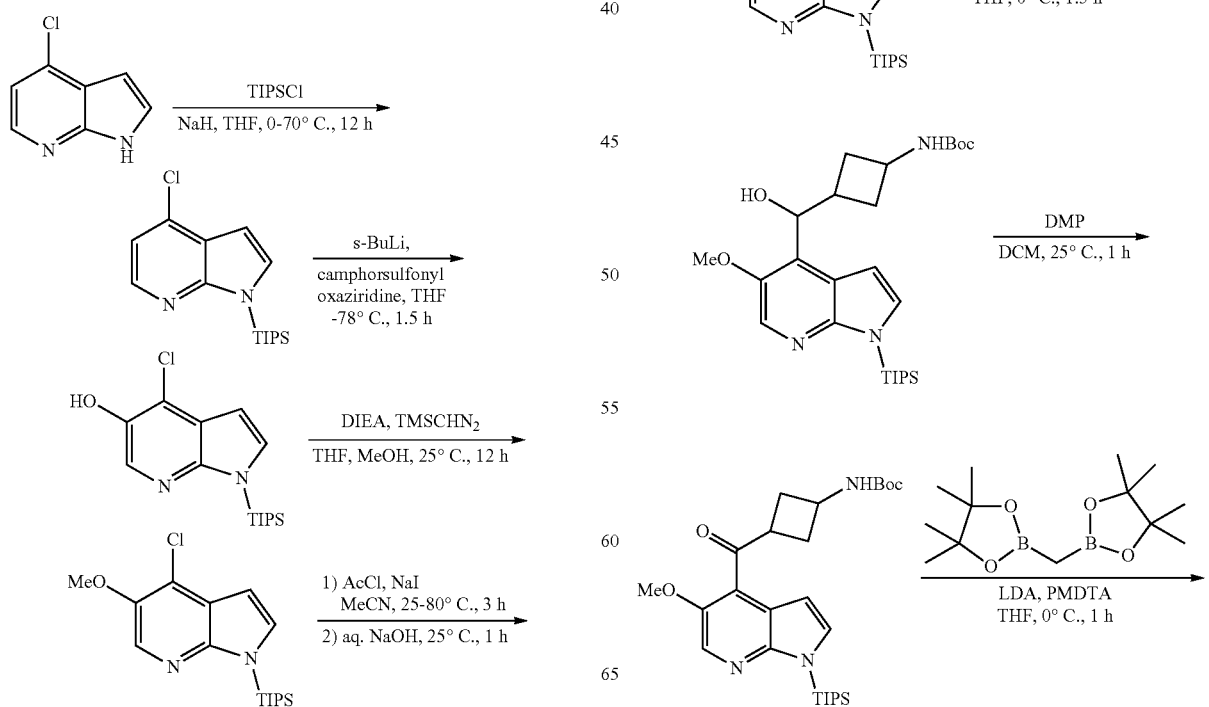

-continued

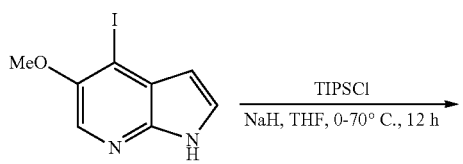

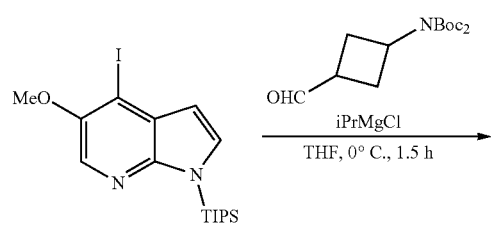

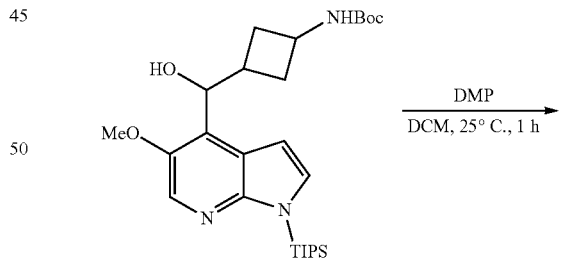

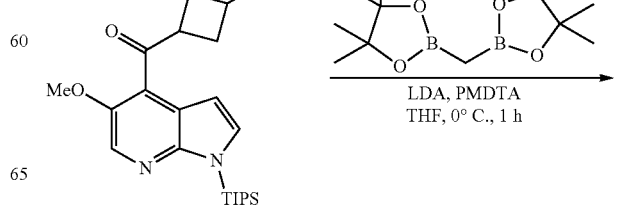

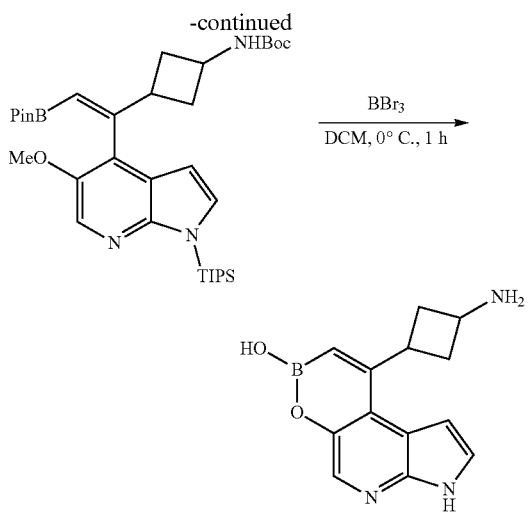

Preparation of (4-chloropyrrolo[2,3-b]pyridin-1-yl)-triisopropyl-silane

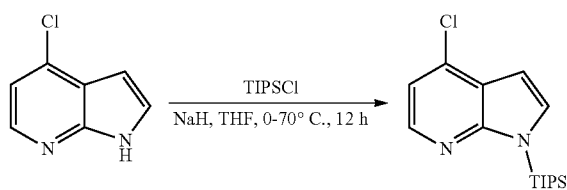

To a solution of 4-chloro-1H-pyrrolo[2,3-b]pyridine (10 g, 65.54 mmol, 1 eq) in DMF (200 mL), NaH (3.93 g, 98.31 mmol, 60% purity, 1.5 eq) was added in portions at 0° C., and the resulting mixture was stirred at 0° C. for 30 min. Then, TIPSCl (25.27 g, 131.08 mmol, 28.05 mL, 2 eq) was added dropwise at 0° C. under a N$_2$ atmosphere, and the resulting mixture was heated to 70° C. for 12 h. The reaction mixture was quenched by adding saturated aq. NH$_4$Cl (100 mL) and extracted with EtOAc (100 mL×3). The combined organic layers were washed with brine (100 mL×2), dried over Na$_2$SO$_4$, filtered and concentrated under reduced pressure to give a residue, which was purified by column chromatography (SiO$_2$, Petroleum ether/Ethyl acetate=20/1 to 10/1) to give (4-chloropyrrolo[2,3-b]pyridin-1-yl)-triisopropyl-silane (19 g, 61.50 mmol, 93.84% yield) as a yellow oil. $^1$H NMR (CDCl$_3$, 400 MHz) δ 8.05 (d, J=5.2 Hz, 1H), 7.24 (d, J=3.6 Hz, 1H), 6.97 (d, J=5.2 Hz, 1H), 6.57 (d, J=3.2 Hz, 1H), 1.79-1.73 (m, 3H), 1.03 (d, J=7.6 Hz, 18H).

Preparation of 4-chloro-1-triisopropylsilyl-pyrrolo[2,3-b]pyridin-5-ol

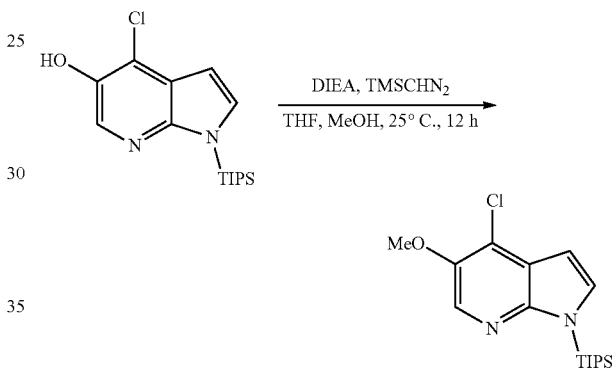

To a solution of (4-chloropyrrolo[2,3-b]pyridin-1-yl)-triisopropyl-silane (2 g, 6.47 mmol, 1 eq) in THF (40 mL), s-BuLi (1.3 M, 10.96 mL, 2.2 eq) was added dropwise at −78° C., and the resulting mixture was stirred for 30 min under a N$_2$ atmosphere. Then camphorsulfonyloxaziridine (2.15 g, 9.39 mmol, 1.45 eq) was added to the mixture at −78° C. under a N$_2$ atmosphere, and the reaction mixture was stirred at −78° C. for 1 h. The reaction was quenched by adding saturated aq. NH$_4$Cl (50 mL) and extracted with EtOAc (50 mL×3). The combined organic layers were washed with brine (100 mL×2), dried over Na$_2$SO$_4$, filtered and concentrated under reduced pressure to give a residue, which was purified by column chromatography (SiO$_2$, Petroleum ether/Ethyl acetate=10/1 to 5/1) to give 4-chloro-1-triisopropylsilyl-pyrrolo[2,3-b]pyridin-5-ol (0.9 g, 2.77 mmol, 42.78% yield) as a yellow oil. $^1$H NMR (CDCl$_3$, 400 MHz) δ 7.99 (s, 1H), 7.24 (d, J=3.2 Hz, 1H), 6.46 (d, J=3.6 Hz, 1H), 5.04 (s, 1H), 1.77-1.70 (m, 3H), 1.03 (d, J=7.6 Hz, 18H).

Preparation of Methyl (4-chloro-5-methoxy-pyrrolo[2,3-b]pyridin-1-yl)-triisopropyl-silane

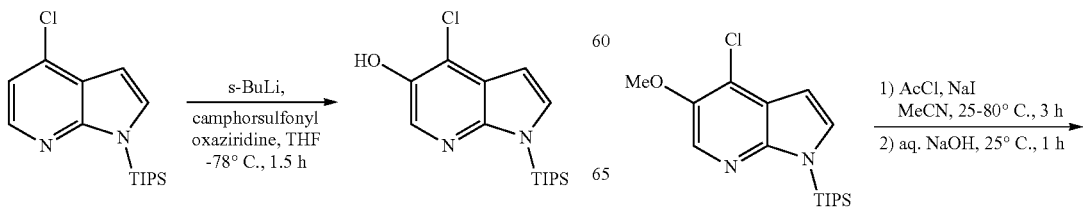

To a mixture of 4-chloro-1-triisopropylsilyl-pyrrolo[2,3-b]pyridin-5-ol (3 g, 9.23 mmol, 1 eq) and DIEA (1.19 g, 9.23 mmol, 1.61 mL, 1 eq) in THF (6 mL)/MeOH (2 mL), TMSCHN$_2$ (2 M, 9.23 mL, 2 eq) was added dropwise at 25° C. under a N$_2$ atmosphere, and the mixture was stirred at 25° C. for 12 h. The reaction was quenched with H$_2$O (150 mL) and extracted with EtOAc (50 mL×3). The combined organic layers were washed with brine (20 mL×2), dried over Na$_2$SO$_4$, filtered and concentrated under reduced pressure to give a residue, which was purified by column chromatography (SiO$_2$, Petroleum ether/Ethyl acetate=15/1 to 5/1) to give (4-chloro-5-methoxy-pyrrolo[2,3-b]pyridin-1-yl)-triisopropyl-silane (2.8 g, 8.26 mmol, 89.47% yield) as a yellow oil. $^1$H NMR (CDCl$_3$, 400 MHz) δ 7.98 (s, 1H), 7.25 (d, J=3.2 Hz, 1H), 6.51 (d, J=3.6 Hz, 1H), 3.92 (s, 3H), 1.79-1.72 (m, 3H), 1.04 (d, J=7.6 Hz, 18H).

Preparation of 4-iodo-5-methoxy-1H-pyrrolo[2,3-b]pyridine

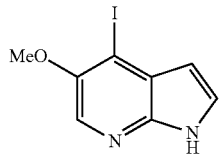

To a mixture of (4-chloro-5-methoxy-pyrrolo[2,3-b]pyridin-1-yl)-triisopropyl-silane (5.3 g, 15.64 mmol, 1 eq) and acetyl chloride (3.68 g, 46.91 mmol, 3.35 mL, 3 eq) in CH₃CN (20 mL), NaI (23.44 g, 156.37 mmol, 10 eq) was added in one portion at 25° C. under a N₂ atmosphere. The mixture was stirred at 80° C. for 3 h. The reaction was quenched by adding 2N aq. K₂CO₃ (50 mL) and extracted with EtOAc (50 mL×3). The combined organic layers were washed with brine (20 mL×2), dried over Na₂SO₄, filtered and concentrated under reduced pressure to give a residue. The residue was dissolved in THF (50 mL) and 2 N aq. NaOH (10 mL) was added. The mixture was stirred at 25° C. for 1 h. H₂O (50 mL) was added to the reaction mixture, and the aqueous phase was extracted with EtOAc (50 mL×3). The combined organic layers were washed with brine (20 mL×2), dried over Na₂SO₄, filtered and concentrated under reduced pressure to give a residue, which was purified by trituration with MTBE (50 mL) to give 4-iodo-5-methoxy-1H-pyrrolo[2,3-b]pyridine (3.5 g, 12.77 mmol, 81.67% yield) as a yellow solid. ¹H NMR (DMSO-d₆, 400 MHz) δ 11.82 (s, 1H), 7.97 (s, 1H), 7.55 (d, J=3.2 Hz, 1H), 6.16 (d, J=3.2 Hz, 1H), 3.90 (s, 3H).

Preparation of (4-iodo-5-methoxy-pyrrolo[2,3-b]pyridin-1-yl)-triisopropyl-silane

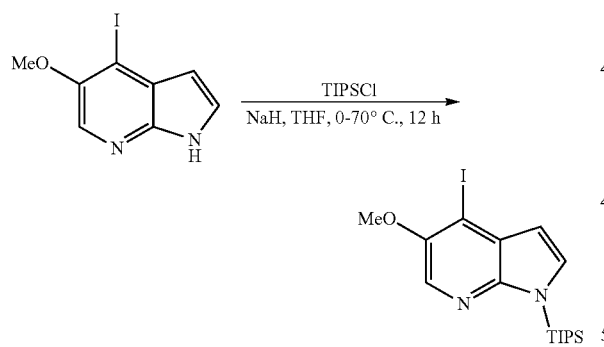

To a solution of 4-iodo-5-methoxy-1H-pyrrolo[2,3-b]pyridine (5 g, 18.24 mmol, 1 eq) in THF (200 mL), NaH (1.61 g, 40.14 mmol, 60% purity, 2.2 eq) was added portionwise at 0° C., and the mixture was stirred at 0° C. for 30 min. TIPSCl (5.28 g, 27.37 mmol, 5.86 mL, 1.5 eq) was added dropwise to the mixture at 0° C. and then heated to 70° C. for 12 h. The reaction mixture was quenched by adding saturated aq. NH₄Cl (50 mL) and extracted with EtOAc (20 mL×3). The combined organic layers were washed with brine (100 mL×2), dried over Na₂SO₄, filtered and concentrated under reduced pressure to give a residue, which was purified by column chromatography (SiO2, Petroleum ether/Ethyl acetate=20/1 to 10/1) to give (4-iodo-5-methoxy-pyrrolo[2,3-b]pyridin-1-yl)-triisopropyl-silane (6 g, 13.94 mmol, 76.41% yield) as a yellow oil. ¹H NMR (CDCl₃, 400 MHz) δ 7.81 (s, 1H), 7.28 (d, J=3.2 Hz, 1H), 6.33 (d, J=3.6 Hz, 1H), 3.91 (s, 3H), 1.78-1.72 (m, 3H), 1.04 (d, J=7.2 Hz, 18H).

Preparation of Tert-Butyl N-[3-[hydroxy-(5-methoxy-1-triisopropylsilyl-pyrrolo[2,3-b]pyridin-4-yl)methyl]cyclobutyl]carbamate

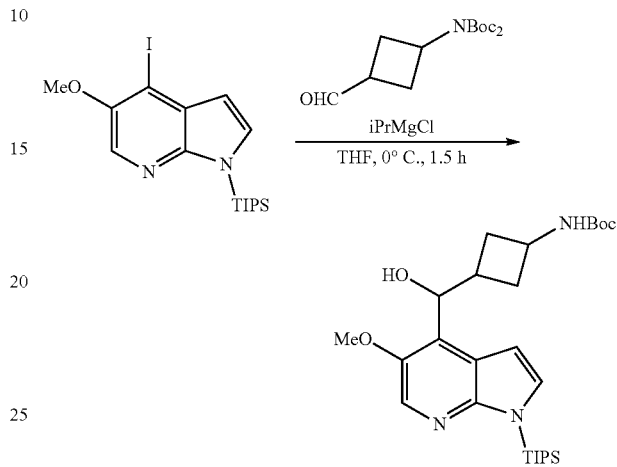

To a mixture of (4-iodo-5-methoxy-pyrrolo[2,3-b]pyridin-1-yl)-triisopropyl-silane (2 g, 4.65 mmol, 1 eq) in THF (30 mL), i-PrMgCl (2 M, 5.81 mL, 2.5 eq) was added dropwise at 0° C., and the resulting mixture was stirred at 0° C. for 30 min under a N₂ atmosphere. Then, tert-butyl N-tert-butoxycarbonyl-N-(3-formylcyclobutyl)carbamate (1.53 g, 5.11 mmol, 1.1 eq) was added in one portion, and the mixture was stirred at 0° C. for 1 h. The reaction mixture was quenched with saturated aq. NH₄Cl (50 mL) and extracted with EtOAc (50 mL×3). The combined organic layers were washed with brine (50 mL×2), dried over Na₂SO₄, filtered and concentrated under reduced pressure to give a residue, which was purified by column chromatography (SiO2, Petroleum ether/Ethyl acetate=10/1 to 3/1) to give tert-butyl N-[3-[hydroxy-(5-methoxy-1-triisopropylsilyl-pyrrolo[2,3-b]pyridin-4-yl)methyl]cyclobutyl]carbamate (1.8 g, 3.57 mmol, 76.90% yield) as a yellow oil. ¹H NMR (CDCl₃, 400 MHz) δ 7.94 (s, 1H), 7.20 (d, J=3.6 Hz, 1H), 6.59 (d, J=3.6 Hz, 1H), 4.96 (d, J=6.4 Hz, 1H), 4.66-4.64 (m, 1H), 3.88 (s, 3H), 2.47-2.41 (m, 2H), 2.40-2.39 (m, 1H), 1.81-1.71 (m, 5H), 1.35 (s, 9H), 1.03 (d, J=7.6 Hz, 18H).

Preparation of Tert-Butyl N-[3-(5-methoxy-1-triisopropylsilyl-pyrrolo[2,3-b] pyridine-4-carbonyl)cyclobutyl]carbamate

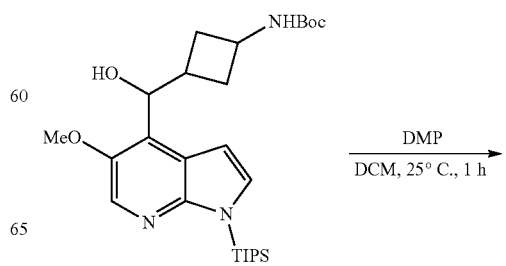

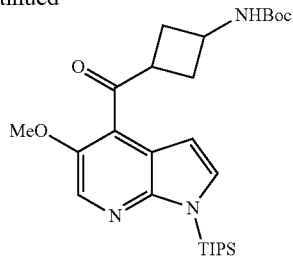

To a mixture of tert-butyl N-[3-[hydroxy-(5-methoxy-1-triisopropylsilyl-pyrrolo [2,3-b]pyridin-4-yl)methyl]cyclobutyl]carbamate (1.8 g, 3.57 mmol, 1 eq) in DCM (40 mL), DMP (1.82 g, 4.29 mmol, 1.33 mL, 1.2 eq) was added portionwise at 25° C. under a $N_2$ atmosphere, and the mixture was stirred at 25° C. for 1 h. $H_2O$ (50 mL) was added and the reaction mixture was extracted with EtOAc (50 mL×3). The combined organic layers were washed with brine (50 mL×2), dried over $Na_2SO_4$, filtered and concentrated under reduced pressure to give a residue, which was purified by column chromatography ($SiO_2$, Petroleum ether/Ethyl acetate=10/1 to 5/1) to give tert-butyl N-[3-(5-methoxy-1-triisopropylsilyl-pyrrolo[2,3-b]pyridine-4-carbonyl)cyclobutyl]carbamate (1.5 g, 2.99 mmol, 83.67% yield) as a yellow oil. $^1$H NMR (CDCl$_3$, 400 MHz) δ 8.04 (s, 1H), 7.32 (d, J=3.2 Hz, 1H), 6.73 (d, J=3.6 Hz, 1H), 4.11-4.07 (m, 1H), 3.91 (s, 3H), 3.64-3.61 (m, 1H), 2.57-2.55 (m, 2H), 2.13-2.08 (m, 2H), 1.77-1.71 (m, 3H), 1.36 (s, 9H), 1.03 (d, J=7.6 Hz, 18H).

Preparation of Tert-Butyl N-[3-[(Z)-1-(5-methoxy-1-triisopropylsilyl-pyrrolo [2,3-b]pyridin-4-yl)-2-(4,4,5,5-tetramethyl-1,3,2-dioxaborolan-2-yl)vinyl]cyclobutyl]carbamate

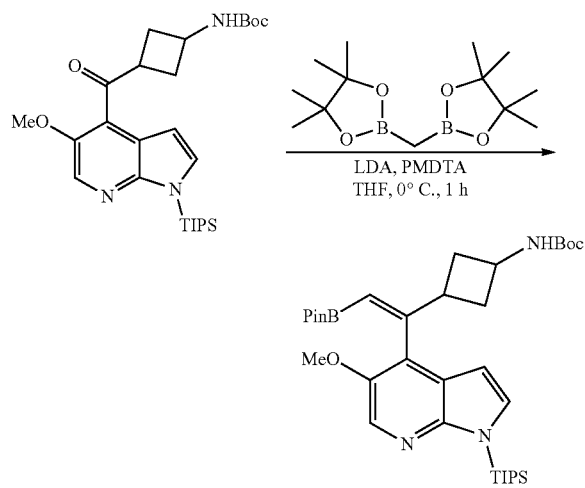

To a mixture of LDA (2 M, 6.98 mL, 7 eq) and N'-[2-(dimethylamino)ethyl]-N,N,N'-trimethyl-ethane-1,2-diamine (460.71 mg, 2.66 mmol, 555.08 uL, 4 eq) in THF (10 mL), a solution of 4,4,5,5-tetramethyl-2-[(4,4,5,5-tetramethyl-1,3,2-dioxaborolan-2-yl)methyl]-1,3,2-dioxaborolane (2.67 g, 9.97 mmol, 5 eq) in THF (10 mL) was added dropwise at 0° C., and the mixture stirred at 0° C. for 10 min. Then, tert-butyl N-[3-(5-methoxy-1-triisopropylsilyl-pyrrolo[2,3-b]pyridine-4-carbonyl) cyclobutyl]carbamate (1 g, 1.99 mmol, 1 eq) in THF (10 mL) was added to the mixture dropwise at 0° C., and the resulting mixture was stirred at 0° C. for 1 h. The reaction mixture was quenched by adding sat. aq. NH$_4$Cl (50 mL) and extracted with EtOAc (30 mL×3). The combined organic layers were washed with brine (30 mL×2), dried over Na$_2$SO$_4$, filtered and concentrated under reduced pressure to give a residue, which was purified by column chromatography (SiO$_2$, Petroleum ether/Ethyl acetate=12/1 to 8/1) to give tert-butyl N-[3-[(Z)-1-(5-methoxy-1-triisopropylsilyl-pyrrolo[2,3-b]pyridin-4-yl)-2-(4,4,5,5-tetramethyl-1,3,2-dioxaborolan-2-yl)vinyl]cyclobutyl]carbamate (0.95 g, 1.52 mmol, 76.18% yield) as a yellow oil. $^1$H NMR (CDCl$_3$, 400 MHz) δ 7.94 (s, 1H), 7.12 (d, J=3.6 Hz, 1H), 6.22 (d, J=3.6 Hz, 1H), 5.61 (s, 1H), 4.63-4.62 (m, 1H), 4.53-4.38 (m, 1H), 3.81 (s, 3H), 2.47-2.45 (m, 2H), 2.25-2.20 (m, 2H), 1.81-1.73 (m, 5H), 1.36 (s, 9H), 1.05 (s, 18H).

Preparation of 9-((1s,3s)-3-aminocyclobutyl)-[1,2]oxaborinino[5,6-d]pyrrolo[2,3-b] pyridin-7(3H)-ol

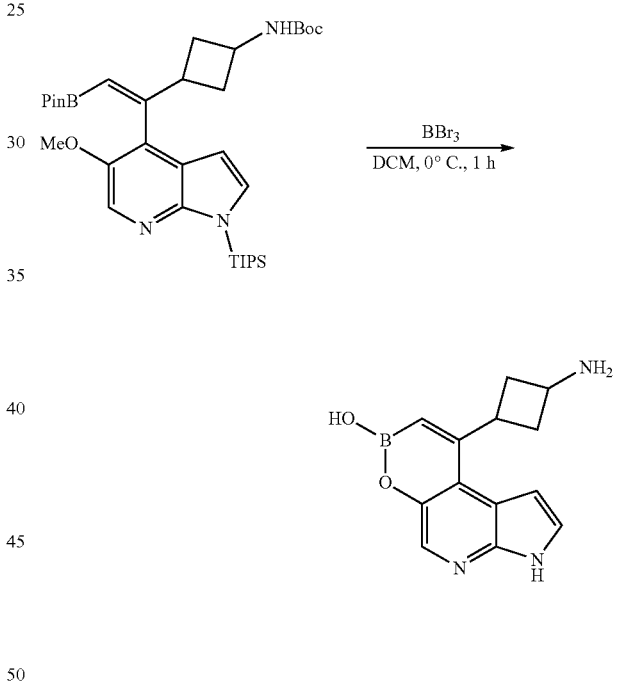

To a mixture of tert-butyl N-[3-[(E)-1-(5-methoxy-1-triisopropylsilyl-pyrrolo[2,3-b]pyridin-4-yl)-2-(4,4,5,5-tetramethyl-1,3,2-dioxaborolan-2-yl)vinyl]cyclobutyl]carbamate (0.9 g, 1.44 mmol, 1 eq) in DCM (10 mL), BBr$_3$ (1.08 g, 4.32 mmol, 415.77 uL, 3 eq) was added in one portion at 0° C. under a N$_2$ atmosphere, and the resulting mixture was stirred at 0° C. for 1 h. Then, the reaction mixture was quenched by adding H$_2$O (10 mL) and extracted with EtOAc (10 mL×3) to remove impurities. The aqueous layer was directly freeze-dried to give 9-((1s,3s)-3-aminocyclobutyl)-[1,2]oxaborinino[5,6-d]pyrrolo[2,3-b]pyridin-7(3H)-ol (0.5 g, crude) as a white solid, which was used in the next step. $^1$H NMR (DMSO-d$_6$, 400 MHz) δ 8.25 (s, 1H), 7.56 (d, J=3.2 Hz, 1H), 6.89 (d, J=3.6 Hz, 1H), 6.27 (s, 1H), 4.20-4.01 (m, 1H), 3.89-3.85 (m, 2H), 2.64-2.62 (m, 1H), 2.17-2.08 (m, 2H).

Synthesis of Intermediate Tert-Butyl N-tert-butoxycarbonyl-N-(3-formylcyclobutyl)carbamate

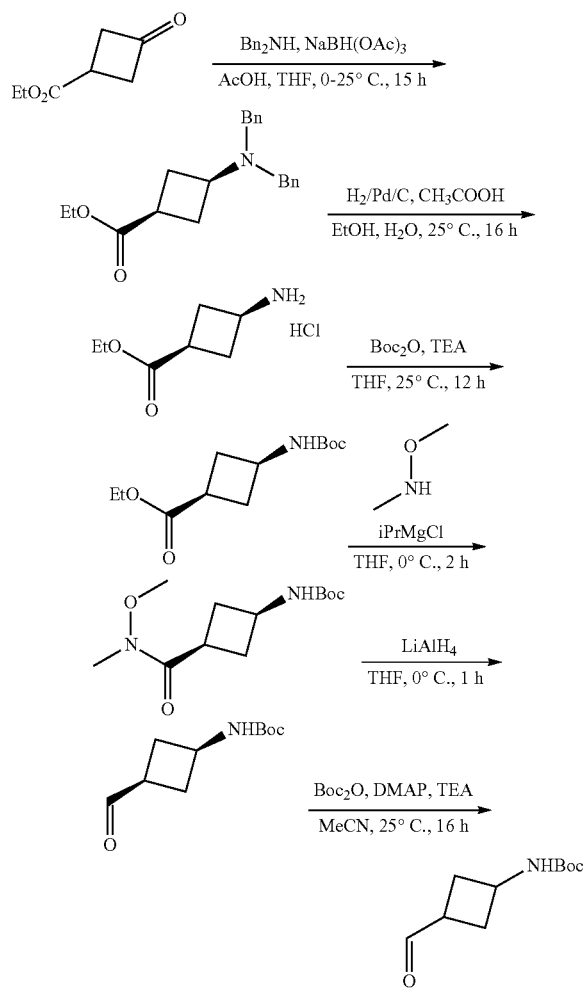

Preparation of ethyl 3-(dibenzylamino)cyclobutanecarboxylate

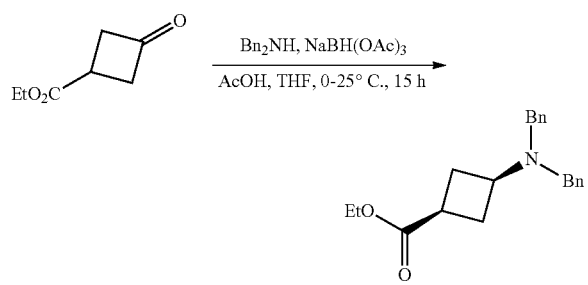

To a mixture of ethyl 3-oxocyclobutanecarboxylate (25 g, 175.87 mmol, 1 eq) and AcOH (15.84 g, 263.80 mmol, 15.09 mL, 1.5 eq) in THF (500 mL), N-benzyl-1-phenylmethanamine (52.04 g, 263.80 mmol, 50.53 mL, 1.5 eq) was added in one portion at 0° C., and the resulting mixture was stirred at 0° C. for 1 h. Then, NaBH(OAc)$_3$ (55.91 g, 263.80 mmol, 1.5 eq) was added to the reaction in portions at 0° C., and the resulting mixture was stirred at 25° C. for 14 h. The solvent was removed under reduced pressure, and the pH of the mixture was adjusted to 9 by adding saturated aq. Na$_2$CO$_3$. The mixture was extracted with EtOAc (500 mL×3). The combined organic layers were washed with brine (500 mL×2), dried over anhydrous Na$_2$SO$_4$, filtered and concentrated under reduced pressure to give a residue, which was purified by flash silica gel chromatography (ISCO®; 330 g SepaFlash® Silica Flash Column, Eluent of 0-10% Ethyl acetate/Petroleum ethergradient @ 100 mL/min) to give ethyl 3-(dibenzylamino)cyclobutanecarboxylate (150 g, 463.78 mmol, 65.93% yield) as a colorless oil.

$^1$H NMR (CDCl$_3$, 400 MHz) δ 7.32-7.26 (m, 8H), 7.24-7.22 (m, 2H), 4.13 (q, J=6.8 Hz, 2H), 3.51 (s, 4H), 3.14-3.09 (m, 1H), 2.67-2.62 (m, 1H), 2.23-2.14 (m, 4H), 1.23 (t, J=6.8 Hz, 3H).

Preparation of Ethyl 3-aminocyclobutanecarboxylate

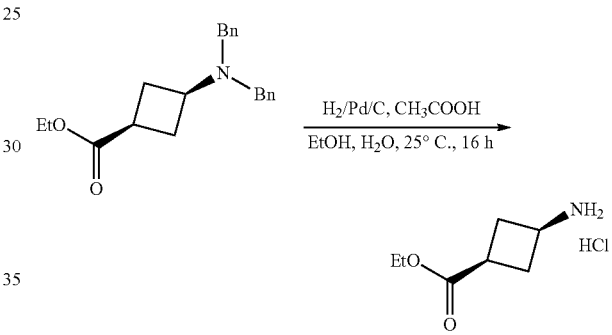

To a solution of ethyl 3-(dibenzylamino)cyclobutanecarboxylate (59 g, 182.42 mmol, 1 eq) in EtOH (1000 mL) and H$_2$O (60 mL), AcOH (10.95 g, 182.42 mmol, 10.43 mL, 1 eq) was added along with Pd/C (20 g, 182.42 mmol, 10% purity). The suspension was degassed in vacuo and purged with H$_2$ three times. The mixture was stirred under a H$_2$ atmosphere (45 psi) at 25° C. for 16 h. Then, the reaction mixture was filtered and concentrated under reduced pressure. To the residue, 4 N HCl/EtOAc (300 mL) was added and a white solid precipitated. The white solid was collected by filtration and dried in vacuo to give ethyl 3-aminocyclobutanecarboxylate (48 g, 267.19 mmol, 73.24% yield, HCl) as a white solid. $^1$H NMR (DMSO-d$_6$, 400 MHz) δ 8.46 (br, 3H), 4.05 (q, J=6.8 Hz, 2H), 3.59-3.55 (m, 1H), 2.96-2.92 (m, 1H), 2.42-2.38 (m, 2H), 2.32-2.26 (m, 2H), 1.19-1.15 (t, J=6.8 Hz, 3H)

Preparation of Ethyl 3-(tert-butoxycarbonylamino)cyclobutanecarboxylate

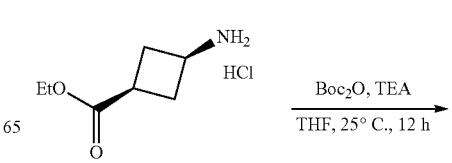

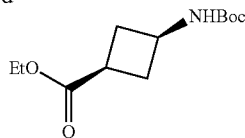

To a mixture of ethyl 3-aminocyclobutanecarboxylate (24 g, 133.60 mmol, 1 eq, HCl) and TEA (40.56 g, 400.79 mmol, 55.79 mL, 3 eq) in THF (300 mL), (Boc)$_2$O (43.74 g, 200.40 mmol, 46.04 mL, 1.5 eq) was added dropwise at 25° C. The mixture was stirred at 25° C. for 12 h under a N$_2$ atmosphere. Then, the reaction mixture was poured into saturated aq. NaHCO$_3$ (200 mL) and extracted with EtOAc (200 mL×3). The combined organic layers were washed with brine (200 mL×2), dried over anhydrous Na$_2$SO$_4$, filtered and concentrated in vacuo to give a residue, which was purified by flash silica gel chromatography (ISCO®; 330 g SepaFlash® Silica Flash Column, Eluent of 0-10% Ethyl acetate/Petroleum ethergradient @ 100 mL/min) to give ethyl 3-(tert-butoxycarbonylamino)cyclobutanecarboxylate (50 g, 205.51 mmol, 76.91% yield) as a white solid. $^1$H NMR (CDCl$_3$, 400 MHz) δ 4.86 (br, 1H), 4.14-4.09 (m, 3H), 2.78-2.69 (m, 1H), 2.59-2.57 (m, 2H), 2.11-2.04 (m, 2H), 1.42 (s, 9H), 1.24 (t, J=6.8 Hz, 3H).

Preparation of Tert-Butyl N-[3-[methoxy(methyl)carbamoyl]cyclobutyl]carbamate

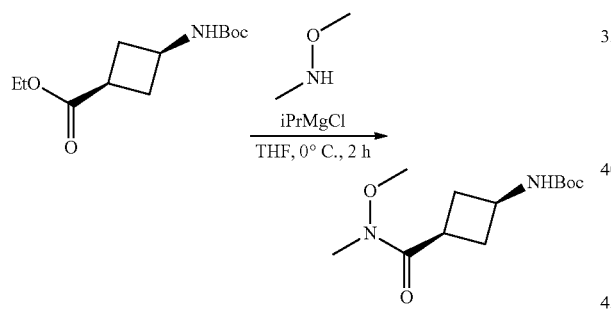

To a mixture of ethyl 3-(tert-butoxycarbonylamino)cyclobutanecarboxylate (25 g, 102.75 mmol, 1 eq) and N-methoxymethanamine (20.05 g, 205.51 mmol, 2 eq, HCl) in THF (250 mL), i-PrMgCl (2 M, 205.51 mL, 4 eq) was added dropwise at 0° C. The mixture was stirred at 0° C. for 2 h. The reaction mixture was poured into saturated aq. NH$_4$Cl (250 mL) and extracted with EtOAc (200 mL×3). The combined organic layers were washed with brine (200 mL×2), dried over anhydrous Na$_2$SO$_4$, filtered and concentrated under reduced pressure to give a residue, which was purified by flash silica gel chromatography (ISCO®; 330 g SepaFlash® Silica Flash Column, Eluent of 0-30% Ethyl acetate/Petroleum ethergradient @ 100 mL/min) to give tert-butyl N-[3-[methoxy(methyl)carbamoyl]cyclobutyl]carbamate (44 g, 170.34 mmol, 82.88% yield) as a white solid. $^1$H NMR (CDCl$_3$, 400 MHz) δ 5.03 (br, 1H), 4.20-4.00 (m, 1H), 3.63 (s, 3H), 3.16-3.15 (m, 4H), 2.51-2.49 (m, 2H), 2.15-2.07 (m, 2H), 1.41 (s, 9H).

Preparation of Tert-Butyl N-(3-formylcyclobutyl)carbamate

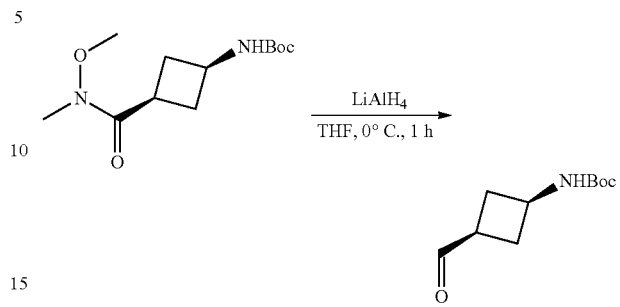

To a mixture of tert-butyl N-[3-[methoxy(methyl)carbamoyl]cyclobutyl]carbamate (15 g, 58.07 mmol, 1 eq) in THF (150 mL), LiAlH$_4$ (2.64 g, 69.68 mmol, 1.2 eq) was added in portions at 0° C. The mixture was stirred at 0° C. for 1 h and quenched by adding Na$_2$SO$_4$.10H$_2$O (50 g) while stirring. The resulting mixture was filtered through a pad of celite to remove the insoluble impurities. The filtrate was washed with HCl 50 mL (1 N), dried over anhydrous Na$_2$SO$_4$, filtered and concentrated under reduced pressure to give a residue, which was purified by flash silica gel chromatography (ISCO®; 330 g SepaFlash® Silica Flash Column, Eluent of 0-30% Ethyl acetate/Petroleum ethergradient @ 100 mL/min) to give tert-butyl N-(3-formylcyclobutyl)carbamate (9 g, 45.17 mmol, 38.89% yield) as a white solid. $^1$H NMR (CDCl$_3$, 400 MHz) δ 9.69 (s, 1H), 4.72 (br. s, 1H), 4.19-4.11 (m, 1H), 2.92-2.86 (m, 1H), 2.58-2.53 (m, 2H), 2.11-2.03 (m, 2H), 1.44 (s, 9H).

Preparation of Tert-Butyl N-tert-butoxycarbonyl-N-(3-formylcyclobutyl)carbamate

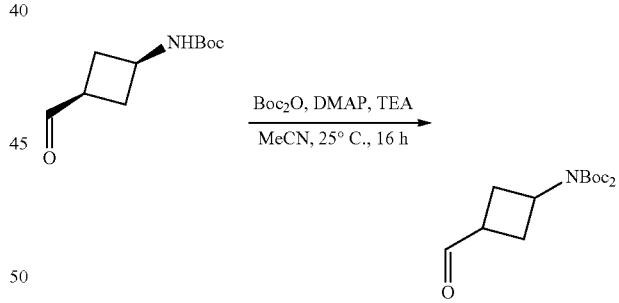

To a mixture of tert-butyl N-(3-formylcyclobutyl)carbamate (9 g, 45.17 mmol, 1 eq) in MeCN (90 mL), TEA (13.71 g, 135.51 mmol, 18.86 mL, 3 eq), DMAP (2.76 g, 22.59 mmol, 0.5 eq) and Boc$_2$O (14.79 g, 67.76 mmol, 15.57 mL, 1.5 eq) were added in one portion at 25° C. The resulting mixture was stirred at 25° C. for 16 h. Then, the mixture was poured into H$_2$O (100 mL) and extracted with EtOAc (100 mL×3). The combined organic layers were washed with brine (100 mL×2), dried over anhydrous Na$_2$SO$_4$, filtered and concentrated under reduced pressure to give a residue, which was purified by flash silica gel chromatography (ISCO®; 120 g SepaFlash® Silica Flash Column, Eluent of 0-30% Ethyl acetate/Petroleum ethergradient @100 mL/min) to give tert-butyl N-tert-butoxycarbonyl-N-(3-formylcyclobutyl)carbamate (4 g, 13.36 mmol, 29.58% yield) as a yellow oil. ¹H NMR (CDCl₃, 400 MHz) δ 9.68 (s, 1H), 4.48-4.38 (m, 1H), 2.83-2.81 (m, 1H), 2.58-2.49 (m, 4H), 1.51 (s, 18H).

Preparation of N-(3-(7-hydroxy-3,7-dihydro-[1,2] oxaborinino[5,6-d]pyrrolo [2,3-b]pyridin-9-yl)cyclobutyl)propane-1-sulfonamide

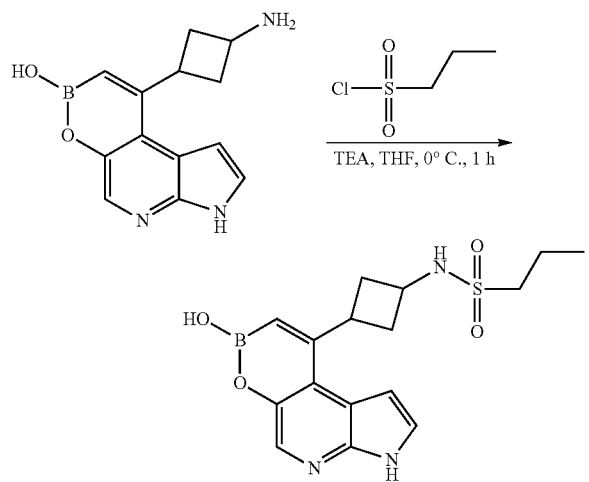

This substance (yield: 9.04%, a white solid) was prepared as a racemic mixture by following General Procedure A. ¹H NMR (DMSO-d₆, 400 MHz) δ 11.81 (s, 1H), 8.93 (s, 1H), 8.25 (s, 1H), 7.57 (s, 1H), 7.45 (d, J=8.4 Hz, 1H), 6.93 (s, 1H), 6.22 (s, 1H), 3.97-3.96 (m, 1H), 3.70-3.69 (m, 1H), 2.97-2.95 (m, 2H), 2.93-2.73 (m, 2H), 2.02-2.00 (m, 2H), 1.69-1.66 (m, 2H), 0.98 (t, J=7.6 Hz, 3H). MS (ESI): mass calcd. For C₁₆H₂₀BN₃O₄S, 361.13, m/z. found 362.1 [M+H]⁺. Purity by HPLC: 92.73% (220 nm), 96.17% (254 nm).

Preparation of N-(trans-3-(7-hydroxy-3,7-dihydro-[1,2]oxaborinino[5,6-d]pyrrolo[2,3-b]pyridin-9-yl) cyclobutyl)cyclopropanesulfonamide and N-(cis-3-(7-hydroxy-3,7-dihydro-[1,2]oxaborinino[5,6-d]pyrrolo[2,3-b]pyridin-9-yl)cyclobutyl) cyclopropanesulfonamide

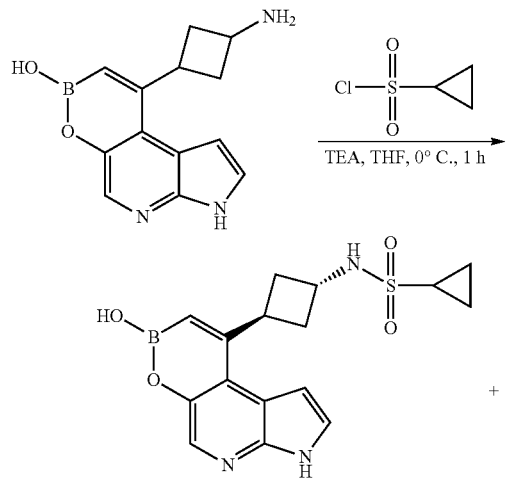

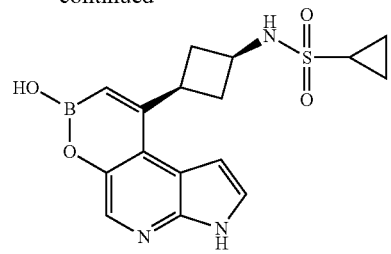

The title compounds were prepared by following General Procedure A, which was purified by prep-HPLC (column: Nano-micro Kromasil C18 100*30 mm 8 um; mobile phase: [water (0.1% TFA)-ACN]; B %: 15%-35%,10 min) to give N-(trans-3-(7-hydroxy-3,7-dihydro-[1,2]oxaborinino[5,6-d] pyrrolo[2,3-b]pyridin-9-yl)cyclobutyl) cyclopropanesulfonamide (yield: 5.68%, a white solid) and N-(cis-3-(7-hydroxy-3,7-dihydro-[1,2]oxaborinino[5,6-d]pyrrolo[2,3-b]pyridin-9-yl)cyclobutyl) cyclopropanesulfonamide (yield: 7.1%, a white solid).

N-(trans-3-(7-hydroxy-3,7-dihydro-[1,2]oxaborinino[5,6-d]pyrrolo[2,3-b]pyridin-9-yl)cyclobutyl) cyclopropanesulfonamide: ¹H NMR (DMSO-d₆, 400 MHz) δ 11.82 (s, 1H), 8.88 (br. s, 1H), 8.28 (s, 1H), 7.67 (d, J=9.6 Hz, 1H), 7.57 (s, 1H), 6.66 (s, 1H), 6.41 (s, 1H), 3.95-3.88 (m, 1H), 3.86-3.82 (m, 2H), 2.63-2.60 (m, 3H), 2.58-2.47 (m, 1H), 0.93-0.89 (m, 4H). MS (ESI): mass calcd. For C₁₆H₁₈BN₃O₄S, 359.11, m/z. found 361.0 [M+H]⁺. Purity by HPLC: 95.41% (220 nm), 95.07% (254 nm).

N-(cis-3-(7-hydroxy-3,7-dihydro-[1,2]oxaborinino[5,6-d]pyrrolo[2,3-b]pyridin-9-yl)cyclobutyl) cyclopropanesulfonamide: ¹H NMR (DMSO-d₆, 400 MHz) δ 11.80 (s, 1H), 8.26 (s, 1H), 7.57 (s, 1H), 7.67 (d, J=9.6 Hz, 1H), 6.94 (s, 1H), 6.24 (s, 1H), 4.02-3.99 (m, 1H), 3.73-3.71 (m, 2H), 2.76-2.75 (m, 2H), 2.25-2.20 (m, 1H), 2.07-2.04 (m, 1H), 0.95-0.93 (m, 4H). MS (ESI): mass calcd. For C₁₆H₁₈BN₃O₄S, 359.11, m/z. found 361.0 [M+H]⁺. Purity by HPLC: 94.92% (220 nm), 92.89% (254 nm).

Preparation of N-(trans-3-(7-hydroxy-3,7-dihydro-[1,2]oxaborinino[5,6-d]pyrrolo[2,3-b]pyridin-9-yl) cyclobutyl)ethanesulfonamide and N-(cis-3-(7-hydroxy-3,7-dihydro-[1,2]oxaborinino[5,6-d]pyrrolo[2,3-b]pyridin-9-yl)cyclobutyl)ethanesulfonamide

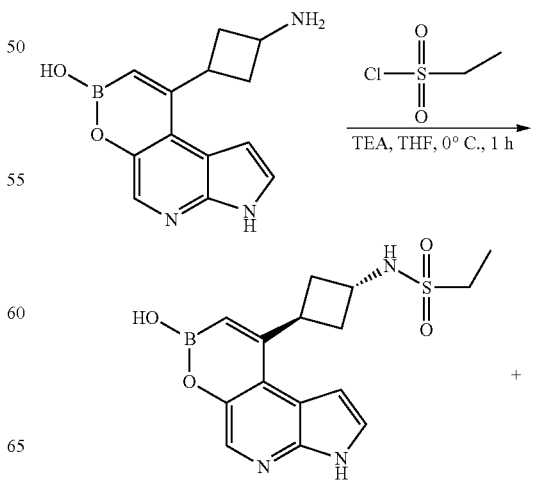

-continued

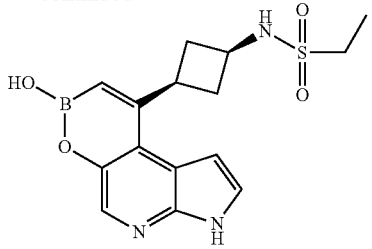

The title compounds were prepared by following General Procedure A. N-(trans-3-(7-hydroxy-3,7-dihydro-[1,2]oxaborinino[5,6-d]pyrrolo[2,3-b]pyridin-9-yl)cyclobutyl) ethanesulfonamide (yield: 2.69%): $^1$H NMR (DMSO-$d_6$+$D_2$O, 400 MHz) δ 8.27 (s, 1H), 7.56 (d, J=3.2 Hz, 1H), 6.64 (d, J=3.2 Hz, 1H), 6.41 (s, 1H), 3.92-3.91 (m, 1H), 3.82-3.80 (m, 1H), 2.97-2.87 (m, 4H), 2.06-1.98 (m, 2H), 1.18 (t, J=7.6 Hz, 3H). MS (ESI): mass calcd. For $C_{15}H_{18}BN_3O_4S$, 347.11, m/z. found 348.1 [M+H]$^+$. HPLC: 92.87% (220 nm), 92.85% (254 nm).

N-(cis-3-(7-hydroxy-3,7-dihydro-[1,2]oxaborinino[5,6-d]pyrrolo[2,3-b]pyridin-9-yl)cyclobutyl)ethanesulfonamide (yield: 5.14%): $^1$H NMR (DMSO-$d_6$, 400 MHz) δ 11.80 (s, 1H), 8.27 (s, 1H), 7.56 (d, J=3.2 Hz, 1H), 7.45 (d, J=9.2 Hz, 1H), 6.92 (d, J=3.2 Hz, 1H), 6.23 (s, 1H), 4.00-3.94 (m, 1H), 3.60-3.70 (m, 1H), 2.99-2.89 (m, 2H), 2.74-2.72 (m, 2H), 2.06-1.98 (m, 2H), 1.19 (t, J=7.2 Hz, 3H). MS (ESI): mass calcd. For $C_{15}H_{18}BN_3O_4S$, 347.11, m/z. found 348.1 [M+H]$^+$. HPLC: 92.08% (220 nm), 91.79% (254 nm).

Preparation of N-(trans-3-(7-hydroxy-3,7-dihydro-[1,2]oxaborinino[5,6-d]pyrrolo [2,3-b]pyridin-9-yl) cyclobutyl)propane-1-sulfonamide and N-(cis-3-(7-hydroxy-3,7-dihydro-[1,2]oxaborinino[5,6-d]pyrrolo [2,3-b]pyridin-9-yl)cyclobutyl)propane-1-sulfonamide

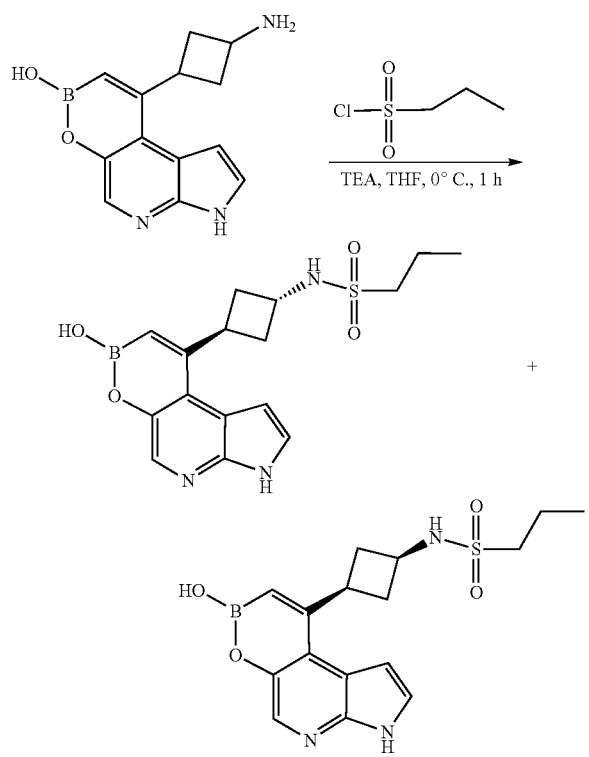

The title compounds were prepared by following General Procedure A, which were purified by prep-HPLC (column: Phenomenex Synergi C18 150*25*10 um; mobile phase: [water (0.1% TFA)-ACN]; B %: 25%-41%,8 min).

N-(trans-3-(7-hydroxy-3,7-dihydro-[1,2]oxaborinino[5,6-d]pyrrolo [2,3-b]pyridin-9-yl)cyclobutyl)propane-1-sulfonamide (yield: 2.1%): $^1$H NMR (DMSO-$d_6$+$D_2$O, 400 MHz) δ 8.23 (s, 1H), 7.52 (d, J=3.8 Hz, 1H), 6.61 (d, J=3.8 Hz, 1H), 6.38 (s, 1H), 3.78-3.87 (m, 1H), 3.74-3.77 (m, 1H), 2.85-2.89 (m, 2H), 1.81-1.79 (m, 1H), 1.65-1.56 (m, 3H), 1.50-1.40 (m, 1H), 0.88-0.84 (m, 3H). MS (ESI): mass calcd. For $C_{16}H_{20}BN_3O_4S$, 361.13, m/z. found 362.1 [M+H]$^+$. HPLC: 94.36% (220 nm), 86.74% (254 nm).

N-(cis-3-(7-hydroxy-3,7-dihydro-[1,2]oxaborinino[5,6-d]pyrrolo [2,3-b]pyridin-9-yl)cyclobutyl)propane-1-sulfonamide (Yield: 20.7%): $^1$H NMR (DMSO-$d_6$, 400 MHz) δ 11.80 (s, 1H), 8.89 (br, 1H), 8.25 (s, 1H), 7.57 (t, J=2.8 Hz, 1H), 7.45 (d, J=8.8 Hz, 1H), 6.92 (s, 1H), 6.23 (s, 1H), 4.01-3.94 (m, 1H), 3.71-3.67 (m, 1H), 2.96-2.92 (m, 2H), 2.75-2.73 (m, 2H), 2.05-1.98 (m, 2H), 1.70-1.65 (m, 2H), 0.97 (t, J=7.6 Hz, 3H). MS (ESI): mass calcd. For $C_{16}H_{20}BN_3O_4S$, 361.13, m/z. found 362.2 [M+H]$^+$. HPLC: 99.97% (220 nm), 100% (254 nm).

Preparation of 4-fluoro-N-(3-(7-hydroxy-3,7-dihydro-[1,2]oxaborinino[5,6-d]pyrrolo[2,3-b]pyridin-9-yl)cyclobutyl)benzenesulfonamide

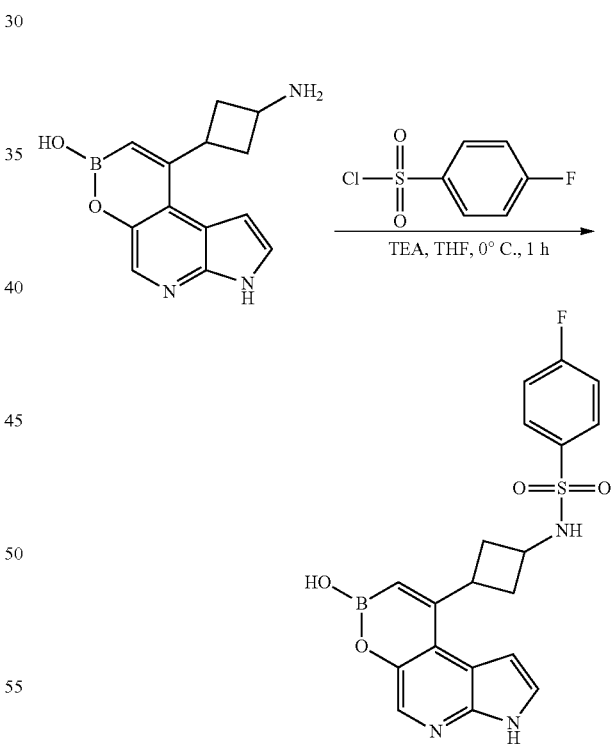

The title compound was prepared by following General Procedure A as a white solid, yield: 7.82%. $^1$H NMR (DMSO-$d_6$, 400 MHz) δ 11.77 (s, 1H), 8.22 (s, 1H), 8.05 (d, J=8.8 Hz, 1H), 7.90-7.86 (m, 2H), 7.54-7.52 (m, 1H), 7.43 (t, J=8.8 Hz, 2H), 6.81 (s, 1H), 6.09 (s, 1H), 3.93-3.91 (m, 1H), 2.43-2.41 (m, 3H), 1.81-1.76 (m, 2H). MS (ESI): mass calcd. For $C_{19}H_{17}BFN_3O_4S$, 413.10, m/z. found 414.1 [M+H]$^+$. HPLC: 75.39% (220 nm), 92.97% (254 nm).

Preparation of N-(cis-3-(7-hydroxy-3,7-dihydro-[1,2]oxaborinino[5,6-d]pyrrolo[2,3-b]pyridin-9-yl)cyclobutyl)butane-1-sulfonamide

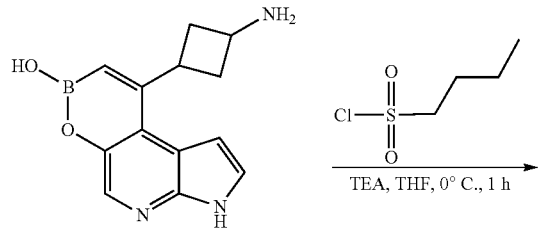

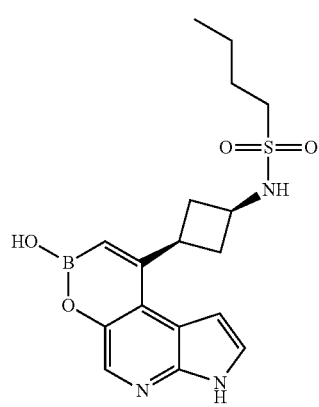

The title compound was prepared by following General Procedure A, yield: 5.9%. ¹H NMR (DMSO-d₆, 400 MHz) δ 11.78 (s, 1H), 8.93 (s, 1H), 8.24 (s, 1H), 7.56 (s, 1H), 7.43 (d, J=8.8 Hz, 1H), 6.91 (s, 1H), 6.22 (s, 1H), 3.97-3.96 (m, 1H), 3.68-3.67 (m, 1H), 2.97-2.93 (m, 2H), 2.74-2.72 (m, 2H), 2.02-2.00 (m, 2H), 1.65-1.63 (m, 2H), 1.41-1.35 (m, 2H), 0.88 (t, J=7.2 Hz, 3H). MS (ESI): mass calcd. For $C_{17}H_{22}BN_3O_4S$, 375.14, m/z. found 376.1 [M+H]⁺. HPLC: 88.14% (220 nm), n/a (254 nm).

Preparation of N-(cis-3-(7-hydroxy-3,7-dihydro-[1,2]oxaborinino[5,6-d]pyrrolo[2,3-b]pyridin-9-yl)cyclobutyl)-3-methoxypropane-1-sulfonamide

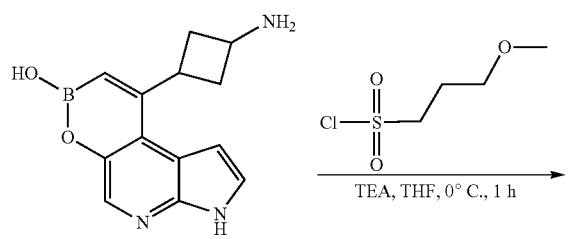

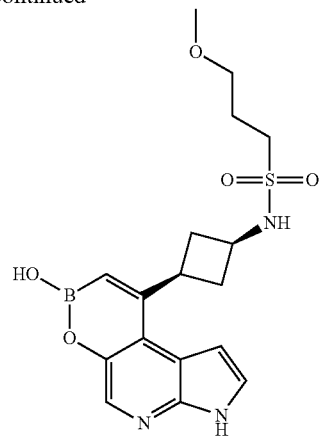

The title compound was prepared by following General Procedure A, yield: 6.1%. ¹H NMR (DMSO-d₆, 400 MHz) δ 11.78 (s, 1H), 8.92 (br, 1H), 8.24 (s, 1H), 7.56 (s, 1H), 7.48 (d, J=8.4 Hz, 1H), 6.92 (s, 1H), 6.22 (s, 1H), 3.99-3.95 (m, 1H), 3.69-3.67 (m, 1H), 3.41-3.38 (m, 2H), 3.21 (s, 3H), 2.99 (t, J=8.0 Hz, 2H), 2.74-2.72 (m, 2H), 2.02-2.00 (m, 2H), 1.89-1.85 (m, 2H). MS (ESI): mass calcd. For $C_{17}H_{22}BN_3O_5S$, 391.14, m/z. found 392.0 [M+H]⁺. HPLC: 82.46% (220 nm), 71.61% (254 nm).

Preparation of 1-cyclobutyl-N-((cis-3-(7-hydroxy-3,7-dihydro-[1,2]oxaborinino[5,6-d]pyrrolo[2,3-b]pyridin-9-yl)cyclobutyl)methanesulfonamide

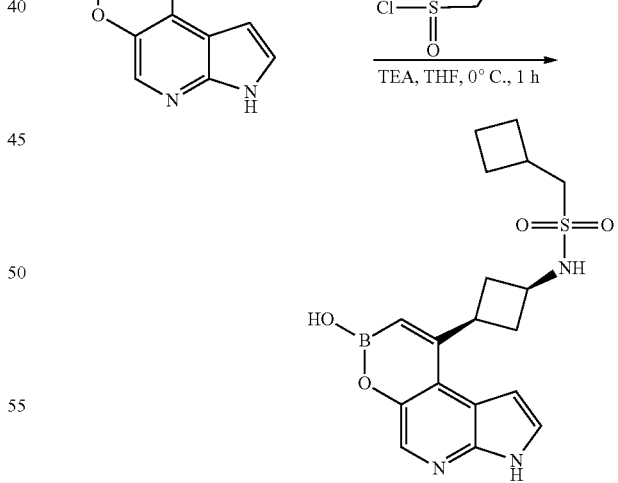

The title compound was prepared by following General Procedure A, yield: 5.7%. ¹H NMR (DMSO-de, 400 MHz) δ 11.81 (s, 1H), 8.94 (s, 1H), 8.25 (s, 1H), 7.57 (s, 1H), 7.41 (d, J=8.8 Hz, 1H), 6.92 (s, 1H), 6.22 (s, 1H), 3.99-3.95 (m, 1H), 3.69-3.67 (m, 1H), 3.68 (d, J=6.8 Hz, 2H), 2.73-2.72 (m, 2H), 2.10-2.00 (m, 5H), 1.84-1.79 (m, 4H). MS (ESI): mass calcd. For $C_{18}H_{22}BN_3O_4S$, 387.14, m/z. found 388.1 [M+H]⁺. HPLC: 87.51% (220 nm), 96.59% (254 nm).

187

Preparation of N-(cis-3-(7-hydroxy-3,7-dihydro-[1,2]oxaborinino[5,6-d]pyrrolo[2,3-b]pyridin-9-yl)cyclobutyl)-3-methylbutane-1-sulfonamide

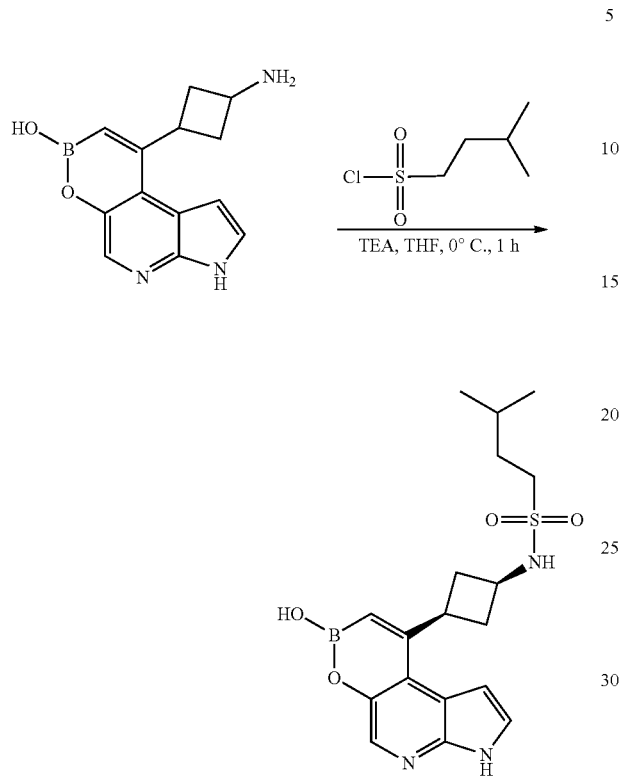

The title compound was prepared by following General Procedure A, yield: 7.2%. ¹H NMR (DMSO-d₆, 400 MHz) δ 11.78 (s, 1H), 8.90 (s, 1H), 8.24 (s, 1H), 7.56 (s, 1H), 7.44 (d, J=9.2 Hz, 1H), 6.92 (s, 1H), 6.22 (s, 1H), 4.56 (q, J=6.8 Hz, 1H), 3.99-3.97 (m, 1H), 3.69-3.67 (m, 1H), 2.97-2.93 (m, 2H), 2.74-2.72 (m, 2H), 2.03-2.02 (m, 2H), 1.67-1.63 (m, 2H), 0.88 (d, J=6.4 Hz, 6H). MS (ESI): mass calcd. For $C_{18}H_{24}BN_3O_4S$, 389.16, m/z. found 390.1 [M+H]⁺. HPLC: 91.94% (220 nm), 77.19% (254 nm).

Preparation of 2-cyclopropyl-N-(cis-3-(7-hydroxy-3,7-dihydro-[1,2]oxaborinino[5,6-d]pyrrolo[2,3-b]pyridin-9-yl)cyclobutyl)ethane-1-sulfonamide

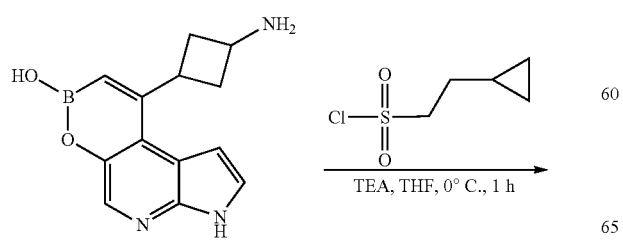

188

-continued

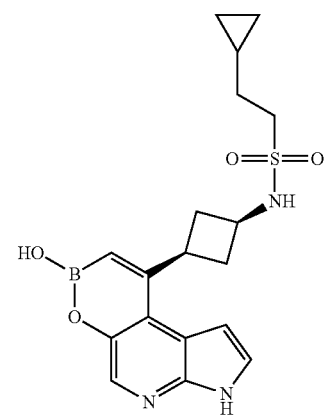

The title compound was prepared by following General Procedure A, yield: 13.6%. ¹H NMR (DMSO-d₆, 400 MHz) δ 11.69 (s, 1H), 8.81 (s, 1H), 8.16 (s, 1H), 7.48 (t, J=2.8 Hz, 1H), 7.33 (d, J=9.2 Hz, 1H), 6.83 (s, 1H), 6.14 (s, 1H), 3.94-3.89 (m, 1H), 3.63-3.59 (m, 1H), 2.97-2.93 (m, 2H), 2.66-2.64 (m, 2H), 1.92-1.90 (m, 1H), 1.48-1.46 (m, 2H), 1.29-1.27 (m, 1H), 0.74-0.73 (m, 1H), 0.36-0.33 (m, 2H), 0.02-0.01 (m, 2H). MS (ESI): mass calcd. For $C_{18}H_{22}BN_3O_4S$, 387.14, m/z. found 388.1 [M+H]⁺. HPLC: 89.42% (220 nm), 84.39% (254 nm).

Preparation of 4-fluoro-N-(trans-3-(7-hydroxy-3,7-dihydro-[1,2]oxaborinino[5,6-d]pyrrolo[2,3-b]pyridin-9-yl)cyclobutyl)benzenesulfonamide and 4-fluoro-N-(cis-3-(7-hydroxy-3,7-dihydro-[1,2]oxaborinino[5,6-d]pyrrolo[2,3-b]pyridin-9-yl)cyclobutyl)benzenesulfonamide

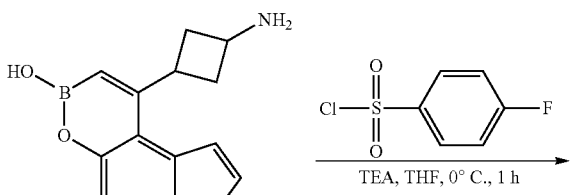

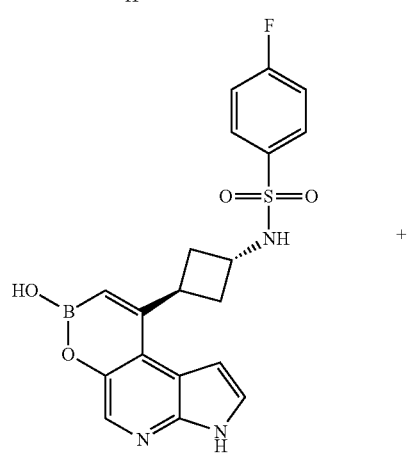

+

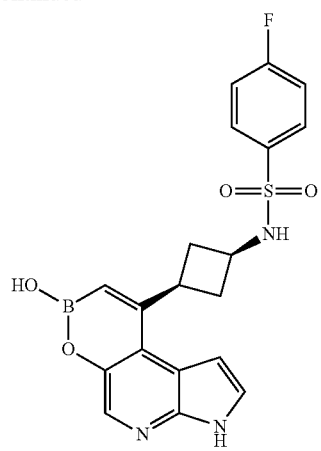

The title compounds were prepared by following General Procedure A. 4-fluoro-N-(trans-3-(7-hydroxy-3,7-dihydro-[1,2]oxaborinino[5,6-d]pyrrolo[2,3-b]pyridin-9-yl)cyclobutyl) benzenesulfonamide (yield: 5.8%): $^1$H NMR (DMSO-$d_6$, 400 MHz) δ 11.83 (s, 1H), 8.30 (d, J=8.4 Hz, 1H), 8.25 (s, 1H), 7.88-7.84 (m, 2H), 7.53 (t, J=2.8 Hz, 1H), 7.42 (t, J=9.2 Hz, 2H), 6.53 (s, 1H), 6.27 (s, 1H), 3.95-3.84 (m, 1H), 3.76-3.70 (m, 1H), 2.37-2.30 (m, 2H), 2.21-2.16 (m, 2H). MS (ESI): mass calcd. For $C_{19}H_{17}BFN_3O_4S$, 413.10, m/z. found 414.1 [M+H]$^+$. HPLC: 88.30% (220 nm), 97.09% (254 nm).

4-fluoro-N-(cis-3-(7-hydroxy-3,7-dihydro-[1,2]oxaborinino[5,6-d]pyrrolo[2,3-b]pyridin-9-yl)cyclobutyl)benzenesulfonamide (yield: 14.4%): $^1$H NMR (DMSO-$d_6$, 400 MHz) δ 11.80 (s, 1H), 8.23 (s, 1H), 8.06 (d, J=8.8 Hz, 1H), 7.92-7.88 (m, 2H), 7.55 (t, J=2.8 Hz, 1H), 7.45 (t, J=8.8 Hz, 2H), 6.83 (s, 1H), 6.11 (s, 1H), 3.97-3.91 (m, 1H), 3.59-3.58 (m, 1H), 2.45-2.43 (m, 2H), 1.86-1.78 (m, 2H). MS (ESI): mass calcd. For $C_{19}H_{17}BFN_3O_4S$, 413.10, m/z. found 414.1 [M+H]$^+$. HPLC: 99.31% (220 nm), 99.44% (254 nm).

Preparation of 9-((1R,2s,3S,5s,7s)-5-bromoadamantan-2-yl)-[1,2]oxaborinino[5,6-d]pyrrolo[2,3-b]pyridin-7(3H)-ol

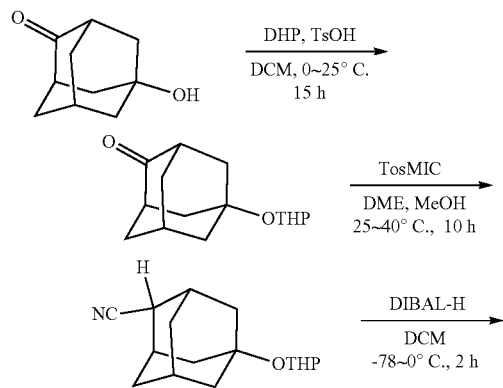

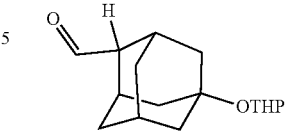
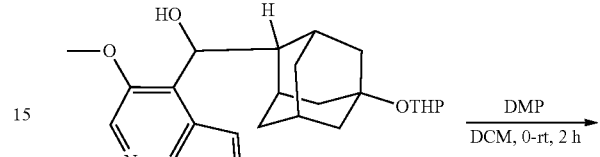
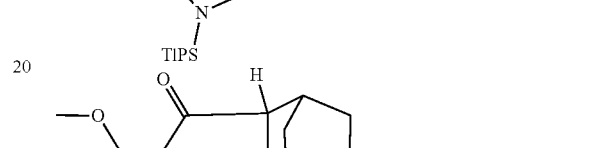
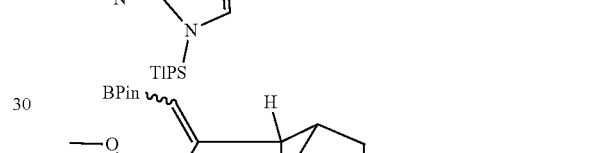
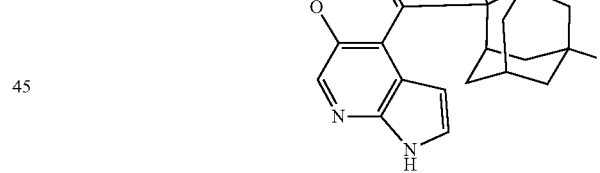

Preparation of 5-tetrahydropyran-2-yloxyadamantan-2-one

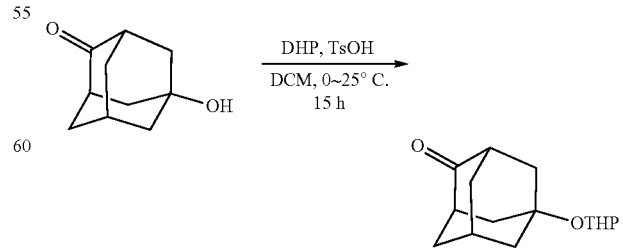

To a mixture of 3,4-dihydro-2H-pyran (25.3 g, 300.81 mmol, 27.50 mL, 5 eq) in DCM (100 mL), TsOH (104 mg, 602 μmol, 0.01 eq) and 5-hydroxyadamantan-2-one (10.0 g, 60.16 mmol, 1 eq) were added at 0° C. The resulting mixture was stirred at room temperature for 15 h. H₂O (100 mL) was added to quench the reaction, which was extracted with DCM (80 mL×2). The combined organic layers were washed with brine (100 mL×2), dried over anhydrous Na₂SO₄, filtered and concentrated in vacuo to give a residue. The obtained crude product was purified by flash silica gel chromatography (ISCO®; 120 g SepaFlash® Silica Flash Column, Eluent of 30~45% Ethyl acetate/Petroleum ether-gradient @ 100 mL/min) to give 5-tetrahydropyran-2-yloxy-adamantan-2-one (13.0 g, 51.93 mmol, 86.32% yield) as a colorless oil. ¹H NMR (CDCl₃, 400 MHz) δ 4.86-4.84 (m, 1H), 3.97-3.92 (m, 1H), 3.48-3.44 (m, 1H), 2.63-2.61 (m, 2H), 2.33-2.31 (m, 1H), 2.12-1.95 (m, 14H), 1.54-1.52 (m, 2H).

Preparation of 5-tetrahydropyran-2-yloxyadamantane-2-carbonitrile

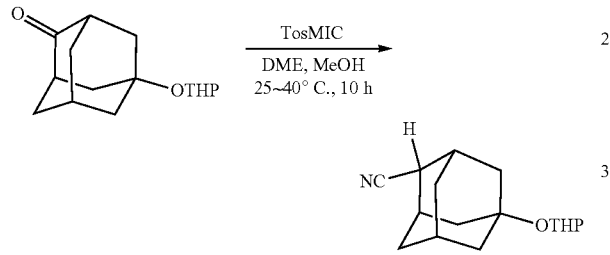

To a mixture of 5-tetrahydropyran-2-yloxyadamantan-2-one (13.0 g, 51.93 mmol, 1 eq) and 1-(isocyanomethylsulfonyl)-4-methyl-benzene (15.2 g, 77.90 mmol, 1.5 eq) in DME (90 mL), t-BuOK (17.5 g, 155.79 mmol, 3 eq) and MeOH (7.49 g, 233.69 mmol, 9.50 mL, 4.50 eq) were added in one portion at room temperature. The resulting mixture was stirred at 40° C. for 10 h. Then, H₂O (50 mL) was added into the reaction mixture, which was extracted with EtOAc (70 mL×2). The combined organic layers were washed with brine (70 mL×2), dried over anhydrous Na₂SO₄, filtered and concentrated in vacuo to give a residue, which was purified by flash silica gel chromatography (ISCO®; 80 g SepaFlash® Silica Flash Column, Eluent of 30~40% Ethyl acetate/Petroleum ethergradient @ 100 mL/min) to get 5-tetrahydropyran-2-yloxyadamantane-2-carbonitrile (6.00 g, 22.96 mmol, 44.21% yield) as a yellow oil. ¹H NMR (CDCl₃, 400 MHz) δ 4.89-4.83 (m, 1H), 3.99-3.92 (m, 1H), 3.49-3.44 (m, 1H), 2.83-2.77 (m, 1H), 2.41-2.40 (m, 2H), 2.30-2.20 (m, 2H), 2.19-2.17 (m, 1H), 1.92-1.85 (m, 7H), 1.55-1.53 (m, 3H), 1.52-1.50 (m, 4H).

Preparation of 5-tetrahydropyran-2-yloxyadamantane-2-carbaldehyde

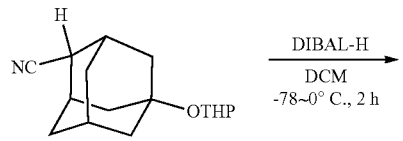

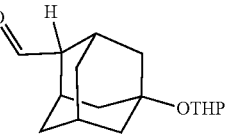

To a mixture of 5-tetrahydropyran-2-yloxyadamantane-2-carbonitrile (6.00 g, 22.96 mmol, 1 eq) in DCM (60 mL), DIBAL-H (1 M, 45.90 mL, 2 eq) was added dropwise at −78° C. under N₂. The resulting mixture was stirred at 0° C. for 2 h. The reaction was then quenched by adding Na₂SO₄.10H₂O (30 g). The reaction mixture was filtered, and the filtrate was concentrated in vacuo to give a residue. The residue was purified by flash silica gel chromatography (ISCO®; 80 g SepaFlash® Silica Flash Column, Eluent of 25-30% Ethyl acetate/Petroleum ethergradient @ 120 mL/min) to give 5-tetrahydropyran-2-yloxyadamantane-2-carbaldehyde (4.80 g, 18.16 mmol, 79.09% yield) as a yellow oil. ¹H NMR (CDCl₃, 400 MHz) δ 9.72 (m, 1H), 4.87-4.78 (m, 1H), 3.95-3.91 (m, 1H), 3.46-3.42 (m, 1H), 2.65-2.60 (m, 2H), 2.30-2.25 (m, 1H), 2.13-2.05 (m, 1H), 1.86-1.49 (m, 16H).

Preparation of (5-methoxy-1-triisopropylsilyl-pyrrolo[2,3-b]pyridin-4-yl)-(5-tetrahydro pyran-2-yloxy-2-adamantyl)methanol

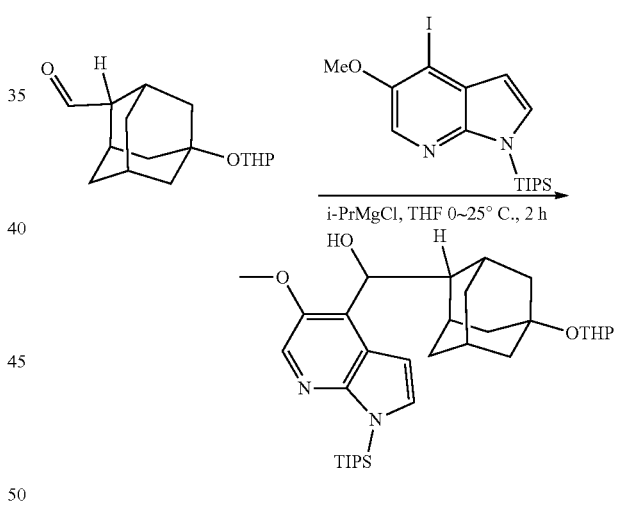

To a mixture of (4-iodo-5-methoxy-pyrrolo[2,3-b]pyridin-1-yl)-triisopropyl-silane (2.00 g, 4.65 mmol, 1 eq) in THF (40 mL), i-PrMgCl (2 M, 3.00 mL, 1.3 eq) was added dropwise at 0° C. under a N₂ atmosphere, and the resulting mixture was stirred at 0° C. for 1 h. Then, 5-tetrahydropyran-2-yloxyadamantane-2-carbaldehyde (1.47 g, 5.58 mmol, 1.2 eq) was added at 0° C., and the reaction mixture was stirred at room temperature for 1 hour. The reaction was quenched by adding sat.aq NH₄Cl (10 mL), and the resulting mixture was extracted with EtOAc (20 mL×2). The combined organic layers were washed with brine (15 mL×2), dried over anhydrous Na₂SO₄, filtered and concentrated in vacuo to give a residue. The obtained residue was purified by column chromatography (SiO₂, Petroleum ether/Ethyl acetate=10/1 to 6/1) to give (5-methoxy-1-triisopropylsilyl-pyrrolo[2,3-b]pyridin-4-yl)-(5-tetrahydropyran-2-yloxy-2- adamantyl)methanol (2.80 g, crude) as a colorless oil, which was used directly in the next step.

Preparation of (5-methoxy-1-triisopropylsilyl-pyrrolo[2,3-b]pyridin-4-yl)-(5-tetrahydro pyran-2-yloxy-2-adamantyl)methanone

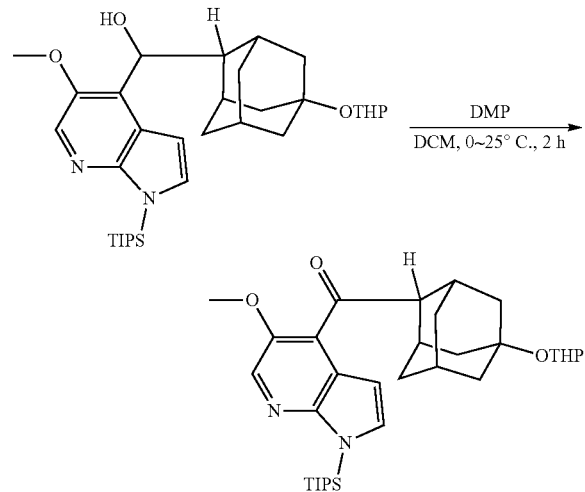

To a mixture of (5-methoxy-1-triisopropylsilyl-pyrrolo[2,3-b]pyridin-4-yl)-(5-tetrahydropyran-2-yloxy-2-adamantyl)methanol (2.80 g, 4.92 mmol, 1 eq) in DCM (15 mL), Dess-Martin (3.13 g, 7.38 mmol, 2.29 mL, 1.5 eq) was added in one portion at 0° C. The mixture was stirred at room temperature for 2 h. Then, H₂O (10 mL) was added into the reaction mixture, which was extracted with EtOAc (10 mL×2). The combined organic layers were washed with brine (10 mL×2), dried over anhydrous Na₂SO₄, filtered and concentrated in vacuo to give a residue. The obtained residue was purified by column chromatography (SiO₂, Petroleum ether/Ethyl acetate=8/1 to 6/1) to give (5-methoxy-1-triisopropylsilyl-pyrrolo[2,3-b]pyridin-4-yl)-(5-tetrahydropyran-2-yloxy-2-adamantyl)methanone (1.10 g, 1.94 mmol, 39.43% yield) as a yellow gum. ¹H NMR (DMSO-de, 400 MHz) δ 8.22 (s, 1H), 7.56 (dd, J=10.4, 3.6 Hz, 1H), 6.51 (dd, J=9.2, 3.6 Hz, 1H), 4.89-4.75 (m, 2H), 3.94 (s, 3H), 3.80-3.78 (m, 2H), 1.82-1.38 (m, 22H), 0.97 (d, J=7.6 Hz, 18H).

Preparation of triisopropyl-[5-methoxy-4-[(E)-1-(5-tetrahydropyran-2-yloxy-2-adamantyl)-2-(4,4,5,5-tetramethyl-1,3,2-dioxaborolan-2-yl)vinyl]pyrrolo[2,3-b]pyridin-1-yl]silane

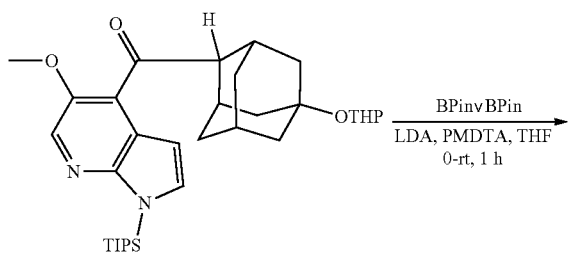

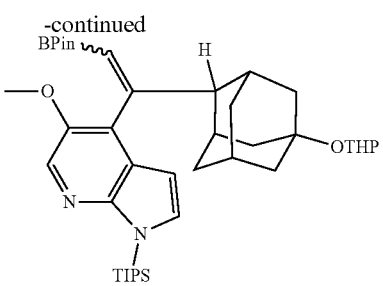

To a mixture of N'-[2-(dimethylamino)ethyl]-N,N,N'-trimethyl-ethane-1,2-diamine (122 mg, 706 μmol, 4 eq) and LDA (2 M, 620 uL, 7 eq) in THF (5 mL), 4,4,5,5-tetramethyl-2-[(4,4,5,5-tetramethyl-1,3,2-dioxaborolan-2-yl)methyl]-1,3,2-dioxaborolane (473 mg, 1.76 mmol, 10 eq) was added at 0° C. and stirred for 10 min. A solution of (5-methoxy-1-triisopropylsilyl-pyrrolo[2,3-b]pyridin-4-yl)-(5-tetrahydropyran-2-yloxy-2-adamantyl)methanone (100 mg, 176 μmol, 1 eq) in THF (5 mL) was then added into the reaction mixture dropwise at 0° C. The resulting mixture was stirred at room temperature for 50 min. The reaction was quenched with sat.aq NH₄Cl (5 mL), which was extracted with EtOAc (5 mL×2). The combined organic layers were washed with brine (5 mL×2), dried over anhydrous Na₂SO₄, filtered and concentrated in vacuo to give a residue. The obtained residue was purified by flash silica gel chromatography (ISCO®; 4 g SepaFlash® Silica Flash Column, Eluent of 10-18% Ethyl acetate/Petroleum ethergradient @36 mL/min) to give triisopropyl-[5-methoxy-4-[(E)-1-(5-tetrahydropyran-2-yloxy-2-adamantyl)-2-(4,4,5,5-tetramethyl-1,3,2-dioxaborolan-2-yl)vinyl]pyrrolo[2,3-b]pyridin-1-yl]silane (100 mg, 145 μmol, 82.05% yield) as a yellow gum. ¹H NMR (CDCl₃, 400 MHz) δ 8.00 (s, 1H), 7.17 (s, 1H), 6.41 (dd, J=10.8, 3.2 Hz, 1H), 5.85 (s, 1H), 4.83 (m, 1H), 3.97-3.86 (m, 5H), 3.44-3.43 (m, 2H), 3.03-2.88 (m, 1H), 2.14-1.45 (m, 20H), 1.25 (s, 12H), 1.14 (d, J=7.6 Hz, 18H).

Preparation of 9-((1R,2s,3S,5s,7s)-5-bromoadamantan-2-yl)-[1,2]oxaborinino[5,6-d]pyrrolo[2,3-b]pyridin-7(3H)-ol

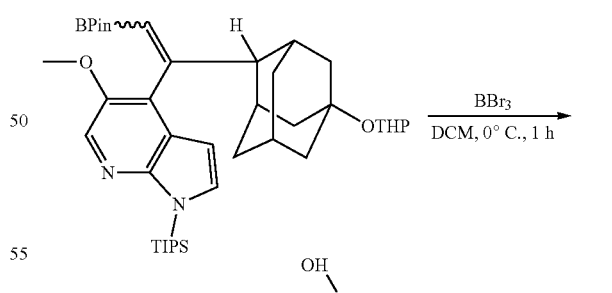

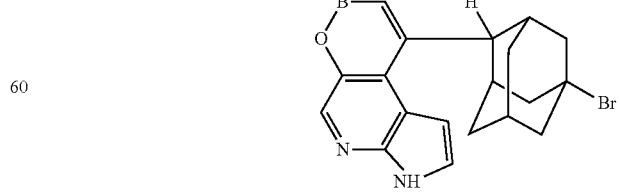

To a mixture of triisopropyl-[5-methoxy-4-[(E)-1-(5-tetrahydropyran-2-yloxy-2-adamantyl)-2-(4,4,5,5-tetramethyl- 1,3,2-dioxaborolan-2-yl)vinyl]pyrrolo[2,3-b]pyridin-1-yl] silane (120 mg, 174 μmol, 1 eq) in DCM (3 mL), BBr$_3$ (305 mg, 1.22 mmol, 120 uL, 7 eq) was added in one portion at 0° C. under a N$_2$ atmosphere. The resulting mixture was stirred at 0° C. for 1 h. The reaction was then quenched by adding H$_2$O (3 mL), which was extracted with EtOAc (3 mL×2). The combined organic layers were washed with brine (3 mL×2), dried over anhydrous Na$_2$SO$_4$, filtered and concentrated in vacuo to give a residue. The obtained residue was purified by prep-HPLC (column: Phenomenex Luna C18 100*30 mm*5 um; mobile phase: [water (0.1% TFA)-ACN]; B %: 45%-75%,10 min) to give 9-((1R,2s,3S,5s,7s)-5-bromoadamantan-2-yl)-[1,2]oxaborinino[5,6-d]pyrrolo[2,3-b]pyridine-7(3H)-ol (6 mg, 14 μmol, 7.89% yield, 91.20% purity) as a white solid. $^1$H NMR (DMSO-d$_6$, 400 MHz) δ 11.81-11.79 (m, 1H), 8.71 (br, 1H), 8.26 (s, 1H), 7.58-7.55 (m, 1H), 6.66-6.61 (m, 1H), 6.40 (s, 1H), 3.68-3.52 (m, 1H), 2.67 (m, 1H), 2.35-2.32 (m, 2H), 2.22-2.21 (m, 2H), 1.95-1.92 (m, 2H), 1.52-1.51 (m, 4H), 1.20-1.15 (m, 2H). MS (ESI): mass calcd. For C$_{19}$H$_{20}$BBrN$_2$O$_2$ 398.08, m/z. found 399.1 [M+H]$^+$. HPLC: 91.2% (220 nm), 77.93% (254 nm).

Preparation of 9-(cis-4-methylpiperidin-3-yl)-[1,2]oxaborinino[5,6-d] pyrrolo [2,3-b]pyridin-7(3H)-ol

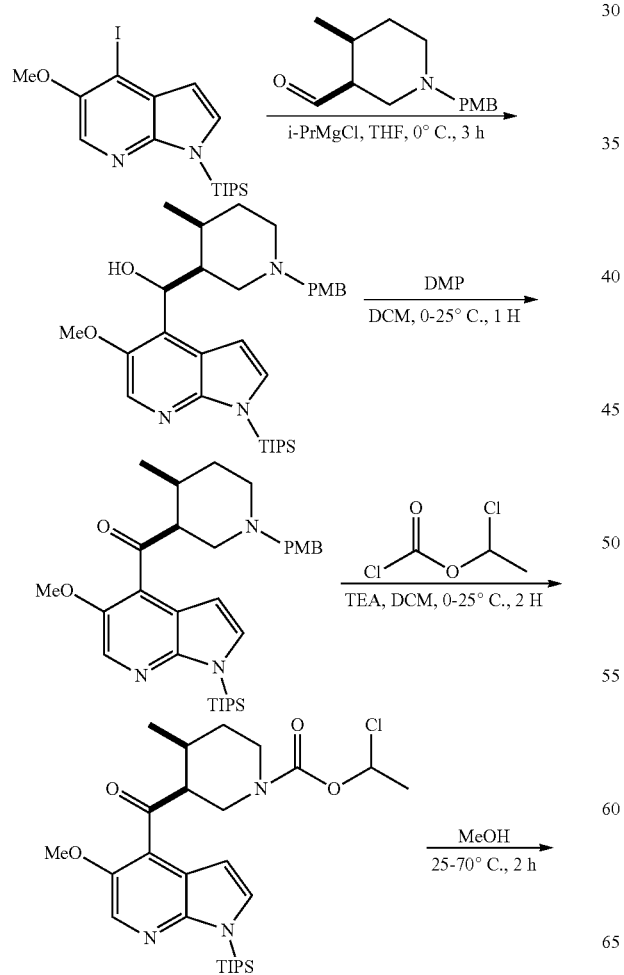

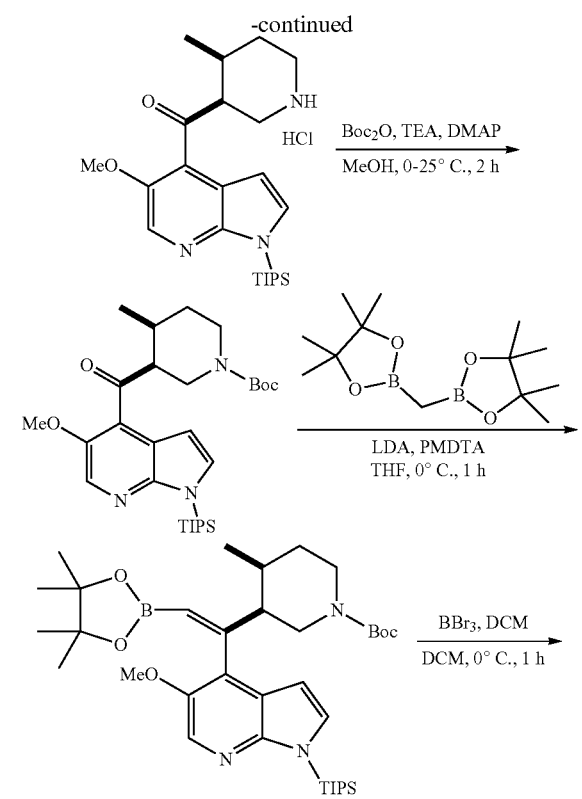

Preparation of Key Intermediate cis-1-[(4-methoxyphenyl)methyl]-4-methyl-piperidine-3-carbaldehyde

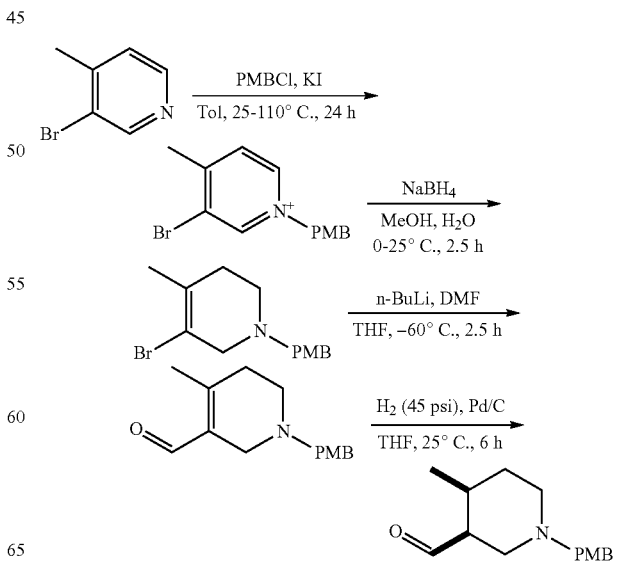

Preparation of 3-bromo-1-[(4-methoxyphenyl) methyl]-4-methyl-pyridin-1-ium

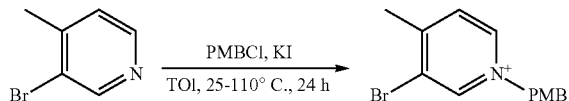

To a mixture of 3-bromo-4-methyl-pyridine (25.0 g, 145 mmol, 16.1 mL, 1 eq) in toluene (300 mL), 1-(chloromethyl)-4-methoxy-benzene (25.0 g, 160 mmol, 21.8 mL, 1.1 eq) and KI (2.41 g, 14.5 mmol, 0.1 eq) were added at room temperature under a $N_2$ atmosphere. The resulting mixture was heated to 110° C. and stirred for 24 h. The reaction mixture was then concentrated in vacuo to give 3-bromo-1-[(4-methoxyphenyl)methyl]-4-methyl-pyridin-1-ium (80.0 g, crude) as a brown solid. $^1$H NMR (DMSO-$d_6$, 400 MHz) δ 9.71 (s, 1H), 9.15 (dd, J=6.4, 1.2 Hz, 1H), 8.15 (d, J=6.4 Hz, 1H), 7.60 (d, J=8.8 Hz, 2H), 6.99 (d, J=8.8 Hz, 2H), 5.75 (s, 2H), 3.75 (s, 3H), 2.59 (s, 3H).

Preparation of 5-bromo-1-[(4-methoxyphenyl) methyl]-4-methyl-3,6-dihydro-2H-pyridine

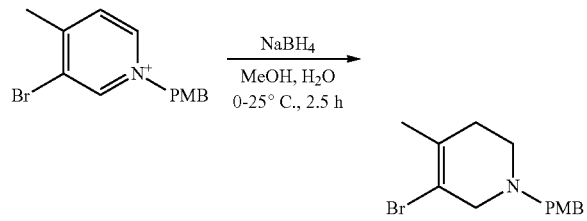

To a solution of 3-bromo-1-[(4-methoxyphenyl)methyl]-4-methyl-pyridin-1-ium (80.0 g, 273 mmol, 1 eq) in MeOH (500 mL), NaBH$_4$ (15.5 g, 409 mmol, 1.5 eq) was added portionwise at 0° C. over a 1 h period, and the resulting mixture was stirred at 0° C. for additional half hour. Then, H$_2$O (500 mL) was added to this reaction mixture at 0° C. and was stirred at 25° C. for 1 h. The solvent was removed in vacuo, and the remaining aqueous phase was extracted with EtOAc (200 mL×3). The combined organic phases were washed with brine (100 mL×2), dried over anhydrous Na$_2$SO$_4$, filtered and concentrated vacuo to yield a residue. The residue was purified by column chromatography (SiO$_2$, Petroleum ether/Ethyl acetate=10/1 to 5/1) to give 5-bromo-1-[(4-methoxyphenyl)methyl]-4-methyl-3,6-dihydro-2H-pyridine (50.0 g, 169 mmol, 61.86% yield) as a green oil. $^1$H NMR (CDCl$_3$, 400 MHz) δ 7.27 (d, J=8.4 Hz, 2H), 6.90 (d, J=8.4 Hz, 2H), 3.85 (s, 3H), 3.57 (s, 2H), 3.24 (s, 2H), 2.65 (t, J=5.6 Hz, 2H), 2.50-2.20 (m, 2H), 1.84 (s, 3H).

Preparation of 1-[(4-methoxyphenyl)methyl]-4-methyl-3,6-dihydro-2H-pyridine-5-carbaldehyde

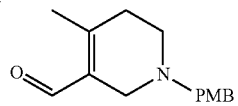

To a mixture of 5-bromo-1-[(4-methoxyphenyl)methyl]-4-methyl-3,6-dihydro-2H-pyridine (20.0 g, 67.5 mmol, 1 eq) in THF (200 mL), n-BuLi (2.5 M, 54.0 mL, 2 eq) was added dropwise at −60° C. over a 1 h period, and the resulting mixture was stirred at −60° C. for an additional half hour. Then, DMF (169 mmol, 13.0 mL, 2.5 eq) was added into the reaction mixture dropwise at −60° C. and stirred for 1 h. The reaction mixture was quenched by adding sat. aq. NH$_4$Cl (300 mL) at 0° C., diluted with EtOAc (50 mL), and extracted with EtOAc (100 mL×3). The combined organic layers were washed with brine (80 mL×3), dried over anhydrous Na$_2$SO$_4$, filtered and concentrated in vacuo to give a residue. The residue was purified by flash silica gel chromatography (ISCO®; 220 g SepaFlash® Silica Flash Column, Eluent of 0~57% Ethyl acetate/Petroleum ether-gradient @ 100 mL/min) to give 1-[(4-methoxyphenyl) methyl]-4-methyl-3,6-dihydro-2H-pyridine-5-carbaldehyde (10.0 g, 40.8 mmol, 60.37% yield) as a yellow oil. $^1$H NMR (CDCl$_3$, 400 MHz) δ 10.07 (s, 1H), 7.25 (d, J=8.4 Hz, 2H), 6.86 (d, J=8.4 Hz, 2H), 3.81 (m, 3H), 3.57 (s, 2H), 3.16 (s, 2H), 2.51 (t, J=5.6 Hz, 2H), 2.40-2.25 (m, 2H), 2.16 (s, 3H).

Preparation of (3R,4R)-1-[(4-methoxyphenyl) methyl]-4-methyl-piperidine-3-carbaldehyde

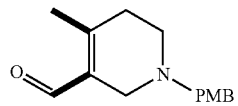

To a solution of 1-[(4-methoxyphenyl)methyl]-4-methyl-3,6-dihydro-2H-pyridine-5-carbaldehyde (5.00 g, 20.4 mmol, 1 eq) in THF (200 mL), Pd/C (1.28 g, 1.02 mmol, 10% purity, 0.05 eq) was added at 25° C. under N$_2$ atmosphere. The reaction mixture was stirred at 25° C. under H$_2$ (45 psi) atmosphere for 6 h. The reaction mixture was filtered, and the filtrate was concentrated under reduced pressure to give a residue. The residue was purified by flash silica gel chromatography (ISCO®; 120 g SepaFlash® Silica Flash Column, Eluent of 0-30% Ethyl acetate/Petroleum ethergradient @ 80 mL/min) to give cis-1-[(4-methoxyphenyl)methyl]-4-methyl-piperidine-3-carbaldehyde (6.50 g, 26.3 mmol, 64.47% yield) as a yellow oil. $^1$H NMR (CDCl$_3$, 400 MHz) δ 9.66 (d, J=2.4 Hz, 1H), 7.21 (d, J=8.4 Hz, 2H), 6.86 (d, J=8.4 Hz, 2H), 3.81 (s, 3H), 3.46 (d, J=2.0 Hz, 2H), 2.92-2.80 (m, 1H), 2.81-2.78 (m, 1H), 2.26-2.20 (m, 1H), 2.06-2.00 (m, 2H), 1.77-1.65 (m, 2H), 1.40-1.31 (m, 1H), 1.02 (d, J=6.4 Hz, 3H).

Preparation of [cis-1-[(4-methoxyphenyl)methyl]-4-methyl-3-piperidyl]-(5-methoxy-1-triisopropylsilyl-pyrrolo[2,3-b]pyridin-4-yl)methanol

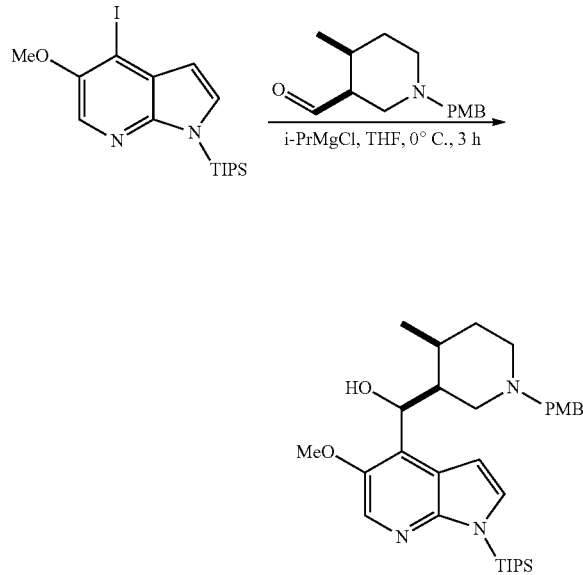

To a mixture of (4-iodo-5-methoxy-pyrrolo[2,3-b]pyridin-1-yl)-triisopropyl-silane (10.0 g, 23.2 mmol, 1 eq) in THF (90 mL), i-PrMgCl (2 M, 29.0 mL, 2.5 eq) was added dropwise at 0° C. over half an hour under a N₂ atmosphere. The resulting mixture was stirred at 0° C. for 1 h. Then, a solution of cis-1-[(4-methoxyphenyl)methyl]-4-methyl-piperidine-3-carbaldehyde (7.47 g, 30.2 mmol, 1.3 eq) in THF (30 mL) was added into the reaction mixture dropwise at 0° C., and the resulting mixture was stirred at 0° C. for 1.5 h. The reaction was quenched by adding sat. aq. NH₄Cl (150 mL) and extracted with EtOAc (80 mL×3). The combined organic phases were washed with brine (60 mL×3), dried over Na₂SO₄, filtered and concentrated in vacuo to give [cis-1-[(4-methoxyphenyl)methyl]-4-methyl-3-piperidyl]-(5-methoxy-1-triisopropylsilyl-pyrrolo[2,3-b]pyridin-4-yl)methanol (16.0 g, crude) as a yellow oil, which was used in the next step directly without purification.

Preparation of [cis-1-[(4-methoxyphenyl)methyl]-4-methyl-3-piperidyl]-(5-methoxy-1-triisopropylsilyl-pyrrolo[2,3-b]pyridin-4-yl)methanone

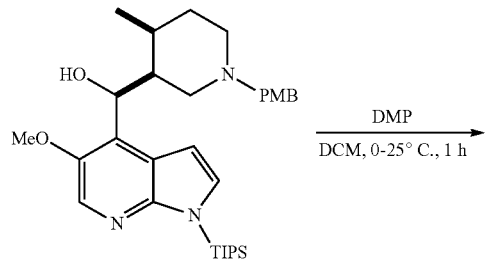

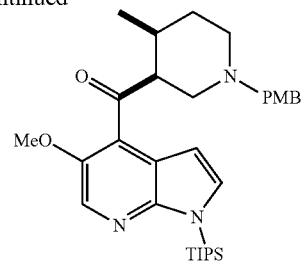

To a mixture of [cis-1-[(4-methoxyphenyl)methyl]-4-methyl-3-piperidyl]-(5-methoxy-1-triisopropylsilyl-pyrrolo[2,3-b]pyridin-4-yl)methanol (8.00 g, 9.42 mmol, 65% purity, 1 eq) in DCM (100 mL), Dess-Martin reagent (4.80 g, 11.3 mmol, 1.2 eq) was added at 0° C., and the resulting mixture was stirred at 25° C. for 1 h. The reaction was then quenched by adding H₂O (150 mL), which was then extracted with DCM (80 mL×3). The combined organic layers were washed with brine (60 mL×3), dried over anhydrous Na₂SO₄, filtered and concentrated in vacuo to give a residue. The obtained residue was purified by flash silica gel chromatography (ISCO®; 120 g SepaFlash® Silica Flash Column, Eluent of 0~30% Ethyl acetate/Petroleum ethergradient @100 mL/min) to give [cis-1-[(4-methoxyphenyl)methyl]-4-methyl-3-piperidyl]-(5-methoxy-1-triisopropylsilyl-pyrrolo[2,3-b]pyridin-4-yl)methanone (7.50 g, 13.6 mmol, 72.38% yield) as a yellow oil. ¹H NMR (CDCl₃, 400 MHz) δ 8.08 (s, 1H), 7.38 (d, J=3.2 Hz, 1H), 7.31 (d, J=8.0 Hz, 2H, 1H), 8.87 (d, J=8.4 Hz, 2H), 6.70 (d, J=3.2 Hz, 1H), 3.86 (s, 3H), 3.81 (s, 3H), 3.69-3.70 (m, 1H), 3.62-3.56 (m, 1H), 3.41-3.38 (m, 1H), 3.24-3.21 (m, 1H), 2.33-2.23 (m, 2H), 1.85-1.74 (m, 4H), 1.69-1.58 (m, 1H), 1.12-1.10 (m, 19H), 1.08-1.04 (m, 1H), 0.90 (d, J=6.8 Hz, 3H).

Preparation of 1-chloroethyl cis-3-(5-methoxy-1-triisopropylsilyl-pyrrolo[2,3-b]pyridine-4-carbonyl)-4-methyl-piperidine-1-carboxylate

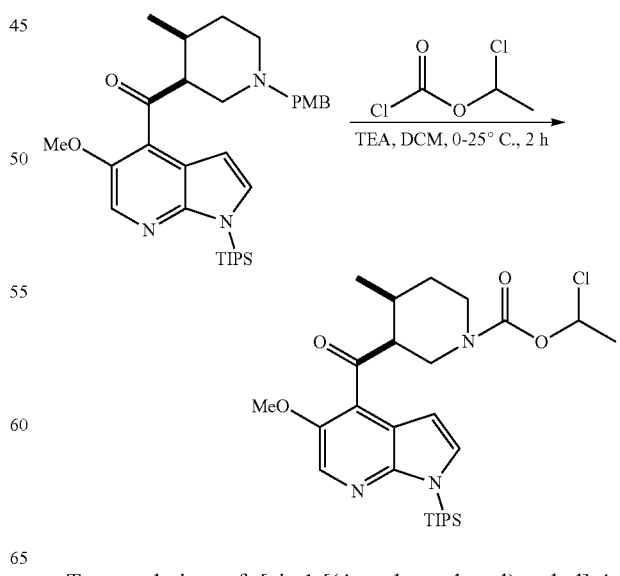

To a solution of [cis-1-[(4-methoxyphenyl)methyl]-4-methyl-3-piperidyl]-(5-methoxy-1-triisopropylsilyl-pyrrolo

[2,3-b]pyridin-4-yl)methanone (2.50 g, 4.55 mmol, 1 eq) in DCM (50 mL), TEA (36.4 mmol, 5.10 mL, 8 eq) and 1-chloroethyl carbonochloridate (2.60 g, 18.2 mmol, 4 eq) were added at 0° C. sequentially, and the resulting reaction was stirred at 25° C. for 2 h. The reaction mixture was concentrated in vacuo to give 1-chloroethyl cis-3-(5-methoxy-1-triisopropylsilyl-pyrrolo[2,3-b]pyridine-4-carbonyl)-4-methyl-piperidine-1-carboxylate (8.00 g, crude) as brown oil, which was used directly in the next step without purification.

Preparation of (5-methoxy-1-triisopropylsilyl-pyrrolo[2,3-b]pyridin-4-yl)-[cis-4-methyl-3-piperidyl]methanone

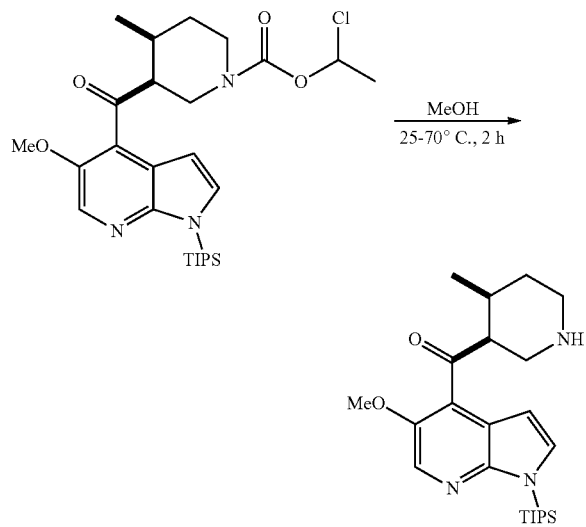

A solution of 1-chloroethyl cis-3-(5-methoxy-1-triisopropylsilyl-pyrrolo[2,3-b] pyridine-4-carbonyl)-4-methyl-piperidine-1-carboxylate (4.00 g, 7.46 mmol, 1 eq) in MeOH (50 mL) was heated to 70° C. and stirred at that temperature for 2 h. Then, the reaction mixture was concentrated in vacuo to give (5-methoxy-1-triisopropylsilyl-pyrrolo[2,3-b] pyridine-4-yl)-[cis-4-methyl-3-piperidyl]methanone (7.00 g, crude), which was used directly in next step without purification.

Preparation of Tert-Butyl cis-3-(5-methoxy-1-triisopropylsilyl-pyrrolo [2,3-b]pyridine-4-carbonyl)-4-methyl-piperidine-1-carboxylate

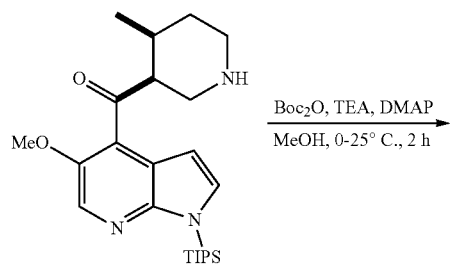

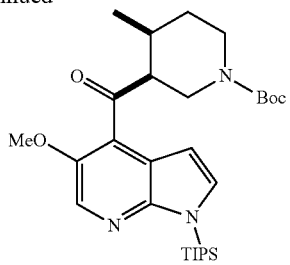

To a solution of (5-methoxy-1-triisopropylsilyl-pyrrolo[2,3-b]pyridin-4-yl)-[cis-4-methyl-3-piperidyl]methanone (3.50 g, 7.51 mmol, 1 eq), TEA (18.8 mmol, 2.60 mL, 2.5 eq) and DMAP (0.459 g, 3.75 mmol, 0.5 eq) in MeOH (50 mL), Boc$_2$O (4.10 g, 18.8 mmol, 4.30 mL, 2.5 eq) was added dropwise at 0° C., and the resulting mixture was stirred at 25° C. for 2 h. The reaction mixture was then filtered, and the filtrate was concentrated in vacuo to give a residue. The residue was purified by flash silica gel chromatography (ISCO®; 120 g SepaFlash® Silica Flash Column, Eluent of 0-10% Ethyl acetate/Petroleum ethergradient @ 100 mL/min) to give tert-butyl cis-3-(5-methoxy-1-triisopropylsilyl-pyrrolo[2,3-b] pyridine-4-carbonyl)-4-methyl-piperidine-1-carboxylate (6.00 g, 11.3 mmol, 75.42% yield) as a yellow oil. $^1$H NMR (CDCl$_3$, 400 MHz) δ 8.14 (s, 1H), 7.38 (d, J=3.2 Hz, 1H), 6.70 (d, J=3.6 Hz, 1H), 4.03 (s, 3H), 3.35-3.15 (m, 2H), 2.82-2.76 (m, 1H), 2.20-2.05 (m, 1H), 1.86-1.78 (m, 3H), 1.74-1.67 (m, 1H), 1.50-1.40 (m, 11H), 1.26-1.21 (m, 1H), 1.12-1.10 (m, 18H), 0.91 (d, J=6.4 Hz, 3H).

Preparation of Tert-Butyl cis-3-[(Z)-1-(5-methoxy-1-triisopropylsilyl-pyrrolo[2,3-b] pyridin-4-yl)-2-(4,4,5,5-tetramethyl-1,3,2-dioxaborolan-2-yl)vinyl]-4-methyl-piperidine-1-carboxylate

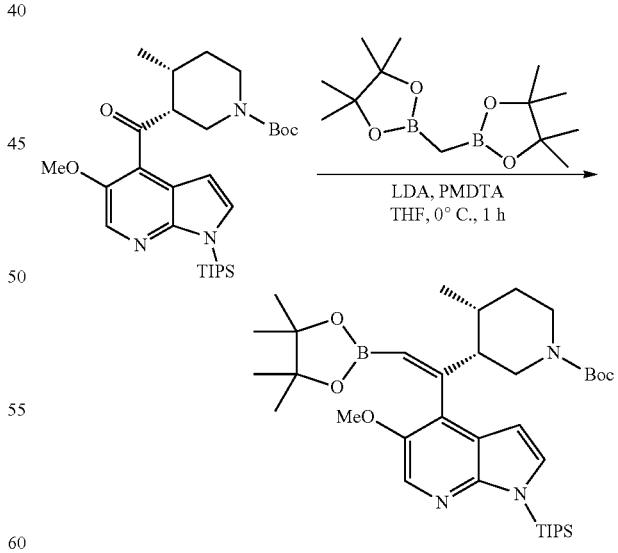

To a solution of LDA (2 M, 17.0 mL, 3 eq) in THF (60 mL), N'-[2-(dimethylamino)ethyl]-N,N,N'-trimethyl-ethane-1,2-diamine (3.93 g, 22.7 mmol, 4.70 mL, 2 eq) and a solution of 4,4,5,5-tetramethyl-2-[(4,4,5,5-tetramethyl-1,3,2-dioxaborolan-2-yl)methyl]-1,3,2-dioxaborolane (9.10 g, 34.0 mmol, 3 eq) in THF (20 mL) were added dropwise in sequence at 0° C. under a N₂ atmosphere. The resulting mixture was stirred at 0° C. for 20 min. Then, a solution of tert-butyl cis-3-(5-methoxy-1-triisopropylsilyl-pyrrolo[2,3-b]pyridine-4-carbonyl)-4-methyl-piperidine-1-carboxylate (6.00 g, 11.3 mmol, 1 eq) in THF (20 mL) was added into this mixture dropwise at 0° C. The resulting mixture was stirred at 0° C. for 40 min. The reaction was quenched by adding sat. aq. NH₄Cl (150 mL), and extracted with EtOAc (60 mL×3). The combined organic phases were washed with brine (40 mL×3), dried over anhydrous Na₂SO₄, filtered and concentrated in vacuo to give a residue. The residue was purified by flash silica gel chromatography (ISCO®; 120 g SepaFlash® Silica Flash Column, Eluent of 0-8% Ethyl acetate/Petroleum ethergradient @ 100 mL/min) to give tert-butyl(3S,4R)-3-[(Z)-1-(5-methoxy-1-triisopropylsilyl-pyrrolo[2,3-b]pyridin-4-yl)-2-(4,4,5,5-tetramethyl-1,3,2-dioxaborolan-2-yl)vinyl]-4-methyl-piperidine-1-carboxylate (8.00 g, crude) as a yellow oil.

Preparation of 9-(cis-4-methylpiperidin-3-yl)-[1,2]oxaborinino[5,6-d] pyrrolo [2,3-b]pyridin-7(3H)-ol

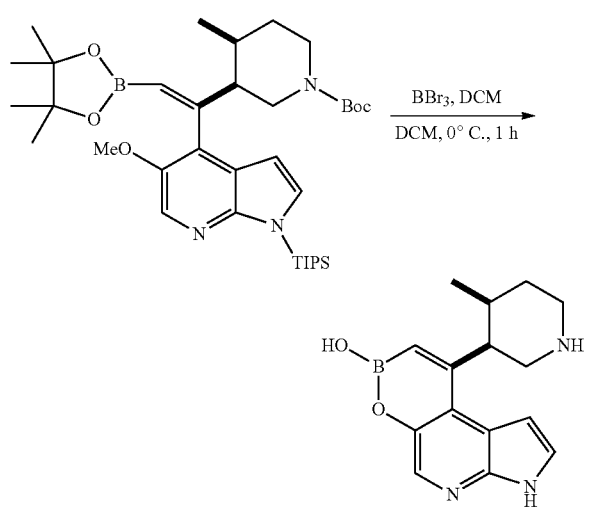

To a mixture of tert-butyl cis-3-[(Z)-1-(5-methoxy-1-triisopropylsilyl-pyrrolo [2,3-b]pyridin-4-yl)-2-(4,4,5,5-tetramethyl-1,3,2-dioxaborolan-2-yl)vinyl]-4-methyl-piperidine-1-carboxylate (8.00 g, 12.24 mmol, 1 eq) in DCM (80 mL), BBr₃ (9.20 g, 36.7 mmol, 3.50 mL, 3 eq) was added dropwise at 0° C. under a N₂ atmosphere, and the resulting mixture was stirred at 0° C. for 1 h. The reaction was quenched by adding H₂O (40 mL) slowly, and the solvent was removed in vacuo to yield an aqueous solution. The solution was directly freeze-dried to give a yellow residue, and the residue was triturated with THF (40 mL) to give 9-(cis-4-methylpiperidin-3-yl)-[1,2]oxaborinino [5,6-d]pyrrolo[2,3-b]pyridin-7(3H)-ol (4.40 g, crude, HBr salt) as a yellow solid. ¹H NMR (DMSO-d₆, 400 MHz) δ 11.97 (s, 1H), 9.11 (s, 1H), 8.94 (s, 1H), 8.29 (s, 1H), 7.66-7.64 (m, 1H), 7.20 (s, 1H), 6.43 (s, 1H), 3.63-3.62 (m, 1H), 3.15-3.12 (m, 2H), 2.98-2.95 (m, 1H), 2.13-2.09 (m, 2H), 1.99-1.96 (m, 1H), 1.70-1.67 (m, 1H), 0.79 (d, J=6.4 Hz, 3H). MS (ESI): mass calcd. For C₁₅H₁₉BClN₃O₂ 319.13, m/z. found 284.2 [M+H]⁺. HPLC: 96.11% (220 nm), 99.53% (254 nm).

Preparation of 3-(cis-3-(7-hydroxy-3,7-dihydro-[1,2]oxaborinino[5,6-d]pyrrolo [2,3-b]pyridin-9-yl)-4-methylpiperidin-1-yl)-3-oxopropanenitrile

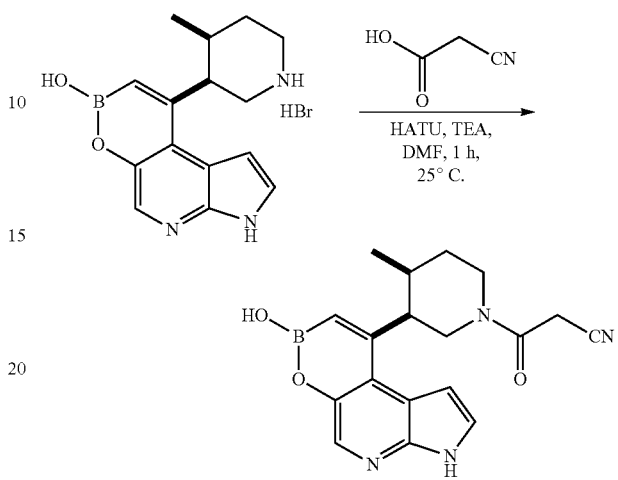

A mixture of 2-cyanoacetic acid (56 mg, 659 μmol, 1.2 eq) and HATU (250 mg, 659 μmol, 1.2 eq) in DMF (1 mL) was stirred at 25° C. for 20 min. Then, TEA (166 mg, 1.65 mmol, 3 eq) and 9-(cis-4-methylpiperidin-3-yl)-[1,2] oxaborinino[5,6-d]pyrrolo[2,3-b]pyridin-7(3H)-ol (200 mg, 549 μmol, 1 eq, HBr) were added into the reaction mixture at room temperature under a N₂ atmosphere. The resulting mixture was stirred at room temperature for 40 min. Then reaction was quenched by adding H₂O (5 mL) and extracted with EtOAc (10 mL×3). The combined organic layers were washed with brine (10 mL), dried over anhydrous Na₂SO₄, filtered and concentrated in vacuo to give a residue. The residue was purified by prep-HPLC (column: Phenomenex Gemini-NX C18 75*30 mm*3 um; mobile phase: [water (0.1% TFA)-ACN]; B %: 5%-40%,8 min) to give 3-(cis-3-(7-hydroxy-3,7-dihydro-[1,2]oxaborinino[5,6-d]pyrrolo[2,3-b]pyridine-9-yl)-4-methylpiperidin-1-yl)-3-oxopropanenitrile (59 mg, 168.49 μmol, 30.67% yield) as a white solid. ¹H NMR (DMSO-d₆, 400 MHz) δ 11.88 (s, 1H), 8.94 (s, 1H), 88.22 (s, 1H), 7.61-7.57 (m, 1H), 6.91-6.76 (m, 1H), 6.34 (s, 1H), 4.63-4.60 (m, 1H), 4.21-4.06 (m, 2H), 3.80-3.76 (m, 1H), 3.30-3.17 (m, 3H), 2.08-2.01 (m, 1H), 1.88-1.84 (m, 1H), 1.52-1.46 (m, 1H), 0.79 (d, J=6.4 Hz, 3H). MS (ESI): mass calcd. For C₁₈H₁₉BN₄O₃ 350.16, m/z. found 351.2 [M+H]⁺. HPLC: 100% (220 nm), 100% (254 nm).

Preparation of Tert-Butyl cis-3-(7-hydroxy-3,7-dihydro-[1,2]oxaborinino[5,6-d]pyrrolo[2,3-b]pyridin-9-yl)-4-methylpiperidine-1-carboxylate

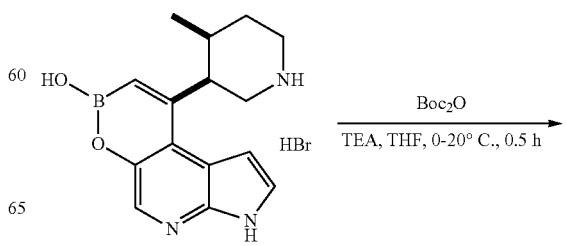

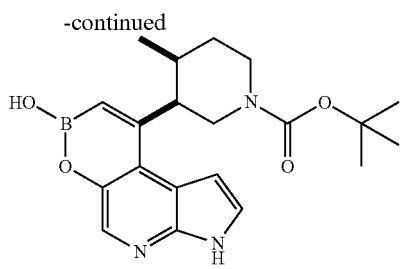

To a solution of 9-(cis-4-methylpiperidin-3-yl)-[1,2]oxaborinino[5,6-d]pyrrolo[2,3-b]pyridin-7(3H)-ol (250 mg, 687 μmol, 1 eq, HBr) in THF (5 mL), TEA (2.06 mmol, 287 uL, 3 eq) and Boc$_2$O (300 mg, 1.37 mmol, 316 uL, 2 eq) were added at 0° C., and the resulting mixture was stirred at 20° C. for 0.5 h. The reaction mixture was then concentrated in vacuo to give a residue, which was purified by prep-HPLC (column: Phenomenex Gemini-NX C18 75*30 mm*3 um; mobile phase: [water (10 mM NH$_4$HCO$_3$)-ACN]; B %: 25%-45%,6 min) to give tert-butyl 3-(7-hydroxy-3,7-dihydro-[1,2]oxaborinino[5,6-d]pyrrolo[2,3-b]pyridin-9-yl)-4-methylpiperidine-1-carboxylate (33 mg, 81.3 μmol, 11.84% yield, 94.41% purity) as a white solid. $^1$H NMR (DMSO-d$_6$, 400 MHz) δ 11.88 (s, 1H), 8.92 (s, 1H), 8.27 (s, 1H), 7.58 (s, 1H), 6.78 (s, 1H), 6.28 (s, 1H), 4.26-4.23 (m, 1H), 4.17-4.06 (m, 1H), 3.17-3.09 (m, 1H), 3.00-2.73 (m, 1H), 2.67-2.59 (m, 1H), 2.07-2.02 (m, 1H), 1.86-1.79 (m, 1H), 1.36 (s, 9H), 1.30-1.24 (m, 1H), 0.79 (d, J=6.4 Hz, 3H). MS (ESI): mass calcd. For C$_{20}$H$_{26}$BN$_3$O$_4$ 383.20, m/z. found 384.2 [M+H]$^+$. HPLC: 94.41% (220 nm), 96.48% (254 nm).

Preparation of 1-(cis-3-(7-hydroxy-3,7-dihydro-[1,2]oxaborinino[5,6-d]pyrrolo[2,3-b]pyridin-9-yl)-4-methylpiperidin-1-yl)butan-1-one

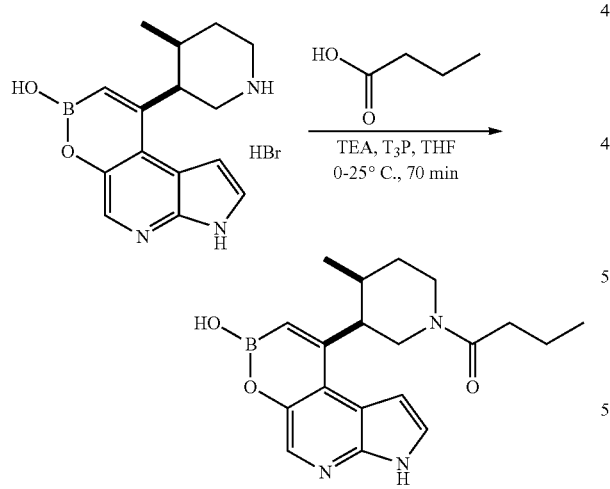

To a solution of 9-(cis-4-methylpiperidin-3-yl)-[1,2]oxaborinino[5,6-d]pyrrolo [2,3-b]pyridin-7(3H)-ol (250 mg, 687 μmol, 1 eq, HBr) and butyric acid (121 mg, 1.37 mmol, 126 uL, 2 eq) in THF (5 mL), TEA (2.06 mmol, 287 uL, 3 eq) was added at 0° C., and the resulting mixture was stirred at 0° C. for 10 min. Then, T$_3$P (2.06 mmol, 1.20 mL, 50% purity, 3 eq) was added into the above mixture dropwise at 0° C., and the resulting mixture was stirred at 25° C. for 1 h. The reaction was quenched by H$_2$O (10 mL) and extracted with EtOAc (8 mL×3). The combined organic layers were washed with brine (5 mL×3), dried over anhydrous Na$_2$SO$_4$, filtered and concentrated in vacuo to give a residue. The residue was purified by prep-HPLC (column: Waters Xbridge Prep OBD C18 150*40 mm*10 um; mobile phase: [water (10 mM NH$_4$HCO$_3$)-ACN]; B %: 25%-50%,8 min) to give 1-(cis-3-(7-hydroxy-3,7-dihydro-[1,2]oxaborinino[5,6-d]pyrrolo[2,3-b]pyridin-9-yl)-4-methylpiperidin-1-yl)butan-1-one (14 mg, 36.0 μmol, 5.24% yield, 90.78% purity) as a white solid. $^1$H NMR (DMSO-d$_6$, T=273+80K, 400 MHz) δ 11.67 (s, 1H), 8.68 (s, 1H), 8.27 (s, 1H), 7.57-7.44 (m 1H), 6.79 (s, 1H), 6.33 (s, 1H), 4.74-4.04 (m, 1H), 3.33-3.17 (m, 1H), 2.69-2.64 (m, 1H), 2.33-2.24 (m, 2H), 2.11-2.03 (m, 1H), 1.93-1.86 (m, 1H), 1.64-1.46 (m, 2H), 1.41-1.14 (m, 2H), 0.99-0.82 (m, 7H). MS (ESI): mass calcd. For C$_{19}$H$_{24}$BN$_3$O$_3$ 353.19, m/z. found 352.1 [M−H]$^−$. HPLC: 90.78% (220 nm), 94.68% (254 nm).

Preparation of cis-3-(7-hydroxy-3,7-dihydro-[1,2]oxaborinino[5,6-d]pyrrolo [2,3-b]pyridin-9-yl)-4-methylpiperidin-1-yl)(phenyl)methanone

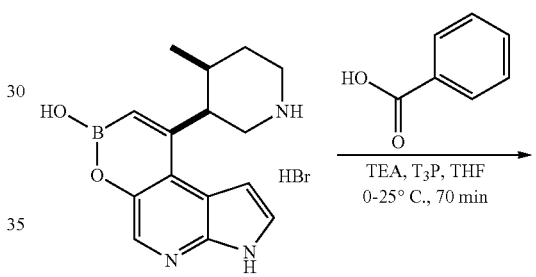

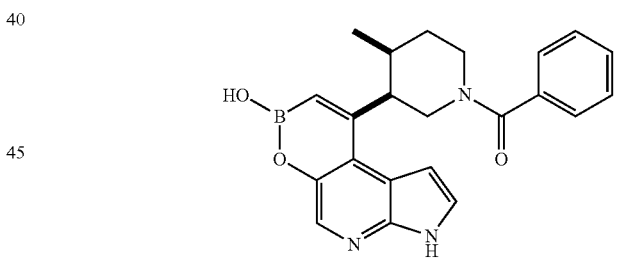

This substance was prepared using the same procedure employed for preparation of 1-(cis-3-(7-hydroxy-3,7-dihydro-[1,2]oxaborinino[5,6-d]pyrrolo[2,3-b]pyridin-9-yl)-4-methylpiperidin-1-yl)butan-1-one. Yield: 15.7%. $^1$H NMR (DMSO-d$_6$, T=273+80K, 400 MHz) δ 11.62 (s, 1H), 8.69 (s, 1H), 8.24 (s, 1H), 7.52-7.38 (m, 6H), 6.77 (s, 1H), 6.35 (s, 1H), 4.33-4.09 (m, 1H), 3.40-3.25 (m, 1H), 3.20-3.16 (m, 1H), 2.94-2.82 (m, 1H), 2.58-2.55 (m, 1H), 2.20-2.06 (m, 1H), 1.89-1.86 (m, 1H), 1.53-1.42 (m, 1H), 0.83 (d, J=6.4 Hz, 3H). MS (ESI): mass calcd. For C$_{22}$H$_{22}$BN$_3$O$_3$ 387.18, m/z. found 386.1 [M−H]$^−$. HPLC: 94.50% (220 nm), 95.55% (254 nm).

Preparation of cis-N-ethyl-3-(7-hydroxy-3,7-dihydro-[1,2]oxaborinino[5,6-d]pyrrolo[2,3-b]pyridin-9-yl)-4-methylpiperidine-1-carboxamide

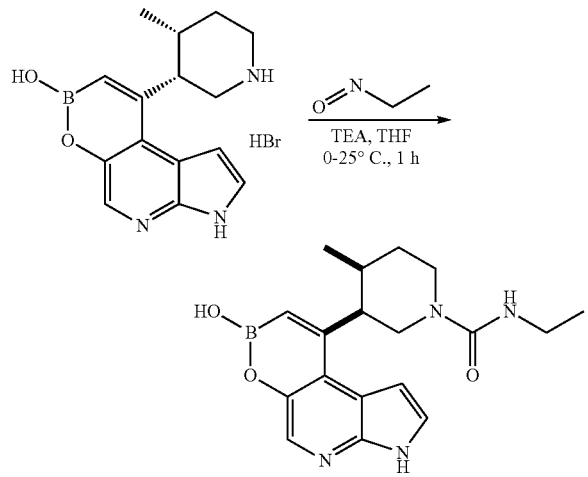

To a solution of 9-(cis-4-methylpiperidin-3-yl)-[1,2]oxaborinino[5,6-d]pyrrolo [2,3-b]pyridin-7(3H)-ol (500 mg, 1.37 mmol, 1 eq, HBr) and TEA (4.12 mmol, 574 uL, 3 eq) in THF (6 mL), isocyanatoethane (195 mg, 2.75 mmol, 217 uL, 2 eq) was added at 0° C., and the resulting mixture was stirred at 25° C. for 1 h. The reaction was quenched by adding H₂O (10 mL) and extracted with EtOAc (8 mL×3). The combined organic layers were washed with brine (5 mL×3), dried over anhydrous Na₂SO₄, filtered and concentrated in vacuo to give a residue, which was purified by prep-HPLC (column: Welch Xtimate C18 250*70 mm #10 um; mobile phase: [water (10 mM NH₄HCO₃)-ACN]; B %: 15%-35%,30 min) to give cis-N-ethyl-3-(7-hydroxy-3,7-dihydro-[1,2]oxaborinino[5,6-d]pyrrolo[2,3-b]pyridin-9-yl)-4-methylpiperidine-1-carboxamide (65 mg, 179 μmol, 13.00% yield, 97.33% purity) as a white solid. ¹H NMR (DMSO-d₆, 400 MHz) δ 11.85 (s, 1H), 8.90 (s, 1H), 8.26 (s, 1H), 7.55 (t, J=3.2 Hz, 1H), 6.20 (s, 1H), 6.46 (t, J=5.2 Hz, 1H), 6.28 (s, 1H), 4.23 (d, J=13.2 Hz, 1H), 4.09 (d, J=13.2 Hz, 1H), 3.18-3.14 (m, 1H), 3.10-3.00 (m, 2H), 2.81 (t, J=12.0 Hz, 1H), 2.54-2.52 (m, 1H), 2.03-1.92 (m, 1H), 1.79 (d, J=10.0 Hz, 1H), 1.35-1.24 (m, 1H), 0.99 (t, J=6.80 Hz, 3H), 0.76 (d, J=6.4 Hz, 3H). MS (ESI): mass calcd. For C₁₈H₂₃BN₄O₃ 354.19, m/z. found 355.2 [M+H]⁺. HPLC: 97.33% (220 nm), 93.56% (254 nm).

Preparation of 1-(cis-3-(7-hydroxy-3,7-dihydro-[1,2]oxaborinino[5,6-d]pyrrolo[2,3-b]pyridin-9-yl)-4-methylpiperidin-1-yl)ethanone

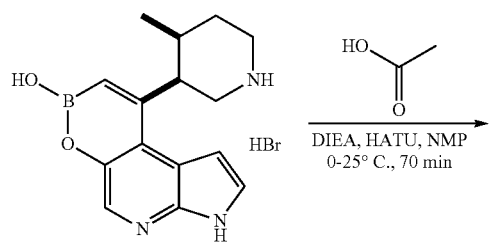

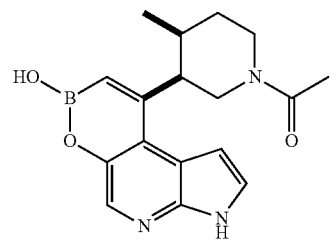

To a solution of AcOH (2.75 mmol, 160 uL, 2 eq) in NMP (2 mL), HATU (783 mg, 2.06 mmol, 1.5 eq) was added at 25° C., and the reaction mixture was stirred at 25° C. for 10 min. Then, a solution of 9-((3S,4R)-4-methylpiperidin-3-yl)-[1,2]oxaborinino[5,6-d]pyrrolo[2,3-b]pyridin-7(3H)-ol (500 mg, 1.37 mmol, 1 eq, HBr) and DIEA (4.12 mmol, 718 uL, 3 eq) in NMP (4 mL) was added into the reaction mixture dropwise at 0° C., and the resulting mixture was stirred at 25° C. for 1 h. The reaction was quenched by adding H₂O (0.1 mL), and the solvent was removed in vacuo to give a residue. The residue was purified by prep-HPLC (column: Kromasil C18 (250*50 mm*10 um); mobile phase: [water (10 mM NH₄HCO₃)-ACN]; B %: 15%-45%, 10 min) to give 1-(3-(7-hydroxy-3,7-dihydro-[1,2]oxaborinino[5,6-d]pyrrolo[2,3-b]pyridin-9-yl)-4-methylpiperidin-1-yl)ethanone (35.9 mg, 110 μmol, 8.04% yield) as a white solid. ¹H NMR (DMSO-ds, T=273+80K, 400 MHz) δ 11.67 (br, 1H), 8.73 (s, 1H), 8.27 (s, 1H), 7.5 (br, 1H), 6.81 (s, 1H), 6.33 (s, 1H), 4.79-4.67 (m, 1H), 3.97-3.93 (m, 1H), 3.35-3.24 (m, 1H), 2.99-2.67 (s, 1H), 2.45-2.43 (m, 1H), 2.13-1.87 (m, 5H), 1.42-1.33 (m, 1H), 0.83 (br, 3H). MS (ESI): mass calcd. For C₁₇H₂₀BN₃O₃ 325.16, m/z. found 326.2 [M+H]⁺. HPLC: 98.87% (220 nm), 99.81% (254 nm).

Preparation of 9-(5-hydroxyadamantan-2-yl)-[1,2]oxaborinino[5,6-d]pyrrolo[2,3-b]pyridine-7(3H)-ol

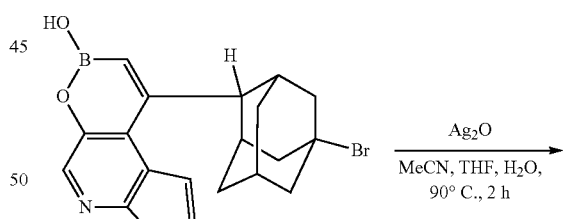

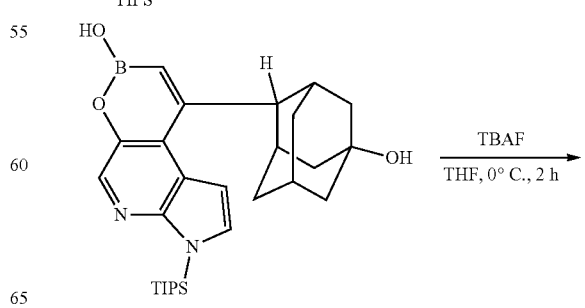

-continued

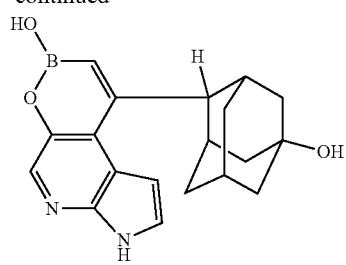

Preparation of 9-(5-hydroxyadamantan-2-yl)-3-(triisopropylsilyl)-[1,2]oxaborinino [5,6-d]pyrrolo[2,3-b]pyridine-7(3H)-ol

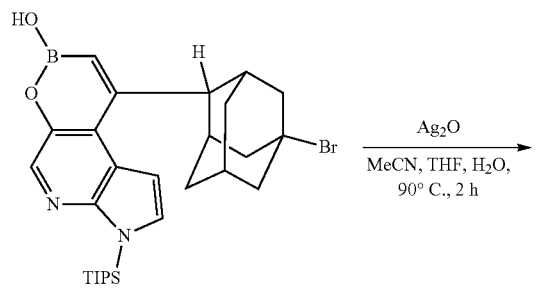

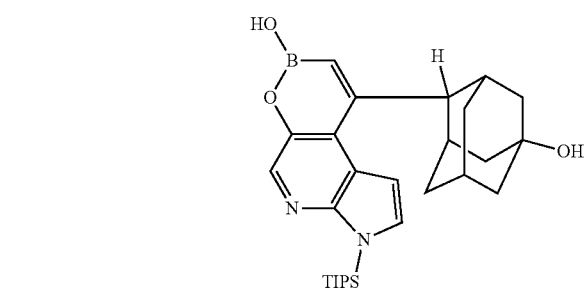

To a mixture of 9-(5-bromoadamantan-2-yl)-3-(triisopropylsilyl)-[1,2]oxaborinino[5,6-d]pyrrolo[2,3-b]pyridin-7(3H)-ol (500 mg, 900 μmol, 1 eq) in H$_2$O (3 mL), THF (1.5 mL), and MeCN (3 mL), Ag$_2$O (312 mg, 1.35 mmol, 1.5 eq) was added in portions at 90° C. The resulting mixture was stirred at 90° C. for 2 h. The reaction mixture was then cooled to 25° C. and filtered, and the filtrate was dried over anhydrous Na$_2$SO$_4$, filtered and concentrated in vacuo to give a residue. The residue was triturated with MeCN (3 mL), dried in vacuo to give 9-(5-hydroxyadamantan-2-yl)-3-(triisopropylsilyl)-[1,2]oxaborinino[5,6-d]pyrrolo[2,3-b]pyridine-7(3H)-ol (0.26 g, 528 μmol, 58.64% yield) as a yellow solid. $^1$H NMR (CDCl$_3$, 400 MHz) δ 8.92-8.89 (m, 1H), 8.25 (s, 1H), 7.61-7.57 (m, 1H), 6.84-6.76 (m, 1H), 6.53 (s, 1H), 6.46-6.44 (m, 1H), 4.54-4.41 (m, 1H), 3.45-3.37 (m, 1H), 2.50-2.48 (m, 1H), 2.07-2.01 (m, 1H), 1.80-1.72 (m, 7H), 1.63-1.61 (m, 3H), 1.45-1.39 (m, 3H), 1.06 (d, J=7.6 Hz, 18H).

Preparation of 9-(5-hydroxyadamantan-2-yl)-[1,2]oxaborinino[5,6-d]pyrrolo[2,3-b]pyridine-7(3H)-ol

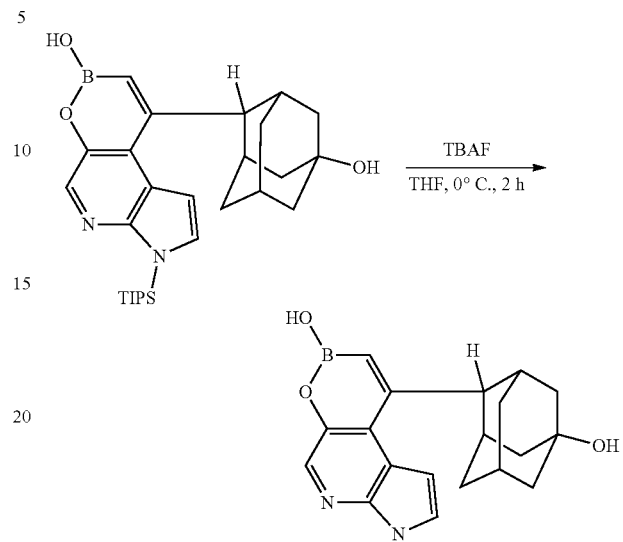

To a mixture of 9-(5-hydroxyadamantan-2-yl)-3-(triisopropylsilyl)-[1,2]oxaborinino[5,6-d]pyrrolo[2,3-b]pyridin-7(3H)-ol (200 mg, 406 μmol, 1 eq) in THF (3 mL), TBAF (110 mg, 406 μmol, 1 eq) was added in one portion at 0° C., and the resulting mixture was stirred at 0° C. for 2 h. The reaction was quenched with H$_2$O (3 mL) and extracted with EtOAc (3 mL×2). The combined organic layers were washed with brine (3 mL×2), dried over anhydrous Na$_2$SO$_4$, filtered and concentrated in vacuo to give a residue. The residue was purified by Prep-TLC (SiO$_2$, DCM:MeOH=20:1) to give the crude product. The crude product was further purified by Prep-HPLC (column: Waters Xbridge BEH C18 100*30 mm*10 um; mobile phase: [water (10 mM NH$_4$HCO$_3$)-ACN]; B %: 15%-45%,8 min) to give 9-(5-hydroxyadamantan-2-yl)-[1,2]oxaborinino[5,6-d]pyrrolo[2,3-b]pyridin-7(3H)-ol (10 mg, 28 μmol, 3.44% yield, 93.83% purity) as a white solid. $^1$H NMR (DMSO-d$_6$, 400 MHz) δ 11.76 (br, 1H), 8.87 (s, 1H), 8.25 (s, 1H), 7.57-7.54 (m, 1H), 6.66-6.60 (m, 1H), 6.42 (s, 1H), 4.39 (s, 1H), 3.45-3.35 (m, 1H), 2.50-2.48 (m, 1H), 2.29-2.21 (m, 1H), 2.02-1.94 (m, 3H), 1.79-1.76 (m, 4H), 1.65-1.63 (m, 2H), 1.46-1.34 (m, 2H). MS (ESI): mass calcd. For C$_{19}$H$_{21}$BN$_2$O$_3$ 336.19, m/z. found 335.1 [M–H]$^-$. HPLC: 93.83% (220 nm), 98.06% (254 nm).

Preparation of 1-(trans-4-(7-hydroxy-3,7-dihydro-[1,2]oxaborinino[5,6-d]pyrrolo [2,3-b]pyridin-9-yl)cyclohexyl)-N-methylmethanesulfonamide

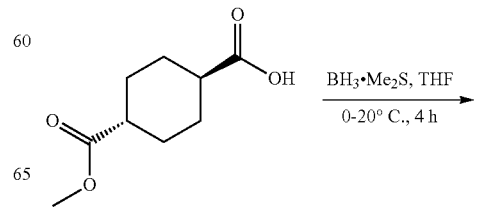

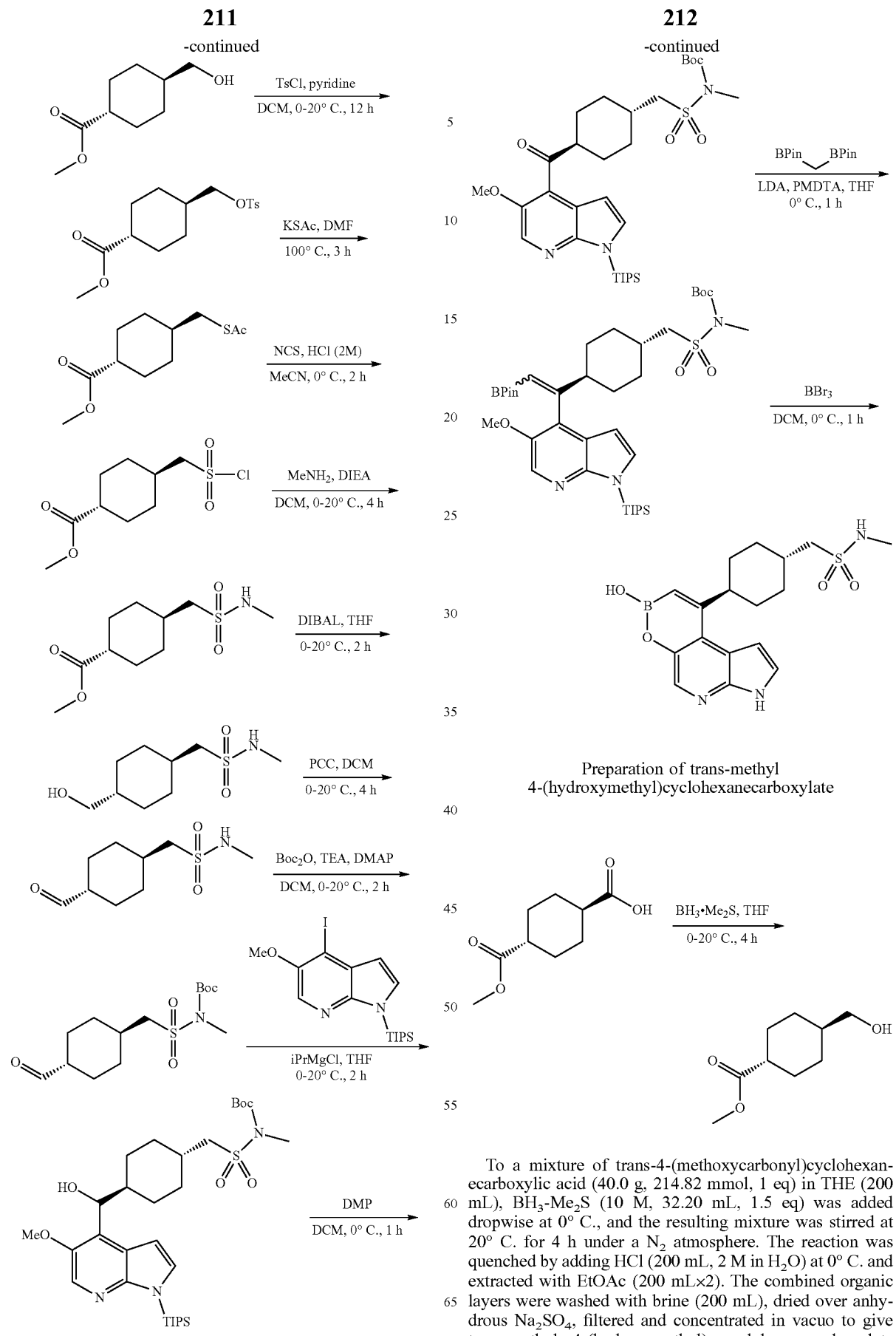

Preparation of trans-methyl 4-(hydroxymethyl)cyclohexanecarboxylate

To a mixture of trans-4-(methoxycarbonyl)cyclohexanecarboxylic acid (40.0 g, 214.82 mmol, 1 eq) in THF (200 mL), BH$_3$·Me$_2$S (10 M, 32.20 mL, 1.5 eq) was added dropwise at 0° C., and the resulting mixture was stirred at 20° C. for 4 h under a N$_2$ atmosphere. The reaction was quenched by adding HCl (200 mL, 2 M in H$_2$O) at 0° C. and extracted with EtOAc (200 mL×2). The combined organic layers were washed with brine (200 mL), dried over anhydrous Na$_2$SO$_4$, filtered and concentrated in vacuo to give trans-methyl 4-(hydroxymethyl) cyclohexanecarboxylate (31.0 g, 180.00 mmol, 83.79% yield) as a yellow oil. $^1$H NMR (CDCl$_3$, 400 MHz) δ 3.68 (s, 3H), 3.46 (d, J=6.0 Hz, 2H), 2.28-2.19 (m, 1H), 2.04-1.96 (m, 2H), 1.92-1.87 (m, 2H), 1.50-1.39 (m, 3H), 1.05-0.97 (m, 2H).

Preparation of Methyl Trans-Methyl 4-((tosyloxy)methyl)

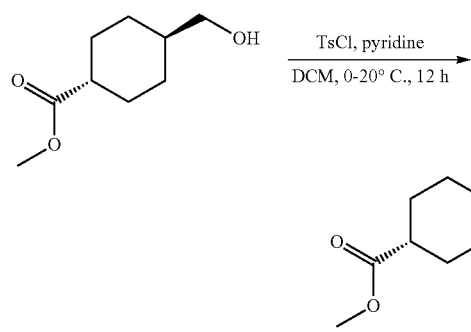

To a solution of methyl trans-methyl 4-(hydroxymethyl) cyclohexanecarboxylate (30.0 g, 174.19 mmol, 1 eq) in DCM (300 mL), 4-methylbenzenesulfonyl chloride (34.9 g, 182.90 mmol, 1.05 eq), DMAP (6.4 g, 52.26 mmol, 0.3 eq) and pyridine (16.5 g, 209.03 mmol, 16.80 mL, 1.2 eq) were added in sequence at 0° C. The resulting mixture was stirred at 20° C. for 12 h. The reaction was quenched by adding sat. NH$_4$Cl (300 mL) at 0° C. and extracted with DCM (100 mL×3). The combined organic layers were washed with brine (300 mL×2), dried over anhydrous Na$_2$SO$_4$, filtered and concentrated in vacuo to give a residue. The residue was purified by column chromatography (SiO$_2$, Petroleum ether/ Ethyl acetate=1/0 to 10/1) to give methyl trans-methyl 4-((tosyloxy)methyl)cyclohexanecarboxylate (38.0 g, 116.42 mmol, 66.83% yield) as a white solid. $^1$H NMR (CDCl$_3$, 400 MHz) δ 7.79 (d, J=8.0 Hz, 2H), 7.35 (d, J=8.0 Hz, 2H), 3.83 (d, J=6.4 Hz, 2H), 3.66 (s, 3H), 2.46 (s, 3H), 2.25-2.16 (m, 1H), 2.03-1.98 (m, 2H), 1.81-1.76 (m, 2H), 1.71-1.61 (m, 1H), 1.42-1.37 (m, 2H), 1.03-0.96 (m, 2H).

Preparation of Trans-Methyl 4-((acetylthio)methyl)cyclohexanecarboxylate

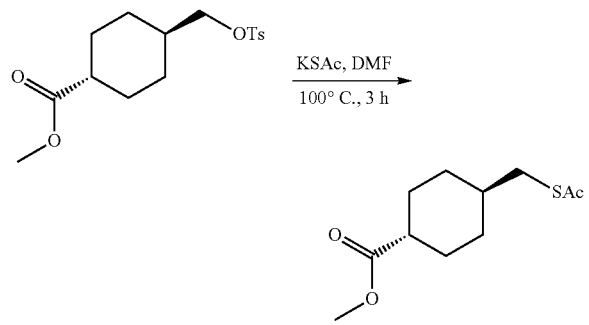

A solution of methyl (1r,4r)-methyl 4-((tosyloxy)methyl) cyclohexanecarboxylate (38.0 g, 116.42 mmol, 1 eq) and acetylsulfanylpotassium (26.6 g, 232.84 mmol, 2 eq) in DMF (250 mL) was stirred at 100° C. for 3 h. The reaction mixture was quenched by sat. NH$_4$Cl (300 mL) at 0° C. and extracted with EtOAc (200 mL×3). The combined organic layers were washed with brine (300 mL×5), dried over Na$_2$SO$_4$, filtered and concentrated in vacuo to give methyl trans-methyl 4-((acetylthio)methyl)cyclohexanecarboxylate (21.0 g, 91.18 mmol, 78.32% yield) as a yellow gum. $^1$H NMR (CDCl$_3$, 400 MHz) δ 3.66 (s, 3H), 2.80 (d, J=6.8 Hz, 2H), 2.33 (s, 3H), 2.23-2.17 (m, 1H), 2.05-1.97 (m, 2H), 1.91-1.86 (m, 2H), 1.46-1.37 (m, 3H), 1.04-0.98 (m, 2H).

Preparation of Trans-Methyl 4-((chlorosulfonyl)methyl)cyclohexanecarboxylate

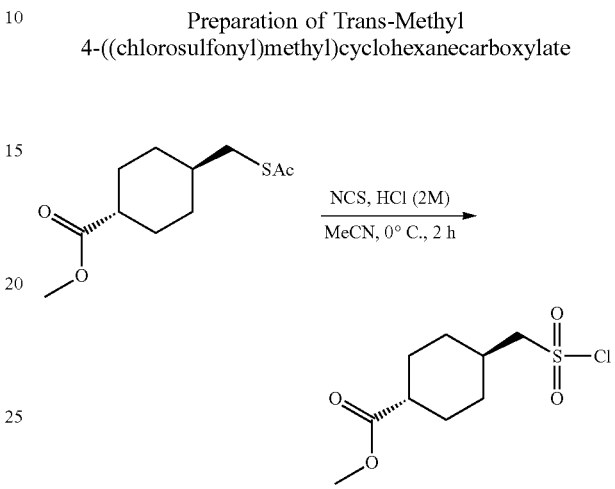

To a solution of methyl trans-methyl 4-((acetylthio) methyl)cyclohexanecarboxylate (10.0 g, 43.42 mmol, 1 eq) in MeCN (100 mL) and HCl (2 M, 32.60 mL, 1.5 eq), NCS (23.2 g, 173.67 mmol, 4 eq) was added in portions, and the resulting mixture was stirred at 0° C. for 2 h. The reaction was quenched by adding H$_2$O (100 mL) at 0° C. and extracted with EtOAc (100 mL×3). The combined organic layers were washed with brine (100 mL×2), dried over anhydrous Na$_2$SO$_4$, filtered and concentrated in vacuo to give methyl trans-methyl 4-((chlorosulfonyl)methyl) cyclohexanecarboxylate (8.00 g, 31.41 mmol, 72.33% yield) as a yellow gum. $^1$H NMR (CDCl$_3$, 400 MHz) δ 3.68 (s, 3H), 3.64 (d, J=6.4 Hz, 2H), 2.29-2.15 (m, 2H), 2.14-2.04 (m, 4H), 1.56-1.50 (m, 2H), 1.26-1.18 (m, 2H).

Preparation of Trans-Methyl 4-((N-methylsulfamoyl)methyl)cyclohexanecarboxylate

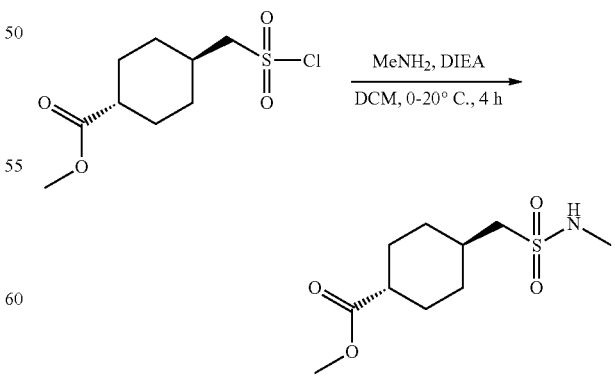

To a solution of trans-methyl 4-((chlorosulfonyl)methyl) cyclohexanecarboxylate (5.00 g, 19.63 mmol, 1 eq) in DCM (50 mL), DIEA (5.10 g, 39.26 mmol, 6.80 mL, 2 eq) and MeNH$_2$ (2 M, 10.80 mL, 1.1 eq) were added dropwise at 0° C. and stirred at 20° C. for 4 h. The reaction mixture was quenched by adding sat. NH$_4$Cl (50 mL) at 0° C. and extracted with DCM (50 mL×3). The combined organic layers were washed with brine (100 mL×2), dried over anhydrous Na$_2$SO$_4$, filtered and concentrated in vacuo to give trans-methyl 4-((N-methylsulfamoyl)methyl) cyclohexanecarboxylate (3.90 g, 15.64 mmol, 79.69% yield) as a yellow gum. $^1$H NMR (CDCl$_3$, 400 MHz) δ 4.23 (q, J=5.2 Hz, 1H), 3.67 (s, 3H), 2.92 (d, J=6.4 Hz, 2H), 2.81 (d, J=5.2 Hz, 3H), 2.29-2.21 (m, 1H), 2.14-2.00 (m, 4H), 2.00-1.91 (m, 1H), 1.55-1.45 (m, 2H), 1.17-1.08 (m, 2H).

Preparation of 1-(trans-4-(hydroxymethyl)cyclohexyl)-N-methylmethanesulfonamide

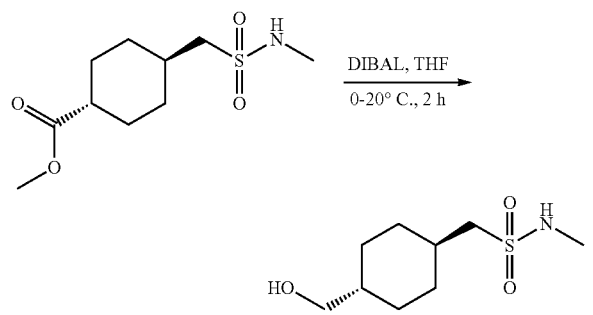

To a mixture of methyl trans-methyl 4-((N-methylsulfamoyl)methyl)cyclohexanecarboxylate (5.00 g, 20.05 mmol, 1 eq) in THF (50 mL), DIBAL-H (1 M, 40.10 mL, 2 eq) was added dropwise at 0° C., and the resulting mixture was stirred at 20° C. for 2 h under a N$_2$ atmosphere. The reaction was quenched with Na$_2$SO$_4$.10H$_2$O (30 g) and filtered. The filtrate was concentrated in vacuum to give 1-(trans-4-(hydroxymethyl)cyclohexyl)-N-methylmethanesulfonamide (3.00 g, 13.56 mmol, 67.59% yield) as a yellow gum. $^1$H NMR (CDCl$_3$, 400 MHz) δ 4.18 (q, J=4.8 Hz, 1H), 3.46 (d, J=6.4 Hz, 2H), 2.92 (d, J=6.0 Hz, 2H), 2.81 (d, J=5.6 Hz, 3H), 2.11-2.04 (m, 2H), 1.97-1.90 (m, 1H), 1.90-1.81 (m, 2H), 1.51-1.42 (m, 1H), 1.20-0.97 (m, 4H).

Preparation of 1-(trans-4-formylcyclohexyl)-N-methylmethanesulfonamide

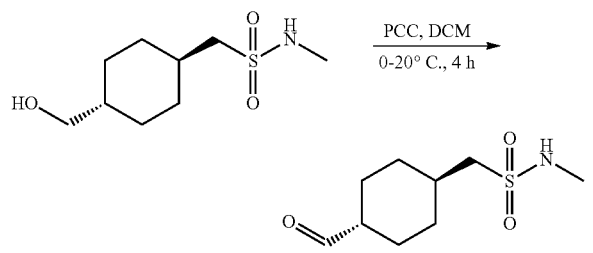

To a mixture of 1-(trans-4-(hydroxymethyl)cyclohexyl)-N-methylmethanesulfonamide (2.00 g, 9.04 mmol, 1 eq) in DCM (30 mL), PCC (3.90 g, 18.07 mmol, 2 eq) was added in portions at 0° C., and the resulting mixture was stirred at 20° C. for 4 h under a N$_2$ atmosphere. The reaction mixture was purified directly by silica gel chromatography (Petroleum ether/Ethyl acetate=20/1 to 3/1) to give 1-((1r,4r)-4-formylcyclohexyl)-N-methylmethanesulfonamide (1.20 g, 5.47 mmol, 60.55% yield) as a yellow oil. $^1$H NMR (CDCl$_3$, 400 MHz) δ 9.62 (d, J=1.2 Hz, 1H), 4.29 (q, J=4.4 Hz, 1H), 2.94 (d, J=6.4 Hz, 2H), 2.81 (d, J=3.2 Hz, 3H), 2.17-1.98 (m, 6H), 1.37-1.32 (m, 2H), 1.19-1.14 (m, 2H).

Preparation of Tert-Butyl ((trans-4-formylcyclohexyl)methyl)sulfonyl(methyl)carbamate

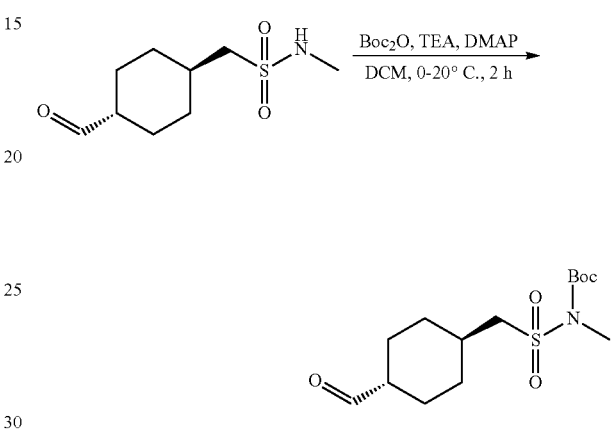

To a mixture of 1-(trans-4-formylcyclohexyl)-N-methylmethanesulfonamide (1.20 g, 5.47 mmol, 1 eq) in DCM (30 mL), Boc$_2$O (2.40 g, 10.94 mmol, 2.50 mL, 2 eq), DMAP (200 mg, 1.64 mmol, 0.3 eq) and TEA (1.40 g, 13.68 mmol, 1.90 mL, 2.5 eq) were added in sequence at 0° C., and the resulting mixture was stirred at 20° C. for 2 h under a N$_2$ atmosphere. The reaction mixture was concentrated in vacuo to give a residue, which was purified by column chromatography (SiO$_2$, Petroleum ether/Ethyl acetate=20/1 to 10/1) to give tert-butyl ((trans-4-formylcyclohexyl)methyl)sulfonyl(methyl)carbamate (1.00 g, 3.13 mmol, 57.21% yield) as a colorless oil. $^1$H NMR (CDCl$_3$, 400 MHz) δ 9.63 (s, 1H), 3.39 (d, J=6.4 Hz, 2H), 3.20 (s, 3H), 2.25-2.17 (m, 1H), 2.15-2.03 (m, 4H), 2.00-1.92 (m, 1H), 1.54 (s, 9H), 1.39-1.33 (m, 2H), 1.23-1.16 (m, 2H).

Preparation of Tert-Butyl ((trans-4-(hydroxy(5-methoxy-1-(triisopropylsilyl)-1H-pyrrolo[2,3-b]pyridin-4-yl)methyl)cyclohexyl)methyl)sulfonyl(methyl)carbamate

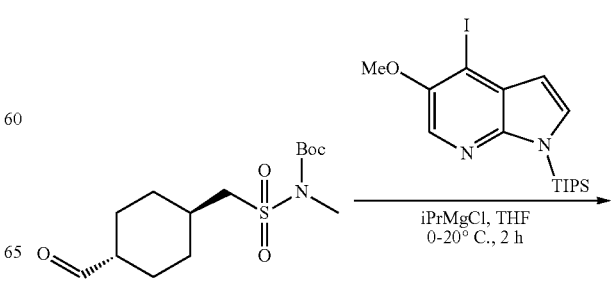

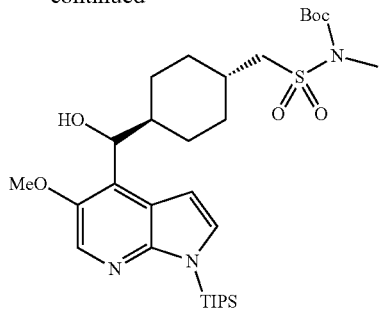

To a solution of (4-iodo-5-methoxy-pyrrolo[2,3-b]pyridin-1-yl)-triisopropyl-silane (1.10 g, 2.56 mmol, 1 eq) in THF (15 mL), i-PrMgCl (2 M, 1.70 mL, 1.3 eq) was added at 0° C., and the resulting mixture was stirred for 1 h. Then, tert-Butyl ((trans-4-formylcyclohexyl)methyl) sulfonyl(methyl)carbamate (980 mg, 3.07 mmol, 1.2 eq) was added at 0° C., and the reaction mixture was stirred at 20° C. for 1 h. The reaction was quenched by adding sat. NH$_4$Cl (20 mL) at 0° C. and extracted with EtOAc (20 mL×2). The combined organic layers were washed with brine (20 mL×2), dried over anhydrous Na$_2$SO$_4$, filtered and concentrated under reduced pressure. The residue was purified by column chromatography (SiO$_2$, Petroleum ether/Ethyl acetate=I/O to 3/1) to give tert-butyl((trans-4-(hydroxy(5-methoxy-1-(triisopropylsilyl)-1H-pyrrolo[2,3-b]pyridin-4-yl)methyl)cyclohexyl)methyl)sulfonyl(methyl)carbamate (850 mg, 1.36 mmol, 53.31% yield) as a colorless oil. $^1$H NMR (CDCl$_3$, 400 MHz) δ 8.04 (s, 1H), 7.28 (d, J=3.6 Hz, 1H), 6.56 (d, J=3.6 Hz, 1H), 4.83 (t, J=8.0 Hz, 1H), 3.96 (s, 3H), 3.36-3.28 (m, 2H), 3.18 (s, 3H), 2.30-2.22 (m, 1H), 2.07-2.02 (m, 1H), 1.90-1.75 (m, 5H), 1.52 (s, 9H), 1.40-1.30 (m, 2H), 1.12 (d, J=7.2 Hz, 18H), 1.10-0.95 (m, 2H), 0.95-0.85 (m, 2H).

Preparation of Tert-Butyl ((trans-4-(5-methoxy-1-(triisopropylsilyl)-1H-pyrrolo[2,3-b]pyridine-4-carbonyl)cyclohexyl)methyl)sulfonyl(methyl)carbamate

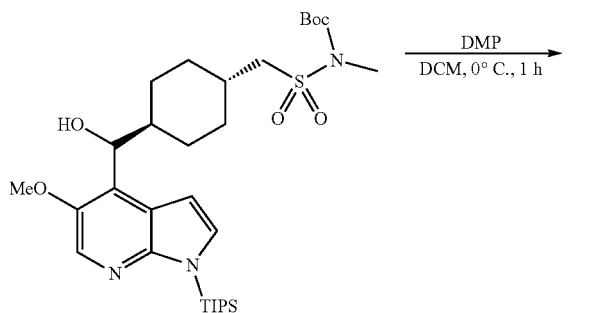

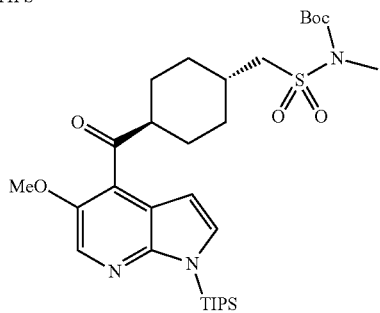

To a solution of tert-butyl tert-butyl ((trans-4-(hydroxy (5-methoxy-1-(triisopropylsilyl)-1H-pyrrolo[2,3-b]pyridin-4-yl)methyl)cyclohexyl)methyl)sulfonyl(methyl)carbamate (850 mg, 1.36 mmol, 1 eq) in DCM (20 mL), DMP (693 mg, 1.63 mmol, 506.13 uL, 1.2 eq) was added at 0° C., and the resulting mixture was stirred for 1 h. The reaction was quenched by adding sat. NH$_4$Cl (20 mL) at 0° C. and extracted with DCM (20 mL×2). The combined organic layers were washed with brine (20 mL×2), dried over anhydrous Na$_2$SO$_4$, filtered and concentrated in vacuo to give a residue, which was purified by column chromatography (SiO$_2$, Petroleum ether/Ethyl acetate=I/O to 3/1) to give tert-butyl ((trans-4-(5-methoxy-1-(triisopropylsilyl)-1H-pyrrolo[2,3-b]pyridine-4-carbonyl)cyclohexyl)methyl) sulfonyl(methyl)carbamate (720 mg, 1.16 mmol, 84.98% yield) as a white solid. $^1$H NMR (CDCl$_3$, 400 MHz) δ 8.12 (s, 1H), 7.37 (d, J=3.6 Hz, 1H), 6.60 (d, J=3.6 Hz, 1H), 3.97 (s, 3H), 3.39 (d, J=6.4 Hz, 2H), 3.20 (s, 3H), 3.19-3.16 (m, 1H), 2.15-2.05 (m, 4H), 2.05-1.95 (m, 1H), 1.85-1.78 (m, 3H), 1.55 (s, 9H), 1.60-1.50 (m, 2H), 1.22-1.17 (m, 2H), 1.12 (d, J=7.6 Hz, 18H).

Preparation of Tert-Butyl ((trans-4-((Z)-1-(5-methoxy-1-(triisopropylsilyl)-1H-pyrrolo [2,3-b] pyridin-4-yl)-2-(4,4,5,5-tetramethyl-1,3,2-dioxaborolan-2-yl)vinyl)cyclohexyl)methyl) sulfonyl (methyl)carbamate

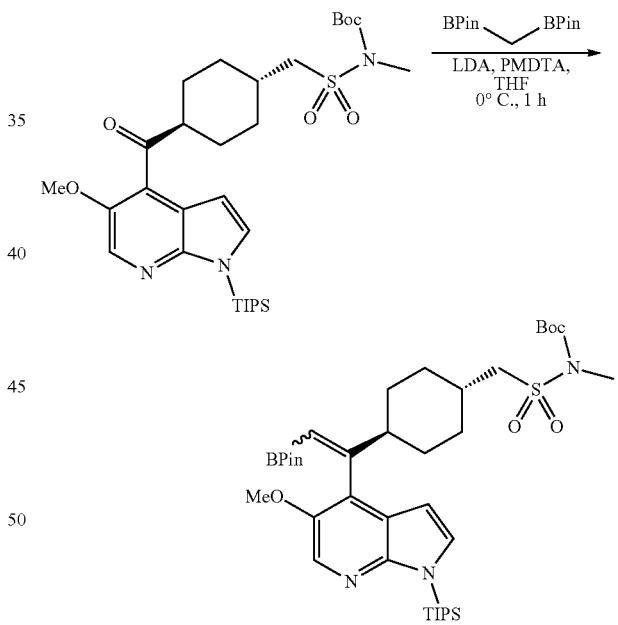

To a solution of LDA (2 M, 0.90 mL, 2.5 eq) in THF (5 mL), a solution of 4,4,5,5-tetramethyl-2-[(4,4,5,5-tetramethyl-1,3,2-dioxaborolan-2-yl)methyl]-1,3,2-dioxaborolane (233 mg, 868.30 μmol, 1.2 eq) and N'-[2-(dimethylamino) ethyl]-N,N,N'-trimethyl-ethane-1,2-diamine (188 mg, 1.09 mmol, 0.230 uL, 1.5 eq) in THF (5 mL) was added dropwise at 0° C., and the resulting mixture was stirred for 10 min. Then, a solution of tert-butyl((trans-4-(5-methoxy-1-(triisopropylsilyl)-1H-pyrrolo[2,3-b]pyridine-4-carbonyl)cyclohexyl)methyl) sulfonyl(methyl)carbamate (450 mg, 723.59 μmol, 1 eq) in THF (5 mL) was added to the above mixture dropwise at 0° C., and the resulting mixture was stirred for additional 1 h. The reaction was quenched by adding sat. NH₄Cl (15 mL) at 0° C. and extracted with EtOAc (15 mL×2). The combined organic layers were washed with brine (15 mL×2), dried over anhydrous Na₂SO₄, filtered and concentrated in vacuo to give a residue, which was purified by column chromatography (SiO₂, Petroleum ether/Ethyl acetate=1/0 to 3/1) to give tert-butyl ((trans-4-((Z)-1-(5-methoxy-1-(triisopropylsilyl)-1H-pyrrolo[2,3-b]pyridin-4-yl)-2-(4,4,5,5-tetramethyl-1,3,2-dioxaborolan-2-yl)vinyl) cyclohexyl)methyl)sulfonyl(methyl)carbamate (290 mg, 233.28 μmol, 32.24% yield, 60% purity) as a white solid.

Preparation of 1-(trans-4-(7-hydroxy-3,7-dihydro-[1,2]oxaborinino[5,6-d]pyrrolo [2,3-b]pyridin-9-yl) cyclohexyl)-N-methylmethanesulfonamide

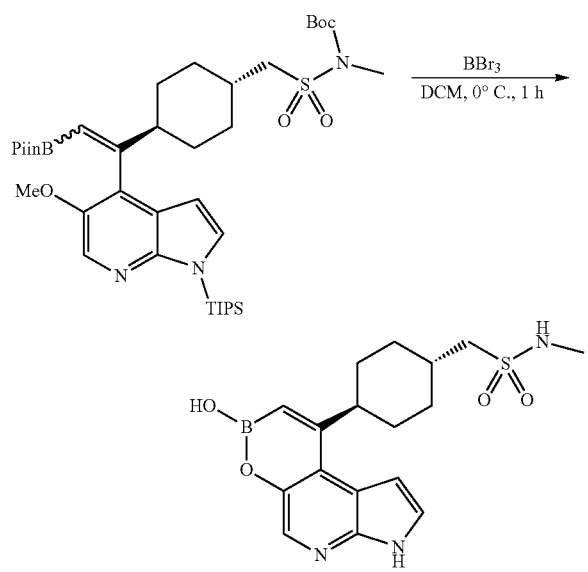

To a solution of tert-butyl ((trans-4-((Z)-1-(5-methoxy-1-(triisopropylsilyl)-1H-pyrrolo[2,3-b] pyridin-4-yl)-2-(4,4,5,5-tetramethyl-1,3,2-dioxaborolan-2-yl)vinyl)cyclohexyl) methyl)sulfonyl (methyl)carbamate (290 mg, 233.28 μmol, 60% purity, 1 eq) in DCM (5 mL), BBr₃ (292 mg, 1.17 mmol, 120 uL, 5 eq) was added at 0° C., and the resulting mixture was stirred for 1 h. The reaction was quenched by H₂O (10 mL) at 0° C. and extracted with DCM (10 mL×2). The combined organic layers were washed with sat. NaHCO₃ (10 mL×2), dried over anhydrous Na₂SO₄, filtered and concentrated in vacuo to give a residue, which was purified by prep-HPLC (column: Phenomenex Luna C18 150*30 mm*5 um; mobile phase: [water (0.1% TFA)-ACN]; B %: 30%-38%,8 min). The product after freeze-drying was further purified by removing TFA residue to give 1-(trans-4-(7-hydroxy-3,7-dihydro-[1,2]oxaborinino[5,6-d] pyrrolo [2,3-b]pyridin-9-yl)cyclohexyl)-N-methylmethanesulfonamide (82 mg, 218.52 μmol, 93.67% yield) as a white solid. ¹H NMR (DMSO-d₆, 400 MHz) δ 11.85 (s, 1H), 8.85 (s, 1H), 8.26 (s, 1H), 7.59 (t, J=2.8 Hz, 1H), 6.91 (q, J=4.8 Hz, 1H), 6.67 (s, 1H), 6.20 (s, 1H), 3.20-3.12 (m, 1H), 3.10 (d, J=6.4 Hz, 2H), 2.59 (d, J=4.8 Hz, 3H), 2.15-2.03 (m, 4H), 2.03-1.93 (m, 1H), 1.47-1.38 (m, 4H). MS (ESI): mass calcd. For C₁₇H₂₂BN₃O₄S, 375.14, m/z. found 376.2 [M+H]⁺. HPLC: 99.34% (220 nm), 99.48% (254 nm).

Preparation of 1-ethyl-3-(3-(7-hydroxy-3,7-dihydro-[1,2]oxaborinino[5,6-d]pyrrolo[2,3-b]pyridin-9-yl) cyclobutyl)urea

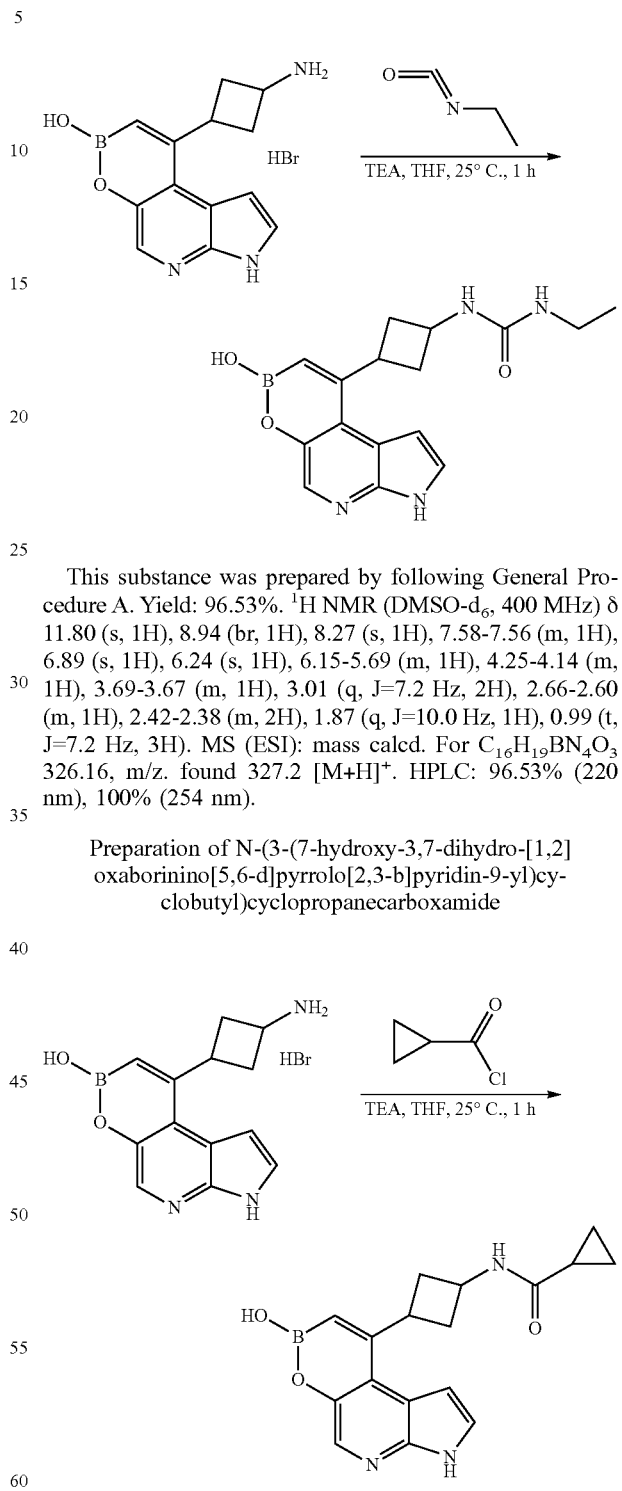

This substance was prepared by following General Procedure A. Yield: 96.53%. ¹H NMR (DMSO-d₆, 400 MHz) δ 11.80 (s, 1H), 8.94 (br, 1H), 8.27 (s, 1H), 7.58-7.56 (m, 1H), 6.89 (s, 1H), 6.24 (s, 1H), 6.15-5.69 (m, 1H), 4.25-4.14 (m, 1H), 3.69-3.67 (m, 1H), 3.01 (q, J=7.2 Hz, 2H), 2.66-2.60 (m, 1H), 2.42-2.38 (m, 2H), 1.87 (q, J=10.0 Hz, 1H), 0.99 (t, J=7.2 Hz, 3H). MS (ESI): mass calcd. For C₁₆H₁₉BN₄O₃ 326.16, m/z. found 327.2 [M+H]⁺. HPLC: 96.53% (220 nm), 100% (254 nm).

Preparation of N-(3-(7-hydroxy-3,7-dihydro-[1,2] oxaborinino[5,6-d]pyrrolo[2,3-b]pyridin-9-yl)cyclobutyl)cyclopropanecarboxamide This substance was prepared by following General Procedure A. Yield: 36.54%. ¹H NMR (DMSO-d₆, 400 MHz) δ 11.81 (s, 1H), 8.93 (br, 1H), 8.34 (d, J=8.4 Hz, 1H), 8.26 (S, 1H), 7.58 (s, 1H), 6.92 (S, 1H), 6.26 (S, 1H), 4.47-4.41 (m, 1H), 4.32-3.99 (m, 1H), 2.70-2.68 (m, 1H), 2.39-2.32 (m, 1H), 1.99-1.95 (m, 2H), 1.57-1.44 (m, 1H), 0.68-0.64 (m, 4H). MS (ESI): mass calcd. For $C_{17}H_{18}BN_3O_3$ 323.14, m/z. found 324.2 $[M+H]^+$. HPLC: 97.11% (220 nm), 96.26% (254 nm).

Preparation of Tert-Butyl (cis-3-(7-hydroxy-3,7-dihydro-[1,2]oxaborinino[5,6-d]pyrrolo[2,3-b]pyridin-9-yl)cyclobutyl)carbamate

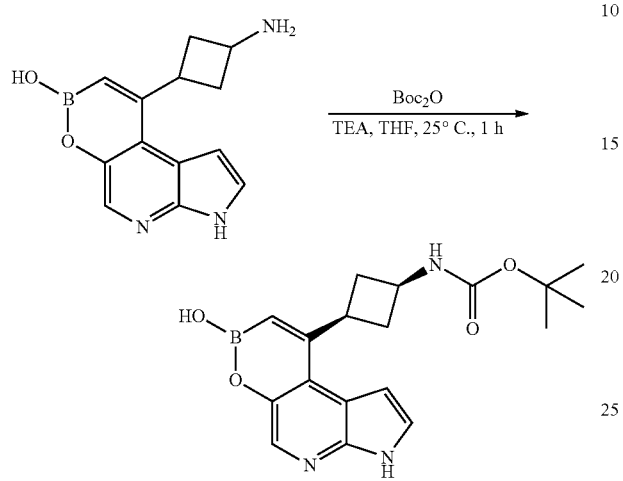

This substance was prepared by following General Procedure A. Yield: 43.09%. $^1$H NMR (DMSO-$d_6$, 400 MHz) δ 11.76 (s, 1H), 8.88 (s, 1H), 8.24 (s, 1H), 7.55 (t, J=2.8 Hz, 1H), 7.14 (d, J=8.4 Hz, 1H), 6.88 (s, 1H), 6.22 (s, 1H), 4.14-4.10 (m, 1H), 3.69-3.67 (m, 1H), 2.64-2.60 (m, 2H), 1.97-1.95 (m, 2H), 1.39 (s, 9H). MS (ESI): mass calcd. For $C_{18}H_{22}BN_3O_4$ 355.17, m/z. found 356.2 $[M+H]^+$. HPLC: 92.71% (220 nm), 96.26% (254 nm).

Preparation of N-(cis-3-(7-hydroxy-3,7-dihydro-[1,2]oxaborinino[5,6-d]pyrrolo[2,3-b]pyridin-9-yl)cyclobutyl)benzenesulfonamide

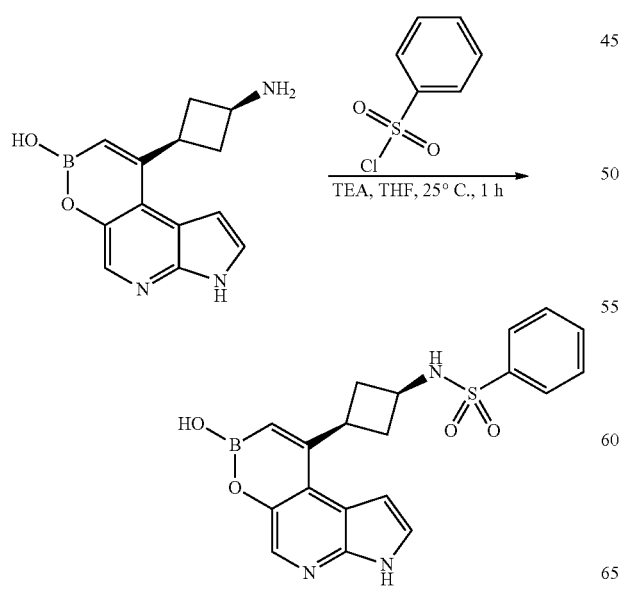

This substance was prepared by following General Procedure A. Yield: 68.88%. $^1$H NMR (DMSO-$d_6$, 400 MHz) δ 11.82 (s, 1H), 8.24 (s, 1H), 8.02 (d, J=6.4 Hz, 1H), 7.85-7.84 (m, 2H), 7.62-7.60 (m, 3H), 7.55-7.53 (m, 1H), 6.83 (s, 1H), 6.12 (s, 1H), 3.97-3.88 (m, 1H), 3.66-3.60 (m, 1H), 2.43-2.41 (m, 2H), 1.85-1.78 (m, 2H). MS (ESI): mass calcd. For $C_{19}H_{18}BN_3O_4S$, 395.11, m/z. found 396.1 $[M+H]^+$. HPLC: 98.81% (220 nm), 96.01% (254 nm).

Preparation of N-(cis-3-(7-hydroxy-3,7-dihydro-[1,2]oxaborinino[5,6-d]pyrrolo[2,3-b]pyridin-9-yl)cyclobutyl)-1-phenylmethanesulfonamide

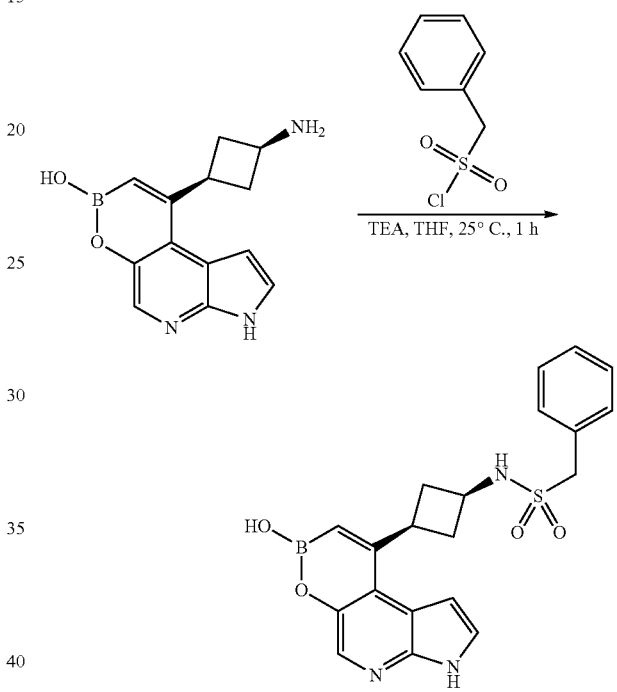

This substance was prepared by following General Procedure A. Yield: 43.98%. $^1$H NMR (DMSO-de, 400 MHz) δ 11.84 (s, 1H), 8.26 (s, 1H), 7.60 (t, J=2.4 Hz, 1H), 7.55 (d, J=8.4 Hz, 1H), 7.40-7.34 (m, 5H), 6.89 (s, 1H), 6.21 (s, 1H), 4.32 (s, 2H), 3.98-3.95 (m, 1H), 3.65-3.64 (m, 1H), 2.69-2.68 (m, 2H), 2.01-1.96 (m, 2H). MS (ESI): mass calcd. For $C_{20}H_{20}BN_3O_4S$, 409.13, m/z found 410.2 $[M+H]^+$. HPLC: 98.98% (220 nm), 97.94% (254 nm).

Preparation of 9-(piperidin-4-yl)-[1,2]oxaborinino[5,6-d]pyrrolo[2,3-b]pyridin-7(3H)-ol

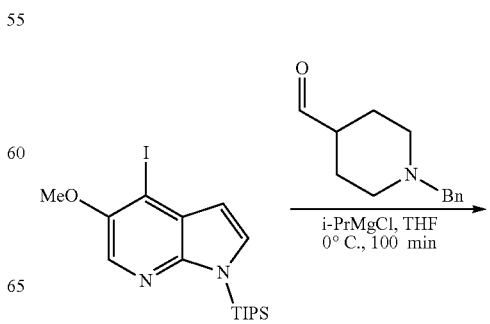

223

-continued

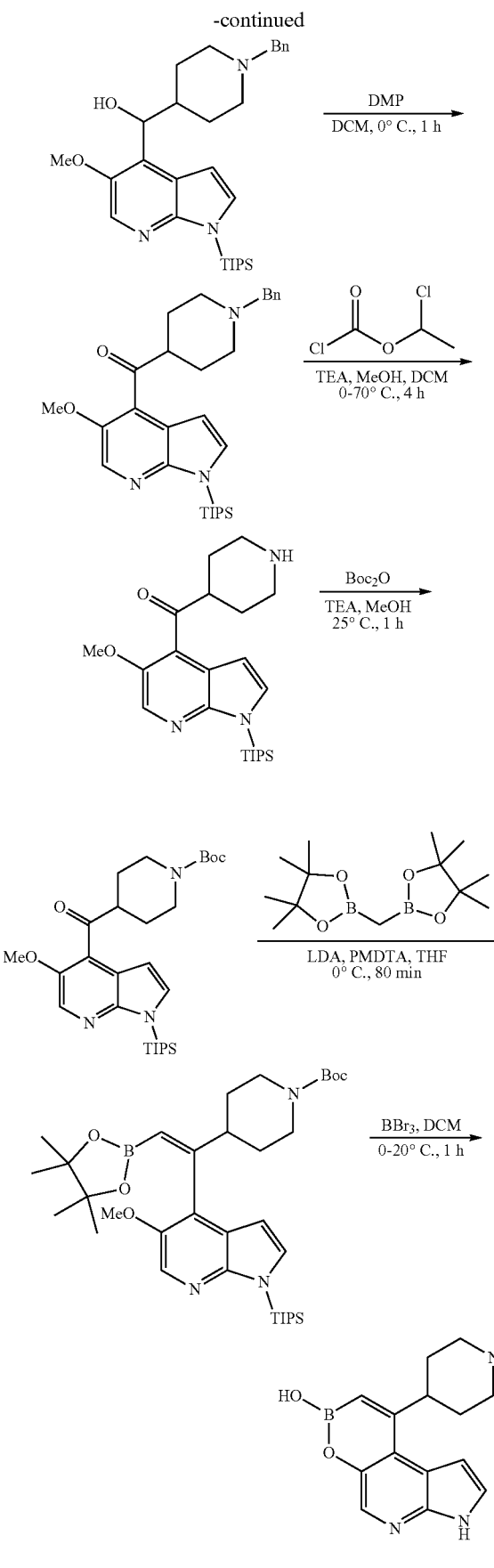

224

Preparation of (1-benzyl-4-piperidyl)-(5-methoxy-1-triisopropylsilyl-pyrrolo[2,3-b]pyridin-4-yl)methanol

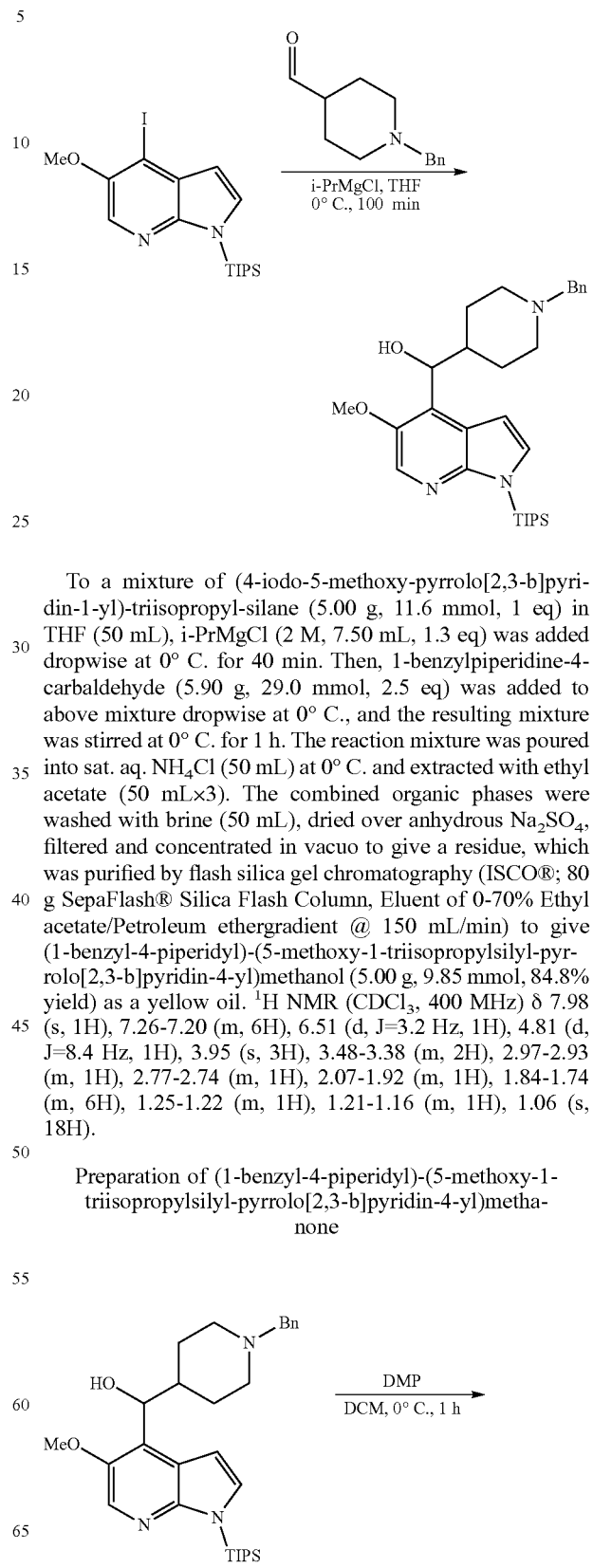

To a mixture of (4-iodo-5-methoxy-pyrrolo[2,3-b]pyridin-1-yl)-triisopropyl-silane (5.00 g, 11.6 mmol, 1 eq) in THF (50 mL), i-PrMgCl (2 M, 7.50 mL, 1.3 eq) was added dropwise at 0° C. for 40 min. Then, 1-benzylpiperidine-4-carbaldehyde (5.90 g, 29.0 mmol, 2.5 eq) was added to above mixture dropwise at 0° C., and the resulting mixture was stirred at 0° C. for 1 h. The reaction mixture was poured into sat. aq. $NH_4Cl$ (50 mL) at 0° C. and extracted with ethyl acetate (50 mL×3). The combined organic phases were washed with brine (50 mL), dried over anhydrous $Na_2SO_4$, filtered and concentrated in vacuo to give a residue, which was purified by flash silica gel chromatography (ISCO®; 80 g SepaFlash® Silica Flash Column, Eluent of 0-70% Ethyl acetate/Petroleum ethergradient @ 150 mL/min) to give (1-benzyl-4-piperidyl)-(5-methoxy-1-triisopropylsilyl-pyrrolo[2,3-b]pyridin-4-yl)methanol (5.00 g, 9.85 mmol, 84.8% yield) as a yellow oil. $^1$H NMR (CDCl$_3$, 400 MHz) δ 7.98 (s, 1H), 7.26-7.20 (m, 6H), 6.51 (d, J=3.2 Hz, 1H), 4.81 (d, J=8.4 Hz, 1H), 3.95 (s, 3H), 3.48-3.38 (m, 2H), 2.97-2.93 (m, 1H), 2.77-2.74 (m, 1H), 2.07-1.92 (m, 1H), 1.84-1.74 (m, 6H), 1.25-1.22 (m, 1H), 1.21-1.16 (m, 1H), 1.06 (s, 18H).

Preparation of (1-benzyl-4-piperidyl)-(5-methoxy-1-triisopropylsilyl-pyrrolo[2,3-b]pyridin-4-yl)methanone

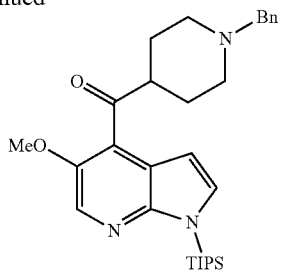

To a mixture of (1-benzyl-4-piperidyl)-(5-methoxy-1-triisopropylsilyl-pyrrolo[2,3-b] pyridin-4-yl)methanol (4.00 g, 7.88 mmol, 1 eq) in DCM (80 mL), (1,1-diacetoxy-3-oxo-1,2-benziodoxol-1-yl) acetate (4.01 g, 9.45 mmol, 1.20 eq) was added portionwise at 0° C., and the resulting mixture was stirred at 0° C. for 1 h. The reaction mixture was poured into sat. aq. NaHCO$_3$ (100 mL) and extracted with DCM (100 mL×3). The combined organic phases were washed with brine (150 mL), dried over anhydrous Na$_2$SO$_4$, filtered and concentrated in vacuo to give a residue, which was purified by flash silica gel chromatography (ISCO®; 80 g SepaFlash® Silica Flash Column, Eluent of 0-70% Ethyl acetate/Petroleum ethergradient @ 150 mL/min) to give (1-benzyl-4-piperidyl)-(5-methoxy-1-triisopropylsilyl-pyrrolo[2,3-b]pyridin-4-yl)methanone (2.00 g, 3.95 mmol, 50.2% yield) as a yellow oil. $^1$H NMR (CDCl$_3$, 400 MHz) δ 8.02 (s, 1H), 7.27-7.17 (m, 6H), 6.49 (d, J=3.2, 1H), 3.88 (s, 3H), 3.44 (s, 2H), 3.12-3.06 (m, 1H), 2.84-2.81 (m, 2H), 2.03-1.97 (m, 2H), 1.85-1.81 (m, 2H), 1.78-1.69 (m, 5H), 1.02 (d, J=7.6, 18H).

Preparation of (5-methoxy-1-triisopropylsilyl-pyrrolo[2,3-b]pyridin-4-yl)-(4-piperidyl) methanone

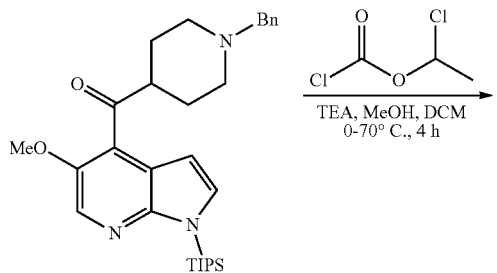

To a solution of (1-benzyl-4-piperidyl)-(5-methoxy-1-triisopropylsilyl-pyrrolo[2,3-b]pyridin-4-yl)methanone (1.50 g, 2.97 mmol, 1 eq) in DCM (15 mL), TEA (2.40 g, 23.7 mmol, 3.30 mL, 8 eq) and 1-chloroethyl carbonochloridate (1.70 g, 11.9 mmol, 4 eq) were added at 0° C., and the reaction was stirred at 25° C. for 2 h. After removing the DCM, the mixture was dissolved in MeOH (15 mL) and the resulting mixture was stirred at 70° C. for 2 h. The reaction mixture was filtered, and the filtrate was concentrated under reduced pressure to give (5-methoxy-1-triisopropylsilyl-pyrrolo[2,3-b]pyridin-4-yl)-(4-piperidyl)methanone (1.20 g, 2.89 mmol, 97.4% yield) as a yellow oil, which was used directly in the next step without purification.

Preparation of Tert-Butyl 4-(5-methoxy-1-triisopropylsilyl-pyrrolo[2,3-b]pyridine-4-carbonyl)piperidine-1-carboxylate

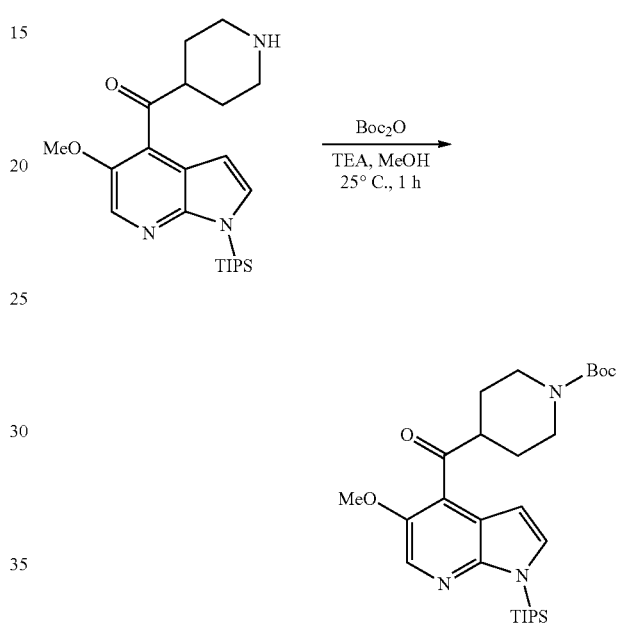

To a mixture of (5-methoxy-1-triisopropylsilyl-pyrrolo[2,3-b]pyridin-4-yl)-(4-piperidyl) methanone (700 mg, 1.68 mmol, 1 eq) in MeOH (10 mL), tert-butoxycarbonyl tert-butyl carbonate (552 mg, 2.53 mmol, 581 uL, 1.5 eq) and TEA (341 mg, 3.37 mmol, 469 uL, 2 eq) were added dropwise in sequence at 25° C., and the resulting mixture was stirred at 25° C. for 1 h. The reaction mixture was poured into ice-water (w/w=1/1) (10 mL), and the aqueous phase was extracted with ethyl acetate (10 mL×3). The combined organic phases were washed with brine (10 mL×3), dried over anhydrous Na$_2$SO$_4$, filtered and concentrated in vacuo to give a residue, which was purified by flash silica gel chromatography (ISCO®; 12 g SepaFlash® Silica Flash Column, Eluent of 0~10% Ethyl acetate/Petroleum ethergradient @ 50 mL/min) to give tert-butyl-4-(5-methoxy-1-triisopropylsilyl-pyrrolo[2,3-b]pyridine-4-carbonyl)piperidine-1-carboxylate (0.5 g, 970 μmol, 57.6% yield) as a yellow oil. $^1$H NMR (CDCl$_3$, 400 MHz) δ 8.12 (s, 1H), 7.37 (d, J=3.2 Hz, 1H), 6.61 (d, J=3.6 Hz, 1H), 3.98 (s, 3H), 3.40-3.34 (m, 1H), 2.90-2.60 (m, 2H), 1.92-1.89 (m, 2H), 1.84-1.78 (m, 5H), 1.69-1.65 (m, 2H), 1.46 (s, 9H), 1.11 (d, J=7.6 Hz, 18H)

227

Preparation of Tert-Butyl 4-[(Z)-1-(5-methoxy-1-triisopropylsilyl-pyrrolo [2,3-b]pyridin-4-yl)-2-(4,4,5,5-tetramethyl-1,3,2-dioxaborolan-2-yl)vinyl]piperidine-1-carboxylate

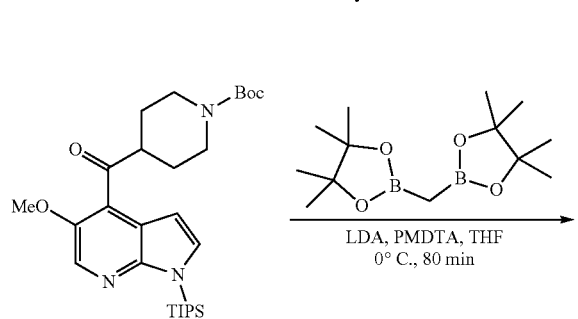

To a mixture of LDA (2 M, 3.80 mL, 3 eq) in THF (10 mL), N'-[2-(dimethylamino)ethyl]-N,N,N'-trimethyl-ethane-1,2-diamine (874 mg, 5.04 mmol, 1.10 mL, 2 eq) and 4,4,5,5-tetramethyl-2-[(4,4,5,5-tetramethyl-1,3,2-dioxaborolan-2-yl)methyl]-1,3,2-dioxaborolane (2.03 g, 7.56 mmol, 3 eq) were added dropwise in sequence at 0° C. under a N₂ atmosphere. The resulting mixture was stirred at 0° C. for 20 min. Then, tert-butyl4-(5-methoxy-1-triisopropylsilyl-pyrrolo[2,3-b]pyridine-4-carbonyl)piperidine-1-carboxylate (1.30 g, 2.52 mmol, 1 eq) in THF (15 mL) was added into the above mixture at 0° C., and the reaction mixture was stirred at 0° C. for 1 h. The reaction mixture was poured into sat. aq. NH₄Cl (25 mL) and extracted with ethyl acetate (30 mL×3). The combined organic phases were washed with brine (30 mL), dried over anhydrous Na₂SO₄, filtered and concentrated in vacuo to give a residue, which was purified by flash silica gel chromatography (ISCO®; 20 g SepaFlash® Silica Flash Column, Eluent of 0-10% Ethyl acetate/Petroleum ethergradient @ 50 mL/min) to give tert-butyl-4-[(Z)-1-(5-methoxy-1-triisopropylsilyl-pyrrolo[2,3-b]pyridin-4-yl)-2-(4,4,5,5-tetramethyl-1,3,2-dioxaborolan-2-yl)vinyl]piperidine-1-carboxylate (1.60 g, 2.50 mmol, 99.2% yield) as a yellow oil. $^1$H NMR (CDCl₃, 400 MHz) δ 8.03 (s, 1H), 7.19 (d, J=3.2 Hz, 1H), 6.30 (d, J=3.6 Hz, 1H), 5.70 (s, 1H), 3.89 (s, 3H), 3.31-3.29 (m, 1H), 2.74-2.51 (m, 3H), 1.92-1.80 (m, 4H), 1.65-1.54 (m, 2H), 1.44 (s, 9H), 1.39-1.26 (m, 2H), 1.24 (s, 12H), 1.13 (s, 18H).

228

Preparation of 9-(piperidin-4-yl)-[1,2]oxaborinino[5,6-d]pyrrolo[2,3-b]pyridin-7(3H)-ol

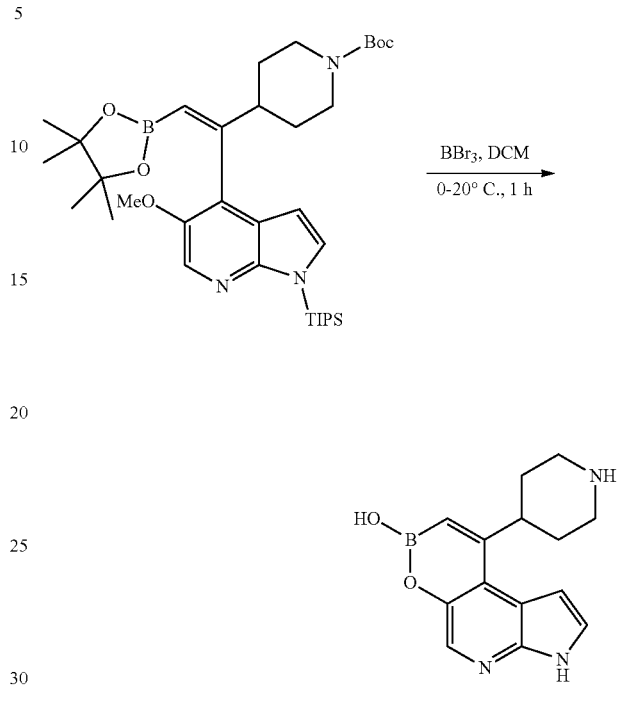

To a mixture of tert-butyl 4-[(Z)-1-(5-methoxy-1-triisopropylsilyl-pyrrolo[2,3-b] pyridin-4-yl)-2-(4,4,5,5-tetramethyl-1,3,2-dioxaborolan-2-yl)vinyl]piperidine-1-carboxylate (1.2 g, 1.88 mmol, 1 eq) in DCM (15 mL), BBr₃ (2.11 g, 8.44 mmol, 813 uL, 4.5 eq) was added dropwise at 0° C., and the resulting mixture was stirred at 20° C. for 1 h. Then, ice-water (w/w=1/1) (20 mL) was added, and the resulting mixture was concentrated in vacuo to yield the aqueous layer, which was directly freeze-dried to give a residue (2 g). The residue was triturated with THF (10 mL) to give the crude product (1.5 g) as HBr salt (off-white solid). $^1$H NMR (DMSO-d₆, 400 MHz) δ 11.84 (s, 1H), 8.83 (s, 1H), 8.25 (s, 1H), 7.58 (s, 1H), 6.69 (d, J=2.8 Hz, 1H), 6.19 (s, 1H), 3.30-3.26 (m, 1H), 3.10-3.07 (m, 2H), 2.78-2.72 (m, 2H), 1.89-1.86 (m, 2H), 1.51-1.42 (m, 2H). MS (ESI): mass calcd. For C₁₄H₁₇BClN₃O₂ 269.13, m/z. found 270.2 [M+H]⁺. HPLC: 98.12% (220 nm), 95.24% (254 nm).

Preparation of 9-(1-(ethylsulfonyl)piperidin-4-yl)-[1,2]oxaborinino[5,6-d]pyrrolo[2,3-b]pyridin-7(3H)-ol

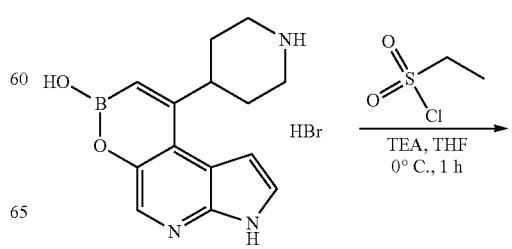

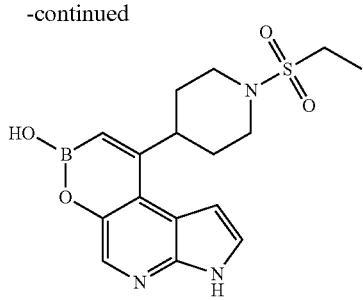

To a mixture of 9-(piperidin-4-yl)-[1,2]oxaborinino[5,6-d]pyrrolo[2,3-b]pyridin-7(3H)-ol (325 mg, 929 μmol, 1 eq HBr) and TEA (282 mg, 2.79 mmol, 3 eq) in THF (3 mL), ethanesulfonyl chloride (239 mg, 1.86 mmol, 2 eq) was added dropwise at 0° C., and the resulting mixture was stirred at 0° C. for 1 h. The reaction mixture was quenched by adding water (0.5 mL), and the formed precipitate was collected by filtration and triturated with EtOH/H$_2$O (1 mL/0.5 mL) at 20° C. for 30 min to give 9-(1-(ethylsulfonyl)piperidin-4-yl)-[1,2]oxaborinino [5,6-d]pyrrolo[2,3-b]pyridin-7(3H)-ol (33.1 mg, 86.7 μmol, 9.33% yield, 94.58% purity) as a white solid. $^1$H NMR (DMSO-d$_6$, 400 MHz) δ 11.89 (s, 1H), 8.92 (s, 1H), 8.27 (s, 1H), 7.59 (t, J=3.2 Hz, 1H), 6.78 (s, 1H), 6.21 (s, 1H), 3.78-3.74 (m, 2H), 3.45-3.39 (m, 1H), 3.21-3.18 (m, 2H), 3.13 (q, J=7.6 Hz, 2H), 2.04 (d, J=12.4 Hz, 2H), 1.63-1.54 (m, 2H), 1.27 (t, J=7.6 Hz, 3H). MS (ESI): mass calcd. For C$_{16}$H$_{20}$BN$_3$O$_4$S, 361.13, m/z. found 362.1 [M+H]$^+$. HPLC: 94.58% (220 nm), 96.67% (254 nm).

Preparation of 9-(1-(propylsulfonyl)piperidin-4-yl)-[1,2]oxaborinino[5,6-d]pyrrolo [2,3-b]pyridin-7(3H)-ol

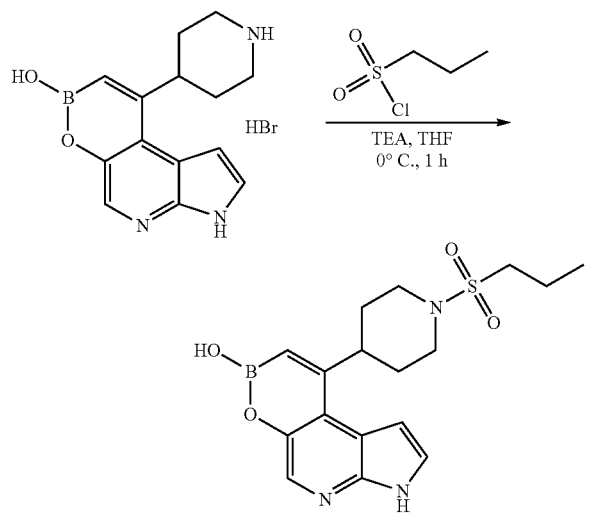

This substance was prepared by following the same procedure employed for the preparation of 9-(1-(ethylsulfonyl)piperidin-4-yl)-[1,2]oxaborinino[5,6-d]pyrrolo[2,3-b]pyridin-7(3H)-ol as a white solid. Yield: 12.0%. $^1$H NMR (DMSO-d$_6$, 400 MHz) δ 11.88 (s, 1H), 8.27 (s, 1H), 7.58 (d, J=3.2 Hz, 1H), 6.78 (d, J=3.2 Hz, 1H), 6.22 (s, 1H), 3.77-3.73 (m, 2H), 3.45-3.44 (m, 1H), 3.19-3.10 (m, 2H), 3.09-3.06 (m, 2H), 2.05 (d, J=12.4 Hz, 2H), 1.75 (q, J=7.6 Hz, 2H), 1.63-1.54 (m, 2H), 1.03 (t, J=7.2 Hz, 3H). MS (ESI): mass calcd. For C$_{17}$H$_{22}$BN$_3$O$_4$S, 375.14, m/z. found 376.1 [M+H]$^+$. HPLC: 98.53% (220 nm), 99.25% (254 nm).

Preparation of 2,2,2-trifluoro-1-(4-(7-hydroxy-3,7-dihydro-[1,2]oxaborinino[5,6-d]pyrrolo[2,3-b]pyridine-9-yl)piperidin-1-yl)ethenone

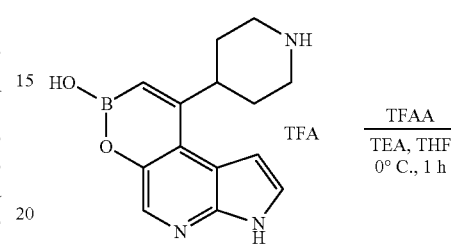

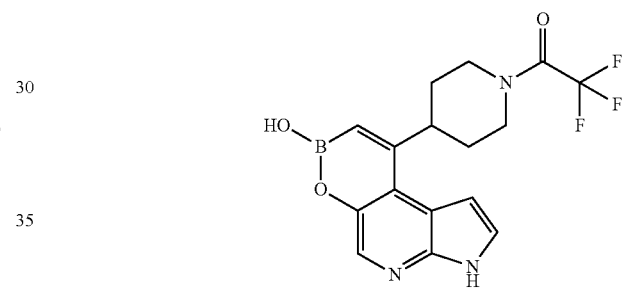

This substance was prepared by following the same procedure employed for the preparation of 9-(1-(ethylsulfonyl)piperidin-4-yl)-[1,2]oxaborinino[5,6-d]pyrrolo[2,3-b] pyridin-7(3H)-ol as a white solid. Yield: 24.5%. $^1$H NMR (DMSO-d$_6$, 400 MHz) δ 11.90 (s, 1H), 8.91 (s, 1H), 8.27 (s, 1H), 7.61 (t, J=3.2 Hz, 1H), 6.83 (s, 1H), 6.19 (s, 1H), 4.50-4.46 (m, 1H), 4.04-4.00 (m, 1H), 3.69-3.62 (m, 2H), 2.56-2.50 (m, 1H), 2.13-1.07 (m, 2H), 1.61-1.50 (m, 2H). MS (ESI): mass calcd. For C$_{16}$H$_{15}$BF$_3$N$_3$O$_3$ 365.12, m/z. found 366.1 [M+H]$^+$. HPLC: 96.35% (220 nm), 97.61% (254 nm).

Preparation of 9-(piperidin-4-yl)-[1,2]oxaborinino[5,6-d]pyrrolo[2,3-b]pyridin-7(3H)-ol

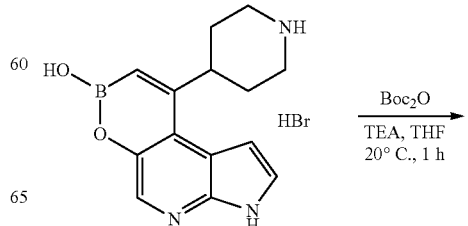

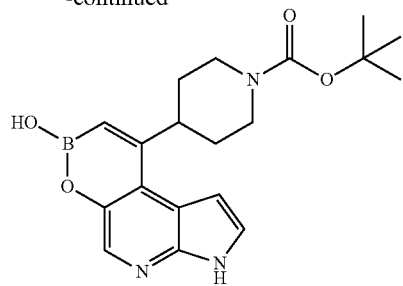

To a mixture of 9-(piperidin-4-yl)-[1,2]oxaborinino[5,6-d]pyrrolo[2,3-b]pyridin-7(3H)-ol (3.63 g, 10.4 mmol, 1 eq) and TEA (3.16 g, 31.2 mmol, 4.3 mL, 3 eq) in THF (30 mL), tert-butoxycarbonyl tert-butyl carbonate (4.54 g, 20.8 mmol, 2 eq) was added dropwise at 20° C., and the resulting mixture was stirred at 20° C. for 1 h. The reaction mixture was then poured into ice-water (w/w=1/1) (20 mL), and the aqueous phase was extracted with ethyl acetate (30 mL×3). The combined organic phases were washed with brine (50 mL), dried over anhydrous $Na_2SO_4$, filtered and concentrated in vacuo to give a crude product (3.00 g) as an off-white solid. $^1$H NMR (DMSO-ds, 400 MHz) δ 11.89 (s, 1H), 8.27 (s, 1H), 7.59 (t, J=3.2 Hz, 1H), 6.75 (s, 1H), 6.19 (s, 1H), 4.14-4.10 (m, 2H), 3.43 (t, J=11.2 Hz, 1H), 3.05-2.95 (m, 2H), 1.97-1.93 (d, m, 2H), 1.50-1.42 (m, 11H). MS (ESI): mass calcd. For $C_{19}H_{22}BN_3O_4$ 369.19, m/z. found 370.1 [M+H]$^+$. HPLC: 98.12% (220 nm), 99.04% (254 nm).

Preparation of 9-(1-(methylsulfonyl)piperidin-4-yl)-[1,2]oxaborinino[5,6-d]pyrrolo [2,3-b]pyridin-7(3H)-ol

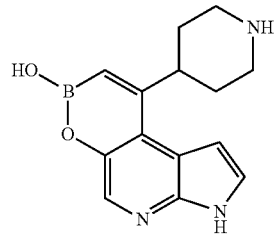

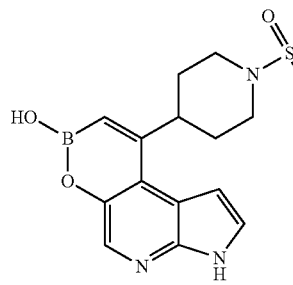

To a mixture of 9-(piperidin-4-yl)-[1,2]oxaborinino[5,6-d]pyrrolo[2,3-b]pyridin-7(3H)-ol (387 mg, 1.11 mmol, 1 eq, HBr) and TEA (338 mg, 3.34 mmol, 466 uL, 3 eq) in THF (3 mL), MsCl (166 mg, 1.45 mmol, 112 uL, 1.3 eq) was added dropwise at 0° C., and the resulting mixture was stirred at 0° C. for 1 h. The reaction mixture was then poured into ice-water (w/w=1/1) (5 mL), and the aqueous phase was extracted with ethyl acetate (5 mL×3). The combined organic phases were washed with brine (10 mL), dried over anhydrous $Na_2SO_4$, filtered and concentrated in vacuo to give a residue, which was purified by prep-HPLC (column: Phenomenex Gemini-NX C18 75*30 mm*3 um; mobile phase: [water (10 mM $NH_4HCO_3$)-ACN]; B %: 20%-50%,8 min) to give 9-(1-(methylsulfonyl)piperidin-4-yl)-[1,2]oxaborinino[5,6-d]pyrrolo[2,3-b]pyridin-7(3H)-ol (23 mg, 66 μmol, 35.7% yield, 96.01% purity) as an off-white solid. $^1$H NMR (DMSO-d$_6$, 400 MHz) δ 11.90 (s, 1H), 8.92 (s, 1H), 8.27 (s, 1H), 7.60 (s, 1H), 6.77 (s, 1H), 6.23 (s, 1H), 3.73 (d, J=11.6 Hz, 2H), 3.42-3.39 (m, 1H), 3.08 (t, J=11.2 Hz, 2H), 2.95 (s, 3H), 2.09-2.05 (m, 2H), 1.67-1.58 (m, 2H). MS (ESI): mass calcd. For $C_{15}H_{18}BN_3O_4S$, 347.11, m/z. found 348.2 [M+H]$^+$. HPLC: 96.01% (220 nm), 98.67% (254 nm).

Preparation of 9-(trans-4-hydroxycyclohexyl)-[1,2]oxaborinino[5,6-d]pyrrolo [2,3-b]pyridin-7(3H)-ol, 9-(cis-4-hydroxycyclohexyl)-[1,2]oxaborinino[5,6-d]pyrrolo [2,3-b]pyridin-7(3H)-ol, 9-(4-bromocyclohexyl)-[1,2]oxaborinino[5,6-d]pyrrolo[2,3-b] pyridine-7(3H)-ol, and 9-(cis-4-bromocyclohexyl)-[1,2]oxaborinino[5,6-d]pyrrolo [2,3-b]pyridin-7(3H)-ol

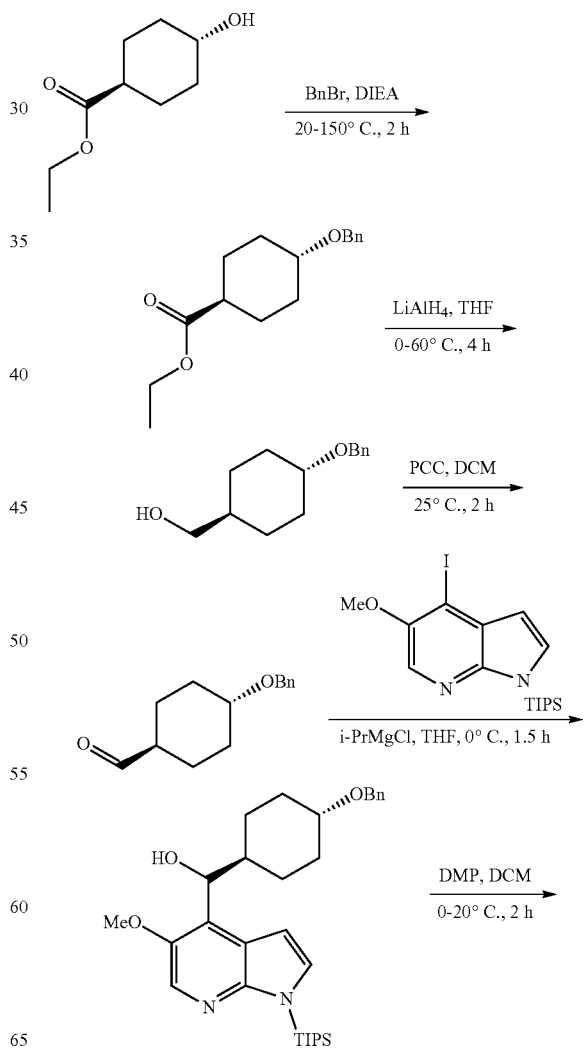

234

Preparation of Trans-Ethyl 4-(benzyloxy)cyclohexanecarboxylate

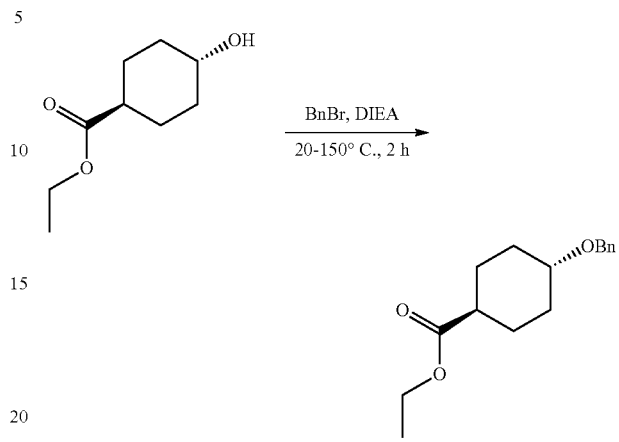

To a mixture of trans-ethyl 4-hydroxycyclohexanecarboxylate (39.0 g, 226 mmol, 1 eq) in DIEA (566 mmol, 98.6 mL, 2.5 eq), BnBr (237 mmol, 28.2 mL, 1.05 eq) was added in one portion at 20° C. under a $N_2$ atmosphere, and the resulting mixture was heated to 150° C. and stirred for 2 h. The reaction mixture was then poured into 1N HCl (800 mL) and was stirred for 5 min. The aqueous phase was extracted with ethyl acetate (500 mL×3). The combined organic phases were washed with brine (200 mL×2), dried over anhydrous $Na_2SO_4$, filtered and concentrated in vacuo to give a residue, which was purified by column chromatography (SiO2, Petroleum ether/Ethyl acetate=10/1 to 5/1) to give trans-ethyl 4-(benzyloxy)cyclohexanecarboxylate (42.0 g, 160.1 mmol, 70.70% yield) as a yellow oil. $^1$H NMR (CDCl$_3$, 400 MHz) δ 7.36-7.32 (m, 4H), 7.31-7.27 (m, 1H), 4.57 (s, 1H), 4.13 (q, J=7.2 Hz, 2H), 3.38-3.31 (m, 1H), 2.29-2.25 (m, 1H), 2.17-2.12 (m, 2H), 2.06-2.01 (m, 2H), 1.52-1.42 (m, 2H), 1.39-1.32 (m, 2H), 1.25 (t, J=7.2 Hz, 3H).

Preparation of (trans-4-(benzyloxy)cyclohexyl)methanol

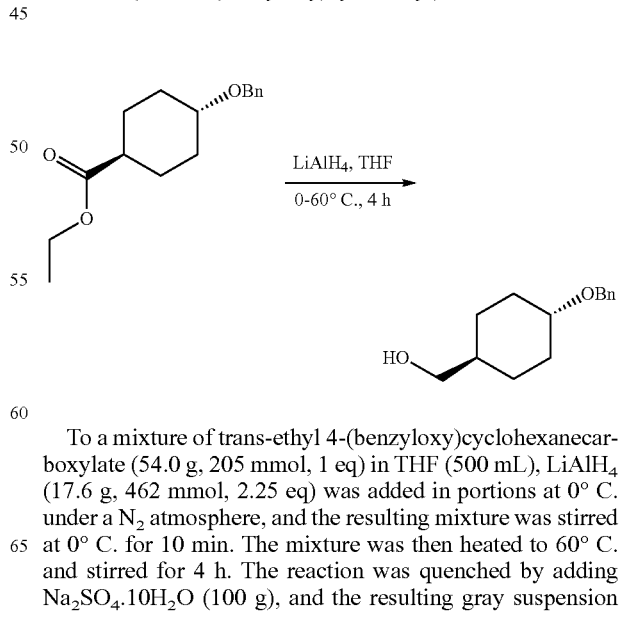

To a mixture of trans-ethyl 4-(benzyloxy)cyclohexanecarboxylate (54.0 g, 205 mmol, 1 eq) in THF (500 mL), LiAlH$_4$ (17.6 g, 462 mmol, 2.25 eq) was added in portions at 0° C. under a $N_2$ atmosphere, and the resulting mixture was stirred at 0° C. for 10 min. The mixture was then heated to 60° C. and stirred for 4 h. The reaction was quenched by adding $Na_2SO_4 \cdot 10H_2O$ (100 g), and the resulting gray suspension

233

-continued

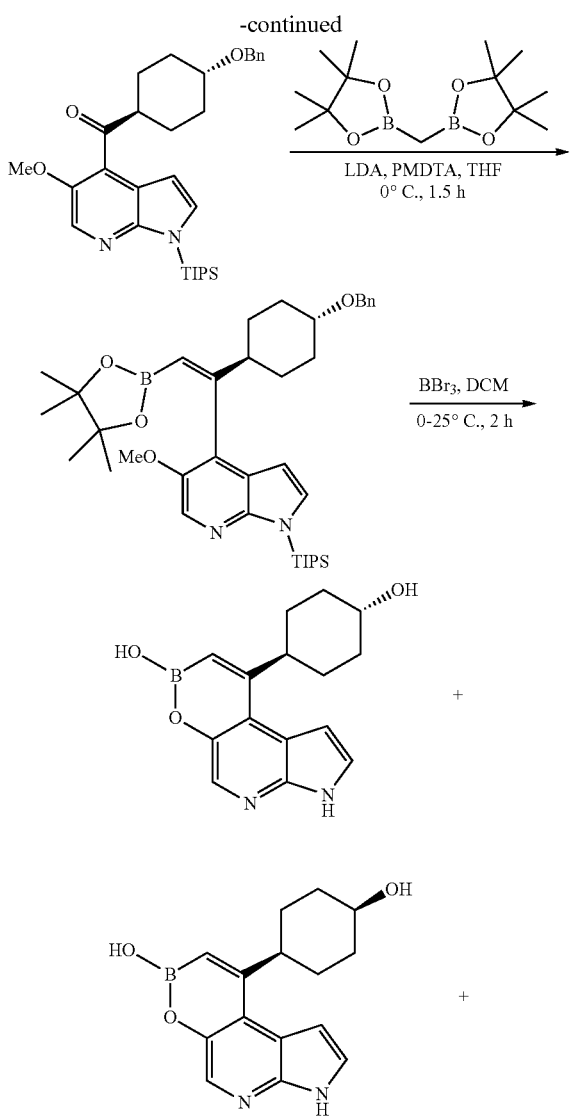

was filtered through a pad of celite and the filter cake was washed with ethyl acetate (500 mL×2). The filtrate was dried over anhydrous Na₂SO₄, filtered and concentrated in vacuo to give the crude product, which was triturated with petroleum ether/Ethyl acetate=10/1 (100 mL) at 20° C. for 30 min to give (trans-4-(benzyloxy)cyclohexyl)methanol (40.0 g, 181 mmol, 88.21% yield) as a white solid. ¹H NMR (CDCl₃, 400 MHz) δ 7.36-7.33 (m, 4H), 7.30-7.27 (m, 1H), 4.58 (s, 2H), 3.44 (d, J=6.4 Hz, 2H), 3.35-3.28 (m, 1H), 2.17-2.13 (m, 2H), 1.88-1.83 (m, 2H), 1.52-1.43 (m, 1H), 1.38-1.27 (m, 2H), 1.00-0.93 (m, 2H).

Preparation of trans-4-(benzyloxy)cyclohexanecarbaldehyde

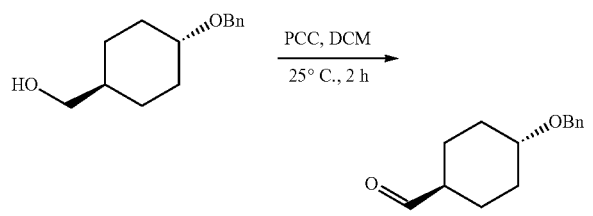

To a mixture of (trans-4-(benzyloxy)cyclohexyl)methanol (10.0 g, 45.4 mmol, 1 eq) in DCM (200 mL), PCC (19.6 g, 90.8 mmol, 2 eq) was added in portions at 25° C. under a N₂ atmosphere, and the resulting mixture was stirred at 25° C. for 2 h. Then, the reaction mixture was poured onto the silica gel column, eluted with (8-15% Ethyl acetate/Petroleum ether) to give trans-4-(benzyloxy)cyclohexanecarbaldehyde (19.0 g, 87.04 mmol, 63.92% yield) as a yellow oil. ¹H NMR (CDCl₃, 400 MHz) δ 9.56 (s, 1H), 7.28-7.20 (m, 4H), 7.20-7.18 (m, 1H), 4.48 (s, 2H), 3.29-3.24 (m, 1H), 2.07-2.02 (m, 1H), 1.99-1.97 (m, 2H), 1.97-1.95 (m, 2H), 1.35-1.25 (m, 4H).

Preparation of (trans-4-(benzyloxy)cyclohexyl)(5-methoxy-1-(triisopropylsilyl)-1H-pyrrolo[2,3-b]pyridin-4-yl)methanol

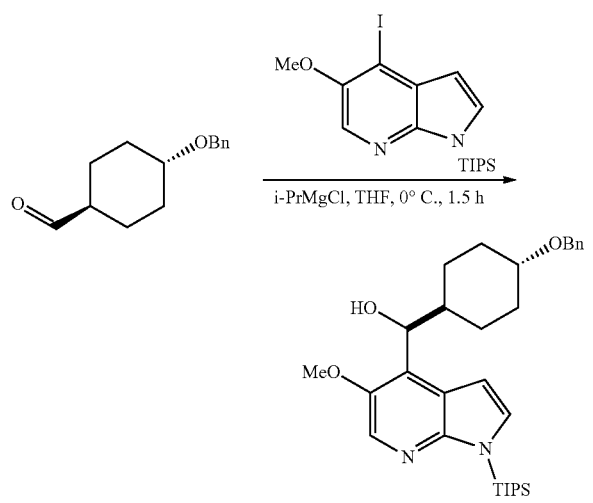

To a solution of (4-iodo-5-methoxy-pyrrolo[2,3-b]pyridin-1-yl)-triisopropyl-silane (2.00 g, 4.65 mmol, 1 eq) in THF (25 mL), i-PrMgCl (2 M, 3.0 mL, 1.3 eq) was added dropwise at 0° C. After addition, the mixture was stirred at this temperature for additional 30 min. Then, trans-4-(benzyloxy)cyclohexanecarbaldehyde (1.52 g, 6.97 mmol, 1.5 eq) was added into the above mixture at 0° C. dropwise, and the resulting mixture was stirred at 0° C. for 1 h. The reaction was quenched by adding sat. aq NH₄Cl (20 mL) and extracted with ethyl acetate (10 mL×3). The combined organic phases were washed with brine (10 mL×2), dried over anhydrous Na₂SO₄, filtered and concentrated in vacuo to give a residue, which was purified by column chromatography (SiO2, Petroleum ether/Ethyl acetate=10/1 to 5/1) to give (trans-4-(benzyloxy)cyclohexyl) (5-methoxy-1-(triisopropylsilyl)-1H-pyrrolo[2,3-b]pyridin-4-yl)methanol (2.50 g, crude) as a yellow oil.

Preparation of (trans-4-(benzyloxy)cyclohexyl)(5-methoxy-1-(triisopropylsilyl)-1H-pyrrolo[2,3-b]pyridin-4-yl)methanone

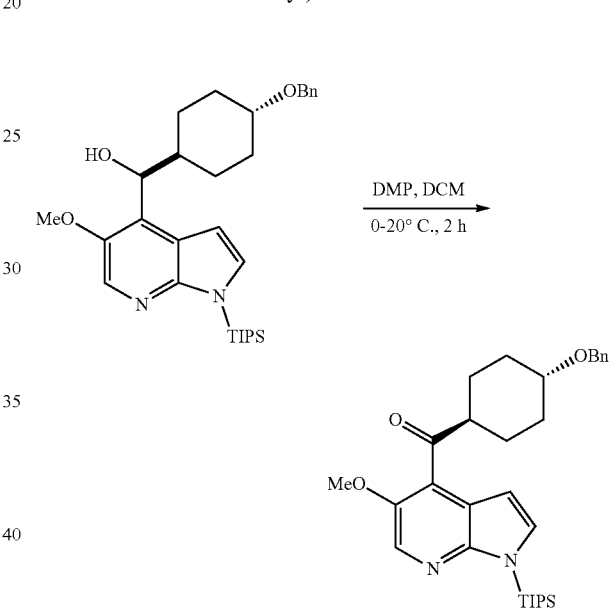

To a mixture of (4-(benzyloxy)cyclohexyl)(5-methoxy-1-(triisopropylsilyl)-1H-pyrrolo[2,3-b]pyridin-4-yl)methanol (2.00 g, 3.83 mmol, 1 eq) in DCM (30 mL), DMP (1.95 g, 4.59 mmol, 1.2 eq) was added in portions at 0° C. under a N₂ atmosphere, and the resulting mixture was stirred at 20° C. for 2 h. Then, the reaction mixture was poured into ice-water (w/w=1/1) (50 mL), and the pH of the aqueous phase was adjusted to 6-7 with sat. aq. NaHCO₃. The aqueous phase was extracted with DCM (30 mL×3), and the combined organic phases were washed with brine (30 mL×2), dried over anhydrous Na₂SO₄, filtered and concentrated in vacuo to give a residue, which was purified by flash silica gel chromatography (ISCO®; 20 g SepaFlash® Silica Flash Column, Eluent of 8-15% Ethyl acetate/Petroleum ethergradient @ 75 mL/min) to give (trans-4-(benzyloxy) cyclohexyl)(5-methoxy-1-(triisopropylsilyl)-1H-pyrrolo[2, 3-b]pyridin-4-yl)methanone (1.8 g, 3.46 mmol, 90.35% yield) as a yellow oil. ¹H NMR (CDCl₃, 400 MHz) δ 8.12-8.10 (m, 1H), 7.37-7.32 (m, 5H), 7.28-7.27 (m, 1H), 6.61-6.60 (m, 1H), 4.59-4.51 (m, 2H), 3.98-3.96 (m, 3H), 3.44-3.37 (m, 1H), 3.28-3.18 (m, 1H), 2.19-2.05 (m, 2H), 1.87-1.84 (m, 2H), 1.83-1.79 (m, 3H), 1.55-1.27 (m, 4H), 1.12-1.10 (m, 18H).

Preparation of 4-((E)-1-(trans-4-(benzyloxy)cyclo-
hexyl)-2-(4,4,5,5-tetramethyl-1,3,2-dioxaborolan-2-
yl)vinyl)-5-methoxy-1-(triisopropylsilyl)-1H-pyrrolo
[2,3-b]pyridine[2,3-b]pyridin-1-yl]-triisopropyl-
silane

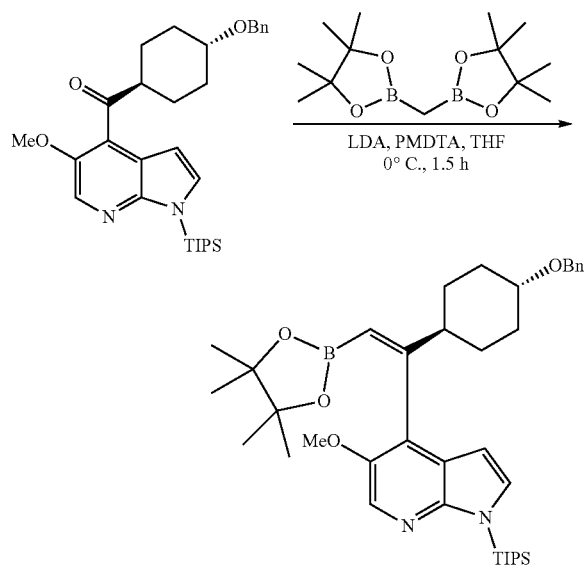

To a solution of LDA (2 M, 4.30 mL, 3 eq) in THF (15 mL), N'-[2-(dimethylamino)ethyl]-N,N,N'-trimethyl-ethane-1,2-diamine (5.76 mmol, 1.20 mL, 2 eq) and a solution of 4,4,5,5-tetramethyl-2-[(4,4,5,5-tetramethyl-1,3,2-dioxaborolan-2-yl) methyl]-1,3,2-dioxaborolane (2.32 g, 8.64 mmol, 3 eq) in THF (10 mL) were added in sequence at 0° C., and the resulting mixture was stirred at 0° C. for 30 min. Then, to the above mixture a solution of (trans-4-(benzyloxy)cyclohexyl)(5-methoxy-1-(triisopropylsilyl)-1H-pyrrolo[2,3-b]pyridin-4-yl)methanone (1.50 g, 2.88 mmol, 1 eq) THF (10 mL) was added dropwise in at 0° C., and the resulting mixture was stirred at 0° C. for 1 h. The reaction was quenched by adding sat. NH$_4$Cl (50 mL) and extracted with ethyl acetate (15 mL×3). The combined organic phases were washed with brine (20 mL), dried over anhydrous Na$_2$SO$_4$, filtered and concentrated in vacuo to give a residue, which was purified by flash silica gel chromatography (ISCO®; 20 g Sepa Flash® Silica Flash Column, Eluent of 5-15% Ethyl acetate/Petroleum ethergradient @ 70 mL/min) to give 4-((E)-1-(trans-4-(benzyloxy)cyclohexyl)-2-(4,4,5,5-tetramethyl-1,3,2-dioxaborolan-2-yl)vinyl)-5-methoxy-1-(triisopropylsilyl)-1H-pyrrolo[2,3-b]pyridine[2,3-b]pyridin-1-yl]-triisopropyl-silane (2.30 g, crude) as a yellow oil.

Preparation of 9-(trans-4-hydroxycyclohexyl)-[1,2]
oxaborinino[5,6-d]pyrrolo [2,3-b]pyridin-7(3H)-ol,
9-(cis-4-hydroxycyclohexyl)-[1,2]oxaborinino[5,6-d]
pyrrolo [2,3-b]pyridin-7(3H)-ol, 9-(4-bromocyclo-
hexyl)-[1,2]oxaborinino[5,6-d]pyrrolo[2,3-b] pyri-
dine-7(3H)-ol, and 9-(cis-4-bromocyclohexyl)-[1,2]
oxaborinino[5,6-d]pyrrolo [2,3-b]pyridin-7(3H)-ol To a mixture of 4-((E)-1-(trans-4-(benzyloxy)cyclohexyl)-2-(4,4,5,5-tetramethyl-1,3,2-dioxaborolan-2-yl)vinyl)-5-methoxy-1-(triisopropylsilyl)-1H-pyrrolo[2,3-b]pyridine (1.1 g, 1.71 mmol, 1 eq) in DCM (20 mL), BBr$_3$ (8.53 mmol, 0.80 mL, 5 eq) was added dropwise at 0° C. under a N$_2$ atmosphere, and the resulting mixture was stirred at 25° C. for 2 h. The reaction was quenched by adding MeOH (30 mL) at 0° C. Then, the reaction mixture was filtered, and the filtrate was concentrated in vacuo to give a residue, which was purified by prep-HPLC (column: Phenomenex luna C18 250*50 mm*10 um; mobile phase: [water (0.1% TFA)-ACN]; B %: 20%-60%,35 min) to give 9-(trans-4-hydroxycyclohexyl)-[1,2]oxaborinino [5,6-d]pyrrolo[2,3-b]pyridin-7(3H)-ol (27.4 mg, 91.40 µmol, 5.36% yield, 94.77% purity) as an off-white solid. $^1$H NMR (DMSO-d$_6$, 400 MHz) δ 11.85 (s, 1H), 8.84 (s, 1H), 8.25 (s, 1H), 7.59 (t, J=2.8 Hz, 1H), 6.66 (s, 1H), 6.19 (s, 1H), 4.67 (d, J=4.4 Hz, 1H), 3.54-3.49 (m, 1H), 3.18-3.12 (m, 1H), 2.02-1.95 (m, 4H), 1.47-1.40 (m, 4H). MS (ESI): mass calcd. For C$_{15}$H$_{17}$BN$_2$O$_3$ 284.13, m/z. found 285.1 [M+H]$^+$. HPLC: 94.77% (220 nm), 95.95% (254 nm); 9-(cis-4-hydroxycyclohexyl)-[1,2]oxaborinino[5,6-d]pyrrolo[2,3-b] pyridin-7(3H)-ol (13.3 mg, 43.85 µmol, 2.57% yield, 93.67% purity) as a yellow solid. $^1$H NMR (DMSO-d$_6$, 400 MHz) δ 11.83 (s, 1H), 8.83 (s, 1H), 8.25 (s, 1H), 7.57 (t, J=3.6 Hz, 1H), 6.69 (s, 1H), 6.22 (s, 1H), 4.43 (d, J=3.2 Hz, 1H), 4.00-3.99 (m, 1H), 3.24-3.20 (m, 1H), 1.83-1.70 (m, 8H). MS (ESI): mass calcd. For C$_{15}$H$_{17}$BN$_2$O$_3$ 284.13, m/z found 285.1 [M+H]$^+$. HPLC: 93.67% (220 nm), 86.05% (254 nm); 9-(4-bromocyclohexyl)-[1,2]oxaborinino[5,6-d] pyrrolo[2,3-b]pyridin-7(3H)-ol (165 mg, 467.45 µmol, 27.40% yield, 98.31% purity) as an off-white solid. $^1$H NMR (DMSO-d$_6$, 400 MHz) δ 11.84 (s, 1H), 8.86 (s, 1H), 8.27 (s, 1H), 7.58 (t, J=3.2 Hz, 1H), 6.72 (s, 1H), 6.26 (s, 1H), 5.01-4.99 (m, 1H), 3.86-3.85 (m, 1H), 2.26-2.22 (m, 2H), 2.16-2.11 (m, 2H), 1.89-1.87 (m, 4H). MS (ESI): mass calcd. For C$_{15}$H$_{16}$BBrN$_2$O$_2$ 346.05, m/z. found 347.0 [M+H]$^+$. HPLC: 98.31% (220 nm), 99.61% (254 nm); 9-(cis-4-bromocyclohexyl)-[1,2]oxaborinino[5,6-d]pyrrolo[2,3-b] pyridine-7(3H)-ol (100 mg, 270.85 µmol, 15.88% yield, 93.99% purity) as an off-white solid. $^1$H NMR (DMSO-d$_6$, 400 MHz) δ 11.86 (s, 1H), 8.87 (s, 1H), 8.25 (s, 1H), 7.59 (s, 1H), 6.73 (d, J=3.2 Hz, 1H), 6.17 (s, 1H), 4.40-4.33 (m, 1H), 3.34-3.33 (m, 1H), 2.42-2.38 (m, 2H), 2.15-2.07 (m, 2H), 2.01-1.97 (m, 2H), 1.61-1.54 (m, 2H). MS (ESI): mass calcd. For C$_{15}$H$_{16}$BBrN$_2$O$_2$ 346.05, m/z. found 347.0 [M+H]$^+$. HPLC: 93.99% (220 nm), 94.36% (254 nm).

Preparation of 3-Ethyl-1-((1R,2s,3S,5s,7s)-5-hy-
droxyadamantan-2-yl)-3,7-dihydro-4H-pyrrolo[3',2':
5,6]pyrido-[3,4-d][1,2,3]diazaborinin-4-ol

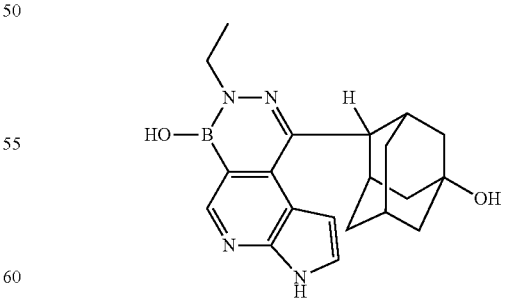

The title compound was prepared by following the experimental procedures in Example 8 above. The analytical data of this compound are shown as following. $^1$H NMR (DMSO-d$_6$+D$_2$O, 400 MHz): δ 9.00 (S, 1H), 7.63-7.61 (m, 1H), 6.81 & 6.76 (two d, J=3.2 Hz, 1H), 3.90-3.85 (m, 2H), 3.60 & 3.51 (two s, 1H), 2.38-2.33 (m, 2H), 2.19-2.16 (m, 2H), 2.00-1.93 (m, 3H), 1.80-1.70 (m, 2H), 1.68-1.50 (m, 2H), 1.35-1.15 (m, 2H), 1.13-1.07 (m, 3H). HPLC purity: 92.08% (220 nm) and 98.11% (254 nm). MS (ESI+): m/z=365.2 [M+H]$^+$.

Preparation of 4-Hydroxy-1-((1R,2s,3S,5s,7s)-5-hydroxyadamantan-2-yl)-4,7-dihydro-3H-pyrrolo[3',2':5,6]-pyrido[3,4-d][1,2,3]diazaborinine-3-carbaldehyde

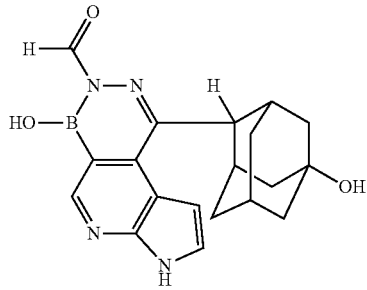 [SMILES: O=CN1N=C(C2C3CC4CC2CC(O)(C4)C3)c2c(cnc3[nH]ccc23)B1O]

The title compound was prepared by following the experimental procedures in Example 8 above. The analytical data of this compound are shown as following. $^1$H NMR (DMSO-d$_6$, 400 MHz): δ 12.33 (s, 1H), 9.37 (s, 1H), 9.08 (s, 1H), 7.77 (s, 1H), 6.82 (d, J=2.8 Hz, 1H), 4.24 (s, 1H), 3.63 (s, 1H), 3.05-2.90 (m, 3H), 2.28-2.22 (m, 2H), 1.98-1.93 (m, 2H), 1.80-1.75 (m, 2H), 1.61 (s, 2H), 1.37-1.34 (m, 2H). HPLC purity: 89.43% (220 nm) and 94.69% (254 nm). MS (ESI+): m/z=365.2 [M+H]$^+$.

Preparation of 3-Cyclopropyl-1-((1R,2s,3S,5s,7s)-5-hydroxyadamantan-2-yl)-3,7-dihydro-4H-pyrrolo-[3',2':5,6]pyrido[3,4-d][1,2,3]diazaborinin-4-ol

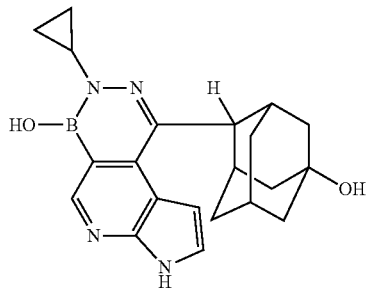 [SMILES: OB1c2cnc3[nH]ccc3c2C(C2C3CC4CC2CC(O)(C4)C3)=NN1C1CC1]

The title compound was prepared by following the experimental procedures in Example 8 above. The analytical data of this compound are shown as following. $^1$H NMR (DMSO-d$_6$+D$_2$O, 400 MHz): δ 9.01 (s, 1H), 7.63-7.60 (m, 1H), 6.79 & 6.74 (two d, 2.8 Hz, 1H), 3.68-3.67 (m, 1H), 3.59 & 3.50 (two s, 1H), 2.33-2.26 (m, 2H), 2.10-1.85 (m, 4H), 1.78-1.62 (m, 2H), 1.62-1.45 (m, 3H), 1.39-1.24 (m, 2H), 1.00-0.92 (m, 2H), 0.83-0.81 (m, 2H). HPLC purity: 91.02% (220 nm) and 96.35% (254 nm). MS (ESI+): m/z=377.2 [M+H]$^+$.

Synthetic Examples

Following the general and specific synthetic teaching of the present disclosure, the following examples may be made, some of which have been synthesized and characterized as set forth herein:

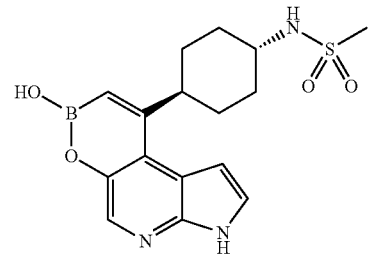

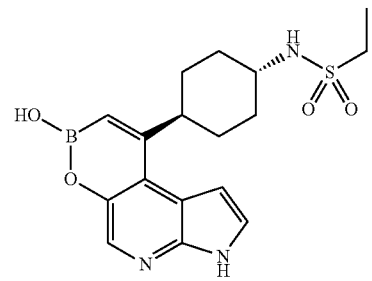

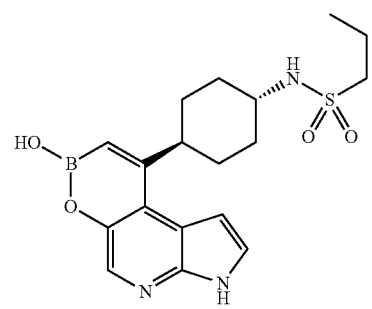

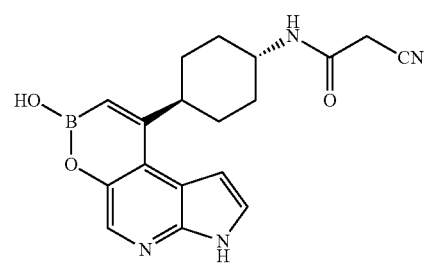

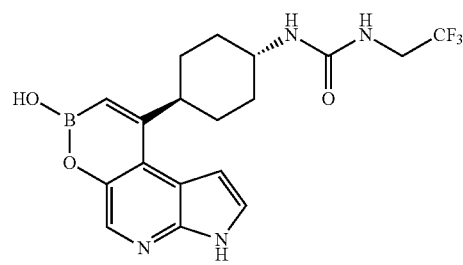

241
-continued
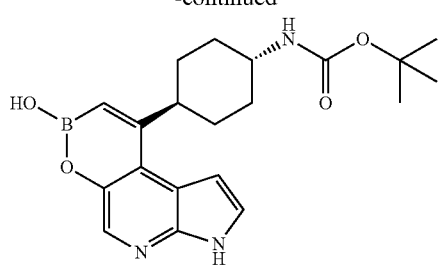
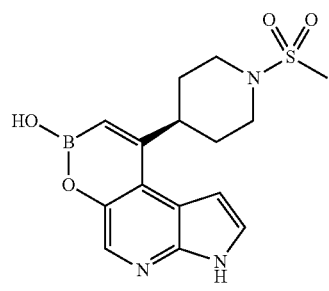
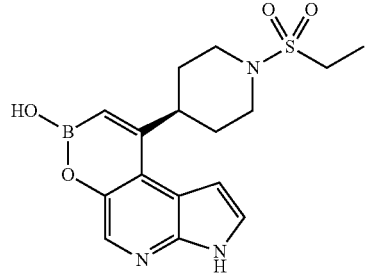
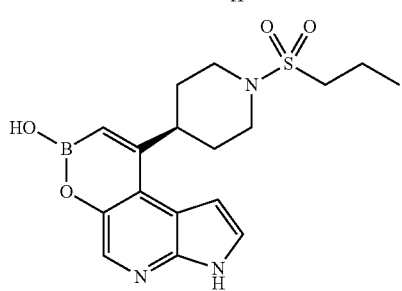
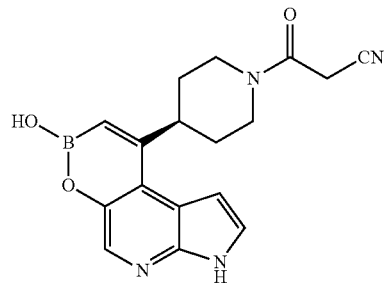
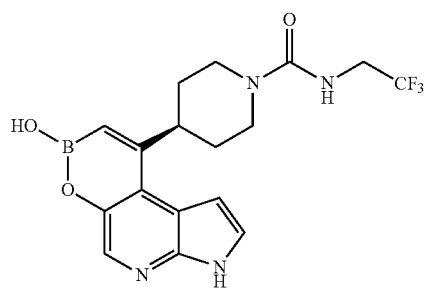
242
-continued
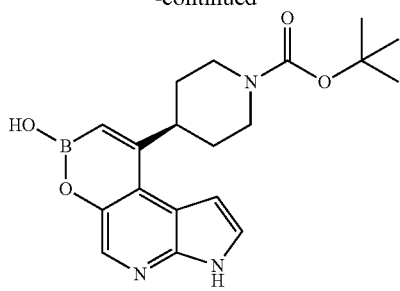
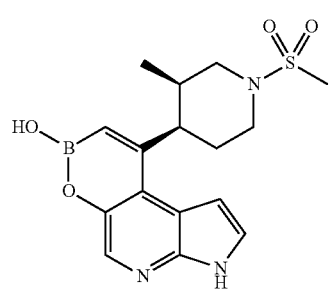
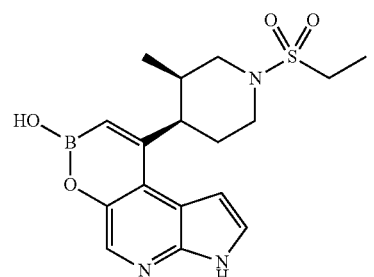
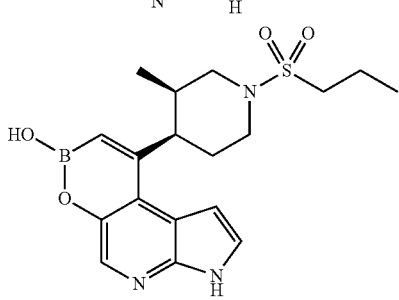
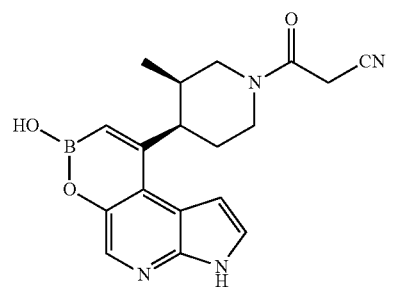
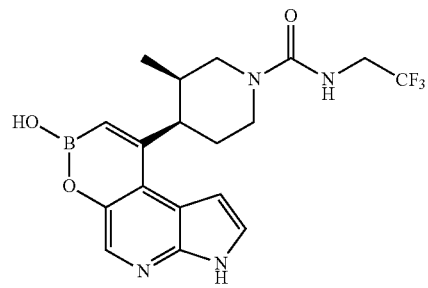

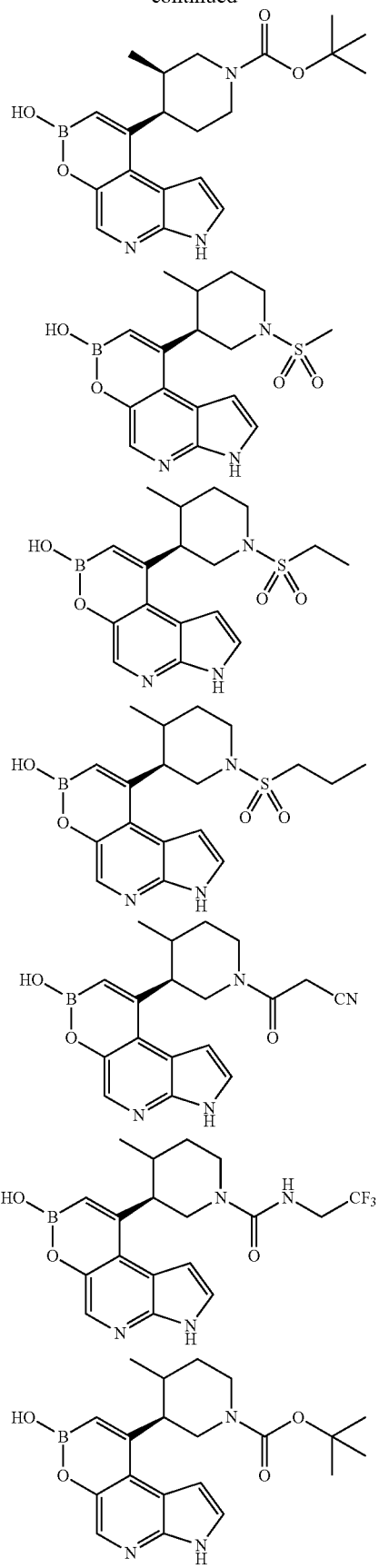
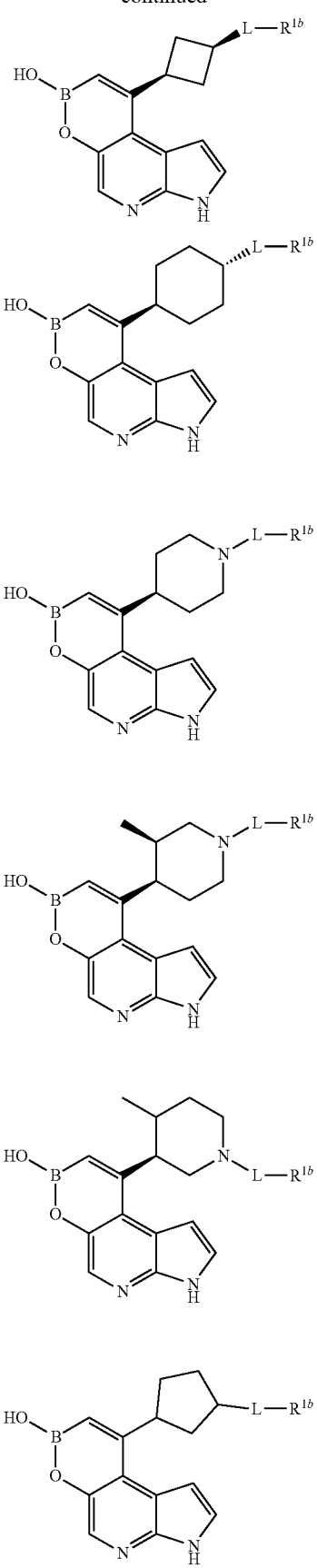

245
-continued
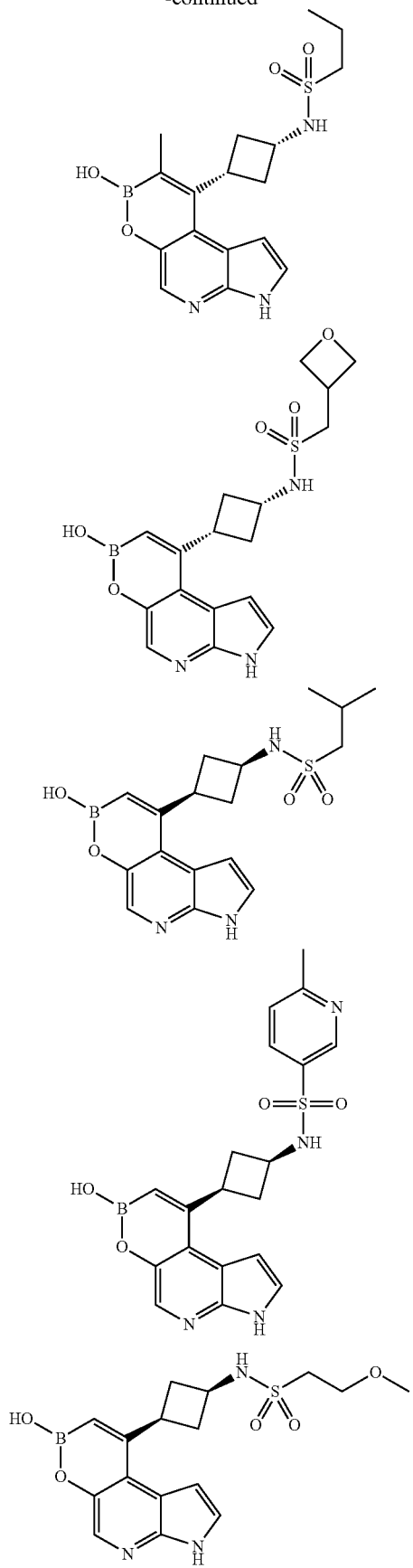
246
-continued
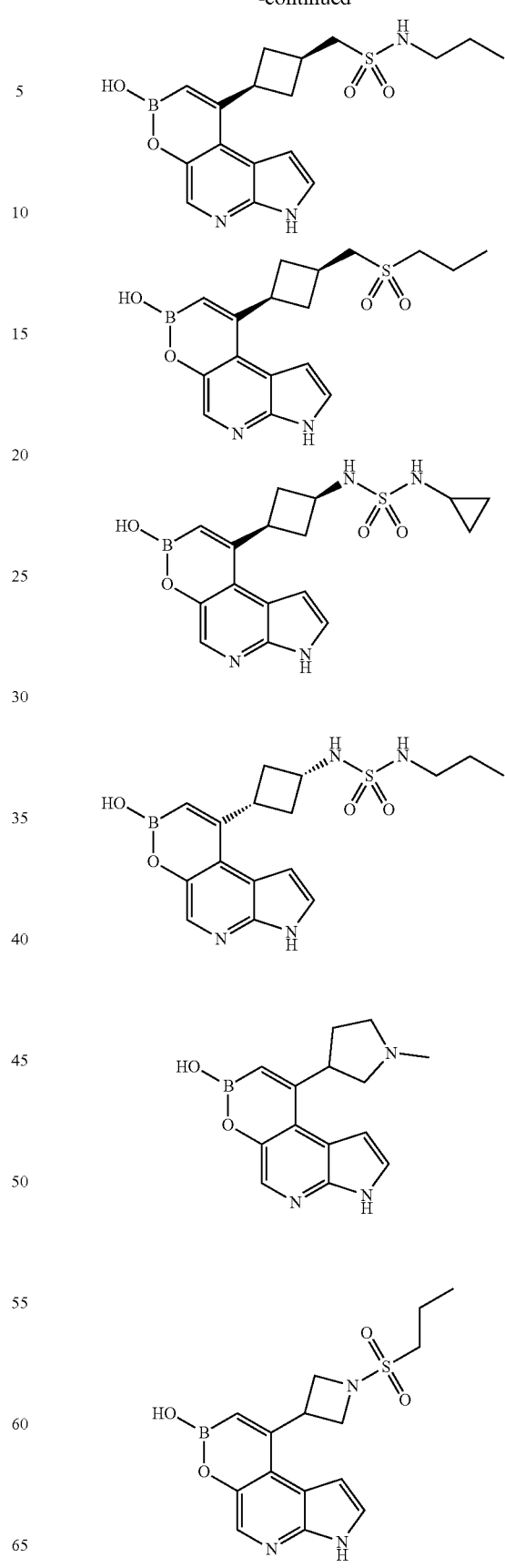

247
-continued
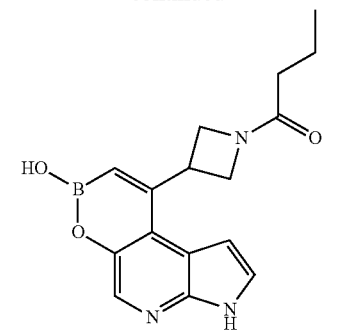
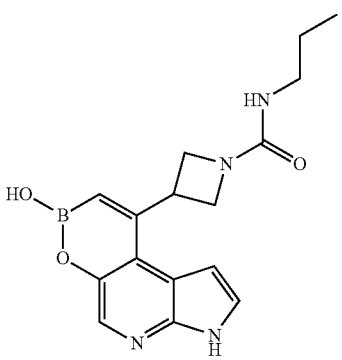
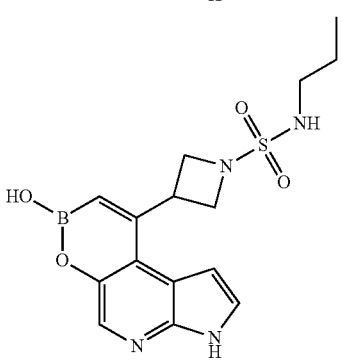
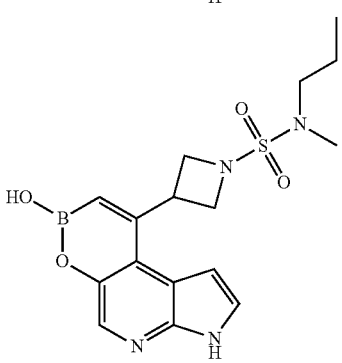
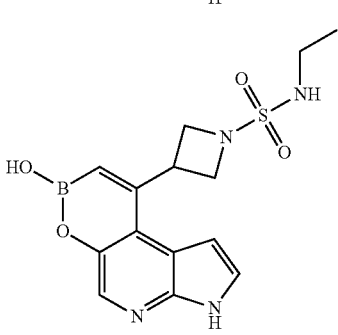
248
-continued
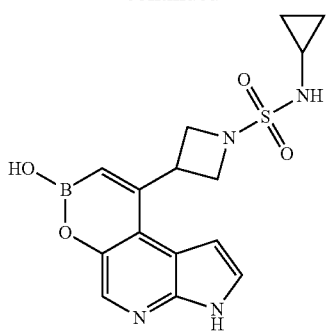
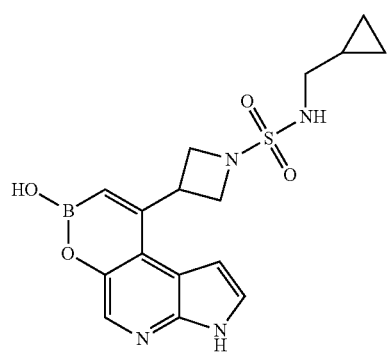
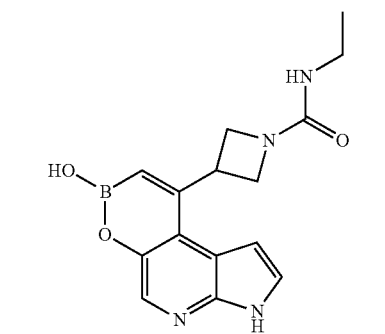
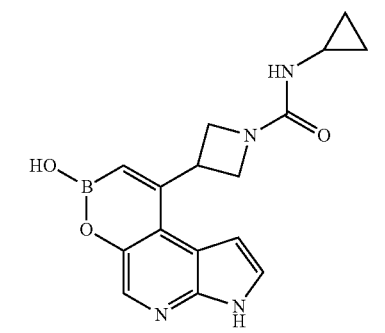
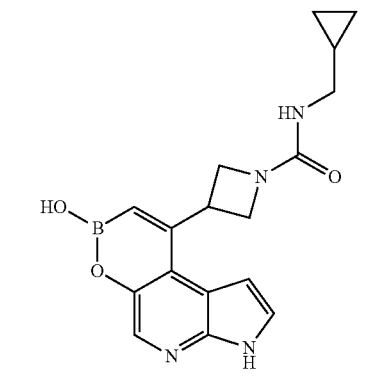

-continued

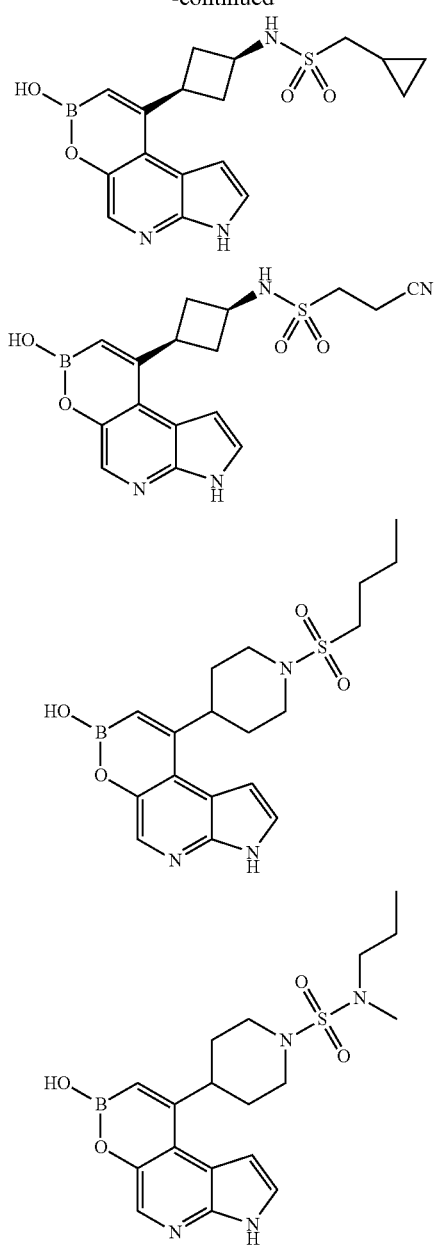

-continued

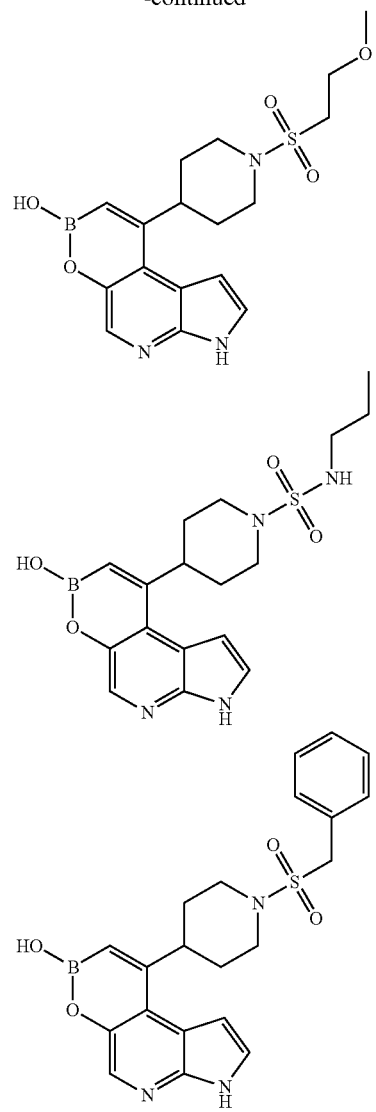

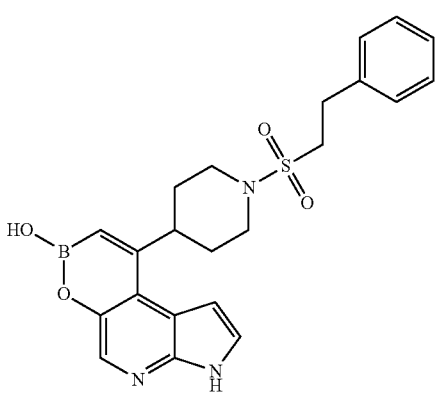

Biological Examples

The compounds of the present disclosure were tested in multiple assays. The results are compiled in FIG. 1 and FIG. 2.

Biochemical Kinase Assay Protocol (JAK, TYK2)

Reagent: Base Reaction buffer; 20 mM Hepes (pH 7.5), 10 mM MgCl2, 1 mM EGTA, 0.02% Brij™ 35, 0.02 mg/ml BSA, 0.1 mM Na3VO4, 2 mM DTT, 1% DMSO, where required cofactors are added individually to each kinase reaction.

Reaction Procedure:
1. Prepare indicated substrate in freshly prepared Base Reaction Buffer
2. Deliver any required cofactors to the substrate solution above
3. Deliver indicated kinase into the substrate solution and gently mix
4. Deliver compounds in DMSO into the kinase reaction mixture by Acoustic technology (Echo550; nanoliter range), incubate for 20 minutes at room temperature 5. Deliver 33P-ATP into the reaction mixture to initiate the reaction.
6. Incubate kinase reaction for 2 hours at room temperature
7. Reactions are spotted onto P81 ion exchange paper
8. Detect kinase activity by filter-binding method.

Prophetic Cytokine inhibition Assay Protocol for IL-4 and IL-13

The test compounds are solubilized in DMSO, then diluted to make appropriate stocks for use in the assay, and diluted in culture medium to 20× assay concentrations. PBMC's are plated and allowed to settle for 1 hour at 37° C., 5% CO2. Test compounds and controls are added to the settled PBMC's and incubated for 1 hour at 37° C., 5% CO2. The PBMC's are then be treated with PHA (10 pg/mL) and incubated for 24 hours at 37° C., 5% CO2. DMSO is used as a positive control and dexamethasone (100 nM) was used as a reference inhibitor control. After the main incubation, cell culture supernatants are harvested and assayed for the cytokines listed above, using standard Luminex protocols. Levels of cytokine induction are interpolated from standard curves using 5-parameter non-linear regression analyses, where y=(A+((B−A)/(1+(((B−E)/(E−A))*((x/C)^D))))). The interpolated data is normalized to DMSO controls and analyzed to determine IC50 values using 4-parameter non-linear regression analyses, where y=(A+((B−A)/(1+((C/x)^D))))

Cytokine Function assay protocols for IL-4/pSTAT6 and GM-CSF/pSTAT5:

GM-CSF/pSTAT5:

Whole blood from a healthy donor was lysed to remove red blood cells. Cells were plated onto a 96w plate. Compound was added and incubated for 1 hour (at 37° C.). After 1 hour, cells were stimulated with GM-CSF for 15 minutes. Cells were fixed and stained with anti pSTAT5 antibody. After staining, cells were read on Beckman-Coulter Cyto-FLEX.

IL-4/pSTAT6:

PBMC from a healthy donor was plated onto a 96w plate. Compound was added and incubated for 1 hour (at 37° C.). After 1 hour, cells were stimulated with IL-4 for 15 minutes. Cells were fixed and stained with anti-pSTAT6 antibody. After staining, cells were read on Beckman-Coulter Cyto-FLEX.

Figure 2:
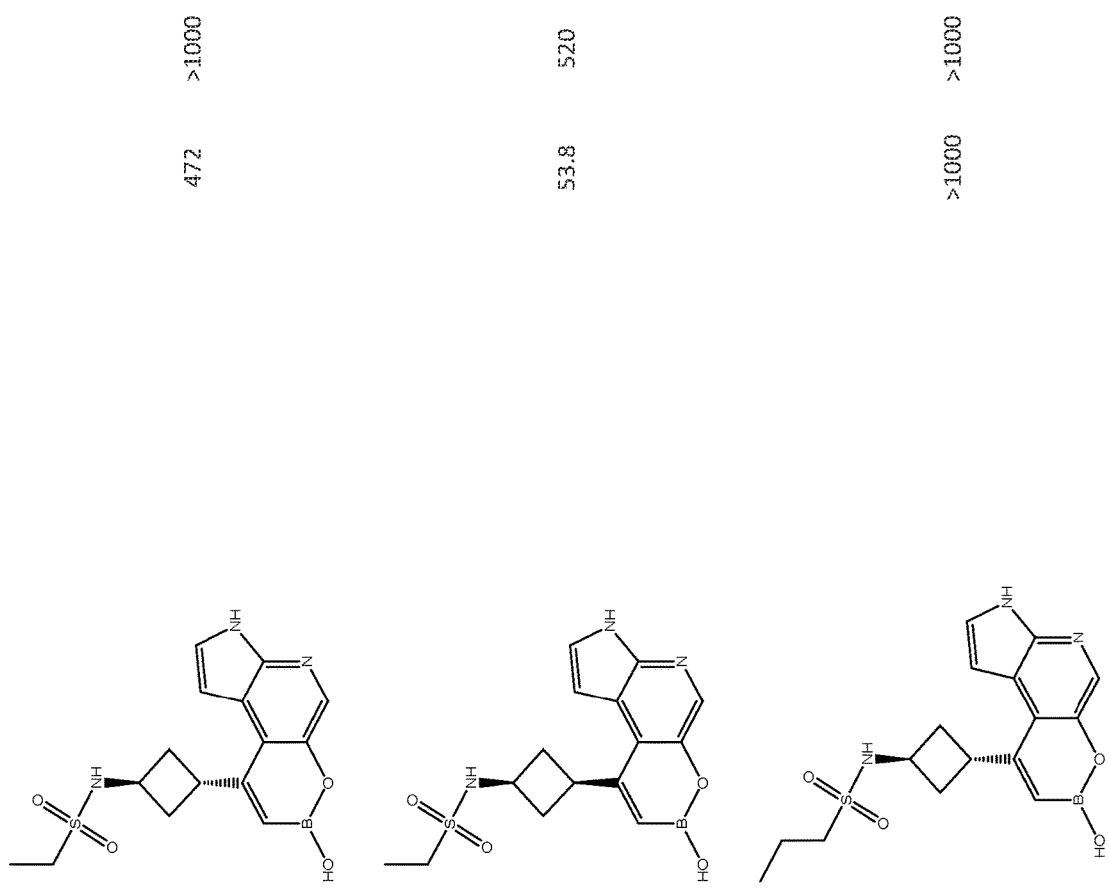
FIG. 2 represents a table of examples of biological activity of the compounds of the present disclosure.
Figure 2:
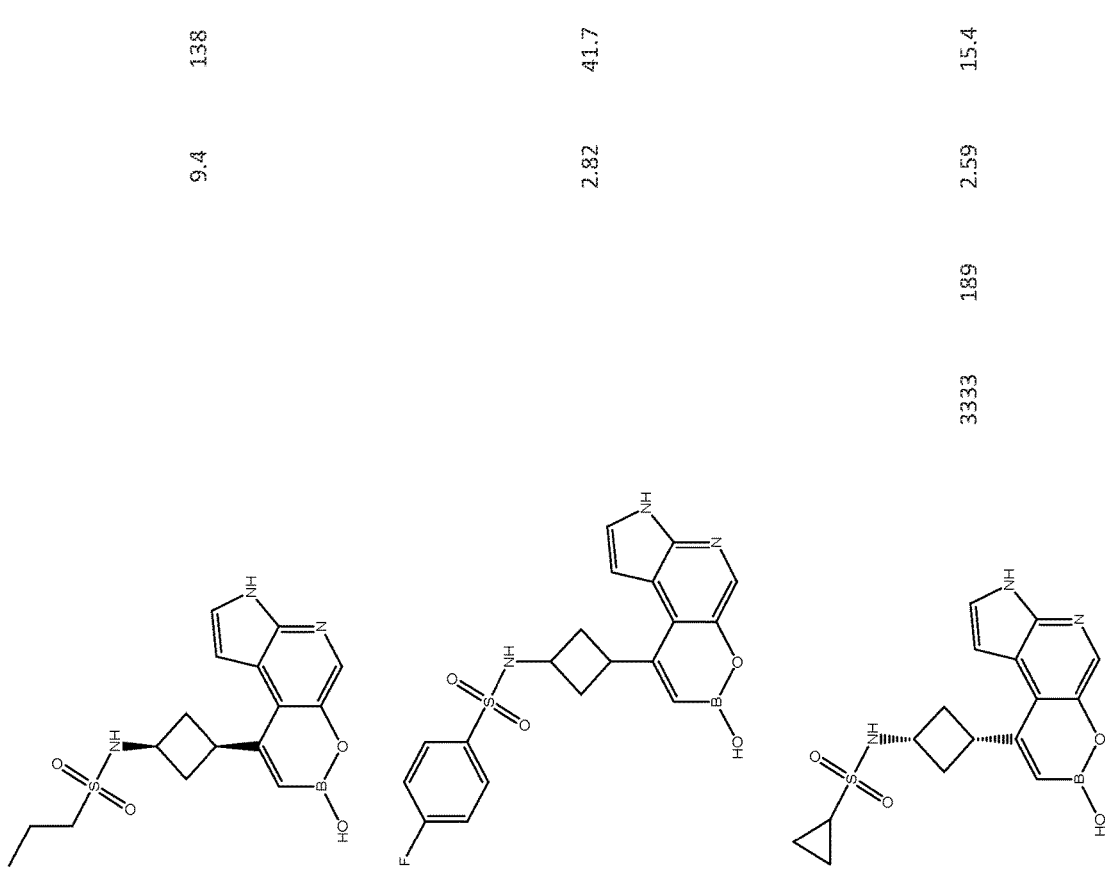
Figure 2:
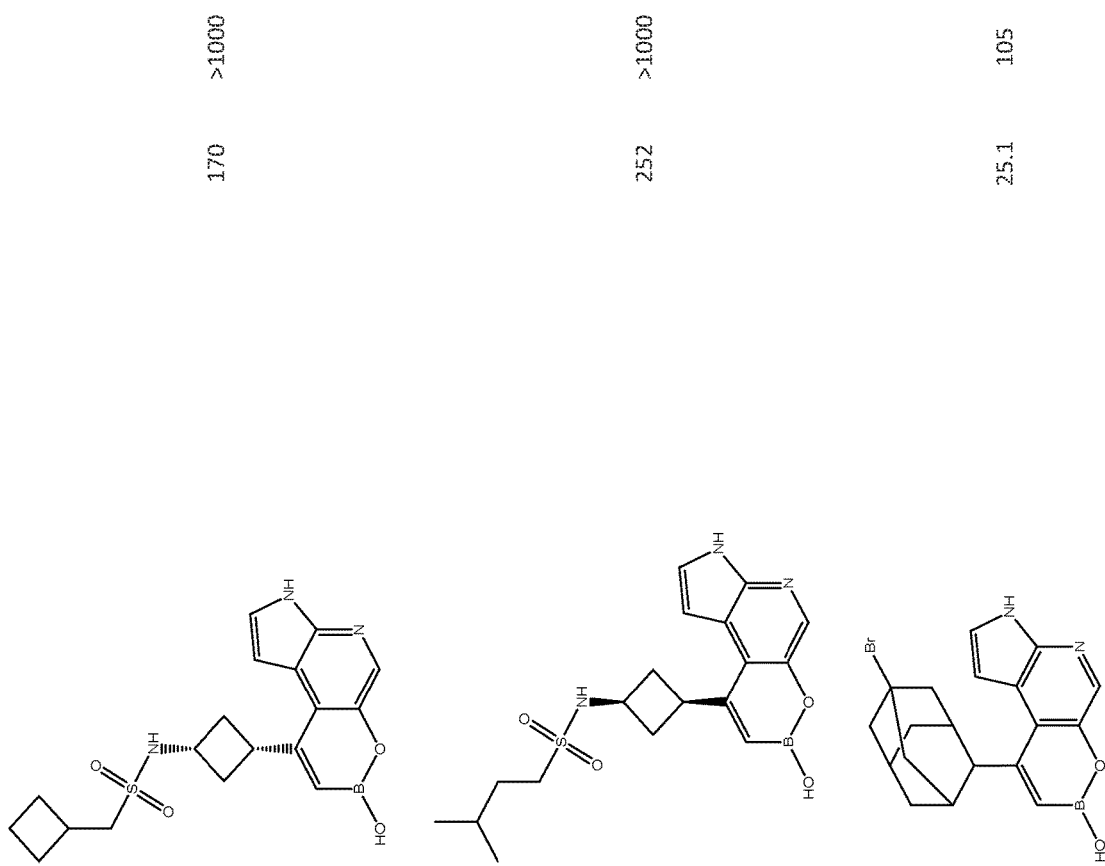
Figure 2:
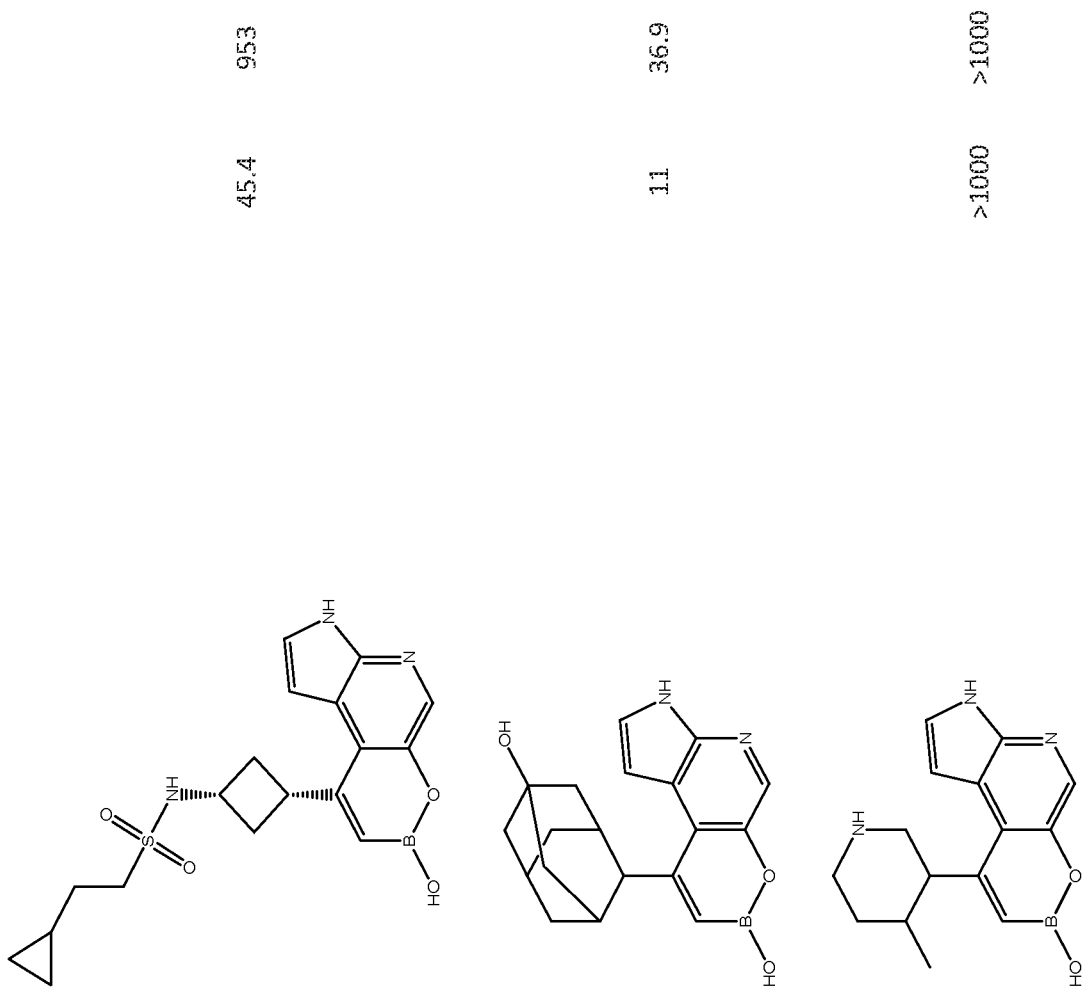
Figure 2:
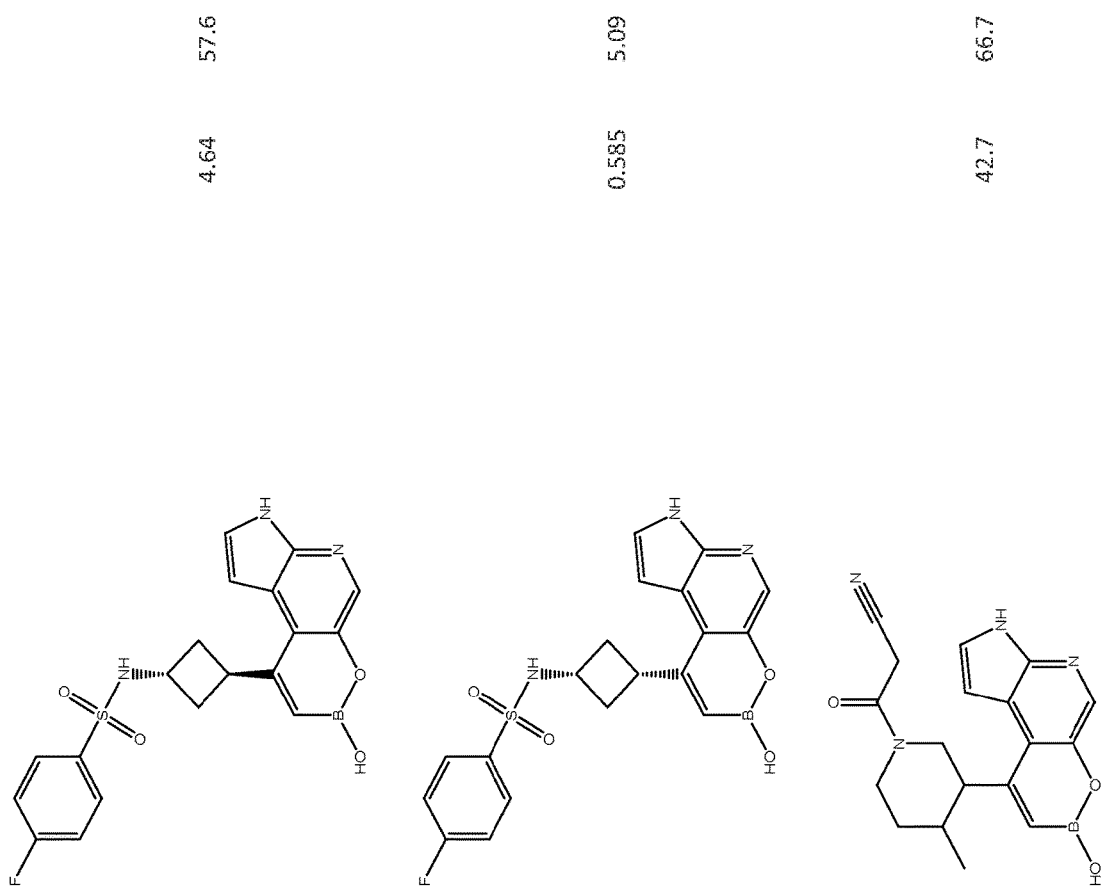
Figure 2:
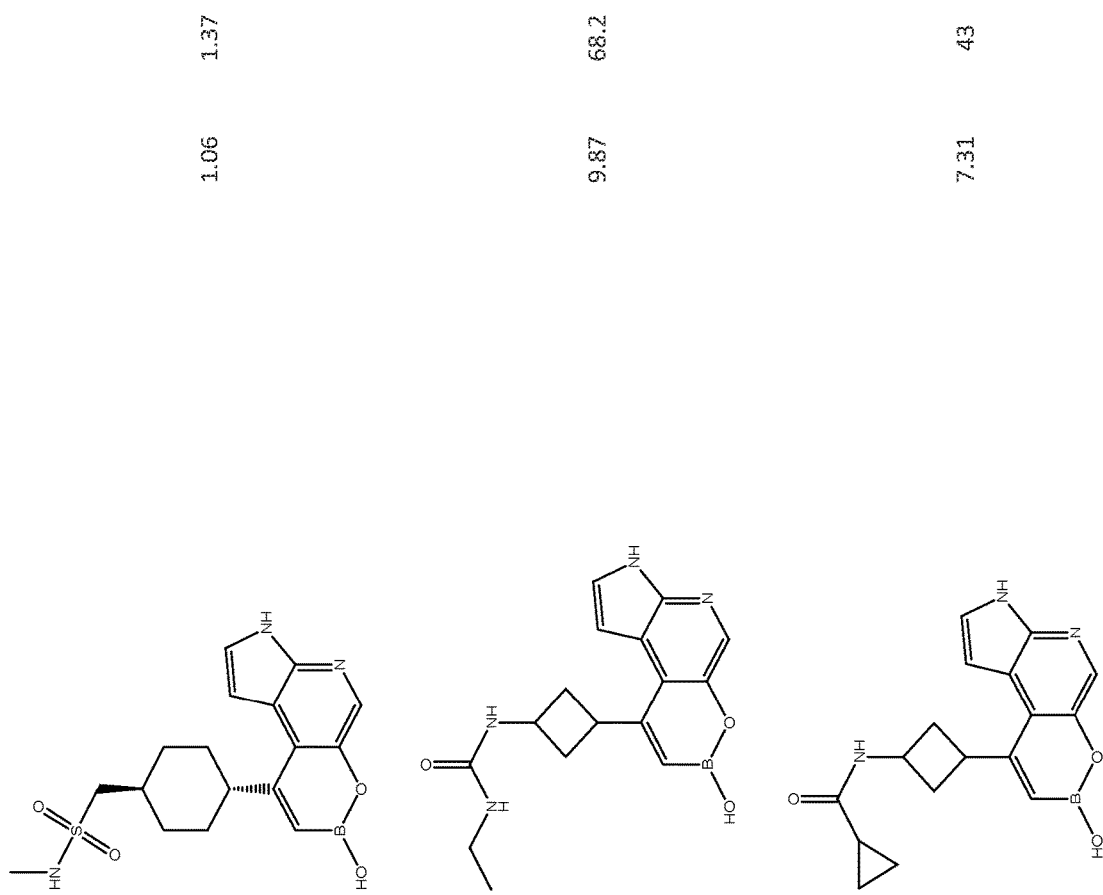
Figure 2:
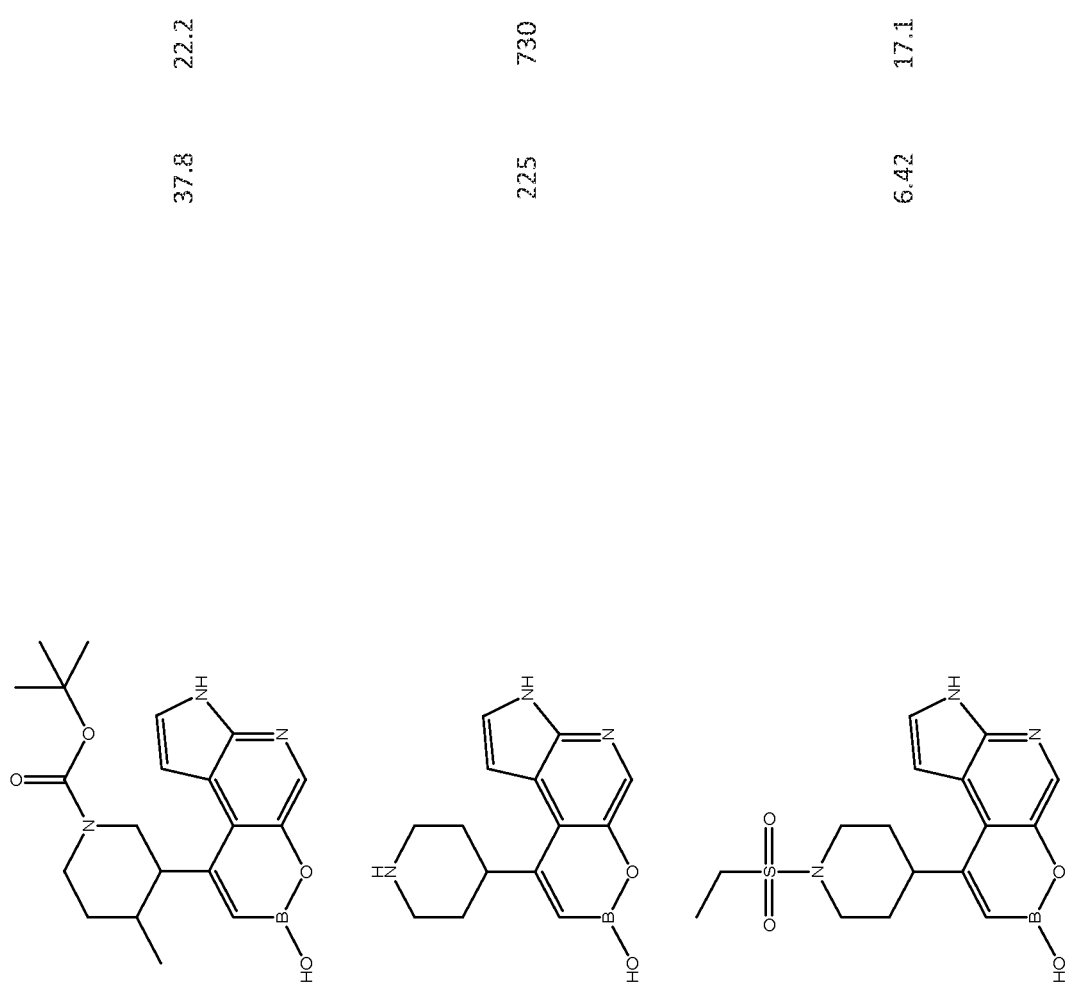
Figure 2:
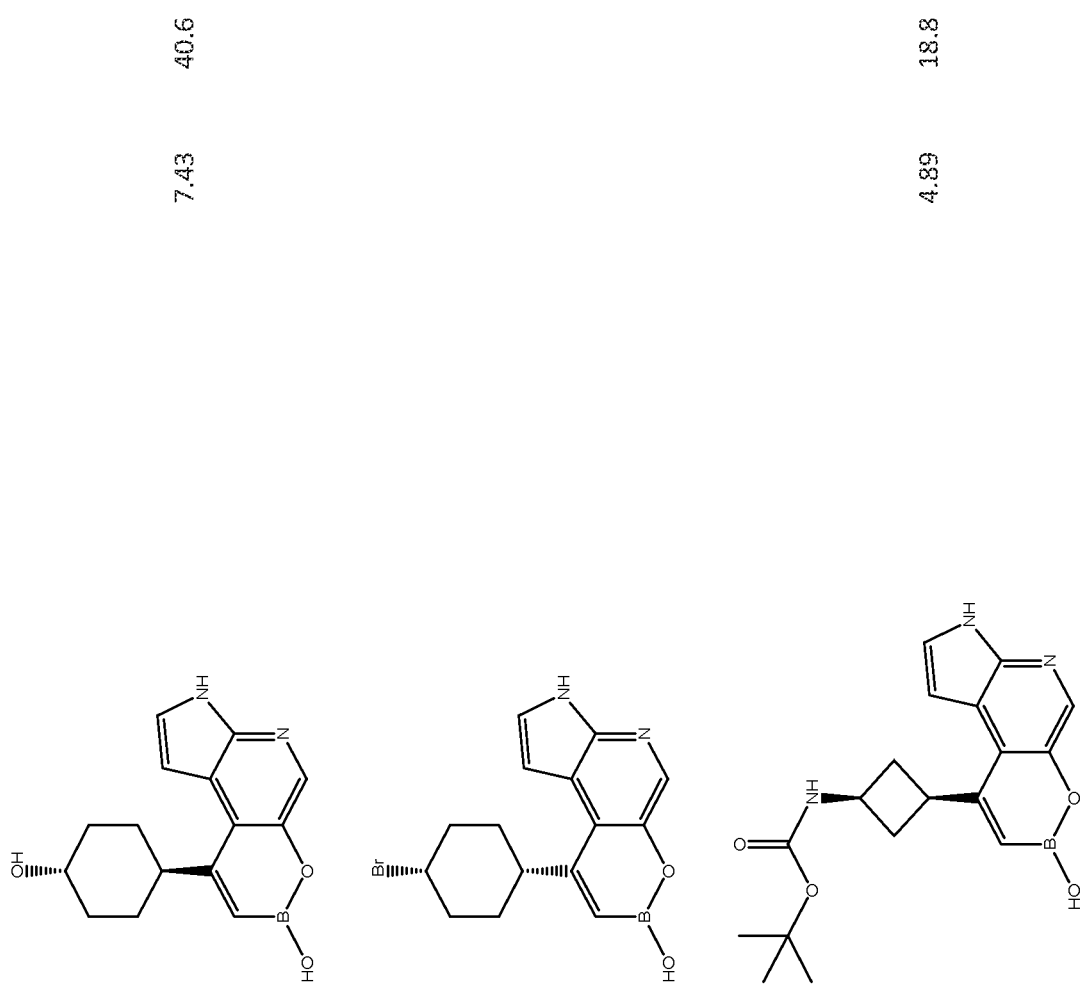
Figure 2:
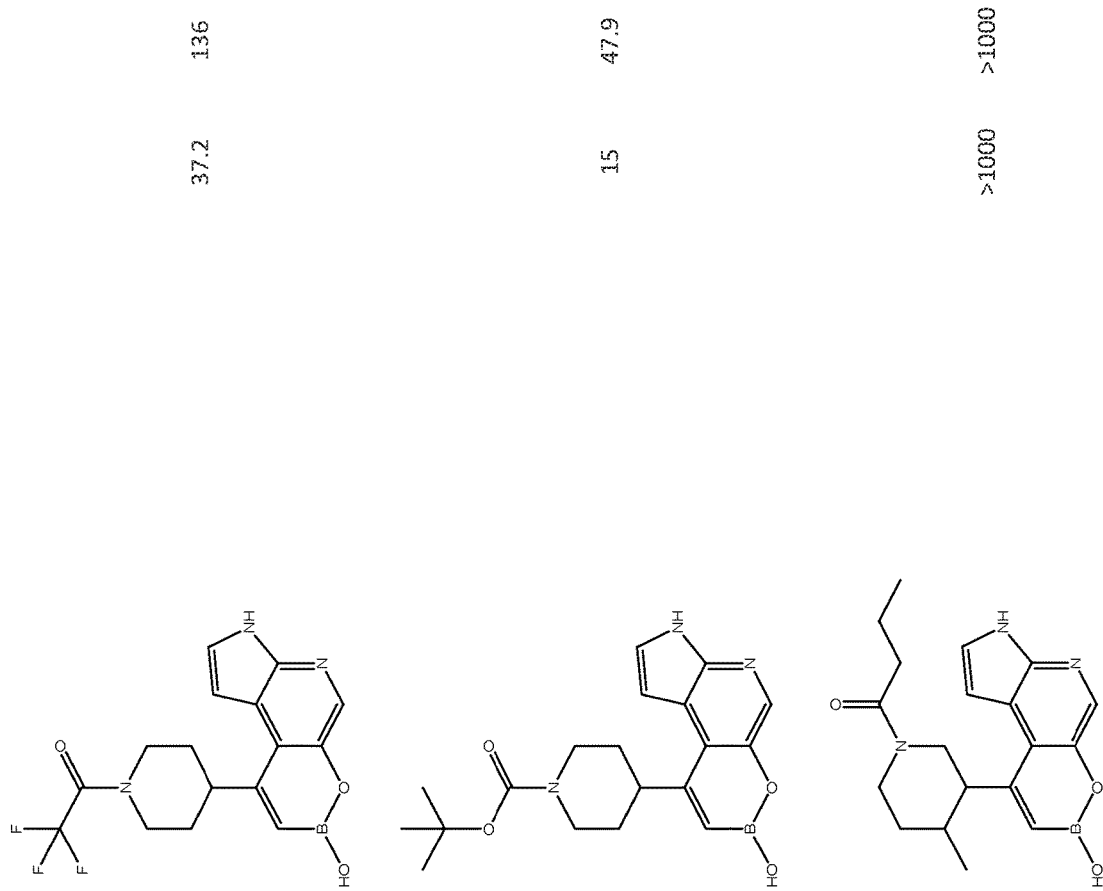
Figure 2:
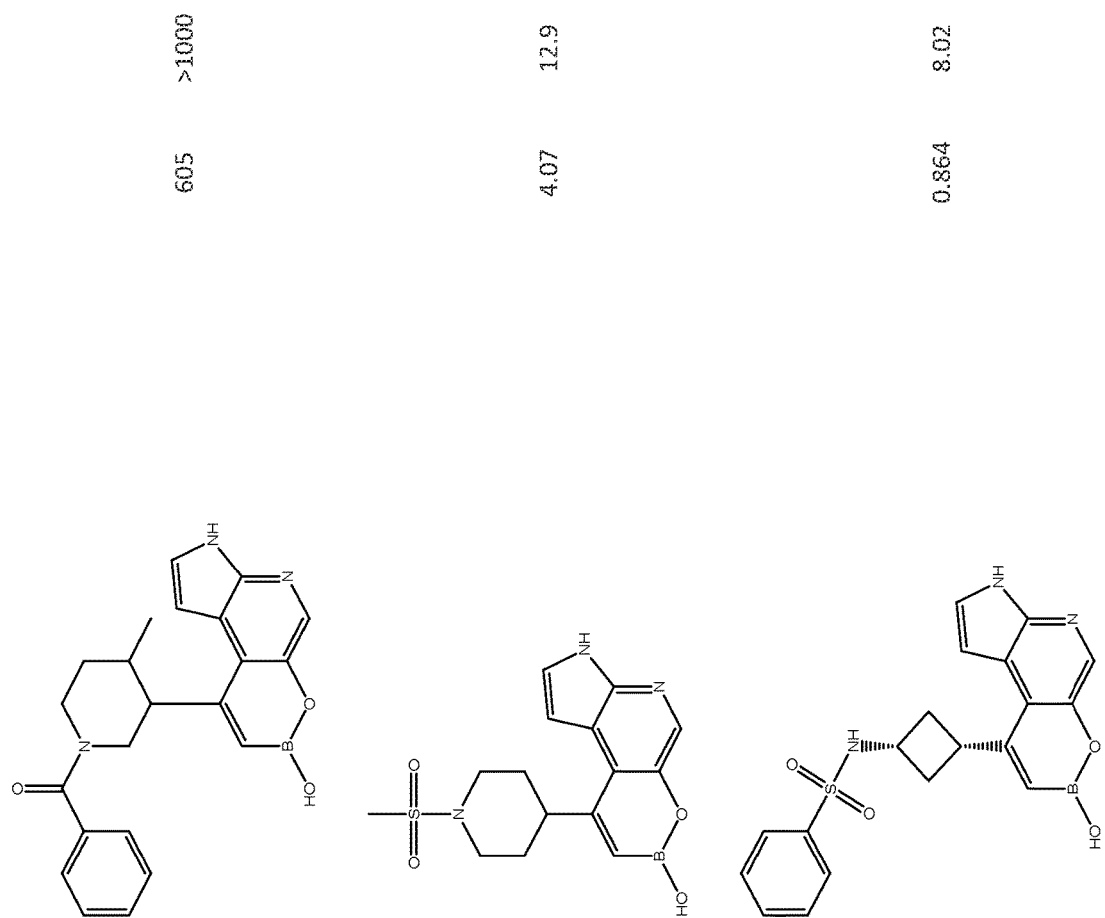
Figure 2:
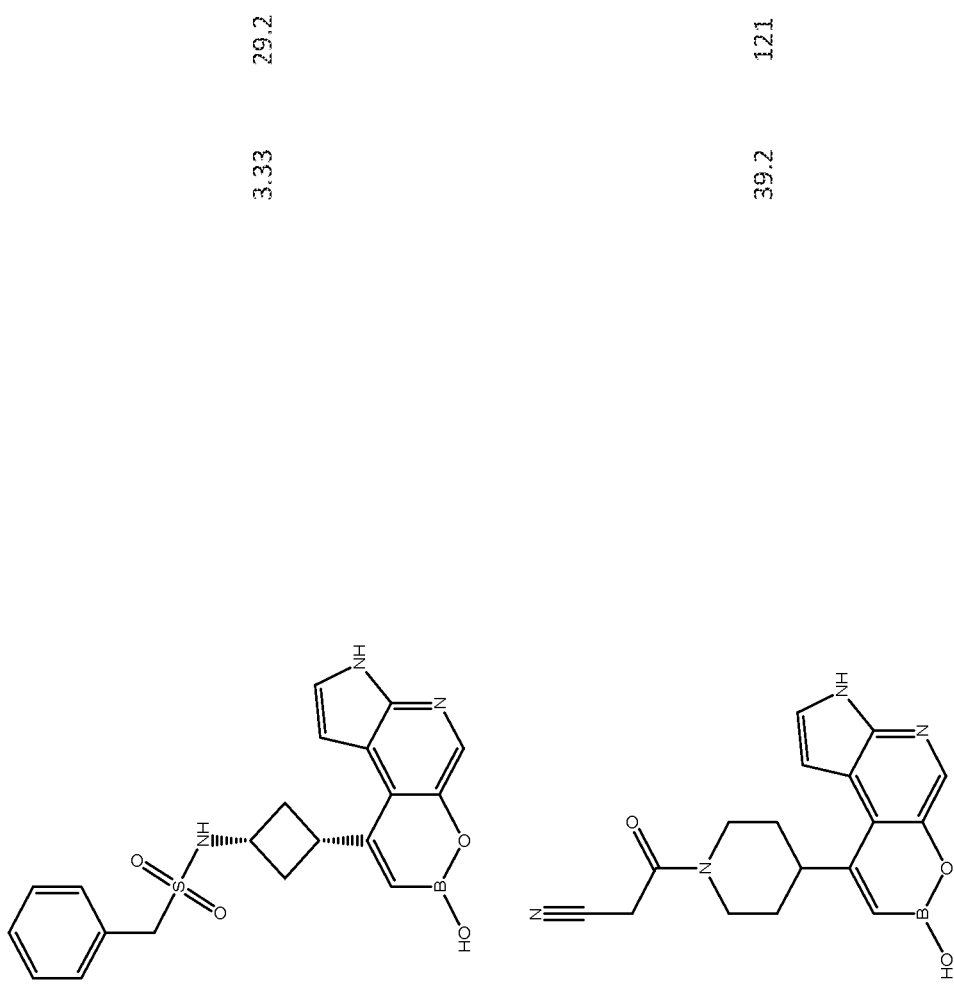
Figure 2:
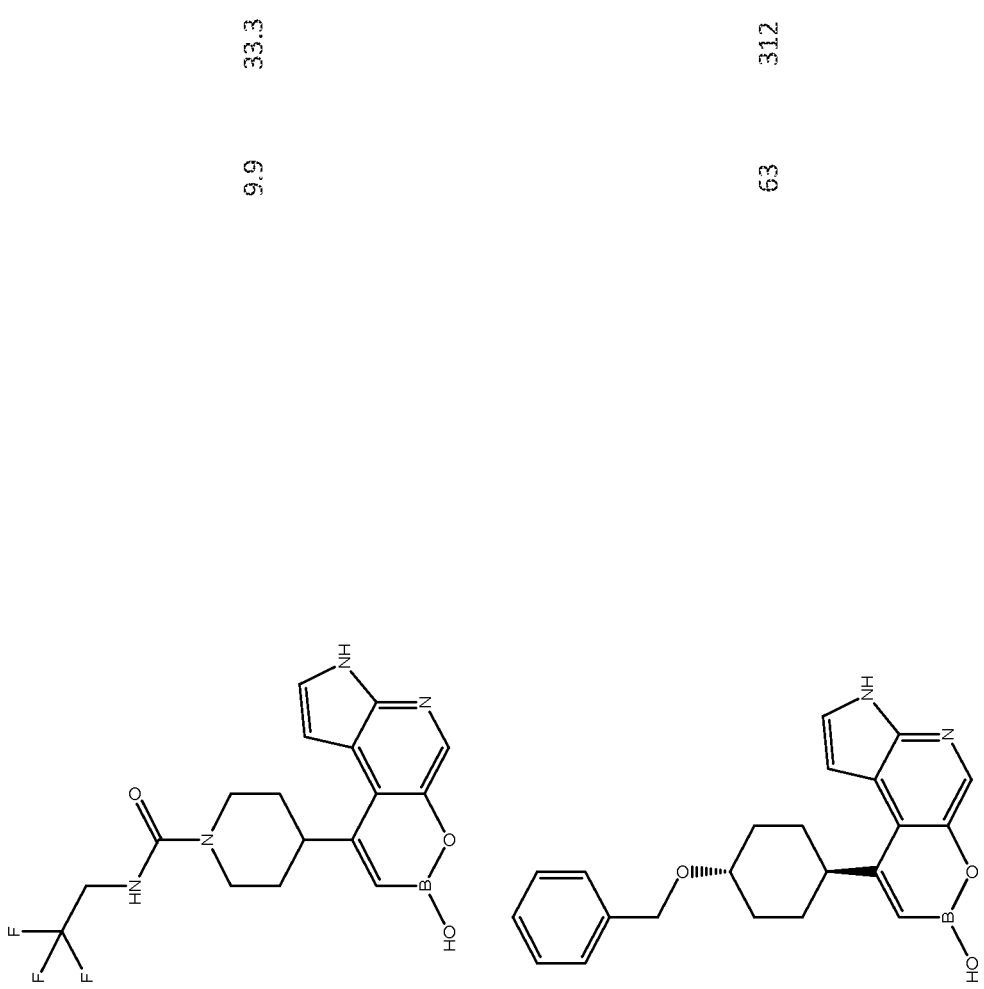
Figure 2:
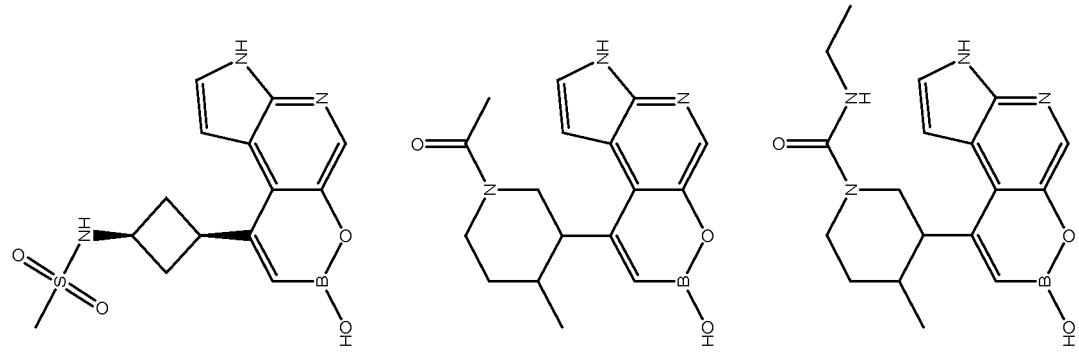
Figure 2:
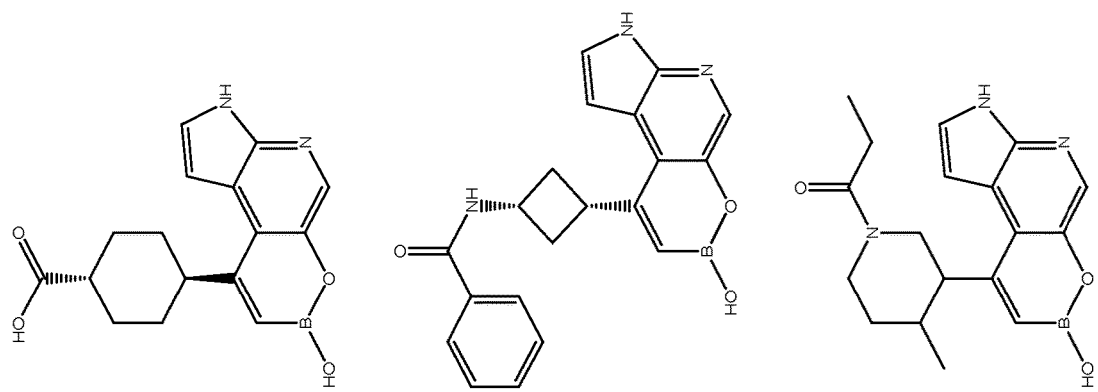
Figure 2:
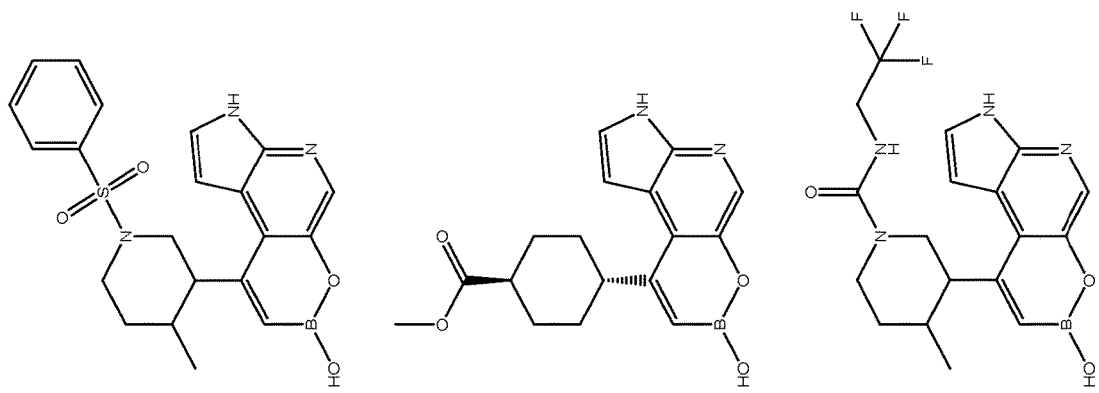
Figure 2:
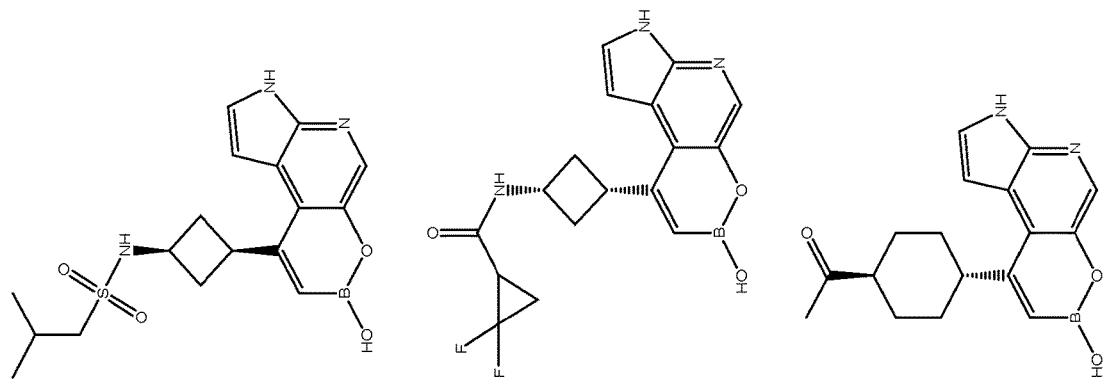
Figure 2:
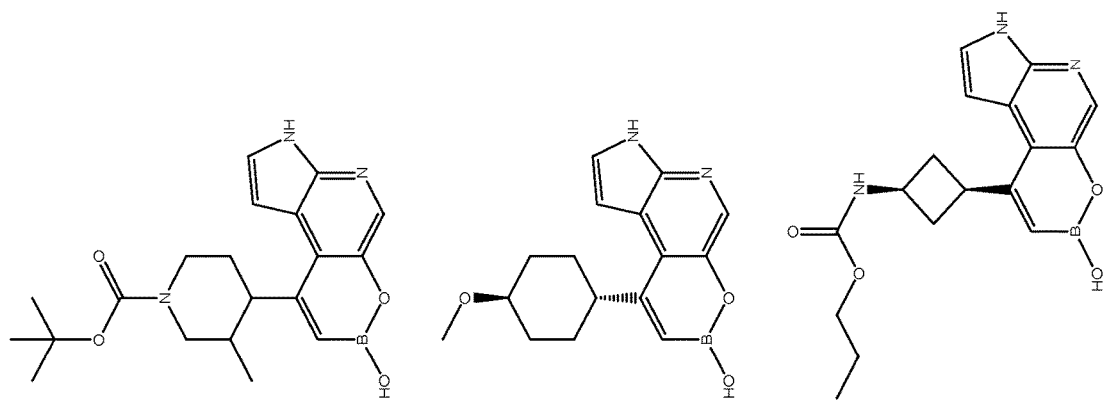
Figure 2:
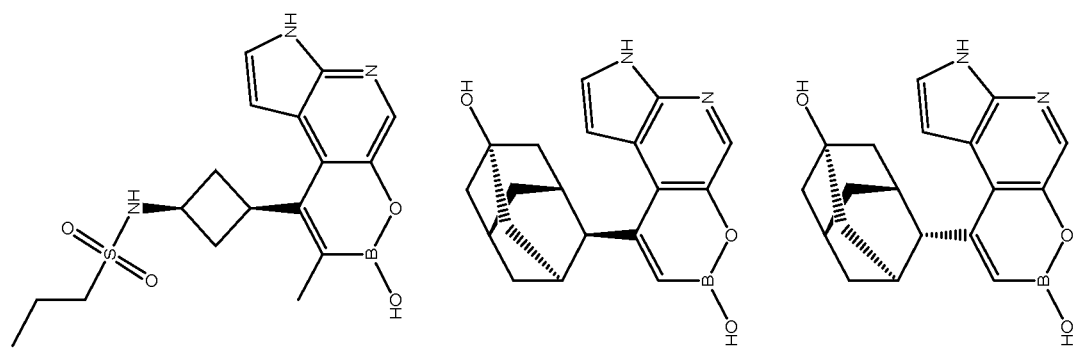
Figure 2:
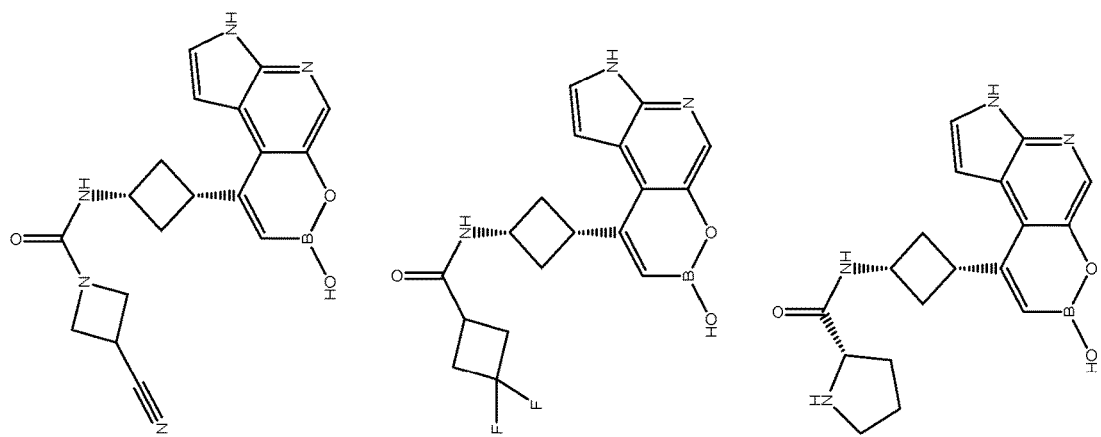
Figure 2:
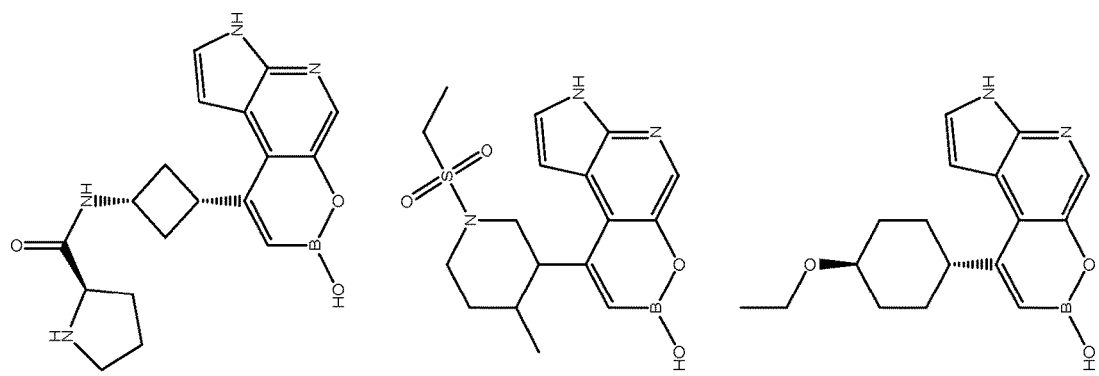

The results are provided in FIGS. 1 and 2. As demonstrated, the compounds of the present disclosure are potent JAK inhibitors. As such, the compounds may be used for the treatment or control of inflammation, auto-immune diseases, cancer, and other disorders and indications where modulation of JAK would be desirable.

Activity of Diazaborane Derivatives (Compounds of Formula (I))

Compounds of the present Formula (I) were tested in the Biochemical Kinase Assay Protocol. The results are provided in FIG. 1. One embodiment of compounds of Formula (I) the present disclosure with preferred activity include:

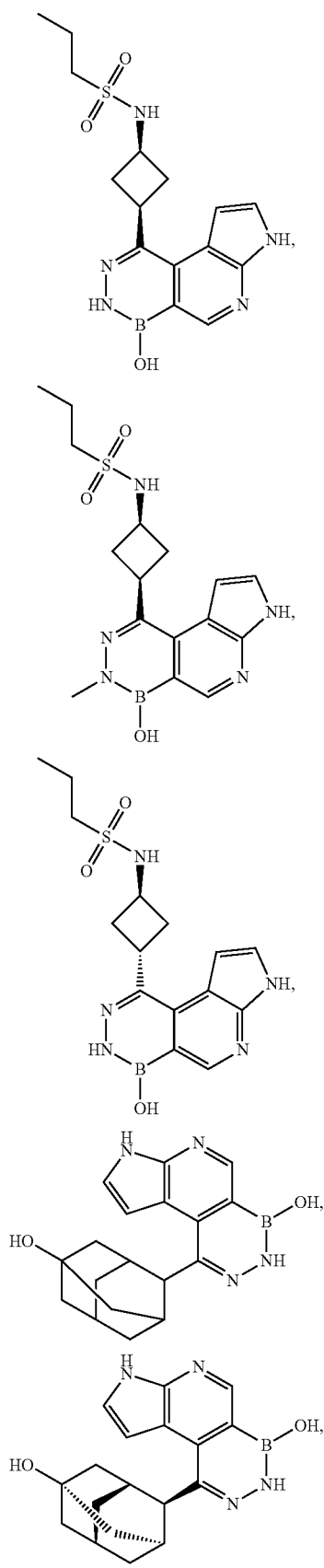

-continued
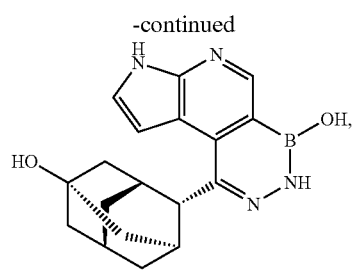
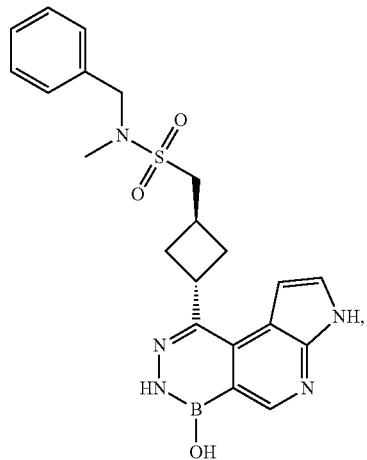
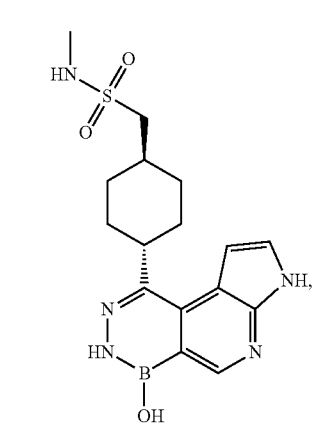
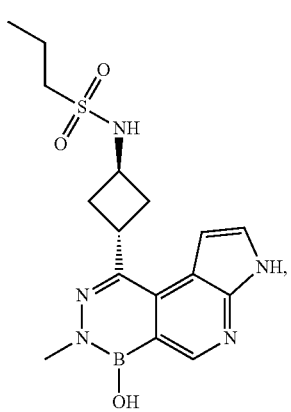
-continued
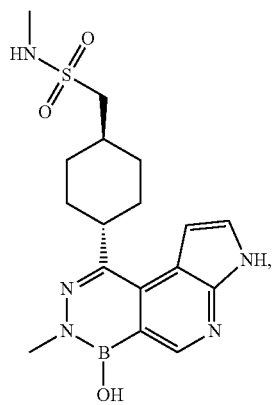
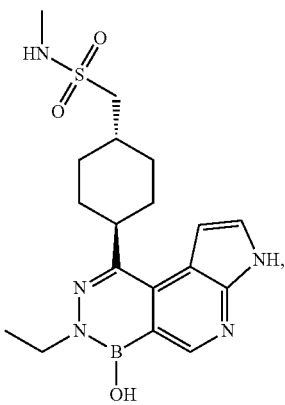
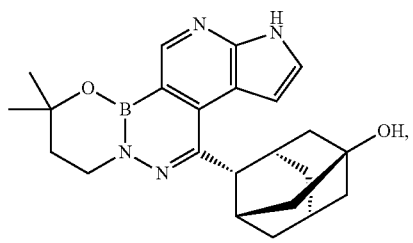
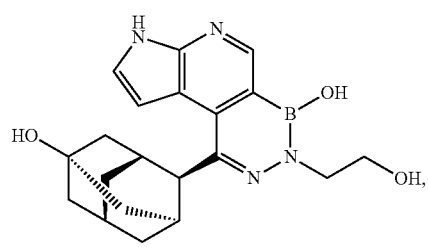
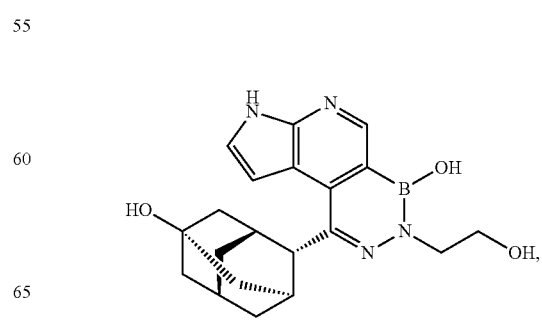

255
-continued
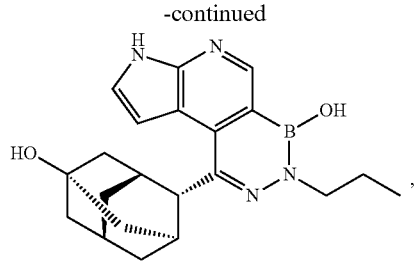
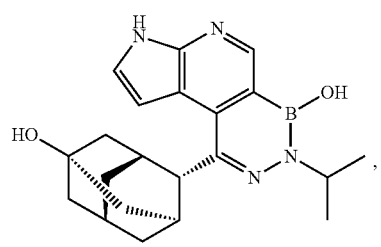
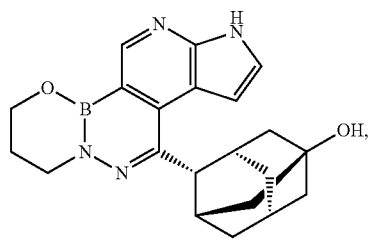
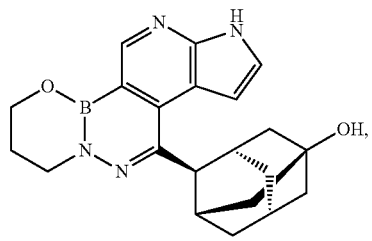
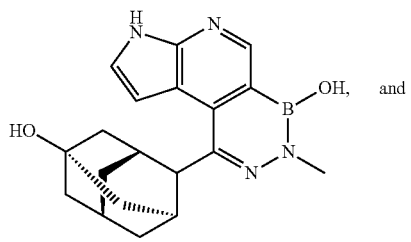 and
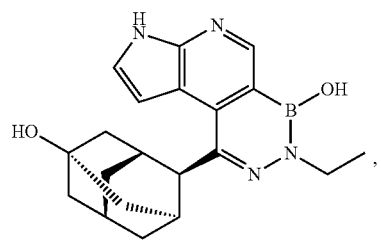
Activity of Oxoborininol Derivatives (Compounds of Formula (II))
Compounds of the present Formula (I) were tested in the Biochemical Kinase Assay Protocol. The results are provided in FIG. 2. One embodiment of compounds of Formula (II) the present disclosure with preferred activity include:
256
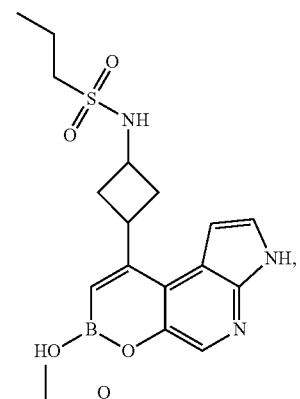
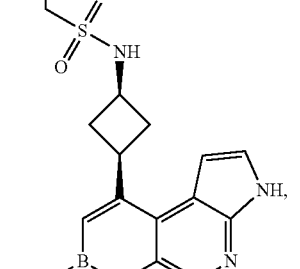
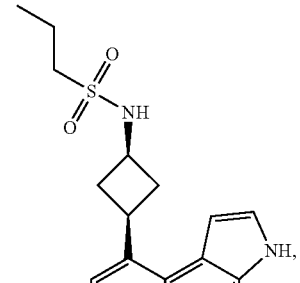
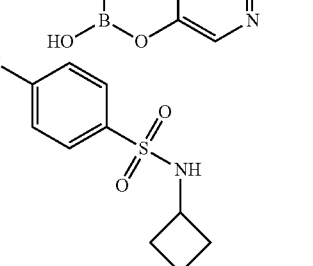
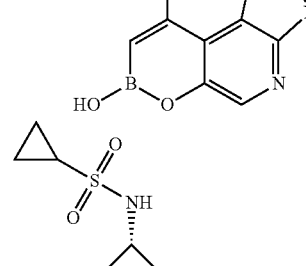
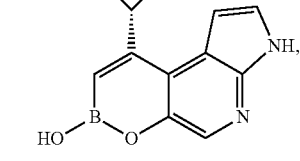

257
-continued
258
-continued
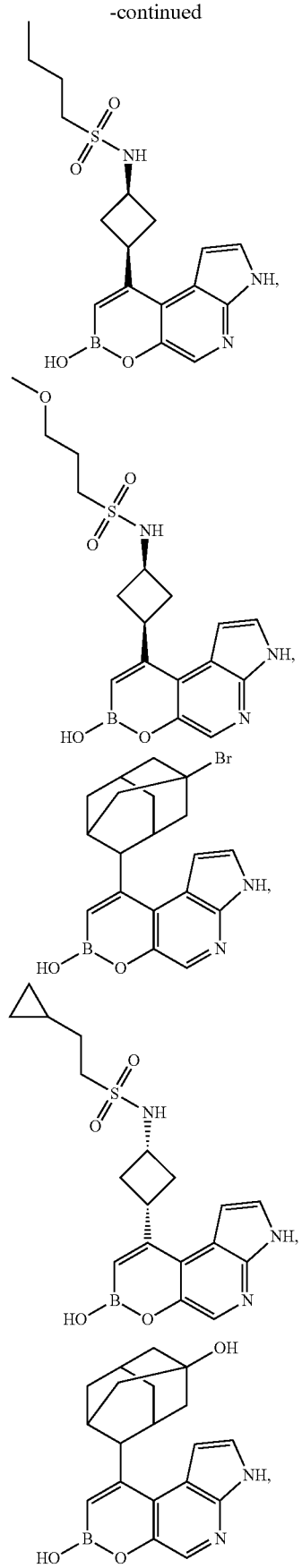
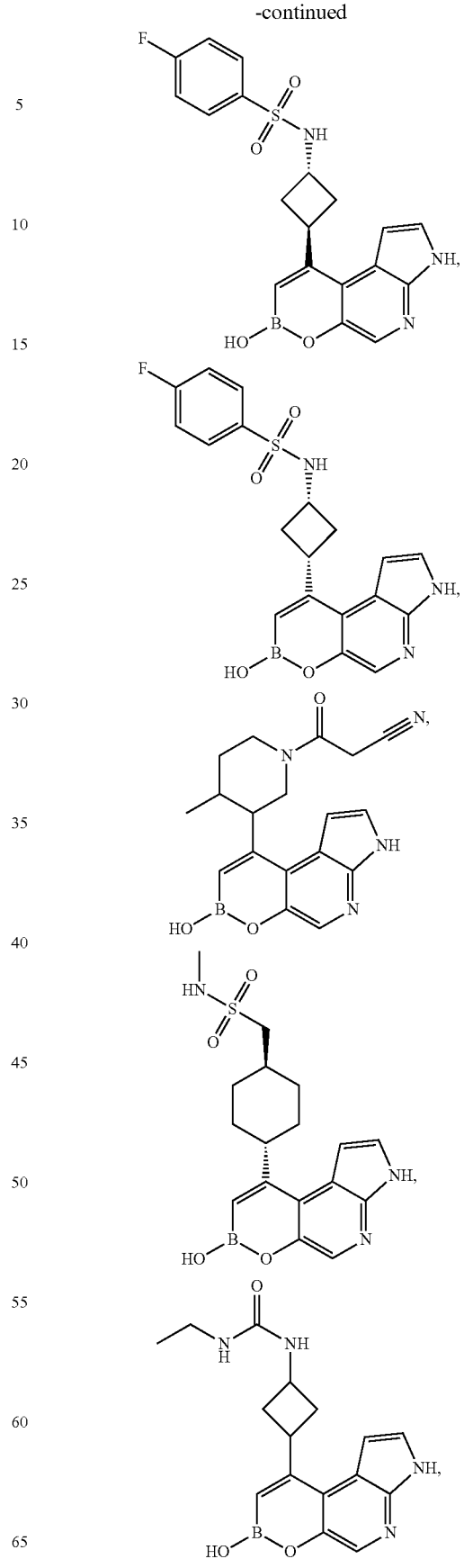

259
-continued
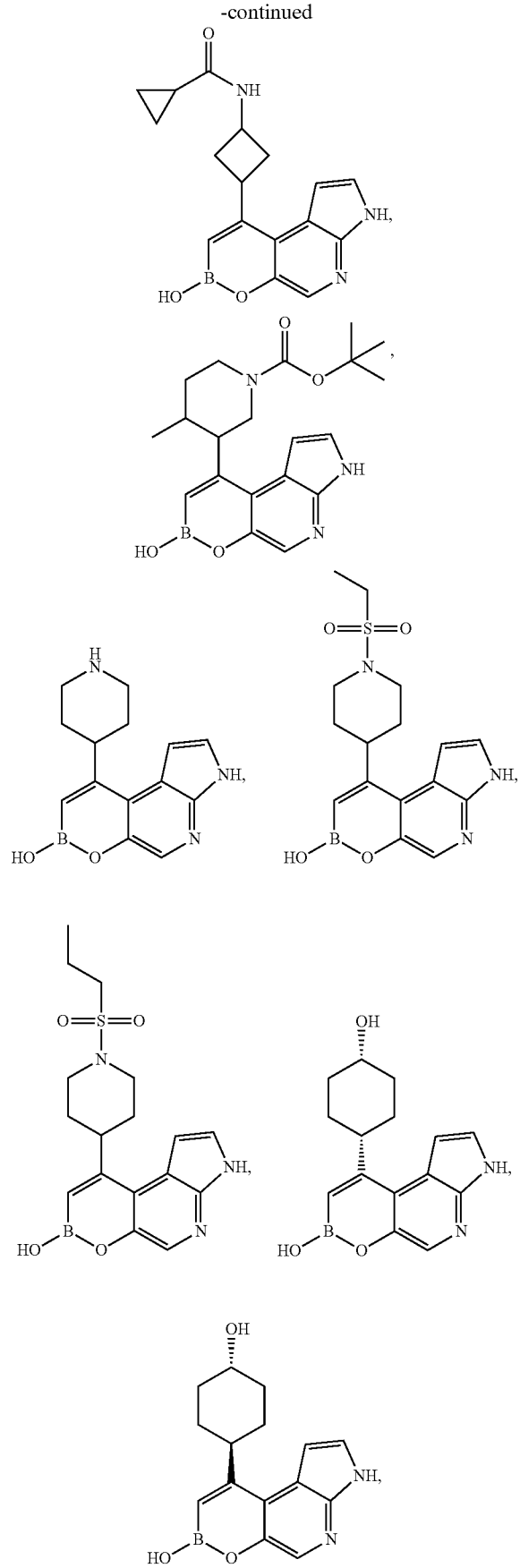
260
-continued
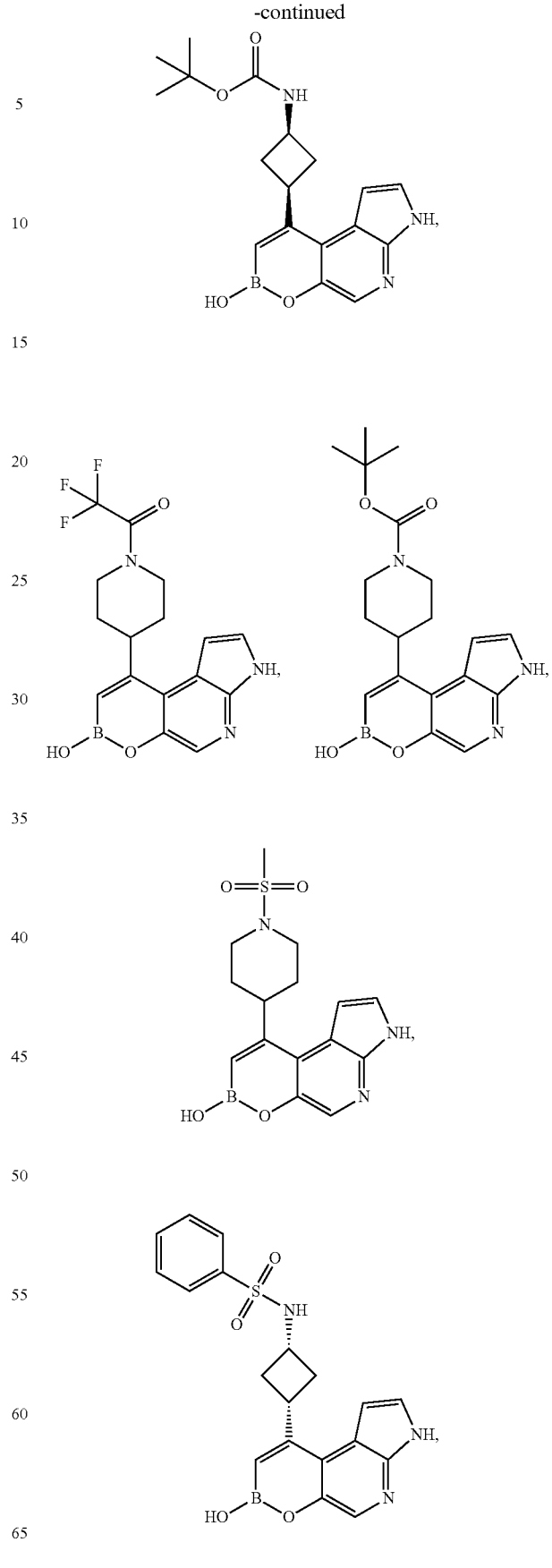

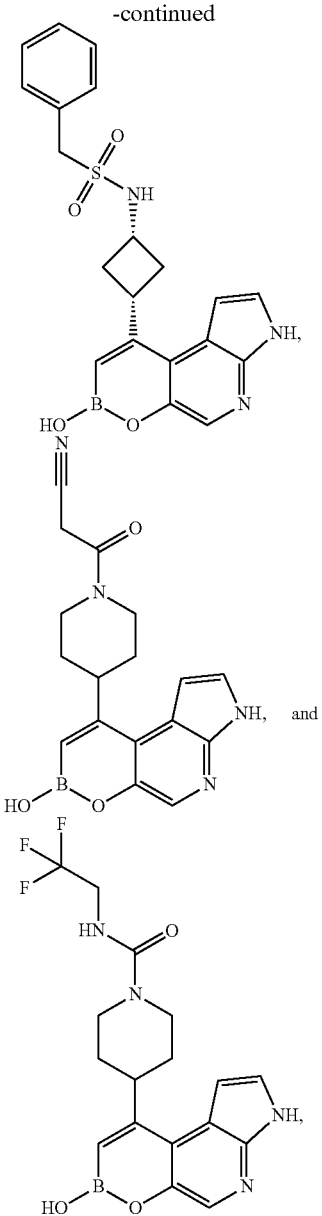

All publications, patents, and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

That which is claimed is:

1. A compound of formula (II):

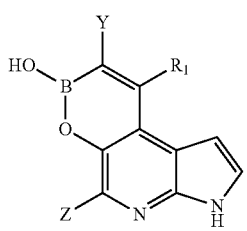

wherein:
Z is selected from the group consisting of hydrogen, fluorine, and $CH_3$;
Y is selected from the group consisting of hydrogen, halogen, $C_{1-6}$ alkyl, $C_{2-6}$ alkenyl, $C_{2-6}$ alkynyl, $C_{3-6}$ cycloalkyl, and $(CH_2)_3OH$, or Y and the oxygen atom depicted as OH together form a 6 to 8 membered ring;
each $R^1$ independently is selected from the group consisting of unsubstituted or substituted:
(i) $C_1$-$C_{15}$ alkyl,
(ii) $C_{2-15}$ alkenyl,
(iii) $C_{2-15}$ alkynyl,
(iv) $C_1$-$C_{15}$ alkyl, wherein one or more carbon atom, including the carbon atom attached to the depicted ring, is replaced with a heteroatom selected from O, N, S, or Si, and wherein each N, S, or Si may be oxidized, and wherein the N may be quarternized,
(v) $C_{2-15}$ alkenyl, wherein one or more carbon atom, including the carbon atom attached to the depicted ring, is replaced with a heteroatom selected from O, N, S, or Si, and wherein each N, S, or Si may be oxidized, and wherein the N may be quarternized,
(vi) $C_{2-15}$ alkynyl, wherein one or more carbon atom, including the carbon atom attached to the depicted ring, is replaced with a heteroatom selected from O, N, S, or Si, and wherein each N, S, or Si may be oxidized, and wherein the N may be quarternized,
(vii) $C_{3-15}$ cycloalkyl,
(viii) heterocyclyl,
(ix) aryl, and
(x) heteroaryl,
or a stereoisomer, enantiomer, or tautomer thereof, or a veterinary or pharmaceutically acceptable salt thereof.

2. The compound of claim 1, wherein Y is hydrogen.

3. The compound of claim 1, wherein Z is hydrogen.

4. The compound of claim 1, wherein Y is hydrogen and Z is hydrogen.

5. The compound of claim 1, wherein $R^1$ is (a) unsubstituted or substituted $C_{3-15}$ cycloalkyl, or (b) unsubstituted or substituted heterocyclyl.

6. The compound of claim 5, wherein $R^1$ individually is unsubstituted or substituted cyclopropyl, cyclobutyl, cyclopentyl, cyclohexyl, bicyclo[1.1.1]pentyl, adamantyl, or heterocyclyl.

7. The compound of claim 5 wherein each $R^1$ is a substituted 3- to 6-membered heterocyclyl, wherein at least one heteroatom is a N.

8. The compound of claim 5, wherein $R^1$ is pyrrolidinyl, piperidinyl, or tetrahydropyranyl.

9. The compound of claim 1, wherein each $R^1$ individually is substituted with one or more substituent selected from the group consisting of halogen, haloalkyl, R', OR', OH, SH, SR', $NO_2$, CN, C(O)R', C(O)(alkyl substituted with one or more of halogen, haloalkyl, $NH_2$, OH, SH, CN, and $NO_2$), C(O)OR', OC(O)R', CON(R')$_2$, OC(O)N(R')$_2$, $NH_2$, NHR', N(R')$_2$, NHCOR', NHCOH, NHCONH$_2$, NHCONHR', NHCON(R')$_2$, NR'CON(R')$_2$, NR'COR', NR'COH, NHCO$_2$H, NHCO$_2$R', NR'CO$_2$R', NHC(S)NH$_2$, NHC(S)NHR', NHC(S)N(R')$_2$, NR'C(S)N(R')$_2$, CO$_2$R', CO$_2$H, CHO, CONH$_2$, CONHR', CON(R')$_2$, S(O)$_2$H, S(O)$_2$R', SO$_2$NH$_2$, S(O)H, S(O)R', SO$_2$NHR', SO$_2$N(R')$_2$, NHS(O)$_2$H, NR'S(O)$_2$H, NHS(O)$_2$R', NR'S(O)$_2$R', N(R')SO$_2$N(R')$_2$, and =O, wherein each of the preceding may be linked to $R^1$ through an alkylene linker, $(CH_2)_x$, where x is 1, 2, or 3, and wherein each R' is the same or different and is hydrogen, alkyl, alkenyl, alkynyl, haloalkyl, haloalkenyl, haloalkynyl, hydroxyalkyl, hydroxyalkenyl, hydroxyalkynyl, cycloalkyl, cycloalkyl substituted by one or more halogens, cycloalkylalkyl, aryl, aryl substituted with one or more halogen, arylalkyl, heterocyclyl, heterocyclylalkyl, heteroaryl, or heteroarylalkyl.

10. The compound of claim 9, wherein each $R^1$ is substituted
a) with one substitutent; or
b) substituted with two substituents, each of which may be substituted from the same or different atoms, as valency allows.

11. The compound of claim 9, wherein the alkylene linker, $(CH_2)_x$, where x is 1, 2, or 3, may itself be further substituted with one or more of alkyl, cycloalkyl, aryl, aralkyl, heteroaryl, heteroarylalkyl, heterocyclyl, or heterocyclylalkyl.

12. The compound of claim 1, wherein $R^1$ is substituted with NHSO$_2$H, NHS(O)$_2$(C$_1$-C$_6$ alkyl), NHS(O)$_2$(C$_1$-C$_6$ partially or fully fluorinated alkyl), NHS(O)$_2$(C$_1$-C$_6$ alkenyl), NHS(O)$_2$(C$_1$-C$_6$ partially or fully fluorinated alkenyl), NHS(O)$_2$(C$_1$-C$_6$ alkynyl), NHS(O)$_2$(C$_1$-C$_6$ partially or fully fluorinated alkynyl), NHS(O)$_2$(C$_1$-C$_6$ cycloalkyl), NHS(O)$_2$(C$_1$-C$_6$ partially or fully fluorinated cycloalkyl), NHSO$_2$(aryl), NHSO$_2$(heterocyclyl), NHSO$_2$(heteroaryl), OH, CH$_2$S(O)$_2$NH(C$_1$-C$_6$ alkyl), CH$_2$S(O)$_2$NH(C$_1$-C$_6$ partially or fully fluorinated alkyl), CH$_2$S(O)$_2$N(C$_1$-C$_6$ alkyl)$_2$, CH$_2$S(O)$_2$N(C$_1$-C$_6$ partially fluorinated alkyl)$_2$, N(C$_1$-C$_6$ alkyl)$_2$, or N(C$_1$-C$_6$ partially fluorinated alkyl)$_2$.

13. The compound of claim 1, wherein $R^1$ is substituted with NHSO$_2$R', wherein R' is hydrogen, alkyl, haloalkyl, alkenyl, alkynyl, cycloalkyl, aryl, heterocyclyl, or heteroaryl.

14. The compound of claim 13, wherein R' is $C_{1-8}$ alkyl, $C_{2-8}$ alkenyl, or $C_{2-8}$ alkynyl.

15. The compound of claim 1, wherein $R^1$ is $R^{1a}$-L-$R_{1b}$, wherein
$R^{1a}$ is independently any $R^1$ group as defined,
L is a polar linking group, and
$R^{1b}$ is independently any $R^1$ group as defined.

16. The compound of claim 15, wherein
(i) $R^{1a}$ is $C_{3-15}$ cycloalkyl,
L is —(CH$_2$)$_p$-L$^1$-,
wherein p is 0, 1, or 2,
L$^1$ is selected from the group consisting of —O—, —C(O)—, —C(O)O—, —OC(O)—, —C(O)N(R')—, —OC(O)N(R')—, —N(R')—, —N(R')C(O)N(R')—, —N(R')C(S)N(R')—, —N(R')C(O)—, —N(R')C(O)O—, —SO$_2$—, —S(O)—, —SO$_2$N(R')—, —N(R')SO$_2$—,
and —N(R')SO$_2$(NR')—; and $R^{1b}$ is selected from the group consisting of unsubstituted or substituted $C_{1-8}$ alkyl, $C_{2-8}$ alkenyl, $C_{2-8}$ alkynyl, $C_{3-15}$ cycloalkyl, heterocyclyl, aryl, arylalkyl, heteroaryl, or heteroarylalkyl;

or (ii) $R^{1a}$ is heterocyclyl;
L is —(CH$_2$)$_p$-L$^1$-,
wherein p is 0, 1, or 2,
L$^1$ is selected from the group consisting of —O—, —C(O)—, —C(O)O—, —OC(O)—, —C(O)N(R')—, —OC(O)N(R')—, —N(R')—, —N(R')C(O)N(R')—, —N(R')C(S)N(R')—, —N(R')C(O)—, —N(R')C(O)O—, —SO$_2$—, —S(O)—, —SO$_2$N(R')—, —N(R')SO$_2$—,
and —N(R')SO$_2$(NR')—; and $R^{1b}$ is selected from the group consisting of unsubstituted or substituted $C_{1-8}$ alkyl, $C_{2-8}$ alkenyl, $C_{2-8}$ alkynyl, $C_{3-15}$ cycloalkyl, heterocyclyl, aryl, arylalkyl, heteroaryl, or heteroarylalkyl, wherein each R' individually is the same or different and is hydrogen, alkyl, alkenyl, alkynyl, haloalkyl, haloalkenyl, haloalkynyl, hydroxyalkyl, hydroxyalkenyl, hydroxyalkynyl, cycloalkyl, cycloalkyl substituted by one or more halogens, cycloalkylalkyl, aryl, aryl substituted with one or more halogen, arylalkyl, heterocyclyl, heterocyclylalkyl, heteroaryl, or heteroarylalkyl.

17. The compound of claim 16, wherein L$^1$ is selected from the group consisting of —O—, —C(O)—, —C(O)O—, —C(O)N(R')—, —NR'C(O)—, —NR'C(O)O—, —SO$_2$—, —SO$_2$N(R')—, —N(R')C(O)N(R')—, and —N(R')SO$_2$—.

18. The compound of claim 16, wherein $R_{1a}$ is selected from the group consisting of unsubstituted or substituted cyclobutyl, cyclohexyl, bicyclo[1.1.1]pentyl, pyrrolidinyl, and piperidinyl.

19. The compound of claim 16, wherein $R^{1b}$ is (a) unsubstituted or (b) substituted.

20. The compound of claim 19, wherein $R^{1b}$ is substituted with at least one of fluorine, OCH$_3$, or CN.

21. The compound of claim 16, wherein Z and Y are both hydrogen.

22. A compound selected from the group consisting of:

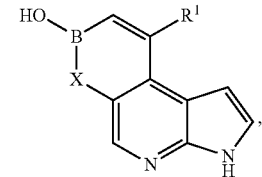

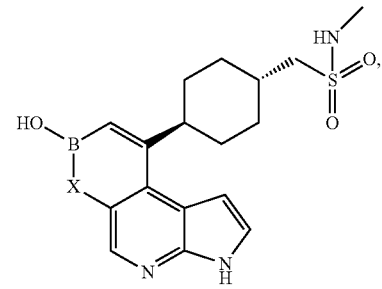

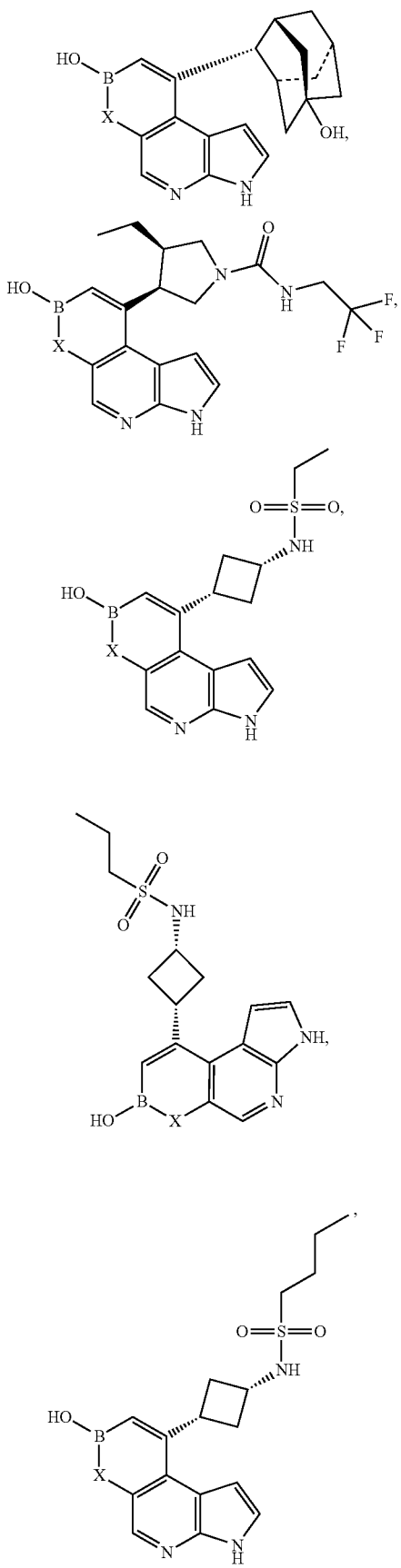

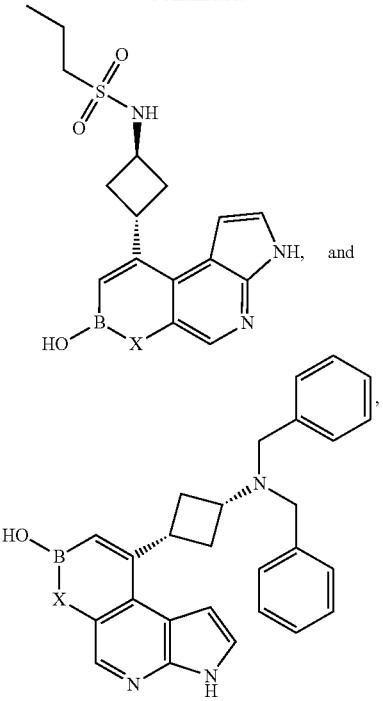

wherein each X independently is selected from the group consisting of O and NR$^a$;

each R$^a$ independently is selected from the group consisting of hydrogen, $C_1$-$C_{15}$ alkyl, $C_{2-15}$ alkenyl, $C_{2-15}$ alkynyl, $C_{3-15}$ cycloalkyl, and aryl; and R$^1$ is selected from the group consisting of unsubstituted or substituted:

(i) $C_1$-$C_{15}$ alkyl, (ii) $C_{2-15}$ alkenyl, (iii) $C_{2-15}$ alkynyl, (iv) $C_1$-$C_{15}$ alkyl, wherein one or more carbon atom, including the carbon atom attached to the depicted ring, is replaced with a heteroatom selected from O, N, S, or Si, and wherein each N, S, or Si may be oxidized, and wherein the N may be quarternized, (v) $C_{2-15}$ alkenyl, wherein one or more carbon atom, including the carbon atom attached to the depicted ring, is replaced with a heteroatom selected from O, N, S, or Si, and wherein each N, S, or Si may be oxidized, and wherein the N may be quarternized, (vi) $C_{2-15}$ alkynyl, wherein one or more carbon atom, including the carbon atom attached to the depicted ring, is replaced with a heteroatom selected from O, N, S, or Si, and wherein each N, S, or Si may be oxidized, and wherein the N may be quarternized, (vii) $C_{3-15}$ cycloalkyl, (viii) heterocyclyl, (ix) aryl, and (x) heteroaryl, or a stereoisomer, enantiomer, or tautomer thereof, or a veterinary or pharmaceutically acceptable salt thereof.

23. The compound of claim 22, wherein X is oxygen.

24. The compound of claim 1, wherein R$^1$ is selected from the group consisting of:

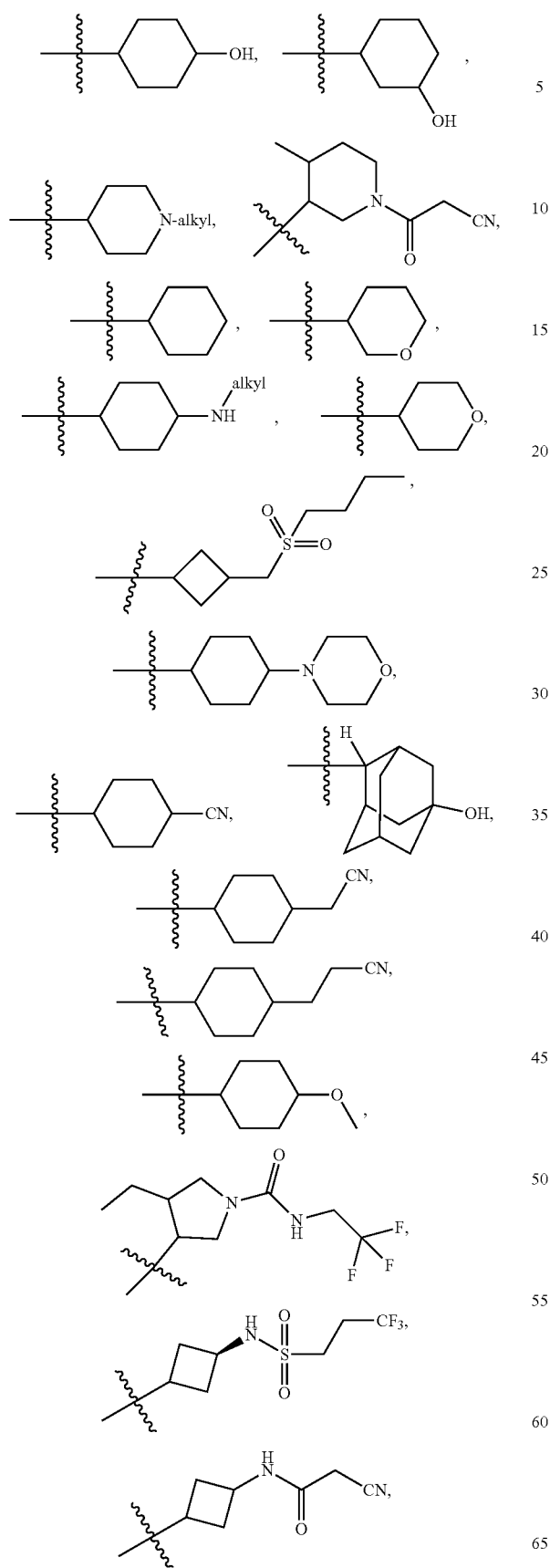
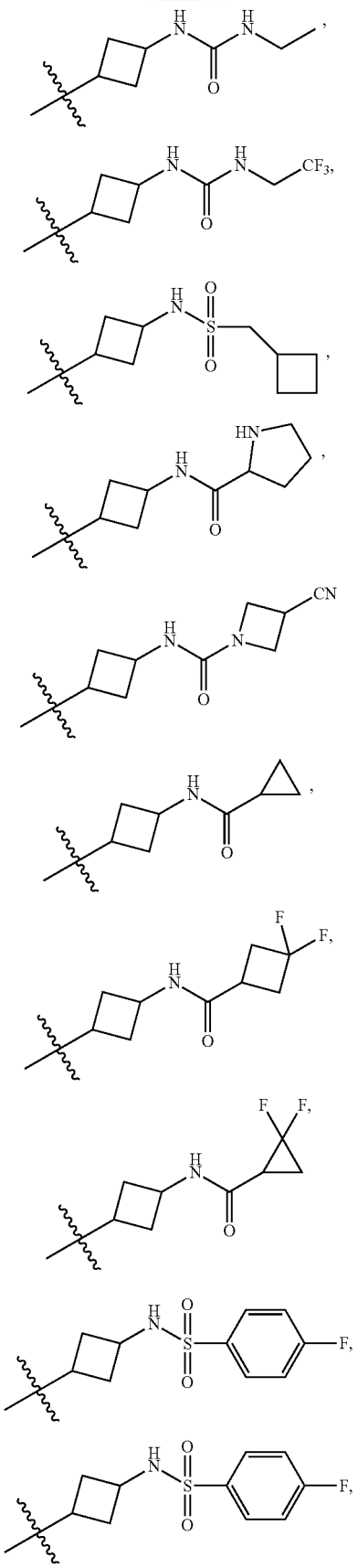

-continued
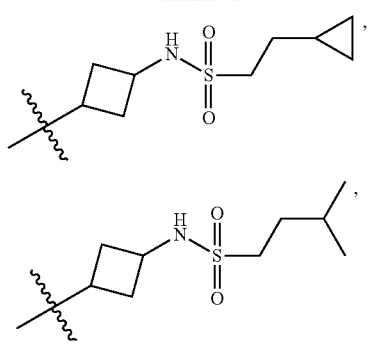
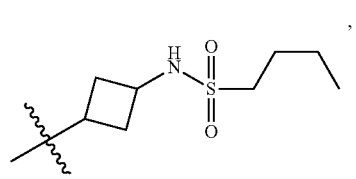
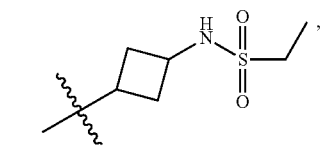
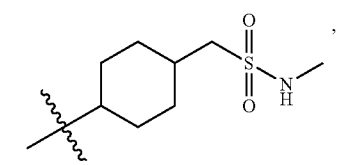
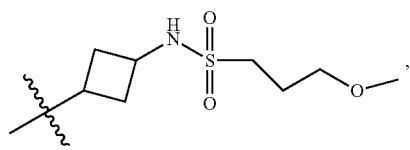
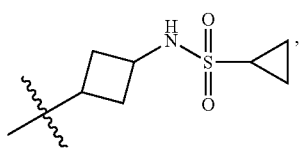
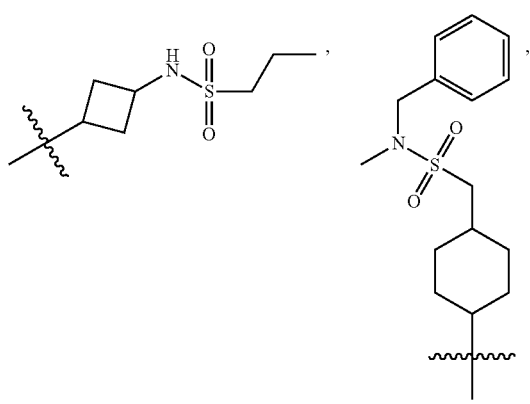
-continued
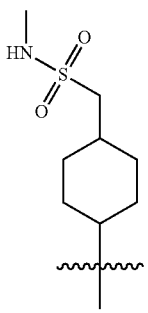, and 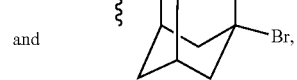
or a stereoisomer, enantiomer, or tautomer thereof, or a veterinary or pharmaceutically acceptable salt thereof.
25. A compound of claim 1, selected from the group consisting of:
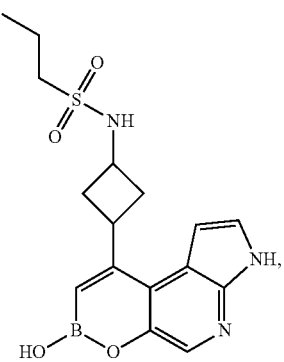
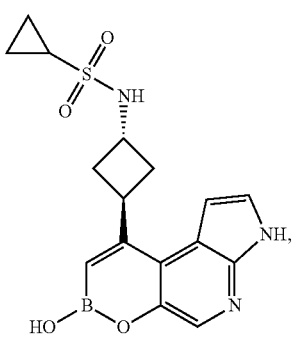
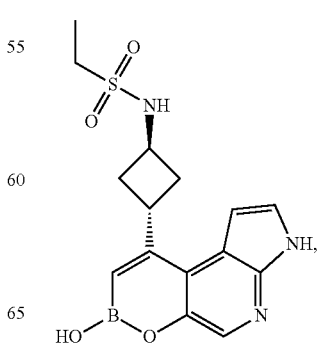 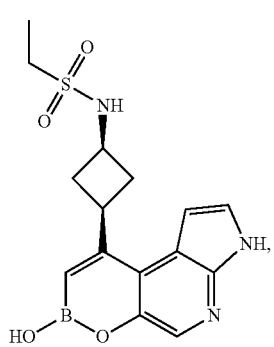

271
-continued
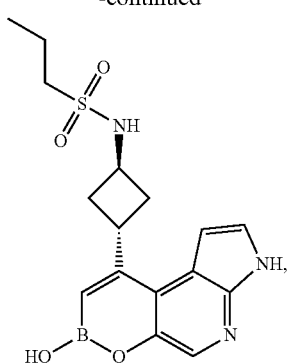
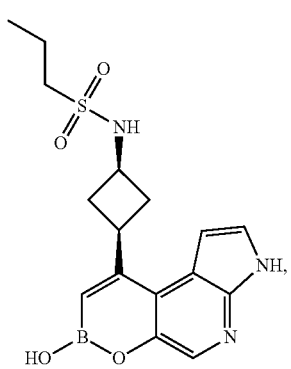
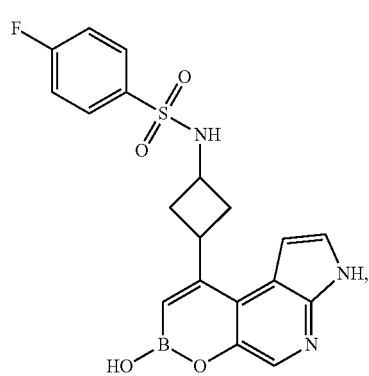
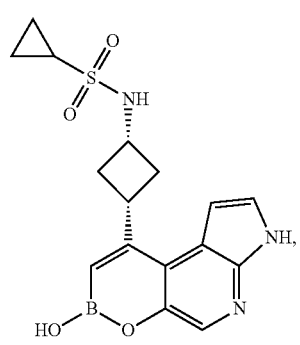
272
-continued
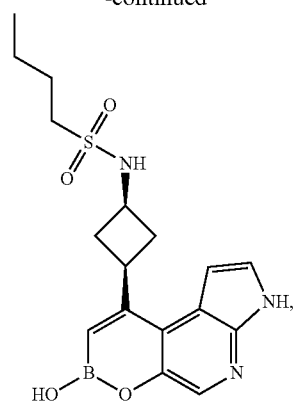
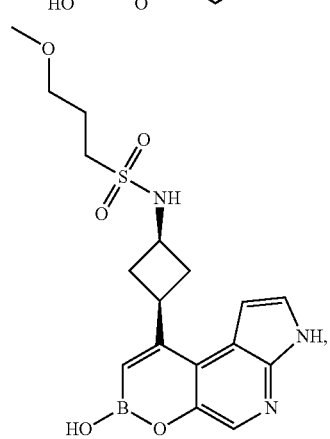
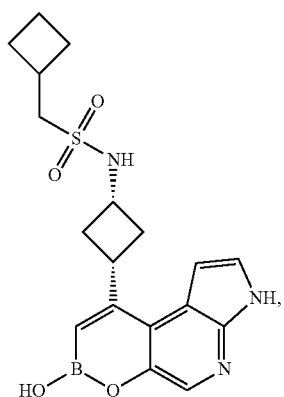
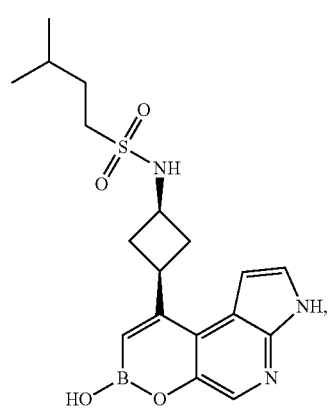

273
-continued
274
-continued
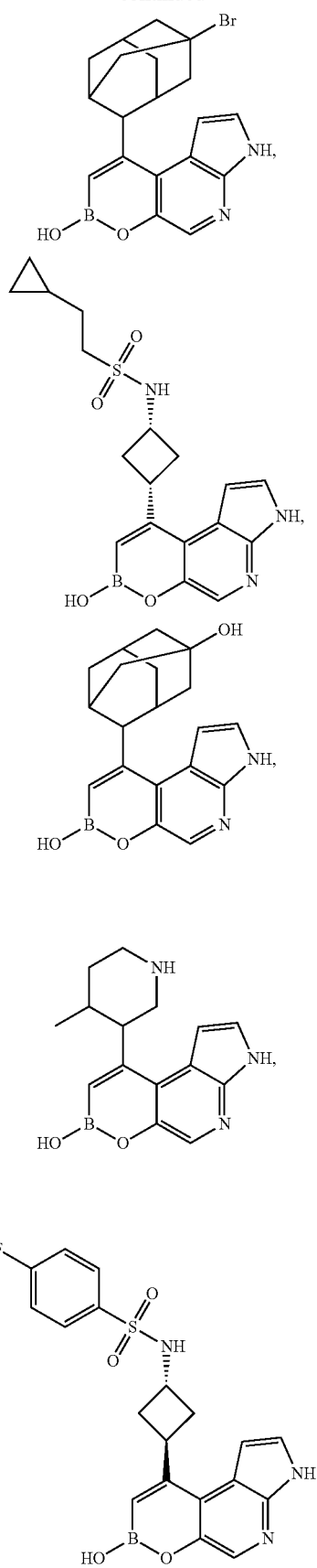
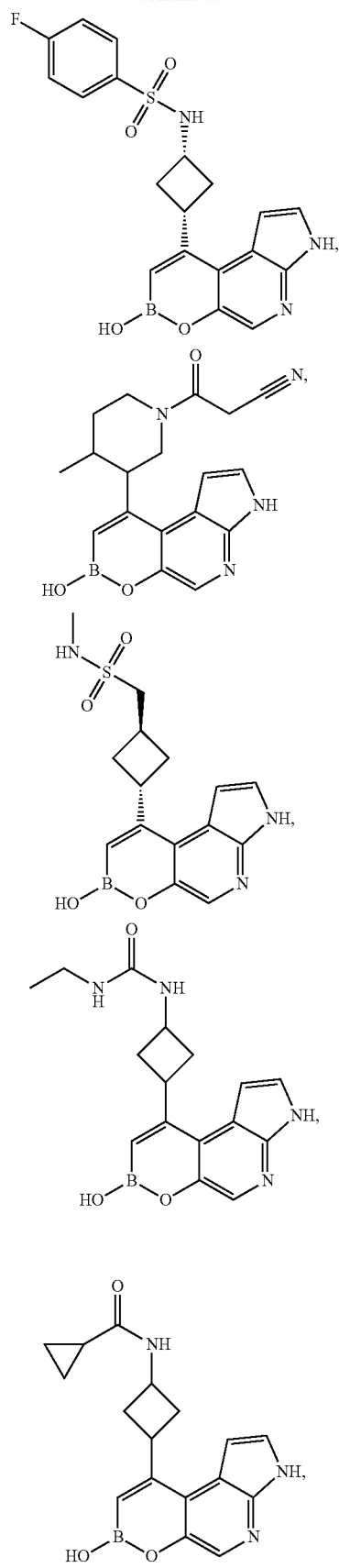

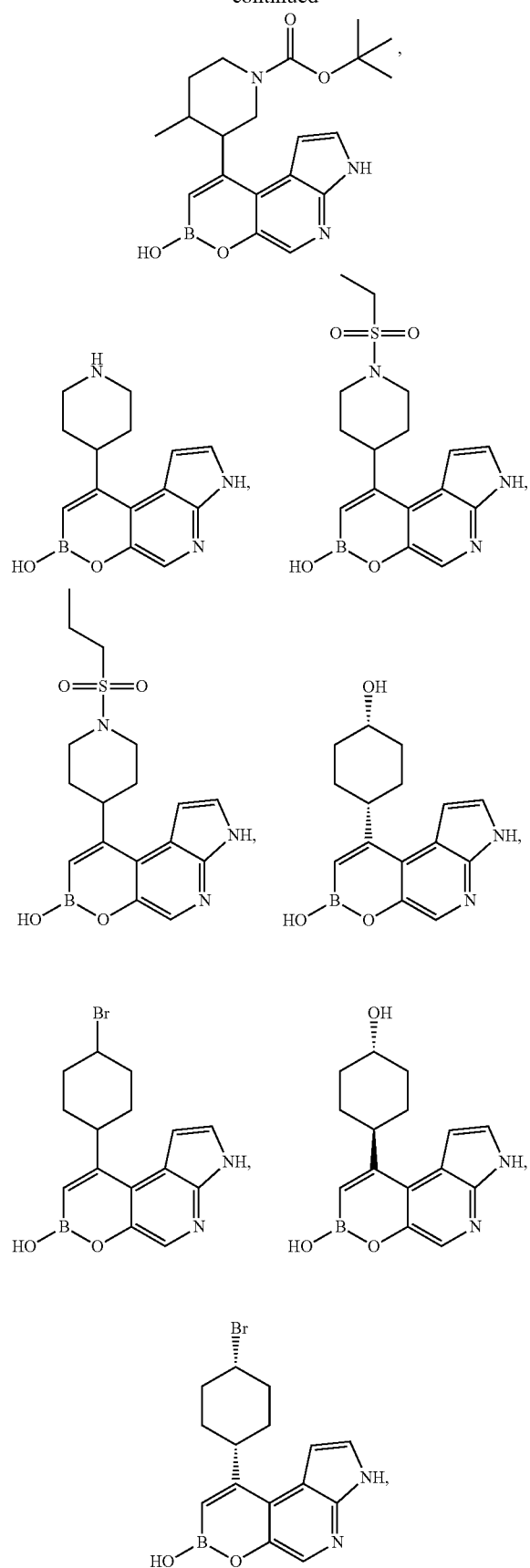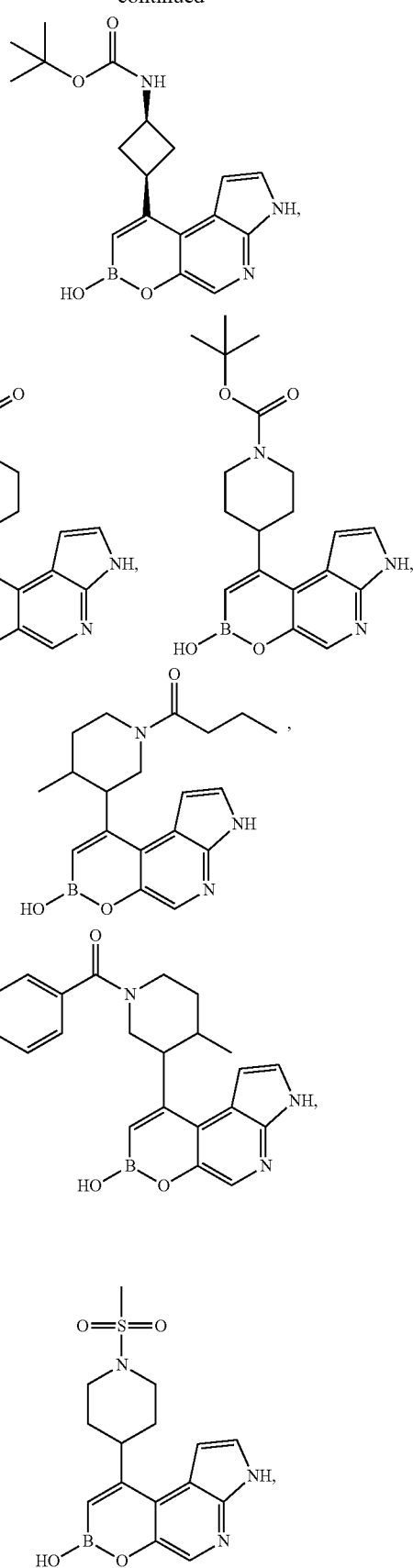

277
-continued
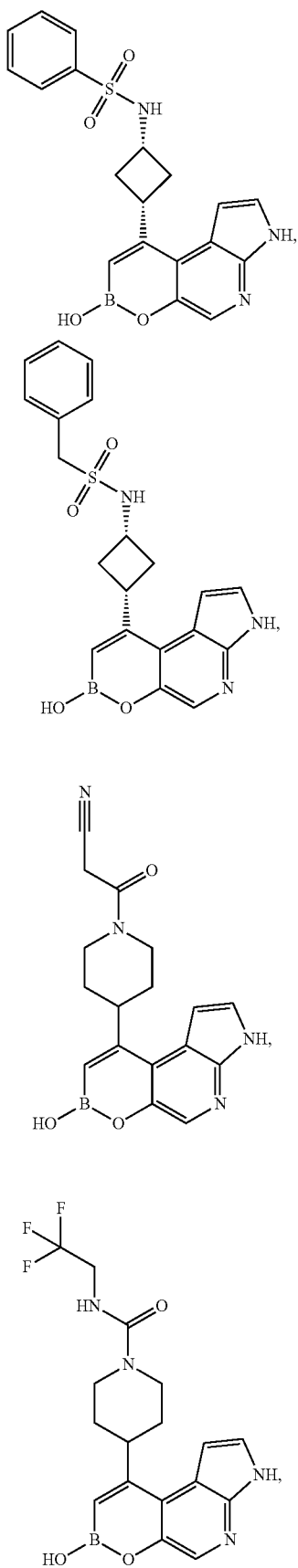
278
-continued
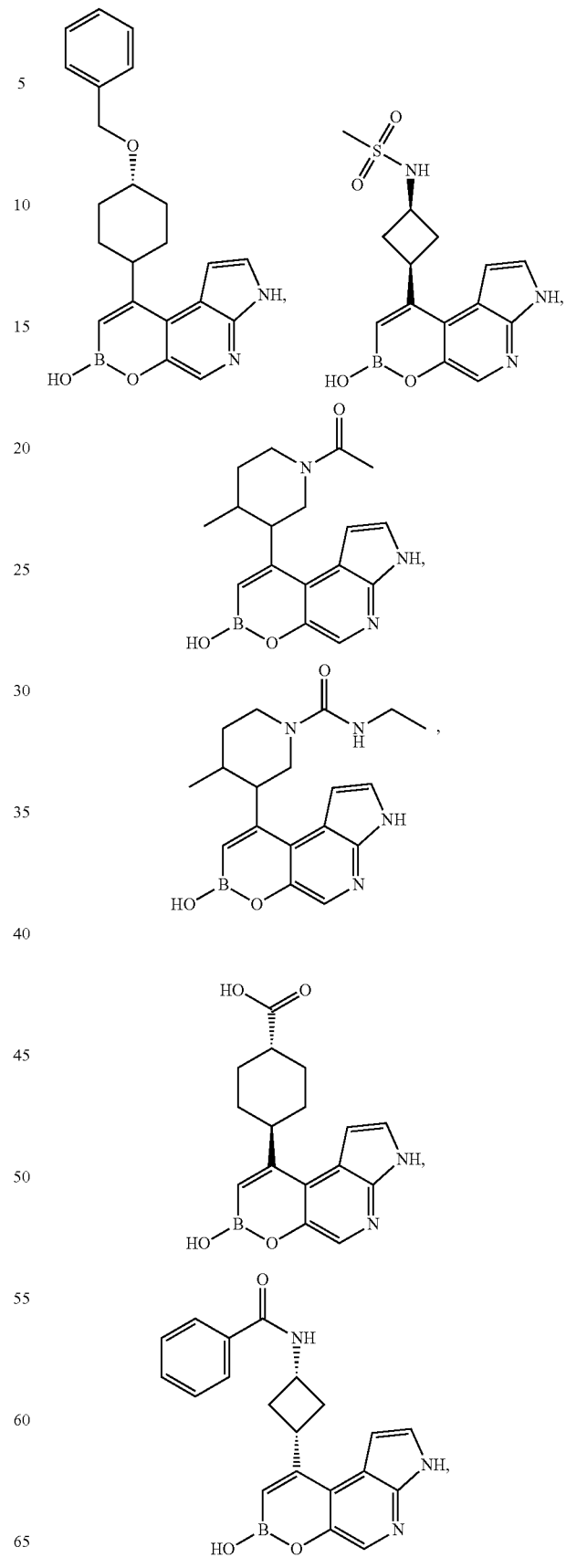

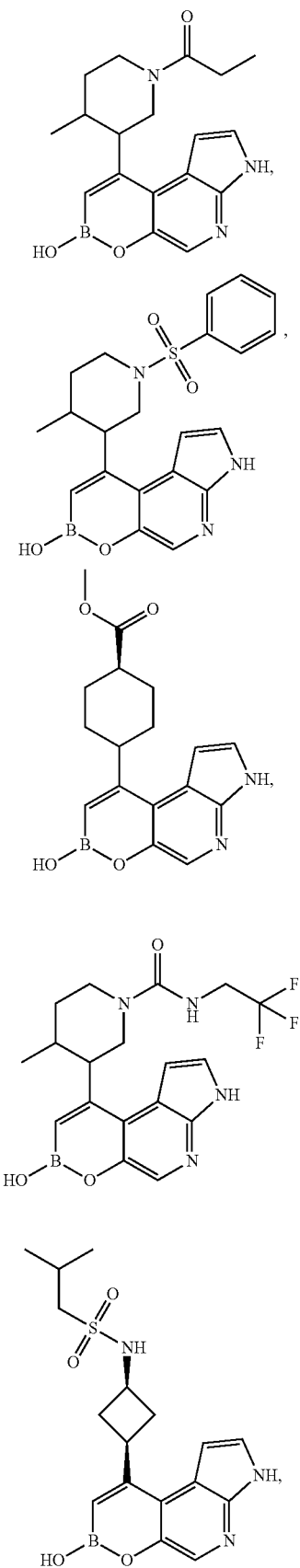
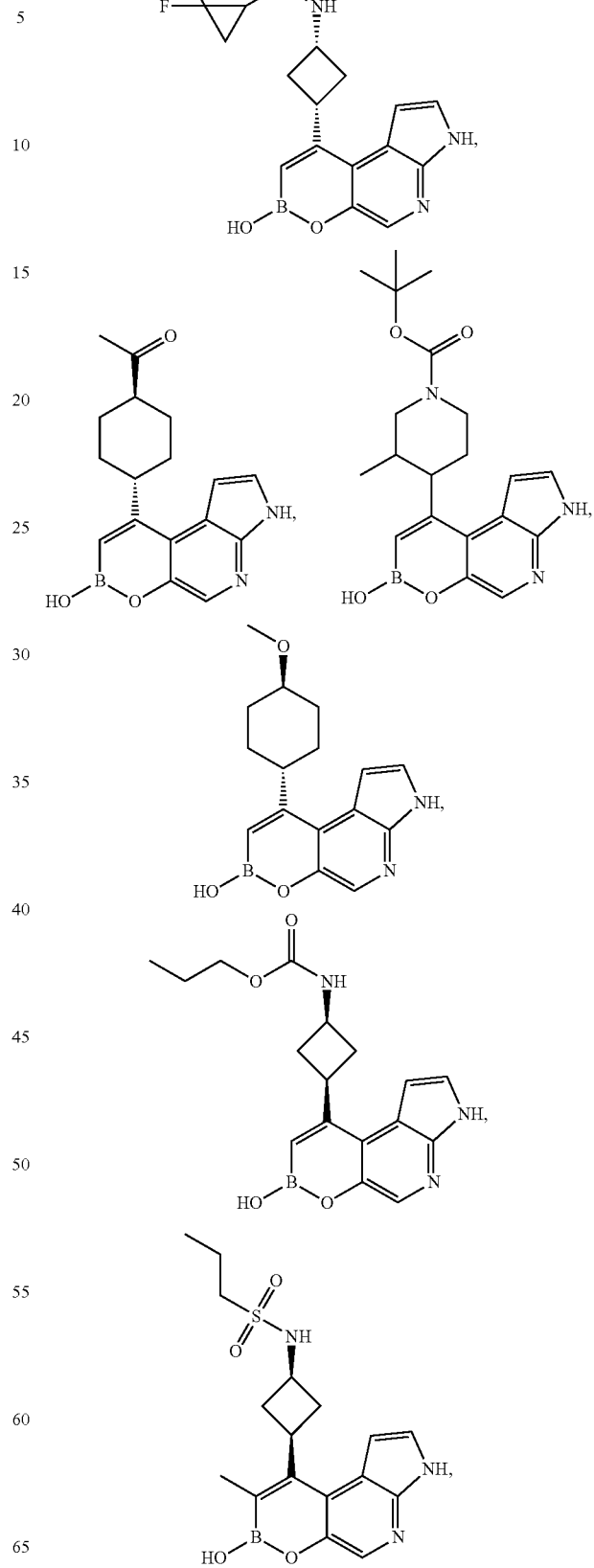

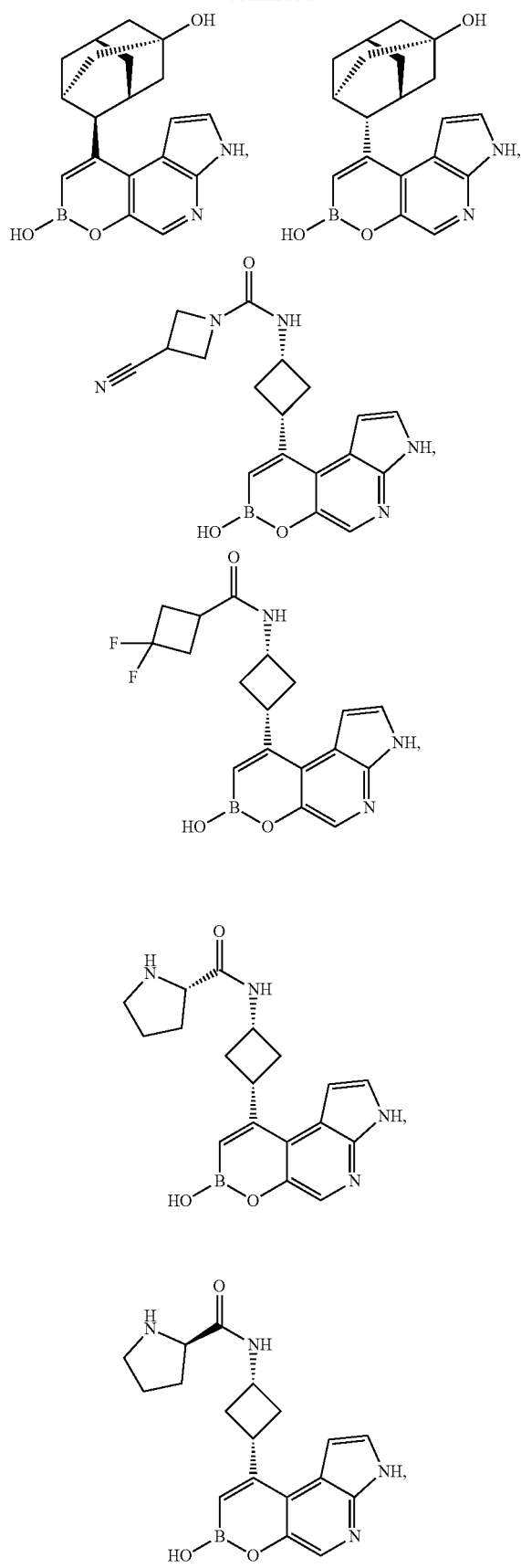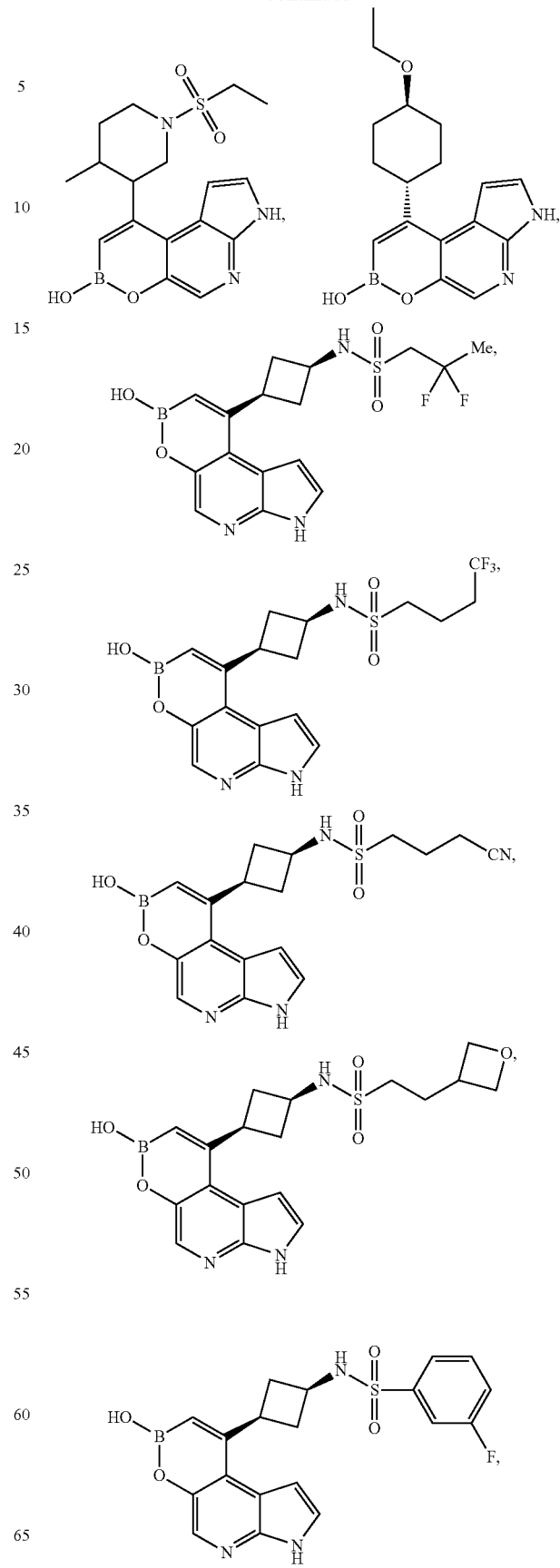

283 -continued
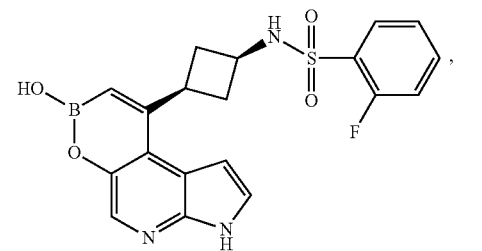
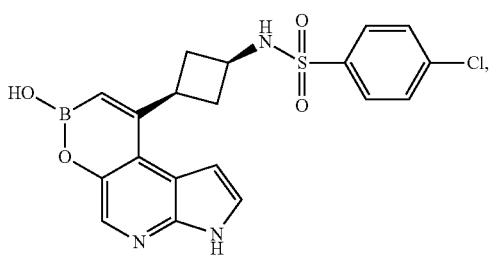
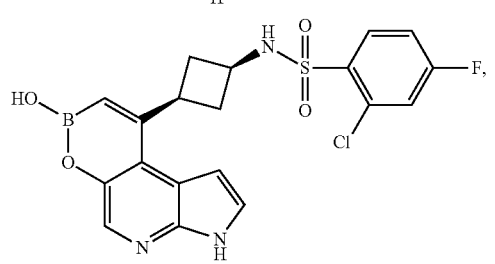
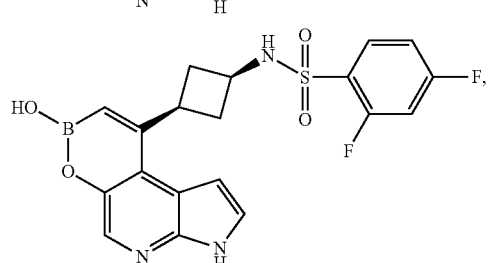
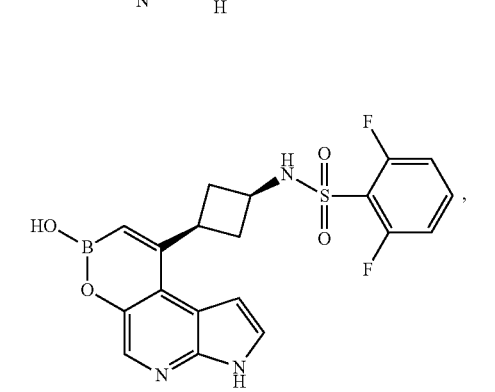
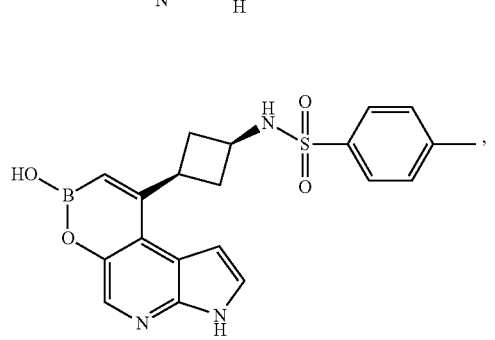
284 -continued
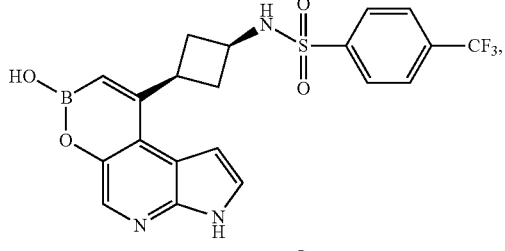
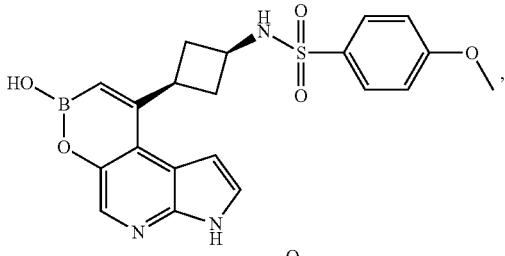
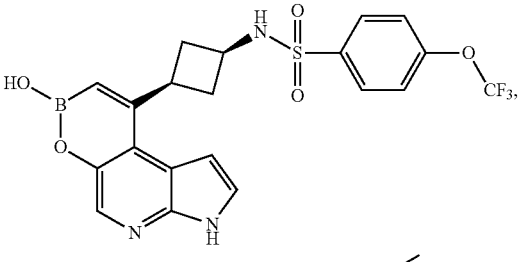
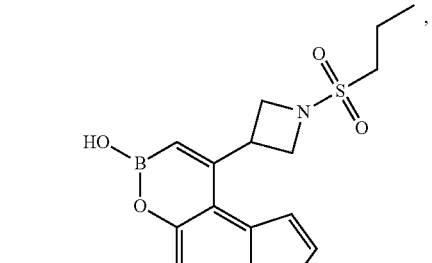
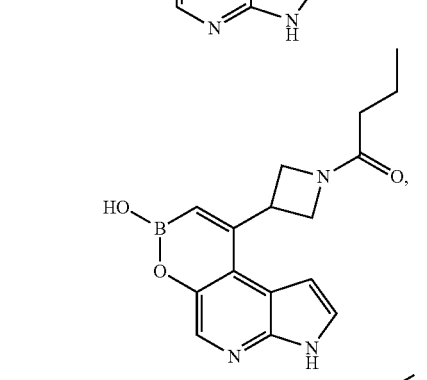
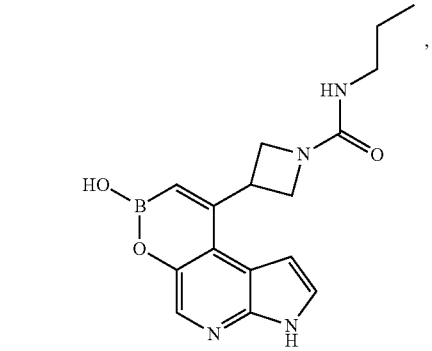

285
-continued
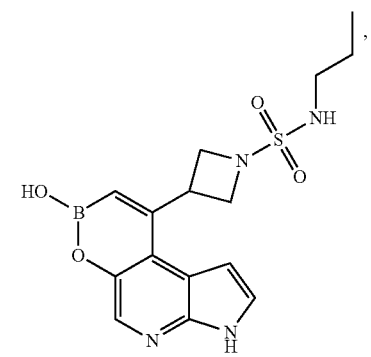
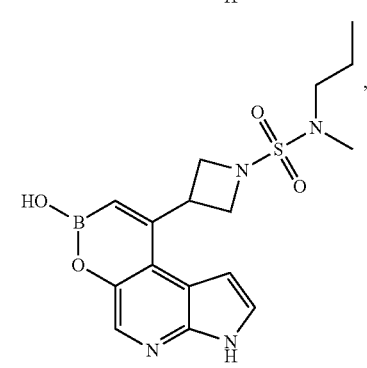
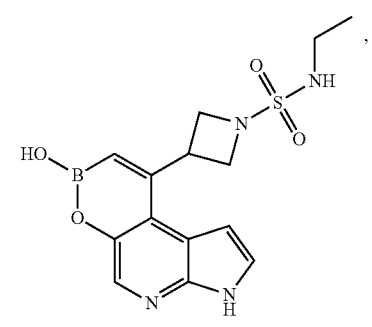
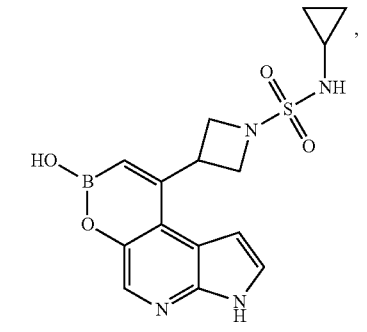
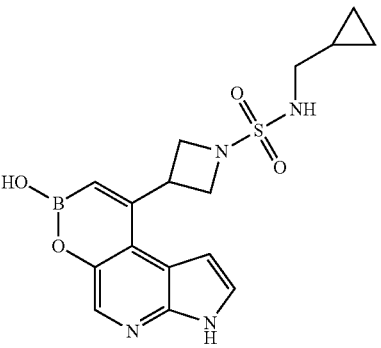
286
-continued
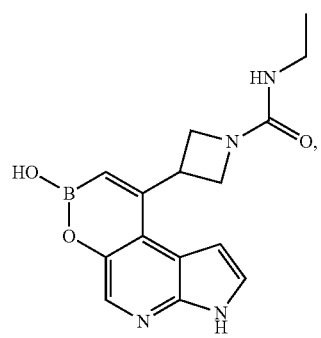
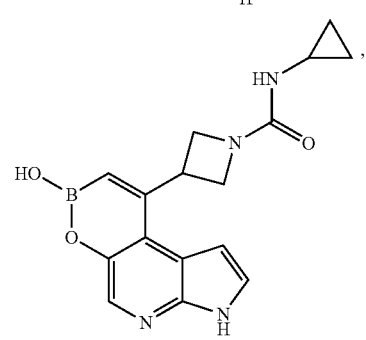
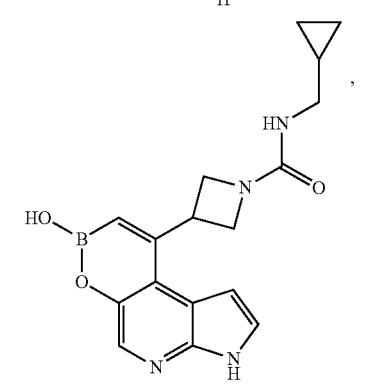
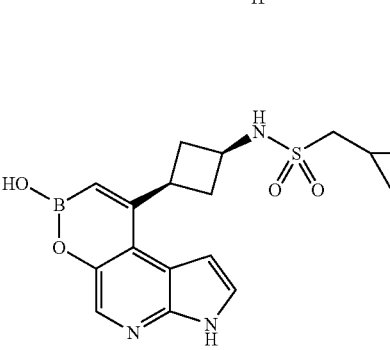
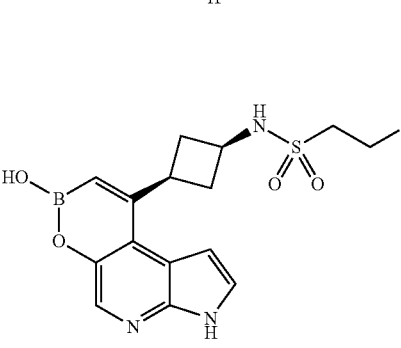

287
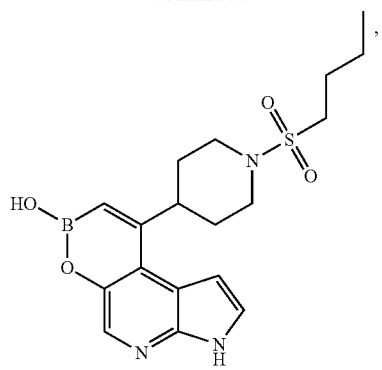
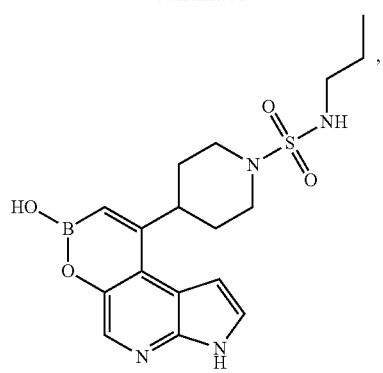
288
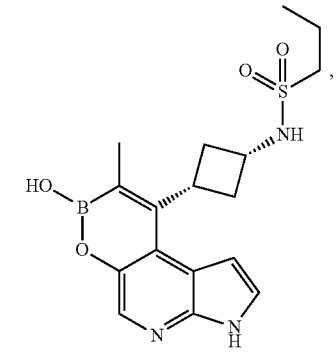
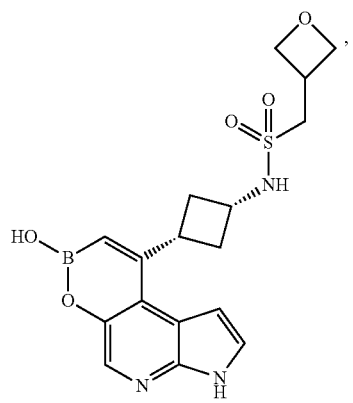

289
-continued
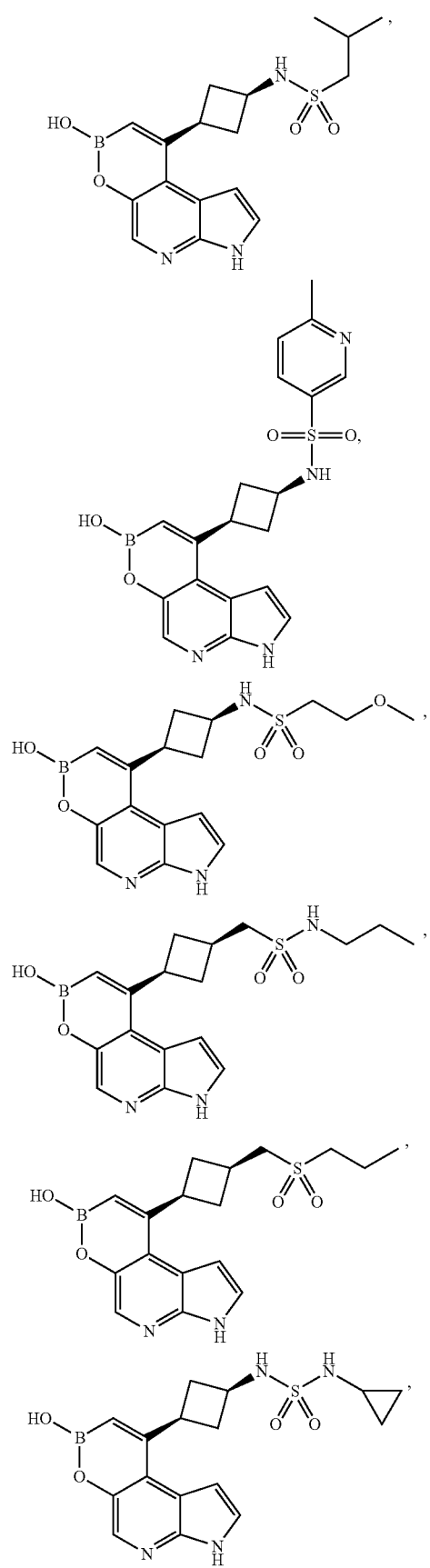
290
-continued
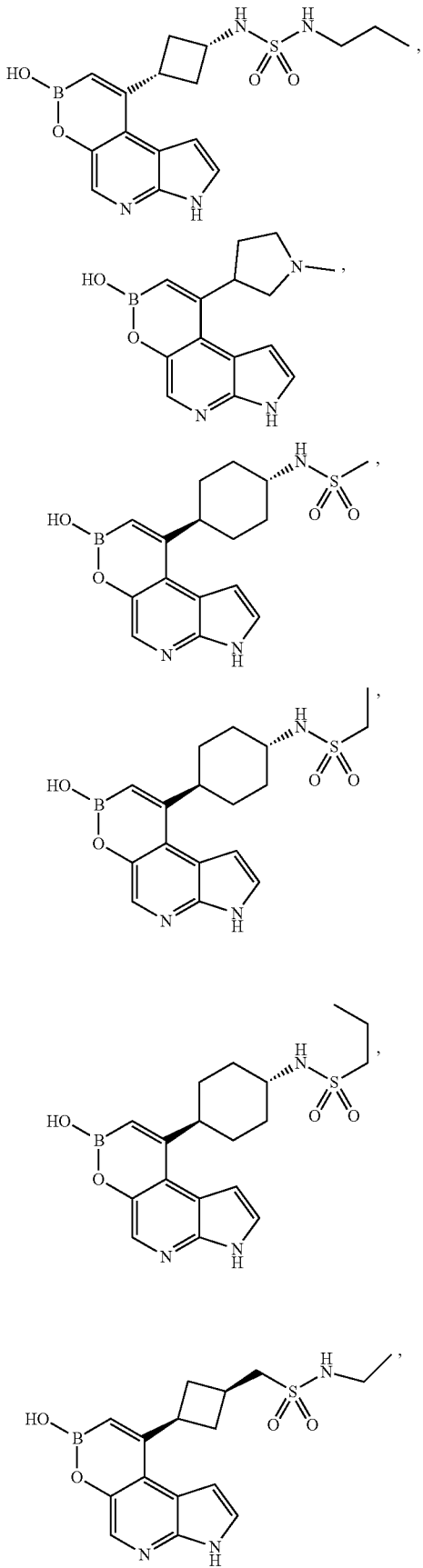

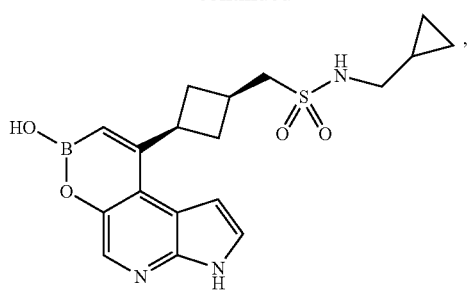
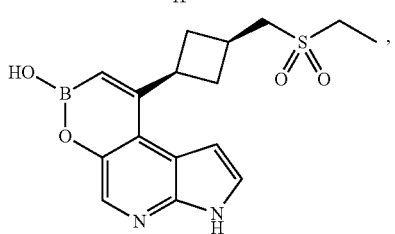
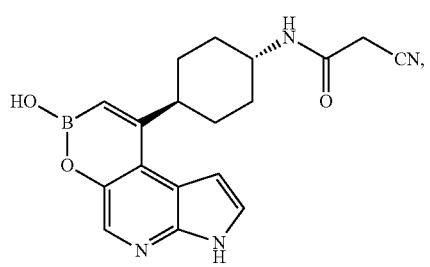
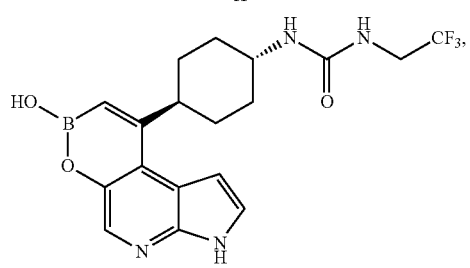
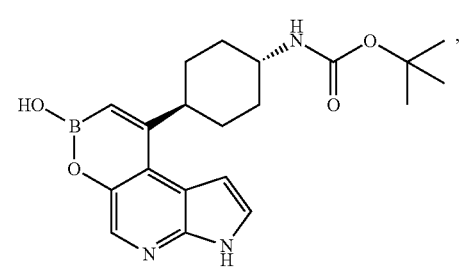
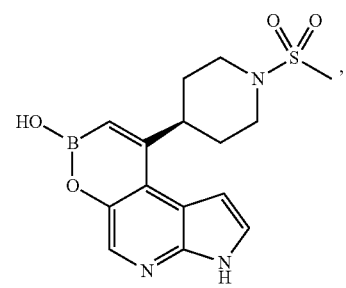
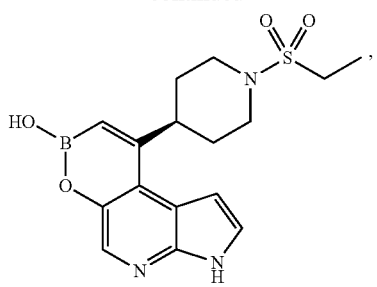
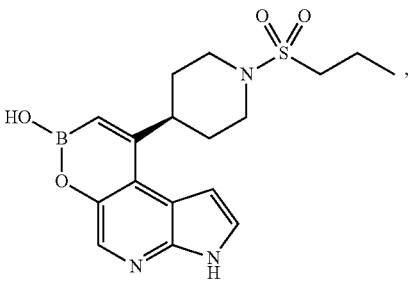
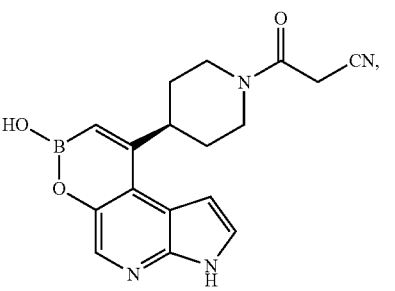
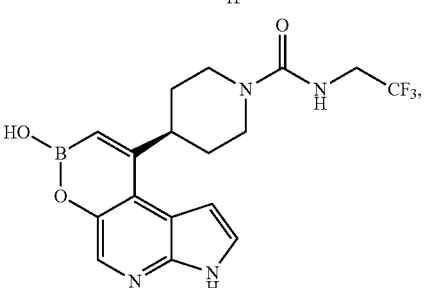
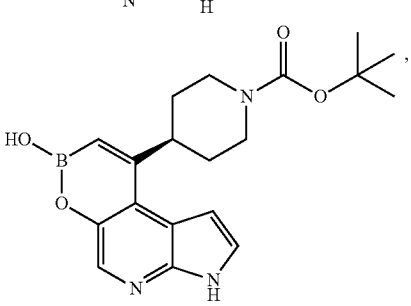
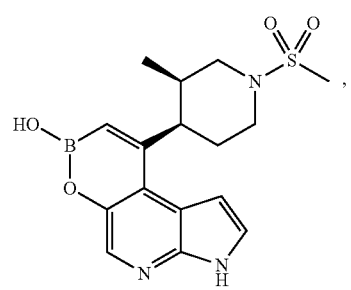

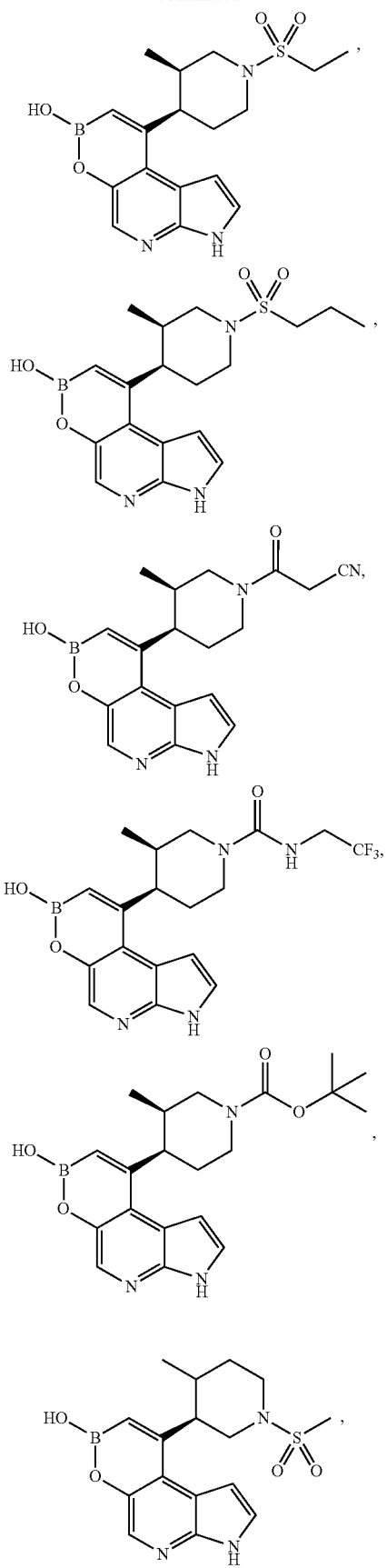
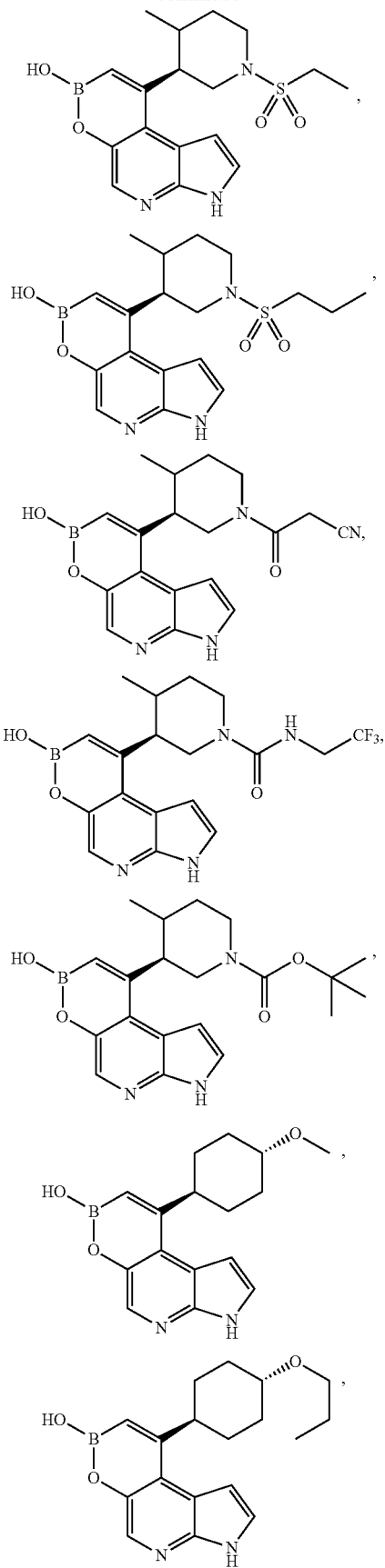

295
-continued
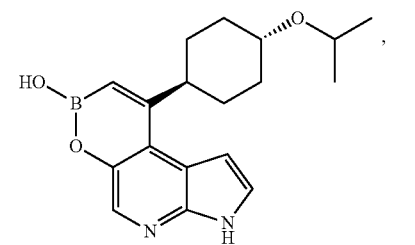
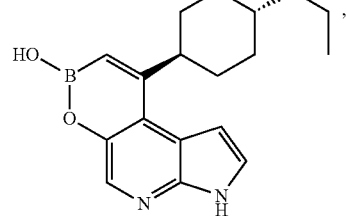
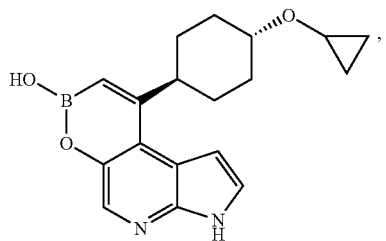
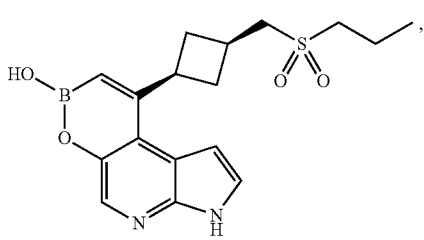
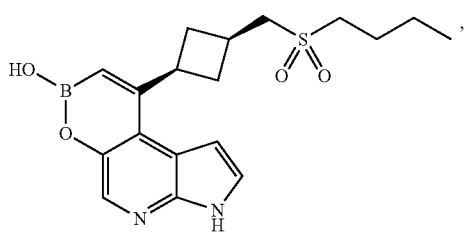
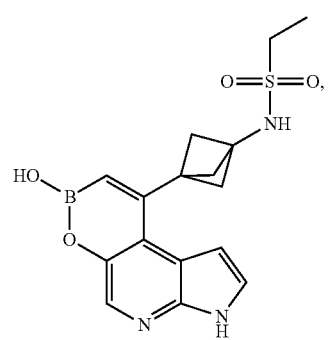
296
-continued
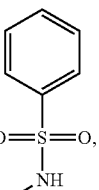
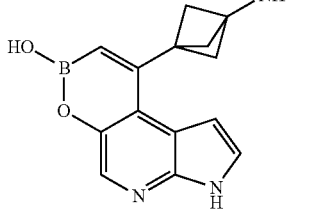
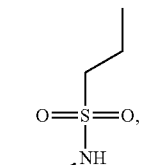
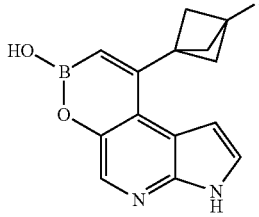
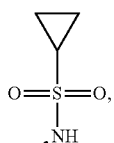
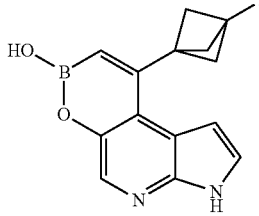
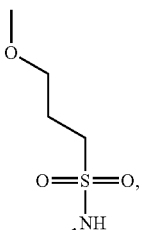
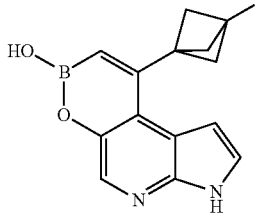

297
-continued
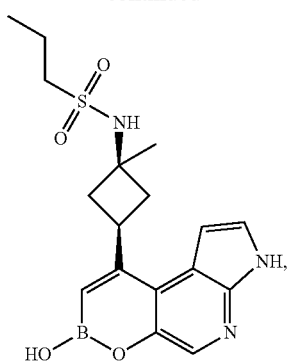
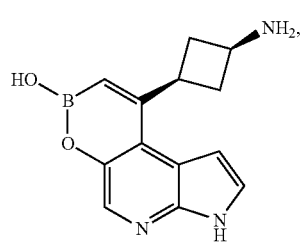
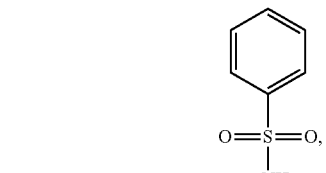
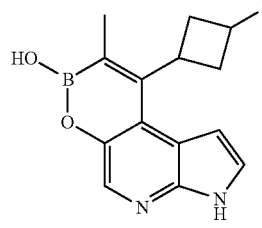
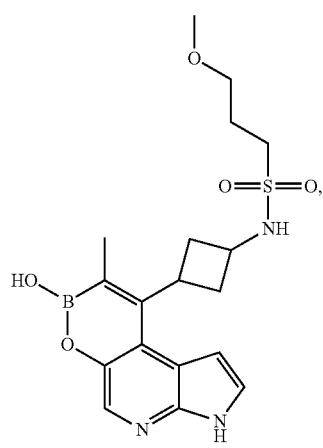
298
-continued
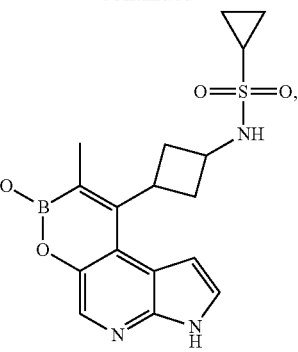
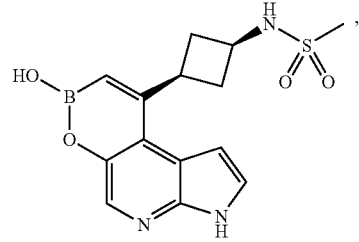
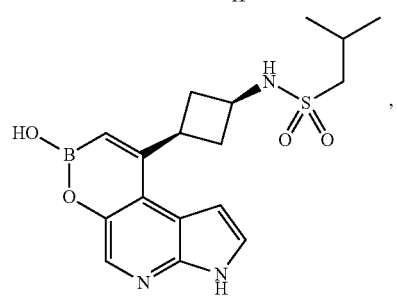
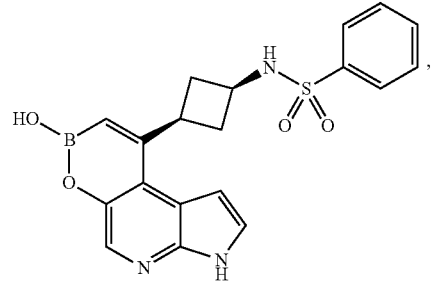
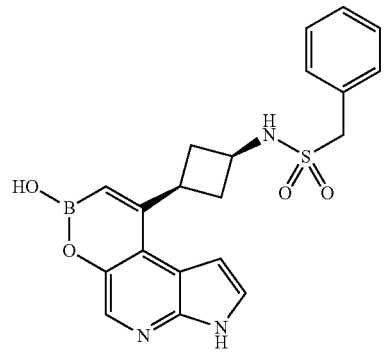

299
-continued
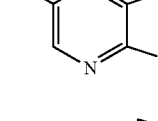
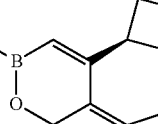
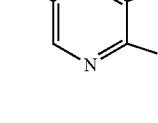
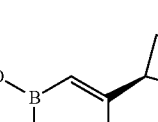
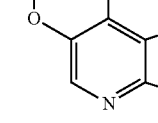
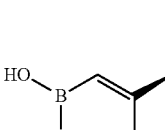
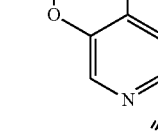
300
-continued
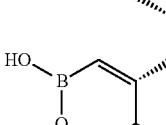
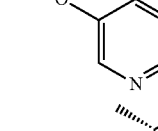
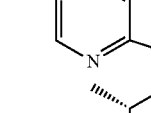
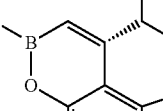
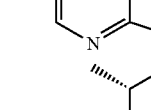
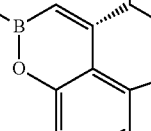
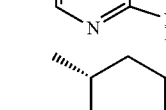

301
-continued
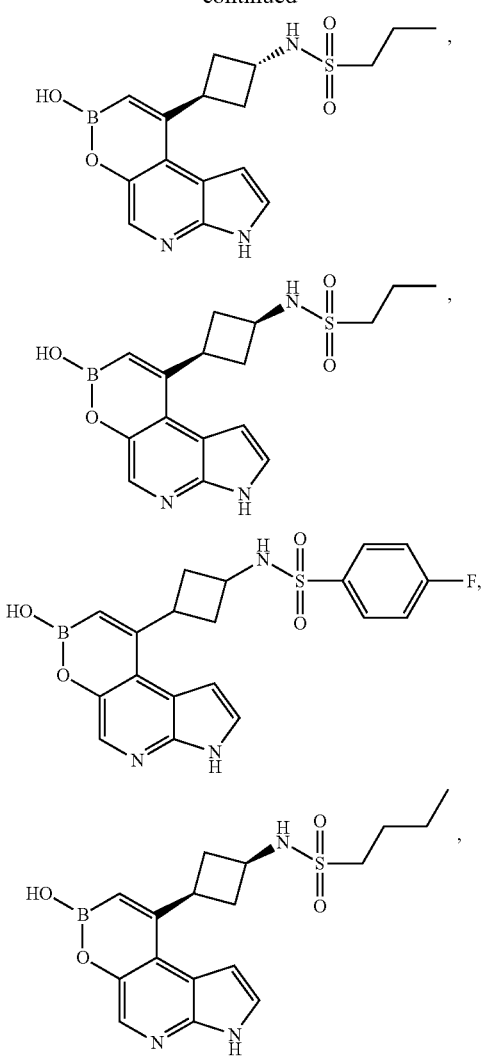
302
-continued
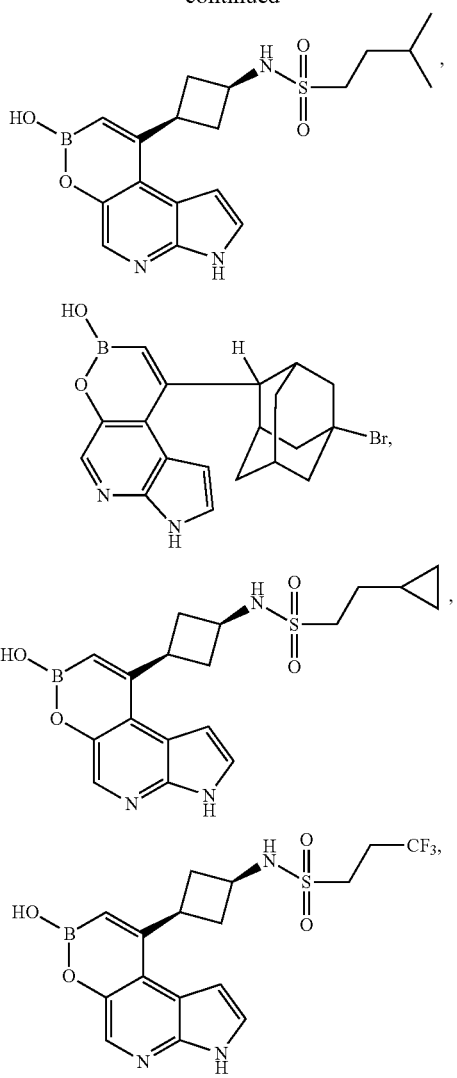
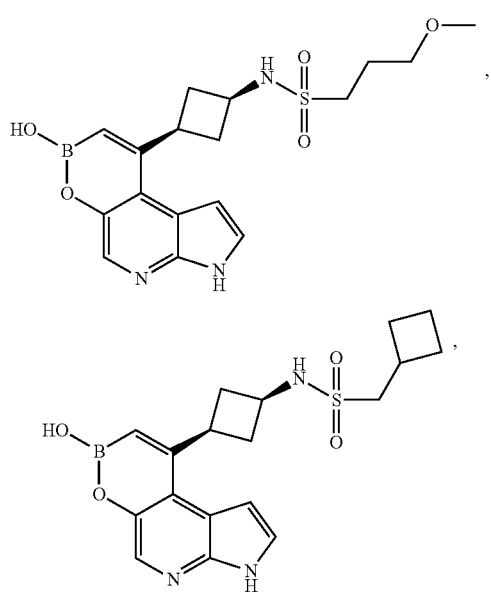
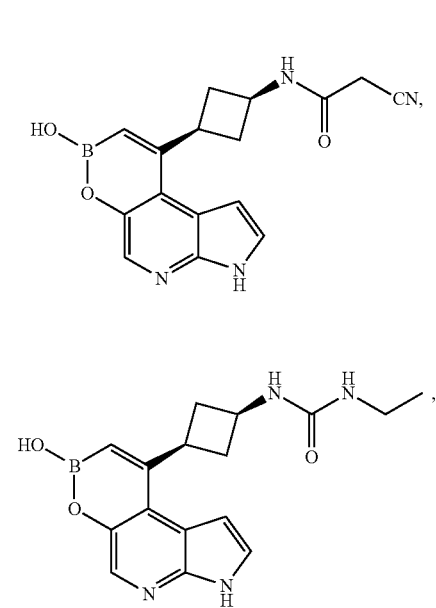

303
-continued
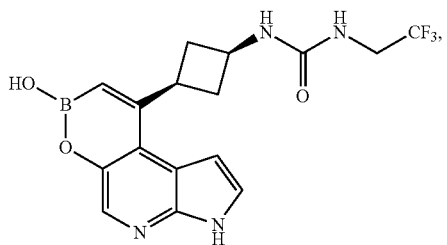
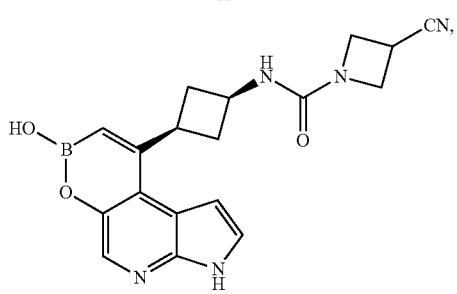
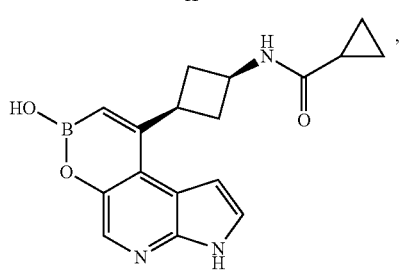
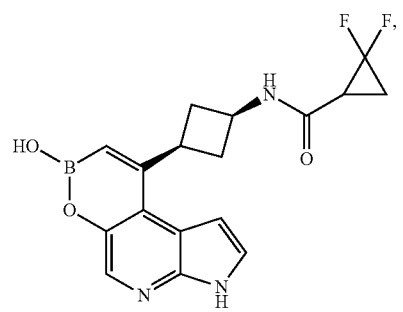
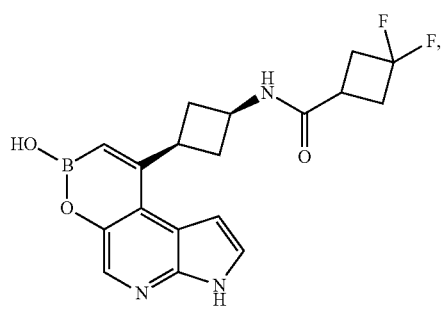
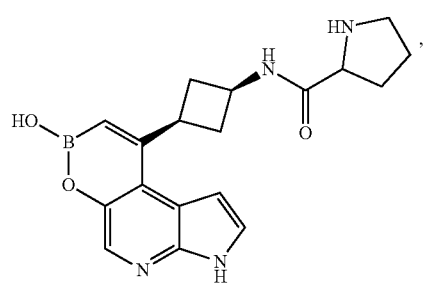
304
-continued
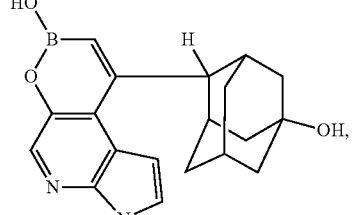
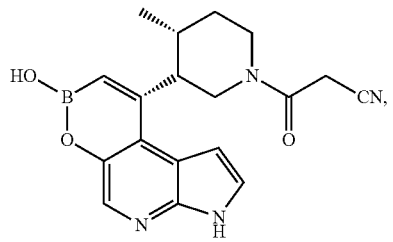
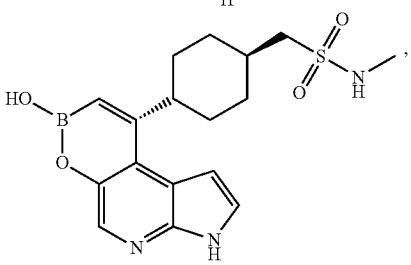
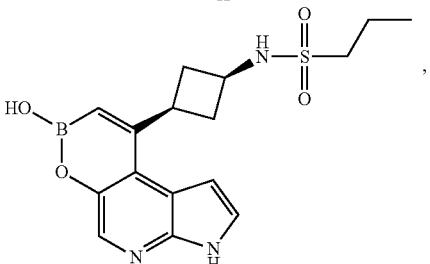
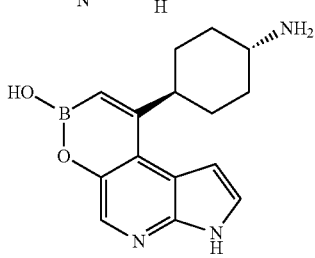
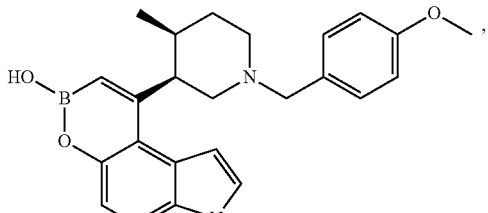
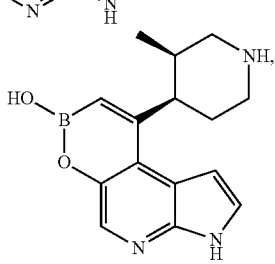

305
-continued
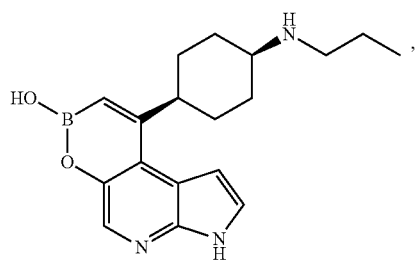
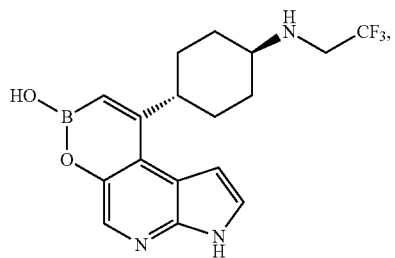
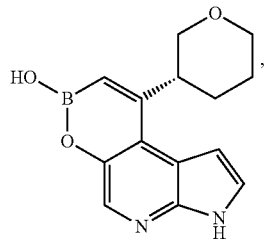
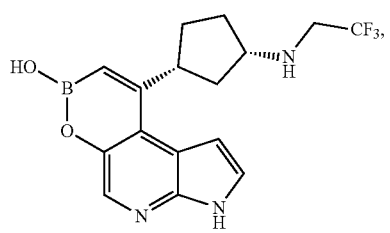
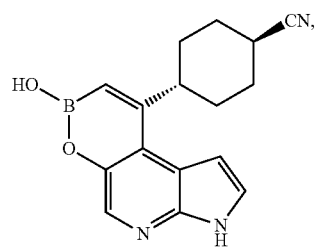
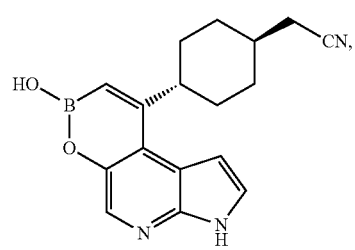
306
-continued
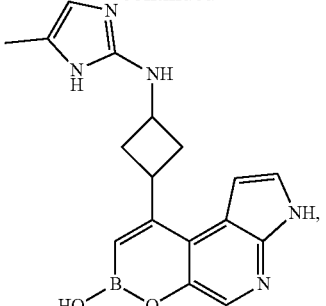
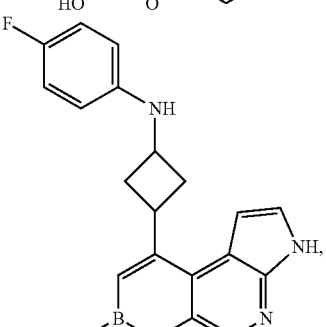
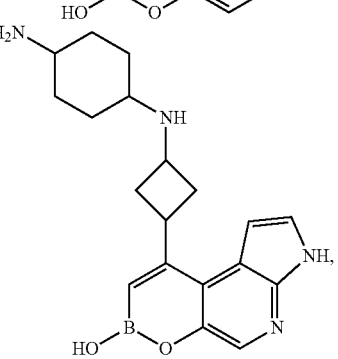
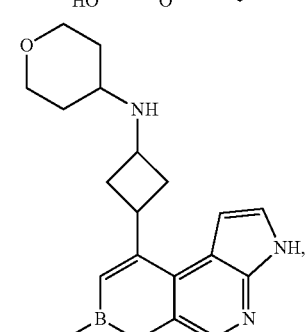
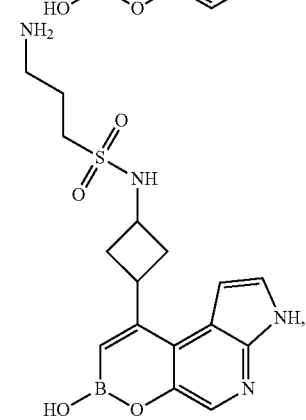

-continued

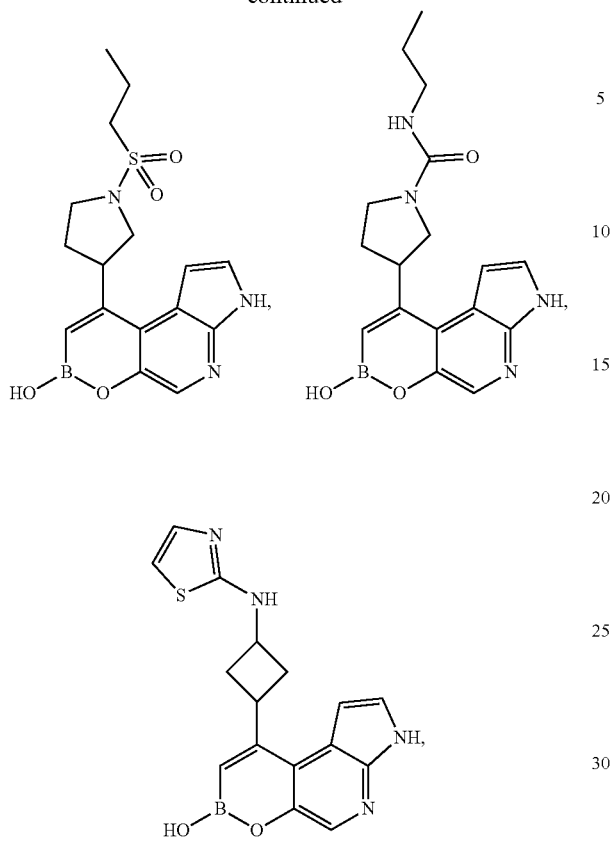

or a stereoisomer, enantiomer, or tautomer thereof, or a veterinary or pharmaceutically acceptable salt thereof.

26. A compound of formula (III), (IV), or (V):

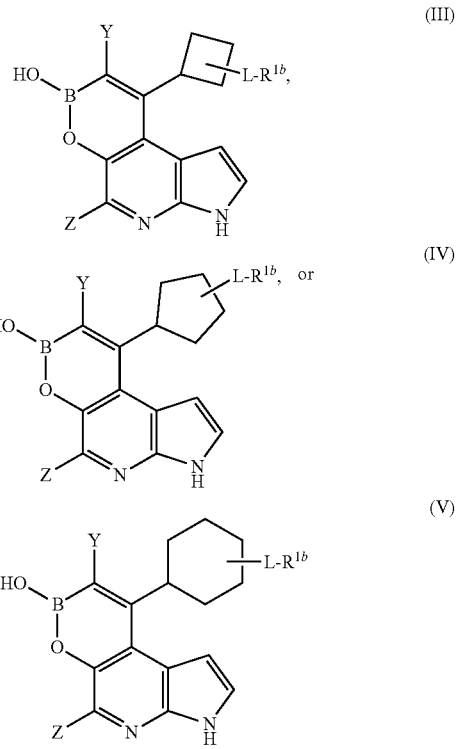

wherein
each Y independently is selected from the group consisting of hydrogen, $C_1$-$C_6$ alkyl, $C_{2-6}$ alkenyl, and $C_{2-6}$ alkynyl;
each Z independently is selected from the group consisting of hydrogen, $C_1$-$C_6$ alkyl, $C_{2-6}$ alkenyl, and $C_{2-6}$ alkynyl; and
each L independently is selected from the group consisting of —NR'SO$_2$—, —CH$_2$SO$_2$NR'—, —NR'C(O)—, and —NR'C(O)NR'—,
where each R' and $R^{1b}$ independently is selected from the group consisting of hydrogen, deuterium, $C_1$-$C_6$ alkyl, $C_2$-$C_6$ alkenyl, $C_2$-$C_6$ alkynyl, $C_3$-$C_6$ cycloalkyl, aryl, aryl-$C_1$-$C_6$ alkyl, aryl-$C_2$-$C_6$ alkenyl, aryl-$C_1$-$C_6$ alkynyl, heteroaryl, $C_1$-$C_6$ alkyl-heteroaryl, $C_2$-$C_6$ alkenyl-heteroaryl, $C_2$-$C_6$ alkynyl-heteroaryl, heteroaryl-$C_1$-$C_6$ alkyl, heteroaryl-$C_2$-$C_6$ alkenyl, heteroaryl-$C_1$-$C_6$ alkynyl, heterocyclyl-$C_1$-$C_6$ alkyl, heterocyclyl-$C_2$-$C_6$ alkenyl, and heterocyclyl-$C_1$-$C_6$ alkynyl,
or a stereoisomer, enantiomer, or tautomer thereof, or a veterinary or pharmaceutically acceptable salt thereof.

27. The compound of claim 26, selected from formula (III'), (IV'), or (V'):

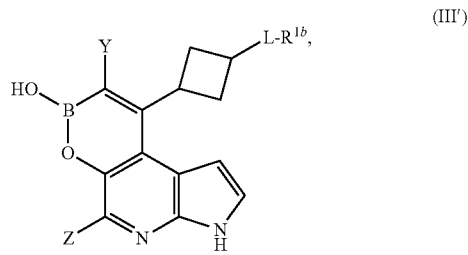

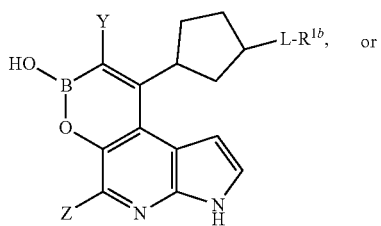
28. The compound of claim 1, selected from the group consisting of:
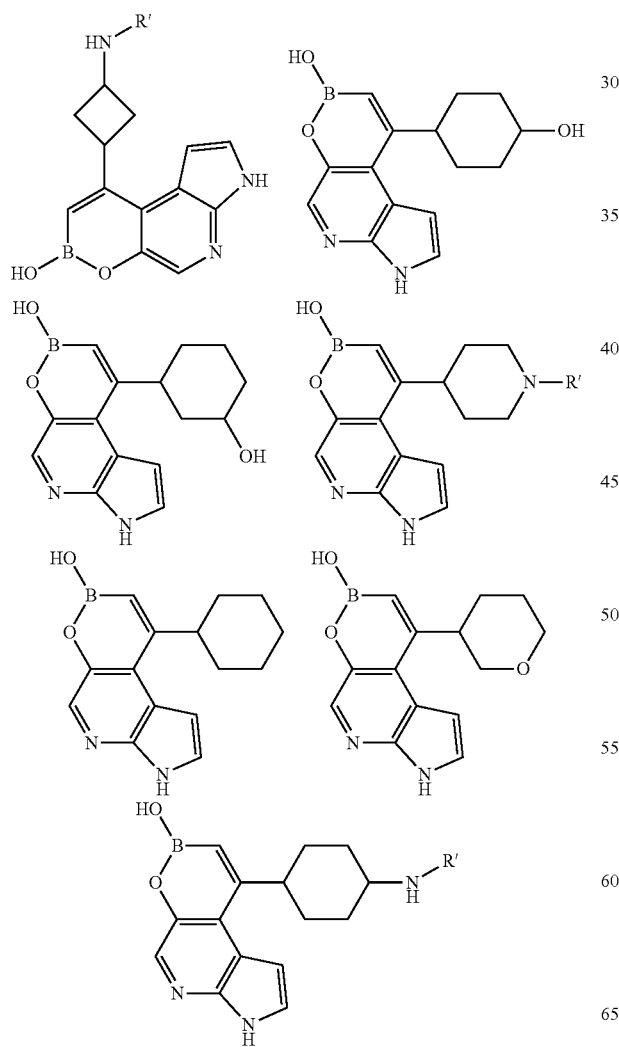
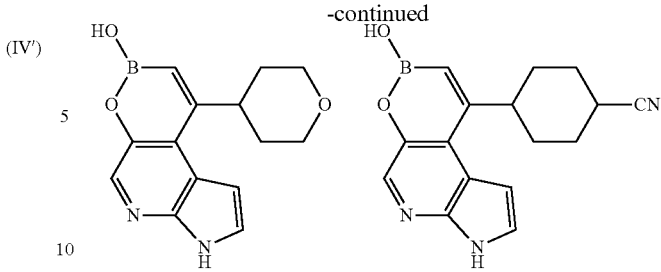
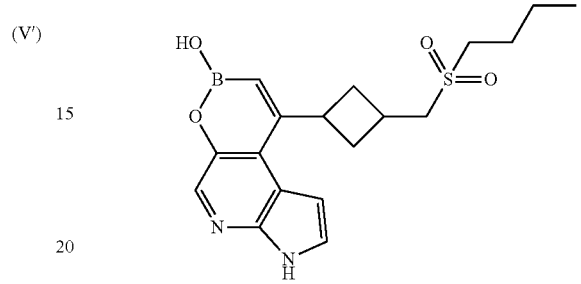
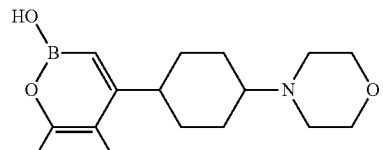
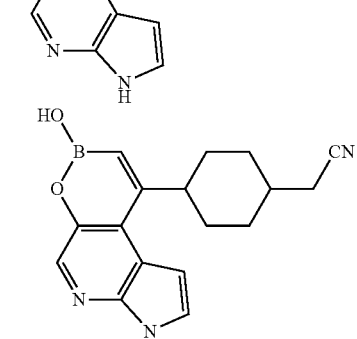
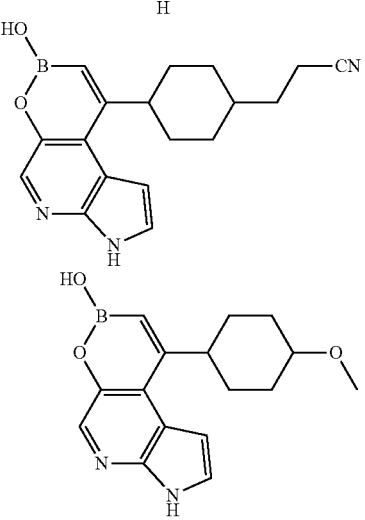
and
wherein
each R' independently is selected from the group consisting of hydrogen, substituted or unsubstituted $C_1$-$C_{15}$ alkyl, substituted or unsubstituted $C_{2-15}$ alkenyl, substituted or unsubstituted $C_{2-15}$ alkynyl, substituted or unsubstituted $C_{3-15}$ cycloalkyl, substituted or unsubstituted heteroaryl, substituted or unsubstituted heterocyclyl, and substituted or unsubstituted aryl,
or a stereoisomer, enantiomer, or tautomer thereof,
or a veterinary or pharmaceutically acceptable salt thereof.
29. The compound of claim 21, wherein R' is H.
30. A compound selected from the group consisting of:
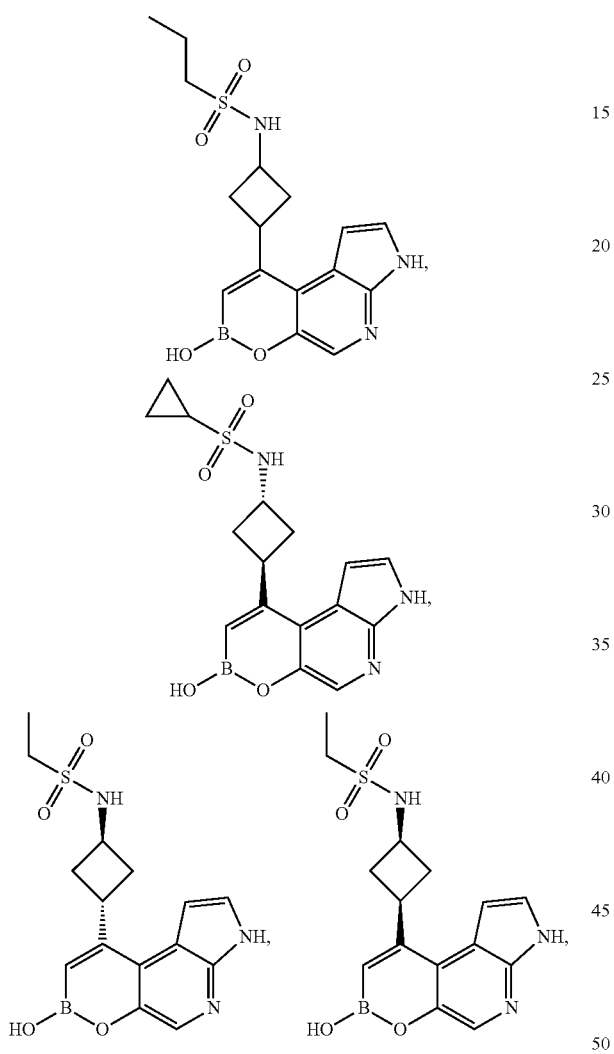
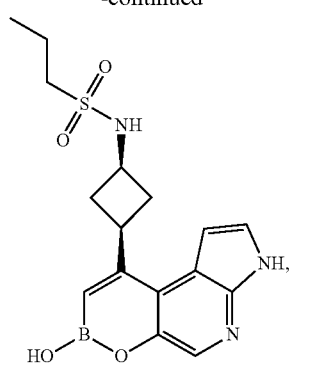
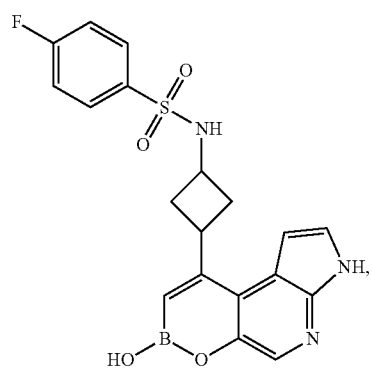
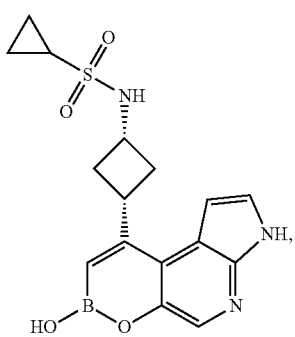
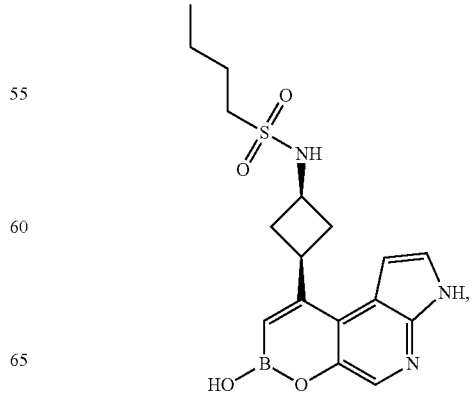

313
-continued
314
-continued
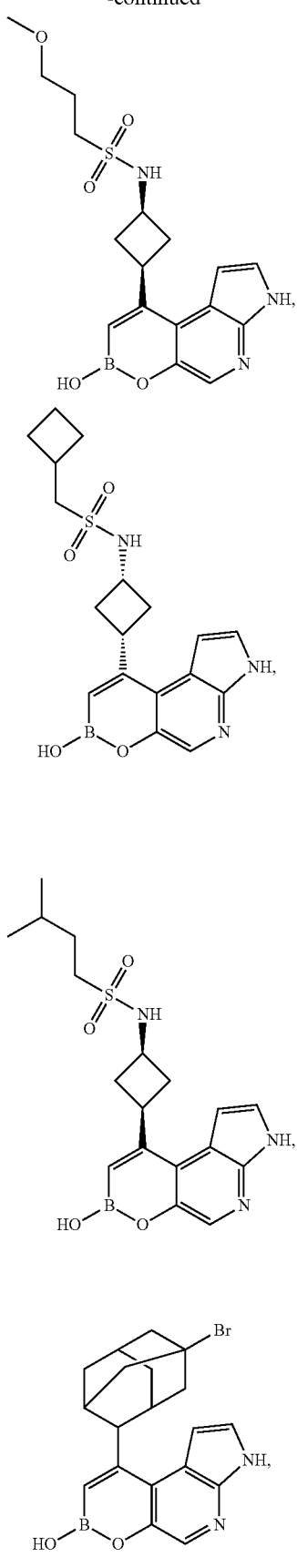
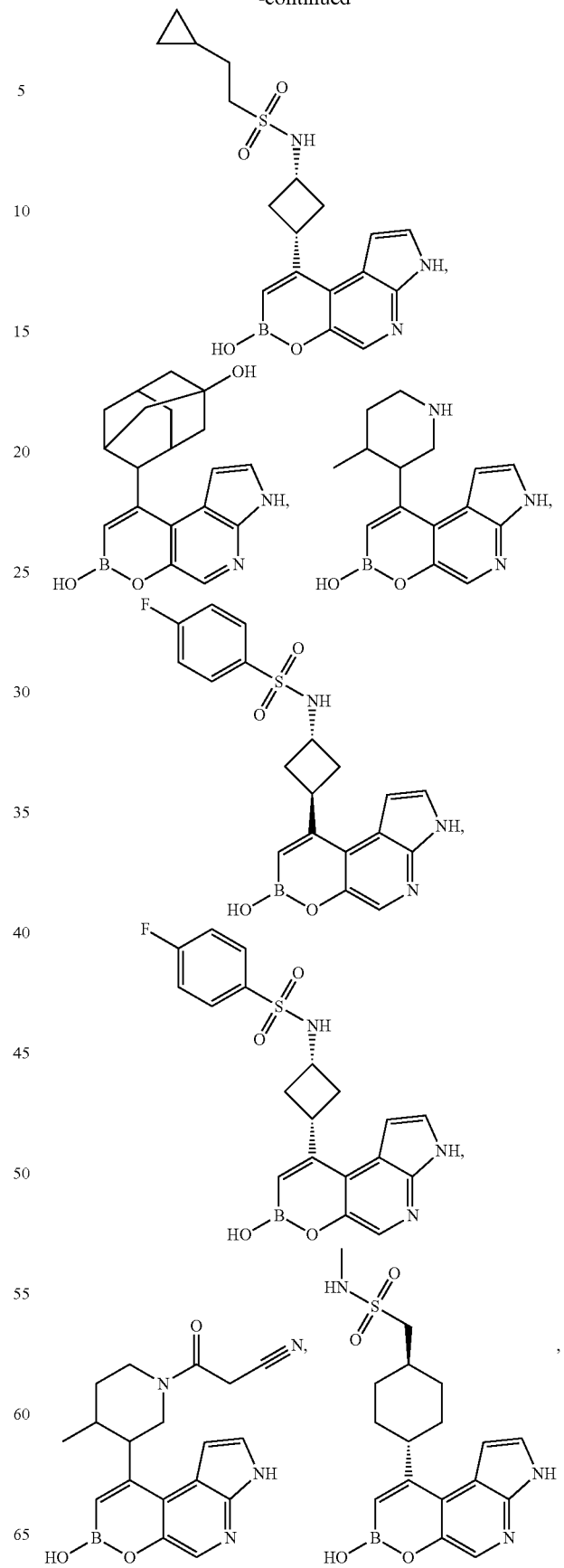

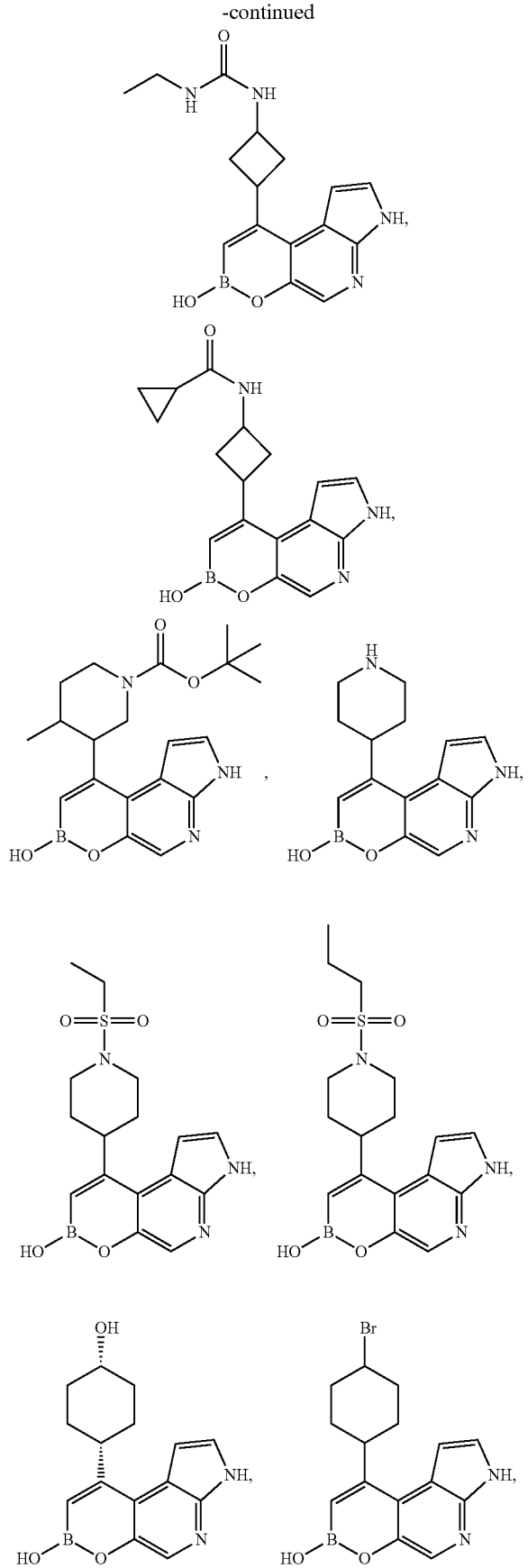

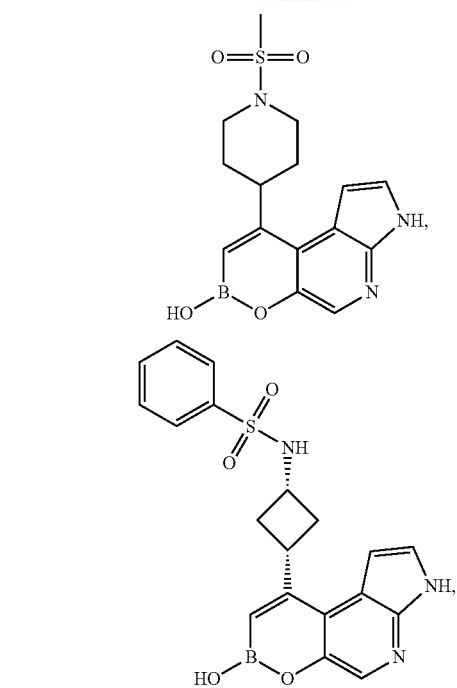
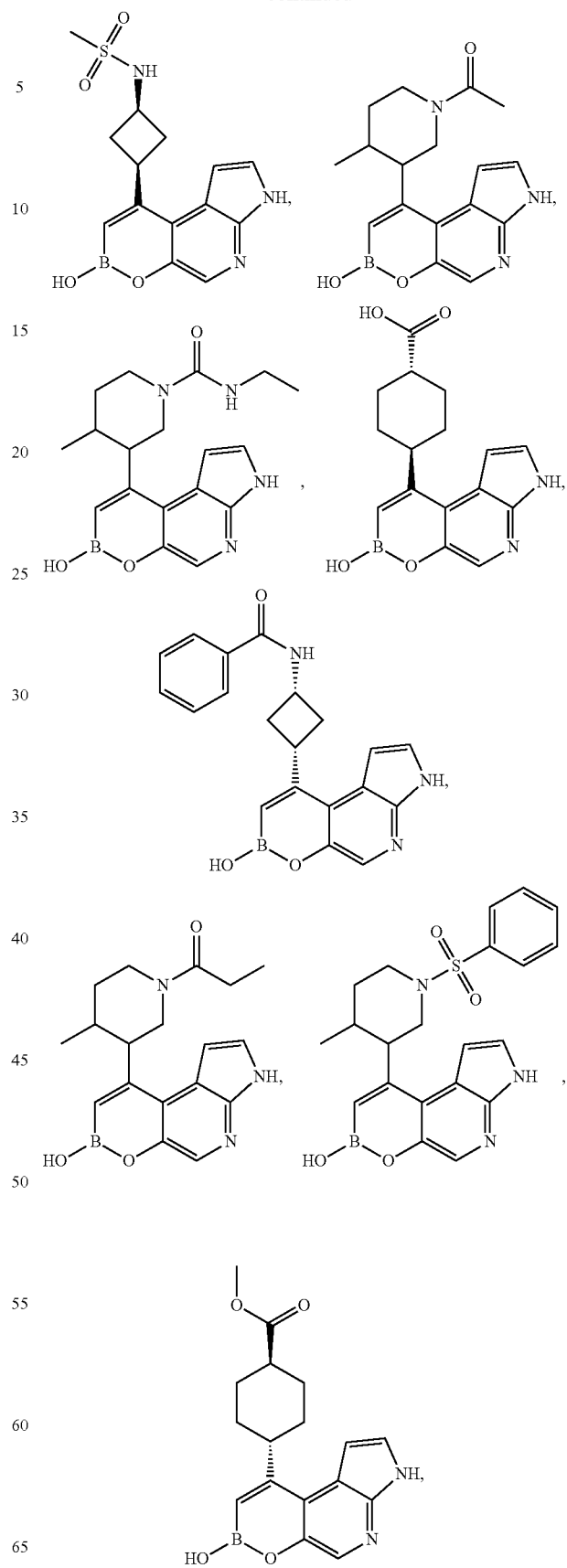

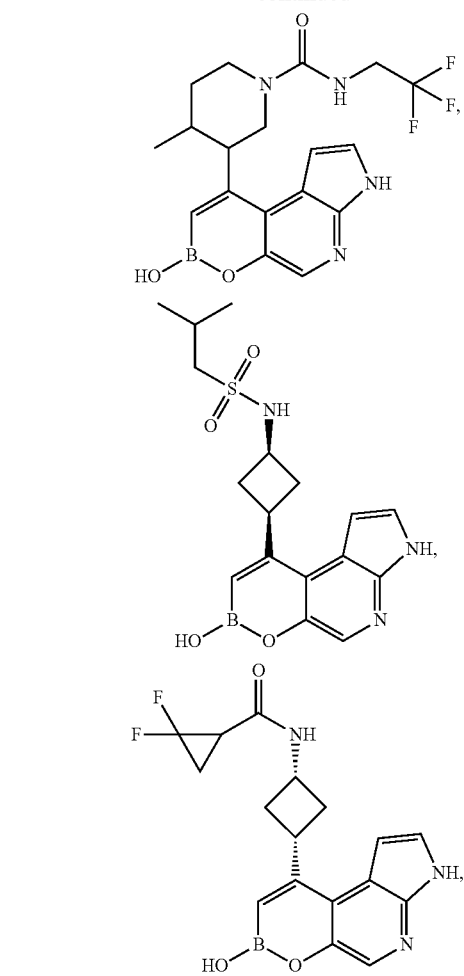
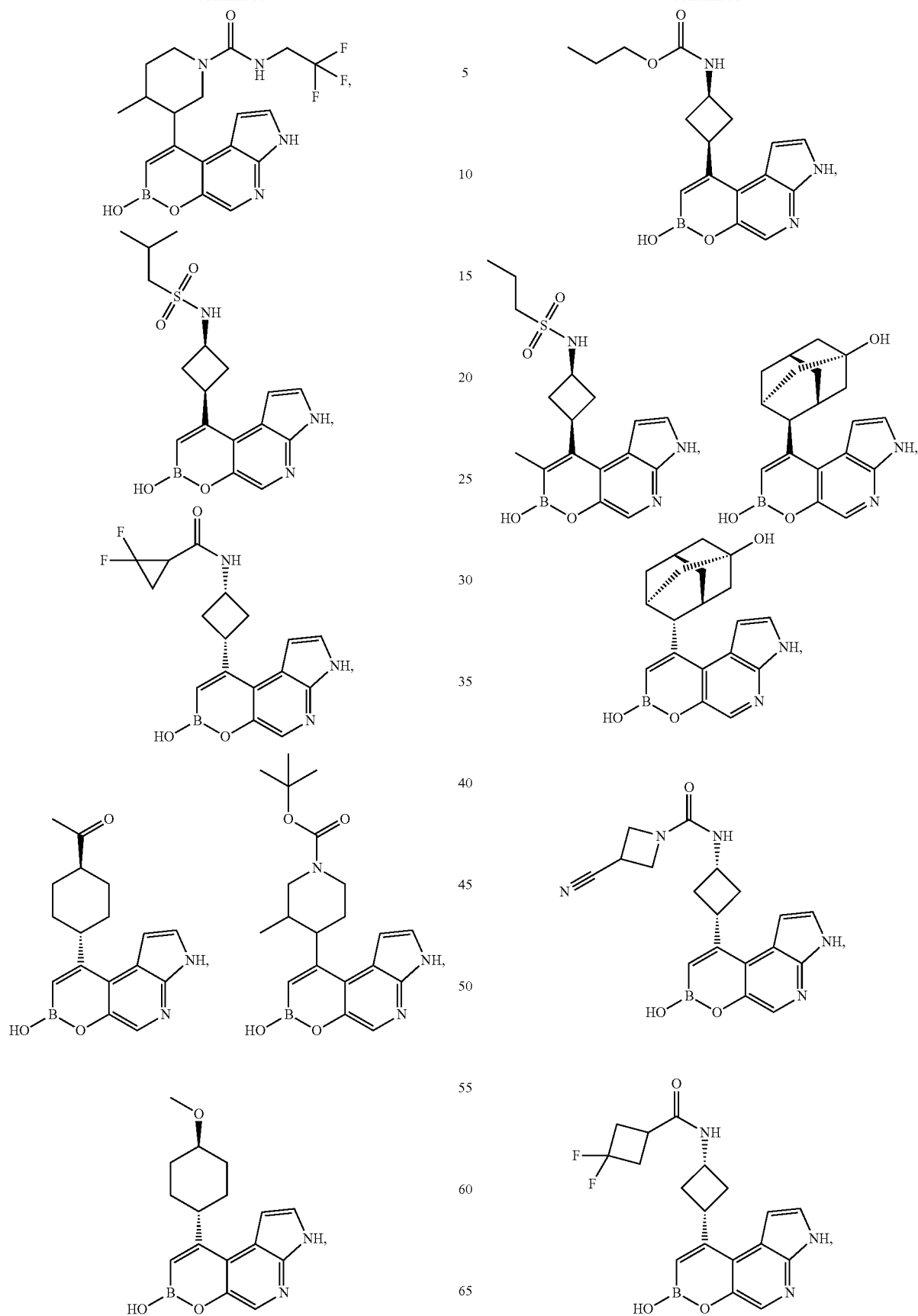

321
-continued
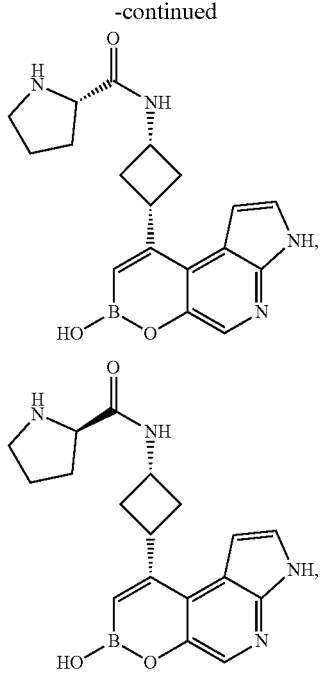
322
-continued
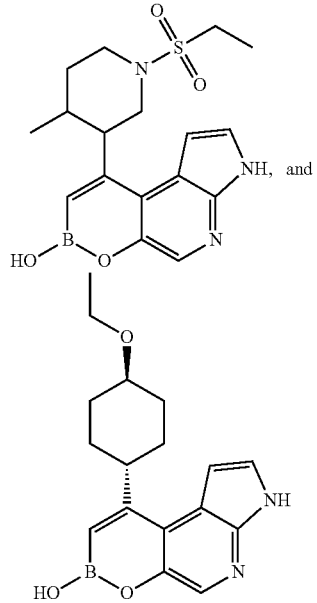
or a stereoisomer, enantiomer, or tautomer thereof, or a veterinary or pharmaceutically acceptable salt thereof.
\* \* \* \* \*